US012344850B2

(12) United States Patent
Cheng et al.

(10) Patent No.: US 12,344,850 B2
(45) Date of Patent: Jul. 1, 2025

(54) MORPHOGENIC REGULATORS AND METHODS OF USING THE SAME

(71) Applicant: Pairwise Plants Services, Inc., Durham, NC (US)

(72) Inventors: Ming Cheng, Cary, NC (US); Qingchun Shi, Cary, NC (US); Thomas J. Poorten, Durham, NC (US); Brian Charles Wilding Crawford, Cary, NC (US); Sathya Sheela Jali, Cary, NC (US); Doug Heckart, Wake Forest, NC (US); Yongjoo Kim, Durham, NC (US)

(73) Assignee: Pairwise Plants Services, Inc., Durham, NC (US)

( * ) Notice: Subject to any disclaimer, the term of this patent is extended or adjusted under 35 U.S.C. 154(b) by 112 days.

(21) Appl. No.: 17/630,973

(22) PCT Filed: Jul. 30, 2020

(86) PCT No.: PCT/US2020/044268
§ 371 (c)(1),
(2) Date: Jan. 28, 2022

(87) PCT Pub. No.: WO2021/022043
PCT Pub. Date: Feb. 4, 2021

(65) Prior Publication Data
US 2022/0259609 A1  Aug. 18, 2022

Related U.S. Application Data

(60) Provisional application No. 62/880,131, filed on Jul. 30, 2019.

(51) Int. Cl.
*C12N 15/82* (2006.01)

(52) U.S. Cl.
CPC ....... *C12N 15/821* (2013.01); *C12N 15/8216* (2013.01)

(58) Field of Classification Search
CPC . C12N 15/821; C12N 15/8216; C07K 14/415
See application file for complete search history.

(56) References Cited

U.S. PATENT DOCUMENTS

| | | | |
|---|---|---|---|
| 4,751,180 A | 6/1988 | Cousens et al. | |
| 4,935,233 A | 6/1990 | Bell et al. | |
| 5,459,252 A | 10/1995 | Conkling et al. | |
| 5,604,121 A | 2/1997 | Hilder et al. | |
| 5,625,136 A | 4/1997 | Koziel et al. | |
| 5,641,876 A | 6/1997 | McElroy et al. | |
| 5,786,538 A | 7/1998 | Barone | |
| 5,789,156 A | 8/1998 | Bujard et al. | |
| 5,814,618 A | 9/1998 | Bujard et al. | |
| 6,007,988 A | 12/1999 | Choo et al. | |
| 6,013,453 A | 1/2000 | Choo et al. | |
| 6,040,504 A | 3/2000 | Rice et al. | |
| 6,503,717 B2 | 1/2003 | Case et al. | |
| 6,511,808 B2 | 1/2003 | Wolffe et al. | |
| 6,919,619 B2 | 7/2005 | Sylvester et al. | |
| 7,141,424 B2 | 11/2006 | Shin et al. | |
| 7,166,770 B2 | 1/2007 | Hohn et al. | |
| 7,256,322 B2 | 8/2007 | Lowe et al. | |
| 7,575,917 B2 * | 8/2009 | Gilbertson | C12N 15/8212 800/278 |
| 7,579,516 B2 | 8/2009 | Boudreau | |
| 7,897,372 B2 | 3/2011 | Duchateau et al. | |
| 8,021,867 B2 | 9/2011 | Smith et al. | |
| 8,119,361 B2 | 2/2012 | Smith et al. | |
| 8,119,381 B2 | 2/2012 | Smith et al. | |
| 8,440,432 B2 | 5/2013 | Voytas et al. | |
| 8,450,471 B2 | 5/2013 | Voytas et al. | |
| 8,586,363 B2 | 11/2013 | Voytas et al. | |
| 8,586,526 B2 | 11/2013 | Gregory et al. | |
| 8,592,645 B2 | 11/2013 | Dekelver et al. | |
| 8,697,853 B2 | 4/2014 | Voytas et al. | |
| 8,704,041 B2 | 4/2014 | Gordon-Kamm et al. | |
| 8,912,138 B2 | 12/2014 | Gregory et al. | |
| 8,921,112 B2 | 12/2014 | Cai et al. | |
| 9,017,967 B2 | 4/2015 | Bonas et al. | |
| 9,790,490 B2 | 10/2017 | Zhang et al. | |
| 9,982,053 B2 | 5/2018 | Pantaleo et al. | |

(Continued)

FOREIGN PATENT DOCUMENTS

| | | | |
|---|---|---|---|
| CN | 109943585 A | 6/2019 | |
| EP | 0255378 A2 | 2/1988 | |

(Continued)

OTHER PUBLICATIONS

Ng, Pauline C., and Steven Henikoff. "Predicting deleterious amino acid substitutions." Genome research 11.5 (2001): 863-874. (Year: 2001).*
Gordon-Kamm, Bill, et al. "Using morphogenic genes to improve recovery and regeneration of transgenic plants." Plants 8.2 (2019): 38. (Year: 2019).*
Potsenkovskaia, Elina, et al. "Novel NF-Y genes expressed during somatic embryogenesis in Medicago truncatula." Plant Gene 31 (2022): 100364. (Year: 2022).*
Liu, Ye, et al. "Computational approaches for predicting variant impact: An overview from resources, principles to applications." Frontiers in genetics 13 (2022): 981005. (Year: 2022).*
Olsen, Addie Nina, et al. "NAC transcription factors: structurally distinct, functionally diverse." Trends in plant science 10.2 (2005): 79-87. (Year: 2005).*

(Continued)

*Primary Examiner* — Charles Logsdon
*Assistant Examiner* — Kelsey L McWilliams
(74) *Attorney, Agent, or Firm* — Myers Bigel, P.A.

(57) ABSTRACT

Methods and compositions for generating transgene-free plants are described. In particular, the transgene-free plants are regenerated by transient expression of morphogenic regulators in a plant cell that is precisely edited using a gene-editing methodology. Also, provided are transformed plants, plant cell, tissues, and seeds in which a target gene is edited, but non-transgenic.

16 Claims, 1 Drawing Sheet
Specification includes a Sequence Listing.

(56) References Cited

U.S. PATENT DOCUMENTS

| | | |
|---|---|---|
| 10,113,163 B2 | 10/2018 | Liu et al. |
| 10,167,457 B2 | 1/2019 | Liu et al. |
| 10,421,972 B2 | 9/2019 | Lira et al. |
| 2002/0160940 A1 | 10/2002 | Case et al. |
| 2007/0209089 A1 | 9/2007 | Richael |
| 2013/0185823 A1 | 7/2013 | Kuang et al. |
| 2017/0219596 A1 | 8/2017 | Tanenbaum et al. |
| 2018/0273960 A1 | 9/2018 | Cigan et al. |
| 2019/0017067 A1 | 1/2019 | Hummel et al. |

FOREIGN PATENT DOCUMENTS

| | | | |
|---|---|---|---|
| EP | 0342926 A2 | 11/1989 | |
| EP | 0452269 A2 | 10/1991 | |
| WO | 9301294 A1 | 1/1993 | |
| WO | 9307278 A1 | 4/1993 | |
| WO | 9509233 A1 | 4/1995 | |
| WO | 9741228 A2 | 11/1997 | |
| WO | 9942587 A1 | 8/1999 | |
| WO | 0173087 A1 | 10/2001 | |
| WO | 2004099366 A2 | 11/2004 | |
| WO | 2008042156 A1 | 4/2008 | |
| WO | 2011017293 A2 | 2/2011 | |
| WO | 2012010976 A1 | 1/2012 | |
| WO | 2015089419 A2 | 6/2015 | |
| WO | 2015161276 A2 | 10/2015 | |
| WO | 2017070632 A2 | 4/2017 | |
| WO | 2018086623 A1 | 5/2018 | |
| WO | 2018136783 A1 | 7/2018 | |
| WO | 2018205995 A1 | 11/2018 | |
| WO | 2018213708 A1 | 11/2018 | |
| WO | 2018213726 A1 | 11/2018 | |
| WO | WO-2019060383 A1 * | 3/2019 | ............... A01H 1/06 |
| WO | 2019075295 A1 | 4/2019 | |
| WO | 2019103034 A1 | 5/2019 | |

OTHER PUBLICATIONS

Guo, Haiwei H., Juno Choe, and Lawrence A. Loeb. "Protein tolerance to random amino acid change." Proceedings of the National Academy of Sciences 101.25 (2004): 9205-9210. (Year: 2004).*

Zhang, James Z. "Overexpression analysis of plant transcription factors." Current opinion in plant biology 6.5 (2003): 430-440. (Year: 2003).*

Keskin, Ozlem, et al. "A new, structurally nonredundant, diverse data set of protein-protein interfaces and its implications." Protein Science 13.4 (2004): 1043-1055 (Year: 2004).*

Thornton, Janet M., et al. "From structure to function: approaches and limitations." nature structural biology 7.11 (2000): 991-994 (Year: 2000).*

Sloan, Jeremy, et al. "Structural basis for the complex DNA binding behavior of the plant stem cell regulator WUSCHEL." Nature Communications 11.1 (2020): 2223. (Year: 2020).*

UniProt Accession A0A2P6RLV6_ROSCH dated May 23, 2018 (Year: 2018).*

International Search Report and the Written Opinion of the International Searching Authority corresponding to International Patent Application No. PCT/US2020/044268 (18 pages) (mailed Feb. 2, 2021).

NCBI Reference Sequence: XP_021816108.1 "protein WUSCHEL [*Prunus avium*]" www.ncbi.nlm.nih.gov (2 pages) (Jul. 26, 2017).

Partial European Search Report corresponding to European Patent Application No. 20847567.3 (13 pages) (dated Aug. 1, 2023).

Shirasawa et al. "The genome sequence of sweet cherry (*Prunus avium*) for use in genomics-assisted breeding" DNA Research, 24(5):499-508 (2017).

Svitashev et al. "Genome editing in maize directed by CRISPR-Cas9 ribonucleoprotein complexes" Nature Communications, 7(13274):1-7 (2016).

Uniprot database accession No. F6KQH2 "SubName: Full= Adenylate isopentenyltransferase" (1 page) (Jul. 27, 2011).

Akiyoshi et al. "T-DNA of Agrobacterium tumefaciens encodes an enzyme of cytokinin biosynthesis" Proceedings of the National Academy of Sciences USA, 81:5994-5998 (1984).

Bolduc et al. "Unraveling the KNOTTED1 regulatory network in maize meristems" Genes & Development, 26:1685-1690 (2012).

Boutilier et al. "Ectopic Expression of Baby Boom Triggers a Conversion from Vegetative to Embryonic Growth" Plant Cell, 14:1737-1749 (2002).

GenBank Accession No. AAA24927.1 "FoKI endonuclease [*Planomicrobium okeanokoites*]" www.ncbi.nlm.nih.gov (2 pages) (Apr. 26, 1993).

Gordon-Kamm et al. "Using morphogenic genes to improve recovery and regeneration of transgenic plants" Plants, 8(38):1-18 (2019).

Haecker et al. "Expression dynamics of WOX genes mark cell fate decisions during early embryonic patterning in *Arabidopsis thaliana*" Development, 131:657-668 (2004).

Hoerster et al. "Use of non-integrating Zm-Wus2 vectors to enhance maize transformation" In Vitro Cellular & Developmental Biology—Plant, 56:265-279 (2020).

Kakimoto, Tatsuo "Identification of plant cytokinin biosynthetic enzymes as dimethylallyl diphosphate:ATP/ADP isopentenyltransferases" Plant & Cell Physiology, 42(7):677-685 (2001).

Kunkel et al. "Inducible isopentenyl transferase as a high efficiency marker for plant transformation" Nature Biotechnology, 17:916-919 (1999).

Kyo et al. "Coexpression of WUSCHEL related homeobox (WOX) 2 with WOX8 or WOX9 promotes regeneration from leaf segments and free cells in Nicotiana tabacum L" Plant Biotechnology, 35:23-30 (2018).

Laux et al. "The WUSCHEL gene is required for shoot and floral meristem integrity in *Arabidopsis*" Development, 122:87-96 (1996).

Long et al. "miR156-SPL modules regulate induction of somatic embryogenesis in citrus callus" Journal of Experimental Botany, 69(12):2979-2993 (2018).

Lowe et al. "Morphogenic Regulators Baby boom and Wuschel Improve Monocot Transformation" The Plant Cell, 28:1998-2015 (2016).

Lowe et al. "Rapid genotype 'independent' *Zea mays* L. (maize) transformation via direct somatic embryogenesis" In Vitro Cellular & Developmental Biology—Plant, 54(3):240-252 (2018).

Maher et al. "Plant gene editing through de novo induction of meristems" Nature Biotechnology, 38:84-89 (2020).

Nelson-Vasilchik et al. "Transformation of Recalcitrant Sorghum Varieties Facilitated by Baby Boom and Wuschel2" Current Protocols in Plant Biology, 3:e20076 (2018).

Nishimura et al. "Over-Expression of Tobacco knotted 1-Type Class1 Homeobox Genes Alters Various Leaf Morphology" Plant & Cellular Physiology, 41(5):583-590 (2000).

Srinivasan et al. "Heterologous expression of the Baby Boom AP2/ERF transcription factor enhances the regeneration capacity of tobacco (*Nicotiana tabacum* L.)" Planta, 225:341-351 (2007).

Zhang et al. "An Intrinsic MicroRNA Timer Regulates Progressive Decline in Shoot regenerative Capacity in Plants" Plant Cell, 27(2):349-360 (2015).

* cited by examiner

| 1 | 2 | 3 | 4 | 5 | 6 | 7 | 8 | 9 | 10 |
|---|---|---|---|---|---|---|---|---|----|
| 11 | 12 | 13 | 14 | 15 | 16 | 17 | 18 | 19 | 20 |
| 21 | 22 | 23 | 24 | 25 | 26 | 27 | 28 | 29 | 30 |
| 31 | 32 | 33 | 34 | 35 | 36 | 37 | 38 | 39 | 40 |
| 41 | 42 | 43 | 44 | 45 | 46 | | | | |
| 47 | 48 | 49 | 50 | 51 | 52 | 53 | 54 | 55 | 56 |
| 57 | 58 | 59 | 60 | 61 | 62 | 63 | 64 | 65 | 66 |
| 67 | 68 | 69 | 70 | 71 | 72 | 73 | 74 | 75 | 76 |
| 77 | 78 | 79 | 80 | 81 | 82 | 83 | 84 | 85 | 86 |
| 87 | 88 | 89 | 90 | 91 | 92 | 93 | 94 | 95 | 96 |
| 97 | 98 | 99 | 100 | 101 | 102 | 103 | 104 | 105 | 106 |

MORPHOGENIC REGULATORS AND METHODS OF USING THE SAME

STATEMENT REGARDING ELECTRONIC FILING OF A SEQUENCE LISTING

A Sequence Listing in ASCII text format, submitted under 37 C.F.R. § 1.821, entitled 1499-39_ST25.txt, 541,101 bytes in size, generated on Feb. 10, 2025, and filed via EFS-Web, is provided in lieu of a paper copy. This Sequence Listing is hereby incorporated by reference into the specification for its disclosures.

FIELD

The present disclosure relates to morphogenic regulators and methods of using the same. The present disclosure further relates to next generation plant breeding, including breeding for vegetative propagated crops, along with methods and compositions for producing transgene-free plants, optionally in which a target gene is edited.

BACKGROUND

Recombinant DNA technology has emerged as a powerful tool for editing genes and genetic elements in vectors to produce novel recombinant DNA products. Due to the continuous improvement of DNA technology and the application of *Agrobacterium* for transgene delivery, transgenic plants have been successfully generated over two decades and genetically modified (GM) plant products have been commercialized to meet high demands of modern society. Not surprisingly, genetic transformation in plants has become a routine practice so that there are more than one hundred agricultural crops to have been genetically modified around the world.

The International Service for the Acquisition of Agri-Biotech Applications (ISAAA) reported that about 160 million hectares were used for cultivating transgenic crops in 2011, which was a 94-fold increase within five years from 1996. There is no doubt that GM technology has become an important plant breeding tool as an answer to a threat of food security in developing countries.

Along with rapid growth of transgenic crop cultivation and production, GM plants have raised concerns from regulatory agencies and the public in some countries, including Europe. One of main concerns is that a piece of foreign DNA and/or a selectable marker gene (usually an antibiotic- or herbicide-resistant gene) remains in the genomes of GM plants. There have been a few approaches to producing transgene-free transgenic plants. One approach is to segregate away integration of a transgene and/or a piece of foreign DNA by conventional breeding methods, for example, by backcrossing the transgenic plants with its parent and achieving offspring with a genetic identity which is closer to that of the parent. In this way, a desired trait in the transgenic plants can be transferred to the favored genetic background of another variety, while undesired foreign DNA can be eliminated.

The aforementioned segregating-away approach has been applied to row crops for removal of unwanted foreign DNA and/or transgene(s); however, they are not particularly adopted to vegetative propagated crops due to their heterozygotic nature and/or multiploidy. The recurrent crossing method to segregate away the transgene(s) is practically and economically undesirable for heterozygotic and/or multiploid plants because the crossings would be technically challenging and/or selection of progeny with only the desired traits and/or gene of interest (GOI) would require multiple rounds of crossing to generate pure and/or near-isogenic lines, which could result in genetic drift, such as loss of beneficial alleles. Also, conventional genetic engineering methods still have not given solutions to the technical challenges of identifying random mutations caused by integration of foreign DNAs in a host genome and removing them in a selective, efficient, and economic manner. Therefore, there is a great need in the art for a method of creating transgene-free plants with high heterozygosity and/or multiploidy, along with introduction of targeted genetic modification by employing new targeted genome engineering technologies.

SUMMARY OF THE DISCLOSURE

One aspect of the present disclosure is directed to an isolated polynucleotide comprising a nucleotide sequence having at least 90%, 95%, or 98% sequence identity to the nucleotide sequence of any one of SEQ ID NOs:1-18 or SEQ ID NOs:28-49. In some embodiments, the isolated polynucleotide comprises a nucleotide sequence having at least 90%, 95%, or 98% sequence identity to the nucleotide sequence of any one of SEQ ID NOs:1-18. In some embodiments, the isolated polynucleotide comprises the nucleotide sequence of any one of SEQ ID NOs:1-18 or SEQ ID NOs:28-49. In some embodiments, the isolated polynucleotide comprises the nucleotide sequence of any one of SEQ ID NOs:1-18.

Another aspect of the present disclosure is directed to an isolated polynucleotide encoding an amino acid sequence having at least 90%, 95%, or 98% sequence identity to the polypeptide sequence of any one of SEQ ID NOs:19-27 or SEQ ID NOs:50-60. In some embodiments, the isolated polynucleotide encodes an amino acid sequence having at least 90%, 95%, or 98% sequence identity to the polypeptide sequence of any one of SEQ ID NOs:19-27. In some embodiments, the isolated polynucleotide encodes the polypeptide sequence of any one of SEQ ID NOs:19-27 or SEQ ID NOs:50-60. In some embodiments, the isolated polynucleotide encodes the polypeptide sequence of any one of SEQ ID NOs:19-27.

A further aspect of the present disclosure is directed to an isolated polypeptide comprising an amino acid sequence having at least 90%, 95%, or 98% sequence identity to the amino acid sequence of any one of SEQ ID NOs:19-27 or SEQ ID NOs:50-60. In some embodiments, the isolated polypeptide comprises an amino acid sequence having at least 90%, 95%, or 98% sequence identity to the amino acid sequence of any one of SEQ ID NOs:19-27. In some embodiments, the isolated polypeptide comprises the amino acid sequence of any one of SEQ ID NOs:19-27 or SEQ ID NOs:50-60. In some embodiments, the isolated polypeptide comprises the amino acid sequence of any one of SEQ ID NOs:19-27.

Another aspect of the present disclosure is directed to a method for transforming a plant cell, the method comprising: introducing a polynucleotide or a polypeptide comprising a heterologous morphogenic regulator into the plant cell, thereby transforming the plant cell.

A further aspect of the present disclosure is directed to a method of improving or increasing regeneration frequency in a group of plant cells, the method comprising: introducing a polynucleotide comprising a heterologous morphogenic regulator into a plant cell in the group of plant cells, thereby improving or increasing regeneration frequency in the group of plant cells.

An additional aspect of the present disclosure is directed to a plant cell, plant part, and/or plant comprising: an edited polynucleotide, wherein the plant cell, plant part, and/or plant is transgene-free.

A further aspect of the present disclosure is directed to a plant cell comprising: a polynucleotide comprising a heterologous morphogenic regulator.

Another aspect of the present disclosure is directed to a group of plant cells comprising: a first plant cell comprising a polynucleotide comprising a heterologous morphogenic regulator; and a second plant cell comprising a polynucleotide encoding gene editing machinery or a gene editing complex (e.g., a ribonucleoprotein) that is capable of modifying at least one target nucleic acid.

The present disclosure can provide a solution to the aforementioned problem of conventional breeding and/or genetic engineering methods to avoid integrating undesired transgenes and/or foreign DNA pieces from stably integrated transgenic plants. In some embodiments, the present disclosure provides a method of modulating and/or modifying a target nucleic acid using a gene-editing system. Furthermore, the disclosure teaches a method of stimulating regeneration of a gene-edited plant or plant part from a plant cell, optionally in which a target nucleic acid is stably and precisely edited. The regeneration of a gene-edited plant or plant part can be induced, as elaborated upon herein, by at least one transiently expressed morphogenic regulator taught in the present disclosure.

The present disclosure further provides expression cassettes and/or vectors comprising a polynucleotide and/or polypeptide of the present invention, and cells comprising a polynucleotide and/or polypeptide of the present invention.

It is noted that aspects of the invention described with respect to one embodiment, may be incorporated in a different embodiment although not specifically described relative thereto. That is, all embodiments and/or features of any embodiment can be combined in any way and/or combination. Applicant reserves the right to change any originally filed claim and/or file any new claim accordingly, including the right to be able to amend any originally filed claim to depend from and/or incorporate any feature of any other claim or claims although not originally claimed in that manner. These and other objects and/or aspects of the present invention are explained in detail in the specification set forth below. Further features, advantages and details of the present invention will be appreciated by those of ordinary skill in the art from a reading of the figures and the detailed description of the preferred embodiments that follow, such description being merely illustrative of the present invention.

BRIEF DESCRIPTION OF THE FIGURES

FIG. 1 illustrates GUS assay results of one hundred and six shoots induced by the ipt gene expression. From one hundred six ipt-induced shoots, seven samples were GUS-positive, but the other ninety-nine samples were GUS-negative.

DETAILED DESCRIPTION

The present disclosure now will be described hereinafter with reference to the accompanying drawings and examples, in which embodiments of the invention are shown. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. Thus, the invention contemplates that in some embodiments of the invention, any feature or combination of features set forth herein can be excluded or omitted. To illustrate, if the specification states that a composition comprises components A, B and C, it is specifically intended that any of A, B or C, or a combination thereof, can be omitted and disclaimed singularly or in any combination. In addition, numerous variations and additions to the various embodiments suggested herein will be apparent to those skilled in the art in light of the instant disclosure, which do not depart from the instant invention. Hence, the following descriptions are intended to illustrate some particular embodiments of the invention, and not to exhaustively specify all permutations, combinations and variations thereof.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

All publications, patent applications, patents and other references cited herein are incorporated by reference in their entireties for the teachings relevant to the sentence and/or paragraph in which the reference is presented.

As used in the description of the invention and the appended claims, the singular forms "a," "an" and "the" are intended to include the plural forms as well, unless the context clearly indicates otherwise.

Also as used herein, "and/or" refers to and encompasses any and all possible combinations of one or more of the associated listed items, as well as the lack of combinations when interpreted in the alternative ("or").

The term "about," as used herein when referring to a measurable value such as an amount or concentration and the like, is meant to encompass variations of $\pm 10\%$, $\pm 5\%$, $\pm 1\%$, $\pm 0.5\%$, or even $\pm 0.1\%$ of the specified value as well as the specified value. For example, "about X" where X is the measurable value, is meant to include X as well as variations of $\pm 10\%$, $\pm 5\%$, $\pm 1\%$, $\pm 0.5\%$, or even $\pm 0.1\%$ of X. A range provided herein for a measureable value may include any other range and/or individual value therein.

As used herein, phrases such as "between X and Y" and "between about X and Y" should be interpreted to include X and Y. As used herein, phrases such as "between about X and Y" mean "between about X and about Y" and phrases such as "from about X to Y" mean "from about X to about Y."

Recitation of ranges of values herein are merely intended to serve as a shorthand method of referring individually to each separate value falling within the range, unless otherwise indicated herein, and each separate value is incorporated into the specification as if it were individually recited herein. For example, if the range 10 to 15 is disclosed, then 11, 12, 13, and 14 are also disclosed.

The term "comprise," "comprises" and "comprising" as used herein, specify the presence of the stated features, integers, steps, operations, elements, and/or components, but do not preclude the presence or addition of one or more other features, integers, steps, operations, elements, components, and/or groups thereof.

As used herein, the transitional phrase "consisting essentially of" means that the scope of a claim is to be interpreted to encompass the specified materials or steps recited in the claim and those that do not materially affect the basic and novel characteristic(s) of the claimed invention. Thus, the term "consisting essentially of" when used in a claim of this invention is not intended to be interpreted to be equivalent to "comprising."

As used herein, the terms "increase," "increasing," "enhance," "enhancing," "improve" and "improving" (and grammatical variations thereof) describe an elevation in a specified parameter or value of at least about 5%, 10%, 15%, 20%, 25%, 30%, 35%, 40%, 45%, 50%, 55%, 60%, 65%, 70%, 75%, 80%, 85%, 90%, 95%, 100%, 150%, 200%, 300%, 400%, 500% or more as compared to a control.

As used herein, the terms "reduce," "reduced," "reducing," "reduction," "diminish," and "decrease" (and grammatical variations thereof), describe, for example, a decrease in a specified parameter or value of at least about 5%, 10%, 15%, 20%, 25%, 30%, 35%, 40%, 45%, 50%, 55%, 60%, 65%, 70%, 75%, 80%, 85%, 90%, 95%, 97%, 98%, 99%, or 100% as compared to a control. In particular embodiments, the reduction can result in no or essentially no (i.e., an insignificant amount, e.g., less than about 10% or even 5%) detectable activity or amount.

A "heterologous" or a "recombinant" nucleotide sequence is a nucleotide sequence not naturally associated with a host cell into which it is introduced, including non-naturally occurring multiple copies of a naturally occurring nucleotide sequence.

A "native" or "wild type" nucleic acid, nucleotide sequence, polypeptide or amino acid sequence refer to a naturally occurring or endogenous nucleic acid, nucleotide sequence, polypeptide or amino acid sequence. Thus, for example, a "wild type mRNA" is an mRNA that is naturally occurring in or endogenous to the reference organism. A "homologous" nucleic acid sequence is a nucleotide sequence naturally associated with a host cell into which it is introduced.

As used herein, the terms "nucleic acid," "nucleic acid molecule," "nucleotide sequence" and "polynucleotide" refer to RNA or DNA that is linear or branched, single or double stranded, or a hybrid thereof. The term also encompasses RNA/DNA hybrids. When dsRNA is produced synthetically, less common bases, such as inosine, 5-methylcytosine, 6-methyladenine, hypoxanthine and others can also be used for antisense, dsRNA, and ribozyme pairing. For example, polynucleotides that contain C-5 propyne analogues of uridine and cytidine have been shown to bind RNA with high affinity and to be potent antisense inhibitors of gene expression. Other modifications, such as modification to the phosphodiester backbone, or the 2'-hydroxy in the ribose sugar group of the RNA can also be made.

As used herein, the term "nucleotide sequence" refers to a heteropolymer of nucleotides or the sequence of these nucleotides from the 5' to 3' end of a nucleic acid molecule and includes DNA or RNA molecules, including cDNA, a DNA fragment or portion, genomic DNA, synthetic (e.g., chemically synthesized) DNA, plasmid DNA, mRNA, and anti-sense RNA, any of which can be single stranded or double stranded. The terms "nucleotide sequence" "nucleic acid," "nucleic acid molecule," "nucleic acid construct," "recombinant nucleic acid," "oligonucleotide" and "polynucleotide" are also used interchangeably herein to refer to a heteropolymer of nucleotides. Nucleic acid molecules and/or nucleotide sequences provided herein are presented herein in the 5' to 3' direction, from left to right and are represented using the standard code for representing the nucleotide characters as set forth in the U.S. sequence rules, 37 CFR §§ 1.821-1.825 and the World Intellectual Property Organization (WIPO) Standard ST.25. A "5' region" as used herein can mean the region of a polynucleotide that is nearest the 5' end of the polynucleotide. Thus, for example, an element in the 5' region of a polynucleotide can be located anywhere from the first nucleotide located at the 5' end of the polynucleotide to the nucleotide located halfway through the polynucleotide. A "3' region" as used herein can mean the region of a polynucleotide that is nearest the 3' end of the polynucleotide. Thus, for example, an element in the 3' region of a polynucleotide can be located anywhere from the first nucleotide located at the 3' end of the polynucleotide to the nucleotide located halfway through the polynucleotide.

As used herein, the term "gene" refers to a nucleic acid molecule capable of being used to produce mRNA, antisense RNA, miRNA, anti-microRNA antisense oligodeoxyribonucleotide (AMO) and the like. Genes may or may not be capable of being used to produce a functional protein or gene product. Genes can include both coding and noncoding regions (e.g., introns, regulatory elements, promoters, enhancers, termination sequences and/or 5' and 3' untranslated regions).

A polynucleotide, gene, or polypeptide may be "isolated" by which is meant a nucleic acid or polypeptide that is substantially or essentially free from components normally found in association with the nucleic acid or polypeptide, respectively, in its natural state. In some embodiments, such components include other cellular material, culture medium from recombinant production, and/or various chemicals used in chemically synthesizing the nucleic acid or polypeptide.

The term "mutation" refers to point mutations (e.g., missense, or nonsense, or insertions or deletions of single base pairs that result in frame shifts), insertions, deletions, and/or truncations. When the mutation is a substitution of a residue within an amino acid sequence with another residue, or a deletion or insertion of one or more residues within a sequence, the mutations are typically described by identifying the original residue followed by the position of the residue within the sequence and by the identity of the newly substituted residue.

The terms "complementary" or "complementarity," as used herein, refer to the natural binding of polynucleotides under permissive salt and temperature conditions by base-pairing. For example, the sequence "A-G-T" (5' to 3') binds to the complementary sequence "T-C-A" (3' to 5'). Complementarity between two single-stranded molecules may be "partial," in which only some of the nucleotides bind, or it may be complete when total complementarity exists between the single stranded molecules. The degree of complementarity between nucleic acid strands has significant effects on the efficiency and strength of hybridization between nucleic acid strands.

"Complement" as used herein can mean 100% complementarity with the comparator nucleotide sequence or it can mean less than 100% complementarity (e.g., "substantially complementary," e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, and the like, complementarity).

A "portion" or "fragment" of a nucleotide sequence or polypeptide sequence will be understood to mean a nucleotide or polypeptide sequence of reduced length (e.g., reduced by 1, 2, 3, 4, 5, 6, 7, 8, 9, 10, 11, 12, 13, 14, 15, 16, 17, 18, 19, 20 or more residue(s) (e.g., nucleotide(s) or peptide(s))

relative to a reference nucleotide or polypeptide sequence, respectively, and comprising, consisting essentially of and/or consisting of a nucleotide or polypeptide sequence of contiguous residues, respectively, identical or almost identical (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identical) to the reference nucleotide or polypeptide sequence. Such a nucleic acid fragment or portion according to the invention may be, where appropriate, included in a larger polynucleotide of which it is a constituent. As an example, a repeat sequence of guide nucleic acid of this invention may comprise a portion of a wild type CRISPR-Cas repeat sequence (e.g., a wild type Type V CRISPR Cas repeat, e.g., a repeat from the CRISPR Cas system that includes, but is not limited to, Cas12a (Cpf1), Cas12b, Cas12c (C2c3), Cas12d (CasY), Cas12e (CasX), Cas12g, Cas12h, Cas12i, C2c1, C2c4, C2c5, C2c8, C2c9, C2c10, Cas14a, Cas14b, and/or Cas14c, and the like).

Different nucleic acids or proteins having homology are referred to herein as "homologues." The term homologue includes homologous sequences from the same and other species and orthologous sequences from the same and other species. "Homology" refers to the level of similarity between two or more nucleic acid and/or amino acid sequences in terms of percent of positional identity (i.e., sequence similarity or identity). Homology also refers to the concept of similar functional properties among different nucleic acids or proteins. Thus, the compositions and methods of the invention further comprise homologues to the nucleotide sequences and polypeptide sequences of this invention. "Orthologous" and "orthologs" as used herein, refers to homologous nucleotide sequences and/or amino acid sequences in different species that arose from a common ancestral gene during speciation. A homologue or ortholog of a nucleotide sequence of this invention has a substantial sequence identity (e.g., at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5% or 100%) to said nucleotide sequence of the invention.

As used herein "sequence identity" refers to the extent to which two optimally aligned polynucleotide or polypeptide sequences are invariant throughout a window of alignment of components, e.g., nucleotides or amino acids. "Identity" can be readily calculated by known methods including, but not limited to, those described in: *Computational Molecular Biology* (Lesk, A. M., ed.) Oxford University Press, New York (1988); *Biocomputing: Informatics and Genome Projects* (Smith, D. W., ed.) Academic Press, New York (1993); *Computer Analysis of Sequence Data, Part I* (Griffin, A. M., and Griffin, H. G., eds.) Humana Press, New Jersey (1994); *Sequence Analysis in Molecular Biology* (von Heinje, G., ed.) Academic Press (1987); and *Sequence Analysis Primer* (Gribskov, M. and Devereux, J., eds.) Stockton Press, New York (1991).

As used herein, the term "percent sequence identity" or "percent identity" refers to the percentage of identical nucleotides in a linear polynucleotide sequence of a reference ("query") polynucleotide molecule (or its complementary strand) as compared to a test ("subject") polynucleotide molecule (or its complementary strand) when the two sequences are optimally aligned. In some embodiments, "percent identity" can refer to the percentage of identical amino acids in an amino acid sequence as compared to a reference polypeptide.

As used herein, the phrase "substantially identical," or "substantial identity" in the context of two nucleic acid molecules, nucleotide sequences or protein sequences, refers to two or more sequences or subsequences that have at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5% or 100% nucleotide or amino acid residue identity, when compared and aligned for maximum correspondence, as measured using one of the following sequence comparison algorithms or by visual inspection. In some embodiments of the invention, the substantial identity exists over a region of consecutive nucleotides of a nucleotide sequence of the invention that is about 10 nucleotides to about 20 nucleotides, about 10 nucleotides to about 25 nucleotides, about 10 nucleotides to about 30 nucleotides, about 15 nucleotides to about 25 nucleotides, about 30 nucleotides to about 40 nucleotides, about 50 nucleotides to about 60 nucleotides, about 70 nucleotides to about 80 nucleotides, about 90 nucleotides to about 100 nucleotides, or more nucleotides in length, and any range therein, up to the full length of the sequence. In some embodiments, the nucleotide sequences can be substantially identical over at least about 20 nucleotides (e.g., about 20, 21, 22, 23, 24, 25, 26, 27, 28, 29, 30, 31, 32, 33, 34, 35, 36, 37, 38, 39, 40 nucleotides). In some embodiments, a substantially identical nucleotide or protein sequence performs substantially the same function as the nucleotide (or encoded protein sequence) to which it is substantially identical.

For sequence comparison, typically one sequence acts as a reference sequence to which test sequences are compared. When using a sequence comparison algorithm, test and reference sequences are entered into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

Optimal alignment of sequences for aligning a comparison window are well known to those skilled in the art and may be conducted by tools such as the local homology algorithm of Smith and Waterman, the homology alignment algorithm of Needleman and Wunsch, the search for similarity method of Pearson and Lipman, and optionally by computerized implementations of these algorithms such as GAP, BESTFIT, FASTA, and TFASTA available as part of the GCG WISCONSIN PACKAGE® (Accelrys Inc., San Diego, CA) software suite for sequence analysis. An "identity fraction" for aligned segments of a test sequence and a reference sequence is the number of identical components which are shared by the two aligned sequences divided by the total number of components in the reference sequence segment, e.g., the entire reference sequence or a smaller defined part of the reference sequence. Percent sequence identity is represented as the identity fraction multiplied by 100. The comparison of one or more polynucleotide sequences may be to a full-length polynucleotide sequence or a portion thereof, or to a longer polynucleotide sequence. For purposes of this invention "percent identity" may also be determined using BLASTX version 2.0 for translated nucleotide sequences and BLASTN version 2.0 for polynucleotide sequences.

Two nucleotide sequences may also be considered substantially complementary when the two sequences hybridize to each other under stringent conditions. In some representative embodiments, two nucleotide sequences considered to be substantially complementary hybridize to each other under highly stringent conditions.

"Stringent hybridization conditions" and "stringent hybridization wash conditions" in the context of nucleic acid hybridization experiments such as Southern and Northern hybridizations are sequence dependent, and are different under different environmental parameters. An extensive guide to the hybridization of nucleic acids is found in Tijssen *Laboratory Techniques in Biochemistry and Molecular Biology-Hybridization with Nucleic Acid Probes* part I chapter 2 "Overview of principles of hybridization and the strategy of nucleic acid probe assays" Elsevier, New York (1993). Generally, highly stringent hybridization and wash conditions are selected to be about 5° C. lower than the thermal melting point ($T_m$) for the specific sequence at a defined ionic strength and pH.

The $T_m$ is the temperature (under defined ionic strength and pH) at which 50% of the target sequence hybridizes to a perfectly matched probe. Very stringent conditions are selected to be equal to the $T_m$ for a particular probe. An example of stringent hybridization conditions for hybridization of complementary nucleotide sequences which have more than 100 complementary residues on a filter in a Southern or northern blot is 50% formamide with 1 mg of heparin at 42° C., with the hybridization being carried out overnight. An example of highly stringent wash conditions is 0.1 5M NaCl at 72° C. for about 15 minutes. An example of stringent wash conditions is a 0.2×SSC wash at 65° C. for 15 minutes (see, Sambrook, infra, for a description of SSC buffer). Often, a high stringency wash is preceded by a low stringency wash to remove background probe signal. An example of a medium stringency wash for a duplex of, e.g., more than 100 nucleotides, is 1×SSC at 45° C. for 15 minutes. An example of a low stringency wash for a duplex of, e.g., more than 100 nucleotides, is 4-6×SSC at 40° C. for 15 minutes. For short probes (e.g., about 10 to 50 nucleotides), stringent conditions typically involve salt concentrations of less than about 1.0 M Na ion, typically about 0.01 to 1.0 M Na ion concentration (or other salts) at pH 7.0 to 8.3, and the temperature is typically at least about 30° C. Stringent conditions can also be achieved with the addition of destabilizing agents such as formamide. In general, a signal to noise ratio of 2× (or higher) than that observed for an unrelated probe in the particular hybridization assay indicates detection of a specific hybridization. Nucleotide sequences that do not hybridize to each other under stringent conditions are still substantially identical if the proteins that they encode are substantially identical. This can occur, for example, when a copy of a nucleotide sequence is created using the maximum codon degeneracy permitted by the genetic code.

A polynucleotide and/or recombinant nucleic acid construct of this invention can be codon optimized for expression. In some embodiments, a polynucleotide, nucleic acid construct, expression cassette, and/or vector of the present invention (e.g., that comprises/encodes a nucleic acid binding domain (e.g., a DNA binding domain such as a sequence-specific DNA binding domain from a polynucleotide-guided endonuclease, a zinc finger nuclease, a transcription activator-like effector nuclease (TALEN), an Argonaute protein, and/or a CRISPR-Cas effector protein), a guide nucleic acid, a cytosine deaminase, adenine deaminase, and/or a heterologous morphogenic regulator) may be codon optimized for expression in an organism (e.g., an animal, a plant, a fungus, an archaeon, or a bacterium). In some embodiments, the codon optimized nucleic acid constructs, polynucleotides, expression cassettes, and/or vectors of the invention have about 70% to about 99.9% (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5%. 99.9% or 100%) identity or more to the reference nucleic acid constructs, polynucleotides, expression cassettes, and/or vectors but which have not been codon optimized.

In any of the embodiments described herein, a polynucleotide or nucleic acid construct of the invention may be operatively associated with a variety of promoters and/or other regulatory elements for expression in a an organism or cell thereof (e.g., a plant and/or a cell of a plant). Thus, in some embodiments, a polynucleotide or nucleic acid construct of this invention may further comprise one or more promoters, introns, enhancers, and/or terminators operably linked to one or more nucleotide sequences. In some embodiments, a promoter may be operably associated with an intron (e.g., Ubi1 promoter and intron). In some embodiments, a promoter associated with an intron maybe referred to as a "promoter region" (e.g., Ubi1 promoter and intron).

By "operably linked" or "operably associated" as used herein in reference to polynucleotides, it is meant that the indicated elements are functionally related to each other, and are also generally physically related. Thus, the term "operably linked" or "operably associated" as used herein, refers to nucleotide sequences on a single nucleic acid molecule that are functionally associated. Thus, a first nucleotide sequence that is operably linked to a second nucleotide sequence means a situation when the first nucleotide sequence is placed in a functional relationship with the second nucleotide sequence. For instance, a promoter is operably associated with a nucleotide sequence if the promoter effects the transcription or expression of said nucleotide sequence. Those skilled in the art will appreciate that the control sequences (e.g., promoter) need not be contiguous with the nucleotide sequence to which it is operably associated, as long as the control sequences function to direct the expression thereof. Thus, for example, intervening untranslated, yet transcribed, nucleic acid sequences can be present between a promoter and the nucleotide sequence, and the promoter can still be considered "operably linked" to the nucleotide sequence.

As used herein, the term "linked," or "fused" in reference to polypeptides, refers to the attachment of one polypeptide to another. A polypeptide may be linked or fused to another polypeptide (at the N-terminus or the C-terminus) directly (e.g., via a peptide bond) or through a linker (e.g., a peptide linker).

The term "linker" in reference to polypeptides is art-recognized and refers to a chemical group, or a molecule linking two molecules or moieties, e.g., two domains of a fusion protein, such as, for example, a CRISPR-Cas effector protein and a peptide tag and/or a polypeptide of interest. A linker may be comprised of a single linking molecule (e.g., a single amino acid) or may comprise more than one linking molecule. In some embodiments, the linker can be an organic molecule, group, polymer, or chemical moiety such as a bivalent organic moiety. In some embodiments, the linker may be an amino acid or it may be a peptide. In some embodiments, the linker is a peptide. In some embodiments, a peptide linker useful with this invention may be about 2 to about 100 or more amino acids in length. In some embodiments, a peptide linker may be a GS linker.

In some embodiments, two or more polynucleotide molecules may be linked by a linker that can be an organic molecule, group, polymer, or chemical moiety such as a bivalent organic moiety. A polynucleotide may be linked or fused to another polynucleotide (at the 5' end or the 3' end) via a covalent or non-covalent linkage or binding, including e.g., Watson-Crick base-pairing, or through one or more linking nucleotides. In some embodiments, a polynucleotide motif of a certain structure may be inserted within another polynucleotide sequence (e.g. extension of the hairpin structure in guide RNA). In some embodiments, the linking nucleotides may be naturally occurring nucleotides. In some embodiments, the linking nucleotides may be non-naturally occurring nucleotides.

A "promoter" is a nucleotide sequence that controls or regulates the transcription of a nucleotide sequence (e.g., a coding sequence) that is operably associated with the promoter. The coding sequence controlled or regulated by a promoter may encode a polypeptide and/or a functional RNA. Typically, a "promoter" refers to a nucleotide sequence that contains a binding site for RNA polymerase II and directs the initiation of transcription. In general, promoters are found 5', or upstream, relative to the start of the coding region of the corresponding coding sequence. A promoter may comprise other elements that act as regulators of gene expression; e.g., a promoter region. These include a TATA box consensus sequence, and often a CAAT box consensus sequence (Breathnach and Chambon, (1981) *Annu. Rev. Biochem.* 50:349). In plants, the CAAT box may be substituted by the AGGA box (Messing et al., (1983) in Genetic Engineering of Plants, T. Kosuge, C. Meredith and A. Hollaender (eds.), Plenum Press, pp. 211-227). In some embodiments, a promoter region may comprise at least one intron (e.g., SEQ ID NO:61 or SEQ ID NO:62).

Promoters useful with this invention can include, for example, constitutive, inducible, temporally regulated, developmentally regulated, chemically regulated, tissue-preferred and/or tissue-specific promoters for use in the preparation of recombinant nucleic acid molecules, e.g., "synthetic nucleic acid constructs" or "protein-RNA complex." These various types of promoters are known in the art.

The choice of promoter may vary depending on the temporal and spatial requirements for expression, and also may vary based on the host cell to be transformed. Promoters for many different organisms are well known in the art. Based on the extensive knowledge present in the art, the appropriate promoter can be selected for the particular host organism of interest. Thus, for example, much is known about promoters upstream of highly constitutively expressed genes in model organisms and such knowledge can be readily accessed and implemented in other systems as appropriate.

In some embodiments, a promoter functional in a plant may be used with the constructs of this invention. Non-limiting examples of a promoter useful for driving expression in a plant include the promoter of the RubisCo small subunit gene 1 (PrbcS1), the promoter of the actin gene (Pactin), the promoter of the nitrate reductase gene (Pnr) and the promoter of duplicated carbonic anhydrase gene 1 (Pdca1) (See, Walker et al. *Plant Cell Rep.* 23:727-735 (2005); Li et al. *Gene* 403:132-142 (2007); Li et al. *Mol Biol. Rep.* 37:1143-1154 (2010)). PrbcS1 and Pactin are constitutive promoters and Pnr and Pdca1 are inducible promoters. Pnr is induced by nitrate and repressed by ammonium (Li et al. *Gene* 403:132-142 (2007)) and Pdca1 is induced by salt (Li et al. *Mol Biol. Rep.* 37:1143-1154 (2010)).

Examples of constitutive promoters useful for plants include, but are not limited to, cestrum virus promoter (cmp) (U.S. Pat. No. 7,166,770), the rice actin 1 promoter (Wang et al. (1992) *Mol. Cell. Biol.* 12:3399-3406; as well as U.S. Pat. No. 5,641,876), CaMV 35S promoter (Odell et al. (1985) *Nature* 313:810-812), CaMV 19S promoter (Lawton et al. (1987) *Plant Mol. Biol.* 9:315-324), nos promoter (Ebert et al. (1987) *Proc. Natl. Acad. Sci USA* 84:5745-5749), Adh promoter (Walker et al. (1987) *Proc. Natl. Acad. Sci. USA* 84:6624-6629), sucrose synthase promoter (Yang & Russell (1990) *Proc. Natl. Acad. Sci. USA* 87:4144-4148), and the ubiquitin promoter. The constitutive promoter derived from ubiquitin accumulates in many cell types. Ubiquitin promoters have been cloned from several plant species for use in transgenic plants, for example, sunflower (Binet et al., 1991. *Plant Science* 79: 87-94), maize (Christensen et al., 1989. *Plant Molec. Biol.* 12: 619-632), and *arabidopsis* (Norris et al. 1993. *Plant Molec. Biol.* 21:895-906). The maize ubiquitin promoter (UbiP) has been developed in transgenic monocot systems and its sequence and vectors constructed for monocot transformation are disclosed in the European patent publication EP0342926. The ubiquitin promoter is suitable for the expression of the nucleotide sequences of the invention in transgenic plants, especially monocotyledons. Further, the promoter expression cassettes described by McElroy et al. (*Mol. Gen. Genet.* 231: 150-160 (1991)) can be easily modified for the expression of the nucleotide sequences of the invention and are particularly suitable for use in monocotyledonous hosts.

In some embodiments, tissue specific/tissue preferred promoters can be used for expression of a heterologous polynucleotide in a plant cell. Tissue specific or preferred expression patterns include, but are not limited to, green tissue specific or preferred, root specific or preferred, stem specific or preferred, flower specific or preferred or pollen specific or preferred. Promoters suitable for expression in green tissue include many that regulate genes involved in photosynthesis and many of these have been cloned from both monocotyledons and dicotyledons. In one embodiment, a promoter useful with the invention is the maize PEPC promoter from the phosphoenol carboxylase gene (Hudspeth & Grula, *Plant Molec. Biol.* 12:579-589 (1989)). Non-limiting examples of tissue-specific promoters include those associated with genes encoding the seed storage proteins (such as 0-conglycinin, cruciferin, napin and phaseolin), zein or oil body proteins (such as oleosin), or proteins involved in fatty acid biosynthesis (including acyl carrier protein, stearoyl-ACP desaturase and fatty acid desaturases (fad 2-1)), and other nucleic acids expressed during embryo development (such as Bce4, see, e.g., Kridl et al. (1991) *Seed Sci. Res.* 1:209-219; as well as EP Patent No. 255378). Tissue-specific or tissue-preferential promoters useful for the expression of the nucleotide sequences of the invention in plants, particularly maize, include but are not limited to those that direct expression in root, pith, leaf or pollen. Such promoters are disclosed, for example, in WO 93/07278, incorporated by reference herein for its disclosure of promoters. Other non-limiting examples of tissue specific or tissue preferred promoters useful with the invention the cotton rubisco promoter disclosed in U.S. Pat. No. 6,040, 504; the rice sucrose synthase promoter disclosed in U.S. Pat. No. 5,604,121; the root specific promoter described by de Framond (FEBS 290:103-106 (1991); European patent EP 0452269 to Ciba-Geigy); the stem specific promoter described in U.S. Pat. No. 5,625,136 (to Ciba-Geigy) and which drives expression of the maize trpA gene; the cestrum yellow leaf curling virus promoter disclosed in WO 01/73087; and pollen specific or preferred promoters including, but not limited to, ProOsLPS10 and ProOsLPS11 from rice (Nguyen et al. *Plant Biotechnol. Reports* 9(5):297-306 (2015)), ZmSTK2_USP from maize (Wang et al. *Genome* 60(6):485-495 (2017)), LAT52 and LAT59 from tomato (Twell et al. *Development* 109(3):705-713 (1990)), Zm13 (U.S. Pat. No. 10,421,972), PLA$_2$-δ promoter from *arabidopsis* (U.S. Pat. No. 7,141,424), and/or the ZmC5 promoter from maize (International PCT Publication No. WO1999/042587.

Additional examples of plant tissue-specific/tissue preferred promoters include, but are not limited to, the root hair-specific cis-elements (RHEs) (KIM ET AL. *The Plant Cell* 18:2958-2970 (2006)), the root-specific promoters RCc3 (Jeong et al. *Plant Physiol.* 153:185-197 (2010)) and RB7 (U.S. Pat. No. 5,459,252), the lectin promoter (Lindstrom et al. (1990) *Der. Genet.* 11:160-167; and Vodkin (1983) *Prog. Clin. Biol. Res.* 138:87-98), corn alcohol dehydrogenase 1 promoter (Dennis et al. (1984) *Nucleic Acids Res.* 12:3983-4000), S-adenosyl-L-methionine synthetase (SAMS) (Vander Mijnsbrugge et al. (1996) *Plant and Cell Physiology,* 37(8):1108-1115), corn light harvesting complex promoter (Bansal et al. (1992) *Proc. Natl. Acad. Sci. USA* 89:3654-3658), corn heat shock protein promoter (O'Dell et al. (1985) *EMBO J.* 5:451-458; and Rochester et al. (1986) *EMBO J.* 5:451-458), pea small subunit RuBP carboxylase promoter (Cashmore, "Nuclear genes encoding the small subunit of ribulose-1,5-bisphosphate carboxylase" pp. 29-39 In: *Genetic Engineering of Plants* (Hollaender ed., Plenum Press 1983; and Poulsen et al. (1986)*Mol. Gen. Genet.* 205:193-200), Ti plasmid mannopine synthase promoter (Langridge et al. (1989) *Proc. Natl. Acad. Sci. USA* 86:3219-3223), Ti plasmid nopaline synthase promoter (Langridge et al. (1989), supra), *petunia* chalcone isomerase promoter (van Tunen et al. (1988) *EMBO J.* 7:1257-1263), bean glycine rich protein 1 promoter (Keller et al. (1989) *Genes Dev.* 3:1639-1646), truncated CaMV 35S promoter (O'Dell et al. (1985) *Nature* 313:810-812), potato patatin promoter (Wenzler et al. (1989) *Plant Mol. Biol.* 13:347-354), root cell promoter (Yamamoto et al. (1990) *Nucleic Acids Res.* 18:7449), maize zein promoter (Kriz et al. (1987) *Mol. Gen. Genet.* 207:90-98; Langridge et al. (1983) *Cell* 34:1015-1022; Reina et al. (1990) *Nucleic Acids Res.* 18:6425; Reina et al. (1990) *Nucleic Acids Res.* 18:7449; and Wandelt et al. (1989) *Nucleic Acids Res.* 17:2354), globulin-1 promoter (Belanger et al. (1991) *Genetics* 129:863-872), α-tubulin cab promoter (Sullivan et al. (1989) *Mol. Gen. Genet.* 215:431-440), PEPCase promoter (Hudspeth & Grula (1989) *Plant Mol. Biol.* 12:579-589), R gene complex-associated promoters (Chandler et al. (1989) *Plant Cell* 1:1175-1183), and chalcone synthase promoters (Franken et al. (1991) *EMBO J* 10:2605-2612).

Useful for seed-specific expression is the pea vicilin promoter (Czako et al. (1992) *Mol. Gen. Genet.* 235:33-40; as well as the seed-specific promoters disclosed in U.S. Pat. No. 5,625,136. Useful promoters for expression in mature leaves are those that are switched at the onset of senescence, such as the SAG promoter from *Arabidopsis* (Gan et al. (1995) *Science* 270:1986-1988).

In addition, promoters functional in chloroplasts can be used. Non-limiting examples of such promoters include the bacteriophage T3 gene 9 5' UTR and other promoters disclosed in U.S. Pat. No. 7,579,516. Other promoters useful with the invention include but are not limited to the S-E9 small subunit RuBP carboxylase promoter and the Kunitz trypsin inhibitor gene promoter (Kti3).

Additional regulatory elements useful with this invention include, but are not limited to, introns, enhancers, termination sequences and/or 5' and 3' untranslated regions.

An intron useful with this invention can be an intron identified in and isolated from a plant and then inserted into an expression cassette to be used in transformation of a plant. As would be understood by those of skill in the art, introns can comprise the sequences required for self-excision and are incorporated into nucleic acid constructs/expression cassettes in frame. An intron can be used either as a spacer to separate multiple protein-coding sequences in one nucleic acid construct, or an intron can be used inside one protein-coding sequence to, for example, stabilize the mRNA. If they are used within a protein-coding sequence, they are inserted "in-frame" with the excision sites included. Introns may also be associated with promoters to improve or modify expression. As an example, a promoter/intron combination useful with this invention includes but is not limited to that of the maize Ubi1 promoter and intron.

Non-limiting examples of introns useful with the present invention include introns from the ADHI gene (e.g., Adh1-S introns 1, 2 and 6), the ubiquitin gene (Ubi1), the RuBisCO small subunit (rbcS) gene, the RuBisCO large subunit (rbcL) gene, the actin gene (e.g., actin-1 intron), the pyruvate dehydrogenase kinase gene (pdk), the nitrate reductase gene (nr), the duplicated carbonic anhydrase gene 1 (Tdca1), the psbA gene, the atpA gene, or any combination thereof.

"Gene editing machinery" and a "gene editing complex" as used herein can each be referred to as an editing system. "Gene editing machinery" and a "gene editing complex" useful with this invention can be any site-specific (sequence-specific) genome editing system now known or later developed, which system can introduce mutations in a target specific manner. For example, gene editing machinery or a gene editing complex can include, but are not limited to, a CRISPR-Cas editing system, a meganuclease editing system, a zinc finger nuclease (ZFN) editing system, a transcription activator-like effector nuclease (TALEN) editing system, a base editing system and/or a prime editing system, each of which can comprise one or more polypeptides and/or one or more polynucleotides that when present and/or expressed as a system in a cell can modify (mutate) a target nucleic acid in a sequence specific manner. In some embodiments, an editing system (e.g., site- or sequence-specific editing system) can comprise one or more polynucleotides and/or one or more polypeptides, including but not limited to a nucleic acid binding domain (DNA binding domain), a nuclease, and/or other polypeptide, and/or a polynucleotide.

In some embodiments, an editing system can comprise one or more sequence-specific nucleic acid binding domains (e.g., DNA binding domains) that can be from, for example, a polynucleotide-guided endonuclease, a CRISPR-Cas endonuclease (e.g., CRISPR-Cas effector protein), a zinc finger nuclease, a transcription activator-like effector nuclease (TALEN) and/or an Argonaute protein. In some embodiments, an editing system can comprise one or more cleavage domains (e.g., nucleases) including, but not limited to, an endonuclease (e.g., Fok1), a polynucleotide-guided endonuclease, a CRISPR-Cas endonuclease (e.g., CRISPR-Cas effector protein), a zinc finger nuclease, and/or a transcription activator-like effector nuclease (TALEN).

A "nucleic acid binding domain" as used herein includes a DNA binding domain and may be a site- or sequence-specific nucleic acid binding domain. In some embodiments, a nucleic acid binding domain may be a sequence-specific nucleic acid binding domain such as, but not limited to, a sequence-specific binding domain from, for example, a polynucleotide-guided endonuclease, a CRISPR-Cas effector protein (e.g., CRISPR-Cas endonuclease), a zinc finger nuclease, a transcription activator-like effector nuclease (TALEN) and/or an Argonaute protein. In some embodiments, a nucleic acid binding domain comprises a cleavage domain (e.g., a nuclease domain) such as, but not limited to, an endonuclease (e.g., Fok1), a polynucleotide-guided endonuclease, a CRISPR-Cas endonuclease, a zinc finger nuclease, and/or a transcription activator-like effector nuclease (TALEN). In some embodiments, the nucleic acid binding domain is a polypeptide that can associate (e.g., form a complex) with one or more nucleic acid molecules (e.g., form a complex with a guide nucleic acid as described herein) that can direct or guide the nucleic acid binding domain to a specific target nucleotide sequence (e.g., a gene locus of a genome) that is complementary to the one or more nucleic acid molecules (or a portion or region thereof), thereby causing the nucleic acid binding domain to bind to the nucleotide sequence at the specific target site. In some embodiments, the nucleic acid binding domain is a CRISPR-Cas effector protein as described herein. In some embodiments, reference is made to specifically to a CRISPR-Cas effector protein for simplicity, but a nucleic acid binding domain as described herein may be used.

In some embodiments, a gene editing complex comprises a ribonucleoprotein such as an assembled ribonucleoprotein complex (e.g., that comprises a CRISPR-Cas effector protein and a guide nucleic acid). A gene editing complex, as used herein, may be assembled when introduced into a plant cell or may assemble into a complex (e.g., a covalently and/or non-covalently bound complex) after and/or during introduction into a plant cell. Exemplary ribonucleoproteins and methods of use thereof include, but are not limited to, those described in Malnoy et al., (2016) Front. Plant Sci. 7:1904; Subburaj et al., (2016) Plant Cell Rep. 35:1535; Woo et al., (2015) Nat. Biotechnol. 33:1162; Liang et al., (2017) Nat. Commun. 8:14261; Svitashev et al., Nat. Commun. 7, 13274 (2016); Zhang et al., (2016) Nat. Commun. 7:12617; Kim et al., (2017) Nat. Commun. 8:14406.

In some embodiments, a polynucleotide and/or a nucleic acid construct of the invention can be an "expression cassette" or can be comprised within an expression cassette. As used herein, "expression cassette" means a recombinant nucleic acid molecule comprising, for example, a nucleic acid construct of the invention (e.g., a polynucleotide comprising a heterologous morphogenic regulator, a polynucleotide encoding a CRISPR-Cas effector protein, a polynucleotide encoding a CRISPR-Cas fusion protein, a polynucleotide encoding a cytosine deaminase, a polynucleotide encoding an adenine deaminase, and/or a polynucleotide comprising a guide nucleic acid), wherein the nucleic acid construct is operably associated with at least a control sequence (e.g., a promoter). Thus, some embodiments of the invention provide expression cassettes designed to express, for example, a nucleic acid construct of the invention. When an expression cassette comprises more than one polynucleotide, the polynucleotides may be operably linked to a single promoter that drives expression of all of the polynucleotides or the polynucleotides may be operably linked to one or more different promoters (e.g., three polynucleotides may be driven by one, two or three promoters in any combination). Thus, for example, a polynucleotide comprising a heterologous morphogenic regulator, a polynucleotide encoding a CRISPR-Cas effector protein, a polynucleotide encoding a deaminase, and a polynucleotide comprising a guide nucleic acid comprised in an expression cassette may each be operably associated with a single promoter or one or more of the polynucleotide(s) may be operably associated with separate promoters (e.g., two or three promoters) in any combination. In some embodiments, two or more different expression cassettes can be provided that one or more polynucleotides. For example, a first expression cassette may be provided that comprises a polynucleotide comprising a heterologous morphogenic regulator and a second expression cassette may be provided that comprises a polynucleotide encoding a CRISPR-Cas effector protein, a polynucleotide encoding a deaminase, and a polynucleotide comprising a guide nucleic acid that may each be operably associated with a single promoter or one or more of the polynucleotide(s) may be operably associated with separate promoters (e.g., two or three promoters) in any combination. The first expression cassette may comprise one or more polynucleotides that are the same as or different than one or more polynucleotides in the second expression cassette and vice versa.

In some embodiments, an expression cassette comprising the polynucleotides/nucleic acid constructs of the invention may be optimized for expression in an organism (e.g., an animal, a plant, a bacterium and the like).

An expression cassette comprising a nucleic acid construct of the invention may be chimeric, meaning that at least one of its components is heterologous with respect to at least one of its other components (e.g., a promoter from the host organism operably linked to a polynucleotide of interest to be expressed in the host organism, wherein the polynucleotide of interest is from a different organism than the host or is not normally found in association with that promoter). An expression cassette may also be one that is naturally occurring but has been obtained in a recombinant form useful for heterologous expression.

An expression cassette can optionally include a transcriptional and/or translational termination region (i.e., termination region) and/or an enhancer region that is functional in the selected host cell. A variety of transcriptional terminators and enhancers are known in the art and are available for use in expression cassettes. Transcriptional terminators are responsible for the termination of transcription and correct mRNA polyadenylation. A termination region and/or the enhancer region may be native to the transcriptional initiation region, may be native to a gene encoding a CRISPR-Cas effector protein or a gene encoding a deaminase, may be native to a host cell, or may be native to another source (e.g., foreign or heterologous to the promoter, to a gene encoding the CRISPR-Cas effector protein or a gene encoding the deaminase, to a host cell, or any combination thereof).

An expression cassette of the invention also can include a polynucleotide encoding a selectable marker, which can be used to select a transformed host cell. As used herein, "selectable marker" means a polynucleotide sequence that when expressed imparts a distinct phenotype to the host cell expressing the marker and thus allows such transformed cells to be distinguished from those that do not have the marker. Such a polynucleotide sequence may encode either a selectable or screenable marker, depending on whether the marker confers a trait that can be selected for by chemical means, such as by using a selective agent (e.g., an antibiotic and the like), or on whether the marker is simply a trait that one can identify through observation or testing, such as by screening (e.g., fluorescence). Many examples of suitable selectable markers are known in the art and can be used in the expression cassettes described herein.

The expression cassettes, the nucleic acid molecules/constructs and polynucleotide sequences described herein can be used in connection with vectors. The term "vector" refers to a composition for transferring, delivering or introducing a nucleic acid (or nucleic acids) into a cell. A vector comprises a nucleic acid construct comprising the nucleotide sequence(s) to be transferred, delivered or introduced. Vectors for use in transformation of host organisms are well known in the art. Non-limiting examples of general classes of vectors include viral vectors, plasmid vectors, phage vectors, phagemid vectors, cosmid vectors, fosmid vectors, bacteriophages, artificial chromosomes, minicircles, or *Agrobacterium* binary vectors in double or single stranded linear or circular form which may or may not be self transmissible or mobilizable. In some embodiments, a viral vector can include, but is not limited, to a retroviral, lentiviral, adenoviral, adeno-associated, or herpes simplex viral vector. A vector as defined herein can transform a prokaryotic or eukaryotic host either by integration into the cellular genome or exist extrachromosomally (e.g. autonomous replicating plasmid with an origin of replication). Additionally included are shuttle vectors by which is meant a DNA vehicle capable, naturally or by design, of replication in two different host organisms, which may be selected from actinomycetes and related species, bacteria and eukaryotic (e.g. higher plant, mammalian, yeast or fungal cells). In some embodiments, the nucleic acid in the vector is under the control of, and operably linked to, an appropriate promoter or other regulatory elements for transcription in a host cell. The vector may be a bi-functional expression vector which functions in multiple hosts. In the case of genomic DNA, this may contain its own promoter and/or other regulatory elements and in the case of cDNA this may be under the control of an appropriate promoter and/or other regulatory elements for expression in the host cell. Accordingly, a nucleic acid construct of this invention and/or expression cassettes comprising the same may be comprised in vectors as described herein and as known in the art.

As used herein, "contact," "contacting," "contacted," and grammatical variations thereof, refer to placing the components of a desired reaction together under conditions suitable for carrying out the desired reaction (e.g., transformation, transcriptional control, genome editing, nicking, and/or cleavage). Thus, for example, a target nucleic acid may be contacted with a nucleic acid construct of the invention encoding, for example, a nucleic acid binding domain (e.g., a DNA binding domain such as a sequence-specific DNA binding protein (e.g., polynucleotide-guided endonuclease, a CRISPR-Cas effector protein (e.g., CRISPR-Cas endonuclease), a zinc finger nuclease, a transcription activator-like effector nuclease (TALEN) and/or an Argonaute protein)), a guide nucleic acid, a deaminase (e.g., a cytosine and/or adenine deaminase), and a heterologous morphogenic regulator, under conditions whereby the CRISPR-Cas effector protein and heterologous morphogenic regulator are expressed, and the CRISPR-Cas effector protein forms a complex with the guide nucleic acid, the complex hybridizes to the target nucleic acid, and optionally the deaminase is recruited to the CRISPR-Cas effector protein (and thus, to the target nucleic acid) or the deaminase is fused to the CRISPR-Cas effector protein, thereby modifying the target nucleic acid. In some embodiments, the deaminase and the CRISPR-Cas effector protein localize at the target nucleic acid, optionally through covalent and/or non-covalent interactions.

As used herein, "modifying" or "modification" in reference to a target nucleic acid includes editing (e.g., mutating), covalent modification, exchanging/substituting nucleic acids/nucleotide bases, deleting, cleaving, nicking, and/or transcriptional control of a target nucleic acid.

"Recruit," "recruiting" or "recruitment" as used herein refer to attracting one or more polypeptide(s) or polynucleotide(s) to another polypeptide or polynucleotide (e.g., to a particular location in a genome) using protein-protein interactions, RNA-protein interactions, and/or chemical interactions. Protein-protein interactions can include, but are not limited to, peptide tags (epitopes, multimerized epitopes) and corresponding affinity polypeptides, RNA recruiting motifs and corresponding affinity polypeptides, and/or chemical interactions. Example chemical interactions that may be useful with polypeptides and polynucleotides for the purpose of recruitment can include, but are not limited to, rapamycin-inducible dimerization of FRB-FKBP; Biotin-streptavidin interaction; SNAP tag (Hussain et al. *Curr Pharm Des.* 19(30):5437-42 (2013)); Halo tag (Los et al. *ACS Chem Biol.* 3(6):373-82 (2008)); CLIP tag (Gautier et al. *Chemistry & Biology* 15:128-136 (2008)); DmrA-DmrC heterodimer induced by a compound (Tak et al. *Nat Methods* 14(12):1163-1166 (2017)); Bifunctional ligand approaches (fuse two protein-binding chemicals together) (Voß et al. *Curr Opin Chemical Biology* 28:194-201 (2015)) (e.g. dihyrofolate reductase (DHFR) (Kopyteck et al. *Cell Chem Biol* 7(5):313-321 (2000)).

"Introducing," "introduce," "introduced" (and grammatical variations thereof) in the context of a polynucleotide of interest, polypeptide of interest, and/or editing system means presenting a nucleotide sequence of interest (e.g., polynucleotide, a nucleic acid construct, and/or a guide nucleic acid), a polypeptide of interest, and/or an editing system (e.g., a polynucleotide, polypeptide, and/or ribonucleoprotein) to a host organism or cell of said organism (e.g., host cell; e.g., a plant cell) in such a manner that the nucleotide sequence of interest, polypeptide of interest, and/or editing system gains access to the interior of a cell. Thus, for example, a polynucleotide comprising a heterologous morphogenic regulator and/or a nucleic acid construct encoding a CRISPR-Cas effector protein, a guide nucleic acid, and a deaminase may be introduced into a cell of an organism, thereby transforming the cell with the polynucleotide comprising a heterologous morphogenic regulator and/or the CRISPR-Cas effector protein, guide nucleic acid, and deaminase. Another example is that a polynucleotide comprising a heterologous morphogenic regulator and/or an editing system comprising a ribonucleoprotein may be introduced into a cell of an organism, thereby transforming the cell with the polynucleotide comprising a heterologous morphogenic regulator and/or the ribonucleoprotein. The ribonucleoprotein may comprise a CRISPR-Cas effector domain, guide nucleic acid, and optionally a deaminase domain. In some embodiments, a polypeptide comprising a heterologous morphogenic regulator and/or an editing system comprising a ribonucleoprotein may be introduced into a cell of an organism, thereby transforming the cell with the polypeptide comprising a heterologous morphogenic regulator and/or the ribonucleoprotein.

The term "transformation" as used herein refers to the introduction of a heterologous nucleic acid, polypeptide, and/or ribonucleoprotein into a cell. Transformation of a cell may be stable or transient. Thus, in some embodiments, a host cell or host organism may be stably transformed with a polynucleotide/nucleic acid molecule of the invention. In some embodiments, a host cell or host organism may be transiently transformed with a nucleic acid construct, a polypeptide and/or a ribonucleoprotein of the invention.

"Transient transformation" or "transiently transformed" in the context of a polynucleotide, polypeptide, and/or ribonucleoprotein means that a polynucleotide, polypeptide, and/or ribonucleoprotein is introduced into the cell and does not integrate into the genome of the cell.

By "stably introducing" or "stably introduced" in the context of a polynucleotide that is introduced into a cell is intended that the introduced polynucleotide is stably incorporated into the genome of the cell, and thus the cell is stably transformed with the polynucleotide.

"Stable transformation" or "stably transformed" as used herein means that a nucleic acid molecule is introduced into a cell and integrates into the genome of the cell. As such, the integrated nucleic acid molecule is capable of being inherited by the progeny thereof, more particularly, by the progeny of multiple successive generations. "Genome" as used herein includes the nuclear and the plastid genome, and therefore includes integration of the nucleic acid into, for example, the chloroplast or mitochondrial genome. Stable transformation as used herein can also refer to a transgene that is maintained extrachromasomally, for example, as a minichromosome or a plasmid.

Transient transformation may be detected by, for example, an enzyme-linked immunosorbent assay (ELISA) or Western blot, which can detect the presence of a peptide or polypeptide encoded by one or more transgene introduced into an organism. Stable transformation of a cell can be detected by, for example, a Southern blot hybridization assay of genomic DNA of the cell with nucleic acid sequences which specifically hybridize with a nucleotide sequence of a transgene introduced into an organism (e.g., a plant). Stable transformation of a cell can be detected by, for example, a Northern blot hybridization assay of RNA of the cell with nucleic acid sequences which specifically hybridize with a nucleotide sequence of a transgene introduced into a host organism. Stable transformation of a cell can also be detected by, e.g., a polymerase chain reaction (PCR) or other amplification reactions as are well known in the art, employing specific primer sequences that hybridize with target sequence(s) of a transgene, resulting in amplification of the transgene sequence, which can be detected according to standard methods Transformation can also be detected by direct sequencing and/or hybridization protocols well known in the art.

Accordingly, in some embodiments, nucleotide sequences, polynucleotides, nucleic acid constructs, and/or expression cassettes of the invention may be expressed transiently and/or they can be stably incorporated into the genome of the host organism. Thus, in some embodiments, a nucleic acid construct of the invention may be transiently introduced into a cell with a guide nucleic acid and as such, no DNA maintained in the cell.

A nucleic acid construct, polypeptide, and/or ribonucleoprotein of the invention can be introduced into a cell by any method known to those of skill in the art. In some embodiments of the invention, transformation of a cell comprises nuclear transformation. In other embodiments, transformation of a cell comprises plastid transformation (e.g., chloroplast transformation). In some embodiments of the invention, transformation of a cell comprises particle bombardment. In still further embodiments, the recombinant nucleic acid construct of the invention can be introduced into a cell via conventional breeding techniques.

Procedures for transforming both eukaryotic and prokaryotic organisms are well known and routine in the art and are described throughout the literature (See, for example, Jiang et al. 2013. *Nat. Biotechnol.* 31:233-239; Ran et al. *Nature Protocols* 8:2281-2308 (2013)).

A nucleotide sequence, polypeptide, and/or ribonucleoprotein therefore can be introduced into a host organism or its cell in any number of ways that are well known in the art. The methods of the invention do not depend on a particular method for introducing one or more nucleotide sequence(s), polypeptide(s), and/or ribonucleoprotein(s) into the organism, only that they gain access to the interior of at least one cell of the organism. Where more than one nucleotide sequence, polypeptide, and/or ribonucleoprotein is to be introduced, they can be assembled as part of a single construct (e.g., a single nucleic acid construct,) or as separate constructs. Accordingly, a nucleotide sequence, polypeptide, and/or ribonucleoprotein can be introduced into the cell of interest in a single transformation event, and/or in separate transformation events, or, alternatively, where relevant, a nucleotide sequence can be incorporated into a plant, for example, as part of a breeding protocol.

The terms "genetically engineered host cell," "recombinant host cell," and "recombinant strain" are used interchangeably herein and refer to host cells that have been genetically engineered by a method of the present disclosure. Thus, the terms include a host cell (e.g., bacteria, yeast cell, fungal cell, CHO, human cell, plant cell, protoplast derived from plant, callus, etc.) that has been genetically altered, modified, or engineered, such that it exhibits an altered, modified, or different genotype and/or phenotype (e.g., when the genetic modification affects coding nucleic acid sequences), as compared to the naturally-occurring host cell from which it was derived. It is understood that the terms refer not only to the particular recombinant host cell in question, but also to the progeny or potential progeny of such a host cell.

The term "genetically engineered" may refer to any manipulation of a host cell's genome (e.g., by insertion or deletion of nucleic acids).

The term "next generation plant breeding" refers to a host of plant breeding tools and methodologies that are available to today's breeder. A key distinguishing feature of next generation plant breeding is that the breeder is no longer confined to relying upon observed phenotypic variation, in order to infer underlying genetic causes for a given trait. Rather, next generation plant breeding may include the utilization of molecular markers and marker assisted selection (MAS), such that the breeder can directly observe movement of alleles and genetic elements of interest from one plant in the breeding population to another, and is not confined to merely observing phenotype. Further, next generation plant breeding methods are not confined to utilizing natural genetic variation found within a plant population. Rather, the breeder utilizing next generation plant breeding methodology can access a host of modern genetic engineering tools that directly alter/change/edit the plant's underlying genetic architecture in a targeted manner, in order to bring about a phenotypic trait of interest. In aspects, the plants bred with a next generation plant breeding methodology are indistinguishable from a plant that was bred in a traditional manner, as the resulting end product plant could theoretically be developed by either method. In particular aspects, a next generation plant breeding methodology may result in a plant that comprises: a genetic modification that is a deletion of any size; a genetic modification that is a single base pair substitution; a genetic modification that is an introduction of nucleic acid sequences from within the plant's natural gene pool (e.g. any plant that could be crossed or bred with a plant of interest) or from editing of nucleic acid sequences in a plant to correspond to a sequence known to occur in the plant's natural gene pool; and offspring of said plants.

The term "traditional plant breeding" refers to the utilization of natural variation found within a plant population as a source for alleles and genetic variants that impart a trait of a interest to a given plant. Traditional breeding methods make use of crossing procedures that rely largely upon observed phenotypic variation to infer causative allele association. That is, traditional plant breeding relies upon observations of expressed phenotype of a given plant to infer underlying genetic cause. These observations are utilized to inform the breeding procedure in order to move allelic variation into germplasm of interest. Further, traditional plant breeding has also been characterized as comprising random mutagenesis techniques, which can be used to introduce genetic variation into a given germplasm. These random mutagenesis techniques may include chemical and/or radiation-based mutagenesis procedures. Consequently, one key feature of traditional plant breeding, is that the breeder does not utilize a genetic engineering tool that directly alters/changes/edits the plant's underlying genetic architecture in a targeted manner, in order to introduce genetic diversity and bring about a phenotypic trait of interest.

As used herein, the term "endogenous gene," refers to a naturally occurring gene, in the location in which it is naturally found within the host cell genome. An endogenous gene as described herein can include alleles of naturally occurring genes that have been mutated according to any of a method of the present disclosure, i.e. an endogenous gene could have been modified at some point by traditional plant breeding methods and/or next generation plant breeding methods.

As used herein, the term "exogenous" refers to a substance coming from some source other than its native source. For example, the terms "exogenous protein," or "exogenous gene" refer to a protein or gene from a non-native source, and that has been artificially supplied to a biological system. As used herein, the term "exogenous" is used interchangeably with the term "heterologous," and refers to a substance coming from some source other than its native source.

As used herein, the term "heterologous" refers to a substance coming from some source or location other than its native source or location. In some embodiments, the term "heterologous nucleic acid" refers to a nucleic acid sequence that is not naturally found in the particular organism. For example, the term "heterologous promoter" may refer to a promoter that has been taken from one source organism and utilized in another organism, in which the promoter is not naturally found. However, the term "heterologous promoter" may also refer to a promoter that is from within the same source organism, but has merely been moved to a novel location, in which said promoter is not normally located.

As used herein, the term "nucleotide change" refers to, e.g., nucleotide substitution, deletion, and/or insertion, as is well understood in the art. For example, mutations contain alterations that produce single nucleotide substitutions, silent substitutions, additions, or deletions, but do not alter the properties or activities of the encoded protein or how the proteins are made.

As used herein, the term "protein modification" refers to, e.g., amino acid substitution, amino acid modification, deletion, and/or insertion, as is well understood in the art.

As used herein, the term "codon optimization" implies that the codon usage of a DNA or RNA is adapted to that of a cell or organism of interest to improve the transcription rate of said recombinant nucleic acid in the cell or organism of interest. The skilled person is well aware of the fact that a target nucleic acid can be modified at one position due to the codon degeneracy, whereas this modification will still lead to the same amino acid sequence at that position after translation, which is achieved by codon optimization to take into consideration the species-specific codon usage of a target cell or organism.

As used herein, the term "naturally occurring" as applied to a nucleic acid, a polypeptide, a cell, or an organism, refers to a nucleic acid, polypeptide, cell, or organism that is found in nature. The term "naturally occurring" may refer to a gene or sequence derived from a naturally occurring source. Thus, for the purposes of this disclosure, a "non-naturally occurring" sequence is a sequence that has been synthesized, mutated, engineered, edited, or otherwise modified to have a different sequence from known natural sequences. In some embodiments, the modification may be at the protein level (e.g., amino acid substitutions, deletions, or insertions). In other embodiments, the modification may be at the DNA level (e.g., nucleotide substitutions, deletions, or insertions).

As used herein, the phrases "recombinant construct", "expression construct", "chimeric construct", and "recombinant DNA construct" are used interchangeably herein. A recombinant construct comprises an artificial combination of nucleic acid fragments, e.g., regulatory and coding sequences that are not found together in nature. For example, a chimeric construct may comprise regulatory sequences and coding sequences that are derived from different sources, or regulatory sequences and coding sequences derived from the same source, but arranged in a manner different than that found in nature. Such construct may be used by itself or may be used in conjunction with a vector. If a vector is used then the choice of vector is dependent upon the method that will be used to transform host cells as is well known to those skilled in the art. For example, a plasmid vector can be used. The skilled artisan is well aware of the genetic elements that must be present on the vector in order to successfully transform, select and propagate host cells comprising any of the isolated nucleic acid fragments of the disclosure. The skilled artisan will also recognize that different independent transformation events will result in different levels and patterns of expression (Jones et al., (1985) EMBO J. 4:2411-2418; De Almeida et al., (1989) Mol. Gen. Genetics 218:78-86), and thus that multiple events must be screened in order to obtain lines displaying the desired expression level and pattern. Such screening may be accomplished by Southern analysis of DNA, Northern analysis of mRNA expression, immunoblotting analysis of protein expression, or phenotypic analysis, among others. Vectors can be plasmids, viruses, bacteriophages, pro-viruses, phagemids, transposons, artificial chromosomes, and the like, that replicate autonomously or can integrate into a chromosome of a host cell. A vector can also be a naked RNA polynucleotide, a naked DNA polynucleotide, a polynucleotide composed of both DNA and RNA within the same strand, a poly-lysine-conjugated DNA or RNA, a peptide-conjugated DNA or RNA, a liposome-conjugated DNA, or the like, that is not autonomously replicating. As used herein, the term "expression" refers to the production of a functional end-product e.g., an mRNA or a protein (precursor or mature).

In some embodiments, an editing system of the present invention comprises a CRISPR-Cas effector protein. As used herein, a "CRISPR-Cas effector protein" is a protein or polypeptide or domain thereof that cleaves, cuts, or nicks a nucleic acid, binds a nucleic acid (e.g., a target nucleic acid and/or a guide nucleic acid), and/or that identifies, recognizes, or binds a guide nucleic acid as defined herein. In some embodiments, a CRISPR-Cas effector protein may be an enzyme (e.g., a nuclease, endonuclease, nickase, etc.) or portion thereof and/or may function as an enzyme. In some embodiments, a CRISPR-Cas effector protein refers to a CRISPR-Cas nuclease polypeptide or domain thereof that comprises nuclease activity or in which the nuclease activity has been reduced or eliminated, and/or comprises nickase activity or in which the nickase has been reduced or eliminated, and/or comprises single stranded DNA cleavage activity (ss DNAse activity) or in which the ss DNAse activity has been reduced or eliminated, and/or comprises self-processing RNAse activity or in which the self-processing RNAse activity has been reduced or eliminated. A CRISPR-Cas effector protein may bind to a target nucleic acid. A CRISPR-Cas effector protein may be a Type I, II, III, IV, V, or VI CRISPR-Cas effector protein. In some embodiments, a CRISPR-Cas effector protein may be from a Type I CRISPR-Cas system, a Type II CRISPR-Cas system, a Type III CRISPR-Cas system, a Type IV CRISPR-Cas system, Type V CRISPR-Cas system, or a Type VI CRISPR-Cas system. In some embodiments, a CRISPR-Cas effector protein of the invention may be from a Type II CRISPR-Cas system or a Type V CRISPR-Cas system. In some embodiments, a CRISPR-Cas effector protein may be a Type II CRISPR-Cas effector protein, for example, a Cas9 effector protein. In some embodiments, a CRISPR-Cas effector protein may be Type V CRISPR-Cas effector protein, for example, a Cas12 effector protein. In some embodiments, a CRISPR-Cas effector protein may be a Cas12a polypeptide or domain thereof and optionally may have an amino acid sequence of any one of SEQ ID NOs:115-131 and/or a nucleotide sequence of any one of SEQ ID NOs:132-134.

In some embodiments, a CRISPR-Cas effector protein may be or include, but is not limited to, a Cas9, C2c1, C2c3, Cas12a (also referred to as Cpf1), Cas12b, Cas12c, Cas12d, Cas12e, Cas13a, Cas13b, Cas13c, Cas13d, Cas1, Cas1B, Cas2, Cas3, Cas3', Cas3", Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4 (dinG), and/or Csf5 nuclease, optionally wherein the CRISPR-Cas effector protein may be a Cas9, Cas12a (Cpf1), Cas12b, Cas12c (C2c3), Cas12d (CasY), Cas12e (CasX), Cas12g, Cas12h, Cas12i, C2c4, C2c5, C2c8, C2c9, C2c10, Cas14a, Cas14b, and/or Cas14c effector protein.

In some embodiments, a CRISPR-Cas effector protein useful with the invention may comprise a mutation in its nuclease active site (e.g., RuvC, HNH, e.g., RuvC site of a Cas12a nuclease domain; e.g., RuvC site and/or HNH site of a Cas9 nuclease domain). A CRISPR-Cas effector protein having a mutation in its nuclease active site, and therefore, no longer comprising nuclease activity, is commonly referred to as "dead," e.g., dCas9. In some embodiments, a CRISPR-Cas effector protein domain or polypeptide having a mutation in its nuclease active site may have impaired activity or reduced activity as compared to the same CRISPR-Cas effector protein without the mutation, e.g., a nickase, e.g, Cas9 nickase, Cas12a nickase.

A CRISPR Cas9 effector protein or CRISPR Cas9 effector domain useful with this invention may be any known or later identified Cas9 nuclease. In some embodiments, a CRISPR Cas9 polypeptide can be a Cas9 polypeptide from, for example, *Streptococcus* spp. (e.g., *S. pyogenes*, *S. thermophilus*), *Lactobacillus* spp., *Bifidobacterium* spp., *Kandleria* spp., *Leuconostoc* spp., *Oenococcus* spp., *Pediococcus* spp., *Weissella* spp., and/or *Olsenella* spp. In some embodiments, a CRISPR-Cas effector protein may be a Cas9 polypeptide or domain thereof and optionally may have a nucleotide sequence of any one of SEQ ID NOs:63-73 and/or an amino acid sequence of any one of SEQ ID NOs:74-75.

In some embodiments, the CRISPR-Cas effector protein may be a Cas9 polypeptide derived from *Streptococcus pyogenes* and recognizes the PAM sequence motif NGG, NAG, NGA (Mali et al, Science 2013; 339(6121): 823-826). In some embodiments, the CRISPR-Cas effector protein may be a Cas9 polypeptide derived from *Streptococcus thermophiles* and recognizes the PAM sequence motif NGGNG and/or NNAGAAW (W=A or T) (See, e.g., Horvath et al, Science, 2010; 327(5962): 167-170, and Deveau et al, J Bacteriol 2008; 190(4): 1390-1400). In some embodiments, the CRISPR-Cas effector protein may be a Cas9 polypeptide derived from *Streptococcus mutans* and recognizes the PAM sequence motif NGG and/or NAAR (R=A or G) (See, e.g., Deveau et al, J BACTERIOL 2008; 190(4): 1390-1400). In some embodiments, the CRISPR-Cas effector protein may be a Cas9 polypeptide derived from *Streptococcus aureus* and recognizes the PAM sequence motif NNGRR (R=A or G). In some embodiments, the CRISPR-Cas effector protein may be a Cas9 protein derived from *S. aureus*, which recognizes the PAM sequence motif N GRRT (R=A or G). In some embodiments, the CRISPR-Cas effector protein may be a Cas9 polypeptide derived from *S. aureus*, which recognizes the PAM sequence motif N GRRV (R=A or G). In some embodiments, the CRISPR-Cas effector protein may be a Cas9 polypeptide that is derived from *Neisseria meningitidis* and recognizes the PAM sequence motif N GATT or N GCTT (R=A or G, V=A, G or C) (See, e.g., Hou et ah, PNAS 2013, 1-6). In the aforementioned embodiments, N can be any nucleotide residue, e.g., any of A, G, C or T. In some embodiments, the CRISPR-Cas effector protein may be a Cas13a protein derived from Leptotrichia shahii, which recognizes a protospacer flanking sequence (PFS) (or RNA PAM (rPAM)) sequence motif of a single 3' A, U, or C, which may be located within the target nucleic acid.

A Type V CRISPR-Cas effector protein useful with embodiments of the invention may be any Type V CRISPR-Cas nuclease. A Type V CRISPR-Cas nuclease useful with this invention as an effector protein can include, but is not limited, to Cas12a (Cpf1), Cas12b, Cas12c (C2c3), Cas12d (CasY), Cas12e (CasX), Cas12g, Cas12h, Cas12i, C2c1, C2c4, C2c5, C2c8, C2c9, C2c10, Cas14a, Cas14b, and/or Cas14c nuclease. In some embodiments, a Type V CRISPR-Cas nuclease polypeptide or domain useful with embodiments of the invention may be a Cas12a polypeptide or domain. In some embodiments, a Type V CRISPR-Cas effector protein or domain useful with embodiments of the invention may be a nickase, optionally, a Cas12a nickase.

In some embodiments, the CRISPR-Cas effector protein may be derived from Cas12a, which is a Type V Clustered Regularly Interspaced Short Palindromic Repeats (CRISPR)-Cas nuclease. Cas12a differs in several respects from the more well-known Type II CRISPR Cas9 nuclease. For example, Cas9 recognizes a G-rich protospacer-adjacent motif (PAM) that is 3' to its guide RNA (gRNA, sgRNA, crRNA, crDNA, CRISPR array) binding site (protospacer, target nucleic acid, target DNA) (3'-NGG), while Cas12a recognizes a T-rich PAM that is located 5' to the target nucleic acid (5'-TTN, 5'-TTTN. In fact, the orientations in which Cas9 and Cas12a bind their guide RNAs are very nearly reversed in relation to their N and C termini. Furthermore, Cas12a enzymes use a single guide RNA (gRNA, CRISPR array, crRNA) rather than the dual guide RNA (sgRNA (e.g., crRNA and tracrRNA)) found in natural Cas9 systems, and Cas12a processes its own gRNAs. Additionally, Cas12a nuclease activity produces staggered DNA double stranded breaks instead of blunt ends produced by Cas9 nuclease activity, and Cas12a relies on a single RuvC domain to cleave both DNA strands, whereas Cas9 utilizes an HNH domain and a RuvC domain for cleavage.

A CRISPR Cas12a effector protein/domain useful with this invention may be any known or later identified Cas12a polypeptide (previously known as Cpf1) (see, e.g., U.S. Pat. No. 9,790,490, which is incorporated by reference for its disclosures of Cpf1 (Cas12a) sequences). The term "Cas12a", "Cas12a polypeptide" or "Cas12a domain" refers to an RNA-guided nuclease comprising a Cas12a polypeptide, or a fragment thereof, which comprises the guide nucleic acid binding domain of Cas12a and/or an active, inactive, or partially active DNA cleavage domain of Cas12a. In some embodiments, a Cas12a useful with the invention may comprise a mutation in the nuclease active site (e.g., RuvC site of the Cas12a domain). A Cas12a domain or Cas12a polypeptide having a mutation in its nuclease active site, and therefore, no longer comprising nuclease activity, is commonly referred to as dead Cas12a (e.g., dCas12a). In some embodiments, a Cas12a domain or Cas12a polypeptide having a mutation in its nuclease active site may have impaired activity, e.g., may have nickase activity.

In some embodiments, a CRISPR-Cas effector protein may be optimized for expression in an organism, for example, in an animal, a plant, a fungus, an archaeon, or a bacterium. In some embodiments, a CRISPR-Cas effector protein (e.g., Cas12a polypeptide/domain or a Cas9 polypeptide/domain) may be optimized for expression in a plant.

Any deaminase domain/polypeptide useful for base editing may be used with this invention. A "cytosine deaminase" and "cytidine deaminase" as used herein refer to a polypeptide or domain thereof that catalyzes or is capable of catalyzing cytosine deamination in that the polypeptide or domain catalyzes or is capable of catalyzing the removal of an amine group from a cytosine base. Thus, a cytosine deaminase may result in conversion of cystosine to a thymidine (through a uracil intermediate), causing a C to T conversion, or a G to A conversion in the complementary strand in the genome. Thus, in some embodiments, the cytosine deaminase encoded by the polynucleotide of the invention generates a C→T conversion in the sense (e.g., "+"; template) strand of the target nucleic acid or a G→A conversion in antisense (e.g., "−", complementary) strand of the target nucleic acid. In some embodiments, a cytosine deaminase encoded by a polynucleotide of the invention generates a C to T, G, or A conversion in the complementary strand in the genome.

A cytosine deaminase useful with this invention may be any known or later identified cytosine deaminase from any organism (see, e.g., U.S. Pat. No. 10,167,457 and Thuronyi et al. *Nat. Biotechnol.* 37:1070-1079 (2019), each of which is incorporated by reference herein for its disclosure of cytosine deaminases). Cytosine deaminases can catalyze the hydrolytic deamination of cytidine or deoxycytidine to uridine or deoxyuridine, respectively. Thus, in some embodiments, a deaminase or deaminase domain useful with this invention may be a cytidine deaminase domain, catalyzing the hydrolytic deamination of cytosine to uracil. In some embodiments, a cytosine deaminase may be a variant of a naturally-occurring cytosine deaminase, including, but not limited to, a primate (e.g., a human, monkey, chimpanzee, gorilla), a dog, a cow, a rat or a mouse. Thus, in some embodiments, an cytosine deaminase useful with the invention may be about 70% to about 100% identical to a wild type cytosine deaminase (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identical, and any range or value therein, to a naturally occurring cytosine deaminase).

In some embodiments, a cytosine deaminase useful with the invention may be an apolipoprotein B mRNA-editing complex (APOBEC) family deaminase. In some embodiments, the cytosine deaminase may be an APOBEC1 deaminase, an APOBEC2 deaminase, an APOBEC3A deaminase, an APOBEC3B deaminase, an APOBEC3C deaminase, an APOBEC3D deaminase, an APOBEC3F deaminase, an APOBEC3G deaminase, an APOBEC3H deaminase, an APOBEC4 deaminase, a human activation induced deaminase (hAID), an rAPOBEC1, FERNY, and/or a CDA1, optionally a pmCDA1, an atCDA1 (e.g., At2g19570), and evolved versions of the same. In some embodiments, the cytosine deaminase may be an APOBEC1 deaminase having the amino acid sequence of SEQ ID NO:76. In some embodiments, the cytosine deaminase may be an APOBEC3A deaminase having the amino acid sequence of SEQ ID NO:77. In some embodiments, the cytosine deaminase may be an CDA1 deaminase, optionally a CDA1 having the amino acid sequence of SEQ ID NO:78. In some embodiments, the cytosine deaminase may be a FERNY deaminase, optionally a FERNY having the amino acid sequence of SEQ ID NO:79. In some embodiments, the cytosine deaminase may be a rAPOBEC1 deaminase, optionally a rAPOBEC1 deaminase having the amino acid sequence of SEQ ID NO:80. In some embodiments, the cytosine deaminase may be a hAID deaminase, optionally a hAID having the amino acid sequence of SEQ ID NO:81 or SEQ ID NO:82. In some embodiments, a cytosine deaminase useful with the invention may be about 70% to about 100% identical (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5% or 100% identical) to the amino acid sequence of a naturally occurring cytosine deaminase (e.g., "evolved deaminases") (see, e.g., SEQ ID NO:83, SEQ ID NO:84, SEQ ID NO:85). In some embodiments, a cytosine deaminase useful with the invention may be about 70% to about 99.5% identical (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 99.5% identical) to the amino acid sequence of any one of SEQ ID NOs:76-85 (e.g., at least 80%, at least 85%, at least 90%, at least 92%, at least 95%, at least 96%, at least 97%, at least 98%, at least 99%, or at least 99.5% identical to the amino acid sequence of any one of SEQ ID NOs:76-85). In some embodiments, a polynucleotide encoding a cytosine deaminase may be codon optimized for expression in a plant and the codon optimized polypeptide may be about 70% to 99.5% identical to the reference polynucleotide.

An "adenine deaminase" and "adenosine deaminase" as used herein refer to a polypeptide or domain thereof that catalyzes or is capable of catalyzing the hydrolytic deamination (e.g., removal of an amine group from adenine) of adenine or adenosine. In some embodiments, an adenine deaminase may catalyze the hydrolytic deamination of adenosine or deoxyadenosine to inosine or deoxyinosine, respectively. In some embodiments, the adenosine deaminase may catalyze the hydrolytic deamination of adenine or adenosine in DNA. In some embodiments, an adenine deaminase encoded by a nucleic acid construct of the invention may generate an A→G conversion in the sense (e.g., "+"; template) strand of the target nucleic acid or a T→C conversion in the antisense (e.g., "−", complementary) strand of the target nucleic acid. An adenine deaminase useful with this invention may be any known or later identified adenine deaminase from any organism (see, e.g., U.S. Pat. No. 10,113,163, which is incorporated by reference herein for its disclosure of adenine deaminases).

In some embodiments, an adenosine deaminase may be a variant of a naturally-occurring adenine deaminase. Thus, in some embodiments, an adenosine deaminase may be about 70% to 100% identical to a wild type adenine deaminase (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identical, and any range or value therein, to a naturally occurring adenine deaminase). In some embodiments, the deaminase or deaminase does not occur in nature and may be referred to as an engineered, mutated or evolved adenosine deaminase. Thus, for example, an engineered, mutated or evolved adenine deaminase polypeptide or an adenine deaminase domain may be about 70% to 99.9% identical to a naturally occurring adenine deaminase polypeptide/domain (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8% or 99.9% identical, and any range or value therein, to a naturally occurring adenine deaminase polypeptide or adenine deaminase domain). In some embodiments, the adenosine deaminase may be from a bacterium, (e.g., *Escherichia coli, Staphylococcus aureus, Haemophilus influenzae, Caulobacter crescentus*, and the like). In some embodiments, a polynucleotide encoding an adenine deaminase polypeptide/domain may be codon optimized for expression in a plant.

In some embodiments, an adenine deaminase domain may be a wild type tRNA-specific adenosine deaminase domain, e.g., a tRNA-specific adenosine deaminase (TadA) and/or a mutated/evolved adenosine deaminase domain, e.g., mutated/evolved tRNA-specific adenosine deaminase domain (TadA*). In some embodiments, a TadA domain may be from *E. coli*. In some embodiments, the TadA may be modified, e.g., truncated, missing one or more N-terminal and/or C-terminal amino acids relative to a full-length TadA (e.g., 1, 2, 3, 4, 5, 6, 7, 8, 9, 10, 11, 12, 13, 14, 15, 6, 17, 18, 19, or 20 N-terminal and/or C terminal amino acid residues may be missing relative to a full length TadA. In some embodiments, a TadA polypeptide or TadA domain does not comprise an N-terminal methionine. In some embodiments, a wild type *E. coli* TadA comprises the amino acid sequence of SEQ ID NO:86. In some embodiments, a mutated/evolved *E. coli* TadA* comprises the amino acid sequence of SEQ ID NOs:87-90 (e.g., SEQ ID NOs: 87, 88, 89, or 90). In some embodiments, a polynucleotide encoding a TadA/TadA* may be codon optimized for expression in a plant. In some embodiments, an adenine deaminase may comprise all or a portion of an amino acid sequence of any one of SEQ ID NOs:91-96. In some embodiments, an adenine deaminase may comprise all or a portion of an amino acid sequence of any one of SEQ ID NOs:86-96.

In some embodiments, a nucleic acid construct of this invention may further encode a glycosylase inhibitor (e.g., a uracil glycosylase inhibitor (UGI) such as uracil-DNA glycosylase inhibitor). Thus, in some embodiments, a nucleic acid construct encoding a CRISPR-Cas effector protein and a cytosine deaminase and/or adenine deaminase may further encode a glycosylase inhibitor, optionally wherein the glycosylase inhibitor may be codon optimized for expression in a plant. In some embodiments, the invention provides fusion proteins comprising a CRISPR-Cas effector polypeptide and a UGI and/or one or more polynucleotides encoding the same, optionally wherein the one or more polynucleotides may be codon optimized for expression in a plant. In some embodiments, the invention provides fusion proteins comprising a CRISPR-Cas effector polypeptide, a deaminase domain (e.g., an adenine deaminase domain and/or a cytosine deaminase domain) and optionally a UGI and/or one or more polynucleotides encoding the same, optionally wherein the one or more polynucleotides may be codon optimized for expression in a plant. In some embodiments, the invention provides fusion proteins, wherein a CRISPR-Cas effector polypeptide, a deaminase domain, and/or a UGI may be fused to any combination of peptide tags and affinity polypeptides as described herein, which may thereby recruit the deaminase domain and/or UGI to the CRISPR-Cas effector polypeptide and to a target nucleic acid. In some embodiments, a guide nucleic acid may be linked to a recruiting RNA motif and one or more of the deaminase domain and/or UGI may be fused to an affinity polypeptide that is capable of interacting with the recruiting RNA motif, thereby recruiting the deaminase domain and UGI to a target nucleic acid.

A "uracil glycosylase inhibitor" useful with the invention may be any protein or polypeptide that is capable of inhibiting a uracil-DNA glycosylase base-excision repair enzyme. In some embodiments, a UGI domain comprises a wild type UGI or a fragment thereof. In some embodiments, a UGI domain useful with the invention may be about 70% to about 100% identical (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5% or 100% identical and any range or value therein) to the amino acid sequence of a naturally occurring UGI domain. In some embodiments, a UGI domain may comprise the amino acid sequence of SEQ ID NO:97 or a polypeptide having about 70% to about 99.5% identity to the amino acid sequence of SEQ ID NO:97 (e.g., at least 80%, at least 85%, at least 90%, at least 92%, at least 95%, at least 96%, at least 97%, at least 98%, at least 99%, or at least 99.5% identical to the amino acid sequence of SEQ ID NO:97). For example, in some embodiments, a UGI domain may comprise a fragment of the amino acid sequence of SEQ ID NO:97 that is 100% identical to a portion of consecutive nucleotides (e.g., 10, 15, 20, 25, 30, 35, 40, 45, 50, 55, 60, 65, 70, 75, 80 consecutive nucleotides; e.g., about 10, 15, 20, 25, 30, 35, 40, 45, to about 50, 55, 60, 65, 70, 75, 80 consecutive nucleotides) of the amino acid sequence of SEQ ID NO:97. In some embodiments, a UGI domain may be a variant of a known UGI (e.g., SEQ ID NO:97) having about 70% to about 99.5% identity (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5% identity, and any range or value therein) to the known UGI. In some embodiments, a polynucleotide encoding a UGI may be codon optimized for expression in a plant (e.g., a plant) and the codon optimized polypeptide may be about 70% to about 99.5% identical to the reference polynucleotide.

The nucleic acid constructs of the invention comprising a CRISPR-Cas effector protein or a fusion protein thereof may be used in combination with a guide nucleic acid (e.g., guide RNA (gRNA), CRISPR array, CRISPR RNA, crRNA), designed to function with the encoded CRISPR-Cas effector protein or domain, to modify a target nucleic acid. A guide nucleic acid useful with this invention may comprise at least one spacer sequence and at least one repeat sequence. The guide nucleic acid is capable of forming a complex with the CRISPR-Cas nuclease domain encoded and expressed by a nucleic acid construct of the invention and the spacer sequence is capable of hybridizing to a target nucleic acid, thereby guiding the complex to the target nucleic acid, wherein the target nucleic acid may be modified (e.g., cleaved or edited) and/or modulated (e.g., modulating transcription) by a deaminase (e.g., a cytosine deaminase and/or adenine deaminase, optionally present in and/or recruited to the complex).

As an example, a nucleic acid construct encoding a Cas9 domain linked to a cytosine deaminase domain (e.g., a fusion protein) may be used in combination with a Cas9 guide nucleic acid to modify a target nucleic acid, wherein the cytosine deaminase domain of the fusion protein deaminates a cytosine base in the target nucleic acid, thereby editing the target nucleic acid. In a further example, a nucleic acid construct encoding a Cas9 domain linked to an adenine deaminase domain (e.g., a fusion protein) may be used in combination with a Cas9 guide nucleic acid to modify a target nucleic acid, wherein the adenine deaminase domain of the fusion protein deaminates an adenosine base in the target nucleic acid, thereby editing the target nucleic acid. In some embodiments, a CRISPR-Cas effector protein (e.g., Cas9) is not fused to a cytosine deaminase and/or adenine deaminase.

Likewise, a nucleic acid construct encoding a Cas12a domain (or other selected CRISPR-Cas nuclease, e.g., C2c1, C2c3, Cas12b, Cas12c, Cas12d, Cas12e, Cas13a, Cas13b, Cas13c, Cas13d, Cas1, Cas1B, Cas2, Cas3, Cas3', Cas3", Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4 (dinG), and/or Csf5) may be linked to a cytosine deaminase domain or adenine deaminase domain (e.g., fusion protein) and may be used in combination with a Cas12a guide nucleic acid (or the guide nucleic acid for the other selected CRISPR-Cas nuclease) to modify a target nucleic acid, wherein the cytosine deaminase domain or adenine deaminase domain of the fusion protein deaminates a cytosine base or adenosine base, respectively, in the target nucleic acid, thereby editing the target nucleic acid.

A "guide nucleic acid," "guide RNA," "gRNA," "CRISPR RNA/DNA" "crRNA" or "crDNA" as used herein means a nucleic acid that comprises at least one spacer sequence, which is complementary to (and hybridizes to) a target DNA (e.g., protospacer), and at least one repeat sequence (e.g., a repeat of a Type V Cas12a CRISPR-Cas system, or a fragment or portion thereof, a repeat of a Type II Cas9 CRISPR-Cas system, or fragment thereof; a repeat of a Type V C2c1 CRISPR Cas system, or a fragment thereof, a repeat of a CRISPR-Cas system of, for example, C2c3, Cas12a (also referred to as Cpf1), Cas12b, Cas12c, Cas12d, Cas12e, Cas13a, Cas13b, Cas13c, Cas13d, Cas1, Cas1B, Cas2, Cas3, Cas3', Cas3", Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4 (dinG), and/or Csf5, or a fragment thereof), wherein the repeat sequence may be linked to the 5' end and/or the 3' end of the spacer sequence. In some embodiments, the guide nucleic acid comprises DNA. In some embodiments, the guide nucleic acid comprises RNA (e.g., is a guide RNA). The design of a gRNA of this invention may be based on a Type I, Type II, Type III, Type IV, Type V, or Type VI CRISPR-Cas system.

In some embodiments, a Cas12a gRNA may comprise, from 5' to 3', a repeat sequence (full length or portion thereof ("handle"); e.g., pseudoknot-like structure) and a spacer sequence.

In some embodiments, a guide nucleic acid may comprise more than one repeat sequence-spacer sequence (e.g., 2, 3, 4, 5, 6, 7, 8, 9, 10, or more repeat-spacer sequences) (e.g., repeat-spacer-repeat, e.g., repeat-spacer-repeat-spacer-repeat-spacer-repeat-spacer-repeat-spacer, and the like). The guide nucleic acids of this invention are synthetic, human-made and not found in nature. A gRNA can be quite long and may be used as an aptamer (like in the MS2 recruitment strategy) or other RNA structures hanging off the spacer.

A "repeat sequence" as used herein, refers to, for example, any repeat sequence of a wild-type CRISPR Cas locus (e.g., a Cas9 locus, a Cas12a locus, a C2c1 locus, etc.) or a repeat sequence of a synthetic crRNA that is functional with the CRISPR-Cas effector protein encoded by the nucleic acid constructs of the invention. A repeat sequence useful with this invention can be any known or later identified repeat sequence of a CRISPR-Cas locus (e.g., Type I, Type II, Type III, Type IV, Type V or Type VI) or it can be a synthetic repeat designed to function in a Type I, II, III, IV, V or VI CRISPR-Cas system. A repeat sequence may comprise a hairpin structure and/or a stem loop structure. In some embodiments, a repeat sequence may form a pseudoknot-like structure at its 5' end (i.e., "handle"). Thus, in some embodiments, a repeat sequence can be identical to or substantially identical to a repeat sequence from wild-type Type I CRISPR-Cas loci, Type II, CRISPR-Cas loci, Type III, CRISPR-Cas loci, Type IV CRISPR-Cas loci, Type V CRISPR-Cas loci and/or Type VI CRISPR-Cas loci. A repeat sequence from a wild-type CRISPR-Cas locus may be determined through established algorithms, such as using the CRISPRfinder offered through CRISPRdb (see, Grissa et al. *Nucleic Acids Res.* 35(Web Server issue):W52-7). In some embodiments, a repeat sequence or portion thereof is linked at its 3' end to the 5' end of a spacer sequence, thereby forming a repeat-spacer sequence (e.g., guide nucleic acid, guide RNA/DNA, crRNA, crDNA).

In some embodiments, a repeat sequence comprises, consists essentially of, or consists of at least 10 nucleotides depending on the particular repeat and whether the guide nucleic acid comprising the repeat is processed or unprocessed (e.g., about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 to 100 or more nucleotides, or any range or value therein; e.g., about). In some embodiments, a repeat sequence comprises, consists essentially of, or consists of about 10 to about 20, about 10 to about 30, about 10 to about 45, about 10 to about 50, about 15 to about 30, about 15 to about 40, about 15 to about 45, about 15 to about 50, about 20 to about 30, about 20 to about 40, about 20 to about 50, about 30 to about 40, about 40 to about 80, about 50 to about 100 or more nucleotides.

A repeat sequence linked to the 5' end of a spacer sequence can comprise a portion of a repeat sequence (e.g., 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35 or more contiguous nucleotides of a wild type repeat sequence). In some embodiments, a portion of a repeat sequence linked to the 5' end of a spacer sequence can be about five to about ten consecutive nucleotides in length (e.g., about 5, 6, 7, 8, 9, 10 nucleotides) and have at least 90% sequence identity (e.g., at least about 90%, 91%, 92%, 93%, 94%, 95%, 96%, 97%, 98%, 99%, or more) to the same region (e.g., 5' end) of a wild type CRISPR Cas repeat nucleotide sequence. In some embodiments, a portion of a repeat sequence may comprise a pseudoknot-like structure at its 5' end (e.g., "handle").

A "spacer sequence" as used herein is a nucleotide sequence that is complementary to a target nucleic acid (e.g., target DNA) (e.g, protospacer). The spacer sequence can be fully complementary or substantially complementary (e.g., at least about 70% complementary (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more)) to a target nucleic acid. Thus, in some embodiments, the spacer sequence can have one, two, three, four, or five mismatches as compared to the target nucleic acid, which mismatches can be contiguous or noncontiguous. In some embodiments, the spacer sequence can have 70% complementarity to a target nucleic acid. In other embodiments, the spacer nucleotide sequence can have 80% complementarity to a target nucleic acid. In still other embodiments, the spacer nucleotide sequence can have 85%, 90%, 95%, 96%, 97%, 98%, 99% or 99.5% complementarity, and the like, to the target nucleic acid (protospacer). In some embodiments, the spacer sequence is 100% complementary to the target nucleic acid. A spacer sequence may have a length from about 15 nucleotides to about 30 nucleotides (e.g., 15, 16, 17, 18, 19, 20, 21, 22, 23, 24, 25, 26, 27, 28, 29, or 30 nucleotides, or any range or value therein). Thus, in some embodiments, a spacer sequence may have complete complementarity or substantial complementarity over a region of a target nucleic acid (e.g., protospacer) that is at least about 15 nucleotides to about 30 nucleotides in length. In some embodiments, the spacer is about 20 nucleotides in length. In some embodiments, the spacer is about 21, 22, or 23 nucleotides in length.

In some embodiments, the 5' region of a spacer sequence of a guide nucleic acid may be identical to a target DNA, while the 3' region of the spacer may be substantially complementary to the target DNA (e.g., Type V CRISPR-Cas), or the 3' region of a spacer sequence of a guide nucleic acid may be identical to a target DNA, while the 5' region of the spacer may be substantially complementary to the target DNA (e.g., Type II CRISPR-Cas), and therefore, the overall complementarity of the spacer sequence to the target DNA may be less than 100%. Thus, for example, in a guide for a Type V CRISPR-Cas system, the first 1, 2, 3, 4, 5, 6, 7, 8, 9, 10 nucleotides in the 5' region (i.e., seed region) of, for example, a 20 nucleotide spacer sequence may be 100% complementary to the target DNA, while the remaining nucleotides in the 3' region of the spacer sequence are substantially complementary (e.g., at least about 70% complementary) to the target DNA. In some embodiments, the first 1 to 8 nucleotides (e.g., the first 1, 2, 3, 4, 5, 6, 7, 8, nucleotides, and any range therein) of the 5' end of the spacer sequence may be 100% complementary to the target DNA, while the remaining nucleotides in the 3' region of the spacer sequence are substantially complementary (e.g., at least about 50% complementary (e.g., 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more)) to the target DNA.

As a further example, in a guide for a Type II CRISPR-Cas system, the first 1, 2, 3, 4, 5, 6, 7, 8, 9, 10 nucleotides in the 3' region (i.e., seed region) of, for example, a 20 nucleotide spacer sequence may be 100% complementary to the target DNA, while the remaining nucleotides in the 5' region of the spacer sequence are substantially complementary (e.g., at least about 70% complementary) to the target DNA. In some embodiments, the first 1 to 10 nucleotides (e.g., the first 1, 2, 3, 4, 5, 6, 7, 8, 9, 10 nucleotides, and any range therein) of the 3' end of the spacer sequence may be 100% complementary to the target DNA, while the remaining nucleotides in the 5' region of the spacer sequence are substantially complementary (e.g., at least about 50% complementary (e.g., at least about 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more or any range or value therein)) to the target DNA. A recruiting guide RNA further comprises one or more recruiting motifs as described herein, which may be linked to the 5' end of the guide or the 3' end or it may be inserted into the recruiting guide nucleic acid (e.g., within the hairpin loop).

In some embodiments, a seed region of a spacer may be about 8 to about 10 nucleotides in length, about 5 to about 6 nucleotides in length, or about 6 nucleotides in length.

A "target nucleic acid", "target DNA," "target nucleotide sequence," "target region," and a "target region in the genome" are used interchangeably herein and refer to a region of a plant's genome that is targeted by an editing system (or a component thereof) as described herein. In some embodiments, a target nucleic acid is fully complementary (100% complementary) or substantially complementary (e.g., at least 70% complementary (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more)) to a spacer sequence in a guide nucleic acid of this invention. A target region useful for a CRISPR-Cas system may be located immediately 3' (e.g., Type V CRISPR-Cas system) or immediately 5' (e.g., Type II CRISPR-Cas system) to a PAM sequence in the genome of the organism (e.g., a plant genome). A target region may be selected from any region of at least 15 consecutive nucleotides (e.g., 16, 17, 18, 19, 20, 21, 22, 23, 24, 25, 26, 27, 28, 29, 30 nucleotides, and the like) located immediately adjacent to a PAM sequence.

A "protospacer sequence" refers to the target double stranded DNA and specifically to the portion of the target DNA (e.g., or target region in the genome) that is fully or substantially complementary (and hybridizes) to the spacer sequence of the CRISPR repeat-spacer sequences (e.g., guide nucleic acids, CRISPR arrays, crRNAs).

In the case of Type V CRISPR-Cas (e.g., Cas12a) systems and Type II CRISPR-Cas (Cas9) systems, the protospacer sequence is flanked by (e.g., immediately adjacent to) a protospacer adjacent motif (PAM). For Type IV CRISPR-Cas systems, the PAM is located at the 5' end on the non-target strand and at the 3' end of the target strand (see below, as an example).

```
5'-NNNNNNNNNNNNNNNNNNNN-3'    RNA Spacer          (SEQ ID NO: 98)
   ||||||||||||||||||||
3'AAANNNNNNNNNNNNNNNNNNNN-5'  Target strand       (SEQ ID NO: 99)
   ||||
5'TTTNNNNNNNNNNNNNNNNNNNN-3'  Non-target strand   (SEQ ID NO: 100)
```

In the case of Type II CRISPR-Cas (e.g., Cas9) systems, the PAM is located immediately 3' of the target region. The PAM for Type I CRISPR-Cas systems is located 5' of the target strand. There is no known PAM for Type III CRISPR-Cas systems. Makarova et al. describes the nomenclature for all the classes, types and subtypes of CRISPR systems (*Nature Reviews Microbiology* 13:722-736 (2015)). Guide structures and PAMs are described in by R. Barrangou (*Genome Biol.* 16:247 (2015)).

Canonical Cas12a PAMs are T rich. In some embodiments, a canonical Cas12a PAM sequence may be 5'-TTN, 5'-TTTN, or 5'-TTTV. In some embodiments, canonical Cas9 (e.g., *S. pyogenes*) PAMs may be 5'-NGG-3'. In some embodiments, non-canonical PAMs may be used but may be less efficient.

Additional PAM sequences may be determined by those skilled in the art through established experimental and computational approaches. Thus, for example, experimental approaches include targeting a sequence flanked by all possible nucleotide sequences and identifying sequence members that do not undergo targeting, such as through the transformation of target plasmid DNA (Esvelt et al. 2013. *Nat. Methods* 10:1116-1121; Jiang et al. 2013. *Nat. Biotechnol.* 31:233-239). In some aspects, a computational approach can include performing BLAST searches of natural spacers to identify the original target DNA sequences in bacteriophages or plasmids and aligning these sequences to determine conserved sequences adjacent to the target sequence (Briner and Barrangou. 2014. *Appl. Environ. Microbiol.* 80:994-1001; Mojica et al. 2009. *Microbiology* 155:733-740).

In some embodiments, the present invention provides expression cassettes and/or vectors comprising the nucleic acid constructs of the invention (e.g., one or more components of an editing system of the invention). In some embodiments, expression cassettes and/or vectors comprising the nucleic acid constructs of the invention and/or one or more guide nucleic acids may be provided. In some embodiments, a nucleic acid construct of the invention comprising a heterologous morphogenic regulator and encoding a base editor (e.g., a construct comprising a CRISPR-Cas effector domain and a deaminase domain (e.g., a fusion protein)) or the components for base editing (e.g., a CRISPR-Cas effector domain fused to a peptide tag or an affinity polypeptide, a deaminase domain fused to a peptide tag or an affinity polypeptide, and/or a UGI fused to a peptide tag or an affinity polypeptide), may be comprised on the same or on a separate expression cassette or vector from that comprising the one or more guide nucleic acids. When the nucleic acid construct encoding a base editor or the components for base editing is/are comprised on separate expression cassette(s) or vector(s) from that comprising the guide nucleic acid, a target nucleic acid may be contacted with (e.g., provided with) the expression cassette(s) or vector(s) encoding the base editor or components for base editing in any order from one another and the guide nucleic acid, e.g., prior to, concurrently with, or after the expression cassette comprising the guide nucleic acid is provided (e.g., contacted with the target nucleic acid).

Fusion proteins of the invention may comprise a sequence-specific DNA binding domain, a CRISPR-Cas effector protein, and/or a deaminase fused to a peptide tag or an affinity polypeptide that interact with the peptide tag, as known in the art, for use in recruiting the deaminase to the target nucleic acid. Methods of recruiting may also comprise a guide nucleic acids linked to an RNA recruiting motif and a deaminase fused to an affinity polypeptide capable of interacting with the RNA recruiting motif, thereby recruiting the deaminase to the target nucleic acid. Alternatively, chemical interactions may be used to recruit a polypeptide (e.g., a deaminase) to a target nucleic acid.

A peptide tag (e.g., epitope) useful with this invention may include, but is not limited to, a GCN4 peptide tag (e.g., Sun-Tag), a c-Myc affinity tag, an HA affinity tag, a His affinity tag, an S affinity tag, a methionine-His affinity tag, an RGD-His affinity tag, a FLAG octapeptide, a strep tag or strep tag II, a V5 tag, and/or a VSV-G epitope. Any epitope that may be linked to a polypeptide and for which there is a corresponding affinity polypeptide that may be linked to another polypeptide may be used with this invention as a peptide tag. In some embodiments, a peptide tag may comprise 1 or 2 or more copies of a peptide tag (e.g., repeat unit, multimerized epitope (e.g., tandem repeats)) (e.g., 1, 2, 3, 4, 5, 6, 7, 8, 9, 10, 11, 12, 13, 14, 15, 16, 17, 18, 19, 20, 21, 22, 23, 24, 25 or more repeat units. In some embodiments, an affinity polypeptide that interacts with/binds to a peptide tag may be an antibody. In some embodiments, the antibody may be a scFv antibody. In some embodiments, an affinity polypeptide that binds to a peptide tag may be synthetic (e.g., evolved for affinity interaction) including, but not limited to, an affibody, an anticalin, a monobody and/or a DARPin (see, e.g., Sha et al., *Protein Sci.* 26(5): 910-924 (2017)); Gilbreth (*Curr Opin Struc Biol* 22(4):413-420 (2013)), U.S. Pat. No. 9,982,053, each of which are incorporated by reference in their entireties for the teachings relevant to affibodies, anticalins, monobodies and/or DARPins.

In some embodiments, a guide nucleic acid may be linked to an RNA recruiting motif, and a polypeptide to be recruited (e.g., a deaminase) may be fused to an affinity polypeptide that binds to the RNA recruiting motif, wherein the guide binds to the target nucleic acid and the RNA recruiting motif binds to the affinity polypeptide, thereby recruiting the polypeptide to the guide and contacting the target nucleic acid with the polypeptide (e.g., deaminase). In some embodiments, two or more polypeptides may be recruited to a guide nucleic acid, thereby contacting the target nucleic acid with two or more polypeptides (e.g., deaminases).

In some embodiments of the invention, a guide RNA may be linked to one or to two or more RNA recruiting motifs (e.g., 1, 2, 3, 4, 5, 6, 7, 8, 9, 10 or more motifs; e.g., at least 10 to about 25 motifs), optionally wherein the two or more RNA recruiting motifs may be the same RNA recruiting motif or different RNA recruiting motifs. In some embodiments, an RNA recruiting motif and corresponding affinity polypeptide may include, but is not limited to, a telomerase Ku binding motif (e.g., Ku binding hairpin) and the corresponding affinity polypeptide Ku (e.g., Ku heterodimer), a telomerase Sm7 binding motif and the corresponding affinity polypeptide Sm7, an MS2 phage operator stem-loop and the corresponding affinity polypeptide MS2 Coat Protein (MCP), a PP7 phage operator stem-loop and the corresponding affinity polypeptide PP7 Coat Protein (PCP), an SfMu phage Com stem-loop and the corresponding affinity polypeptide Com RNA binding protein, a PUF binding site (PBS) and the affinity polypeptide *Pumilio*/fem-3 mRNA binding factor (PUF), and/or a synthetic RNA-aptamer and the aptamer ligand as the corresponding affinity polypeptide. In some embodiments, the RNA recruiting motif and corresponding affinity polypeptide may be an MS2 phage operator stem-loop and the affinity polypeptide MS2 Coat Protein (MCP). In some embodiments, the RNA recruiting motif and corresponding affinity polypeptide may be a PUF binding site (PBS) and the affinity polypeptide *Pumilio*/fem-3 mRNA binding factor (PUF). Exemplary RNA recruiting motifs and corresponding affinity polypeptides that may be useful with this invention can include, but are not limited to, SEQ ID NOs:101-111.

In some embodiments, the components for recruiting polypeptides and nucleic acids may include those that function through chemical interactions that may include, but are not limited to, rapamycin-inducible dimerization of FRB-FKBP; Biotin-streptavidin; SNAP tag; Halo tag; CLIP tag; DmrA-DmrC heterodimer induced by a compound; bifunctional ligand (e.g., fusion of two protein-binding chemicals together; e.g. dihyrofolate reductase (DHFR).

In some embodiments, the nucleic acid constructs, expression cassettes or vectors of the invention that are optimized for expression in a plant may be about 70% to 100% identical (e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5% or 100%) to the nucleic acid constructs, expression cassettes or vectors comprising the same polynucleotide(s) but which have not been codon optimized for expression in a plant.

As described herein, a "peptide tag" may be employed to recruit one or more polypeptides. A peptide tag may be any polypeptide that is capable of being bound by a corresponding affinity polypeptide. A peptide tag may also be referred to as an "epitope" and when provided in multiple copies, a "multimerized epitope." Example peptide tags can include, but are not limited to, a GCN4 peptide tag (e.g., Sun-Tag), a c-Myc affinity tag, an HA affinity tag, a His affinity tag, an S affinity tag, a methionine-His affinity tag, an RGD-His affinity tag, a FLAG octapeptide, a strep tag or strep tag II, a V5 tag, and/or a VSV-G epitope. In some embodiments, a peptide tag may also include phosphorylated tyrosines in specific sequence contexts recognized by SH2 domains, characteristic consensus sequences containing phosphoserines recognized by 14-3-3 proteins, proline rich peptide motifs recognized by SH3 domains, PDZ protein interaction domains or the PDZ signal sequences, and an AGO hook motif from plants. Peptide tags are disclosed in WO2018/136783 and U.S. Patent Application Publication No. 2017/0219596, which are incorporated by reference for their disclosures of peptide tags. Peptide tags that may be useful with this invention can include, but are not limited to, SEQ ID NO:112 and SEQ ID NO:113. An affinity polypeptide useful with peptide tags includes, but is not limited to, SEQ ID NO:114.

A peptide tag may comprise or be present in one copy or in 2 or more copies of the peptide tag (e.g., multimerized peptide tag or multimerized epitope) (e.g., about 2, 3, 4, 5, 6, 7, 8, 9, 10, 11, 12, 13, 14, 15, 16, 17, 18, 9, 20, 21, 22, 23, 24, or 25 or more peptide tags). When multimerized, the peptide tags may be fused directly to one another or they may be linked to one another via one or more amino acids (e.g., 1, 2, 3, 4, 5, 6, 7, 8, 9, 10, 11, 12, 13, 14, 15, 16, 17, 18, 19, 20 or more amino acids, optionally about 3 to about 10, about 4 to about 10, about 5 to about 10, about 5 to about 15, or about 5 to about 20 amino acids, and the like, and any value or range therein. Thus, in some embodiments, a CRISPR-Cas effector protein of the invention may comprise a CRISPR-Cas effector protein domain fused to one peptide tag or to two or more peptide tags, optionally wherein the two or more peptide tags are fused to one another via one or more amino acid residues. In some embodiments, a peptide tag useful with the invention may be a single copy of a GCN4 peptide tag or epitope or may be a multimerized GCN4 epitope comprising about 2 to about 25 or more copies of the peptide tag (e.g., about 2, 3, 4, 5, 6, 7, 8, 9, 10, 11, 12, 13, 14, 15, 16, 17, 18, 19, 20, 21, 22, 23, 24, 25 or more copies of a GCN4 epitope or any range therein).

In some embodiments, a peptide tag may be fused to a CRISPR-Cas polypeptide or domain. In some embodiments, a peptide tag may be fused or linked to the C-terminus of a CRISPR-Cas effector protein to form a CRISPR-Cas fusion protein. In some embodiments, a peptide tag may be fused or linked to the N-terminus of a CRISPR-Cas effector protein to form a CRISPR-Cas fusion protein. In some embodiments, a peptide tag may be fused within a CRISPR-Cas effector protein (e.g., a peptide tag may be in a loop region of a CRISPR-Cas effector protein). In some embodiments, peptide tag may be fused to a cytosine deaminase and/or to an adenine deaminase.

An "affinity polypeptide" (e.g., "recruiting polypeptide") refers to any polypeptide that is capable of binding to its corresponding peptide tag, peptide tag, or RNA recruiting motif. An affinity polypeptide for a peptide tag may be, for example, an antibody and/or a single chain antibody that specifically binds the peptide tag, respectively. In some embodiments, an antibody for a peptide tag may be, but is not limited to, an scFv antibody. In some embodiments, an affinity polypeptide may be fused or linked to the N-terminus of a deaminase (e.g., a cytosine deaminase or an adenine deaminase). In some embodiments, the affinity polypeptide is stable under the reducing conditions of a cell or cellular extract.

The nucleic acid constructs of the invention and/or guide nucleic acids may be comprised in one or more expression cassettes as described herein. In some embodiments, a nucleic acid construct of the invention may be comprised in the same or in a separate expression cassette or vector from that comprising a guide nucleic acid and/or a recruiting guide nucleic acid.

When used in combination with guide nucleic acids and recruiting guide nucleic acids, the nucleic acid constructs of the invention (and expression cassettes and vectors comprising the same) may be used to modify a target nucleic acid and/or its expression. A target nucleic acid may be contacted with a nucleic acid construct of the invention and/or expression cassettes and/or vectors comprising the same prior to, concurrently with or after contacting the target nucleic acid with the guide nucleic acid/recruiting guide nucleic acid (and/or expression cassettes and vectors comprising the same.

The term "seed region" refers to the critical portion of a crRNA's or guide RNA's guide sequence that is most susceptible to mismatches with their targets. In some embodiments, a single mismatch in the seed region of a crRNA/gRNA can render a CRISPR complex inactive at that binding site. In some embodiments, the seed regions for Cas9 endonucleases are located along the last ~12 nts of the 3' portion of the guide sequence, which correspond (hybridize) to the portion of the protospacer target sequence that is adjacent to the PAM. In some embodiments, the seed regions for Cpf1 endonucleases are located along the first ~5 nts of the 5' portion of the guide sequence, which correspond (hybridize) to the portion of the protospacer target sequence adjacent to the PAM.

The term "modified" refers to a substance or compound (e.g., a cell, a polynucleotide sequence, and/or a polypeptide sequence) that has been altered or changed as compared to the corresponding unmodified substance or compound. For example, a modified polynucleotide can be a nucleic acid that has been edited (e.g., mutated such as by substituting and/or deleting a nucleic acid) and/or changed compared to its unmodified or native sequence and/or structure.

An "edited polynucleotide" as used herein refers to a polynucleotide that has been edited (e.g., mutated such as by substituting and/or deleting a nucleic acid) and/or changed compared to its unmodified or native sequence and/or structure. The term "gene edited plant, part or cell" as used herein refers to a plant, part or cell that comprises one or more endogenous genes that are edited by an editing system. An editing system of the present disclosure may comprise a targeting element and/or an editing element. The targeting element may be capable of recognizing and/or may be configured to recognize a target genomic sequence. The editing element may be capable of modifying and/or may be configured to modify a target nucleic acid, e.g., by substitution or insertion of one or more nucleotides, deletion of one or more nucleotides, alteration of a nucleotide sequence to include a regulatory sequence, insertion of a transgene at a safe harbor genomic site or other specific location in the genome, or any combination thereof. The targeting element and the editing element can be on the same nucleic acid molecule or different nucleic acid molecules. In some embodiments, the editing element is capable of precise genome editing by insertion and/or deletion of at least one nucleotide using a CRISPR/Cas system. In some embodiments, the editing element is capable of precise genome editing by substitution of a single nucleotide using a base editor, such cytosine base editor (CBE) and/or adenine base editor (ABE), which is directly or indirectly fused to a CRISPR-associated effector protein.

The terms "transgene" or "transgenic" as used herein refer to at least one nucleic acid sequence that is taken from the genome of one organism, or produced synthetically, and which is then introduced into a host cell or organism or tissue of interest and which is subsequently integrated into the host's genome by means of "stable" transformation or transfection approaches. In contrast, the term "transient" transformation or transfection or introduction refers to a way of introducing molecular tools including at least one nucleic acid (DNA, RNA, single-stranded or double-stranded or a mixture thereof) and/or at least one amino acid sequence, optionally comprising suitable chemical or biological agents, to achieve a transfer into at least one compartment of interest of a cell, including, but not restricted to, the cytoplasm, an organelle, including the nucleus, a mitochondrion, a vacuole, a chloroplast, or into a membrane, resulting in transcription and/or translation and/or association and/or activity of the at least one molecule introduced without achieving a stable integration or incorporation and thus inheritance of the respective at least one molecule introduced into the genome of a cell. The terms "transgene-free" refers to a condition in which a transgene is not present or found in the genome of a host cell or tissue or organism of interest.

As used herein, the term "tissue culture" indicates a composition comprising isolated cells of the same or a different type or a collection of such cells organized into parts of a plant. Exemplary types of tissue cultures are protoplasts, calli, plant clumps, and plant cells that can generate tissue culture that are intact in plants or parts of plants, such as embryos, pollen, flowers, seeds, leaves, stems, roots, root tips, anthers, pistils, meristematic cells, axillary buds, ovaries, seed coat, endosperm, hypocotyls, cotyledons and the like. The term "plant organ" refers to plant tissue or a group of tissues that constitute a morphologically and functionally distinct part of a plant. "Progeny" comprises any subsequent generation of a plant.

General methods in molecular and cellular biochemistry can be found in such standard textbooks as Molecular Cloning: A Laboratory Manual, 3rd Ed. (Sambrook et al., HaRBor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998), the disclosures of which are incorporated herein by reference.

As mentioned above, segregating to eliminate transgenes in vegetative propagated crops such as caneberries and cherries is not a preferred practice after a target gene is edited. Particularly, the heterozygotic nature of these crops requires several years or decades in the case of woody crops such as cherries, to breed newly edited traits to a desired elite cultivar for commercial production using traditional breeding methods. The present disclosure provides a solution to obtain transgene-free edited plants such as by transiently expressing the gene editing machinery (optionally, a Cas9 endonuclease and gRNA) in the plant cells and also by co-expressing at least one morphogenic regulator to regenerate edited cells without the aid of selection. The present disclosure also teaches methods for culturing plant tissues for transformation and regeneration as well as identification of the gene-edited event in the transformed plant, plant tissue, and plant cell.

A method of the present invention may comprise modifying a target nucleic acid using a nucleic acid construct of the invention, and/or an expression cassette and/or vector comprising the same. A method of the present invention may be carried out in an in vivo system (e.g., in a cell or in an organism) or in an in vitro system (e.g., cell free). A method, composition, and/or system of the present invention may generate and/or provide allelic diversity, optionally in a semi-random way. In some embodiments, a method of the present invention comprises determining a desired or preferred phenotype using and/or based on the modified target nucleic acid. A method of the present invention may provide one or more modified target nucleic acid(s), and the one or more modified target nucleic acid(s) may be analyzed for a desired or preferred phenotype.

According to some embodiments, a morphogenic regulator is provided. A morphogenic regulator may be present in and/or used in a composition, system, and/or method of the present invention. A "morphogenic regulator" as used herein refers to a nucleic acid sequence, gene, or polypeptide that can cause and/or stimulate morphogenesis in a cell in which it is present and expressed. A morphogenic regulator of the present invention may be used to regenerate a plant from a transformed plant cell. In some embodiments, ectopic overexpression of a morphogenic regulator involved in either embryo and/or meristem development stimulates growth of transgenic plants. Due to pleiotropic deleterious effect of some morphogenic regulators under a condition of constitutive expression, the present disclosure teaches the initial stimulating of morphogenic regulators while later restricting or eliminating their expression in the plant. In some embodiments, methods of controlling ectopic overexpression include, but are not limited to the use of transient expression, inducible promoters, tissue-specific promoters, and excision of the morphogenic regulators.

In some embodiments, ectopic overexpression of morphogenic regulators induce morphogenic growth response to enhance and/or improve transformation efficiencies, which may allow for transformation of numerous recalcitrant crops and/or successful regeneration of transformed plants. In some embodiments, transient expression of morphogenic regulators enhances and/or improves transformation efficiencies. In some embodiments, transient expression of a morphogenic regulator as described herein provides an increase and/or improvement in plant transformation efficiency and/or rate. In other embodiments, transient expression of morphogenic regulators provides an increase and/or improvement in a plant regeneration process and/or rate. In some embodiments, introduction of a polypeptide comprising a morphogenic regulator onto and/or into a plant cell provides an increase and/or improvement in plant transformation efficiency and/or rate and/or a plant regeneration process and/or rate. In some embodiments, the use of morphogenic regulators can solve current issues with plant genome modification and regeneration of genetically-modified plants and/or gene-edited plants. In some embodiments, plant transformation and regeneration improvements can be distinguished by their impact on either improving transformation efficiencies, or improving the regeneration process to recover transgenic plants.

Exemplary morphogenic regulators include, but are not limited to, a Wuschel (WUS) gene (e.g., from blackberry and/or cherry), Baby boom (BBM, e.g., from blackberry and/or cherry), Knotted1 (KN1) gene (e.g., from maize, blackberry, and/or cherry), isopentenyl transferase (ipt) gene (e.g., from *Agrobacterium tumefaciens*, blackberry, and/or cherry), CLAVATA3 (CLV3) mutant, miR156 (e.g., from citrus), AtGRF5 (e.g., from *Arabidopsis thaliana*), NTT (e.g., from *Arabidopsis thaliana*, blackberry, and/or cherry), HDZipII (e.g., from *Arabidopsis thaliana*, blackberry, and/or cherry), and orthologs or polypeptides thereof. Further exemplary morphogenic regulators include, but are not limited to those described in U.S. Pat. No. 7,256,322; *Plant Cell* 14:1737-1749 (2002); *Plant Cell Physiol.* 41(5) 583-590 (2000); *Plant Physiol.* 161(3):1076-1085 (2013); *J Exp Bot.* 69(12):2979-2993 (2018); *Plant Cell* 27(2):349-360 (2015); and *Plant Physiol.* 167(3):817-832 (2015).

In some embodiments, homologs and orthologs of WUS, BBM, KN1, IPT, CLV3, miR156, GRF5, NTT, and HDZipII genes are identified and used for improving plant transformation and/or regeneration in a plant of interest.

Further exemplary morphogenic regulators include, but are not limited to, those having a nucleotide sequence having at least 90%, 91%, 92%, 93%, 94%, 95%, 96%, 97%, 98%, 99%, or 100% sequence identity to the nucleotide sequence of any one of SEQ ID NOs:1-18 or SEQ ID NOs:28-49. In some embodiments, a nucleotide sequence of the present invention may encode an amino acid sequence having at least 90%, 91%, 92%, 93%, 94%, 95%, 96%, 97%, 98%, 99%, or 100% sequence identity to the polypeptide sequence of any one of SEQ ID NOs:19-27 or SEQ ID NOs:50-60. Exemplary morphogenic regulators may have an amino acid sequence having at least 90%, 91%, 92%, 93%, 94%, 95%, 96%, 97%, 98%, 99%, or 100% sequence identity to the polypeptide sequence of any one of SEQ ID NOs:19-27 or SEQ ID NOs:50-60. A polynucleotide comprising a morphogenic regulator may be operably associated with a heterologous promoter. Compositions, systems, and/or methods of the present invention may provide a cell, plant part, plant, expression cassette, and/or vector comprising a polynucleotide comprising a morphogenic regulator as described herein and/or a polypeptide comprising a morphogenic regulator as described herein. In some embodiments, the cell, plant part, plant, expression cassette, and/or vector also includes an editing system (e.g., a polynucleotide encoding gene editing machinery or a gene editing complex (e.g., a ribonucleoprotein)), and/or a polynucleotide encoding a selectable marker.

The catabolic enzyme isopentenyl transferase (IPT) directs the synthesis of cytokinins and plays a major role in controlling cytokinin levels in plant tissues. Multiple routes have been proposed for cytokinin biosynthesis. Transfer RNA degradation has been suggested to be a source of cytokinin, because some tRNA molecules contain an isopentenyladenosine (iPA) residue at the site adjacent to the anticodon (Swaminathan, et al., (1977) *Biochemistry* 16:1355-1360). The modification is catalyzed by tRNA isopentenyl transferase (tRNA IPT; EC 2.5.1.8), which has been identified in various organisms such as *Escherichia coli, Saccharomyces cerevisiae, Lactobacillus acidophilus, Homo sapiens*, and *Zea mays* (Bartz, et al., (1972) *Biochemie* 54:31-39; Kline, et al., (1969) *Biochemistry* 8:4361-4371; Holtz, et al., (1975) *Hoppe-Seyler's Z. Physiol. Chem.* 356:1459-1464; Golovko, et al., (2000) *Gene* 258:85-93; and, Holtz, et al., (1979) *Hoppe-Seyler's Z. Physiol. Chem.* 359:89-101). However, this pathway is not considered to be the main route for cytokinin synthesis (Chen, et al., (1997) *Physiol. Plant* 101:665-673 and McGraw, et al., (1995) *Plant Hormones, Physiology, Biochemistry and Molecular Biology*. Ed. Davies, 98-117, Kluwer Academic Publishers, Dordrecht).

The current knowledge of cytokinin biosynthesis in plants is largely deduced from studies on a possible analogous system in *Agrobacterium tumefaciens*. Cells of *A. tumefaciens* are able to infect certain plant species by inducing tumor formation in host plant tissues (Van Montagu, et al., (1982) *Curr Top Microbiol Immunol* 96:237-254; Hansen, et al., (1999). *Curr Top Microbiol Immunol* 240:21-57). To do so, the *A. tumefaciens* cells synthesize and secrete cytokinins which mediate the transformation of normal host plant tissues into tumors or calli. This process is facilitated by the *A. tumefaciens* tumor-inducing plasmid which contains genes encoding the necessary enzyme and regulators for cytokinin biosynthesis. Biochemical and genetic studies revealed that Gene 4 of the tumor-inducing plasmid encodes an isopentenyl transferase (IPT), which converts AMP and DMAPP into isopentenyladenosine-5'-monophosphate (iPMP), the active form of cytokinins (Akiyoshi, et al., (1984) *Proc. Natl. Acad. Sci. USA* 81:5994-5998). Overexpression of the *Agrobacterium* ipt gene in a variety of transgenic plants has been shown to cause an increased level of cytokinins and elicit typical cytokinin responses in the host plant (Hansen, et al., (1999) *Curr Top Microbiol Immunol* 240:21-57). Therefore, it has been postulated that plant cells use machinery similar to that of *A. tumefaciens* cells for cytokinin biosynthesis. *Arabidopsis* IPT homologs have recently been identified in *Arabidopsis* and *Petunia* (Takei, et al., (2001) *J. Biol. Chem.* 276:26405-26410 and Kakimoto, (2001) *Plant Cell Physiol.* 42:677-685). Overexpression of the *Arabidopsis* IPT homologs in plants elevated cytokinin levels and elicited typical cytokinin responses in planta and under tissue culture conditions (Kakimoto, (2001) *Plant Cell Physiol.* 42:677-685).

In view of the influence of cytokinins on a wide variety of plant developmental processes, including root architecture, shoot and leaf development, and seed set, the ability to manipulate cytokinin levels in higher plant cells, and thereby drastically affect plant growth and productivity, offers significant commercial value (Mok, et al., (1994) *Cytokinins. Chemistry, Action and Function.* CRC Press, Boca Raton, Fla., pp. 155-166).

In some embodiments, the morphogenic regulator is an ipt gene encoding isopentenyl transferase. Isopentenyl transferase (ipt) gene is a cytokinin biosynthetic gene isolated from *Agrobacterium tumefaciens*.

In some embodiments, overexpression of a morphogenic regulator (e.g., an ipt gene) in transgenic plant cells induces shoot formation in media without additional plant growth regulators. In some embodiments, non-transgenic plants may be regenerated from the hormone-free media and they may be morphologically normal. In some embodiments, these non-transgenic plants are derived from cells where a morphogenic regulator was transiently expressed. In some embodiments, these non-transgenic plants are from the cells adjacent to the transformed cells which redistributed the cytokinin to the adjacent wild type cells.

Compositions, systems, and/or methods of the present invention may produce non-transgenic plants that are derived from cells under a condition of in which a morphogenic regulator is transiently expressed. In some embodiments, an expression cassette comprising gene editing machinery (Cas variants, Cpf1, gRNA targeting PDS or other genes) is transformed or co-transformed with another expression cassette comprising a morphogenic regulator. In some embodiments, the resultant transgenic (with an edited polynucleotide, but without expression of the morphogenic regulator) and non-transgenic (with anedited polynucleotide, and with expression of the morphogenic regulator) plants can be analyzed for transgene integration and gene editing efficiency.

A method of the present invention may comprise introducing a polynucleotide or a polypeptide comprising a heterologous morphogenic regulator into a plant cell, thereby transforming the plant cell. A "heterologous morphogenic regulator" as used herein refers to a morphogenic regulator as described herein that is heterologous to the plant cell in which the morphogenic regulator is being or has been introduced, or to a morphogenic regulator as described herein that is present at a different protein concentration than it would normally be present in the plant cell to which the morphogenic regulator is being or has been introduced. Compared to a control, the method may improve or increase regeneration frequency in a group of plant cells in which at least one of the plant cells is transformed with the polynucleotide or polypeptide comprising a heterologous morphogenic regulator. A "group of plant cells" as used herein refers to two more plant cells. In some embodiments, regeneration frequency may be improved or increased in a group of plant cells that are not transformed with a polynucleotide or polypeptide comprising a heterologous morphogenic regulator, but are in proximity to a cell comprising the polynucleotide or polypeptide comprising a heterologous morphogenic regulator. The method may include introducing an editing system into the same plant cell or a different plant cell as the heterologous morphogenic regulator. The step of introducing the polynucleotide or polypeptide comprising the heterologous morphogenic regulator and the step of introducing the editing system may be performed concurrently or sequentially in any order. A plant cell may be stably transformed with a polynucleotide comprising a heterologous morphogenic regulator and/or may be stably transformed with an editing system (e.g., a polynucleotide encoding a gene editing machinery or a gene editing complex such as a ribonucleoprotein). A plant cell may be transiently transformed with a polynucleotide or polypeptide comprising a heterologous morphogenic regulator and/or may be stably transformed with an editing system (e.g., a polynucleotide encoding a gene editing machinery or a gene editing complex).

A method of the present invention may not introduce (i.e., may be devoid of introducing) a polynucleotide encoding a selectable marker. Accordingly, a plant cell comprising the polynucleotide or polypeptide comprising a heterologous morphogenic regulator and/or editing system may not comprise a polynucleotide encoding a selectable marker. In some embodiments, a method of the present invention comprises introducing a polynucleotide encoding a selectable marker into the same plant cell or a different plant cell as the heterologous morphogenic regulator and/or editing system. A selectable marker may be stably or transiently transformed in a cell and/or method of the present invention.

A single polynucleotide may comprise a polynucleotide comprising a heterologous morphogenic regulator, a polynucleotide encoding an editing system, and/or a polynucleotide encoding a selectable marker, or two or more polynucleotides may include one or more of a polynucleotide comprising a heterologous morphogenic regulator, a polynucleotide encoding an editing system, and/or a polynucleotide encoding a selectable marker. In some embodiments, a first polynucleotide comprises a polynucleotide comprising a heterologous morphogenic regulator and a second polynucleotide comprises a polynucleotide encoding editing system.

A method of the present invention may stimulate embryogenesis and/or organogenesis in a plant cell. In some embodiments, a method of the present invention stimulates embryogenesis and/or organogenesis in a plant cell comprising a polynucleotide or polypeptide comprising a heterologous morphogenic regulator and optionally an editing system and/or selectable marker. In some embodiments, a plant cell and/or method of the present invention stimulates embryogenesis and/or organogenesis in a plant cell that does not comprise (i.e., is devoid of) a polynucleotide or polypeptide comprising a heterologous morphogenic regulator or does not have the heterologous morphogenic regulator at a same concentration (e.g., protein concentration) in the plant cell. For example, a method of the present invention may introduce a polynucleotide comprising a heterologous morphogenic regulator into a plant cell and the plant cell comprising the polynucleotide comprising a heterologous morphogenic regulator may stably or transiently express the polynucleotide comprising a heterologous morphogenic regulator. In stably or transiently expressing the polynucleotide comprising a heterologous morphogenic regulator, the plant cell may stimulate embryogenesis and/or organogenesis in a plant cell that does not comprise (i.e., is devoid of) a polynucleotide comprising a heterologous morphogenic regulator. The plant cell devoid of the polynucleotide comprising a heterologous morphogenic regulator may be a neighboring plant cell.

A "neighboring plant cell" as used herein refers to the location of a plant cell relative to another plant cell (i.e., the reference plant cell), and a neighboring plant cell is one that is in physical contact with, adjacent to, and/or in chemical communication with (e.g., receives cytokines from) the reference plant cell. The neighboring plant cell may be a plant cell that is from a different plant species or genotype than that of the transformed cell comprising the heterologous morphogenic regulator as described herein (e.g., the reference plant cell). In some embodiments, a neighboring plant cell is a plant cell in which a plasmodesmata (e.g., a primary and/or secondary plasmodesmata) connects the plant cell to the reference plant cell and/or in which a plasmodesmata traverses or passes through the cell wall of both the reference plant cell and neighboring plant cell. In some embodiments, a neighboring plant cell is the plant cell that is immediately adjacent to the reference plant call and middle lamella contacts or joins the cell walls of the two plant cells. In some embodiments, a neighboring plant cell is a plant cell in which an apoplast is formed by a portion of the cell wall of the reference plant cell and by a portion of the cell wall of the neighboring plant cell. In some embodiments, a neighboring plant cell is a plant cell in which 0, 1, 2, 3, 4, 5, 6, 7, 8, 9, 10, 11, 12, 13, 14, 15, 16, 17, 18, 19, 20, or more plant cells are between the cell wall of the neighboring plant cell and the cell wall of the reference plant cell. In some embodiments, a neighboring plant cell is one that is in the same explant as the reference plant cell and/or all cells in an explant are considered to be a neighboring plant cell. A neighboring plant cell may be devoid of a polynucleotide or a polypeptide comprising a heterologous morphogenic regulator, devoid of an editing system, and/or devoid of a selectable marker. In some embodiments, a first plant cell is transiently transformed with a polynucleotide or a polypeptide comprising a heterologous morphogenic regulator and the first plant cell stimulates a neighboring plant cell that is transiently transformed with an editing system to multiply and/or regenerate.

According to some embodiments, a composition, system, and/or method of the present invention causes or induces one or more plant cell(s) to multiply to provide one or more transgene-free plant cell(s), optionally using a plant cell in which a polynucleotide or a polypeptide comprising a heterologous morphogenic regulator has been introduced. The one or more transgene-free plant cell(s) may be undifferentiated plant cells or tissue or may be a callus. The one or more transgene-free plant cell(s) may be cultured explants. The one or more transgene-free cell(s) may form and/or may be grown to form one or more organ(s) and/or plant part(s). In some embodiments, a composition, system, and/or method of the present invention regenerates a transgene-free plant part or transgene-free plant, optionally using a plant cell in which a polynucleotide or a polypeptide comprising a heterologous morphogenic regulator has been introduced. In some embodiments, a transgene-free plant cell, a transgene-free plant part, and/or transgene-free plant is produced (e.g., regenerated) from the plant cell in which a polynucleotide or a polypeptide comprising a heterologous morphogenic regulator has been introduced. In some embodiments, the plant cell in which a polynucleotide or polypeptide comprising a heterologous morphogenic regulator has been introduced stimulates and/or initiates one or more neighboring plant cell(s) to multiply and/or regenerate to provide a transgene-free plant cell, a transgene-free plant part, or transgene-free plant. A method of the present invention may include, responsive to a step of introducing a polynucleotide or a polypeptide comprising a heterologous morphogenic regulator into a plant cell and optionally responsive to introducing an editing system into the same plant cell or a different plant cell (e.g., a neighboring plant cell), producing a plant cell, plant part and/or plant that is non-transgenic. A transgene-free plant cell, plant part and/or plant of the present invention may comprise an edited polynucleotide. The edited polynucleotide may be responsive to introducing an editing system into the same plant cell or a different plant cell (e.g., a neighboring plant cell) as the plant cell in which a polynucleotide or a polypeptide comprising a heterologous morphogenic regulator is introduced.

A composition, system, and/or method of the present invention may induce shoot formation, optionally using a plant cell in which a polynucleotide or a polypeptide comprising a heterologous morphogenic regulator and/or editing system has been introduced. In some embodiments, the method comprises expressing the heterologous morphogenic regulator in the plant cell and inducing shoot formation from the plant cell or a neighboring plant cell. The shoot formation may comprise apical dominance and/or roots.

A method of the present invention may include growing (e.g., culturing) a plant cell in the presence of and/or in contact with (e.g., on) media devoid of plant growth regulators and/or hormones (e.g., hormone-free media). The plant cell may comprise a polynucleotide or a polypeptide comprising a heterologous morphogenic regulator, editing system, and/or a selectable marker. In some embodiments, growing the plant cell comprises growing the plant cell in the presence of, in contact with, and/or on media devoid of plant growth regulators and/or hormones and producing a plant part and/or plant from the plant cell.

In some embodiments, a method of the present invention comprises transiently expressing an editing system in a plant cell and regenerating plant cells comprising an edited polynucleotide, optionally without the aid of selection (e.g., without using or introducing a selection marker). A polynucleotide encoding the editing system may be introduced into the plant cell or a neighboring plant cell, and/or the editing system may be introduced into the plant cell or a neighboring plant cell as an assembled ribonucleoprotein complex. In some embodiments, the editing system comprises a CRISPR-Cas effector protein (e.g., Cas9/Cas12a) and a guide nucleic acid.

In some embodiments, a method of the present invention comprises introducing (e.g., delivering) a polynucleotide or a polypeptide comprising a heterologous morphogenic regulator and a polynucleotide encoding a selectable marker to a plant cell, and regenerating a stably transformed plant under herbicide and/or antibiotic selection. In some embodiments, the method comprises introducing an editing system. In some embodiments, an editing system is not introduced.

In some embodiments, a method of the present invention comprises introducing (e.g., delivering) a polynucleotide or a polypeptide comprising a heterologous morphogenic regulator to a plant cell and does not include introducing a selectable marker to the plant cell. The method further includes regenerating a stably transformed plant without selection. In some embodiments, the method comprises introducing an editing system. In some embodiments, an editing system is not introduced.

In some embodiments, a composition, system and/or method of the present invention provides a genetic trigger for embryogenesis, organogenesis, and/or regeneration. In some embodiments, a composition, system and/or method of the present invention stimulates or causes transformed cells to multiply and/or regenerate faster and/or more efficiently than non-transformed cells. This may allow for transformed shoots to be more efficiently found among the regenerated shoots even without a selection system to inhibit the regeneration of untransformed cells.

In some embodiments, a method of the present invention comprises introducing (e.g., delivering) a polynucleotide or a polypeptide comprising a heterologous morphogenic regulator to a plant cell, and inducing a neighboring plant cell to multiply and/or regenerate. Certain types of morphogenic regulators (e.g., wuschel or WUS) organize embryo development on a concentration gradient from high to low. For this reason, cells that are transiently or stably transformed can induce their neighboring plant cells to organize an embryo and regenerate. Accordingly, a polynucleotide or a polypeptide comprising a heterologous morphogenic regulator may be introduced separately from another transgene and/or separately from an editing system. In some embodiments, the cells that receive the polynucleotide or polypeptide comprising a heterologous morphogenic regulator cause or induce neighboring plant cells, some of which have received the separate transgene and/or editing system, to multiply and/or regenerate. This can be with or without editing tools (e.g., an editing system) and/or with or without a selectable marker in the neighboring plant cells.

In some embodiments, a method of the present invention directly expresses transgenes encoding polynucleotides that initiate and/or define embryo identity. A composition, system, and/or method of the present invention may reduce or eliminate the dependence of a plant cell on media growth regulators and/or hormone supplements for regeneration. Media hormone supplementation enables many cells in a tissue, whether transformed or not, the potential to regenerate. However, an advantage of a composition, system, and/or method of the present invention can be that by introducing a polynucleotide or a polypeptide comprising a heterologous morphogenic regulator into a plant cell, the potential to regenerate is now tied to the transformation identity itself, representing a powerful approach to selectively encourage transformed cells to regenerate preferentially over untransformed cells. A polypeptide, polynucleotide, composition, system, and/or method of the present invention may increase or improve regeneration efficiency by about 2-, 4-, 6-, 8-, 10-, 20-, 30-, 40-, 50-, 60-, 70-, 80-, 90-100-, 200-, 300-, 400-, 500-, 600-, 700-, 800-, 900-, or 1000-fold compared to a control (e.g., a composition, system, cell (e.g., plant cell), and/or method that is devoid of a polypeptide and/or polynucleotide of the present invention).

A composition, system and/or method of the present invention may provide and/or produce a plant part and/or plant such as responsive to a step of introducing a polynucleotide or a polypeptide comprising a heterologous morphogenic regulator into a plant cell and optionally responsive to introducing an editing system into the same plant cell or a different plant cell (e.g., a neighboring plant cell) and responsive to growing plant cells. The plant part and/or plant may be morphologically normal compared to a control plant part and/or plant (e.g., compared to a non-transformed plant part or plant). Methods for determining morphological structures are known to those of skill in the art.

A composition, system and/or method of the present invention may comprise and/or introduce a morphogenic regulator as described herein. In some embodiments, the heterologous morphogenic regulator is a Knotted 1 (KN1), Baby Boom (BBM), Wuschel (WUS) or Wuschel-related homeobox (WOX) gene, or an ortholog thereof. In some embodiments, the morphogenic regulator is ipt or an ortholog thereof. In some embodiments, the morphogenic regulator is kn1 or an orthology thereof, optionally kn1 homeobox gene of maize. The maize transcription factor KN1 functions in plant meristems, self-renewing structures consisting of stem cells and their immediate daughters, which is associated with cytokinins accumulation through the positive regulation of cytokinin synthesis genes. In some embodiments, kn1 gene can be assessed to see if its transient expression is able to enhance plant regeneration and consequently increase gene editing occurrences. In some embodiments, the morphogenic regulator is WUS. In some embodiments, the morphogenic regulator is BBM. In some embodiments, the morphogenic regulator is CLV3. In some embodiments, the morphogenic regulator is miR156. In some embodiments, the morphogenic regulator is GRF5. In some embodiments, the morphogenic regulator is NTT. In some embodiments, the morphogenic regulator is HDZipII.

In some embodiments, the polynucleotide comprising the heterologous morphogenic regulator has at least 90%, 91%, 92%, 93%, 94%, 95%, 96%, 97%, 98%, 99%, or 100% sequence identity to the nucleotide sequence of any one of SEQ ID NOs:1-18 or SEQ ID NOs:28-49, optionally wherein the polynucleotide comprising the heterologous morphogenic regulator comprises the nucleotide sequence of any one of SEQ ID NOs:1-18 or SEQ ID NOs:28-49. In some embodiments, the polynucleotide comprising the heterologous morphogenic regulator has at least 90%, 91%, 92%, 93%, 94%, 95%, 96%, 97%, 98%, 99%, or 100% sequence identity to the nucleotide sequence of any one of SEQ ID NOs:1-18, optionally wherein the polynucleotide comprising the heterologous morphogenic regulator comprises the nucleotide sequence of any one of SEQ ID NOs:1-18. A polynucleotide comprising the heterologous morphogenic regulator may be operably associated with a promoter (e.g., a heterologous promoter). In some embodiments, the polynucleotide comprising the heterologous morphogenic regulator encodes an amino acid sequence having at least 90%, 91%, 92%, 93%, 94%, 95%, 96%, 97%, 98%, 99%, or 100% sequence identity to the polypeptide sequence of any one of SEQ ID NOs:19-27 or SEQ ID NOs:50-60, optionally wherein the polynucleotide comprising the heterologous morphogenic regulator encodes the polypeptide sequence of any one of SEQ ID NOs:19-27 or SEQ ID NOs:50-60. In some embodiments, the polynucleotide comprising the heterologous morphogenic regulator encodes an amino acid sequence having at least 90%, 91%, 92%, 93%, 94%, 95%, 96%, 97%, 98%, 99%, or 100% sequence identity to the polypeptide sequence of any one of SEQ ID NOs:19-27, optionally wherein the polynucleotide comprising the heterologous morphogenic regulator encodes the polypeptide sequence of any one of SEQ ID NOs:19-27. In some embodiments, the polypeptide comprising the heterologous morphogenic regulator has an amino acid sequence having at least 90%, 91%, 92%, 93%, 94%, 95%, 96%, 97%, 98%, 99%, or 100% sequence identity to the polypeptide sequence of any one of SEQ ID NOs:19-27 or SEQ ID NOs:50-60, optionally wherein the polypeptide comprising the heterologous morphogenic regulator has the polypeptide sequence of any one of SEQ ID NOs:19-27 or SEQ ID NOs:50-60. In some embodiments, the polypeptide comprising the heterologous morphogenic regulator has an amino acid sequence having at least 90%, 91%, 92%, 93%, 94%, 95%, 96%, 97%, 98%, 99%, or 100% sequence identity to the polypeptide sequence of any one of SEQ ID NOs:19-27, optionally wherein the polypeptide comprising the heterologous morphogenic regulator has the polypeptide sequence of any one of SEQ ID NOs:19-27. In some embodiments, the present disclosure provides a delivery of one or more components of an editing system directly to the plant cell. This is of interest, inter alia, for the generation of non-transgenic plants. In some embodiments, one or more of the components of the editing system is prepared outside the plant or plant cell and delivered to the cell. In some embodiments, the editing system is prepared in vitro prior to introduction to the plant cell. A base-editing fusion protein may be prepared by various methods known by one of skill in the art and include recombinant production. After expression, the CRISPR-Cas effector protein may be isolated, refolded if needed, purified and optionally treated to remove any purification tags if a tag such as a His-tag is present in the fusion protein. Once crude, partially purified, or more completely purified CRISPR-Cas effector protein is obtained, the protein may be introduced to the plant cell.

In some embodiments, the CRISPR-Cas effector protein is mixed with a guide nucleic acid that targets a target nucleic acid to form a pre-assembled ribonucleoprotein.

The individual components or pre-assembled ribonucleoprotein can be introduced into the plant cell via electroporation, by bombardment with targeted gene-editing system coated particles, by chemical transfection and/or by some other means of transport across a cell membrane. For instance, transfection of a plant protoplast with a pre-assembled CRISPR-Cas9 ribonucleoprotein has been demonstrated to ensure targeted modification of the plant genome (as described by Woo et al. Nature Biotechnology, 2015; 33(11):1162-1164).

In some embodiments, an editing system and/or one or more component(s) thereof may be introduced into a plant cell using nanoparticles. The editing system and/or components thereof, either as protein or nucleic acid or in a combination thereof, can be uploaded onto and/or packaged in nanoparticles and applied to the plants (such as for instance described in WO2008/042156 and US2013/0185823). In particular, the disclosure teaches nanoparticles uploaded with or packed with DNA molecule(s) encoding the CRISPR-Cas effector protein, DNA molecule(s) encoding cytosine deaminase (which may be fused to the CRISPR-Cas protein or a linker), and DNA molecules encoding the guide RNA and/or isolated guide RNA as described in WO2015/089419.

Further means of introducing one or more components of an editing system to a plant cell is by using cell penetrating peptides (CPP). Accordingly, some embodiments of the disclosure comprise compositions comprising a cell penetrating peptide linked to the gene-editing fusion protein. In some embodiments, a sequence-specific nucleic acid binding domain (e.g., a CRISPR Cas effector protein) and/or guide nucleic acid is coupled to one or more CPPs to effectively transport them inside plant protoplasts. Ramakrishna (Genome Res. 2014 June; 24(6): 1020-7 for Cas9 in human cells). In some embodiments, a sequence-specific nucleic acid binding domain (e.g., a CRISPR Cas effector protein) and/or guide nucleic acid are encoded by one or more circular or non-circular DNA molecule(s) which are coupled to one or more CPPs for plant protoplast delivery. The plant protoplasts are then regenerated to plant cells and further to plants. CPPs are generally described as short peptides of fewer than 35 amino acids either derived from proteins or from chimeric sequences which are capable of transporting biomolecules across cell membrane in a receptor independent manner. CPP can be cationic peptides, peptides having hydrophobic sequences, amphipathic peptides, peptides having proline-rich and anti-microbial sequence, and chimeric or bipartite peptides (Pooga and Langel 2005). CPPs are able to penetrate biological membranes and as such trigger the movement of various biomolecules across cell membranes into the cytoplasm and to improve their intracellular routing, and hence facilitate interaction of the biomolecule with the target.

In some embodiments, the methods described herein are used to modify a endogenous nucleic acid and/or gene and/or to modify their expression without the permanent introduction of any foreign gene including those encoding the editing system components into the genome of the plant, so as to avoid the presence of foreign DNA in the genome of the plant. In some embodiments, this may be provided by transient expression of the editing system components. In some embodiments, one or more of the components are expressed on one or more viral vectors which produce sufficient a sequence-specific nucleic acid binding domain (e.g., a CRISPR Cas effector protein), and guide nucleic acid to consistently steadily ensure modification of a nucleic acid of interest according to a method described herein. In some embodiments, transient expression of the editing system components is ensured in plant protoplasts and thus not integrated into the genome. The limited window of expression can be sufficient to allow the editing system to ensure modification of a target nucleic acid as described herein.

In some embodiments, the different components of the editing system are introduced in the plant cell, protoplast or plant tissue either separately or in mixture, with the aid of delivering molecules such as nanoparticles or CPP molecules as described herein above.

The expression of the editing system components can induce targeted modification of the genome. The different strategies described herein can allow CRISPR-mediated targeted genome editing without requiring the introduction of the editing system components into the plant genome. Components which are transiently introduced into the plant cell are used for editing a target nucleic acid and become non-functional naturally as they are stably integrated into a host genome.

In some embodiments, plant cells which have an edited polynucleotide and that are produced or obtained by any of the methods described herein, can be cultured to regenerate a whole plant that possesses the transformed or modified genotype and thus the desired phenotype. Conventional regeneration techniques are well known to those skilled in the art. Particular examples of such regeneration techniques rely on manipulation of certain phytohormones in a tissue culture growth medium, and typically relying on a biocide and/or herbicide marker which has been introduced together with the desired nucleotide sequences. In some embodiments, plant regeneration is obtained from cultured protoplasts, plant callus, explants, organs, pollens, embryos or parts thereof (see e.g. Evans et al. (1983), Handbook of Plant Cell Culture, Klee et al (1987) Ann. Rev. of Plant Phys.). However, the regeneration efficiency and ratio is very low.

In some embodiments, transformed or improved plants as described herein can be self-pollinated to provide seed for homozygous trait-improved plants of the disclosure, which have a desired trait such as seedlessness, reduced seed size, reduced endocarp tissue, or less lignified endocarp (homozygous for the DNA modification) or crossed with non-transgenic plants or different trait-improved plants to provide seed for heterozygous plants. Where a recombinant DNA was introduced into the plant cell, the resulting plant of such a crossing is a plant which is heterozygous for the recombinant DNA molecule. Both such homozygous and heterozygous plants obtained by crossing from the trait-improved plants and comprising the genetic modification (which can be a recombinant DNA) are referred to herein as "progeny". Alternatively, gene-edited plants can be obtained by one of the methods described herein using an editing system whereby no foreign DNA is incorporated into the genome using transient expression/delivery or whereby foreign DNA is incorporated into the genome using stable transformation but removed/segregated away upon crossing. Progeny of such plants, obtained by further breeding may also contain the genetic modification such as nucleotide substitutions. Breedings may be performed by any breeding methods that are commonly used for different crops (e.g., Allard, Principles of Plant Breeding, John Wiley & Sons, NY, U. of CA, Davis, CA, 50-98 (1960). However, this approach cannot be applied to plants and/or crops with high heterozygosity and/or multiploidy.

Developing a method to generate CRISPR-mediated non-transgenic events is highly desirable for many applications of genome editing, particularly for asexually propagated, heterozygous, perennial crop plants. It has been reported that pre-assembled CRISPR/Cas9 ribonucleoproteins can be delivered into protoplasts to induce mutations, without the need for stable integration of CRISPR/Cas9 genes into the host-plant genome (Malnoy et al. 2016, Subburaj et al. 2016, Woo et al. 2015). Particle bombardment has also been used to deliver CRISPR/Cas9 ribonucleoproteins to wheat and maize cells, producing non-transgenic mutants (Liang et al. 2017, Svitashev et al 2016, Zhang et al. 2016, Kim 2017).

A method for production and expedient screening of CRISPR/Cas9-mediated non-transgenic mutant plants via transient T-DNA expression has been reported using tobacco as a model species (Che et al 2018). The mutant rate of non-transgenic plant from total regenerated plants was <0.5% when no selection was applied. The present disclosure teaches that transient expression of a morphogenic regulator in dicot species is demonstrated to enhance regeneration and may subsequently increase gene editing efficiency.

As mentioned above, transient expression of an editing system via *Agrobacterium*-mediated T-DNA delivery was reported to generate edited events without transgene integration, the overall efficiency was low due to the lack of selection (Chen et al. 2018). The present disclosure teaches use of transient expression of morphogenic regulator(s) to enhance the regeneration of edited cells without transgene integration. In some embodiments, morphogenic regulators are transiently transformed using *Agrobacterium*-mediated T-DNA delivery along with gene editing machinery that generates edited events.

In some embodiments, a gene-edited plant cell produced according to a method of the present is grown, multiplied, and/or regenerated in a medium without growth hormones, in which case, for example, at most 2%, at most 1%, at most 0.9%, at most 0.8%, at most 0.7%, at most 0.6%, at most 0.5%, at most 0.4%, at most 0.3%, at most 0.2%, at most 0.1%, at most 0.05%, at most 0.01%, at most 0.005%, at most 0.001%, at most 0.0005%, or at most 0.0001% or lower of the transformed cells are regenerated into a whole plants. In some embodiments, a gene-edited plant cell produced according to a method of the present invention is transformed with an expression cassette comprising one or more (e.g., 1, 2, 3, 4, 5, or more) morphogenic regulator(s) (such as WUS, BBN, KN1, IPT, CLV3, miR156, GRF5, NTT, and/or HDZipII) and regenerated in a medium without growth hormones, in which case, for example, at least 1%, at least 2%, at least 3%, at least 4%, at least 5%, at least 6%, at least 7%, at least 8%, at least 9%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% or higher, of the transformed cells are regenerated into a whole plants.

In some embodiments of the present invention, transient expression of at least one morphogenic regulator in a transformed cell is capable of regenerating a plant without regeneration-inducing hormones added.

In some embodiments, transient expression of at least one morphogenic regulator in a transformed cell is capable of regenerating a plant in combination with addition of regeneration-inducing hormones in an improved, enhanced and/or synergistic manner.

In some embodiments, a plant cell of interest can be co-transformed with an expression cassette comprising one or more gene editing components/machinery and another expression cassette comprising at least one morphogenic regulator. In embodiments, the transient expression of at least one morphogenic regulator increases, enhances, improves transformation efficiency of the gene-editing system. In further embodiments, the transient expression of at least one morphogenic regulator increases, enhances, improves regeneration of the gene-edited plant cell. In further embodiments, the transient expression of at least one morphogenic regulator increases, enhances, improves regeneration of the gene-edited plant cell even in a culture medium without hormones such as regeneration-inducing hormones.

In other embodiments, the morphogenic regulators taught in the present disclosure can be used as a positive selection marker that gives rise to plant regeneration in a hormone-less culture medium. This allows for avoidance of use of a selectable marker gene (usually an antibiotic- or herbicide-resistant gene), which can make the transformed cells and/or regenerated plants transgenic due to undesired DNA pieces that is stably integrated and inherited.

In some embodiments, transient expression of morphogenic regulators in a plant cell transformed with the gene-editing machinery taught in the present disclosure increases, improves, and/or enhance plant transformation efficiency at least 0.5%, at least 1%, at least 2%, at least 3%, at least 4%, at least 5%, at least 6%, at least 7%, at least 8%, at least 9%, at least 10%, at least 12%, at least 15%, at least 18%, at least 20%, at least 30%, at least 40%, at least 50%, at least 60%, at least 70%, at least 80%, at least 90%, at least 100%, at least 150%, at least 200%, at least 250%, at least 300%, at least 400%, at least 500% or higher than a plant cell transformed with the gene-editing machinery, but without morphogenic regulator expression.

In some embodiments, transient expression of morphogenic regulators in a plant cell transformed with the gene-editing machinery taught in the present disclosure increases, improves, and/or enhance plant regeneration at least 0.5%, at least 1%, at least 2%, at least 3%, at least 4%, at least 5%, at least 6%, at least 7%, at least 8%, at least 9%, at least 10%, at least 12%, at least 15%, at least 18%, at least 20%, at least 30%, at least 40%, at least 50%, at least 60%, at least 70%, at least 80%, at least 90%, at least 100%, at least 150%, at least 200%, at least 250%, at least 300%, at least 400%, at least 500% or higher than a plant cell transformed with the gene-editing machinery, but without morphogenic regulator expression.

In some embodiments, the modified plant cells described herein demonstrate an altered expression and/or function of one or more endogenous target genes.

In some embodiments, the expression of an endogenous target gene in a particular pathway is reduced in the modified plant cells. In some embodiments, the expression of a plurality (e.g., two or more) of endogenous target genes in a particular pathway are reduced in the modified plant cells. For example, the expression of 2, 3, 4, 5, 6, 7, 8, 9, 10, or more endogenous target genes in a particular pathway may be reduced. In some embodiments, the expression of an endogenous target gene in one pathway and the expression of an endogenous target genes in another pathway is reduced in the modified plant cells. In some embodiments, the expression of a plurality of endogenous target genes in one pathway and the expression of a plurality of endogenous target genes in another pathway are reduced in the modified plant cells. For example, the expression of 2, 3, 4, 5, 6, 7, 8, 9, 10, or more endogenous target genes in one pathway may be reduced and the expression of 2, 3, 4, 5, 6, 7, 8, 9, 10, or more endogenous target genes in another particular pathway may be reduced. In some embodiments, the expression of a plurality of endogenous target genes in a plurality of pathways is reduced. For example, the expression of one endogenous gene from each of a plurality of pathways (e.g., 2, 3, 4, 5, 6, 7, 8, 9, 10, or more pathways) may be reduced. In additional aspects, the expression of a plurality of endogenous genes (e.g., 2, 3, 4, 5, 6, 7, 8, 9, 10, or more genes) from each of a plurality of pathways (e.g., 2, 3, 4, 5, 6, 7, 8, 9, 10, or more pathways) may be reduced.

In some embodiments, the function of a protein encoded by an endogenous target gene in a particular pathway is altered in the modified plant cells. In some embodiments, the functions of proteins encoded by a plurality (e.g., two or more) of endogenous target genes in a particular pathway are altered in the modified plant cells. For example, the function of proteins encoded by 2, 3, 4, 5, 6, 7, 8, 9, 10, or more endogenous target genes in a particular pathway may be altered. In some embodiments, the function of a protein encoded by an endogenous target gene in one pathway and the function of an endogenous target genes in another pathway is altered in the modified plant cells. In some embodiments, the functions of proteins encoded by a plurality of endogenous target genes in one pathway and the function of proteins encoded by a plurality of endogenous target genes in another pathway are altered in the modified plant cells. For example, the function of proteins encoded by 2, 3, 4, 5, 6, 7, 8, 9, 10, or more endogenous target genes in one pathway may be altered and the function of proteins encoded by 2, 3, 4, 5, 6, 7, 8, 9, 10, or more endogenous target genes in another particular pathway may be altered. In some embodiments, the functions of proteins encoded by a plurality of endogenous target genes in a plurality of pathways are altered. For example, the function of a protein encoded by one endogenous gene from each of a plurality of pathways (e.g., 2, 3, 4, 5, 6, 7, 8, 9, 10, or more pathways) may be altered. In additional aspects, the function of proteins encoded by a plurality of endogenous genes (e.g., 2, 3, 4, 5, 6, 7, 8, 9, 10, or more genes) from each of a plurality of pathways (e.g., 2, 3, 4, 5, 6, 7, 8, 9, 10, or more pathways) may be altered.

Gene editing generally refers to the process of modifying the nucleotide sequence of a genome, preferably in a precise or pre-determined manner. Examples of methods of gene editing described herein include methods of using site-directed nucleases to cut deoxyribonucleic acid (DNA) at precise target locations in the genome, thereby creating single-strand or double-strand DNA breaks at particular locations within the genome. Such breaks can be and regularly are repaired by natural, endogenous cellular processes, such as homology-directed repair (HDR) and non-homologous end joining (NHEJ). These two main DNA repair processes consist of a family of alternative pathways. NHEJ directly joins the DNA ends resulting from a double-strand break, sometimes with the loss or addition of nucleotide sequence, which may disrupt or enhance gene expression. HDR utilizes a homologous sequence, or donor sequence, as a template for inserting a defined DNA sequence at the break point. The homologous sequence can be in the endogenous genome, such as a sister chromatid. Alternatively, the donor can be an exogenous nucleic acid, such as a plasmid, a single-strand oligonucleotide, a double-stranded oligonucleotide, a duplex oligonucleotide or a virus, that has regions of high homology with the nuclease-cleaved locus, but which can also contain additional sequence or sequence changes including deletions that can be incorporated into the cleaved target locus. A third repair mechanism can be microhomology-mediated end joining (MMEJ), also referred to as "Alternative NHEJ," in which the genetic outcome is similar to NHEJ in that small deletions and insertions can occur at the cleavage site. MMEJ can make use of homologous sequences of a few basepairs flanking the DNA break site to drive a more favored DNA end joining repair outcome, and recent reports have further elucidated the molecular mechanism of this process; see, e.g., Cho and Greenberg, Nature 518, 174-76 (2015); Kent et al., Nature Structural and Molecular Biology, Adv. Online doi:10.1038/nsmb.2961 (2015); Mateos-Gomez et al., Nature 518, 254-57 (2015); Ceccaldi et al., Nature 528, 258-62 (2015). In some instances, it may be possible to predict likely repair outcomes based on analysis of potential microhomologies at the site of the DNA break.

"Recombination" refers to a process of exchange of genetic information between two polynucleotides, including but not limited to, donor capture by non-homologous end joining (NHEJ) and homologous recombination. For the purposes of this disclosure, "homologous recombination (HR)" refers to the specialized form of such exchange that takes place, for example, during repair of double-strand breaks in cells via homology-directed repair (HDR) mechanisms. This process requires nucleotide sequence homology, uses a "donor" molecule as a template to repair a "target" molecule (i.e., the one that experienced the double-strand break), and is variously known as "non-crossover gene conversion" or "short tract gene conversion," because it leads to the transfer of genetic information from the donor to the target. Without wishing to be bound by any particular theory, such transfer can involve mismatch correction of heteroduplex DNA that forms between the broken target and the donor, and/or synthesis-dependent strand annealing, in which the donor is used to resynthesize genetic information that will become part of the target, and/or related processes. Such specialized HR often results in an alteration of the sequence of the target molecule such that part or all of the sequence of the donor polynucleotide is incorporated into the target polynucleotide.

Gene editing methods contemplated in various embodiments comprise engineered nucleases, designed to bind and cleave a target DNA sequence in a gene of interest. The engineered nucleases contemplated in particular embodiments, can be used to introduce a double-strand break in a target polynucleotide sequence, which may be repaired (i) by non-homologous end joining (NHEJ) in the absence of a polynucleotide template, e.g., a donor repair template, or (ii) by homology directed repair (HDR), i.e., homologous recombination, in the presence of a donor repair template. Engineered nucleases contemplated in certain embodiments, can also be engineered as nickases, which generate single-stranded DNA breaks that can be repaired using the cell's base-excision-repair (BER) machinery or homologous recombination in the presence of a donor repair template.

Gene editing via sequence-specific nucleases is known in the art. See references (1) Carroll, D. (2011) Genome engineering with zinc-finger nucleases. Genetics, 188, 773-82; (2) Wood, A. J. et al. (2011) Targeted gene editing across species using ZFNs and TALENs. Science (New York, N.Y.), 333, 307; (3) Perez-Pinera, P. et al. (2012) Advances in targeted gene editing. Current opinion in chemical biology, 16, 268-77, each of which is hereby incorporated by reference in their entireties.

A nuclease-mediated double-stranded DNA (dsDNA) break in the genome can be repaired by two main mechanisms: Non-Homologous End Joining (NHEJ), which frequently results in the introduction of non-specific insertions and deletions (indels), or homology directed repair (HDR), which incorporates a homologous strand as a repair template. See Symington, L. S. and Gautier, J. (2011) Double-strand break end resection and repair pathway choice. Annual review of genetics, 45, 247-71, which is hereby incorporated by reference in its entirety.

When a sequence-specific nuclease is delivered along with a homologous donor DNA construct containing the desired mutations, gene targeting efficiencies are increased by 1000-fold compared to just the donor construct alone. See Urnov et al. (2005) Highly efficient endogenous human gene correction using designed zinc-finger nucleases. Nature, 435, 646-51, which is hereby incorporated by reference in its entirety.

In some embodiments, the gene editing techniques of the present disclosure are used for plants that are modified using any gene editing tool, including, but not limited to: ZFNs, TALENS, CRISPR, and Mega nuclease technologies. In some embodiments, the gene editing tools of the present disclosure comprise proteins or polynucleotides which have been custom designed to target and cut at specific deoxyribonucleic acid (DNA) sequences. In some embodiments, gene editing proteins are capable of directly recognizing and binding to selected DNA sequences. In other embodiments, the gene editing tools of the present disclosure form complexes, wherein nuclease components rely on nucleic acid molecules for binding and recruiting the complex to the target DNA sequence.

In some embodiments, the single component gene editing tools comprise a binding domain capable of recognizing specific DNA sequences in the genome of the plant and a nuclease that cuts double-stranded DNA. The rationale of gene editing technology taught in the present disclosure is the use of a tool that allows the introduction of site-specific mutations in the plant genome or the site-specific integration of genes.

Many methods are available for delivering genes into plant cells, e.g. transfection, electroporation, viral vectors and *Agrobacterium* mediated transfer. Genes can be expressed transiently from a plasmid vector. Once expressed, the genes generate the targeted mutation that will be stably inherited, even after the degradation of the plasmid containing the gene.

Customizable nucleases can be used to make targeted double-stranded breaks (DSB) in living cells, the repair of which can be exploited to induce desired sequence changes. Two competing pathways effect repairs in most cells, including plant cells. Repair of a nuclease-induced DSB by non-homologous end joining (NHEJ) leads to the introduction of insertion/deletion mutations (indels) with high frequencies.

By contrast, DSB repair by homology directed repair (HDR) with a user-supplied "donor template" DNA can lead to the introduction of specific alterations (e.g., point mutations and insertions) or the correction of mutant sequences back to wild-type.

In some embodiments, a plant cell of interest is generated by gene editing accomplished with engineered nucleases targeting one or more loci that contributes to a target gene of interest. Without wishing to be bound to any particular theory, it is contemplated that engineered nucleases are designed to precisely disrupt one or more target genes of interest through gene editing and, once nuclease activity and specificity are validated, lead to predictable disruption of target gene expression and/or function.

The engineered nucleases described herein generate single-stranded DNA nicks or double-stranded DNA breaks (DSB) in a target sequence. Furthermore, a DSB can be achieved in the target DNA by the use of two nucleases generating single-stranded micks (nickases). Each nickase cleaves one strand of the DNA and the use of two or more nickases can create a double strand break (e.g., a staggered double-stranded break) in a target DNA sequence. In other embodiments, the nucleases are used in combination with a donor repair template, which is introduced into the target sequence at the DNA break-site via homologous recombination at a DSB.

Engineered nucleases described herein that are suitable for gene editing comprise one or more DNA binding domains and one or more DNA cleavage domains (e.g., one or more endonuclease and/or exonuclease domains), and optionally, one or more linkers contemplated herein. An "engineered nuclease" refers to a nuclease comprising one or more DNA binding domains and one or more DNA cleavage domains, wherein the nuclease has been designed and/or modified to bind a DNA binding target sequence adjacent to a DNA cleavage target sequence. The engineered nuclease may be designed and/or modified from a naturally occurring nuclease or from a previously engineered nuclease.

Illustrative examples of nucleases that may be engineered to bind and cleave a target sequence include, but are not limited to homing endonucleases (meganucleases), mega-TALs, transcription activator-like effector nucleases (TALENs), zinc finger nucleases (ZFNs), and clustered regularly-interspaced short palindromic repeats (CRISPR)/Cas nuclease systems.

In some embodiments, the nucleases contemplated herein comprise one or more heterologous DNA-binding and cleavage domains (e.g., ZFNs, TALENs, megaTALs), (Boissel et al., 2014; Christian et al., 2010). In other embodiments, the DNA-binding domain of a naturally-occurring nuclease may be altered to bind to a selected target site (e.g., a meganuclease that has been engineered to bind to site different than the cognate binding site). For example, meganucleases have been designed to bind target sites different from their cognate binding sites (Boissel et al., 2014). In particular embodiments, a nuclease requires a nucleic acid sequence to target the nuclease to a target site (e.g., CRISPR/Cas).

(i) TALEN

Transcription activator-like effector nucleases (TALENs) comprise a nonspecific DNA-cleaving nuclease (e.g., a Fok I cleavage domain) fused to a DNA-binding domain that can be easily engineered so that TALENs can target essentially any sequence (See, e.g., Joung and Sander, Nature Reviews Molecular Cell Biology 14:49-55 (2013)). Methods for generating engineered TALENs are known in the art, see, e.g., the fast ligation-based automatable solid-phase highthroughput (FLASH) system described in U.S. Ser. No. 61/610,212, and Reyon et al., Nature Biotechnology 30,460-465 (2012); as well as the methods described in Bogdanove & Voytas, Science 333, 1843-1846 (2011); Bogdanove et al., Curr Opin Plant Biol 13, 394-401 (2010); Scholze & Boch, J. Curr Opin Microbiol (2011); Boch et al., Science 326, 1509-1512 (2009); Moscou & Bogdanove, Science 326, 1501 (2009); Miller et al., Nat Biotechnol 29, 143-148 (2011); Morbitzer et al., T. Proc Natl Acad Sci USA 107, 21617-21622 (2010); Morbitzer et al., Nucleic Acids Res 39, 5790-5799 (2011); Zhang et al., Nat Biotechnol 29, 149-153 (2011); Geissler et al., PLoS ONE 6, e19509 (2011); Weber et al., PLoS ONE 6, e19722 (2011); Christian et al., Genetics 186, 757-761 (2010); Li et al., Nucleic Acids Res 39, 359-372 (2011); Mahfouz et al., Proc Natl Acad Sci USA 108, 2623-2628 (2011); Mussolino et al., Nucleic Acids Res (2011); Li et al., Nucleic Acids Res 39, 6315-6325 (2011); Cermak et al., Nucleic Acids Res 39, e82 (2011); Wood et al., Science 333, 307 (2011); Hockemeye et al. Nat Biotechnol 29, 731-734 (2011); Tesson et al., Nat Biotechnol 29, 695-696 (2011); Sander et al., Nat Biotechnol 29, 697-698 (2011); Huang et al., Nat Biotechnol 29, 699-700 (2011); and Zhang et al., Nat Biotechnol 29, 149-153 (2011); all of which are incorporated herein by reference in their entirety.

In some embodiments, a TALEN that binds to and cleaves a target region of a locus that contributes to a target gene of interest. A "TALEN" refers to an engineered nuclease comprising an engineered TALE DNA binding domain contemplated elsewhere herein and an endonuclease domain (or endonuclease half-domain thereof), and optionally comprise one or more linkers and/or additional functional domains, e.g., an end-processing enzymatic domain of an end-processing enzyme that exhibits 5-3' exonuclease, 5-3' alkaline exonuclease, 3-5'exonuclease (e.g., Trex2), 5' flap endonuclease, helicase or template-independent DNA polymerases activity.

In some embodiments, plants of interest are modified through Transcription activator-like (TAL) effector nucleases (TALENs). TALENS are polypeptides with repeat polypeptide arms capable of recognizing and binding to specific nucleic acid regions. By engineering the polypeptide arms to recognize selected target sequences, the TAL nucleases can be use to direct double stranded DNA breaks to specific genomic regions. These breaks can then be repaired via recombination to edit, delete, insert, or otherwise modify the DNA of a host organism. In some embodiments, TALENSs are used alone for gene editing (e.g., for the deletion or disruption of a gene). In other embodiments, TALs are used in conjunction with donor sequences and/or other recombination factor proteins that will assist in the Non-homologous end joining (NHEJ) process to replace the targeted DNA region. For more information on the TAL-mediated gene editing compositions and methods of the present disclosure, see U.S. Pat. Nos. 8,440,432; 8,440,432; 8,450,471; 8,586,526; 8,586,363; 8,592,645; 8,697,853; 8,704,041; 8,921,112; and 8,912,138, each of which is hereby incorporated in its entirety for all purposes.

(ii) MegaTALs

Various illustrative embodiments contemplate a megaTAL nuclease that binds to and cleaves a target region of a locus that contributes to a target gene of interest. A "megaTAL" refers to an engineered nuclease comprising an engineered TALE DNA binding domain and an engineered meganuclease, and optionally comprise one or more linkers and/or additional functional domains, e.g., an end-processing enzymatic domain of an end-processing enzyme that exhibits 5-3' exonuclease, 5-3' alkaline exonuclease, 3-5'exonuclease, 5' flap endonuclease, helicase or template-independent DNA polymerases activity.

A "TALE DNA binding domain" is the DNA binding portion of transcription activator-like effectors (TALE or TAL-effectors), which mimics plant transcriptional activators to manipulate the plant transcriptome (see e.g., Kay et al., 2007. Science 318:648-651). TALE DNA binding domains contemplated in particular embodiments are engineered de novo or from naturally occurring TALEs. Illustrative examples of TALE proteins for deriving and designing DNA binding domains are disclosed in U.S. Pat. No. 9,017,967, and references cited therein, all of which are incorporated herein by reference in their entireties.

In some embodiments, plants of interest are modified through megaTALs. In some embodiments, megaTALs are engineered endonucleases capable of targeting selected DNA sequences and inducing DNA breaks.

(iii) Meganucleases/Homing Endonucleases (HE)

Meganucleases are sequence-specific endonucleases originating from a variety of organisms such as bacteria, yeast, algae and plant organelles. A number of Meganucleases are known in the art, see, e.g., WO 2012010976 (Meganuclease variants cleaving DNA target sequences of the TERT gene); U.S. Pat. Nos. 8,021,867; 8,119,361 and 8,119,381 (I-CreI meganucleases); U.S. Pat. No. 7,897,372 (I-CreI Meganuclease Variants with Modified Specificity).

In some embodiments, a homing endonuclease or meganuclease is engineered to bind to, and to introduce single-stranded nicks or double-strand breaks (DSBs) in, one or more loci that contribute to a target gene of interest. "Homing endonuclease" and "meganuclease" are used interchangeably and refer to naturally-occurring nucleases or engineered meganucleases that recognize 12-45 base-pair cleavage sites and are commonly grouped into five families based on sequence and structure motifs: LAGLIDADG (SED ID NO:135), GIY-YIG, HNH, His-Cys box, and PD-(D/E)XK.

Engineered HEs do not exist in nature and can be obtained by recombinant DNA technology or by random mutagenesis. Engineered HEs may be obtained by making one or more amino acid alterations, e.g., mutating, substituting, adding, or deleting one or more amino acids, in a naturally occurring HE or previously engineered HE. In particular embodiments, an engineered HE comprises one or more amino acid alterations to the DNA recognition interface. Engineered HEs contemplated in particular embodiments may further comprise one or more linkers and/or additional functional domains, e.g., an end-processing enzymatic domain of an end-processing enzyme that exhibits 5-3' exonuclease, 5-3' alkaline exonuclease, 3-5'exonuclease, 5' flap endonuclease, helicase or template-independent DNA polymerases activity.

In some embodiments, plants of interest are modified through meganucleases. In some embodiments, meganucleases are engineered endonucleases capable of targeting selected DNA sequences and inducing DNA breaks. In some embodiments, new meganucleases targeting specific regions are developed through recombinant techniques which combine the DNA binding motifs from various other identified nucleases. In other embodiments, new meganucleases are created through semi-rational mutational analysis, which attempts to modify the structure of existing binding domains to obtain specificity for additional sequences. For more information on the use of meganucleases for genome editing, see Silva et al., 2011 Current Gene Therapy 11 pg 11-27; and Stoddard et al., 2014 Mobile DNA 5 pg 7, each of which is hereby incorporated in its entirety for all purposes.

(iv) ZFN

Zinc-finger nucleases (ZFNs) are composed of programmable, sequence-specific zinc finger DNA-binding modules (see above) linked to a nonspecific DNA cleavage domain, e.g., a Fok I cleavage domain. Methods for making and using ZFNs are known in the art, see, e.g., (Maeder et al., 2008, Mol. Cell, 31:294-301; Joung et al., 2010, Nat. Methods, 7:91-92; Isalan et al., 2001, Nat. Biotechnol., 19:656-660; Sander et al., Nat Methods. 8(1):67-9, 2011; Bhakta et al., Genome Res. 23(3):530-8, 2013). In some embodiments, the ZFNs are described in, or are generated as described in, WO 2011/017293 or WO 2004/099366. Additional suitable ZFNs are described in U.S. Pat. Nos. 6,511,808, 6,013,453, 6,007,988, and 6,503,717 and U.S. patent application 2002/0160940.

In some embodiments, a zinc finger nuclease (ZFN) that binds to and cleaves a target region of a locus that contributes to a target gene of interest. A "ZFN" refers to an engineered nuclease comprising one or more zinc finger DNA binding domains and an endonuclease domain (or endonuclease half-domain thereof), and optionally comprise one or more linkers and/or additional functional domains, e.g., an end-processing enzymatic domain of an end-processing enzyme that exhibits 5-3' exonuclease, 5-3' alkaline exonuclease, 3-5'exonuclease, 5' flap endonuclease, helicase or template-independent DNA polymerases activity.

In one embodiment, targeted double-stranded cleavage is achieved using two ZFNs, each comprising an endonuclease half-domain can be used to reconstitute a catalytically active cleavage domain. In another embodiment, targeted double-stranded cleavage is achieved with a single polypeptide comprising one or more zinc finger DNA binding domains and two endonuclease half-domains.

In one embodiment, a ZFN comprises a TALE DNA binding domain contemplated elsewhere herein, a zinc finger DNA binding domain, and an endonuclease domain (or endonuclease half-domain) contemplated elsewhere herein.

In one embodiment, a ZFN comprises a zinc finger DNA binding domain, and a meganuclease contemplated elsewhere herein.

In particular embodiments, the ZFN comprises a zinger finger DNA binding domain that has one, two, three, four, five, six, seven, or eight or more zinger finger motifs and an endonuclease domain (or endonuclease half-domain). Typically, a single zinc finger motif is about 30 amino acids in length. Zinc fingers motifs include both canonical $C_2H_2$ zinc fingers, and non-canonical zinc fingers such as, for example, $C_3H$ zinc fingers and $C_4$ zinc fingers.

Zinc finger binding domains can be engineered to bind any DNA sequence. Candidate zinc finger DNA binding domains for a given 3 bp DNA target sequence have been identified and modular assembly strategies have been devised for linking a plurality of the domains into a multi-finger peptide targeted to the corresponding composite DNA target sequence. Other suitable methods known in the art can also be used to design and construct nucleic acids encoding zinc finger DNA binding domains, e.g., phage display, random mutagenesis, combinatorial libraries, computer/rational design, affinity selection, PCR, cloning from cDNA or genomic libraries, synthetic construction and the like. (See, e.g., U.S. Pat. No. 5,786,538; Wu et al., PNAS 92:344-348 (1995); Jamieson et al., Biochemistry 33:5689-5695 (1994); Rebar & Pabo, Science 263:671-673 (1994); Choo & Klug, PNAS 91:11163-11167 (1994); Choo & Klug, PNAS 91: 11168-11172 (1994); Desjarlais & Berg, PNAS 90:2256-2260 (1993); Desjarlais & Berg, PNAS 89:7345-7349 (1992); Pomerantz et al., Science 267:93-96 (1995); Pomerantz et al., PNAS 92:9752-9756 (1995); Liu et al., PNAS 94:5525-5530 (1997); Griesman & Pabo, Science 275:657-661 (1997); Desjarlais & Berg, PNAS 91:11-99-11103 (1994)).

Individual zinc finger motifs bind to a three or four nucleotide sequence. The length of a sequence to which a zinc finger binding domain is engineered to bind (e.g., a target sequence) will determine the number of zinc finger motifs in an engineered zinc finger binding domain. For example, for ZFNs in which the zinc finger motifs do not bind to overlapping subsites, a six-nucleotide target sequence is bound by a two-finger binding domain; a nine-nucleotide target sequence is bound by a three-finger binding domain, etc. In particular embodiments, DNA binding sites for individual zinc fingers motifs in a target site need not be contiguous, but can be separated by one or several nucleotides, depending on the length and nature of the linker sequences between the zinc finger motifs in a multi-finger binding domain.

In some embodiments, plants of interest are modified through Zinc Finger Nucleases. Three variants of the ZFN technology are recognized in plant genome engineering (with applications ranging from producing single mutations or short deletions/insertions in the case of ZFN-1 and -2 techniques up to targeted introduction of new genes in the case of the ZFN-3 technique):

ZFN-1: Genes encoding ZFNs are delivered to plant cells without a repair template. The ZFNs bind to the plant DNA and generate site specific double-strand breaks (DSBs). The natural DNA-repair process (which occurs through nonhomologous end-joining, NHEJ) leads to site specific mutations, in one or only a few base pairs, or to short deletions or insertions.

ZFN-2: Genes encoding ZFNs are delivered to plant cells along with a repair template homologous to the targeted area, spanning a few kilo base pairs. The ZFNs bind to the plant DNA and generate site-specific DSBs. Natural gene repair mechanisms generate site-specific point mutations e.g. changes to one or a few base pairs through homologous recombination and the copying of the repair template.

ZFN-3: Genes encoding ZFNs are delivered to plant cells along with a stretch of DNA which can be several kilo base pairs long and the ends of which are homologous to the DNA sequences flanking the cleavage site. As a result, the DNA stretch is inserted into the plant genome in a site specific manner.

(v) FokI

FokI is a type IIs restriction endonuclease that includes a DNA recognition domain and a catalytic (endonuclease) domain. The fusion proteins described herein can include all of FokI or just the catalytic endonuclease domain, e.g., amino acids 388-583 or 408-583 of GenBank Acc. No. AAA24927.1, e.g., as described in WO95/09233, Li et al., Nucleic Acids Res. 39(1): 359-372 (2011); Cathomen and Joung, Mol. Ther. 16: 1200-1207 (2008), or a mutated form of FokI as described in Miller et al. Nat Biotechnol 25: 778-785 (2007); Szczepek et al., Nat Biotechnol 25: 786-793 (2007); or Bitinaite et al., Proc. Natl. Acad. Sci. USA. 95:10570-10575 (1998). See also Tsai et al., Nat Biotechnol. 2014 June; 32(6):569-76

In some embodiments, plants of interest are modified through FokI endonucleases.

Herein, the term "targeted gene-editing system" refers to a protein, nucleic acid, or combination thereof that is capable of substituting, inserting, or deleting one or more nucleotides at a target site and modifying an endogenous target DNA sequence when introduced into a cell, thereby causing one or more amino acid substitutions, insertions, or deletions. In some embodiments, the editing system taught in the present disclosure refers to the targeted gene editing system.

More specifically, the term "targeted base-editing system" refers to a protein, nucleic acid, or combination thereof that is capable of substituting one or more nucleotides at a target site and modifying an endogenous target DNA sequence when introduced into a cell, thereby causing one or more amino acid substitutions.

Numerous gene editing systems suitable for use in the methods of the present disclosure, include, but are not limited to, zinc-finger nuclease systems, TALEN systems, and CRISPR/Cas systems.

In some embodiments, a nuclease-inactivated CRISPR/Cas system having a base deaminase activity is utilized for a targeted base-editing. In other aspects, a nickase is used.

In some embodiments, the targeted base-editing system can mediate a change in the sequence of the endogenous target gene, for example, by introducing one or more point mutations into the endogenous target sequence, such as by substituting C with T (or G with A) or A with G (or T with C) in the endogenous target sequence.

In some embodiments, the targeted gene-editing system may mediate a change in the expression of the protein encoded by the endogenous target gene. In such embodiments, the targeted gene-editing system may regulate the expression of the encoded protein by modifications of the endogenous target DNA sequence, or by acting on the mRNA product encoded by the DNA sequence. In some embodiments, the targeted gene-editing system may result in the expression of a modified endogenous protein. In some embodiments, the modifications to the endogenous DNA sequence mediated by the targeted gene-editing system result in an altered function of the modified endogenous protein as compared to the corresponding endogenous protein in an unmodified plant cell. In such embodiments, the expression level of the modified endogenous protein may be increased, decreased or may be the same, or substantially similar to, the expression level of the corresponding endogenous protein in an unmodified plant cell.

The present disclosure provides a targeted gene-editing system to edit a target nucleotide sequence in the genome of a plant, comprising at least one of the followings; i) a gene editing fusion protein, and a guide RNA; ii) an expression construct comprising a nucleotide sequence encoding a gene editing fusion protein, and a guide RNA; iii) a gene editing fusion protein, and an expression construction comprising a nucleotide sequence encoding a guide RNA; iv) an expression construct comprising a nucleotide sequence encoding a gene editing fusion protein, and an expression construct comprising a nucleotide sequence encoding a guide RNA; v) an expression construct comprising a nucleotide sequence encoding gene editing fusion protein and a nucleotide sequence encoding guide RNA; wherein said gene editing fusion protein contains a CRISPR-associated effector domain and optionally a deaminase domain, said guide RNA can target said gene editing fusion protein to the target sequence in the plant genome.

In some embodiments, the present disclosure provides a polynucleotide encoding a gRNA. In some embodiments, a gRNA-encoding nucleic acid is comprised in an expression vector, e.g., a recombinant expression vector. In some embodiments, the present disclosure provides a polynucleotide encoding a site-directed modifying polypeptide. In some embodiments, the polynucleotide encoding a site-directed modifying polypeptide is comprised in an expression vector, e.g., a recombinant expression vector.

In some embodiments, the targeted gene-editing system comprises a Cas protein as a CRISPR-associated effector domain. Cas molecules of a variety of species can be used in the methods and compositions described herein, including Cas molecules derived from *S. pyogenes, S. aureus, N. meningitidis, S. thermophiles, Acidovorax avenae, Actinobacillus pleuropneumoniae, Actinobacillus succinogenes, Actinobacillus suis, Actinomyces* sp., *Cycliphilus denitrificans, Aminomonas paucivorans, Bacillus cereus, Bacillus smithii, Bacillus thuringiensis, Bacteroides* sp., *Blastopirellula marina, Bradyrhizobium* sp., *Brevibacillus laterospoxus, Campylobacter coli, Campylobacter jejuni, Campylobacter lari, Candidatus puniceispirillum, Clostridium cellulolyticum, Clostridium perfringens, Corynebacterium accolens, Corynebacterium diphtheria, Corynebacterium matruchotii, Dinoroseobacter shibae, Eubacterium dolichum,* Gammaproteobacterium, *Gluconacetobacter diazotrophicus, Haemophilus parainfluenzae, Haemophilus sputomm, Helicobacter canadensis, Helicobacter cinaedi, Helicobacter mustelae, Ilyobacter polytropus, Kingella kingae, Lactobacillus crispatus, Listeria ivanovii, Listeria monocytogenes, Listeriaceae bacterium, Methylocystis* sp., *Methylosinus trichosporium, Mobiluncus mulieris, Neisseria bacilliformis, Neisseria cinerea, Neisseria flavescens, Neisseria lactamica, Neisseria meningitidis, Neisseria* sp., *Neisseria wadsworthii, Nitrosomonas* sp., *Parvibaculum lavamentivorans, Pasteurella multocida, Phascolarctobacterium succinatutens, Ralstonia syzygii, Rhodopseudomonas palustris, Rhodovulum* sp., *Simonsiella muelleri, Sphingomonas* sp., *Sporolactobacillus vineae, Staphylococcus aureus, Staphylococcus lugdunensis, Streptococcus* sp., *Subdoligranulum* sp., *Tistrella mobilis, Treponema* sp., or *Verminephrobacter eiseniae*.

In some embodiments, the Cas protein is a naturally-occurring Cas protein. In other embodiments, the Cas protein is an engineered Cas protein. In some embodiments, the Cas endonuclease is selected from the group consisting of C2C1, C2C3, Cpf1 (also referred to as Cas12a), Cas12b, Cas12c, Cas12d, Cas12e, Cas13a, Cas13b, Cas13c, Cas13d, Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, and Csf4.

In some embodiments, the Cas protein is an endoribonuclease such as a Cas13 protein. In some embodiments, the Cas13 protein is a Cas13a (Abudayyeh et al., Nature 550 (2017), 280-284), Cas13b (Cox et al., Science (2017) 358: 6336, 1019-1027), Cas13c (Cox et al., Science (2017) 358:6336, 1019-1027), or Cas13d (Zhang et al., Cell 175 (2018), 212-223) protein.

In some embodiments, the Cas protein is a wild type or naturally occurring Cas9 protein or a Cas9 ortholog. Wild type Cas9 is a multi-domain enzyme that uses an HNH nuclease domain to cleave the target strand of DNA and a RuvC-like domain to cleave the non-target strand. Binding of WT Cas9 to DNA based on gRNA specificity results in double-stranded DNA breaks that can be repaired by non-homologous end joining (NHEJ) or homology-directed repair (HDR).

In some embodiments, the naturally occurring Cas9 polypeptide is selected from the group consisting of SpCas9, SpCas9-HF1, SpCas9-HF2, SpCas9-HF3, SpCas9-HF4, SaCas9, FnCpf, FnCas9, eSpCas9, and NmeCas9. In some embodiments, the Cas9 protein comprises an amino acid sequence having at least 60%, 65%, 70%, 75%, 80%, 85%, 90%, 95%, 96%, 97%, 98%, 99%, or 100% sequence identity to a Cas9 amino acid sequence described in Chylinski et al., RNA Biology 2013 10:5, 727-737; Hou et al., PNAS Early Edition 2013, 1-6).

In some embodiments, the Cas polypeptide comprises one or more of the following activities: (a) a nickase activity, i.e., the ability to cleave a single strand, e.g., the non-complementary strand or the complementary strand, of a nucleic acid molecule; (b) a double stranded nuclease activity, i.e., the ability to cleave both strands of a double stranded nucleic acid and create a double stranded break, which in an embodiment is the presence of two nickase activities; (c) an endonuclease activity; (d) an exonuclease activity; and/or (e) a helicase activity, i.e., the ability to unwind the helical structure of a double stranded nucleic acid. In other embodiments, the Cas protein may be dead or inactive (e.g. dCas).

In some embodiments, the Cas polypeptide is fused to heterologous polypeptide/proteins that has base deaminase activity.

In some embodiments, different Cas proteins (i.e., Cas9 proteins from various species) may be advantageous to use in the various provided methods in order to capitalize on various enzymatic characteristics of the different Cas proteins (e.g., for different PAM sequence preferences; for increased or decreased enzymatic activity; for an increased or decreased level of cellular toxicity; to change the balance between NHEJ, homology-directed repair, single strand breaks, double strand breaks, etc.).

In some embodiments, the Cas protein is a Cas9 protein derived from S. pyogenes and recognizes the PAM sequence motif NGG, NAG, NGA (Mali et al, Science 2013; 339 (6121): 823-826). In some embodiments, the Cas protein is a Cas9 protein derived from S. thermophiles and recognizes the PAM sequence motif NGGNG and/or NNAGAAW (W=A or T) (See, e.g., Horvath et al, Science, 2010; 327 (5962): 167-170, and Deveau et al, J Bacteriol 2008; 190(4): 1390-1400). In some embodiments, the Cas protein is a Cas9 protein derived from S. mutans and recognizes the PAM sequence motif NGG and/or NAAR (R=A or G) (See, e.g., Deveau et al, J BACTERIOL 2008; 190(4): 1390-1400). In some embodiments, the Cas protein is a Cas9 protein derived from S. aureus and recognizes the PAM sequence motif NNGRR (R=A or G). In some embodiments, the Cas protein is a Cas9 protein derived from S. aureus and recognizes the PAM sequence motif N GRRT (R=A or G). In some embodiments, the Cas protein is a Cas9 protein derived from S. aureus and recognizes the PAM sequence motif N GRRV (R=A or G). In some embodiments, the Cas protein is a Cas9 protein derived from N. meningitidis and recognizes the PAM sequence motif N GATT or N GCTT (R=A or G, V=A, G or C) (See, e.g., Hou et ah, PNAS 2013, 1-6). In the aforementioned embodiments, N can be any nucleotide residue, e.g., any of A, G, C or T. In some embodiments, the Cas protein is a Cas13a protein derived from Leptotrichia shahii and recognizes the PFS sequence motif of a single 3' A, U, or C.

In embodiments, a Cas protein as a CRISPR-associated effector domain is codon-optimized based on plant genomes of the present disclosure.

In some embodiments, the at least one CRISPR-associated effector is selected from at least one of a nuclease, comprising a CRISPR nuclease, including Cas or Cpf1 nucleases.

In some embodiments, the at least one CRISPR-associated effector is a Cas polypeptide. In some embodiments, the at least one CRISPR-associated effector is a Cas polypeptide, wherein the Cas polypeptide comprises a site-specific DNA binding domain linked to at least one base editor. The CRISPR-associated effector or the nucleic acid sequence encoding the same, is selected from the group comprising (i) Cas9, including SpCas9, SaCas9, SaKKH-Cas9, VQR-Cas9, StlCas9, (ii) Cpf1, including AsCpf1, LbCpf1, FnCpf1, (iii) CasX, or (iv) CasY, or any variant or derivative of the aforementioned CRISPR-associated effector, preferably wherein the at least one CRISPR-associated effector comprises a mutation in comparison to the respective wild type sequence so that the resulting CRISPR-associated effector is converted to a single-strand specific DNA nickase, or to a DNA binding effector lacking all DNA cleavage ability, as described below.

Therefore, according to the present disclosure, artificially modified CRISPR nucleases are envisaged, which might indeed not be any "nucleases" in the sense of double-strand cleaving enzymes, but which are nickases or nuclease-dead variants, which still have inherent DNA recognition and thus binding ability.

In some embodiments, the Cas protein described above can be engineered to alter one or more properties of the Cas polypeptide. For example, in some embodiments, the Cas polypeptide comprises altered enzymatic properties, e.g., altered nuclease activity, (as compared with a naturally occurring or other reference Cas molecule) or altered helicase activity. In some embodiments, an engineered Cas polypeptide can have an alteration that alters its size, e.g., a deletion of amino acid sequence that reduces its size without significant effect on another property of the Cas polypeptide. In some embodiments, an engineered Cas polypeptide comprises an alteration that affects PAM recognition. For example, an engineered Cas polypeptide can be altered to recognize a PAM sequence other than the PAM sequence recognized by the corresponding wild type Cas protein. In some embodiments, the targeted gene-editing system comprises a Cas protein as a CRISPR-associated effector domain.

Cas polypeptides with desired properties can be made in a number of ways, including alteration of a naturally occurring Cas polypeptide or parental Cas polypeptide, to provide a mutant or altered Cas polypeptide having a desired property. For example, one or more mutations can be introduced into the sequence of a parental Cas polypeptide (e.g., a naturally occurring or engineered Cas polypeptide). Such mutations and differences may comprise substitutions (e.g., conservative substitutions or substitutions of non-essential amino acids); insertions; or deletions. In some embodiments, a mutant Cas polypeptide comprises one or more mutations (e.g., at least 1, 2, 3, 4, 5, 10, 15, 20, 30, 40 or 50 mutations) relative to a parental Cas polypeptide.

In an embodiment, a mutant Cas polypeptide comprises a cleavage property that differs from a naturally occurring Cas polypeptide. In some embodiments, the Cas is a deactivated Cas (dCas) mutant, which is catalytically dead. In such embodiments, the Cas polypeptide does not comprise any intrinsic enzymatic activity and is unable to mediate target nucleic acid cleavage. In such embodiments, the dCas is fused with a heterologous protein that is capable of modifying the target nucleic acid in a non-cleavage based manner. In some embodiments, the targeted gene-editing system comprises a Cas protein as a CRISPR-associated effector domain.

In some embodiments, the dCas is a dCas9 mutant. In some embodiments, a dCas protein is fused to base deaminase domains (e.g., cytidine deaminase, or adenosine deaminase). In some such cases, the dCas fusion protein is targeted by the gRNA to a specific location (i.e., sequence) in the target nucleic acid and exerts locus-specific modification such as replacing C with T (or G with A) if the fusion protein has cytidine deaminase activity) or replacing A with G (or T with C) if the fusion protein has adenosine deaminase activity.

In some embodiments, the dCas is a dCas13 mutant (Konermann et al., Cell 173 (2018), 665-676). These dCas13 mutants can then be fused to enzymes that modify RNA, including adenosine deaminases (e.g., ADAR1 and ADAR2). Adenosine deaminases convert adenine to inosine, which the translational machinery treats like guanine, thereby creating a functional A to G change in the target sequence.

In some embodiments, the CRISPR-associated effector protein is Cas9 endonuclease. In some embodiments, the CRISPR-associated effector protein is a CRISPR-Cas variant, which is dCas9 mutant or nCas9 nickase mutant. The Cas9 endonuclease has a DNA cleavage domain containing two subdomains: i) the RuvC subdomain cleaving the non-complementary single-stranded chain and ii) the HNH nuclease subdomain cleaving the chain that is complementary to gRNA. Mutations in these subdomains can inactivate Cas9 endonuclease to form deactivated Cas9 (dCas9), which is interchangeably used with "catalytically dead Cas9". The nuclease-inactivated Cas9 retains DNA binding capacity directed by gRNA. Thus, in principle, when fused with an additional protein, the dCas9 can simply target said additional protein to almost any DNA sequence through co-expression with appropriate guide RNA. For example, catalytically dead Cas9 (dCas9), which contains Asp10Ala (D10A) and His840Ala (H840A) mutations that inactivate its nuclease activity, retains its ability to bind DNA in a guide RNA-programmed manner, but does not cleave the DNA backbone (Komor et al., nature (2016), Vol 533:420-424). In some embodiments, conjugation of dCas9 with an enzymatic or chemical catalyst that mediates the direct conversion of one base to another could enable RNA-programmed DNA base editing.

In some embodiments, the mutant Cas9 is a Cas9 nickase (nCas9) mutant. Cas9 nickase mutants comprise only one catalytically active domain (either the RuvC domain (D10A) or the HNH domain (H840A)). The Cas9 nickase mutants retain DNA binding based on gRNA specificity, but are capable of cutting only one strand of DNA resulting in a single-strand break (e.g. a "nick"). In some embodiments, two complementary Cas9 nickase mutants (e.g., one Cas9 nickase mutant with an inactivated RuvC domain, and one Cas9 nickase mutant with an inactivated HNH domain) are expressed in the same cell with two gRNAs corresponding to two respective target sequences; one target sequence on the sense DNA strand, and one on the antisense DNA strand. This dual-nickase system results in staggered double stranded breaks and can increase target specificity, as it is unlikely that two off-target nicks will be generated close enough to generate a double stranded break. In some embodiments, a Cas9 nickase mutant is co-expressed with a nucleic acid repair template to facilitate the incorporation of an exogenous nucleic acid sequence by homology-directed repair.

The dCas9 of the present disclosure can be derived from Cas9 of different species, for example, derived from *S. pyogenes* Cas9 (SpCas9). Mutations in both the RuvC subdomain and the HNH nuclease subdomain of the SpCas9 (includes, for example, D10A and H840A mutations) inactivate *S. pyogenes* Cas9 nuclease, resulting in a nuclease-dead/catalytically dead Cas9 (dCas9). In some embodiments of the present disclosure, the nuclease-inactivated Cas9 comprises the dCas9. In some preferred embodiments, the nuclease-inactivated Cas9 comprises.

Inactivation of one of the subdomains by mutation allows Cas9 to gain nickase activity, i.e., resulting in a Cas9 nickase (nCas9), for example, nCas9 with a D10A mutation only.

In some embodiments, the nuclease-inactivated Cas9 comprises amino acid substitutions D10A and/or H840A relative to wild type Cas9. In some embodiments, the nuclease-inactivated Cas9 of the present disclosure loses nuclease activity completely, which is catalytically dead. In such embodiments, the nuclease-inactivated Cas9 is the dCas9 with D10A and H840A. Therefore, the term "nuclease-inactivated Cas9" refers to dCas9 and/or nCas9.

In other embodiments, the nuclease-inactivated Cas9 of the present disclosure has nickase activity. In some embodiments, the nuclease-inactivated Cas9 is a Cas9 nickase that retains the cleavage activity of the HNH subdomain of Cas9, whereas the cleavage activity of the RuvC subdomain is inactivated. For example, the nuclease-inactivated Cas9 contains an amino acid substitution D10A relative to wild type Cas9. In such embodiments, the nuclease-inactivated Cas9 is the nCas9 with D10A only. In some embodiments of the present disclosure, the nuclease-inactivated Cas9 comprises the nCas9.

In some embodiments, the Cas polypeptides described herein can be engineered to alter the PAM/PFS specificity of the Cas polypeptide. In some embodiments, a mutant Cas polypeptide has a PAM/PFS specificity that is different from the PAM/PFS specificity of the parental Cas polypeptide. For example, a naturally occurring Cas protein can be modified to alter the PAM/PFS sequence that the mutant Cas polypeptide recognizes to decrease off target sites, improve specificity, or eliminate a PAM/PFS recognition requirement. In some embodiments, a Cas protein can be modified to increase the length of the PAM/PFS recognition sequence. In some embodiments, the length of the PAM recognition sequence is at least 4, 5, 6, 7, 8, 9, 10 or 15 amino acids in length. Cas polypeptides that recognize different PAM/PFS sequences and/or have reduced off-target activity can be generated using directed evolution. Exemplary methods and systems that can be used for directed evolution of Cas polypeptides are described, e.g., in Esvelt et al. Nature 2011, 472(7344): 499-503.

Exemplary Cas mutants are described in International PCT Publication No. WO 2015/161276 and Konermann et al., Cell 173 (2018), 665-676, which are incorporated herein by reference in their entireties.

In some embodiments, the deaminase domain is fused to the N-terminus of the nuclease-inactivated Cas9 domain. In some embodiments, the deaminase domain is fused to the C-terminus of the nuclease-inactivated Cas9 domain. In some embodiments, the deaminase domain and the nuclease inactivated Cas9 domain are fused through a linker. The linker can be a non-functional amino acid sequence having no secondary or higher structure, N-terminus and one or more NLSs at the C-terminus. Where there are more than one NLS, each NLS may be selected as independent from other NLSs. In some embodiments, the targeted base-editing fusion protein comprises two NLSs, for example, the two NLSs are located at the N-terminus and the C-terminus, respectively.

In some embodiment, a targeted base modification is a conversion of any nucleotide C, A, T, or G, to any other nucleotide. Any one of a C, A, T or G nucleotide can be exchanged in a site-directed way as mediated by a base editor, or a catalytically active fragment thereof, to another nucleotide. A base editing complex can comprise any base editor, or a base editor domain or catalytically active fragment thereof, which can convert a nucleotide of interest into any other nucleotide of interest in a targeted way.

A base editing domain according to the present disclosure can comprise at least one cytidine deaminase, or a catalytically active fragment thereof. The at least one base editing complex can comprise the cytidine deaminase, or a domain thereof in the form of a catalytically active fragment, as base editor.

According to the present disclosure, cytidine deaminases that can be used in connection with the present disclosure include, but are not limited to, members of the enzyme family known as apolipoprotein B mRNA-editing complex (APOBEC) family deaminase, an activation-induced deaminase (AID), or a cytidine deaminase 1 (CDA1). In particular embodiments, the deaminase in an APOBEC1 deaminase, an APOBEC2 deaminase, an APOBEC3A deaminase, an APOBEC3B deaminase, an APOBEC3C deaminase, and APOBEC3D deaminase, an APOBEC3E deaminase, an APOBEC3F deaminase an APOBEC3G deaminase, an APOBEC3H deaminase, or an APOBEC4 deaminase.

In the methods and systems of the present disclosure, the cytidine deaminase is capable of targeting Cytosine in a DNA single strand. In certain example embodiments the cytodine deaminase may edit on a single strand present outside of the binding component e.g. bound Cas9 and/or Cas13. In other example embodiments, the cytodine deaminase may edit at a localized bubble, such as a localized bubble formed by a mismatch at the target edit site but the guide sequence.

In some embodiments, the cytidine deaminase protein recognizes and converts one or more target cytosine residue(s) in a single-stranded bubble of a DNA-RNA heteroduplex into uracil residues (s). In some embodiments, the cytidine deaminase protein recognizes a binding window on the single-stranded bubble of a DNA-RNA heteroduplex. In some embodiments, the binding window contains at least one target cytosine residue(s). In some embodiments, the binding window is in the range of about 3 bp to about 100 bp. In some embodiments, the binding window is in the range of about 5 bp to about 50 bp. In some embodiments, the binding window is in the range of about 10 bp to about 30 bp. In some embodiments, the binding window is about 1 bp, 2 bp, 3 bp, 5 bp, 7 bp, 10 bp, 15 bp, 20 bp, 25 bp, 30 bp, 40 bp, 45 bp, 50 bp, 55 bp, 60 bp, 65 bp, 70 bp, 75 bp, 80 bp, 85 bp, 90 bp, 95 bp, or 100 bp.

In some embodiments, the cytidine deaminase protein comprises one or more deaminase domains. Not intended to be bound by theory, it is contemplated that the deaminase domain functions to recognize and convert one or more target cytosine (C) residue(s) contained in a single-stranded bubble of a DNA-RNA heteroduplex into (an) uracil (U) residue (s). In some embodiments, the deaminase domain comprises an active center. In some embodiments, the active center comprises a zinc ion. In some embodiments, amino acid residues in or near the active center interact with one or more nucleotide(s) 5' to a target cytosine residue. In some embodiments, amino acid residues in or near the active center interact with one or more nucleotide(s) 3' to a target cytosine residue.

In some embodiments, the cytidine deaminase comprises human APOBEC1 full protein (hAPOBEC1) or the deaminase domain thereof (hAPOBEC1-D) or a C-terminally truncated version thereof (hAPOBEC-T). In some embodiments, the cytidine deaminase is an APOBEC family member that is homologous to hAPOBEC1, hAPOBEC-D or hAPOBEC-T. In some embodiments, the cytidine deaminase comprises human AID1 full protein (hAID) or the deaminase domain thereof (hAID-D) or a C-terminally truncated version thereof (hAID-T). In some embodiments, the cytidine deaminase is an AID family member that is homologous to hAID, hAID-D or hAID-T. In some embodiments, the hAIDT is a hAID which is C-terminally truncated by about 20 amino acids.

In some embodiments, the cytidine deaminase comprises the wild type amino acid sequence of a cytosine deaminase. In some embodiments, the cytidine deaminase comprises one or more mutations in the cytosine deaminase sequence, such that the editing efficiency, and/or substrate editing preference of the cytosine deaminase is changed according to specific needs.

Certain mutations of APOBEC 1 and APOBEC3 proteins have been described in Kim et al., Nature Biotechnology (2017) 35(4):371-377 and Harris et al. Mol. Cell (2002) 10:1247-1253, each of which is incorporated herein by reference in its entirety.

Additional embodiments of the cytidine deaminase are disclosed in WO2017/070632 and WO2018/213726, each of which is incorporated herein by reference in its entirety.

In some embodiments, at least one CRISPR-associated effector is temporarily or permanently linked to at least one base editor to form a targeted base editing complex, which is a base editing fusion protein, wherein the base editing complex mediates the at least one targeted base modification. The at least one CRISPR-associated effector can be non-covalently (temporarily) or covalently (permanently) be attached to at least one base editor. Any component of the at least one base editor can be temporarily or permanently linked to the at least one CRISPR-associated effector.

The adenosine deaminases (e.g. engineered adenosine deaminases, evolved adenosine deaminases) provided herein may be from any organism, such as a bacterium. In some embodiments, the deaminase or deaminase domain is a variant of a naturally-occurring deaminase from an organism. In some embodiments, the deaminase or deaminase domain does not occur in nature. For example, in some embodiments, the deaminase or deaminase domain is at least 50%, at least 55%, at least 60%, at least 65%, at least 70%, at least 75% at least 80%, at least 85%, at least 90%, at least 95%, at least 96%, at least 97%, at least 98%, at least 99%, or at least 99.5% identical to a naturally-occurring deaminase. In some embodiments, the adenosine deaminase is from a bacterium, such as, *E. coli, S. aureus, S. typhi, S. putrefaciens, H. influenzae,* or *C. crescentus.* In some embodiments, the adenosine deaminase is a TadA deaminase. In some embodiments, the TadA deaminase is an *E. coli* TadA deaminase (ecTadA). In some embodiments, the TadA deaminase is a truncated *E. coli* TadA deaminase. For example, the truncated ecTadA may be missing one or more N-terminal amino acids relative to a full-length ecTadA. In some embodiments, the truncated ecTadA may be missing 1, 2, 3, 4, 5, 6, 7, 8, 9, 10, 11, 12, 13, 14, 15, 6, 17, 18, 19, or 20 N-terminal amino acid residues relative to the full length ecTadA. In some embodiments, the truncated ecTadA may be missing 1, 2, 3, 4, 5, 6, 7, 8, 9, 10, 11, 12, 13, 14, 15, 6, 17, 18, 19, or 20 C-terminal amino acid residues relative to the full length ecTadA. In some embodiments, the ecTadA deaminase does not comprise an N-terminal methionine.

Some aspects of the disclosure provide adenosine deaminases. In some embodiments, the adenosine deaminases provided herein are capable of deaminating adenine. In some embodiments, the adenosine deaminases provided herein are capable of deaminating adenine in a deoxyadenosine residue of DNA. The adenosine deaminase may be derived from any suitable organism (e.g., E. coli). In some embodiments, the adenine deaminase is a naturally-occurring adenosine deaminase that includes one or more mutations corresponding to any of the mutations provided herein (e.g., mutations in ecTadA). One of skill in the art will be able to identify the corresponding residue in any homologous protein and in the respective encoding nucleic acid by methods well known in the art, e.g., by sequence alignment and determination of homologous residues. Accordingly, one of skill in the art would be able to generate mutations in any naturally-occurring adenosine deaminase (e.g., having homology to ecTadA) that corresponds to any of the mutations described herein, e.g., any of the mutations identified in ecTadA. In some embodiments, the adenosine deaminase is from a prokaryote. In some embodiments, the adenosine deaminase is from a bacterium. In some embodiments, the adenosine deaminase is from *Escherichia coli, Staphylococcus aureus, Salmonella typhi, Shewanella putrefaciens, Haemophilus influenzae, Caulobacter crescentus*, or *Bacillus subtilis*. In some embodiments, the adenosine deaminase is from *E. coli*.

In other embodiments, adenosine deaminases that can be used that include, but are not limited to, members of the enzyme family known as adenosine deaminases that act on RNA (ADARs), members of the enzyme family known as adenosine deaminases that act on tRNA (ADATs), and other adenosine deaminase domain-containing (ADAD) family members.

According to the present disclosure, the adenosine deaminase is capable of targeting adenine in a RNA/DNA heteroduplex. Indeed, Zheng et al. (Nucleic Acids Res. 2017, 45(6): 3369-3377) has demonstrated that ADARs can carry out adenosine to inosine editing reactions on RNA/DNA heteroduplexes. In particular embodiments, the adenosine deaminase has been modified to increase its ability to edit DNA in a RNA/DNA heteroduplex as detailed herein below.

In some embodiments, the adenosine deaminase is derived from one or more metazoa species, including but not limited to, mammals, birds, frogs, squids, fish, flies and worms. In some embodiments, the adenosine deaminase is a human, squid or *Drosophila* adenosine deaminase.

In some embodiments, the adenosine deaminase is a human ADAR, including hADAR1, hADAR2, hADAR3. In some embodiments, the adenosine deaminase is a *Caenorhabditis elegans* ADAR protein, including ADR-1 and ADR-2. In some embodiments, the adenosine deaminase is a *Drosophila* ADAR protein, including dAdar. In some embodiments, the adenosine deaminase is a squid *Loligo pealeii* ADAR protein, including sqADAR2a and sqADAR2b. In some embodiments, the adenosine deaminase is a human ADAT protein. In some embodiments, the adenosine deaminase is a *Drosophila* ADAT protein. In some embodiments, the adenosine deaminase is a human ADAD protein, including TE R (hADAD1) and TE RL (hADAD2).

In some embodiments, the adenosine deaminase is a TadA protein such as *E. coli* TadA. See Kim et al., Biochemistry 45:6407-6416 (2006); Wolf et al., EMBO J. 21:3841-3851 (2002), each of which is incorporated herein by reference in its entirety. In some embodiments, the adenosine deaminase is mouse ADA (See Grunebaum et al., Curr. Opin. Allergy Clin. Immunol. 13:630-638 (2013)) or human ADAT2 (See Fukui et al., J. Nucleic Acids 2010:260512 (2010)), each of which is incorporated herein by reference in its entirety.

Additional embodiments of the adenosine deaminase are disclosed in U.S. Patent No. 10,113,163 and WO2018/213708, each of which is incorporated herein by reference in its entirety.

In some embodiments, at least one CRISPR-associated effector is temporarily or permanently linked to at least one base editor to form a targeted base editing complex, which is a base editing fusion protein, wherein the base editing complex mediates the at least one targeted base modification. The at least one CRISPR-associated effector can be non-covalently (temporarily) or covalently (permanently) be attached to at least one base editor. Any component of the at least one base editor can be temporarily or permanently linked to the at least one CRISPR-associated effector.

In one aspect the present disclosure provides methods for targeted deamination of adenine in a DNA, more particularly in a locus of interest. The disclosure teaches the adenosine deaminase (AD) protein is recruited specifically to the relevant Adenine in the locus of interest by a CRISPR-Cas complex which can specifically bind to a target sequence. In order to achieve this, the adenosine deaminase protein can either be covalently linked to the CRISPR-Cas enzyme or be provided as a separate protein, but adapted so as to ensure recruitment thereof to the CRISPR-Cas complex.

In particular embodiments, recruitment of the adenosine deaminase to the target locus is ensured by fusing the adenosine deaminase or catalytic domain thereof to the CRISPR-Cas protein, which is a Cas or Cpf1 protein. Methods of generating a fusion protein from two separate proteins are known in the art and typically involve the use of spacers or linkers. The CRISPR-Cas protein can be fused to the adenosine deaminase protein or catalytic domain thereof on either the N- or C-terminal end thereof. In particular embodiments, the CRISPR-Cas protein is a Cas or Cpf1 protein and is linked to the N-terminus of the deaminase protein or its catalytic domain.

In the present disclosure, linker refers to a molecule which joins two entities such as two domains to form a fusion protein. Generally, such molecules have no specific biological activity other than to join or to preserve some minimum distance or other spatial relationship between the proteins. However, in certain embodiments, the linker may be selected to influence some property of the linker and/or the fusion protein such as the folding, net charge, or hydrophobicity of the linker.

Suitable linkers for use in the methods of the present disclosure are well known to those of skill in the art and include, but are not limited to, straight or branched-chain carbon linkers, heterocyclic carbon linkers, or peptide linkers. However, as used herein the linker may also be a covalent bond (carbon-carbon bond or carbon-heteroatom bond). In particular embodiments, the linker is used to separate the CRISPR-Cas protein and the cytidine deaminase by a distance sufficient to ensure that each protein retains its required functional property. Preferred peptide linker sequences adopt a flexible extended conformation and do not exhibit a propensity for developing an ordered secondary structure.

In some embodiments, the linker can be a chemical moiety which can be monomeric, dimeric, multimeric or polymeric. Exemplary linkers are disclosed in Maratea et al. (1985), Gene 40: 39-46; Murphy et al. (1986) Proc. Nat'l. Acad. Sci. USA 83: 8258-62; U.S. Pat. Nos. 4,935,233; and 4,751,180. For example, GlySer linkers GGS, GGGS or GSG can be used. GGS, GSG, GGGS or GGGGS linkers can be used in repeats of 3 such as $(GGS)_3$. In other embodiments, 1, 2, 3, 4, 5, 6, 7, 8, 9, 10, 11, 12 or more of (GGGGS), to provide suitable lengths. In some embodiments, linkers such as $(GGGGS)_1$, $(GGGGS)_2$, $(GGGGS)_3$, $(GGGGS)_4$, $(GGGGS)_5$, $(GGGGS)_6$, $(GGGGS)_7$, $(GGGGS)_8$, $(GGGGS)_9$, $(GGGGS)_{10}$, $(GGGGS)_{11}$, or $(GGGGS)_{12}$ may be used. In other embodiments, the linker is XTEN linker. In particular embodiments, the nuclease-inactivated CRISPR-associated effector protein such as dCas9 or nCas9 is linked to the deaminase protein or its catalytic domain by means of an XTEN linker. In some embodiments, the nuclease-inactivated Cas mutant is linked C-terminally to the N-terminus of a deaminase protein or its catalytic domain by means of an XTEN linker. In addition, N- and C-terminal NLSs can also function as linker.

The present disclosure provides guide RNAs (gRNAs) that direct a site-directed modifying polypeptide to a specific target nucleic acid sequence. A gRNA comprises a nucleic acid-targeting segment and protein-binding segment. The nucleic acid-targeting segment of a gRNA comprises a nucleotide sequence that is complementary to a sequence in the target nucleic acid sequence. As such, the nucleic acid-targeting segment of a gRNA interacts with a target nucleic acid in a sequence-specific manner via hybridization (i.e., base pairing), and the nucleotide sequence of the nucleic acid-targeting segment determines the location within the target nucleic acid that the gRNA will bind. The nucleic acid-targeting segment of a gRNA can be modified (e.g., by genetic engineering) to hybridize to any desired sequence within a target nucleic acid sequence.

The protein-binding segment of a guide RNA interacts with a site-directed modifying polypeptide (e.g. a Cas protein) to form a complex. The guide RNA guides the bound polypeptide to a specific nucleotide sequence within target nucleic acid via the above-described nucleic acid-targeting segment. The protein-binding segment of a guide RNA comprises two stretches of nucleotides that are complementary to one another and which form a double stranded RNA duplex.

In some embodiments, a gRNA comprises two separate RNA molecules. In such embodiments, each of the two RNA molecules comprises a stretch of nucleotides that are complementary to one another such that the complementary nucleotides of the two RNA molecules hybridize to form the double-stranded RNA duplex of the protein-binding segment. In some embodiments, a gRNA comprises a single guide RNA molecule (sgRNA).

The specificity of a gRNA for a target loci is mediated by the sequence of the nucleic acid-binding segment, which comprises about 20 nucleotides that are complementary to a target nucleic acid sequence within the target locus. In some embodiments, the corresponding target nucleic acid sequence is approximately 20 nucleotides in length. In some embodiments, the nucleic acid-binding segments of the gRNA sequences of the present disclosure are at least 90% complementary to a target nucleic acid sequence within a target locus. In some embodiments, the nucleic acid-binding segments of the gRNA sequences of the present disclosure are at least 95%, 96%, 97%, 98%, or 99% complementary to a target nucleic acid sequence within a target locus. In some embodiments, the nucleic acid-binding segments of the gRNA sequences of the present disclosure are 100% complementary to a target nucleic acid sequence within a target locus.

In some embodiments, the target nucleic acid sequence is an RNA target sequence. In some embodiments, the target nucleic acid sequence is a DNA target sequence.

In some embodiments, the targeted gene-editing system comprises two or more gRNA molecules each comprising a DNA-binding segment, wherein at least one of the nucleic acid-binding segments binds to a target DNA sequence of a target gene.

In some embodiments, the guide RNA is a single guide RNA (sgRNA). Methods of constructing suitable sgRNAs according to a given target sequence are known in the art. See e.g., Wang, Y. et al. Simultaneous editing of three homoeoalleles in hexaploid bread wheat confers heritable resistance to powdery mildew. Nat. Biotechnol. 32, 947-951 (2014); Shan, Q. et al. Targeted genome modification of crop plants using a CRISPR-Cas system. Nat. Biotechnol. 31, 686-688 (2013); Liang, Z. et al. Targeted mutagenesis in *Zea mays* using TALENs and the CRISPR/Cas system. J Genet Genomics. 41, 63-68 (2014).

The addition of a uracil DNA glycosylase (UGI) domain further increased the base-editing efficiency. In some embodiments, the targeted base-editing system further comprises a base excision repair (BER) inhibitor. Cellular DNA-repair response to the presence of a U:G pairing in DNA may be responsible for a decrease in nucleobase editing efficiency in plant cells. Uracil DNA glycosylase catalyzes removal of uracil from DNA in plant cells, which may initiate base excision repair, such that the U:G pair is reversed to C:G. In some embodiments, the BER inhibitor is an uracyl glycosylase inhibitor or an active domain thereof.

In some embodiments, the BER inhibitor is an inhibitor of uracil DNA glycosylase (UDG). In some embodiments, the BER inhibitor is an inhibitor of UDG. In some embodiments, the BER inhibitor is a polypeptide inhibitor. In some embodiments, the BER inhibitor is a protein that binds single-stranded DNA. For example, the BER inhibitor may be a *Erwinia tasmaniensis* single-stranded binding protein. In some embodiments, the BER inhibitor is a protein that binds uracil. In some embodiments, the BER inhibitor is a protein that binds uracil in DNA. In some embodiments, the BER inhibitor is a catalytically inactive UDG or binding domain thereof. In some embodiments, the BER inhibitor is a catalytically inactive UDG or binding domain thereof that does not excise uracil from the DNA. Other proteins that are capable of inhibiting (e.g., sterically blocking) UDG are within the scope of this disclosure. Additionally, any proteins that block or inhibit base-excision repair as also within the scope of this disclosure.

Base excision repair may be inhibited by molecules that bind the edited strand, block the edited base, inhibit uracil DNA glycosylase, inhibit base excision repair, protect the edited base, and/or promote fixing of the non-targeted strand. Accordingly, the use of the BER inhibitor described herein can increase the editing efficiency of a cytidine deaminase that is capable of catalyzing a C to U change.

In particular embodiments, the uracil glycosylase inhibitor (UGI) is the uracil DNA glycosylase inhibitor of *Bacillus subtilis* bacteriophage PBS1 or an active fragment thereof, such as an 83 residue protein of *Bacillus subtilis* bacteriophage PBS1.

Suitable UGI protein and nucleotide sequences are provided herein and additional suitable UGI sequences are known to those in the art, and include, for example, those published in Wang et al., Uracil-DNA glycosylase inhibitor gene of bacteriophage PBS2 encodes a binding protein specific for uracil-DNA glycosylase. J. Biol. Chem. 264: 1 163-1 171(1989); Lundquist et al., Site-directed mutagenesis and characterization of uracil-DNA glycosylase inhibitor protein. Role of specific carboxylic amino acids in complex formation with *Escherichia coli* uracil-DNA glycosylase. J. Biol. Chem. 272:21408-21419(1997); Ravishankar et al., X-ray analysis of a complex of *Escherichia coli* uracil DNA glycosylase (EcUDG) with a proteinaceous inhibitor. The structure elucidation of a prokaryotic UDG. Nucleic Acids Res. 26:4880-4887(1998); and Putnam et al., Protein mimicry of DNA from crystal structures of the uracil-DNA glycosylase inhibitor protein and its complex with *Escherichia coli* uracil-DNA glycosylase. J. Mol. Biol. 287:331-346(1999), each of which incorporated herein by reference. Additional embodiments of the uracil glycosylase inhibitor (UGI) are disclosed in WO2018/086623, WO2018/205995, WO2017/70632, and WO2018/213726, each of which is incorporated herein by reference in its entirety.

In some embodiments, the UGI domain comprises a wild type UGI or a UGI. In some embodiments, the UGI proteins provided herein include fragments of UGI and proteins homologous to a UGI or a UGI fragment.

Additional proteins may be uracil glycosylase inhibitors. For example, other proteins that are capable of inhibiting (e.g., sterically blocking) a uracil-DNA glycosylase base-excision repair enzyme are within the scope of this disclosure. Additionally, any proteins that block or inhibit base-excision repair as also within the scope of this disclosure. In some embodiments, a protein that binds DNA is used. In another embodiment, a substitute for UGI is used. In some embodiments, a uracil glycosylase inhibitor is a protein that binds single-stranded DNA. For example, a uracil glycosylase inhibitor may be a *Erwinia tasmaniensis* single-stranded binding protein. In some embodiments, a uracil glycosylase inhibitor is a protein that binds uracil. In some embodiments, a uracil glycosylase inhibitor is a protein that binds uracil in DNA. In some embodiments, a uracil glycosylase inhibitor is a catalytically inactive uracil DNA-glycosylase protein. In some embodiments, a uracil glycosylase inhibitor is a catalytically inactive uracil DNA-glycosylase protein that does not excise uracil from the DNA. As another example, a uracil glycosylase inhibitor is a catalytically inactive UDG.

In some embodiments, the base editing system comprises the following domains; i) the CRISPR-Cas protein (dCas9 or nCas9) and ii) the cytidine deaminase, which can be fused to or linked to a BER inhibitor (e.g., an inhibitor of uracil DNA glycosylase).

Uracil-DNA glycosylase (UDG) is an enzyme that reverts mutations in DNA. The most common mutation is the deamination of cytosine to uracil. UDG repairs these mutations and UDG is crucial in DNA repair. Various uracil-DNA glycosylases and related DNA glycosylases (EC) are present such as uracil-DNA glycosylase, thermophilic uracil-DNA glycosylase, G:T/U mismatch-specific DNA glycosylase (Mug), and single-strand selective monofunctional uracil-DNA glycosylase (SMUG1).

Uracil DNA glycosylases remove uracil from DNA, which can arise either by spontaneous deamination of cytosine or by the misincorporation of dU opposite dA during DNA replication. The prototypical member of this family is *E. coli* UDG, which was among the first glycosylases discovered. Four different uracil-DNA glycosylase activities have been identified in mammalian cells, including UNG, SMUG1, TDG, and MBD4, which vary in substrate specificity and subcellular localization. SMUG1 prefers single-stranded DNA as substrate, but also removes U from double-stranded DNA. In addition to unmodified uracil, SMUG1 can excise 5-hydroxyuracil, 5-hydroxymethyluracil and 5-formyluracil bearing an oxidized group at ring C5.[13] TDG and MBD4 are strictly specific for double-stranded DNA. TDG can remove thymine glycol when present opposite guanine, as well as derivatives of U with modifications at carbon 5.

TDG and SMUG1 are the major enzymes responsible for the repair of the U:G mispairs caused by spontaneous cytosine deamination, whereas uracil arising in DNA through dU misincorporation is mainly dealt with by UNG. MBD4 is thought to correct T:G mismatches that arise from deamination of 5-methylcytosine to thymine in CpG sites.

Uracil arising in DNA either from misincorporation of dUMP or from deamination of cytosine is actively removed through the multistep base excision repair (BER) pathway. BER of uracil is initiated by a uracil DNA glycosylase (UDG) activity that cleaves the N-glycosidic bond and excises uracil as a free base, generating an abasic (apurinic/apyrimidinic, AP) site in the DNA. Repair is completed through subsequent steps that include incision at the AP site, gap tailoring, repair synthesis, and ligation.

In some embodiments, the addition of a Uracil-DNA glycosylase (UDG) such as uracil N-glycosylase (UNG) can induce various mutations at targeted base. In some embodiments, the targeted base-editing system further comprises a Uracil-DNA glycosylase (UDG). Cellular DNA-repair response to the presence of a U:G pairing in DNA may be responsible for a decrease in nucleobase editing efficiency in plant cells. Uracil DNA glycosylase catalyzes removal of uracil from DNA in plant cells, which may initiate base excision repair, such that the U:G pair is reversed to C:G. In other embodiments, removal of uracil from DNA in plant cells are not always reversed to C for C:G paring, but randomized to other bases such as T, A, and G.

In some embodiments, a Uracil-DNA glycosylase (UDG) is fused to the targeted base editing system taught in the present disclosure to introduce a stable and targeted, but randomized single nucleotide substitution in a target gene of interest.

The use of the UDG described herein can increase the base randomization in a targeted single nucleotide of a target gene.

In some embodiments, a UDG is provided in cis. In some embodiments, a UDG is provided in trans. In some embodiments, a UDG is fused to a base editor (or a base editing system) described in the present disclosure. In other embodiments, a UDG trigger a stall DNA replication for base randomization. In other embodiments, a UDG triggers a DNA repair through DNA replication, thereby including base randomization. In further embodiments, naturally occurring UDG variants can be used as a UDG domain. In further embodiments, non-naturally occurring UDG variants can be used as a UDG domain. In further embodiments, a UDG can be genetically engineered to enhance a functional UDG activity.

A nuclear localization signal (NLS), or any other organelle targeting signal, can be further required to ensure proper targeting of the complex. The present disclosure relate to modifying an cytosine in a target locus of interest, whereby the target locus is within a plant cell. In order to improve targeting of the CRISPR-Cas protein and/or the cytidine deaminase protein or catalytic domain thereof used in the methods of the present disclosure to the nucleus, it may be advantageous to provide one or both of these components with one or more nuclear localization sequences (NLSs).

In some embodiments, the NLSs used in the context are heterologous to the proteins. In general, NLS consists of one or more short sequences of positively charged lysine or arginine exposed on the surface of a protein, but other types of NLS are also known in the art.

In some embodiments, the N-terminus of the gene editing fusion protein comprises an NLS with an amino acid sequence. In some embodiments, the C-terminus of the gene-editing fusion protein comprises an NLS.

In addition, the gene editing fusion protein may also include other localization sequences, such as cytoplasmic localization sequences, chloroplast localization sequences, mitochondrial localization sequences, and the like, depending on the location of the DNA to be edited. In order to obtain efficient expression in plants, in some embodiments, the nucleotide sequence encoding the gene editing fusion protein is codon optimized for the plant to be gene edited.

Codon optimization refers to a process of modifying a nucleic acid sequence for enhanced expression in the host cells of interest by replacing at least one codon (e.g. about or more than about 1, 2, 3, 4, 5, 10, 15, 20, 25, 50, or more codons) of the native sequence with codons that are more frequently or most frequently used in the genes of that host cell while maintaining the native amino acid sequence. Various species exhibit particular bias for certain codons of a particular amino acid. Codon bias (differences in codon usage between organisms) often correlates with the efficiency of translation of messenger RNA (mRNA), which is in turn believed to be dependent on, among other things, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization. Codon usage tables are readily available, for example, at the "Codon Usage Database" available at www.kazusa.orjp/codon/and these tables can be adapted in a number of ways. See Nakamura, Y., et al. "Codon usage tabulated from the international DNA sequence databases: status for the year 2000" Nucl. Acids Res. 28:292 (2000).

In some embodiments, the codon-optimized nucleotide sequence encoding the gene editing fusion protein is provided herein. In some embodiments, the guide RNA is a single guide RNA (sgRNA). Methods of constructing suitable sgRNAs according to a given target sequence are known in the art. See e.g., Wang, Y. et al. Simultaneous editing of three homeoalleles in hexaploid bread wheat confers heritable resistance to powdery mildew. *Nat. Biotechnol.* 32, 947-951 (2014); Shan, Q. et al. Targeted genome modification of crop plants using a CRISPR-Cas system. *Nat. Biotechnol.* 31, 686-688 (2013); Liang, Z. et al. Targeted mutagenesis in *Zea mays* using TALENs and the CRISPR/Cas system. *J Genet Genomics.* 41, 63-68 (2014).

In order to ensure appropriate expression in a plant cell, the components of the targeted gene-editing system described herein are typically placed under control of a plant promoter, i.e. a promoter operable in plant cells. The use of different types of promoters is envisaged.

A constitutive plant promoter is a promoter that is able to express the open reading frame (ORF) that it controls in all or nearly all of the plant tissues during all or nearly all developmental stages of the plant (referred to as "constitutive expression"). One non-limiting example of a constitutive promoter is the cauliflower mosaic virus 35S promoter. "Regulated promoter" refers to promoters that direct gene expression not constitutively, but in a temporally- and/or spatially-regulated manner, and includes tissue-specific, tissue-preferred and inducible promoters. Different promoters may direct the expression of a gene in different tissues or cell types, or at different stages of development, or in response to different environmental conditions. In particular embodiments, one or more of the components of the targeted gene-editing system described herein are expressed under the control of a constitutive promoter, such as the cauliflower mosaic virus 35S promoter. Tissue-preferred promoters can be utilized to target enhanced expression in certain cell types within a particular plant tissue, for instance vascular cells in leaves or roots or in specific cells of the seed. Examples of particular promoters for use of the present disclosure can be found in Kawamata et al., (1997) Plant Cell Physiol 38:792-803; Yamamoto et al., (1997) Plant J 12:255-65; Hire et al, (1992) Plant Mol Biol 20:207-18, Kuster et al, (1995) Plant Mol Biol 29:759-72, and Capana et al., (1994) Plant Mol Biol 25:681-91.

Inducible promoters can be of interest to express one or more of the components of the targeted gene-editing system described herein under limited circumstances to avoid non-specific activity of the deaminase. In particular embodiments, one or more elements of the targeted gene-editing system described herein are expressed under control of an inducible promoter.

Examples of promoters that are inducible and that allow for spatiotemporal control of gene editing or gene expression may use a form of energy. The form of energy may include but is not limited to sound energy, electromagnetic radiation, chemical energy and/or thermal energy. Examples of inducible systems include tetracycline inducible promoters (Tet-On or Tet-Off), small molecule two-hybrid transcription activations systems (FKBP, ABA, etc), or light inducible systems (Phytochrome, LOV domains, or cryptochrome), such as a Light Inducible Transcriptional Effector (LITE) that direct changes in transcriptional activity in a sequence-specific manner. The components of a light inducible system may include a fusion protein of the targeted gene-editing system and a light-responsive cytochrome heterodimer (e.g. from *Arabidopsis thaliana*). Further examples of inducible DNA binding proteins and methods for their use are provided in U.S. 61/736,465 and U.S. 61/721,283, which is hereby incorporated by reference in its entirety.

In particular embodiments, transient or inducible expression can be achieved by using, for example, chemical-regulated promotors, i.e. whereby the application of an exogenous chemical induces gene expression. Modulating of gene expression can also be obtained by a chemical-repressible promoter, where application of the chemical represses gene expression. Chemical-inducible promoters include, but are not limited to, the maize ln2-2 promoter, activated by benzene sulfonamide herbicide safeners (De Veylder et al., (1997) Plant Cell Physiol 38:568-77), the maize GST promoter (GST-11-27, WO93/01294), activated by hydrophobic electrophilic compounds used as pre-emergent herbicides, and the tobacco PR-1 a promoter (Ono et al., (2004) Biosci Biotechnol Biochem 68:803-7) activated by salicylic acid. Promoters which are regulated by antibiotics, such as tetracycline-inducible and tetracycline-repressible promoters (Gatz et al., (1991) Mol Gen Genet 227: 229-37; U.S. Pat. Nos. 5,814,618 and 5,789,156) can also be used herein.

In some embodiments, the nucleotide sequence encoding the gene-edited fusion protein and/or the nucleotide sequence encoding the guide RNA is operably linked to a plant expression regulatory element, such as a promoter. Examples of promoters that can be used in the present disclosure include, but are not limited to the cauliflower mosaic virus 35S promoter (Odell et al. (1985) *Nature* 313: 810-812), a maize Ubi-1 promoter, a wheat U6 promoter, a rice U3 promoter, a maize U3 promoter, a rice actin promoter, a TrpPro5 promoter (U.S. patent application Ser. No. 10/377,318; filed on Mar. 16, 2005), a pEMU promoter (Last et al. *Theor. Appl. Genet.* 8 1: 581-588), a MAS promoter (Velten et al. (1984) *EMBO J.* 3: 2723-2730), a maize H3 histone promoter (Lepetit et al. *Mol. Gen. Genet.* 231: 276-285 and Atanassova et al. (1992) *Plant J.* 2 (3): 291-300), and a *Brassica napus* ALS3 (PCT Application WO 97/41228) promoters. Promoters that can be used in the present disclosure also include the commonly used tissue specific promoters as reviewed in Moore et al. (2006) *Plant J.* 45 (4): 651-683.

In the present disclosure, the plants are intended to comprise without limitation angiosperm and gymnosperm plants such as acacia, alfalfa, amaranth, apple, apricot, artichoke, ash tree, asparagus, avocado, banana, barley, beans, beet, birch, beech, blackberry, black raspberry, blueberry, broccoli, Brussel's sprouts, cabbage, cane berry, canola, cantaloupe, carrot, cassava, cauliflower, cedar, a cereal, celery, chestnut, cherry, Chinese cabbage, citrus, Clementine, clover, coffee, corn, cotton, cowpea, cucumber, cypress, eggplant, elm, endive, eucalyptus, fennel, figs, fir, geranium, grape, grapefruit, groundnuts, ground cherry, gum hemlock, hickory, kale, kiwifruit, kohlrabi, larch, lettuce, leek, lemon, lime, locust, pine, maidenhair, maize, mango, maple, melon, millet, mushroom, mustard, nuts, oak, oats, oil palm, okra, onion, orange, an ornamental plant or flower or tree, papaya, palm, parsley, parsnip, pea, peach, peanut, pear, peat, pepper, persimmon, pigeon pea, peach, pine, pineapple, plantain, plum, pomegranate, potato, pumpkin, radicchio, radish, rapeseed, raspberry, rice, rye, sorghum, safflower, sallow, soybean, spinach, spruce, squash, strawberry, sugar beet, sugarcane, sunflower, sweet potato, sweet corn, tangerine, tea, tobacco, tomato, trees, triticale, turf grasses, turnips, vine, walnut, watercress, watermelon, wheat, wild strawberry, yams, yew, and zucchini.

The methods for targeted gene-editing system as described herein can be used to confer desired traits on essentially any plant. A wide variety of plants and plant cell systems may be engineered for the desired physiological and agronomic characteristics described herein using the nucleic acid constructs of the present disclosure and the various transformation methods. In preferred embodiments, target plants and plant cells for engineering include, but are not limited to, those monocotyledonous and dicotyledonous plants, such as crops including grain crops (e.g., wheat, maize, rice, millet, barley), fruit crops (e.g., tomato, apple, grape, peach, pear, plum, raspberry, black raspberry, blackberry, cane berry, cherry, avocado, strawberry, wild strawberry, orange), forage crops (e.g., alfalfa), root vegetable crops (e.g., carrot, potato, sugar beets, yam), leafy vegetable crops (e.g., lettuce, spinach); flowering plants (e.g., petunia, rose, chrysanthemum), conifers and pine trees (e.g., pine fir, spruce); plants used in phytoremediation (e.g., heavy metal accumulating plants); oil crops (e.g., sunflower, rape seed) and plants used for experimental purposes (e.g., *Arabidopsis*). In some embodiments, fruit crops such as tomato, apple, peach, pear, plum, raspberry, black raspberry, blackberry, cane berry, cherry, avocado, strawberry, wild strawberry, grape and orange.

The present disclosure provides methods for targeted editing in a plant cell, tissue, organ or plant. In one aspect, the present disclosure provides methods for producing a gene-edited plant by transient expression of a gene editing system. In another aspect, the present disclosure provides methods for a gene-edited and non-transgenic plant by transient expression of a gene editing system along with transient expression of at least one morphogenic regulator taught in the present disclosure. Therefore, the present disclosure teaches a gene-edited plant that is also transgene-free without any integration of foreign DNAs.

In some embodiments, an editing system as described herein is used to introduce targeted mutations, such as insertions, deletions, or substitutions, thereby causing a nonsense mutation (e.g., premature stop codon) or a missense mutation (e.g., encoding different amino acid residue). This is of interest where the single nucleotide mutations in certain endogenous genes can confer or contribute to a desired trait.

The methods described herein may result in the generation of gene-edited plants that have one or more desirable traits compared to the wild type plant.

In some embodiments, non-transgenic but gene-edited plants, plant parts, or cells are obtained, in that no exogenous DNA sequence is incorporated into the genome of any of the plant cells of the plant. In such embodiments, the gene-edited plants are non-transgenic. Where only the modification of an endogenous gene is ensured and no foreign genes are introduced or maintained in the plant genome, the resulting genetically modified crops contain no foreign genes and can thus basically be considered non-transgenic.

In some embodiments, modification of the target sequence can be accomplished simply by introducing or producing the gene editing protein and guide RNA in plant cells, and the modification can be stably inherited without the need of stable transformation of plants with an editing system. This avoids potential off-target effects of a stable editing system, and also avoids the integration of exogenous nucleotide sequences into the plant genome, and thereby resulting in higher biosafety. In some embodiments, the editing system is the targeted gene editing system. In further embodiments, the plant cells in which the genetic modification is stably inherited without stable transformation is edited by the gene editing system (i.e. the targeted gene editing system) are transformed and regenerated into a whole plant by the transient expression of one or more morphogenic regulators.

In other embodiments, the polynucleotides are delivered into the cell by a DNA virus (e.g., a geminivirus) or an RNA virus (e.g., a tobravirus). In other embodiments, the introducing steps include delivering to the plant cell a T-DNA containing one or more polynucleotide sequences encoding an encoding system (e.g., a CRISPR-Cas effector protein and a guide nucleic acid), where the delivering is via *Agrobacterium*. The polynucleotide sequence encoding the components of CRISPR/Cas system can be operably linked to a promoter, such as a constitutive promoter (e.g., a cauliflower mosaic virus 35S promoter), or a cell specific or inducible promoter in a plant cell of interest described herein. In other embodiments, the polynucleotide is introduced by microprojectile bombardment.

In some embodiments, the gene editing system can be introduced into plants by various methods well known to people skilled in the art. Methods that can be used to introduce the gene editing system of the present disclosure into plants include but not limited to particle bombardment, PEG-mediated protoplast transformation, *Agrobacterium*-mediated transformation, plant virus-mediated transformation, pollen tube approach, and ovary injection approach.

In some embodiments, the introduction is performed in the absence of a selective pressure, thereby avoiding the integration of exogenous nucleotide sequences in the plant genome. In some embodiments, the introduction comprises transforming the gene editing system into isolated plant cells or tissues, and then regenerating the transformed plant cells or tissues into an intact plant by the help of morphogenic regulator expression taught in the present disclosure. Preferably, the regeneration is performed in the absence of a selective pressure, i.e., no selective agent against the selective gene carried on the expression vector is used during the tissue culture. Without the use of a selective agent, the regeneration efficiency of the plant can be increased to obtain a modified plant that does not contain exogenous nucleotide sequences. To increase, enhance, improve the transformation and regeneration of a non-transgenic plant with a desired modification inherited, the morphogenic regulator(s) is transiently expressed in the plant cell.

In other embodiments, the editing system of the present disclosure can be transformed to a particular site on an intact plant, such as leaf, shoot tip, pollen tube, young ear, or hypocotyl. This is particularly suitable for the transformation of plants that are difficult to regenerate by tissue culture. In some embodiments, proteins expressed in vitro and/or RNA molecules transcribed in vitro are directly transformed into the plant. The proteins and/or RNA molecules are capable of achieving gene-editing in plant cells, and are subsequently degraded by the cells to avoid the integration of exogenous nucleotide sequences into the plant genome. Plants that can be gene-edited by the methods includes monocotyledon and dicotyledon. For example, the plant may be a crop plant such as wheat, rice, maize, soybean, sunflower, sorghum, rape, alfalfa, cotton, barley, millet, sugar cane, tomato, tobacco, cassava, or potato. For another example, the plant may be a fruit crops such as tomato, apple, peach, pear, plum, raspberry, black raspberry, blackberry, cane berry, cherry, avocado, strawberry, wild strawberry, grape and orange.

In some embodiments, the target sequence is associated with plant traits such as desired traits, and thereby the gene editing results in the plant having altered traits relative to a wild type plant. In the present disclosure, the target sequence to be modified (e.g., a target nucleic acid) may be located anywhere in the genome, for example, within a functional gene such as a protein-coding gene or, for example, may be located in a gene expression regulatory region such as a promoter region or an enhancer region, and thereby accomplish the functional modification of said gene or accomplish the modification of a gene expression.

In some embodiments, the method further comprises obtaining progeny of the gene-edited plant, which is also non-transgenic. In a further aspect, the disclosure also provides a gene-edited plant or progeny thereof or parts thereof, wherein the plant is obtained by the method described above.

In another aspect, the present disclosure also provides a plant breeding method comprising crossing a first gene-edited plant obtained by the above-mentioned method of the present disclosure with a second plant not containing said genetic modification, thereby introducing said genetic modification into said second plant.

In particular embodiments, the method further includes screening the plant cell after the introducing steps to determine whether the expression of the gene of interest has been modified. In particular embodiments, the methods include the step of regenerating a plant from the plant cell. In further embodiments, the methods include cross breeding the plant to obtain a genetically desired plant lineage.

In some embodiments, significant impact of transient expression of morphogenic regulators on plant transformation and regeneration can be applied for generation of gene-edited plant without foreign DNA integration. The regenerated plant from a gene-edited plant cell is transgene-free and/or DNA integration-free. Transient expression of at least one morphogenic regulators gives rise to successful regeneration of a plant cell of interest.

In other embodiments, significant impact of transient expression of morphogenic regulators on plant transformation and regeneration can be applied for plant regeneration of dicot species, especially those with heterozygotic nature and/or polyploidy.

In some embodiments, transient expression of morphogenic regulators can used to regenerate plants from protoplast cells. In other embodiments, transient expression of morphogenic regulator can be used to regenerate plants from edited callus by the gene-editing system taught in the present disclosure.

As described herein, the nucleic acids of the invention and/or expression cassettes and/or vectors comprising the same may be codon optimized for expression in an organism. An organism useful with this invention may be any organism or cell thereof for which a morphogenic regulator and/or nucleic acid modification may be useful. An organism can include, but is not limited to, any animal, any plant, any fungus, any archaeon, or any bacterium. In some embodiments, the organism may be a plant or cell thereof.

A target nucleic acid of any cell, plant, or plant part may be modified using a composition, system, and/or method of the invention. Any plant (or groupings of plants, for example, into a genus or higher order classification) may be modified using a nucleic acid construct, composition, system, and/or method of this invention including an angiosperm, a gymnosperm, a monocot, a dicot, a C3, C4, CAM plant, a bryophyte, a fern and/or fern ally, a microalgae, and/or a macroalgae. A plant and/or plant part useful with this invention may be a plant and/or plant part of any plant species/variety/cultivar. The term "plant part," as used herein, includes but is not limited to, embryos, pollen, ovules, seeds, leaves, stems, shoots, flowers, branches, fruit, kernels, ears, cobs, husks, stalks, roots, root tips, anthers, plant cells including plant cells that are intact in plants and/or parts of plants, plant protoplasts, plant tissues, plant cell tissue cultures, plant calli, plant clumps, and the like. As used herein, "shoot" refers to the above ground parts including the leaves and stems. Further, as used herein, "plant cell" refers to a structural and physiological unit of the plant, which comprises a cell wall and also may refer to a protoplast. A plant cell can be in the form of an isolated single cell or can be a cultured cell or can be a part of a higher-organized unit such as, for example, a plant tissue or a plant organ.

Non-limiting examples of plants useful with the present invention include turf grasses (e.g., bluegrass, bentgrass, ryegrass, fescue), feather reed grass, tufted hair grass, miscanthus, arundo, switchgrass, vegetable crops, including artichokes, kohlrabi, arugula, leeks, asparagus, lettuce (e.g., head, leaf, romaine), malanga, melons (e.g., muskmelon, watermelon, crenshaw, honeydew, cantaloupe), cole crops (e.g., brussels sprouts, cabbage, cauliflower, broccoli, collards, kale, chinese cabbage, bok choy), cardoni, carrots, napa, okra, onions, celery, parsley, chick peas, parsnips, chicory, peppers, potatoes, cucurbits (e.g., marrow, cucumber, zucchini, squash, pumpkin, honeydew melon, watermelon, cantaloupe), radishes, dry bulb onions, rutabaga, eggplant, salsify, escarole, shallots, endive, garlic, spinach, green onions, squash, greens, beet (sugar beet and fodder beet), sweet potatoes, chard, horseradish, tomatoes, turnips, and spices; a fruit crop such as apples, apricots, cherries, nectarines, peaches, pears, plums, prunes, cherry, quince, fig, nuts (e.g., chestnuts, pecans, pistachios, hazelnuts, pistachios, peanuts, walnuts, macadamia nuts, almonds, and the like), citrus (e.g., clementine, kumquat, orange, grapefruit, tangerine, mandarin, lemon, lime, and the like), blueberries, black raspberries, boysenberries, cranberries, currants, gooseberries, loganberries, raspberries, strawberries, blackberries, grapes (wine and table), avocados, bananas, kiwi, persimmons, pomegranate, pineapple, tropical fruits, pomes, melon, mango, papaya, and lychee, a field crop plant such as clover, alfalfa, timothy, evening primrose, meadow foam, corn/maize (field, sweet, popcorn), hops, jojoba, buckwheat, safflower, quinoa, wheat, rice, barley, rye, millet, sorghum, oats, triticale, sorghum, tobacco, kapok, a leguminous plant (beans (e.g., green and dried), lentils, peas, soybeans), an oil plant (rape, canola, mustard, poppy, olive, sunflower, coconut, castor oil plant, cocoa bean, groundnut, oil palm), duckweed, *Arabidopsis*, a fiber plant (cotton, flax, hemp, jute), *Cannabis* (e.g., *Cannabis sativa, Cannabis indica*, and *Cannabis ruderalis*), *lauraceae* (cinnamon, camphor), or a plant such as coffee, sugar cane, tea, and natural rubber plants; and/or a bedding plant such as a flowering plant, a cactus, a succulent and/or an ornamental plant (e.g., roses, tulips, violets), as well as trees such as forest trees (broad-leaved trees and evergreens, such as conifers; e.g., elm, ash, oak, maple, fir, spruce, cedar, pine, birch, cypress, eucalyptus, willow), as well as shrubs and other nursery stock. In some embodiments, the nucleic acid constructs of the invention and/or expression cassettes and/or vectors encoding the same may be used to modify maize, soybean, wheat, canola, rice, tomato, pepper, sunflower, raspberry, blackberry, black raspberry and/or cherry.

In some embodiments, a plant cell of the present invention and/or that is used in a composition, system and/or method of the present invention is a plant cell is from an asexually propagated, heterozygous, perennial plant. In some embodiments, a plant cell of the present invention and/or that is used in a composition, system and/or method of the present invention is a dicot plant cell, optionally wherein the plant cell is a blackberry, raspberry, or cherry plant cell.

In some embodiments, the invention provides cells (e.g., plant cells, animal cells, bacterial cells, archaeon cells, and the like) comprising a polypeptide, polynucleotide, nucleic acid construct, expression cassette and/or vector of the invention.

The present invention further comprises a kit or kits to carry out the methods of this invention. A kit of this invention can comprise reagents, buffers, and apparatus for mixing, measuring, sorting, labeling, etc, as well as instructions and the like as would be appropriate for modifying a target nucleic acid.

In some embodiments, the invention provides a kit for comprising one or more nucleic acid construct(s) of the invention, expression cassette(s), vector(s), and/or cells comprising the same as described herein, with optional instructions for the use thereof. In some embodiments, a kit may further comprise an editing system (e.g., a CRISPR-Cas guide nucleic acid (corresponding to a CRISPR-Cas effector protein encoded by a polynucleotide of the invention) and/or an expression cassette, vector, and/or cell comprising the same Accordingly, in some embodiments, kits are provided comprising a nucleic acid construct comprising (a) a polynucleotide(s) as provided herein and (b) a promoter that drives expression of the polynucleotide(s) of (a). In some embodiments, the kit may further comprise a nucleic acid construct encoding a guide nucleic acid, wherein the construct comprises a cloning site for cloning of a nucleic acid sequence identical or complementary to a target nucleic acid sequence into backbone of the guide nucleic acid.

In some embodiments, the nucleic acid construct of the invention may be an mRNA that may encode one or more introns within the encoded polynucleotide(s). In some embodiments, the nucleic acid constructs of the invention, and/or an expression cassettes and/or vectors comprising the same, may further encode one or more selectable markers useful for identifying transformants (e.g., a nucleic acid encoding an antibiotic resistance gene, herbicide resistance gene, and the like).

The invention will now be described with reference to the following examples. It should be appreciated that these examples are not intended to limit the scope of the claims to the invention, but are rather intended to be exemplary of certain embodiments. Any variations in the exemplified methods that occur to the skilled artisan are intended to fall within the scope of the invention.

EXAMPLES

The following examples are given for the purpose of illustrating various embodiments of the disclosure and are not meant to limit the present disclosure in any fashion. Changes therein and other uses which are encompassed within the spirit of the disclosure, as defined by the scope of the claims, will occur to those skilled in the art.

Example 1. Transformation of Tobacco Leaves

Transformation can be accomplished by various methods known to be effective in plants, including particle-mediated delivery, *Agrobacterium*-mediated transformation, PEG-mediated delivery, and electroporation.

The tobacco leaves are prepared for transformation with plasmids containing the gene-editing system and/or plasmids containing at least one morphogenic regulator. The expression vector containing the morphogenic regulators such as WUS, BBN, KN1, IPT, CLV3, miR156, GRF5, NTT, and HDZipII is co-bombarded or co-transformed with another expression vector containing the targeted gene editing system, for example, CRISPR/Cas 9 endonuclease with gRNA.

The tobacco leaf transformation can be achieved by the simultaneous expression of the morphogenic regulator and the gene editing machinery after the vacuum infiltration of tobacco leaves with two populations of recombinant *Agrobacterium*.

Example 2. Transient Expression of Morphogenic Regulators

Parameters of the transformation protocol can be modified to ensure that the activity of morphogenic regulators (including, but are not limited to, WUS, BBN, KN1, IPT, CLV3, miR156, GRF5, NTT, and HDZipII) is transient.

One method for transient expression can involve precipitating the expression vector in a manner that allows for transcription and expression, but precludes subsequent release of the DNA, for example, by using the chemical polyethylenimine.

In this example, three expression vectors were constructed to test integration efficiency of a morphogenic regulator; 1) GUS marker gene driven by a constitutive promoter, 2) ipt gene fused with GUS marker gene under control of a native promoter, 3) ipt gene fused with GUS marker gene under control of a constitutive promoter. Each vector was transformed into tobacco leaves (*Nicotiana benthamiana*).

The effect of an isopentenyl transferase (ipt) gene expression under a constitutive promoter could clearly be seen. For example, ipt gene expression induced multiple shoot formation in a hormone-free media when compared to two controls (i) without ipt gene expressed as well as (ii) with ipt gene expressed under a native promoter. The ipt transformed leaf explants showed darker green color and enlargement at 2-4 wks and numerous shoots emerged as early as 4 weeks after inoculation on hormone-free and nonselective medium.

The ipt gene under a constitutive promoter produced significantly more plants that were regenerated in a hormone-free media than the control where a construct without ipt gene was used, indicating that ipt gene enhanced plant regeneration in tobacco.

Over 90% of the plants regenerated were GUS negative in the first experiment. As shown in FIG. 1, GUS assay results of one hundred six shoots induced by the ipt gene expression indicate that about 93.4% (99 out of 106 ipt-induced shoots) were GUS negative, suggesting either that the GUS-negative shoots would not be stably integrated but transiently expressed. However, transgenic nature has not been determined. Thus, molecular analyses are being performed to determine the transgenic nature of these GUS negative plants is in progress.

On the other hand, seven samples were GUS-positive, which may indicate stable integration of ipt-GUS fusion cassette. Furthermore, the GUS-positive ipt-induced shoots generated too many shoots that could be explained by too high level of cytokinin accumulation due to the constitutive ipt gene expression. Thus, the GUS positive samples are considered to be stably integrated into a tobacco genome.

Importantly, molecular analyses are being performed to determine the transgenic nature of these GUS negative plants is in progress.

Example 3. Constructions of Expression Vectors for Gene-Editing System and/or Morphogenic Regulators In this example, the construction of expression vector contains a marker-free T-DNA. Especially, three constructs are being generated and tested for efficiency of gene-editing and/or plant regeneration.
1) Locate both ipt (Morphogenic regulator; Morgen) and gene-editing machinery outside of T-DNA Left Border
2) Locate editing machinery inside of T-DNA, but ipt/Morgen outside of T-DNA Left Border
3) Locate both ipt/Morgen and editing machinery inside of T-DNA An expression vector comprising 1) expression cassette for ipt gene and 2) expression cassette for gene editing system (CRISPR/Cas9 and gRNA) will be transformed into a plant cell of interest in order to generate mutations at the corresponding targeted sites. DNA delivery (such as recombinant DNA, plasmid DNA) for targeted mutagenesis and gene editing in plants are presented herewith.

The gene-editing expression vectors will be transformed into plants of interest such as: black raspberry, blackberry, cane berry, cherry, peach, avocado, strawberry, wild strawberry, apple, tomato, grape, and peach as well as model plants such as *Arabidopsis* and tobacco. The disclosure teaches all types of transformation methods, including using *agrobacterium*-mediated protocols that are known in the art and/or developed by the inventors, as well as biolistic transformation methods. Tissue culture and regeneration of transformed plants will be performed accordingly.

Example 4: Molecular Analysis for Transformed Plants

In this example, the activity of the gene-editing machinery will be examined with efficiency of plant transformation and regeneration by control of transient ipt gene expression on the transformed plants of interest including *Arabidopsis*, black raspberry, cane berry, blackberry, cherry, avocado, strawberry, wild strawberry, peach, grape, apple, tomato and/or tobacco.

Example 5: Inducible Expression of Morphogenic Regulators

In this example, expression vectors were constructed to test inducible ipt expression (GR-LHG4-pOP4::ipt) in tobacco transformation. The vector contained two expression cassettes. The ipt was driven by a pOP4 promoter, whose transcription activity is controlled by the transcription factor LHG4. LHG4 was fused with glucocorticoid receptor (GR), constitutively expressed and located in cytoplasm. GR-LHG4 protein translocates to a cell nucleus upon the application of inducing chemical dexamethasone (Dex). Each vector was transformed into tobacco leaves (*Nicotiana benthamiana*). Leaf segments at about 1 square centimetre were prepared from tobacco plants maintained in vitro. An *Agrobacterium* suspension containing the plasmid was prepared at OD 0.2 as the inoculum. Leaf segments were inoculated by the *Agrobacterium* by submerging in the suspension for 10 minutes and then were transferred to sterile filter paper (1 mL of MS liquid added) for a 2-day co-culture. The leaf explants were then transferred to MS-based agar medium containing no plant growth regulators or selection agent for regeneration. Medium with and without inducing chemical Dex (µM) were compared for the effect of induced ipt expression.

The explants showed darker green color and enlargement at 2-4 wks than the control; and numerous shoots emerged as early as 4 weeks after inoculation on hormone-free and nonselective medium. In addition, numerous shoots emerged as early as 4 weeks on hormone-free nonselective medium supplemented with inducing chemical dexamethasone (Dex). As the control, no shoots were regenerated from the same medium without Dex.

Example 6: Non-transgenic Editing Using Morphogenic Regulators and a Gene-Editing System The efficacy of non-transgenic editing using ipt in the same T-DNA with PDS editing machinery was examined. The vectors contained a sequence encoding LbCpf1 nuclease and gRNA targeting tobacco PDS genes to create deletion mutations. In the same vector, an ipt constitutive expression cassette was built in the same T-DNA with the PDS editing machinery. *Agrobacterium* containing the vector was used for tobacco transformation. Leaf segments at about 1 square centimetre were prepared from tobacco plants maintained in vitro. An *Agrobacterium* suspension containing the plasmid was prepared at OD 0.2 as the inoculum. Leaf segments were inoculated by the *Agrobacterium* by submerging in the suspension for 10 minutes and then were transferred to sterile filter paper (1 mL of MS liquid added) for a 2-day co-culture. The leaf explants were then transferred to MS-based agar medium containing no plant growth regulators or selection agent for regeneration.

The plants that were regenerated with ipt included many shoots when regenerated on the hormone-free nonselective medium. A population of 200 shoots was subjected to molecular determination of transgene integration and gene editing. A total of 7 samples had transgene integration among the 200 (providing 96.5% nontransgenic, which is similar with Example 2). Four samples showed deletion mutations targeted by gRNA, including 3 with transgene integration and 1 without the integration. As the control, 20 shoots regenerated from medium with selection and BAP were used for the same molecular determinations, and photobleaching phenotype was observed on some regenerated shoots.

Example 7: Strong Constitutive Expression

RoKN1 and PavKN1 (strong constitutive expression) in tobacco transformation was tested. Leaf segments at about 1 square centimeter were prepared from tobacco plants maintained in vitro. An *Agrobacterium* suspension containing the plasmid (RoKN1 or PavKN1 expression) was prepared at OD 0.2 as the inoculum. Leaf segments were inoculated by the *Agrobacterium* by submerging in the suspension for 10 minute and transferred to sterile filter paper (1 mL of MS liquid added) for a 2-day co-culture. Then the leaf explants were transferred to MS-based agar medium containing 1 mg/L of BAP and 100 mg/L of spectinomycin as the selective agent. In contrast to expression with ipt, no different phenotype was observed on hormone-free nonselective medium but strong a shooty phenotype was observed on regeneration medium (BAP+selection).

Example 8: Expression of Morphogenic Regulators with Various Promoters

Various morphogenic regulators were tested together with different promoters in tobacco transformation. RoWUS, SorbiWUS, PavWUS, AtBBM, TaBBM-1, TaBBM-2, SobiBBM, RoBBM, and PavBBM were tested. Each gene was driven by a double viral strong constitutive promoter or a weaker promoter (pNOS) for a comparative test. Leaf segments at about 1 square centimetre were prepared from tobacco plants maintained in vitro. An *Agrobacterium* suspension containing each of the plasmids was prepared at OD 0.2 as the inoculum. Leaf segments were inoculated by the *Agrobacterium* by submerging in the suspension for 10 minutes and were then transferred to sterile filter paper (1 mL of MS liquid added) for a 2-day co-culture. Then the leaf explants were transferred to four types of MS-based agar medium for regeneration: 1) hormone-free and selection-free; 2) BAP 1 mg/L and selection free; 3) BAP 1 mg/L and selection; 4) 2, 4D 0.2 mg/L and selection.

The medium conditions post inoculation include 1) hormone-free nonselective 2) BAP w/o selection 3) BAP+ selection 4) 2,4 D+selection. There was no significant morphogenic changes for all tested genes on medium conditions 1), 2) or 3). On the 2,4 D containing medium, somatic embryogenesis was observed from RoWUS, PavWUS and SobiWUS transformed explants, as showed by early globular callus (both promoters), and bipolar structures (strong promoters) and proliferation of shoots from regenerated structure (strong promoter). The level of WUS expression appeared to affect the normal development as informed by visual reporter ZsGreen expression.

Example 9

WOX2-GR and WOX8-GR in tobacco transformation were tested. Results: shoot regeneration was observed from WOX2-GR inoculated explants at the presence of Dex on medium with BAP and selection (image below). Strong shoot proliferations were observed from WOX8-GR inoculated explants at the presence of Dex on medium with BAP and selection.

Example 10

RoWUS was tested in blackberrry transformation. Results: higher efficiency of regeneration was observed in RoWUS transformed leaf petiole explants, as shown by higher number of shoots regenerated per petiole. Both promoter types (constitutive strong and constitutive weak) showed similar gene effect. Two *Agrobacterium* strains were mixed at different ratios and co-infiltrated to blackberry explants. One strain delivered a T-DNA containing the RoWUS expression cassette and the other strain delivered a T-DNA containing a Cas12a expression cassette for genome editing. Many regenerated shoots were obtained due to RoWUS regeneration enhancing capacity. When delivered at a 1:1 ratio of RoWUS T-DNA to Cas12a T-DNA, 36 shoots were recovered and 2 were positive in a qPCR test for presence of a hygromycin selectable marker gene (5.6% efficiency). When delivered at a 1:9 ratio of RoWUS T-DNA to Cas12a T-DNA, 50 shoots were recovered and 5 were positive in a qPCR test for presence of a hygromycin selectable marker gene (10% efficiency). In contrast to these results, a control sample group transformed only with the T-DNA containing the Cas12a expression cassette yielded 41 shoots and only 1 was positive in a qPCR test for presence of a hygromycin selectable marker gene (2.4% efficiency). This indicates that transgenic shoots can be recovered at a higher efficiency when transforming with RoWUS than without it.

REFERENCES

All references, articles, publications, patents, patent publications, and patent applications cited herein are incorporated by reference in their entireties for all purposes. However, mention of any reference, article, publication, patent, patent publication, and patent application cited herein is not, and should not, be taken as an acknowledgment or any form of suggestion that they constitute valid prior art or form part of the common general knowledge in any country in the world.

U.S. Pat. No. 7,256,322 B2
US20180273960 A1
Gordon-Kamm B., Sardesai N., Arling M., Lowe K., Hoerster G., Betts S., and Jones T. Using morphogenic genes to improve recovery and regeneration of transgenic plants. Plants 8(2). Pii: E38 (2019)
Chen et al. A method for the production and expedient screening of CRISPR/Cas9-mediated non-transgenic mutant plants. Hort Research 5:13 (2018)
Carimi F., De Pasquale F. Crescimanno F. G. Somatic embryogenesis and plant regeneration from pistil thin cell layers of citrus. Plant Cell Rep. 18, 935-940 (1999).
Paul H., Belaizi M., Sangwan-Norreel B. S. Somaticembryo genes is in apple. J. Plant Physiol. 143, 78-86 (1994).
Fischer R., Emans, N. Molecular farming of pharmaceutical proteins. Transgenic Res. 9, 279-299 (2000).
Pogue G. P. et al. Production of pharmaceutical □grade recombinant aprotinin and a monoclonal antibody product using plant□based transient expression systems. Plant Biotechnol. J. 8, 638-654 (2010).
Richael C. M., Kalyaeva M., Chretien R. C., Yan H., Adimulam S., Stivison A., Weeks J. T., Rommens C. M., Cytokinin vectors mediate marker-free and backbone-free plant transformation. Transgenic Res. 17:905-917 (2008).

Boutilier K, Offringa R, Sharma V K, Kieft H, Ouellet T, Zhang L, Hattori J, Liu C M, van Lammeren A A, Miki B L, Custers J B, van Lookeren Campagne M M Ectopic expression of BABY BOOM triggers a conversion from vegetative to embryonic growth. Plant Cell 14:1737-1749 (2002)

Nishimura A., Tamaoki M., Sakamoto T., Matsuoka M., Over-Expression of Tobacco knotted 1-Type Class 1 Homeobox Genes Alters Various Leaf Morphology. Plant Cell Physiol. 41(5) 583-590 (2000)

Song X F, Guo P., Ren S.-C, Xu T.-T., and Liu C.-M. Antagonistic Peptide Technology for Functional Dissection of CLV3/ESR Genes in Arabidopsis. Plant Physiol. 161(3):1076-1085 (2013)

Long J. M., Liu C. Y., Feng M. Q., Liu Y., Wu X. M., Guo W. W., miR156-SPLs Module Regulates Somatic Embryogenesis Induction in Citrus Callus. J Exp Bot. 69(12):2979-2993 (2018)

Zhang T. Q., Lian H., Tang H., Dolezal K., Zhou C. M., Yu S., Chen J. H., Chen Q., Liu H., Ljung K., Wang J. W. An intrinsic microRNA timer regulates progressive decline in shoot regenerative capacity in plant. Plant Cell 27(2):349-360 (2015)

Vercruyssen L, Tognetti V. B., Gonzalez N., Van Dingenen J., De Milde L., Bielach A., De Rycke R., Van Breusegem F., Inzé D. GROWTH REGULATING FACTOR5 Stimulates Arabidopsis Chloroplast Division, Photosynthesis, and Leaf Longevity. Plant Physiol. 167(3):817-832 (2015)

Malnoy, M. et al. DNA-free genetically edited grapevine and apple protoplast using CRISPR/Cas9 ribonucleoproteins. Front. Plant Sci. 7, 1904 (2016).

Subburaj, S. et al. Site-directed mutagenesis in Petunia× hybrida protoplast system using direct delivery of purified recombinant Cas9 ribonucleoproteins. Plant Cell Rep. 35, 1535-1544 (2016).

Woo, J. W. et al. DNA-free genome editing in plants with preassembled CRISPR-Cas9 ribonucleoproteins. Nat. Biotechnol. 33, 1162-1164 (2015).

Liang, Z. et al. Efficient DNA-free genome editing of bread wheat using CRISPR/Cas9 ribonucleoprotein complexes. Nat. Commun. 8, 14261 (2017).

Svitashev, S., Schwartz, C., Lenderts, B., Young, J. K. & Cigan, A. M. Genome editing in maize directed by CRISPR-Cas9 ribonucleoprotein complexes. Nat. Commun. 7, 13274 (2016).

Zhang, Y. et al. Efficient and transgene-free genome editing in wheat through transient expression of CRISPR/Cas9 DNA or RNA. Nat. Commun. 7, 12617 (2016).

Kim, H. et al. CRISPR/Cpf1-mediated DNA-free plant genome editing. Nat. Commun. 8, 14406 (2017).

What is claimed is:

1. A method for transforming a plant cell, the method comprising:
   introducing a heterologous morphogenic regulator into the plant cell, wherein the introducing comprises introducing a polynucleotide comprising the heterologous morphogenic regulator and/or a polypeptide comprising the heterologous morphogenic regulator into the plant cell, thereby transforming the plant cell,
   wherein the polynucleotide comprising the heterologous morphogenic regulator encodes an amino acid sequence having at least 95% sequence identity to SEQ ID NO:26 and/or the polypeptide comprising the heterologous morphogenic regulator has at least 95% sequence identity to SEQ ID NO:26.

2. The method of claim 1, further comprising introducing an editing system into the plant cell and/or into a second plant cell.

3. The method of claim 1, further comprising stimulating embryogenesis and/or organogenesis in the plant cell and/or a neighboring plant cell.

4. The method of claim 1, further comprising regenerating a transgene-free plant part or transgene-free plant using the plant cell.

5. The method of claim 1, wherein the plant cell is stably transformed with the polynucleotide encoding the heterologous morphogenic regulator, a polynucleotide encoding an editing system, and/or a polynucleotide encoding a selectable marker.

6. The method of claim 1, wherein the plant cell is transiently transformed with the heterologous morphogenic regulator, an editing system, and/or a polynucleotide encoding a selectable marker.

7. The method of claim 2, wherein the second plant cell is stably transformed with a polynucleotide encoding the editing system and/or a polynucleotide encoding a selectable marker.

8. The method of claim 1, further comprising inducing shoot formation using the plant cell.

9. The method of claim 1, further comprising, responsive to the introducing step(s), producing a plant part and/or plant that is non-transgenic.

10. The method of claim 1, further comprising inducing a neighboring plant cell comprising an editing system to multiply and/or regenerate.

11. The method of claim 10, wherein the plant part or plant comprises an edited polynucleotide and is transgene-free.

12. The method of claim 1, wherein the amino acid sequence is SEQ ID NO:26 and/or the polypeptide comprising the heterologous morphogenic regulator has the sequence of SEQ ID NO:26.

13. The method of claim 1, wherein the plant cell is a dicot plant cell.

14. The method of claim 1, wherein the plant cell is a blackberry, raspberry, or cherry plant cell.

15. The method of claim 1, further comprising introducing a polynucleotide encoding an editing system into a second plant cell, wherein the second plant cell is stably transformed with the polynucleotide encoding the editing system.

16. The method of claim 15, further comprising inducing the second plant cell to multiply and/or regenerate to produce a plant part or plant that comprises an edited polynucleotide and is transgene-free.

* * * * *

UNITED STATES PATENT AND TRADEMARK OFFICE
CERTIFICATE OF CORRECTION

| | | |
|---|---|---|
| PATENT NO. | : 12,344,850 B2 | Page 1 of 1 |
| APPLICATION NO. | : 17/630973 | |
| DATED | : July 1, 2025 | |
| INVENTOR(S) | : Cheng et al. | |

It is certified that error appears in the above-identified patent and that said Letters Patent is hereby corrected as shown below:

In the Specification

Column 12, Line 40: Please correct "0-conglycinin," to read --β-conglycinin,--

Column 25, Line 19: Please correct "dead Cas12a" to read --deadCas12a--

Column 29, Line 54: Please correct "thereof," to read --thereof;--

Column 29, Line 57: Please correct "thereof," to read --thereof;--

Column 45, Line 46: Please correct "90-" to read --90-,--

Column 84, Line 62: Please correct "pharmaceutical □grade" to read --pharmaceutical-grade--

Column 84, Line 64: Please correct "plant□based" to read --plant-based--

Column 85, Line 10: Please correct "knotted 1-Type Class 1" to read --knotted1-Type Class1--

Signed and Sealed this
Thirtieth Day of December, 2025

John A. Squires
*Director of the United States Patent and Trademark Office*

SEQUENCE LISTING

```
<160> NUMBER OF SEQ ID NOS: 135

<210> SEQ ID NO 1
<211> LENGTH: 972
<212> TYPE: DNA
<213> ORGANISM: Rubus occidentalis

<400> SEQUENCE: 1
atggactgcg gcggcccaac aacaaacaag gacaagctcc tcgtcattat gggagccacc      60
ggcgccggca agtcgcggct atccctcgac ctcgccgctt gcttccctcc ggcaaccttc     120
gaagtcatca acgcggataa aatgcaggtc tacaagggac tcgacatcac caccaacaag     180
ctccccgctc cggagcgact cggcgtcccg caccacttgc tcggcgagtt cgactcgctc     240
gacggcgagg ttactcccgc caagtttcgc gagctcgcgg ctcgggtggt ttccggcgtt     300
agtgctcgga ggaaagtgcc tgtgcttgtg ggtgggtcca actcattcat ccacgcgctg     360
gtcgtcgacc ggttcgaacc aggttttaat gtctttgacg gcgactctgt gacagtatcg     420
atctcatcgg agctccggta caattgttgt tttctctggg ttgatgtgtc gtcggtggtg     480
ttgacggagt acttgtcgaa gcgagtagac gaaatgctag actcggggat gttactcgag     540
ctggccgagt tttacaactc ggccgaggaa gactcggtgg ttcgaacggg gataagaaag     600
tccatcggag tagcggagtt cagccggtat tttaggaagc acccgccgcc gggaggtagc     660
gaggaggtgg gggacgatga cccggtacgg agagaagcat ataaggacgc cgtgagggaa     720
attaagctga acacgtgtca gctggcgaag aggcagattg gaaaaatctc acggctgagg     780
ggggcggggt ggaacctacg gaggttagat gcgacggagg cgtttagggc ggcggtgaag     840
tcagatgaaa aagacgggaa taggtggtcg gagatttggg aaagagaggt ggttggacca     900
agcgtgaaga ttgtgaatca tttcttggag gaggagattc aatcaacaaa agtacaaaat     960
caaaagattt ag                                                         972
```

```
<210> SEQ ID NO 2
<211> LENGTH: 972
<212> TYPE: DNA
<213> ORGANISM: Rubus occidentalis

<400> SEQUENCE: 2
atggattgcg gcggacctac taccaataag gataagctgt tggttattat gggcgctacc    60
ggcgccggaa agtctagact gtcattggat cttgctgcct gttttccacc agctacattc   120
gaagttatta atgctgataa gatgcaggtt tacaaaggac tggatatcac aactaacaaa   180
ctgcctgcac cagagcgctt gggtgttcct catcaccttc tgggcgaatt tgattctctt   240
gatggagagg tgaccccagc taagttcaga gaactggcag ctcgcgtggt ttctggcgtt   300
tcagccagac gcaaagtgcc tgttctggtg ggtggctcta attcttttat tcatgccttg   360
gtggttgata gattcgaacc aggctttaat gtgttcgatg gcgattctgt tactgtgtca   420
atctcttcag agcttcgcta taattgctgt tttctgtggg ttgatgtgtc ttcagtggtt   480
cttaccgaat acctgtctaa gagggtggat gagatgttgg attcaggcat gttgcttgaa   540
cttgctgagt tctacaactc tgccgaggaa gattcagtgg ttcgcacagg cattaggaag   600
tctatcggag ttgctgaatt ttcaaggtat ttcagaaaac atccaccacc aggcggctct   660
gaggaagttg gagatgatga tcctgtgagg agagaagcct acaaggatgc agtgcgcgag   720
atcaaattga atacatgcca gcttgccaag aggcagattg gtaaaatctc aagattgcgc   780
ggtgcaggct ggaacctgcg caggttggat gcaactgagg cttttagagc cgctgttaag   840
tctgatgaaa aagatggtaa caggtggtca gagatttggg aaagagaggt ggttggccca   900
tctgtgaaga ttgtgaatca cttcctggag gaagagatcc agtcaactaa ggtgcagaac   960
cagaaaatct ga                                                       972

<210> SEQ ID NO 3
<211> LENGTH: 1074
<212> TYPE: DNA
<213> ORGANISM: Rubus occidentalis

<400> SEQUENCE: 3
atgacacttg attccttccc aactcttcat tattcttatt ataatattac cccccattct    60
ctctcctcgc cggcggtcac cctcactccc ccaccatctc ttccccaaaa gccgcgctgg   120
gcccgaatgg actccggccc agcaacaact acaaccgtcc cactccggca caaggacaag   180
cttgttgtca tcatgggagc caccggagcc ggaaagtccc gtctctcaat cgacctcgcc   240
actcacttcc cttcttgctt cgaaatcatc aactcggaca aaatgcaggt ctacaaggga   300
ctcgacatca ccaccaacaa gattccagtt cccgaccgta tcggagttcc ccaccacctc   360
ctcggtcagt tcgacccgct cgacggggag ctcaccccg ccgagtttcg acaactcgcc   420
ggtcaagccg tttccgccat tacttctcgg cggaaagtgc ccatgcttgt gggtgggtcc   480
aactctctaa tacacgccct cctcgttgac cggttcgaac cgggtgtaga tgtcttcgaa   540
ggcggcgccg ccatatcgtc ggagctcagg tacaattgct gctttctctg ggttgatgtc   600
tccttgacgg ttttagcgga ctacttgtct aagcgagtag acgaaatgct cgactcggga   660 atgtggagg agttggccga ttttgcgac ccggaagatg acgacttggc gattcgaacc   720
gggttgagaa aggctattgg agtaccggag ttcagccggt ttttcaaaaa atacccgccg   780
atttgtcaga gtcagaaggc gaggcccgat gatccggtgc ggagaggagc atataaagaa   840
gcggttaggg ccattaagga caacacgtgt cagctggcca agacgcagat tggaaagatt   900
```

```
ctacggctta gagtggcggg agggtgggac ctacagaggc tagatgcgac cgaggcgttc      960
agggcggtgg tgacgtcaga agacgatgcc ggaaagaggg ggtcagagat atggcagaaa     1020
caggtggtgg aagcaagcgt gaaaattgtg aagcgattct tggagcagga gtag           1074

<210> SEQ ID NO 4
<211> LENGTH: 1074
<212> TYPE: DNA
<213> ORGANISM: Rubus occidentalis

<400> SEQUENCE: 4
atgacattgg attcttttcc tactcttcat tactcatact acaacatcac tcctcactca       60
ctgtcttcac cagcagtgac tctgactcca ccaccatctc tgcctcagaa gccaagatgg      120
gctcgcatgg attctggacc tgccactacc acaactgttc cacttagaca taaggataaa      180
ctggtggtta ttatgggtgc aacaggcgct ggaaaatctc gcctgtcaat cgatttggcc      240
actcactttc cttcttgctt cgagattatc aattcagata agatgcaggt ttacaaaggc      300
ctggatatta ccacaaacaa gatccctgtg ccagatagaa ttggagttcc acatcacctg      360
ttgggtcaat tgatcctct tgatggcgag ctgaccccag ctgaattccg ccagttggcc       420
ggtcaggcag tgtctgctat tacatcaaga cgcaaagtgc ctatgctggt tggcggatct      480
aattcattga tccatgccct tctggttgat aggtttgagc caggcgtgga tgttttcgaa      540
ggtggcgctg ccatctcttc agagcttaga tataactgct gttttcctgtg gtggatgtt     600 tctctgactg tgttggccga ttacttgtca agagagttg atgaaatgct tgattctgga      660
atgcttgagg aactggcaga gttttgtgat cctgaagatg atgatttggc aattaggacc     720
ggtcttagaa aggctatcgg cgtgccagag ttctcaagat ttttcaagaa gtatcctcca     780
atctgccagt ctcagaaagc ccgccctgat gatccagtga ggagaggcgc atacaaggaa     840
gccgttaggg caatcaaaga taacacctgt cagcttgcta agacacagat tggaaaaatc    900
ttgcgcctta gggttgctgg cggctgggat ttgcagcgcc ttgatgctac tgaggccttt      960
agggcagtgg ttacctcaga agatgatgca ggcaagcgct ggtctgagat ttggcagaaa    1020
caggtggttg aagcttctgt gaagatcgtt aaaaggttct tggagcagga atga            1074

<210> SEQ ID NO 5
<211> LENGTH: 1125
<212> TYPE: DNA
<213> ORGANISM: Prunus avium

<400> SEQUENCE: 5
atgacacttc atcccttccc aactcactcc caccaccatt attctaatct caatttctat       60
tcttatatct ctcgtttcca cttgttcccg ccggtcaacc acctctgccc caccactcct      120
tcccatcatc atcctctccc ccacatcaag ccccgccgcg gggcccacat atcctccggc      180
cccaccaccc cacgccaaca acaacagcgc aaggacaagc ttctcattat cttgggcgcc     240
accggcgccg gcaagtcccg cctctccctc gacctcgcca cccgcttccc tttcttcgaa     300
atcgtgaact ccgacaaaat gcaactctac gccggcctcg acatcaccac caacaagctt     360
cccatccccg accgctcgg cgtccccac catctcctcg gcgagttcga ccctcgccac       420
ggcgatttta cgcccgccca attccgcgcc gttgccggtc aagccatttc cagcattacg     480
aatcgaagga aggtgccgat gctcgtcggc ggctccaact ccttcattca tgcgctcctc     540
gtggaccggt cgaaccgggc tccaatgtc ttcgaaccgg gtttcaatgg ctctgtctct      600
tccgagctca ggtataattg ctgttttctg tgggtggacg tgtcgttgac ggtcttgacg     660
```

```
gagtacttgt gcaagcgagt cgacgaaatg ctcgactcgg ggatgttgga cgagttggcc    720
gagttctgcg acccggatcg ccaggacgaa gacgaattga cggcgagtca gacagcgttg    780
agaaaggcga ttggcgtgcc cgagttcact cggtattttg aaaaatatcc accacagggg    840
aggggcggag agggtgatga tcgggagcgg agggaagcat acgaagaggc ggtgagggcg    900
atcaaggaca cacgtgtcag gctggcgaag aggcagatag ggaagatcct acggctgaag    960
ggaggagggt gggacctacg gaggctagat gcaacggacg cgtttagggc ggtggttgcg   1020
acgacgtcgt cggataagga cgacggaaag aggtggtcag agatatggga gaggcaggtt   1080
gtcaaaccaa gcgtgaaggt tgtgaagcgt ttcttggacg agtag                   1125

<210> SEQ ID NO 6
<211> LENGTH: 1125
<212> TYPE: DNA
<213> ORGANISM: Prunus avium

<400> SEQUENCE: 6
atgactcttc atccatttcc tacccactct catcaccatt actcaaatct gaacttctac     60
tcttacattt cacgctttca cctgtttcca ccagttaatc acttgtgccc aactacccct    120
tctcaccatc acccattgcc tcatattaag ccaagacgcg gagcccacat ctcttcaggt    180
ccaacaactc aagacagca gcagcagaga aaggataaac tgttgattat ccttggtgca    240
acaggagctg gcaagtctcg cctgtcattg gatcttgcaa ctaggtttcc attttttcgag    300 atcgtgaact cagataagat gcagctttac gctggcctgg atattaccac aaacaagttg    360
ccaatccctg ataggcttgg cgttcctcat caccttctgg gagaattcga tccaagacat    420
ggcgatttta cccctgccca gttccgcgct gtggctggac aggcaatctc ttcaatcaca    480
aacaggagaa aagtgcctat gctggttggc ggatctaact cttttattca cgccttgctt    540
gtggatcgct tcgagccagg ttctaatgtt tttgaacctg gcttcaacgg atcagtgtct    600
tcagagctta ggtataattg ctgttttctg tgggtggatg tttctcttac agttctgact    660
gagtacctgt gcaagagagt ggatgaaatg ttggattcag gcatgttgga tgagcttgca    720
gaattctgtg atccagatcg ccaggatgag gatgaattga ccgcctctca gacagcactt    780
aggaaagcta ttggagttcc tgagtttact agatatttcg aaaagtaccc acctcagggt    840
cgcggtggcg aaggcgatga tagggagcgc agggaagctt atgaggaagc cgtgagagca    900
atcaaagata cacttgtcag gctggccaag agacagattg gcaaaatcct gagactgaag    960
ggcggcggct gggatctgag aagactggat gctaccgatg cctttagggc agtggttgct   1020
actacctctt cagataagga tgatggaaaa aggtggtctg agatctggga agacaggtg    1080 gttaagccat cagttaaggt ggttaaaaga ttcttggatg agtga                   1125

<210> SEQ ID NO 7
<211> LENGTH: 1173
<212> TYPE: DNA
<213> ORGANISM: Rubus occidentalis

<400> SEQUENCE: 7
atggaggaat acaataacag taatgaaatg gatcatgaga gttcaggtac tcccagagga     60
aatttcctgt acgcatctcc aaatctcgga ggtaactatg gtagaactgc cgcaggtgat    120
cataatcagc agatcaacac cttcatctt caatcaagcg gtggcgagtg ttttcagtcc    180
ggaggaacag cacagcccac cgtgaagacc gaagcagcag gtagcacttc ccaacatgct    240
```

| | | |
|---|---|---|
| ccccacaaat ttcatcatca gtttcctcct ccctcattaa tattgtcaag aggtcagaat | 300 | |
| gatcagctac cagttcagca acaacagcac atagaaaacg agaatgaagt ggaggccatc | 360 | |
| aaggctaaaa tcatcgctca ccctcactac tctaatctct tgcaagctta catggattgc | 420 | |
| caaagggtgg gagctccgtc tgaagtcgtg gctcgtctcg cagctgcgcg ccaggagttt | 480 | |
| gaagcacgac agcgatcttt agtcagttcg agagatgctt cttcgaaaga cccagaactc | 540 | |
| gatcagttca tggaagctta ctatgatatg ttggttaaat atcgggagga actaacaagg | 600 | |
| cccatacaag aagcaatgga tttcatgagg aagattgaaa ctcagcttaa catgctcggc | 660 | |
| aatgacagta gcactactcc tcttcgcatc ttctcggcct cggcgcaaga ggacaaatgt | 720 | |
| gacggaaatg gttcatctga gaggaccagg acaacaata gtggtggaga aactgaagtg | 780 | |
| gccgagatcg atccgagagc cgaagacaga gaactcaaga tcacctcttg agaaagtac | 840 | |
| agtggttact taagtagcct caagcaagaa ctctccaaga aaagaagaa aggcaaattg | 900 | |
| cccaaagatg ccaggcagaa gcttctgagt tggtgggagt tgcactacaa gtggccatat | 960 | |
| ccttcggagt cggagaaggt ggcattggcg gagtcgacag gtttggatca gaagcagata | 1020 | |
| aacaattggt tcataaatca aaggaagcgg cactggaagc catcggagga catgcagttc | 1080 | |
| atggtgatgg atgggttgca cccacagaat gcagcaactc tctacatgga tggacactac | 1140 | |
| attggtgatg gtcattaccg tctcggtccc taa | 1173 | |

<210> SEQ ID NO 8
<211> LENGTH: 1362
<212> TYPE: DNA
<213> ORGANISM: Rubus occidentalis

<400> SEQUENCE: 8

| | | |
|---|---|---|
| atggaggaat acaataacag taatgaaatg gatcatgaga gttcaggtac tcccaggtaa | 60 | |
| gtttctgctt ctacctttga tatatatata ataattatca ttaattagta gtaatataat | 120 | |
| atttcaaata tttttttcaa aataaaagaa tgtagtatat agcaattgct tttctgtagt | 180 | |
| ttataagtgt gtatatttta atttataact tttctaatat atgaccaaaa tttgttgatg | 240 | |
| tgcaggggaa atttcctgta cgcatctcca aatctcggag gtaactatgg tagaactgcc | 300 | |
| gcaggtgatc ataatcagca gatcaacacc tttcatcttc aatcaagcgg tggcgagtgt | 360 | |
| tttcagtccg gaggaacagc acagcccacc gtgaagaccg aagcagcagg tagcacttcc | 420 | |
| caacatgctc cccacaaatt tcatcatcag tttcctcctc cctcattaat attgtcaaga | 480 | |
| ggtcagaatg atcagctacc agttcagcaa caacagcaca tagaaaacga gaatgaagtg | 540 | |
| gaggccatca aggctaaaat catcgctcac cctcactact ctaatctctt gcaagcttac | 600 | |
| atggattgcc aaagggtggg agctccgtct gaagtcgtgg ctcgtctcgc agctgcgcgc | 660 | |
| caggagtttg aagcacgaca gcgatctta gtcagttcga gagatgcttc ttcgaaagac | 720 | |
| ccagaactcg atcagttcat ggaagcttac tatgatatgt tggttaaata tcgggaggaa | 780 | |
| ctaacaaggc ccatacaaga agcaatggat ttcatgagga agattgaaac tcagcttaac | 840 | |
| atgctcggca atgacagtag cactactcct cttcgcatct tctcggcctc ggcgcaagag | 900 | |
| gacaaatgtg acggaaatgg ttcatctgaa gaggaccagg acaacaatag tggtggagaa | 960 | |
| actgaagtgg ccgagatcga tccgagagcc gaagacagag aactcaagaa tcacctcttg | 1020 | |
| agaaagtaca gtggttactt aagtagcctc aagcaagaac tctccaagaa aaagaagaaa | 1080 | |
| ggcaaattgc ccaaagatgc caggcagaag cttctgagtt ggtgggagtt gcactacaag | 1140 | |
| tggccatatc cttcggagtc ggagaaggtg gcattggcgg agtcgacagg tttggatcag | 1200 | |

| | |
|---|---:|
| aagcagataa acaattggtt cataaatcaa aggaagcggc actggaagcc atcggaggac | 1260 |
| atgcagttca tggtgatgga tgggttgcac ccacagaatg cagcaactct ctacatggat | 1320 |
| ggacactaca ttggtgatgg tcattaccgt ctcggtccct aa | 1362 |

<210> SEQ ID NO 9
<211> LENGTH: 1068
<212> TYPE: DNA
<213> ORGANISM: Prunus avium

<400> SEQUENCE: 9

| | |
|---|---:|
| atggaagagt acaaccaaat ggatcatgag agctcaggtg gtagaggaaa tttcctgtac | 60 |
| gcctcaccaa atcttggagg caactatggg agggcaagcc atgatcatca gatgggcatc | 120 |
| aacgcctttc atcttcaatc gagcggtggt ggtgatttcc actctccagg aggagcacac | 180 |
| ccaattaatg tcaagactga agccagcaca tcccatcatg gccatcacaa atttcagtac | 240 |
| aacaacaaca acaataataa taataataat cctcttctgt catcaagagg gcaccaacca | 300 |
| gtagttcaac aacagcataa tctggaccgt caaaacgatg atcacaccct gagctccaac | 360 |
| gaagtggaag ccatcaaagc caagatcatc gcccaccctc agcagcggtc ttcagtggct | 420 |
| tcaagagagg cttcaaaaga tccagaactc gatcagttca tggaagctta ctatgatatg | 480 |
| ttggtgaaat atcgagagga gctaacaagg cccatacaag aagccatgga tttcatgcgg | 540 |
| aggattgaaa ctcagctcaa catgcttggc aacaataatg ctcctcctct tcgcatcttc | 600 |
| tcaccctctg aggacaaatg tgaaggaatt ggttcatctg aagaggagca ggagaatagt | 660 |
| ggtggagaaa cagaagtgcc tgagattgat ccaagagctg aagacagaga gctcaagaac | 720 |
| cacctgttga aaaagtatag tggttactta agtagcctga gcaagagct ttccaagaaa | 780 |
| aagaagaaag ggaaattgcc caaagatgcc aggcagaagc ttctcagttg gtgggagttg | 840 |
| cattacaagt ggcccatatcc ttcagaatcg gagaaggtgg cattggcgga gtcaaccggt | 900 |
| ttggatcaga acaaataaa caattggttc ataaatcaga ggaagaggca ctggaaaccc | 960 |
| tcagaggaca tgcagttcat ggtgatggat ggcctacacc ctcagaatgc ggccctgtat | 1020 |
| atggatggac actacatagg cgatggccac taccgtctgg ggccatga | 1068 |

<210> SEQ ID NO 10
<211> LENGTH: 1068
<212> TYPE: DNA
<213> ORGANISM: Prunus avium

<400> SEQUENCE: 10

| | |
|---|---:|
| atggaagagt acaaccaaat ggatcatgag agctcaggtg gtagaggaaa tttcctgtac | 60 |
| gcctcaccaa atcttggagg caactatggg agggcaagcc atgatcatca gatgggcatc | 120 |
| aacgcctttc atcttcaatc gagcggtggt ggtgatttcc actctccagg aggagcacac | 180 |
| ccaattaatg tcaagactga agccagcaca tcccatcatg gccatcacaa atttcagtac | 240 |
| aacaacaaca acaataataa taataataat cctcttctgt catcaagagg gcaccaacca | 300 |
| gtagttcaac aacagcataa tctggaccgt caaaacgatg atcacaccct gagctccaac | 360 |
| gaagtggaag ccatcaaagc caagatcatc gcccaccctc agcagcggtc ttcagtggct | 420 |
| tcaagagagg cttcaaaaga tccagaactc gatcagttca tggaagctta ctatgatatg | 480 |
| ttggtgaaat atcgagagga gctaacaagg cccatacaag aagccatgga tttcatgcgg | 540 |
| aggattgaaa ctcagctcaa catgcttggc aacaataatg ctcctcctct tcgcatcttc | 600 |

```
tcaccctctg aggacaaatg tgaaggaatt ggttcatctg aagaggagca ggagaatagt      660
ggtggagaaa cagaagtgcc tgagattgat ccaagagctg aagacagaga gctcaagaac      720
cacctgttga aaagtatag tggttactta agtagcctga agcaagagct ttccaagaaa       780
aagaagaaag ggaaattgcc caaagatgcc aggcagaagc ttctcagttg gtgggagttg      840
cattacaagt ggccatatcc ttcagaatcg gagaaggtgg cattggcgga gtcaaccggt      900
ttggatcaga acaaataaa caattggttc ataaatcaga ggaagaggca ctggaaaccc       960
tcagaggaca tgcagttcat ggtgatggat ggcctacacc ctcagaatgc ggccctgtat     1020
atggatggac actacatagg cgatggccac taccgtctgg ggccatga                  1068
```

<210> SEQ ID NO 11
<211> LENGTH: 2103
<212> TYPE: DNA
<213> ORGANISM: Rubus occidentalis

<400> SEQUENCE: 11

```
atgaacatga actggttggg tttctctctt tcccctcaag aagatgatgc tccaatatca       60
caccagctgg ctgaccaaga gacgttagcc tctcgccttg gcttcaactc caatgatcaa      120
atccaaggtg ccggcggtga ggcagattgg aatatgaagg gtgtagacat gaactcatca      180
gatggcaata actacaaaag gacctcatca tcatccgatc tgtcgcctat gctaatggga      240
agcagtacta ctactagtac ttcatgcagc attatcagcc agccaaacct tgaaaatcat      300
catcaacaac aacaactacc aaagcttgaa aacttccttg ccgacattc ttttgcggat       360 catgaccaaa gtagtactag tcatgattac atgttcgata tgaataatgg accgggtgca      420
attagcagta atgttatgaa tacttctaat actaatagta acaatattgg gctgtccatg      480
atcaagactt ggctgaggaa tcaacctcct cagccgcgcg ataacaacca ccagctggag      540
caggagagca agactactaa ggagagcaga atcaaccac agagtagtct atcgctctca       600
atgagtactg gatcgcttca tacagtaaca actgcaactg caggtggtgc cagtgccagt      660
gccggtgccg gggaaactac ctcatcatca ataataata gaaagcagtc gccagttttg       720
acagccacaa caactgatcc ccaaactcaa actactggtg gtgccattga ggctgtgccc      780
agaaaggcca ttgatacatt tggccagagg acttctatat accgtggtgt aaccaggcac      840
agatggacag gtagatatga agctcatcta tgggataata gctgccgaag agagggacaa      900
actcgcaagg gaaggcaagg tggttatgac aaagaagaca aggcagctag agcttatgac      960
ttagcagcat tgaaatattg gggcaccaca accactacca actttccgat cagtacctat     1020
gaaaaagaga tagatgaaat gaagccgatg acaagacagg agtatgttgc atctctgaga     1080
aggaagagta gcgggttttc tcgaggtgca tccatttatc gagggggtaac caggcaccac     1140 cagcatggga gatggcaagc aagaattggt agagttgcag ggaacaaaga tctgtacctt     1200
ggaactttca gtacccaaga ggaagcagct gaggcgtatg acattgctgc cataaagttc     1260
cgaggactca atgcggtaac aaactttgac atgagcagat atgatgtcaa gtccattctg     1320
gagagcagcg cattgcccat tactactggt gcctctgcaa agcgattgaa ggatgttcag     1380
cagcagcctc ctcctccggc agatcatcat catcagatca tgttgtcgtc tgtgctggat     1440
catcacggac agatgatcag atcttcatcg tcaacagagc atgatatcat gggcaatatc     1500
tttcatcagg atgatgatca tctccgtcaa caacttcaga tgggaggcac ccacaatttc     1560
ttccatgatc atgatcacca gcagcgtagc ggccttatgg gattaatgga ttcttcggca     1620
gcagcagctt ctatggaaca cagctcaggc tctaattctg tcatatatag tgttgggggat    1680
```

```
caccatggta ataataatgg atatggaagc aatgctagag ggactggtag tggctatata    1740
atgcccatgg ctatgagtac agttgtggct aatcatggcc aaaatcaagc tgatggaaat    1800
aatatcaatg gtttcggaga tggtgatggt gatgatcagg aagtgaatat taaggcgcag    1860
cagcttggtt atgatcatca tcaaaatgtg tttctgggtt caagtaatac tacagatccc    1920
gcttatcagc atcacgcaag caacaggaac ttgtattatc aacttccagt acatgatgac    1980
cagcatgaat cgtcatcaga agcagtagct actagtagta ctacatgtaa catgaattgg    2040
gttccaacag ctgttccaac tcatcttgct cattctactt ttacagtctg gaacgacaca    2100
tag                                                                  2103

<210> SEQ ID NO 12
<211> LENGTH: 2103
<212> TYPE: DNA
<213> ORGANISM: Rubus occidentalis

<400> SEQUENCE: 12
atgaatatga actggttggg ctttctctct tctccacagg aagatgatgc tcctatttct      60
catcagctgg ccgatcagga aactctggca tctagattgg gcttcaattc aaacgatcag     120
atccagggag ctggcggaga ggccgattgg aatatgaagg gtgtggatat gaactcttca     180
gatggcaata actataagcg cacctcttca tcttcagatc tttctccaat gctgatgggt     240
tcttcaacta ccacatctac atcatgctct attatctcac agccaaattt ggagaaccat     300
caccagcagc agcagttgcc taagcttgaa aatttcttg gcagacattc tttcgccgat     360
cacgatcagt cttcaacctc acacgattac atgtttgata tgaataacgg acctggtgca     420
atctcttcaa acgttatgaa cacttctaac accaactcaa ataacatcgg actgtctatg     480
atcaaaacat ggttgaggaa tcagccacct cagccaagag ataataacca tcagctggag     540
caggaatcta agactaccaa agagtcaagg aaccagcctc agtcttcact gtcattgtct     600
atgtcaactg gttctttgca caccgtgaca actgctacag ccggtggcgc atctgcttca     660
gctggcgctg gcgagactac atcttcatct aataacaata gaaagcagtc accagttttg     720
accgctacta ccacagatcc tcagacacag actaccggag gtgccattga agcagtgcca     780
aggaaagcca tcgatacttt cggacagaga acctctatct atcgcggtgt tacacgccat     840
aggtggactg cagatacgag gctcaccttt gggataatt catgtagacg cgaaggacag     900
actagaaagg gtcgccaggg cggatatgat aaggaagata agctgctag agcttatgat     960 ctggcagctt tgaaatactg gggcacaact accacaacta acttcccaat ctctactat     1020 gagaaggaaa tcgatgagat gaaacctatg accagacagg aatacgtggc ttcactgagg    1080
agaaagtcat ctggattctc tcgcggtgcc tcaatctatc gcggagtgac taggcatcac    1140
cagcatggta ggtggcaggc taggatcggc agagttgccg gaaataagga tctttatctg    1200
ggcacatttt ctactcagga agaggctgca gaggcatacg atattgctgc catcaagttt    1260
cgcggactta atgctgtgac caacttcgat atgtctagat acgatgttaa atcaatcttg    1320
gaatcatctg cccttccaat caccacaggc gcttctgcca agcgcctgaa agatgtgcag    1380
cagcagccac caccaccagc tgatcatcac catcagatta tgttgtcatc tgttcttgat    1440
caccatggac agatgatcag gtcatcttca tctactgagc atgatattat gggtaatatc    1500
ttccatcagg atgatgatca cctgagacag cagttgcaga tgggtggcac ccacaacttt    1560
ttccacgatc atgatcacca gcagcgctct ggtcttatgg gcctgatgga ttcatctgca    1620
```

```
gctgccgcat ctatggaaca ttcatctgga tctaattctg tgatctattc agttggcgat   1680
catcatggca acaataacgg ttatggctct aacgcccgcg aacaggttc aggctacatc    1740 atgcctatgg caatgtctac tgtggttgct aatcacggcc agaaccaggc agatggaaat   1800
aacattaatg gctttggcga tggcgatggc gatgatcagg aagtgaacat caaggctcag   1860
cagcttggtt atgatcacca tcagaatgtt ttcctgggct catctaacac taccgatcca   1920
gcataccagc accatgcttc taataggaac ctttattacc agctgcctgt gcatgatgat   1980
cagcacgagt catcttcaga agcagttgct acatcttcaa aacttgcaa tatgaactgg    2040 gtgccaaccg ccgttcctac acatttggca cactcaacct ttacagtttg aatgatact    2100 tga                                                                2103

<210> SEQ ID NO 13
<211> LENGTH: 1599
<212> TYPE: DNA
<213> ORGANISM: Prunus avium

<400> SEQUENCE: 13
atgggttcca tgaactggtt gggtttctct ctttcccctc aagaagtcgt tcctgctgat     60
ccatccatat ctgagggtga tcatcatcat caacatcatg acggccatga gttatctgat    120
gatcagaccg ccacactagt ctctcgcctt ggcttcaagt actccgatga catctccggt    180
accgatgtca ccgaggctg ctttgatctc acttctcatg atgactcatc cgctactact     240
actgctgctg ctgttcctaa taatcattct cacaaccacc tcatccctcc acctttggc    300 atgcttcatc aagctgctgc attcaacacc accaatattc actcccaagg tgcagattgg   360
agtaatatga actcatcaga tagcagcacc tacaagacga cttcagacca cctgtctatg   420
ctgatgggaa gcaacagttc gtacagaagc caaaaccttg aaaataatca tcaacagcca    480
aagcttgaaa acttccttgg ccgacactcc ttcgttgcgg atgagcacca tcggcggc     540 cagagtagta gtggcacgca tgcatacaat aataatagca ccagcaatac aatcagact     600 cttccgcttt cgatgagtac tggatctcac actcatcata atactactag tactgctgct    660
gctggagaaa cttgttcatc agatcgagat aatacttgta ataataataa caagctggca    720
gttgttagga ccaccgcctc aaccgctcct cccctgggga tcgatagcca gactactagt    780
actactgcta ctgctattga ggccgtgccc agaaagtccg ttgatacttt tggacagagg    840
acttctatat accgtggcac agatggacag gtagatatga agctcatctc tgggataata    900
gttgccggag agaaggacaa actcgcaagg gaaggcaaga tcagcaacta tgagaaagag    960
atagacgaaa tgaagcacat gacgagacag gagtacgttg catctttaag aaggaagagt   1020
agtggctttt ctcgtggtgc atccatttat cgaggggtaa caagacacca ccagcatggg   1080
agatggcaag caaggattgg tcgagtcgca gggaacaaag atctctacct gggaacatt    1140 agctccaact ctgtcatgta tagcactgct actactacta atggaggagg aggaggagga   1200
ggaggagatc atggtggcta tataatccca atgggtacag ttatatctaa tgatcacaat   1260
gatggttttg gagatggcac taatcatgat catcaggtga aggcggtggc gcttggattt    1320
gaaaatgtgt ttggctcaac ttctgcttct gttaatgcta caaatgttac tagggatgct   1380
tataataatc atgcaaggaa cttgtattat cttccgcagc agctgccgca atcgtcatca   1440
gtgtcatcag tatcatcagc aggtgtggcc aagggcggca gcgcatatga tattcatgaa   1500
gcagggcaat gtaacaattg gatgcccaca gcagttccaa cgtcgactaa cagtaacatc   1560
aacatgcctc ctactttcac tgtctggaat gacacataa                          1599
```

<210> SEQ ID NO 14
<211> LENGTH: 1599
<212> TYPE: DNA
<213> ORGANISM: Prunus avium

<400> SEQUENCE: 14

| | | | | | |
|---|---|---|---|---|---|
| atgggctcta | tgaattggct | tggattttct | ctgtctccac | aggaagtggt | gccagccgat | 60 |
| ccttctattt | cagaaggcga | tcatcaccat | cagcaccatg | atggacatga | gctgtctgat | 120 |
| gatcagactg | caaccttggt | gtcacgcctt | ggttttaaat | actctgatga | tatctcaggc | 180 |
| actgatgtta | ccggcggatg | cttcgatttg | acctctcacg | atgattcttc | agcaactacc | 240 |
| acagctgccg | cagttcctaa | taaccactca | cataatcacc | ttattccacc | tccatttggt | 300 |
| atgctgcatc | aggctgccgc | attcaatact | accaacatcc | actctcaggg | cgctgattgg | 360 |
| tcaaacatga | actcttcaga | ttcttctact | tataagacaa | cttctgatca | tttgtcaatg | 420 |
| cttatgggct | ctaattcttc | atacagatca | cagaacttgg | agaataacca | tcagcagcca | 480 |
| aagctggaaa | acttttggg | acgccactct | tcgtggcag | atgaacacca | tattggtggc | 540 |
| cagtcttcat | ctggcactca | tgcttacaat | aacaattcta | catcaaacac | tatccagacc | 600 |
| ctgtctttgt | caatgtctac | cggatctcac | acacaccata | acaccacatc | aacagctgct | 660 |
| gctggcgaga | cttgctcatc | tgatcgcgat | aatacatgta | acaataacaa | taagctggct | 720 |
| gtggttagga | ctaccgcctc | aactgcacct | ccacctggca | ttgattctca | gacaacttca | 780 |
| accacagcta | ccgccatcga | agctgtgcca | agaaagtctg | ttgatacttt | cggacagaga | 840 |
| acctcaatct | atcgcggaac | agatggtcag | gtggatatga | agttgatctc | tggaattatc | 900 |
| gttgccggtg | agaaggataa | acttgcaaga | gaaggcaaga | tttcaaacta | cgagaaggaa | 960 |
| atcgatgaga | tgaagcatat | gaccagacag | gaatacgttg | cttctctgag | aagaaagtct | 1020 |
| tctggctttt | ctcgcggagc | ctcaatctat | cgcggagtga | caaggcacca | tcagcacggt | 1080 |
| aggtggcagg | ctaggatcgg | tagagttgcc | ggcaataagg | atctttatct | gggcaccttc | 1140 |
| tcatctaact | ctgtgatgta | ctcaacagcc | actaccacta | atggcggcgg | cggcggcggc | 1200 |
| ggcggcgatc | atggcggata | cattatccca | atgggcactg | ttatttctaa | tgatcacaac | 1260 |
| gatggatttg | gcgatggcac | taaccatgat | caccaggtga | agcagttgc | tcttggtttt | 1320 |
| gagaatgtgt | tcggctcaac | ttctgcatca | gtgaatgcta | caaacgttac | tagggatgcc | 1380 |
| tataacaatc | atgcaagaaa | cctgtattac | ttgccacagc | agctgcctca | gtcatcttca | 1440 |
| gtgtcttcag | tttcttcagc | tggcgtggcc | aagggtggct | ctgcatacga | tattcacgaa | 1500 |
| gctggacagt | gtaacaattg | gatgccaaca | gctgttccta | catctactaa | ctcaaatatc | 1560 |
| aacatgccac | ctaccttcac | agtgtggaat | gatacttga | | | 1599 |

<210> SEQ ID NO 15
<211> LENGTH: 894
<212> TYPE: DNA
<213> ORGANISM: Rubus occidentalis

<400> SEQUENCE: 15

| | | | | | |
|---|---|---|---|---|---|
| atggaaccac | aatcccagca | accaactgag | gatggaggaa | gcaacaaagc | agctgggagt | 60 |
| gctaacatgc | tttgcaggca | gagcagtacc | aggtggactc | ccactactga | tcagataaga | 120 |
| atcctcaagg | agctttacta | caacaaggga | gttaggtccc | aagtgcaga | gcagattcag | 180 |
| aggatctgtc | tccagctgaa | acggtacgga | aagatcgagg | gaaagaatgt | cttttactgg | 240 |

| | |
|---|---|
| ttccagaacc acaaggctcg agagaggcag aagaagaggt tcacttcgga tgttcatgtg | 300 |
| cccatgcaaa gatcagggct tgttgggaac agtaacgtag ctaattggaa acctgaggat | 360 |
| cagtatctca acatgaacaa caagtactcc aacatttgtc aaggggtttc ttcttctgca | 420 |
| tctgcttctg cttcttcagc tggtgtggtt tcttttaatg gcagatggg gaactatggt | 480 |
| gtttatggat ctatgaacat ggagaagagt tttagggact gttcaatctc agctggagga | 540 |
| ggtaccagta ctactggtgt tggaattggt ggatccatta gtcacaatta cgggtcatgg | 600 |
| gtcggtggta gtgttgaccc gtattcctcc tcatcgtaca ccactactag tactactttc | 660 |
| tttgacaacc aaaaacaaat tttcatggaa gaagaagaag aggatcacca ggagattgaa | 720 |
| acccttcccc tgttccccat gcatggtgag acatctttg gcaacatcaa gacaacttcc | 780 |
| gaaggcggcg gcggcgacta cggctactac tccagcggct ggggcggtag ctctcgcact | 840 |
| tcccttgagc tcagcctcaa ttcctacggc tacaacaacc caactatta ctga | 894 |

<210> SEQ ID NO 16
<211> LENGTH: 894
<212> TYPE: DNA
<213> ORGANISM: Rubus occidentalis

<400> SEQUENCE: 16

| | |
|---|---|
| atggaaccac agtctcagca gcctactgag gatggcggat caaataaggc tgccggatct | 60 |
| gctaacatgc tgtgcaggca gtcttcaaca agatggactc caactaccga tcagatcagg | 120 |
| atcttgaagg aactttacta caataagggc gtgagatcac cttctgccga gcagattcag | 180 |
| cgcatctgtc tgcagttgaa gagatatggc aagattgaag caagaatgt gttttattgg | 240 |
| ttccagaacc ataaggcaag agagcgccag aagaagagat tcacttctga tgtgcacgtt | 300 |
| ccaatgcagc gctcaggtct ggtgggcaat tctaacgttg ctaattggaa gcctgaagat | 360 |
| cagtatttga acatgaataa caagtactca aacatttgcc agggtgtgtc ttcatctgca | 420 |
| tcagcttctg cctcatctgc cggcgtggtg tcttttaatg gccagatggg taactatggc | 480 |
| gtttacggat ctatgaatat ggagaaatct ttccgcgatt gttcaatctc tgcaggtggc | 540 |
| ggaacttcaa caactggcgt gggaattggt ggctcaatct ctcataatta tggctcatgg | 600 |
| gtgggaggtt ctgttgatcc atattcatct tcatcttaca ccacaacttc taccacattt | 660 |
| ttcgataacc agaagcagat tttcatggag gaagaggaag aggatcatca ggaaatcgag | 720 |
| actcttccac tgtttcctat gcacggagaa gatattttcg gtaatatcaa gactacctca | 780 |
| gagggcggag gtggcgatta cggctattac tcatctggat gggggaggttc atctagaaca | 840 |
| tctttggaac tttcactgaa ttcttatggc tacaataacc ctaactatta ctga | 894 |

<210> SEQ ID NO 17
<211> LENGTH: 918
<212> TYPE: DNA
<213> ORGANISM: Prunus avium

<400> SEQUENCE: 17

| | |
|---|---|
| atggaacctc aacaaaccca acaacaacca aatgaagatg cagcaacaa agggactagt | 60 |
| ggtactaatt ttctgtgcag gcaaagcagt acaaggtgga cacccacaag tgatcagatt | 120 |
| agaatattga aggacctttta ctacaacaat ggtgtgaggt ccccaagtgc agagcagatt | 180 |
| cagaggatct ctgctcggct gagacagtac ggcaagattg aaggcaagaa cgttttctat | 240 |
| tggtttcaga accacaaggc tcgtgagagg cagaagaaaa ggttcattga tgtaccagcc | 300 |
| ccacccatca tgcaaagatc agggcttggg attaataata atgctcctac tgcttatgaa | 360 |

```
cccattaatc acagcaacaa gtaccccaac atttctgctt ctgctggggt tcttctgca      420 tctgcttctt cagctggtgt gattgctgtt gggcaaatgg ggagctatgg ctatggatct      480
atgaccatgg agaagagttt tagggactgc tcaatatcag ctgcaggagg tactagtagt      540
ggtcatgttg gtggatctaa taataatatt ggtcacaacg ttggatcatg gttggtgtt       600 gatccatatt cttcacccta cactctcttt gacaagagat catcatcaag acaagtgttt      660
ggtgaccaag aaaatatgat ggatgaagaa gatcatgaat accaagaaaa cctgcaagat      720
tccccagaga ttgagaccct ccctctcttc ccatgcatg gtgaagacat ccatggcttt       780
ggcaacatca gtccacctc cgacagctac tactccggct ggtaccgctc cgacgagggc      840
aacaatggcc gcacttccct tgagctcagc ctcaattcct acggccacat gacccctgat      900
tatttcagct catattaa                                                    918

<210> SEQ ID NO 18
<211> LENGTH: 1107
<212> TYPE: DNA
<213> ORGANISM: Prunus avium

<400> SEQUENCE: 18
atggaacctc aacaaaccca caacaaacca atgaagatg gcagcaacaa aggtaagttt        60
ctgcttctac ctttgatata tatataataa ttatcattaa ttagtagtaa tataatattt      120
caaatatttt tttcaaaata aaagaatgta gtatatagca attgcttttc tgtagtttat      180
aagtgtgtat attttaattt ataactttc taatatatga ccaaaatttg ttgatgtgca      240
gggactagtg gtactaattt tctgtgcagg caaagcagta caaggtggac acccacaagt      300
gatcagatta gaatattgaa ggacctttac tacaacaatg gtgtgaggtc cccaagtgca      360
gagcagattc agaggatctc tgctcggctg agacagtacg gcaagattga aggcaagaac      420
gttttctatt ggtttcagaa ccacaaggct cgtgagaggc agaagaaaag gttcattgat      480
gtaccagccc cacccatcat gcaaagatca gggcttggga ttaataataa tgctcctact      540
gcttatgaac ccattaatca cagcaacaag taccccaaca tttctgcttc tgctggggtt      600
tcttctgcat ctgcttcttc agctggtgtg attgctgttg gcaaatggg gagctatggc       660 tatggatcta tgaccatgga gaagagtttt agggactgct caatatcagc tgcaggaggt      720
actagtagtg gtcatgttgg tggatctaat aataatattg gtcacaacgt ggatcatgg       780 gttggtgttg atccatattc ttcaccctac actctctttg acaagagatc atcatcaaga      840
caagtgtttg gtgaccaaga aaatatgatg gatgaagaag atcatgaata ccaagaaaac      900
ctgcaagatt ccccagagat tgagaccctc cctctcttcc ccatgcatgg tgaagacatc      960
catggctttg gcaacatcaa gtccacctcc gacagctact actccggctg gtatcgctcc     1020
gacgagggca caatggccg cacttccctt gagctcagcc tcaattccta cggccacatg       1080 accctgatt atttcagctc atattaa                                          1107

<210> SEQ ID NO 19
<211> LENGTH: 323
<212> TYPE: PRT
<213> ORGANISM: Rubus occidentalis

<400> SEQUENCE: 19

Met Asp Cys Gly Gly Pro Thr Thr Asn Lys Asp Lys Leu Leu Val Ile
1               5                   10                  15

Met Gly Ala Thr Gly Ala Gly Lys Ser Arg Leu Ser Leu Asp Leu Ala
```

```
            20                  25                  30
Ala Cys Phe Pro Pro Ala Thr Phe Glu Val Ile Asn Ala Asp Lys Met
            35                  40                  45

Gln Val Tyr Lys Gly Leu Asp Ile Thr Thr Asn Lys Leu Pro Ala Pro
        50                  55                  60

Glu Arg Leu Gly Val Pro His His Leu Leu Gly Glu Phe Asp Ser Leu
 65                  70                  75                  80

Asp Gly Glu Val Thr Pro Ala Lys Phe Arg Glu Leu Ala Ala Arg Val
                85                  90                  95

Val Ser Gly Val Ser Ala Arg Arg Lys Val Pro Val Leu Val Gly Gly
            100                 105                 110

Ser Asn Ser Phe Ile His Ala Leu Val Val Asp Arg Phe Glu Pro Gly
            115                 120                 125

Phe Asn Val Phe Asp Gly Asp Ser Val Thr Val Ser Ile Ser Ser Glu
            130                 135                 140

Leu Arg Tyr Asn Cys Cys Phe Leu Trp Val Asp Val Ser Ser Val Val
145                 150                 155                 160

Leu Thr Glu Tyr Leu Ser Lys Arg Val Asp Glu Met Leu Asp Ser Gly
                165                 170                 175

Met Leu Leu Glu Leu Ala Glu Phe Tyr Asn Ser Ala Glu Glu Asp Ser
            180                 185                 190

Val Val Arg Thr Gly Ile Arg Lys Ser Ile Gly Val Ala Glu Phe Ser
            195                 200                 205

Arg Tyr Phe Arg Lys His Pro Pro Gly Gly Ser Glu Glu Val Gly
            210                 215                 220

Asp Asp Asp Pro Val Arg Arg Glu Ala Tyr Lys Asp Ala Val Arg Glu
225                 230                 235                 240

Ile Lys Leu Asn Thr Cys Gln Leu Ala Lys Arg Gln Ile Gly Lys Ile
                245                 250                 255

Ser Arg Leu Arg Gly Ala Gly Trp Asn Leu Arg Leu Asp Ala Thr
            260                 265                 270

Glu Ala Phe Arg Ala Ala Val Lys Ser Asp Glu Lys Asp Gly Asn Arg
            275                 280                 285

Trp Ser Glu Ile Trp Glu Arg Glu Val Val Gly Pro Ser Val Lys Ile
            290                 295                 300

Val Asn His Phe Leu Glu Glu Glu Ile Gln Ser Thr Lys Val Gln Asn
305                 310                 315                 320

Gln Lys Ile

<210> SEQ ID NO 20
<211> LENGTH: 357
<212> TYPE: PRT
<213> ORGANISM: Rubus occidentalis

<400> SEQUENCE: 20

Met Thr Leu Asp Ser Phe Pro Thr Leu His Tyr Ser Tyr Tyr Asn Ile
  1               5                  10                  15

Thr Pro His Ser Leu Ser Ser Pro Ala Val Thr Leu Thr Pro Pro
            20                  25                  30

Ser Leu Pro Gln Lys Pro Arg Trp Ala Arg Met Asp Ser Gly Pro Ala
            35                  40                  45

Thr Thr Thr Thr Val Pro Leu Arg His Lys Asp Lys Leu Val Val Ile
        50                  55                  60

Met Gly Ala Thr Gly Ala Gly Lys Ser Arg Leu Ser Ile Asp Leu Ala
```

```
                65                  70                  75                  80
Thr His Phe Pro Ser Cys Phe Glu Ile Ile Asn Ser Asp Lys Met Gln
                        85                  90                  95

Val Tyr Lys Gly Leu Asp Ile Thr Thr Asn Lys Ile Pro Val Pro Asp
                100                 105                 110

Arg Ile Gly Val Pro His His Leu Leu Gly Gln Phe Asp Pro Leu Asp
                115                 120                 125

Gly Glu Leu Thr Pro Ala Glu Phe Arg Gln Leu Ala Gly Gln Ala Val
        130                 135                 140

Ser Ala Ile Thr Ser Arg Arg Lys Val Pro Met Leu Val Gly Gly Ser
145                 150                 155                 160

Asn Ser Leu Ile His Ala Leu Leu Val Asp Arg Phe Glu Pro Gly Val
                165                 170                 175

Asp Val Phe Glu Gly Gly Ala Ala Ile Ser Ser Glu Leu Arg Tyr Asn
                180                 185                 190

Cys Cys Phe Leu Trp Val Asp Val Ser Leu Thr Val Leu Ala Asp Tyr
                195                 200                 205

Leu Ser Lys Arg Val Asp Glu Met Leu Asp Ser Gly Met Leu Glu Glu
        210                 215                 220

Leu Ala Glu Phe Cys Asp Pro Glu Asp Asp Leu Ala Ile Arg Thr
225                 230                 235                 240

Gly Leu Arg Lys Ala Ile Gly Val Pro Glu Phe Ser Arg Phe Lys
                245                 250                 255

Lys Tyr Pro Pro Ile Cys Gln Ser Gln Lys Ala Arg Pro Asp Asp Pro
                260                 265                 270

Val Arg Arg Gly Ala Tyr Lys Glu Ala Val Arg Ala Ile Lys Asp Asn
        275                 280                 285

Thr Cys Gln Leu Ala Lys Thr Gln Ile Gly Lys Ile Leu Arg Leu Arg
        290                 295                 300

Val Ala Gly Gly Trp Asp Leu Gln Arg Leu Asp Ala Thr Glu Ala Phe
305                 310                 315                 320

Arg Ala Val Val Thr Ser Glu Asp Asp Ala Gly Lys Arg Trp Ser Glu
                325                 330                 335

Ile Trp Gln Lys Gln Val Val Glu Ala Ser Val Lys Ile Val Lys Arg
                340                 345                 350

Phe Leu Glu Gln Glu
            355

<210> SEQ ID NO 21
<211> LENGTH: 374
<212> TYPE: PRT
<213> ORGANISM: Prunus avium

<400> SEQUENCE: 21

Met Thr Leu His Pro Phe Pro Thr His Ser His His Tyr Ser Asn
1               5                   10                  15

Leu Asn Phe Tyr Ser Tyr Ile Ser Arg Phe His Leu Phe Pro Pro Val
                20                  25                  30

Asn His Leu Cys Pro Thr Thr Pro Ser His His Pro Leu Pro His
            35                  40                  45

Ile Lys Pro Arg Arg Gly Ala His Ile Ser Ser Gly Pro Thr Thr Pro
        50                  55                  60

Arg Gln Gln Gln Gln Arg Lys Asp Lys Leu Leu Ile Ile Leu Gly Ala
65                  70                  75                  80
```

```
Thr Gly Ala Gly Lys Ser Arg Leu Ser Leu Asp Leu Ala Thr Arg Phe
                85                  90                  95

Pro Phe Phe Glu Ile Val Asn Ser Asp Lys Met Gln Leu Tyr Ala Gly
            100                 105                 110

Leu Asp Ile Thr Thr Asn Lys Leu Pro Ile Pro Asp Arg Leu Gly Val
        115                 120                 125

Pro His His Leu Leu Gly Glu Phe Asp Pro Arg His Gly Asp Phe Thr
    130                 135                 140

Pro Ala Gln Phe Arg Ala Val Ala Gly Gln Ala Ile Ser Ser Ile Thr
145                 150                 155                 160

Asn Arg Arg Lys Val Pro Met Leu Val Gly Gly Ser Asn Ser Phe Ile
                165                 170                 175

His Ala Leu Leu Val Asp Arg Phe Glu Pro Gly Ser Asn Val Phe Glu
            180                 185                 190

Pro Gly Phe Asn Gly Ser Val Ser Ser Glu Leu Arg Tyr Asn Cys Cys
        195                 200                 205

Phe Leu Trp Val Asp Val Ser Leu Thr Val Leu Thr Glu Tyr Leu Cys
    210                 215                 220

Lys Arg Val Asp Glu Met Leu Asp Ser Gly Met Leu Asp Glu Leu Ala
225                 230                 235                 240

Glu Phe Cys Asp Pro Asp Arg Gln Asp Glu Asp Leu Thr Ala Ser
                245                 250                 255

Gln Thr Ala Leu Arg Lys Ala Ile Gly Val Pro Glu Phe Thr Arg Tyr
            260                 265                 270

Phe Glu Lys Tyr Pro Pro Gln Gly Arg Gly Glu Gly Asp Asp Arg
        275                 280                 285

Glu Arg Arg Glu Ala Tyr Glu Glu Ala Val Arg Ala Ile Lys Asp Asn
    290                 295                 300

Thr Cys Gln Leu Ala Lys Arg Gln Ile Gly Lys Ile Leu Arg Leu Lys
305                 310                 315                 320

Gly Gly Gly Trp Asp Leu Arg Arg Leu Asp Ala Thr Asp Ala Phe Arg
                325                 330                 335

Ala Val Val Ala Thr Thr Ser Ser Asp Lys Asp Asp Gly Lys Arg Trp
            340                 345                 350

Ser Glu Ile Trp Glu Arg Gln Val Val Lys Pro Ser Val Lys Val Val
        355                 360                 365

Lys Arg Phe Leu Asp Glu
    370

<210> SEQ ID NO 22
<211> LENGTH: 446
<212> TYPE: PRT
<213> ORGANISM: Rubus occidentalis

<400> SEQUENCE: 22

Met Glu Glu Tyr Asn Asn Ser Asn Glu Met Asp His Glu Ser Ser Gly
1               5                   10                  15

Thr Pro Arg Val Ser Ala Ser Thr Phe Asp Ile Tyr Ile Ile Ile
            20                  25                  30

Ile Asn Tyr Asn Ile Ser Asn Ile Phe Lys Ile Lys Glu Cys Ser
        35                  40                  45

Ile Gln Leu Leu Phe Cys Ser Leu Val Cys Ile Phe Phe Ile Thr Phe
    50                  55                  60

Leu Ile Tyr Asp Gln Asn Leu Leu Met Cys Arg Gly Asn Phe Leu Tyr
65                  70                  75                  80
```

```
Ala Ser Pro Asn Leu Gly Gly Asn Tyr Gly Arg Thr Ala Ala Gly Asp
                85                  90                  95

His Asn Gln Gln Ile Asn Thr Phe His Leu Gln Ser Ser Gly Gly Glu
            100                 105                 110

Cys Phe Gln Ser Gly Thr Ala Gln Pro Thr Val Lys Thr Glu Ala
        115                 120                 125

Ala Gly Ser Thr Ser Gln His Ala Pro His Lys Phe His His Gln Phe
    130                 135                 140

Pro Pro Pro Ser Leu Ile Leu Ser Arg Gly Gln Asn Asp Gln Leu Pro
145                 150                 155                 160

Val Gln Gln Gln Gln His Ile Glu Asn Glu Asn Glu Val Glu Ala Ile
                165                 170                 175

Lys Ala Lys Ile Ile Ala His Pro His Tyr Ser Asn Leu Leu Gln Ala
            180                 185                 190

Tyr Met Asp Cys Gln Arg Val Gly Ala Pro Ser Glu Val Val Ala Arg
        195                 200                 205

Leu Ala Ala Ala Arg Gln Glu Phe Glu Ala Arg Gln Arg Ser Leu Val
    210                 215                 220

Ser Ser Arg Asp Ala Ser Ser Lys Asp Pro Glu Leu Asp Gln Phe Met
225                 230                 235                 240

Glu Ala Tyr Tyr Asp Met Leu Val Lys Tyr Arg Glu Glu Leu Thr Arg
                245                 250                 255

Pro Ile Gln Glu Ala Met Asp Phe Met Arg Lys Ile Glu Thr Gln Leu
            260                 265                 270

Asn Met Leu Gly Asn Asp Ser Ser Thr Thr Pro Leu Arg Ile Phe Ser
        275                 280                 285

Ala Ser Ala Gln Glu Asp Lys Cys Asp Gly Asn Gly Ser Ser Glu Glu
    290                 295                 300

Asp Gln Asp Asn Asn Ser Gly Gly Glu Thr Glu Val Ala Glu Ile Asp
305                 310                 315                 320

Pro Arg Ala Glu Asp Arg Glu Leu Lys Asn His Leu Leu Arg Lys Tyr
                325                 330                 335

Ser Gly Tyr Leu Ser Ser Leu Lys Gln Glu Leu Ser Lys Lys Lys Lys
            340                 345                 350

Lys Gly Lys Leu Pro Lys Asp Ala Arg Gln Lys Leu Leu Ser Trp Trp
        355                 360                 365

Glu Leu His Tyr Lys Trp Pro Tyr Pro Ser Glu Ser Glu Lys Val Ala
    370                 375                 380

Leu Ala Glu Ser Thr Gly Leu Asp Gln Lys Gln Ile Asn Asn Trp Phe
385                 390                 395                 400

Ile Asn Gln Arg Lys Arg His Trp Lys Pro Ser Glu Asp Met Gln Phe
                405                 410                 415

Met Val Met Asp Gly Leu His Pro Gln Asn Ala Ala Thr Leu Tyr Met
            420                 425                 430

Asp Gly His Tyr Ile Gly Asp Gly His Tyr Arg Leu Gly Pro
        435                 440                 445

<210> SEQ ID NO 23
<211> LENGTH: 355
<212> TYPE: PRT
<213> ORGANISM: Prunus avium

<400> SEQUENCE: 23

Met Glu Glu Tyr Asn Gln Met Asp His Glu Ser Ser Gly Gly Arg Gly
```

```
        1               5                   10                  15
Asn Phe Leu Tyr Ala Ser Pro Asn Leu Gly Gly Asn Tyr Gly Arg Ala
                20                  25                  30
Ser His Asp His Gln Met Gly Ile Asn Ala Phe His Leu Gln Ser Ser
                35                  40                  45
Gly Gly Gly Asp Phe His Ser Pro Gly Gly Ala His Pro Ile Asn Val
             50                 55                  60
Lys Thr Glu Ala Ser Thr Ser His His Gly His His Lys Phe Gln Tyr
 65                 70                  75                  80
Asn Asn Asn Asn Asn Asn Asn Asn Asn Pro Leu Leu Ser Ser Arg
                    85                  90                  95
Gly His Gln Pro Val Val Gln Gln Gln His Asn Leu Asp Arg Gln Asn
                100                 105                 110
Asp Asp His Thr Leu Ser Ser Asn Glu Val Glu Ala Ile Lys Ala Lys
                115                 120                 125
Ile Ile Ala His Pro Gln Gln Arg Ser Ser Val Ala Ser Arg Glu Ala
                130                 135                 140
Ser Lys Asp Pro Glu Leu Asp Gln Phe Met Glu Ala Tyr Tyr Asp Met
145                 150                 155                 160
Leu Val Lys Tyr Arg Glu Leu Thr Arg Pro Ile Gln Glu Ala Met
                    165                 170                 175
Asp Phe Met Arg Arg Ile Glu Thr Gln Leu Asn Met Leu Gly Asn Asn
                180                 185                 190
Asn Ala Pro Pro Leu Arg Ile Phe Ser Pro Ser Glu Asp Lys Cys Glu
                195                 200                 205
Gly Ile Gly Ser Ser Glu Glu Glu Gln Glu Asn Ser Gly Gly Glu Thr
                210                 215                 220
Glu Val Pro Glu Ile Asp Pro Arg Ala Glu Asp Arg Glu Leu Lys Asn
225                 230                 235                 240
His Leu Leu Lys Lys Tyr Ser Gly Tyr Leu Ser Ser Leu Lys Gln Glu
                    245                 250                 255
Leu Ser Lys Lys Lys Lys Gly Lys Leu Pro Lys Asp Ala Arg Gln
                260                 265                 270
Lys Leu Leu Ser Trp Trp Glu Leu His Tyr Lys Trp Pro Tyr Pro Ser
                275                 280                 285
Glu Ser Glu Lys Val Ala Leu Ala Glu Ser Thr Gly Leu Asp Gln Lys
                290                 295                 300
Gln Ile Asn Asn Trp Phe Ile Asn Gln Arg Lys Arg His Trp Lys Pro
305                 310                 315                 320
Ser Glu Asp Met Gln Phe Met Val Met Asp Gly Leu His Pro Gln Asn
                    325                 330                 335
Ala Ala Leu Tyr Met Asp Gly His Tyr Ile Gly Asp Gly His Tyr Arg
                340                 345                 350
Leu Gly Pro
         355

<210> SEQ ID NO 24
<211> LENGTH: 700
<212> TYPE: PRT
<213> ORGANISM: Rubus occidentalis

<400> SEQUENCE: 24

Met Asn Met Asn Trp Leu Gly Phe Ser Leu Ser Pro Gln Glu Asp Asp
1               5                   10                  15
```

-continued

```
Ala Pro Ile Ser His Gln Leu Ala Asp Gln Glu Thr Leu Ala Ser Arg
            20                  25                  30

Leu Gly Phe Asn Ser Asn Asp Gln Ile Gln Gly Ala Gly Gly Glu Ala
        35                  40                  45

Asp Trp Asn Met Lys Gly Val Asp Met Asn Ser Ser Asp Gly Asn Asn
    50                  55                  60

Tyr Lys Arg Thr Ser Ser Ser Asp Leu Ser Pro Met Leu Met Gly
65                  70                  75                  80

Ser Ser Thr Thr Thr Ser Thr Ser Cys Ser Ile Ile Ser Gln Pro Asn
                85                  90                  95

Leu Glu Asn His His Gln Gln Gln Leu Pro Lys Leu Glu Asn Phe
            100                 105                 110

Leu Gly Arg His Ser Phe Ala Asp His Asp Gln Ser Ser Thr Ser His
        115                 120                 125

Asp Tyr Met Phe Asp Met Asn Asn Gly Pro Gly Ala Ile Ser Ser Asn
    130                 135                 140

Val Met Asn Thr Ser Asn Thr Asn Ser Asn Asn Ile Gly Leu Ser Met
145                 150                 155                 160

Ile Lys Thr Trp Leu Arg Asn Gln Pro Pro Gln Pro Arg Asp Asn Asn
                165                 170                 175

His Gln Leu Glu Gln Glu Ser Lys Thr Thr Lys Glu Ser Arg Asn Gln
            180                 185                 190

Pro Gln Ser Ser Leu Ser Leu Ser Met Ser Thr Gly Ser Leu His Thr
        195                 200                 205

Val Thr Thr Ala Thr Ala Gly Gly Ala Ser Ala Ser Ala Gly Ala Gly
    210                 215                 220

Glu Thr Thr Ser Ser Asn Asn Asn Arg Lys Gln Ser Pro Val Leu
225                 230                 235                 240

Thr Ala Thr Thr Thr Asp Pro Gln Thr Gln Thr Thr Gly Gly Ala Ile
                245                 250                 255

Glu Ala Val Pro Arg Lys Ala Ile Asp Thr Phe Gly Gln Arg Thr Ser
            260                 265                 270

Ile Tyr Arg Gly Val Thr Arg His Arg Trp Thr Gly Arg Tyr Glu Ala
        275                 280                 285

His Leu Trp Asp Asn Ser Cys Arg Arg Glu Gly Gln Thr Arg Lys Gly
    290                 295                 300

Arg Gln Gly Gly Tyr Asp Lys Glu Asp Lys Ala Arg Ala Tyr Asp
305                 310                 315                 320

Leu Ala Ala Leu Lys Tyr Trp Gly Thr Thr Thr Thr Asn Phe Pro
                325                 330                 335

Ile Ser Thr Tyr Glu Lys Glu Ile Asp Glu Met Lys Pro Met Thr Arg
            340                 345                 350

Gln Glu Tyr Val Ala Ser Leu Arg Arg Lys Ser Ser Gly Phe Ser Arg
        355                 360                 365

Gly Ala Ser Ile Tyr Arg Gly Val Thr Arg His His Gln His Gly Arg
    370                 375                 380

Trp Gln Ala Arg Ile Gly Arg Val Ala Gly Asn Lys Asp Leu Tyr Leu
385                 390                 395                 400

Gly Thr Phe Ser Thr Gln Glu Glu Ala Ala Glu Ala Tyr Asp Ile Ala
                405                 410                 415

Ala Ile Lys Phe Arg Gly Leu Asn Ala Val Thr Asn Phe Asp Met Ser
            420                 425                 430

Arg Tyr Asp Val Lys Ser Ile Leu Glu Ser Ser Ala Leu Pro Ile Thr
```

```
              435                 440                 445
Thr Gly Ala Ser Ala Lys Arg Leu Lys Asp Val Gln Gln Pro Pro
    450                 455                 460
Pro Pro Ala Asp His His His Gln Ile Met Leu Ser Ser Val Leu Asp
465                 470                 475                 480
His His Gly Gln Met Ile Arg Ser Ser Ser Thr Glu His Asp Ile
                485                 490                 495
Met Gly Asn Ile Phe His Gln Asp Asp Asp His Leu Arg Gln Gln Leu
            500                 505                 510
Gln Met Gly Gly Thr His Asn Phe Phe His Asp His Asp His Gln Gln
            515                 520                 525
Arg Ser Gly Leu Met Gly Leu Met Asp Ser Ser Ala Ala Ala Ser
        530                 535                 540
Met Glu His Ser Ser Gly Ser Asn Ser Val Ile Tyr Ser Val Gly Asp
545                 550                 555                 560
His His Gly Asn Asn Gly Tyr Gly Ser Asn Ala Arg Gly Thr Gly
                565                 570                 575
Ser Gly Tyr Ile Met Pro Met Ala Met Ser Thr Val Val Ala Asn His
            580                 585                 590
Gly Gln Asn Gln Ala Asp Gly Asn Asn Ile Asn Gly Phe Gly Asp Gly
        595                 600                 605
Asp Gly Asp Asp Gln Glu Val Asn Ile Lys Ala Gln Gln Leu Gly Tyr
610                 615                 620
Asp His His Gln Asn Val Phe Leu Gly Ser Ser Asn Thr Thr Asp Pro
625                 630                 635                 640
Ala Tyr Gln His His Ala Ser Asn Arg Asn Leu Tyr Tyr Gln Leu Pro
                645                 650                 655
Val His Asp Gln His Glu Ser Ser Ser Glu Ala Val Ala Thr Ser
            660                 665                 670
Ser Thr Thr Cys Asn Met Asn Trp Val Pro Thr Ala Val Pro Thr His
            675                 680                 685
Leu Ala His Ser Thr Phe Thr Val Trp Asn Asp Thr
        690                 695                 700

<210> SEQ ID NO 25
<211> LENGTH: 532
<212> TYPE: PRT
<213> ORGANISM: Prunus avium

<400> SEQUENCE: 25

Met Gly Ser Met Asn Trp Leu Gly Phe Ser Leu Ser Pro Gln Glu Val
1               5                   10                  15
Val Pro Ala Asp Pro Ser Ile Ser Glu Gly Asp His His Gln His
            20                  25                  30
His Asp Gly His Glu Leu Ser Asp Asp Gln Thr Ala Thr Leu Val Ser
        35                  40                  45
Arg Leu Gly Phe Lys Tyr Ser Asp Asp Ile Ser Gly Thr Asp Val Thr
    50                  55                  60
Gly Gly Cys Phe Asp Leu Thr Ser His Asp Asp Ser Ser Ala Thr Thr
65                  70                  75                  80
Thr Ala Ala Ala Val Pro Asn Asn His Ser His Asn His Leu Ile Pro
                85                  90                  95
Pro Pro Phe Gly Met Leu His Gln Ala Ala Ala Phe Asn Thr Thr Asn
            100                 105                 110
```

```
Ile His Ser Gln Gly Ala Asp Trp Ser Asn Met Asn Ser Asp Ser
        115                 120                 125

Ser Thr Tyr Lys Thr Thr Ser Asp His Leu Ser Met Leu Met Gly Ser
130             135                 140

Asn Ser Ser Tyr Arg Ser Gln Asn Leu Glu Asn Asn His Gln Gln Pro
145             150                 155                 160

Lys Leu Glu Asn Phe Leu Gly Arg His Ser Phe Val Ala Asp Glu His
            165                 170                 175

His Ile Gly Gly Gln Ser Ser Ser Gly Thr His Ala Tyr Asn Asn Asn
        180                 185                 190

Ser Thr Ser Asn Thr Ile Gln Thr Leu Ser Leu Ser Met Ser Thr Gly
    195                 200                 205

Ser His Thr His His Asn Thr Thr Ser Thr Ala Ala Ala Gly Glu Thr
    210                 215                 220

Cys Ser Ser Asp Arg Asp Asn Thr Cys Asn Asn Asn Asn Lys Leu Ala
225             230                 235                 240

Val Val Arg Thr Thr Ala Ser Thr Ala Pro Pro Gly Ile Asp Ser
            245                 250                 255

Gln Thr Thr Ser Thr Thr Ala Thr Ala Ile Glu Ala Val Pro Arg Lys
            260                 265                 270

Ser Val Asp Thr Phe Gly Gln Arg Thr Ser Ile Tyr Arg Gly Thr Asp
            275                 280                 285

Gly Gln Val Asp Met Lys Leu Ile Ser Gly Ile Ile Val Ala Gly Glu
        290                 295                 300

Lys Asp Lys Leu Ala Arg Glu Gly Lys Ile Ser Asn Tyr Glu Lys Glu
305             310                 315                 320

Ile Asp Glu Met Lys His Met Thr Arg Gln Glu Tyr Val Ala Ser Leu
                325                 330                 335

Arg Arg Lys Ser Ser Gly Phe Ser Arg Gly Ala Ser Ile Tyr Arg Gly
            340                 345                 350

Val Thr Arg His His Gln His Gly Arg Trp Gln Ala Arg Ile Gly Arg
            355                 360                 365

Val Ala Gly Asn Lys Asp Leu Tyr Leu Gly Thr Phe Ser Ser Asn Ser
        370                 375                 380

Val Met Tyr Ser Thr Ala Thr Thr Thr Asn Gly Gly Gly Gly Gly
385                 390                 395                 400

Gly Gly Asp His Gly Gly Tyr Ile Ile Pro Met Gly Thr Val Ile Ser
            405                 410                 415

Asn Asp His Asn Asp Gly Phe Gly Asp Gly Thr Asn His Asp His Gln
            420                 425                 430

Val Lys Ala Val Ala Leu Gly Phe Glu Asn Val Phe Gly Ser Thr Ser
        435                 440                 445

Ala Ser Val Asn Ala Thr Asn Val Thr Arg Asp Ala Tyr Asn Asn His
    450                 455                 460

Ala Arg Asn Leu Tyr Tyr Leu Pro Gln Gln Leu Pro Gln Ser Ser Ser
465             470                 475                 480

Val Ser Ser Val Ser Ser Ala Gly Val Ala Lys Gly Gly Ser Ala Tyr
            485                 490                 495

Asp Ile His Glu Ala Gly Gln Cys Asn Asn Trp Met Pro Thr Ala Val
            500                 505                 510

Pro Thr Ser Thr Asn Ser Asn Ile Asn Met Pro Pro Thr Phe Thr Val
            515                 520                 525

Trp Asn Asp Thr
```

<210> SEQ ID NO 26
<211> LENGTH: 297
<212> TYPE: PRT
<213> ORGANISM: Rubus occidentalis

<400> SEQUENCE: 26

Met Glu Pro Gln Ser Gln Gln Pro Thr Glu Asp Gly Gly Ser Asn Lys
1               5                   10                  15

Ala Ala Gly Ser Ala Asn Met Leu Cys Arg Gln Ser Ser Thr Arg Trp
            20                  25                  30

Thr Pro Thr Thr Asp Gln Ile Arg Ile Leu Lys Glu Leu Tyr Tyr Asn
        35                  40                  45

Lys Gly Val Arg Ser Pro Ser Ala Glu Gln Ile Gln Arg Ile Cys Leu
50                  55                  60

Gln Leu Lys Arg Tyr Gly Lys Ile Glu Gly Lys Asn Val Phe Tyr Trp
65                  70                  75                  80

Phe Gln Asn His Lys Ala Arg Glu Arg Gln Lys Lys Arg Phe Thr Ser
                85                  90                  95

Asp Val His Val Pro Met Gln Arg Ser Gly Leu Val Gly Asn Ser Asn
            100                 105                 110

Val Ala Asn Trp Lys Pro Glu Asp Gln Tyr Leu Asn Met Asn Asn Lys
        115                 120                 125

Tyr Ser Asn Ile Cys Gln Gly Val Ser Ser Ala Ser Ala Ser Ala
    130                 135                 140

Ser Ser Ala Gly Val Val Ser Phe Asn Gly Gln Met Gly Asn Tyr Gly
145                 150                 155                 160

Val Tyr Gly Ser Met Asn Met Glu Lys Ser Phe Arg Asp Cys Ser Ile
                165                 170                 175

Ser Ala Gly Gly Gly Thr Ser Thr Gly Val Gly Ile Gly Gly Ser
            180                 185                 190

Ile Ser His Asn Tyr Gly Ser Trp Val Gly Ser Val Asp Pro Tyr
        195                 200                 205

Ser Ser Ser Ser Tyr Thr Thr Ser Thr Thr Phe Phe Asp Asn Gln
210                 215                 220

Lys Gln Ile Phe Met Glu Glu Glu Glu Asp His Gln Glu Ile Glu
225                 230                 235                 240

Thr Leu Pro Leu Phe Pro Met His Gly Glu Asp Ile Phe Gly Asn Ile
                245                 250                 255

Lys Thr Thr Ser Glu Gly Gly Gly Gly Asp Tyr Gly Tyr Tyr Ser Ser
            260                 265                 270

Gly Trp Gly Gly Ser Ser Arg Thr Ser Leu Glu Leu Ser Leu Asn Ser
        275                 280                 285

Tyr Gly Tyr Asn Asn Pro Asn Tyr Tyr
    290                 295

<210> SEQ ID NO 27
<211> LENGTH: 305
<212> TYPE: PRT
<213> ORGANISM: Prunus avium

<400> SEQUENCE: 27

Met Glu Pro Gln Gln Thr Gln Gln Pro Asn Glu Asp Gly Ser Asn
1               5                   10                  15

Lys Gly Thr Ser Gly Thr Asn Phe Leu Cys Arg Gln Ser Ser Thr Arg

```
            20                  25                  30
Trp Thr Pro Thr Ser Asp Gln Ile Arg Ile Leu Lys Asp Leu Tyr Tyr
            35                  40                  45

Asn Asn Gly Val Arg Ser Pro Ser Ala Glu Gln Ile Gln Arg Ile Ser
 50                  55                  60

Ala Arg Leu Arg Gln Tyr Gly Lys Ile Glu Gly Lys Asn Val Phe Tyr
 65                  70                  75                  80

Trp Phe Gln Asn His Lys Ala Arg Glu Arg Gln Lys Lys Arg Phe Ile
                 85                  90                  95

Asp Val Pro Ala Pro Pro Ile Met Gln Arg Ser Gly Leu Gly Ile Asn
            100                 105                 110

Asn Asn Ala Pro Thr Ala Tyr Glu Pro Ile Asn His Ser Asn Lys Tyr
            115                 120                 125

Pro Asn Ile Ser Ala Ser Ala Gly Val Ser Ser Ala Ser Ala Ser Ser
            130                 135                 140

Ala Gly Val Ile Ala Val Gly Gln Met Gly Ser Tyr Gly Tyr Gly Ser
145                 150                 155                 160

Met Thr Met Glu Lys Ser Phe Arg Asp Cys Ser Ile Ser Ala Ala Gly
                165                 170                 175

Gly Thr Ser Ser Gly His Val Gly Gly Ser Asn Asn Ile Gly His
            180                 185                 190

Asn Val Gly Ser Trp Val Gly Val Asp Pro Tyr Ser Ser Pro Tyr Thr
            195                 200                 205

Leu Phe Asp Lys Arg Ser Ser Arg Gln Val Phe Gly Asp Gln Glu
            210                 215                 220

Asn Met Met Asp Glu Glu Asp His Glu Tyr Gln Glu Asn Leu Gln Asp
225                 230                 235                 240

Ser Pro Glu Ile Glu Thr Leu Pro Leu Phe Pro Met His Gly Glu Asp
                245                 250                 255

Ile His Gly Phe Gly Asn Ile Lys Ser Thr Ser Asp Ser Tyr Tyr Ser
            260                 265                 270

Gly Trp Tyr Arg Ser Asp Glu Gly Asn Asn Gly Arg Thr Ser Leu Glu
            275                 280                 285

Leu Ser Leu Asn Ser Tyr Gly His Met Thr Pro Asp Tyr Phe Ser Ser
            290                 295                 300

Tyr
305

<210> SEQ ID NO 28
<211> LENGTH: 723
<212> TYPE: DNA
<213> ORGANISM: Agrobacterium tumefaciens

<400> SEQUENCE: 28
atggatctgc gtctaatttt cggtccaact tgcacaggaa agacgtcgac cgcggtagct     60
cttgcccagc agactgggct tccagtcctt tcgctcgatc gggtccaatg ttgtcctcag    120
ctgtcaaccg gaagcggacg accaacagtg gaagaactga aggaacgag ccgtctatac    180 cttgatgatc ggcctctggt gaagggtatc atcgcagcca agcaagctca tgaaaggctg    240 atggggagg tgtataatta tgaggcccac ggcgggctta ttcttgaggg aggatctatc    300
tcgttgctca agtgcatggc gcaaagcagt tattggagtg cggattttcg ttggcatatt    360
attcgccacg agttagcaga cgaagagacc ttcatgaacg tggccaaggc cagagttaag    420
cagatgttac gccctgctgc aggcctttct attatccaag agttggttga tctttggaaa    480
```

```
gagcctcggc tgaggcccat actgaaagag atcgatggat atcgatatgc catgttgttt    540
gctagccaga accagatcac atccgatatg ctattgcagc ttgacgcaga tatggaggat    600
aagttgattc atgggatcgc tcaggagtat ctcatccatg cacgccgaca agaacagaaa    660
ttccctcgag ttaacgcagc cgcttacgac ggattcgaag gtcatccatt cggaatgtat    720
tag                                                                 723
```

<210> SEQ ID NO 29
<211> LENGTH: 723
<212> TYPE: DNA
<213> ORGANISM: Agrobacterium tumefaciens

<400> SEQUENCE: 29

```
atggatctgc gtctaatttt cggtccaact tgcacaggaa agacgtcgac cgcggtagct     60
cttgcccagc agactgggct tccagtcctt tcgctcgatc gggtccaatg ttgtcctcag    120
ctgtcaaccg gaagcggacg accaacagtg gaagaactga aggaacgag ccgtctatac     180 cttgatgatc ggcctctggt gaagggtatc atcgcagcca agcaagctca tgaaaggctg    240 atggggagg tgtataatta tgaggcccac ggcgggctta ttcttgaggg aggatctatc     300
tcgttgctca gtgcatggc gcaaagcagt tattggagtg cggattttcg ttggcatatt     360
attcgccacg agttagcaga cgaagagacc ttcatgaacg tggccaaggc cagagttaag    420
cagatgttac gccctgctgc aggcctttct attatccaag agttggttga tctttggaaa    480
gagcctcggc tgaggcccat actgaaagag atcgatggat atcgatatgc catgttgttt    540
gctagccaga accagatcac atccgatatg ctattgcagc ttgacgcaga tatggaggat    600
aagttgattc atgggatcgc tcaggagtat ctcatccatg cacgccgaca agaacagaaa    660
ttccctcgag ttaacgcagc cgcttacgac ggattcgaag gtcatccatt cggaatgtat    720
tag                                                                 723
```

<210> SEQ ID NO 30
<211> LENGTH: 957
<212> TYPE: DNA
<213> ORGANISM: Arabidopsis thaliana

<400> SEQUENCE: 30

```
atgaagtgta atgacaaaat ggttgtgatc atgggtgcca ccggttctgg caagtcatca     60
ctctctgttg atctcgcttt acatttaaa gccgagatca tcaactctga caaatgcag     120 ttctacgatg gcttgaagat caccacgaat caatcgacca ttgaagatcg acgtggagtg    180
ccacatcacc ttctcggtga actaaacccg gaggctggag aagtcacagc ggcagaattt    240
cgcgttatgg cggctgaagc catctccgag attactcaac gtaaaaagct cccaatcctt    300
gccggtggat ccaactcata cattcatgct ctccttgcaa atcttatga ccctgaaaac    360 tatccgtttt ctgatcacaa gggctcaatc tgctccgagt tgaaatatga ttgttgtttc    420
atttggatag atgtggatca gtctgtgtta ttcgagtatc tttctttacg tttggatctt    480
atgatgaagt caggtatgtt cgaggagatc gctgagttcc accgctctaa gaaggccccg    540
aaagagccat tgggatatg aaggctata ggagtgcaag agtttgatga ctacctcaaa    600
atgtacaagt gggacaatga catggataaa tgggacccta tgagaaagga ggcttatgag    660
aaggcggtga gagccatcaa agaaaacaca tttcagctca caaaggatca aatcacgaag    720
atcaacaagc tgagaaatgc cgggtgggac ataaagaagg tggatgctac agcatcgttt    780
```

| | |
|---|---:|
| cgagaggcaa ttagggcagc caaggaaggc gaaggtgtag ccgagatgca gagaaagata | 840 |
| tggaacaagg aagtgttgga accgtgtgtg aagattgtca ggagccactt ggaccaaccg | 900 |
| atcaactatt attattatta cttttattta ctaaaaagat ttttaagtct taactag | 957 |

<210> SEQ ID NO 31
<211> LENGTH: 956
<212> TYPE: DNA
<213> ORGANISM: Arabidopsis thaliana

<400> SEQUENCE: 31

| | |
|---|---:|
| atgaagtgca atgataaaat ggtggttatt atgggtgcaa caggttctgg caagtcttca | 60 |
| ctgtcagttg atctggcttt gcatttcaag gccgaaatta tcaattctga taagatgcag | 120 |
| ttctacgatg gcctgaagat tactaccaac cagtcaacta tcgaggatag acgcggtgtg | 180 |
| ccacatcacc tgttgggcga attgaaccct gaggctggag aagtgaccgc tgccgagttt | 240 |
| agagttatgg cagctgaggc tatttctgaa atcacacagc gcaagaaact tccaattctg | 300 |
| gccggcggat ctaattcata tatccatgca cttctggcta agtcttacga tccagaaaac | 360 |
| tatcctttct cagatcacaa aggatctatt tgttcagagt tgaagtacga ttgctgtttt | 420 |
| atttggatcg atgtggatca gtctgttctt ttcgagtatc tttcactgcg cttggatctt | 480 |
| atgatgaaat ctggaatgtt tgaggaaatc gcagagttcc ataggtcaaa gaaagctcca | 540 |
| aaggaacctc ttggcatttg aaagcaatc ggagtgcagg aattcgatga ttacctgaag | 600 |
| atgtataagt gggataatga tatggataag tgggatccta tgcgcaagga agcttacgaa | 660 |
| aaagccgtta gggcaattaa agagaacaca ttccagttga ctaaggatca gatcactaag | 720 |
| attaataagc ttagaaacgc cggatgggat attaagaaag tggatgctac cgcctcattc | 780 |
| agggaagcca tcagagccgc aaaggaaggc gagggtgtgg cagagatgca gaggaagatc | 840 |
| tggaataagg aagtgctgga accatgcgtg aaaattgtta gatctcactt ggatcagcct | 900 |
| atcaattact actactacta cttctatttg cttaagcgct tcctgtcatt gaactg | 956 |

<210> SEQ ID NO 32
<211> LENGTH: 7908
<212> TYPE: DNA
<213> ORGANISM: Zea mays

<400> SEQUENCE: 32

| | |
|---|---:|
| agtgcactgt ctctctccaa aggcagctgc attggcctcc agccttttcc ctactgtgcc | 60 |
| gcgcgccctc ccttctctct aatgatagca tagggagaga aggcatactc cgaggcatcc | 120 |
| ttctcctttc cctctccttc cccaaaccct tttcctcttt ccctcgcccc aagaacttca | 180 |
| tctcatctcc aggcgcccct tttgcgcttg cgcaggagga gctcacgggg acagtgggcg | 240 |
| gagagctcga tcgctgcacc actacttcac tggaggtccg cccactccca tggaggagat | 300 |
| cacccaacac tttggagttg gcgcaagcag ccacggccat ggccacggcc agcaccacca | 360 |
| tcatcaccac caccaccacc cgtgggcatc ctccctcagc gccgtcgtag cgccgctgcc | 420 |
| gccgcaaccg ccaagcgcag gcctgccgct gaccctgaac acggtggcgg ccactgggaa | 480 |
| cagcggcggt agcggcaacc cggtgctgca gcttgccaac ggtggcggcc tcctcgacgc | 540 |
| atgcgtcaag gcgaaggagc cctcgtcgtc gtctccctac gcaggcgacg tcgaggccat | 600 |
| caaggccaag atcatctcgc acccacacta ctactcgctc ctcactgcct acctcgagtg | 660 |
| caacaaggca agcaagacta gtagccgcag tctaacaata gctctcctgc ttccggttca | 720 |
| gctactgctg ctagcgaagt ttggccacat ctgatgtcaa gagcatggcg catgcacata | 780 |

```
ctttctgctt gcttttacat agcatactat agtttatgca tgctgctcat gtagacatgt    840
gcatctggtg ttcggaactt tctcaaacgg ccgtgggtgt ttgcaggtgg gggcaccacc    900
ggaggtgtcg gcgaggctga cggagatagc gcaggaggtg gaggcgcggc agcgcacggc    960
gctcggcggc ctggccgctg cgacggagcc ggagctggac cagttcatgg tgaggcatct   1020
ttaggtttat ttcacgcgcg cgcagcgcac cattattagt cgttttcagc tcgggctcgg   1080
atttaatttg cgtgtatata tggtaggagg cgtaccacga gatgctggtg aagttcaggg   1140
aggagctgac gaggccgctg caggaggcga tggagttcat gcgaagggtg gagtcgcagc   1200
tgaactcgct ttccatctcc ggaaggtcgc tgcgcaacat cctttcatct ggtactgaag   1260
ttgctgcggc ccatgcccct cttattttat attagatgat tcttggatc ggttgtcgcc    1320
tcatgcagcg atgcatgccc tccctcttgt taaaatcttc ctgtcctctc cttcgtcttg   1380
ctgtcctctt tcttggttga gcatatgttg atgggttttt ttttttgcat ttcaaaaggg   1440
ttaaattttt ccttgatgtg gtttctcagc aattaatttt ggcatctgtg tagttccctt   1500
tttaagagca tcttgctatg catgcatatt ttgagtatag atagctgcgg aacgcagatg   1560
aatgtcttgt ctgcgcttca tgttttttaa tgcgcggcag cattcctaat caggggtttc   1620
gaaagagaat cttctccctg cttgcttttc ctggccatgc atctgtgaga ttcttctctc   1680
tggcttccgt cgatctttgc ttctgctgga aggaaatag tcctcagtca cacatgtgca    1740
ggagcgcagc ttcaatctag catggctgaa agctctctgg ttctttccat acactccatc   1800
ctgcacattc cttgcatata ttctgctgtt aaactgctta gcgacgagga tgaatgaaaa   1860
cacctgtctt ttttactagt gggagtacta atttggctgc tgttgccatg gatgcgttgt   1920
tcatcgtcct ccattatatt gatcgattcc atttggaatg gaacatgtgc atgtgttctg   1980
cgagtagttc ctggctcagc gcagccatct tttcccatga tgggaaccc agggagttcc    2040
cttgttctag ggtttgggaa agggccacag tgtactgggt gctgtggcat tgtgcaagca   2100
cagtctatag ccgaggagtc tcactggcgt atgtcagtga acatagtag tatacacgtt    2160
gtagtagtgg gagatcagag agagagagag atgggagtc atcccccatc tgtcacgcaa    2220
gcttgtggcc agaacattct tgtcatcttt ctcccctca agagatgtag ctacctgttg    2280
tcctagaatc tatagtgttg tggtgtggtc ttccaggtgc gcacacagat ctggccactg   2340
ctggccttag tatttgctaa ttttaaaatg aacacatcag gtagatcgag acgatccatg   2400
gcaagcgtct ttctaatgac ctatcacaag gctatagtaa caactcgtac caccacagtt   2460
acgcacagcc cagagttttt cacttctcgg ttctgttctt cttagagcac tggctatggc   2520
tagtatatat gcatggcagc aacacacaca cacacacaca atcacttcat tactggagca   2580
agttagcgaa gaagctgcca tctgatgtcg tagaatgctg caaaaatgaa aggttcagag   2640
gcaggcatac gggttgaaat ggagcaccgt atgcggcggc ccagttttt gtgttctgac    2700
cggcgcagtg gacaaaatgg cctgtgtgcc tcgagaacca tagagacagt tgcctagcgc   2760
atgagcgctg agcggcccct attatttgat gtgagatctc tctatcaatg gatgtgtgat   2820
ctgctaggtt tatattatat atgcgtctac tatatcccta ccagtccctg tattttctga   2880
cagatagact tctcccccgc gcgttctctc ataaataaat gacggtcaag gaacattgga   2940
tgctttccga ggcgagctag tacaagtttc atctgcgttt gcgtttgtat ttttcagctg   3000
tcaactcaga tttctcctca gctccaactg ttctttgacc ttcttggtac tgttttcttg   3060
gaagaaacta tttgttgacc attttggtt ataataaggc cacagacaaa ctgttgaatt    3120
```

```
taatcacaaa acaacactac tgcgttttt cttttctttt ctgactgatg ttgcacatgt   3180
actccaagat tcttggttgc atgcactctt tcaaggtcat gcaaaagcag ggacaccggg   3240
tgtcacgagt ttccgtttgt ctcgaggtaa gaccaaaaaa gataccggaa gcaaacaaca   3300
taaaacaaag ggtaggatgg aaaagagctg atggatttta caatgtatcg ccagagtgga   3360
aaagacaacg cgactagagg aaaggaacga tctggcactt ccaactgtgt gaattcttcc   3420
atttgatgtg cgtctcgtgc atgtttattt tcttggttac tggaaatcgg gtgcatccat   3480
ttttattcag gattcaatta ttggttactg gagccaggtc cgttcgtttt tattttcctt   3540
ttgagattga ctggatcgat tctctggttc tagtcactta tgctgttggt tttatcgttt   3600
tcatggattt ctattctatc tctcccaata ttcagtatca cataaaatcc tgtgactaga   3660
tttctttatc acatacaatc ttgtttttt attttcttta atttaacact ggatttgttt   3720
gataatatgt tctgaaaaac gttaataaat ttaagcacaa cagccttta aaaatatgta   3780
taattattta ccttgaaacc cagcatcggc cgggaacaag gaaaagaact caaggtttta   3840
aatgcattga aatgaaacat taatggagtg tttggtttga ataatgatgt agtccatcat   3900
cttctcactc ctcactttt tgtttggttt atggaatgga gtgagttaat ccatcaacac   3960
ctcattcctc atagttagtt gtttagtact aatatgtgga atgaagtcat cccaccaaat   4020
ttgaagaatg gactcatgat gcaccacttc attttagata gagtgattca tcaaaccaaa   4080
cacctcataa gggcatgttt ggatcctagg agctaaaaga aaagtgacta aagtttagtc   4140
actttaggag ctaaagatct actaaatagg aaactaaaag tgactagaat agtaaaaggt   4200
atcttttag tcattttag ctcctaagaa ggagctaaat tttagttagt ttggtttagc   4260
tcttggatcc aaacaggccc taagaaaatg tttcgacaac atttgggaca ataaaacagt   4320
tcctaaggat ttctttggca agattaggcc ttctttggaa caaagaaaaa tgaaggaatc   4380
ttgaaggatt gaaatcctat aggaagcttt catatgcaaa gaattgtgtt cctaggatga   4440
tttctaacaa gaggctcatc cccttgaaaa ttgttctttg tgtctatctc tctcctctaa   4500
ttcatgtgtt cttatgttgc attgaaacac tattagaaaa ttttcatgtg ttttaattta   4560
tgtatgattg taagtgtcaa gcagcactat tcctacattt tttctattcc tgtgttttat   4620
cgatactgca tcccaatgaa ggcctaagcg tatcatgcaa tcttttccag aagttttta   4680
gattgctgta taatgacaag gtgcaatgct cttcgttttc ttttttggtt ttcctcattt   4740
tcagcaaggc caccaaattt ttccatgatg ttcttgtctt attcctgtag tatccctcga   4800
aaaaatttca tagcttttcta catccatgtt atctaatgat gttcttcatt tcaaagacag   4860
acacatttgg cataagttct gattggtcac taaaactttg tggtacggtc atttactttt   4920
actatacaca tgtactgtat tcatgcgtac attgtacttt gtccattggg gcctttcctc   4980
tttttaatac aacgggcatc gtttcaaaaa aaatgtgtca gtcgtaactg cacacttctt   5040
tagttttccc cagttaacag catgacggaa tagagttaca gagtctcatg tcaagtcaca   5100
tatatcctca agtcgtttct aaaattaaag taatattttc attgttgctt ccgtaagaat   5160
gcaccacaaa cacaaaatat catttccttt atgcaaatat atatatatga atgtttgttt   5220
ctggcagtgg tgagaagctt ctcactgagc caaaggtttt agggatgcca tgtgctcttt   5280
ttctttttta agtgtagatt aagcaaacct ttataatttt taaactccaa ccagatacct   5340
tttctaaatt cataaatgct ctggactatc ttcacgaaaa aggctttggt aatatgttca   5400
caagcctcct ttatctgtta tcctgggcta gacataggat gtgttgaagc aatacaagcg   5460
gagttgtttc gttaaagcaa aaaaaaaact gtaactttat attggagaat atacatcgtt   5520
```

```
ctcccatatt tgttacagtg ctcataaata gacaaagttt tttttttgaa atcttaagcc    5580
ctgtgtttct ttggttatct tatctctata ttgcttccaa atatgttgtc atcaagatgg    5640
atatagataa ttgtcaaaac gaaaagtgtg catggttcat ttatgccaat tctgaaaagc    5700
ataagttaaa tattaagata ccaataaaga aaaacatatg cagtgttgac tgttgggaaa    5760
agaacaaggt ctgcacatac acttgcaata taaatctttt tacccagcaa taaaaaaacg    5820
atcaaatatc acgcaaacaa agtaatacgt ccagaaacac ccatactttt gaaattcgtc    5880
tttgaaatgc agtaggttca caaaataaaa tggtgcaact gcacatgtcc tttatatctg    5940
tactcaatgg gttttctgga gatgttagat tgattggtgg gacaatatcc taatgcaact    6000
cgcaaattcc caaggccgaa ctcaagtggg agtttggatg attttttttg taagaagca    6060
gatggctgcg ctagtttaca tagaccatca cacttcacaa ttcacattca tgaagtcata    6120
actttgttca cttcttgttt aactatggca tataaaaaca tactgtgtgt tgttttgctt    6180
gtatggaaca tgtattttag ttttttagta aataagttca gtaaatgtct ttgccggaca    6240
aatttcacca atctggctac gaatgatgct tgatcacttc ttttgtttta tctaaaagtt    6300
ccatgtctta tgcttgaagg ctcttctgag gaggatcaag aaggtagcgg aggagagacc    6360
gagctccctg aagttgatgc acatggtgtg gaccaagagc tgaagcacca tctcctgaag    6420
aaatacagtg gctatctaag ctcgctcaag caagaactgt caagaagaa gaagaaaggg    6480
aagctcccca aggaggctcg ccagcagctc cttagctggt gggatcagca ctacaaatgg    6540
ccttacccct cagtacgtct tcttttttatt cttccatttt aactattgtt ggtgacacat    6600
gatttagacg atgccaattc ttcatgaact tttcatagcc agctacccaa tgttagtact    6660
gactgcacat tgtaattcaa gggtaagtat atatatacat aaatcacatt tggcaaatct    6720
aagctacata tgggtctttg atcttccatg acggtctgtt gatctctgat ttgcatatcg    6780
gcatataaaa agtgagccaa atatgtcag agtctaataa tattgatcag ggagtggcag    6840
gtgattattg gtattaattt aaccttattt aaggtatttt gaaacttctg tagcgttctt    6900
actaaatacc attgattta atttaagcaa ctatatattt atctggtgaa aaatgaagcc    6960
ttttctgata tacaaattga agagtctaca atggtttcac ttacatggct gaaacagaaa    7020
atcatagtgc cctgaattgt gtgttgatac tcataagcgc agattcaaat ttgtaatttt    7080
caagtttagg gttctaagtg aaaaaaaaac attgagtcca ggagcataca ctgaactttt    7140
ttttatcat atcttcattt tgttggatgt tttgtatacg gcatatagcc tgtgcttccc    7200
tactggatat gaattaacca actcttccca tcggtgagca ggagactcag aaggtggcac    7260
tggctgagtc taccgggctt gacctgaagc agatcaacaa ctggttcatc aaccagcgga    7320
agcggcactg gaagccatcc gaggagatgc accacctgat gatggacggg taccacacca    7380
ccaatgcctt ctacatggac ggccacttca tcaacgacgg cgggctgtac cggctcggct    7440
agccaccggt atctcgcttc catttcacac cccacggcct agctataaag actaatggtt    7500
ccaggtgtct gaagtactga agacaggggg gctagctatc taatgtttgt gccgcacgca    7560
tgagctgtaa ggaggccatg cttaattatt ctgttgccgt tgctactcta tctatatgcg    7620
cctatgcctc cgtgcatgaa ctatgcttta ggtggttgct gctccacact gtggtggtgt    7680
gcttttgctt ttgtgtggtc gtattgtatg cgtaacctga cagatggatc cctgattgct    7740
acatgtttga ataatttgca tgatctagct agtttctgcc taatctaatg gtacggctca    7800
tgtcttgtca ggtggatttg ttatgtgttt ttttttcaa attgaggctt gtttgttttg    7860
```

| | |
|---|---:|
| ctctcaatcc atccatgtga attgggtgga attaaatgag tttaaatt | 7908 |

<210> SEQ ID NO 33
<211> LENGTH: 1077
<212> TYPE: DNA
<213> ORGANISM: Zea mays

<400> SEQUENCE: 33

| | |
|---|---:|
| atggaggaga tcacccaaca ctttggagtt ggcgcaagca gccacggcca tggccacggc | 60 |
| cagcaccacc atcatcacca ccaccaccac ccgtgggcat cctccctcag cgccgtcgta | 120 |
| gcgccgctgc cgccgcaacc gccaagcgca ggcctgccgc tgaccctgaa cacggtggcg | 180 |
| gccactggga acagcggcgg tagcggcaac ccggtgctgc agcttgccaa cggtggcggc | 240 |
| ctcctcgacg catgcgtcaa ggcgaaggag ccctcgtcgt cgtctcccta cgcaggcgac | 300 |
| gtcgaggcca tcaaggccaa gatcatctcg cacccacact actactcgct cctcactgcc | 360 |
| tacctcgagt gcaacaaggt gggggcacca ccggaggtgt cggcgaggct gacggagata | 420 |
| gcgcaggagg tggaggcgcg gcagcgcacg gcgctcggcg gcctggccgc tgcgacggag | 480 |
| ccggagctgg accagttcat ggaggcgtac cacgagatgc tggtgaagtt caggaggag | 540 |
| ctgacgaggc cgctgcagga ggcgatggag ttcatgcgaa gggtggagtc gcagctgaac | 600 |
| tcgctttcca tctccggaag gtcgctgcgc aacatccttt catctggctc ttctgaggag | 660 |
| gatcaagaag gtagcggagg agagaccgag ctccctgaag ttgatgcaca tggtgtggac | 720 |
| caagagctga agcaccatct cctgaagaaa tacagtggct atctaagctc gctcaagcaa | 780 |
| gaactgtcaa agaagaagaa gaaagggaag ctccccaagg aggctcgcca gcagctcctt | 840 |
| agctggtggg atcagcacta caaatggcct taccccctcag agactcagaa ggtggcactg | 900 |
| gctgagtcta ccgggcttga cctgaagcag atcaacaact ggttcatcaa ccagcggaag | 960 |
| cggcactgga agccatccga ggagatgcac cacctgatga tggacggata ccacaccacc | 1020 |
| aatgccttct acatggacgg ccacttcatc aacgacggcg ggctgtaccg gctcggc | 1077 |

<210> SEQ ID NO 34
<211> LENGTH: 1755
<212> TYPE: DNA
<213> ORGANISM: Arabidopsis thaliana

<400> SEQUENCE: 34

| | |
|---|---:|
| atgaactcga tgaataactg gttaggcttc tctctctctc ctcatgatca aaatcatcac | 60 |
| cgtacggatg ttgactcctc caccaccaga accgccgtag atgttgccgg agggtactgt | 120 |
| tttgatctgg ccgctccctc cgatgaatct tctgccgttc aaacatcttt tctttctcct | 180 |
| ttcggtgtca ccctcgaagc tttcaccaga gacaataata gtcactcccg agattgggac | 240 |
| atcaatggtg gtgcatgcaa taacattaac aataacgaac aaaatggacc aaagcttgag | 300 |
| aatttcctcg gccgcaccac cacgatttac aataccaacg agaccgttgt agatggaaat | 360 |
| ggcgattgtg gaggaggaga cggtggtggt ggcggctcac taggccttc gatgataaaa | 420 |
| acatggctga gtaatcattc ggttgctaat gctaatcatc aagacaatgg taacggtgca | 480 |
| cgaggcttgt ccctctctat gaattcatct actagtgata gcaacaacta caacaacaat | 540 |
| gatgatgtcg tccaagagaa gactattgtt gatgtcgtag aaactacacc gaagaaaact | 600 |
| attgagagtt ttggacaaag gacgtctata taccgcggtg ttacaaggca tcggtggaca | 660 |
| ggtagatacg aggcacattt atgggacaat agttgcaaaa gagaaggcca gactcgcaaa | 720 |
| ggaagacaag tttatctggg aggttatgac aaagaagaaa aagcagctag ggcttacgat | 780 |

```
ttagccgcac taaagtattg gggaaccacc actactacta acttcccctt gagtgaatat      840
gagaaagagg tagaagagat gaagcacatg acgaggcaag agtatgttgc ctctctgcgc      900
aggaaaagta gtggtttctc tcgtggtgca tcgatttatc gaggagtaac aaggcatcac      960
caacatggaa ggtggcaagc taggatcgga agagtcgccg gtaacaaaga cctctacttg     1020
ggaactttcg gcacacagga agaggctgct gaggcttatg acattgcagc cattaaattc     1080
agaggattaa gcgcagtgac taacttcgac atgaacagat acaatgttaa agcaatcctc     1140
gagagcccga gtctacctat tggtagttct gcgaaacgtc tcaaggacgt taataatccg     1200
gttccagcta tgatgattag taataacgtt tcagagagtg caaataatgt tagcggttgg     1260
caaaacactg cgtttcagca tcatcaggga atggatttga gcttattgca gcaacagcag     1320
gagaggtacg ttggttatta caatggagga aacttgtcta ccgagagtac tagggtttgt     1380
ttcaaacaag aggaggaaca acaacacttc ttgagaaact cgccgagtca catgactaat     1440
gttgatcatc atagctcgac ctctgatgat tctgttaccg tttgtggaaa tgttgttagt     1500
tatggtggtt atcaaggatt cgcaatccct gttggaacat cggttaatta cgatcccttt     1560
actgctgctg agattgctta caacgcaaga aatcattatt actatgctca gcatcagcaa     1620
caacagcaga ttcagcagtc gccgggagga gattttccgg tggcgatttc gaataaccat     1680
agctctaaca tgtactttca cggggaaggt ggtggagaag gggctccaac gttttcagtt     1740
tggaacgaca cttag                                                      1755

<210> SEQ ID NO 35
<211> LENGTH: 1755
<212> TYPE: DNA
<213> ORGANISM: Arabidopsis thaliana

<400> SEQUENCE: 35
atgaattcta tgaataactg gttgggcttt tctctttcac cacatgatca gaaccatcac       60
aggactgatg tggattcttc aactaccaga accgccgtgg atgttgcagg cggatactgc      120
tttgatttgg ctgccccatc agatgaatct tcagcagtgc agacttcttt tctgtcacct      180
ttcggcgtta ctcttgaggc tttcaccaga gataataact ctcactcacg cgattgggat      240
attaatggtg gcgcctgcaa taacatcaat aacaatgagc agaatggccc taagctggaa      300
aacttcttgg gaagaacaac taccatctat aatactaacg aaaccgtggt tgatggtaat      360
ggcgattgtg gaggtggcga tggaggtggc ggaggttctc ttggtctgtc aatgatcaaa      420
acctggctgt ctaatcattc agtggctaat gccaaccacc aggataatgg caacggtgct      480
cgcggcttgt ctctttctat gaattcttca acatctgatt caaacaatta caacaataac      540
gatgatgtgt tcaggagaa gactattgtg atgtggttg aaacaactcc aaagaaaaca       600
attgagtctt tggtcagcg cacttcaatc tacaggggcg ttacaaggca tagatggact      660
ggacgctatg aagctcacct gtgggataat tcttgtaaga ggagggcca gactcgcaaa      720
ggaaggcagg tttacttggg cggatatgat aaggaagaga aagcagctag gcctacgat       780
cttgccgcac tgaaatattg ggcaccaca actaccacaa attttcctct ttctgaatac      840
gagaaggaag tggaggagat gaagcatatg acccgccagg agtatgttgc ttctctgaga      900
agaaagtctt caggtttctc taggggcgcc tcaatctata ggggtgtgac aagacatcac      960
cagcacggca gatggcaggc tagaatcgga cgcgttgccg gtaataagga tctgtacttg     1020
ggcacatttg gaactcagga agaggctgcc gaagcatatg atattgcagc tatcaagttt     1080
```

| | |
|---|---|
| agaggcttgt ctgctgtgac taacttcgat atgaatcgct ataacgttaa agccattctt | 1140 |
| gagtctccat cactgcctat cggatcttca gccaagcgcc ttaaagatgt gaataaccca | 1200 |
| gttcctgcaa tgatgatctc taataacgtg tctgaatcag caaataacgt tcaggatgg | 1260 |
| cagaataccg ctttccagca tcaccagggt atggatcttt cactgttgca gcagcagcag | 1320 |
| gaaagatatg tgggatatta caatggtggc aacctgtcta ccgagtcaac aagggtttgc | 1380 |
| tttaagcagg aagaggagca gcagcatttc ttgagaaatt ctccatcaca catgacaaac | 1440 |
| gttgatcatc actcttcaac ctctgatgat tcagtgacag tttgtggcaa tgtggtttct | 1500 |
| tacggaggtt atcaggggttt tgcaattcca gtgggcacct cagttaacta cgatcctttc | 1560 |
| acagccgcag agatcgcata acgctaga aaccattact actacgccca gcaccagcag | 1620 |
| cagcagcaga ttcagcagtc tccaggcgga gatttccctg tggcaatctc aaataaccat | 1680 |
| tcttcaaaca tgtacttcca cggagagggt ggcggagaag gtgctcctac tttctctgtt | 1740 |
| tggaacgata cctga | 1755 |

<210> SEQ ID NO 36
<211> LENGTH: 1986
<212> TYPE: DNA
<213> ORGANISM: Triticum aestivum

<400> SEQUENCE: 36

| | |
|---|---|
| atggcttctg aaacgactg gttggggttc tcgctctccg gccaagaaaa cccacagccg | 60 |
| catcaggata gcccgccgcc cgccggcatc gacatctccg cgccagtga cttctatggc | 120 |
| gtacccacgc agccagctcc cgacgctcaa ctcggcgtgc caggtcatca gccttcatac | 180 |
| gggatcacgg aggacttcaa taggggagct catgaaaccc acgattggaa catgagggt | 240 |
| gatctggact ataacggcgg tgcgtccgag ctctcgatgc tcgtcgggtc gagcgcagtc | 300 |
| ggcggcaaga gggcggccat ggaggccgag accgagccca gcttgaggaa cttcctcggt | 360 |
| tgcaactcgt tcgtctccga gcaagatcag gccggcggct tcttgttctc cggagtcccg | 420 |
| atgaccacca gcagcaacag caacaccggg agcaacacca tggagctctc tatgatcaag | 480 |
| agctggctcc gtgacaacca gctaccccaa gcgccgcacc cgcagtcgca gaccggggcg | 540 |
| cccgcgcagc agccgcaacc ccacgaggag atgggcaccg acgcgagcag cttcgatccg | 600 |
| cggggggagaa acgcgcgtt ggtggtggcg gggagctcgc agagcctggc gctctcgatg | 660 |
| agcacgggtt caggatcgca cttgccaatg gctgtggtca gcggcagtgc cagtggggga | 720 |
| gtctcagaga gcacctcctc ggagaacaag cgagccagcg cgccatgga ttcgccgggc | 780 |
| ggtgcggtag aagctgtcgc gaggaagtcc atcgacacat tcgggcaaag gacgtcgata | 840 |
| tatcgaggtg taacaagaca tagatggaca ggccgttatg aggctcatct ctgggacaat | 900 |
| agctgcagaa gagaagggca gagtcgcaag ggccgacaag tttatcttgg tggctatgac | 960 |
| aaggaggaca aggcagcaag ggcttatgat ttggcagcac tcaagtattg ggtacaaca | 1020 |
| acaactacaa atttcccaat taatacctac gaaaaagagg tggatgaaat gaaacatatg | 1080 |
| actaggcagg aatatatcgc atacttaaga aggaatagca gcggattttc tcgtggtgcg | 1140 |
| tcaaaatatc gtggtgtaac taggcaccat cagcatggga gatggcaagc aagaattggg | 1200 |
| cgggttgcag gaaacaaaga tctctactta ggcaccttca gcaccgagga ggaggcggcg | 1260 |
| gaggcctacg acatcgcggc gatcaagttc gcgggctca acgccgtcac caacttcgac | 1320 |
| atgagtcgct acgacgtcaa gaccatcctc gagagcagca cctgccggt gggtggcgcg | 1380 |
| gctaggcgcc tcaaggaggc cgctgatcat ccggaggccg gcgccacgat ctggcgagcc | 1440 |

```
ggcatggacg gcgccatcat ctcccagctg accgacgtcg ggatgggcgc gtacgcgtcg    1500
taccaccacg gctggccgac catcgcattc cagcagccgt cgccgctctc ggtgcactac    1560
ccatacgtcg cccagccgcc ccgcgggtgg tgcaagcccg agcaggacgc caccgtcgcc    1620
acgcaaagcc tgcaggacct ccagcagctg cacctcggga ccgccgctca caactatttc    1680
caggcatcgt cgagctcaac ggtctacaac ggcggcggcg tcggcgggta ccagcagggc    1740
accggtggca acgccttctt gatgccggct agcaccgttg tggatgaaca ggggcacagc    1800
agcactgccg ccaaccaggg aagcacctgc agctacgggg acgaagaggg gaagctcaat    1860
cttgggtacg atgccatggc gatggcgagc accggcgccg acccatacgc ggcggcgtca    1920
actgtgagca tcgcgagggc gaacgggtac tccaacaact ggagctcgcc gttcagtggc    1980
atgtga                                                                1986
```

<210> SEQ ID NO 37
<211> LENGTH: 1986
<212> TYPE: DNA
<213> ORGANISM: Triticum aestivum

<400> SEQUENCE: 37

```
atggcctcag gaaatgattg gcttggtttt tctctgtcag gccaggagaa ccctcagcca      60
catcaggatt ctccacctcc agcaggaatt gatatctcag gtgcttctga tttctatggc     120
gtgcctactc agcctgcccc agatgcacag ttgggagttc ctggtcacca gccatcttac     180
ggtattactg aggattttaa tagaggcgct catgaaaccc acgattggaa tatgcgcgga     240
gatcttgatt ataacggcgg agcctcagag cttttctatg cggtgggttc ttcagccgtt     300
ggtggcaagc gcgctgccat ggaagcgagg actgaaccta aattggagga ttttcttggc     360
tgcaactcat tcgtgtctga acaggatcag gccggaggtt ttctgttctc aggcgttcca     420
atgactacct cttcaaactc aaacacagga tctaacacta tggaattgtc aatgatcaag     480
tcttggctga gagataacca gttgcctcag gctcctcatc cacagtctca gaccggtgct     540
ccagcacagc agcctcagcc acacgaggaa atgggcacag atgcatcttc attcgatcct     600
agaggccgca atggcgccct tgtggttgca ggctcttcac agtcactggc cttgtctatg     660
tcaacaggct ctggatcaca tctgccaatg gccgtggttt ctggctcagc atctggcgga     720
gtgtcagagt ctacttcttc agaaaacaaa cgcgcttcag gagccatgga ttctcctggt     780
ggcgctgtgg aggcagttgc taggaagtca attgatacct tggacagcg cacatctatc     840 tatagggg tgactaggca tagatggacc ggcagatacg aggcccactt gtgggataat     900
tcatgtagac gcgaaggcca gtctcgcaaa ggaaggcagg tttatcttgg aggttacgat     960
aaggaagata aagcagctcg cgcttatgat ttggccgcac ttaagtactg ggcacaact    1020 accacaacta acttcccaat taacacttac gagaaggaag ttgatgagat gaaacatatg    1080
acccgccagg aatatatcgc ttacctgagg agaaattctt caggattttc aagggggtgcc    1140 tctaaataca ggggagtgac cagacatcac cagcacggta gatggcaggc tagaattggc    1200
cgcgttgccg gaaacaagga tctttatctg ggcacttttt ctacagagga gaggctgcc    1260 gaggcatacg atattgcagc tatcaagttt aggggcttga atgctgtgac aaacttcgat    1320
atgtctagat acgatgttaa aacaatcctt gaatcttcaa ctctgcctgt gggaggagca    1380
gcaaggaggt tgaaggaggc tgccgatcat ccagaagccg gcgcaactat ctggagggct    1440
ggtatggatg gcgccattat ctcacagctt accgatgttg gtatgggcgc ttatgcctct    1500
```

-continued

| | |
|---|---|
| taccatcacg gatggcctac tatcgccttt cagcagcctt caccactgtc tgtgcactat | 1560 |
| ccttacgttg cacagcctcc aagaggatgg tgcaaaccag agcaggatgc aactgtggct | 1620 |
| acccagtctc tgcaggattt gcagcagttg catcttggta cagcagctca caattacttt | 1680 |
| caggcctctt catcttcaac tgtgtataac ggtggcggag ttggtggcta ccagcagggc | 1740 |
| accggtggta atgcattcct gatgccagct tctacagtgg ttgatgaaca gggccactct | 1800 |
| tcaaccgccg caaatcaggg atcaacatgt tcttatggcg atgaagaggg caagctgaac | 1860 |
| ttgggttacg atgcaatggc tatggcctct acaggcgctg atccttatgc tgccgcatca | 1920 |
| actgtttcta ttgcaagagc taatggctac tcaaataact ggtcttcacc attctctggt | 1980 |
| atgtga | 1986 |

<210> SEQ ID NO 38
<211> LENGTH: 1980
<212> TYPE: DNA
<213> ORGANISM: Triticum aestivum

<400> SEQUENCE: 38

| | |
|---|---|
| atggcttctg ggaacgactg gttggggttc tcgctctccg gccaagagaa cccacagccg | 60 |
| catcaggata gctcgccgcc cgccgacatc gacatcgctg cgccagtggc cttctatggc | 120 |
| ctacccacgc agccagctcc cgacgctcaa ctcggtgtgc aggtcatca tcagccttca | 180 |
| tacgggatca cggaggcctt caatagggga gctcatgaaa tccacgattg aacatgagg | 240 |
| ggtgatctgg actacaacgg cggtgcgtcc gagctctcga tgctcgtcgg gtcgagcgca | 300 |
| gttggcggca gagggcggc catggaggcc gagaccgagc ccaagcttga ggacttcctc | 360 |
| gttggcaact cgttcgtctc cgagcaagat caggccggtg gcttcttgtt ctccggtgtc | 420 |
| ccgatggcga ccagcaccaa cagcaacagc aggagcaaca ccatggagct ctctatgatc | 480 |
| aagagctggc tccgtgacaa ccaggtaccc caagcgccgc acccgcagtc gcagaccggg | 540 |
| gcgcccgcg agcagccgca accccacgag gagatgggca ccgacgcgag cagcttcgat | 600 |
| ccgctgggga gaaacggcgc gttggtggtg gcggggagct cgcagagcct ggcgctctcg | 660 |
| atgagcacgg gctcaggatc gcacttgccg atggctgtgc tcggcggcag tcccagtggg | 720 |
| ggagtctcag agagcacctc ctcggagaac aagcgggcca gcggcgccat ggattcgccg | 780 |
| ggcggtgcgg tagaagctgt cgcgaggaag tccatcgaca cattcgggca aggacgtcg | 840 |
| atatatcgag gtgtaacaag acatagatgg acagggcgtt atgaggctca tctctgggac | 900 |
| aatagctgca gaagagaagg gcagagtcgc aagggtaggc aagtttatct gggtggctat | 960 |
| gacaaggagg acaaggcagc aagggcttat gatttggcag cactcaagta ttggggtaca | 1020 |
| acaacaacaa caaatttccc aattaatacc tacgaaaaag aggtggatga atgaaacat | 1080 |
| atgactaggc aggaatacat cgcataccta agaaggaata gcagcggatt ttcccgtggt | 1140 |
| gcgtcaaaat atcgtggtgt aactaggcac catcagcatg ggagatggca agcaagaatt | 1200 |
| gggagggttg caggaaacaa ggatctctac ttaggcacct tcagcaccga ggaggaggcg | 1260 |
| gcggaggcct acgacatcgc ggcgatcaag ttccgtgggc tgaacgccgt caccaacttc | 1320 |
| gacatgagtc gctacgacgt caagaccatc ctcgagagca gcaccctgcc ggtggtggc | 1380 |
| gcggcgaggc gccccaagga ggtcgctgat catccagagg ctggcgccac gatctggcgg | 1440 |
| gccggcatgg acgcggcgt catctcccag ctgaccgacg tcgggatggg cacgtacgcg | 1500 |
| tcgtaccacc acggctggcc aaccatcgca ttccagcagc cctcgccgct gtcggtgcac | 1560 |
| tacccatacg tcgcccagcc gtctcgcggg tggtgcaagc ccgagcagga cgccagcgtc | 1620 |

```
gccacgcaaa gcctgcagga cctccagcag ctgcacctcg ggaccgccgc tcacaactat    1680
ttccaggcat cgtcgagctc cacggtctac aacggcggcg ggtaccagca aggcaccagt    1740
ggcaacgcct tcttgatgcc ggctagcacc gtggtggatg aacaggggca cagcagcact    1800
gccaccaacc agggaagcac atgcagctac ggggacgaag aggggaagct caatctcggg    1860
tacgatgcca tggcgatggc gagcaccggc gccgacccat acgcggcggc gccaactgtg    1920
agcattgcga gggcgaacgg gtactccaac aactggagct cgccgttcaa tggcatgtga    1980
```

<210> SEQ ID NO 39
<211> LENGTH: 1980
<212> TYPE: DNA
<213> ORGANISM: Triticum aestivum

<400> SEQUENCE: 39

```
atggcttctg gaaatgattg gcttggtttt tctctgtcag gccaggagaa cccacagcct      60
catcaggatt cttcaccacc tgccgatatt gatatcgcag gagcttcagg tttctatggc     120
cttccaactc agccagctcc tgatgcccag ctgggagtgc aggtcatca ccagccttct      180 tacggtatta ccgaggcttt taatcgcggc gctcatgaaa tccacgattg gaatatgagg     240
ggcgatctgg attataacgg cggagcctca gagctttcta tgctggtggg ctcttcagca     300
gttggtggca agcgcgctgc catggaagct gagactgaac caaaattgga ggattttctt     360
gtgggaaact cattcgtttc tgaacaggat caggctggag gttttctgtt ctcaggtgtg     420
cctatggcca catctactaa ttctaactca aggtctaata ccatggaact gtcaatgatt     480
aagtcttggt tgagagataa ccaggttcca caggccccac atcctcagtc acagaccgga     540
gcacctgcac agcagccaca gcctcacgag gaaatgggaa cagatgcatc ttcatttgat     600
ccattgggca gaaatggcgc tcttgtggtt gccggctctt cacagtctct ggcattgtca     660
atgtctacag gctcaggatc tcacctgcca atggctgtgt tggcggatc accttctggt      720 ggcgtttcag agtctacttc ttcagaaaac aaacgcgcat caggcgctat ggattctcct     780
ggaggtgctg tggaggctgt tgccaggaag tcaattgata cattcggaca gaggacttct     840
atctatagag gtgtgaccag acatcgctgg acaggcagat acgaggccca cttgtgggat     900
aattcatgca gacgcgaagg acagtctagg aaaggtagac aggtttatct ggcggatac      960 gataaggaag ataaagcagc tcgcgcttat gatttggccg cacttaagta ctggggcact    1020
accacaacta ccaacttccc aattaacact tacgagaagg aagtggatga gatgaaacat    1080
atgacccgcc aggaatatat cgcctacttg aggagaaatt cttcaggatt ctcaggggg     1140 gcatctaaat acagaggagt gacacgccat caccagcacg gtagatggca ggctcgcatt    1200
ggcagggttg ccggaaacaa ggatctttat ctgggcactt tttcaaccga ggaagaggct    1260
gccgaggctt acgatattgc agctatcaag tttagaggac tgaatgccgt gactaacttc    1320
gatatgtctc gctacgatgt taaaactatc cttgaatctt caaccctgcc tgtgggtgga    1380
gcagcacgca ggccaaagga ggttgcagat catcctgaag caggcgctac catttggagg    1440
gctggcatgg atggaggtgt gatctcacag ctgacagatg ttggtatggg cacttatgcc    1500
tcttaccatc acggctggcc aacaattgca ttccagcagc catcaccttt gtctgtgcac    1560
tatccatacg ttgcccagcc ttctagaggt tggtgcaaac ctgagcagga tgcctcagtg    1620
gcaacacagt ctctgcagga tttgcagcag ttgcatcttg aactgctgc ccacaattac     1680 tttcaggctt cttcatcttc aactgtttat aatggcggag gttaccagca gggcacttct    1740
```

| ggcaacgcct | tcctgatgcc | agcatctaca | gtggttgatg | aacagggcca | ttcttcaacc | 1800 |
| gcaacaaatc | agggatcaac | ctgttcttat | ggcgatgaag | agggcaagct | gaacttgggt | 1860 |
| tacgatgcca | tggcaatggc | ttctaccggc | gccgatccat | atgcagctgc | ccctacagtt | 1920 |
| tcaatcgcca | gagcaaatgg | ctactctaat | aactggtctt | cacctttcaa | cggtatgtga | 1980 |

<210> SEQ ID NO 40
<211> LENGTH: 2112
<212> TYPE: DNA
<213> ORGANISM: Sorghum bicolor

<400> SEQUENCE: 40

| atggctactg | tgaacaactg | gctcgctttc | tccctctccc | cgcaggagct | gccgcccacc | 60 |
| cagacggact | ccaccctcat | ctctgccgcc | accaccgacg | atgtctccgg | cgatgtctgc | 120 |
| ttcaacatcc | cccaagattg | gagcatgagg | ggatccgagc | tttcggcgct | cgtcgccgag | 180 |
| ccgaagctgg | aggacttcct | cggcggaatc | tccttctccg | agcagcacca | caaggccaac | 240 |
| tgcaacatga | tccccagcac | tagcagcaca | gcttgctacg | cgagctcggg | tgctaccgcc | 300 |
| ggctaccatc | accagctgta | ccaccagccc | accagctccg | cgctccactt | cgctgactcc | 360 |
| gtcatggtgg | cctcctcggc | cggcggcgtc | cacgacggag | gtgccatgct | cagcgcggcc | 420 |
| agcgctaatg | gtagcgctgg | cgctggcgct | gccagtgcca | atggcagcgg | cagcatcggg | 480 |
| ctgtccatga | tcaagaactg | gctgcggagc | caaccagctc | ccatgcagcc | gagggtggcg | 540 |
| gcggctgaga | gcgtgcaggg | gctctctttg | tccatgaaca | tggcggggggc | gacgcaaggc | 600 |
| gccgctggca | tgccacttct | tgctggagag | gcgggccggg | cgcccgagag | tgtctcgacg | 660 |
| tcggcacagg | gtggagccgt | cgtcacggct | ccaaaggagg | atagcggtgg | cagcggtgtt | 720 |
| gccgccaccg | gcgccctagt | agccgtgagc | acggacacgg | gtggcagcgg | cgcgtcggct | 780 |
| gacaacacgg | caaggaagac | ggtggacacg | ttcgggcagc | gcacgtcgat | ttaccgtggc | 840 |
| gtgacaaggc | atagatggac | tgggagatat | gaagcacatc | tgtgggacaa | cagttgcaga | 900 |
| agggaaggac | aaactcgcaa | gggtcgtcaa | gtctatttag | gtggctatga | taaagaggag | 960 |
| aaagctgcta | gggcttatga | tctggctgct | cttaagtact | ggggtcccac | gacaacaaca | 1020 |
| aattttccag | tgaataacta | cgaaaaggag | ctggaggata | tgaagcacat | gacaaggcag | 1080 |
| gagtttgtag | cgtctctgag | aaggaagagc | agtggtttct | ccagaggtgc | atccatttac | 1140 |
| aggggagtga | ctaggcatca | ccagcatgga | agatggcaag | cacggattgg | acgagttgca | 1200 |
| gggaacaagg | atctctactt | ggccaccttc | agcacgcagg | aggaggcagc | ggaggcatac | 1260 |
| gacattgcgg | cgatcaagtt | ccgcggcctc | aacgccgtca | caaacttcga | catgagccgc | 1320 |
| tacgacgtca | agagcatcct | ggacagcagt | gcgctcccca | tcggcagcgc | cgccaagcgt | 1380 |
| ctcaaggagg | ccgaggccgc | cgcgtccgca | cagcaccatg | ccggcgtggt | gagctacgac | 1440 |
| gtcggccgca | tagcctcaca | gctcggcgac | ggcggcgccc | tggcggcggc | gtacggcgcg | 1500 |
| cactaccatg | gcgcctggcc | gaccatcgcg | ttcagccgga | gcgcggccac | gggcctgtac | 1560 |
| cacccgtacg | cgcagccgat | gcgcgggtgg | tgcaagcagg | agcaggacca | cgcggtgatc | 1620 |
| gcggccgcgc | acagcctgca | ggagctccac | cacctgaacc | tgggtgctgc | cgccggcgcg | 1680 |
| cacgacttct | tctcggcggg | gcagcaggcg | gcgatgcacg | gcctgggtag | catggacaat | 1740 |
| gcatcactcg | agcacagcac | cggctccaac | tccgtcgtgt | acaacggtgt | tggtgatagc | 1800 |
| aacggcagca | ccgtcgtcgg | cagtggtggc | tacatgatgc | ctatgagcgc | tgccacggcg | 1860 |
| acggctacca | cggcaatggt | gagccacgag | caggtgcatg | cacgggcaca | gggtgatcac | 1920 |

```
cacgacgaag ccaagcaggc tgctcagatg gggtacgaga gctacctggt gaacgcagag   1980
aactatggcg gcgggaggat gtctgcggcc tgggcgactg tctcagcgcc accggcggca   2040
agcagcaacg ataacatggc ggacgtcggc catggcggcg cacagctctt cagtgtctgg   2100
aacgatactt aa                                                       2112

<210> SEQ ID NO 41
<211> LENGTH: 2112
<212> TYPE: DNA
<213> ORGANISM: Sorghum bicolor

<400> SEQUENCE: 41
atggccacag tgaataactg gcttgcattt tctctgtcac cacaggaact tccacctaca     60
cagactgatt caactctgat ttctgctgcc actaccgatg atgtgtcagg cgatgtttgc    120
ttcaatatcc cacaggattg gtctatgcgc ggctcagaac tttctgcact ggttgctgaa    180
cctaagttgg aggattttct tggcggaatt ctttctcag agcagcatca caaagccaat     240
tgcaacatga tcccatcaac atcttcaact gcctgttatg catcttcagg tgcaacagct    300
ggctatcatc accagttgta ccatcagcct acttcttcag cccttcactt tgcagattct    360
gtgatggttg cttcttcagc cggtggcgtt catgatggag gtgctatgct ttcagcagct    420
tctgcaaatg gctcagcagg tgcaggagca gcatctgcaa acggatctgg ttcaattggt    480
ttgtcaatga tcaagaattg gcttcgctct cagccagctc ctatgcagcc aagggtggct    540
gccgcagaat ctgttcaggg tctttctctg tctatgaata tggctggcgc cacacaggga    600
gctgccggta tgccactgtt ggcaggagaa aggggaaggg cacctgagtc tgtgtcaacc    660
tctgctcagg gcggagccgt ggttacagca cctaaggagg attcaggtgg ctctggagtt    720
gcagctactg gtgcattggt ggctgttcct accgatacag gaggttcagg agcatctgct    780
gataataccg cccgcaaaac cgtggataca ttcggccaga ggacatcaat ctatagagga    840
gttacaagac atcgctggac tggaagatac gaagctcacc tttgggataa ctcttgcaga    900
cgcgagggcc agaccaggaa gggaagacag gtgtatctgg gcggatacga taaggaggaa    960
aaagccgcaa gggcttatga tttggctgcc cttaaatact ggggcccaac aactaccaca   1020
aattttcctg tgaataacta tgagaaggaa ctggaggata tgaaacacat gaccaggcag   1080
gaatttgttg cttcattgag gagaaagtct tcaggattct caagaggtgc ctctatctat   1140
agaggcgtga cacgccatca ccagcatgga aggtggcagg ctaggatcgg aagggttgca   1200
ggaaacaaag atttgtatct tggcactttc tctacccagg aggaagcagc tgaggcatac   1260
gatattgccg caatcaagtt tagaggattg aatgctgtga ctaacttcga tatgtcacgc   1320
tacgatgtta aatctatcct ggattcttca gccttgccaa tcggctcagc tgccaagagg   1380
cttaaagaag ctgaagcagc tgcctctgct cagcatcacg ccggcgtggt ttcatacgat   1440
gtgggaagaa ttgcctctca gcttggcgat ggtggcgcac tggcagctgc ctatggtgcc   1500
cattaccacg gcgcatggcc aactatcgct tttcagcctt cagcagctac cggactgtat   1560
cacccatacg cccagcctat gagaggttgg tgtaagcagg aacaggatca tgctgttatc   1620
gccgcagctc actctctgca ggagttgcat cacctgaatt tgggtgccgc agctggcgca   1680
catgatttct tttctgctgg tcagcaggcc gcaatgcacg gcctgggatc tatggataat   1740
gcctcattgg agcattctac tggctcaaat tctgtggttt ataacggtgt gggcgattca   1800
aacgatctta ccgtggttgg ttcaggaggt tacatgatgc ctatgtctgc tgccactgcc   1860
```

| | |
|---|---|
| accgcaacta ccgctatggt gtcacatgaa caggttcacg ctagagctca gggcgatcat | 1920 |
| cacgatgagg ccaaacaggc agctcagatg ggatatgaat cttacctggt gaatgctgag | 1980 |
| aactacggag gtggtaggat gtcagcagca tgggcaactg tttctgctcc acctgctgcc | 2040 |
| tcttcaaatg ataacatggc agatgtgggc catggcggag ctcagttgtt ctctgtttgg | 2100 |
| aatgatacct ga | 2112 |

<210> SEQ ID NO 42
<211> LENGTH: 927
<212> TYPE: DNA
<213> ORGANISM: Triticum aestivum

<400> SEQUENCE: 42

| | |
|---|---|
| atggacaagc agagcgtcat gtggagacag ctgcagcacc agcaccacca ggccagcggc | 60 |
| gcggcgggtg gcaatgccgt cgctgctgcc ggtgctggtg cgacgacgac gaccgcgccc | 120 |
| gtccggccga gcggcgcgcg gtggacgccc acgccggagc aggtcaagat cctcaaggac | 180 |
| ctctactacg actgcggcat ccggtcgccc acggcggagc agatccagcg gatcgcggcc | 240 |
| cggctccggc agtacggccg gatcgagggc aagaacgtct tctactggtt ccagaaccac | 300 |
| aaggcccgcg agcgccagaa gaagcgcctc ggcgtcgacg tcaacggctc ccccctcgcc | 360 |
| accgccaccg ccgccgacgt cctcgccctc tcccctccg gtgcggcggc cggcttgtac | 420 |
| ggcgccggca gctgcgccgg tagaggcgcg gctgtccatc cagatgcgag cgccactact | 480 |
| actacttgct ggggagacag caccctgcag gactacatgg gcgcgaggag cacggcggga | 540 |
| gcgggcaacc acgcggcgc cgccgcagca gcacctacgc cgtggccagc tgcgagcttc | 600 |
| cctttctcca ccaaccagac gccgccaatg ccccgccgc gggagctccc gctcttcccg | 660 |
| accgcggag gccggcaaga aagcgccgac gacttcaacg gcagcagcta ccatctccag | 720 |
| cccaacagct cgcagtggtg ggaagctgcc gccgccagca acgccaacgc catggcagtc | 780 |
| gtccatcatc agctgctgca agaacagcac gagcagcagc acagcttta caacagcagc | 840 |
| ggcaaccagc agcagatgat gatgatgatg cccatccagg acgccggcac ctccccggag | 900 |
| ctcactctcc gcgcccctta catgtga | 927 |

<210> SEQ ID NO 43
<211> LENGTH: 927
<212> TYPE: DNA
<213> ORGANISM: Triticum aestivum

<400> SEQUENCE: 43

| | |
|---|---|
| atggataagc agtcagttat gtggaggcag cttcagcatc agcaccacca ggcatctgga | 60 |
| gctgccggcg gaaatgcagt ggcagctgcc ggagccggtg caactaccac aactgcacca | 120 |
| gttcgcccctt caggagctag gtggacacct actccagagc aggttaagat tcttaaagat | 180 |
| ctgtactacg attgcggtat cagatctcca actgctgaac agattcagcg catcgcagct | 240 |
| agactgcgcc agtatggccg cattgaggga aagaatgtgt ttactggtt ccagaaccac | 300 |
| aaagcaaggg aaagacagaa gaaaaggttg ggagtggatg ttaacggttc accacttgct | 360 |
| accgccacag ccgcagatgt tcttgccctg tctccttcag gtgctgccgc aggcctgtat | 420 |
| ggcgctggat cttgtgctgg tagaggcgct gctgtgcatc ctgatgcatc tgctaccaca | 480 |
| actacctgtt ggggcgattc aaccttgcag gattacatgg gagctcgctc tacagccgga | 540 |
| gcaggtaatc atggtggcgc agctgccgca gctcctactc catggcctgc cgcatctttt | 600 |
| ccattctcaa ctaaccagac cccacctatg ccaccaccaa gagagttgcc acttttcct | 660 |

| | |
|---|---|
| actggcggcg gcagacagga atcagccgat gatttcaatg gctcttcata tcatttgcag | 720 |
| cctaactctt cacagtggtg ggaggctgcc gcagcttcaa atgctaacgc catggcagtg | 780 |
| gttcatcacc agctgttgca ggagcagcat gaacagcagc actcttttta taattcttca | 840 |
| ggtaaccagc agcagatgat gatgatgatg ccaatccagg atgctggcac atctccagaa | 900 |
| ctgactttga gagccccta catgtga | 927 |

<210> SEQ ID NO 44
<211> LENGTH: 984
<212> TYPE: DNA
<213> ORGANISM: Sorghum bicolor

<400> SEQUENCE: 44

| | |
|---|---|
| atggcggcca atgtgggcgc gggcaggagt gccgtcggcg gcggcggtgg tggtggagcg | 60 |
| ggtggcactg gcactgctgc tgccagcggc agcgtggcga cgacagcggt gtgccgcccc | 120 |
| atcggctcgc ggtggacgcc gacgcccgag cagatcagga tactcaagga gttctactac | 180 |
| ggctgcggca tccggtcgcc caactcggag cagatccagc gcatcaccgc catgctgcgc | 240 |
| cagcacggca agatcgaggg caagaacgtc ttctactggt tccagaacca caaggcccgc | 300 |
| gaacgccaga agcgccgcct caccaacctc gacgtcaacg tgcccaccgc cgcagccgcc | 360 |
| ggcgcggccg acgccagcac ccacctaggc gtcctctcgc tgtcgtcgcc ttcaggcgcg | 420 |
| gcgcctccct cgcccaccct cggcttctac gccggcaatg gcggcgccgg ctcgaccgtg | 480 |
| ctgctggaca cgagttccga ctgcgctgcc atggccactg agacatgctt cctgcaggac | 540 |
| tacatgggcg tgatgggcac gggcagcgcg gccgccgcgt cgccgtgggc atgcttctcg | 600 |
| tcgtcgaaca ctatgcggc ggccgcggca cgggcaccga cggtgacgcg ggcgcccgag | 660 |
| acgctccctc tcttcccgac gggcggcgac gacagccagc ccggcggcc gcggcacgga | 720 |
| gtcccagttc cagttgcagc aggcgaggcc atccgcggcg gcagcagcag cagcaggtac | 780 |
| ctgccgttct ggggtgccgc gcccacaact gccagtgcca cttccattgg gatccagcag | 840 |
| caacaccagc tgctgcagct gcaagagcag tacagctttt acagcaacgc catgcccggc | 900 |
| accggcagcc aagatgcatc agcagcatcc ctggagctca gcctcagctc ctggtgctcc | 960 |
| ccttaccctg cagggaccat gtga | 984 |

<210> SEQ ID NO 45
<211> LENGTH: 984
<212> TYPE: DNA
<213> ORGANISM: Sorghum bicolor

<400> SEQUENCE: 45

| | |
|---|---|
| atggcggcga acgtggggc aggtcggtca gcggtcgggg gaggggagg gggtggagcg | 60 |
| ggtgggactg gcacagcggc agcgtcaggc tcagttgcca ctaccgcagt gtgcagacca | 120 |
| attggatctc gctggacccc aacacctgag cagattagga tcctgaagga attttattac | 180 |
| ggctgtggaa ttagatcacc taattctgag cagattcaga ggatcactgc tatgttgaga | 240 |
| cagcatggca agatcgaggg aaaaaatgtg ttttattggt tccagaacca caaggcccgc | 300 |
| gaaaggcaga aaagacgcct tacaaatctg gatgtgaatg ttccaacagc tgccgcagct | 360 |
| ggcgccgcag atgcatcaac tcatttggga gtgttgtcac tttcttcacc atctggtgct | 420 |
| gcccccacctt cacctaccct tggtttttat gctggcaatg gcggagccgg atctaccgtt | 480 |
| ctgttggata catcttcaga ttgcgcagct atggcaactg aaacctgctt tctgcaggat | 540 |

| | |
|---|---|
| tacatgggcg tgatgggcac tggatcagcc gcagctgcct ctccttgggc ttgcttctct | 600 |
| tcatctaaca caatggcagc tgccgcagct cgcgcaccaa cagttactag ggctcctgag | 660 |
| actctgccat tgttccctac cggtggcgat gattctcagc caagaagacc aagacatgga | 720 |
| gtgccagttc ctgtggctgc tggcgaggct atcagaggcg gctcatcttc atctcgctac | 780 |
| cttccatttt ggggtgctgc ccctacaact gcatcagcta catctattgg catccagcag | 840 |
| cagcaccagc ttctgcagct gcaggagcag tattcattct actctaacgc catgccagga | 900 |
| actggttcac aggatgcatc tgccgcatct cttgaattgt ccttgtcctc ctggtgctct | 960 |
| ccctatcccg ctggaactat gtga | 984 |

<210> SEQ ID NO 46
<211> LENGTH: 783
<212> TYPE: DNA
<213> ORGANISM: Arabidopsis thaliana

<400> SEQUENCE: 46

| | |
|---|---|
| atggaaaacg aagtaaacgc aggaacagca agcagttcaa gatggaaccc aacgaaagat | 60 |
| cagatcacgc tactggaaaa tctttacaag gaaggaatac gaactccgag cgccgatcag | 120 |
| attcagcaga tcaccggtag gcttcgtgcg tacggccata tcgaaggtaa aaacgtcttt | 180 |
| tactggttcc agaaccataa ggctaggcaa cgccaaaagc agaaacagga gcgcatggct | 240 |
| tacttcaatc gcctcctcca caaaaccctcc cgtttcttct accccctcc ttgctcaaac | 300 |
| gtgggttgtg tcagtccgta ctatttacag caagcaagtg atcatcatat gaatcaacat | 360 |
| ggaagtgtat acacaaacga tcttcttcac agaaacaatg tgatgattcc aagtggtggc | 420 |
| tacgagaaac ggacagtcac acaacatcag aaacaacttt cagacataag aacaacagca | 480 |
| gccacaagaa tgccaatttc tccgagttca ctcagatttg acagatttgc cctccgtgat | 540 |
| aactgttatg ccggtgagga cattaacgtc aattccagtg gacggaaaac actccctctt | 600 |
| tttcctcttc agcctttgaa tgcaagtaat gctgatggta tgggaagttc cagttttgcc | 660 |
| cttggtagtg attctccggt ggattgttct agcgatggag ccggccgaga gcagccgttt | 720 |
| attgatttct tttctggtgg ttctacttct actcgtttcg atagtaatgg taatgggttg | 780 |
| taa | 783 |

<210> SEQ ID NO 47
<211> LENGTH: 783
<212> TYPE: DNA
<213> ORGANISM: Arabidopsis thaliana

<400> SEQUENCE: 47

| | |
|---|---|
| atggaaaacg aagtaaacgc aggaacagca agcagttcaa gatggaaccc aacgaaagat | 60 |
| cagatcacgc tactggaaaa tctttacaag gaaggaatac gaactccgag cgccgatcag | 120 |
| attcagcaga tcaccggtag gcttcgtgcg tacggccata tcgaaggtaa aaacgtcttt | 180 |
| tactggttcc agaaccataa ggctaggcaa cgccaaaagc agaaacagga gcgcatggct | 240 |
| tacttcaatc gcctcctcca caaaaccctcc cgtttcttct accccctcc ttgctcaaac | 300 |
| gtgggttgtg tcagtccgta ctatttacag caagcaagtg atcatcatat gaatcaacat | 360 |
| ggaagtgtat acacaaacga tcttcttcac agaaacaatg tgatgattcc aagtggtggc | 420 |
| tacgagaaac ggacagtcac acaacatcag aaacaacttt cagacataag aacaacagca | 480 |
| gccacaagaa tgccaatttc tccgagttca ctcagatttg acagatttgc cctccgtgat | 540 |
| aactgttatg ccggtgagga cattaacgtc aattccagtg gacggaaaac actccctctt | 600 |

```
tttcctcttc agcctttgaa tgcaagtaat gctgatggta tgggaagttc cagttttgcc      660
cttggtagtg attctccggt ggattgttct agcgatggag ccggccgaga gcagccgttt      720
attgatttct ttctggtgg ttctacttct actcgtttcg atagtaatgg taatggggttg     780 taa                                                                    783
```

```
<210> SEQ ID NO 48
<211> LENGTH: 978
<212> TYPE: DNA
<213> ORGANISM: Arabidopsis thaliana

<400> SEQUENCE: 48
atgtcctcct caaacaaaaa ttggccaagc atgttcaaat ccaaaccttg caacaataat      60
catcatcatc aacatgaaat cgatactcca tcttacatgc actactctaa ttgcaaccta     120
tcatcttcct tttcctcaga tcggatacca gatcctaaac cgagatggaa tcctaaaccg     180
gagcagatta ggatactcga atcaatcttc aattccggta ctattaaccc acctagagag     240
gagattcaaa gaatccggat ccggcttcaa gaatatggtc aaatcggtga cgcaaacgtg     300
ttttactggt ttcaaaaccg gaaatctcga gcaaaacaca gcttcgtgt tcatcacaaa      360 agccctaaaa tgtcaaagaa ggacaagacg gttattccta gtactgacgc tgatcattgt     420
tttggttttg ttaaccaaga aaccggatta tatccggttc aaaacaatga gttggtggta     480
accgaaccgg ccggttttct atttccggtt cataatgatc cgagcgctgc tcaatcagcg     540
tttggttttg gcgattttgt tgtaccggtg gtaacggaag aagggatggc attctctacc     600
gttaataacg gcgttaattt ggagactaac gaaaattttg ataaaattcc ggcgatcaat     660
ttatacggcg gagatggaaa tggcggtgga aattgttttc ctcctttgac tgttccatta     720
accatcaatc aatctcaaga aaacgagat gtaggattat ccggtggtga agacgtcgga      780
gataatgttt atccggtgag aatgacggtg tttattaacg agatgcctat cgaagtagtg     840
tctggattat tcaacgttaa ggcagctttc ggaaacgatg ccgttttgat caactcgttt     900
ggccagccta ttcttacaga tgaatttggt gttacttatc aacctctcca aatggcgca      960 atctattatc ttattag                                                   978
```

```
<210> SEQ ID NO 49
<211> LENGTH: 978
<212> TYPE: DNA
<213> ORGANISM: Arabidopsis thaliana

<400> SEQUENCE: 49
atgtcctcct caaacaaaaa ttggccaagc atgttcaaat ccaaaccttg caacaataat      60
catcatcatc aacatgaaat cgatactcca tcttacatgc actactctaa ttgcaaccta     120
tcatcttcct tttcctcaga tcggatacca gatcctaaac cgagatggaa tcctaaaccg     180
gagcagatta ggatactcga atcaatcttc aattccggta ctattaaccc acctagagag     240
gagattcaaa gaatccggat ccggcttcaa gaatatggtc aaatcggtga cgcaaacgtg     300
ttttactggt ttcaaaaccg gaaatctcga gcaaaacaca gcttcgtgt tcatcacaaa      360 agccctaaaa tgtcaaagaa ggacaagacg gttattccta gtactgacgc tgatcattgt     420
tttggttttg ttaaccaaga aaccggatta tatccggttc aaaacaatga gttggtggta     480
accgaaccgg ccggttttct atttccggtt cataatgatc cgagcgctgc tcaatcagcg     540
tttggttttg gcgattttgt tgtaccggtg gtaacggaag aagggatggc attctctacc     600
```

-continued

```
gttaataacg cgttaatttt ggagactaac gaaaattttg ataaaattcc ggcgatcaat    660
ttatacggcg gagatggaaa tggcggtgga aattgttttc ctcctttgac tgttccatta    720
accatcaatc aatctcaaga aaacgagat gtaggattat ccggtggtga agacgtcgga     780
gataatgttt atccggtgag aatgacggtg tttattaacg agatgcctat cgaagtagtg    840
tctggattat tcaacgttaa ggcagctttc ggaaacgatg ccgttttgat caactcgttt    900
ggccagccta ttcttacaga tgaatttggt gttacttatc aacctctcca aaatggcgca    960
atctattatc ttatttag                                                  978
```

<210> SEQ ID NO 50
<211> LENGTH: 240
<212> TYPE: PRT
<213> ORGANISM: Agrobacterium tumefaciens

<400> SEQUENCE: 50

```
Met Asp Leu Arg Leu Ile Phe Gly Pro Thr Cys Thr Gly Lys Thr Ser
1               5                   10                  15

Thr Ala Val Ala Leu Ala Gln Gln Thr Gly Leu Pro Val Leu Ser Leu
            20                  25                  30

Asp Arg Val Gln Cys Cys Pro Gln Leu Ser Thr Gly Ser Gly Arg Pro
        35                  40                  45

Thr Val Glu Glu Leu Lys Gly Thr Ser Arg Leu Tyr Leu Asp Asp Arg
    50                  55                  60

Pro Leu Val Lys Gly Ile Ile Ala Ala Lys Gln Ala His Glu Arg Leu
65                  70                  75                  80

Met Gly Glu Val Tyr Asn Tyr Glu Ala His Gly Leu Ile Leu Glu
                85                  90                  95

Gly Gly Ser Ile Ser Leu Leu Lys Cys Met Ala Gln Ser Ser Tyr Trp
            100                 105                 110

Ser Ala Asp Phe Arg Trp His Ile Ile Arg His Glu Leu Ala Asp Glu
        115                 120                 125

Glu Thr Phe Met Asn Val Ala Lys Ala Arg Val Lys Gln Met Leu Arg
    130                 135                 140

Pro Ala Ala Gly Leu Ser Ile Ile Gln Glu Leu Val Asp Leu Trp Lys
145                 150                 155                 160

Glu Pro Arg Leu Arg Pro Ile Leu Lys Glu Ile Asp Gly Tyr Arg Tyr
                165                 170                 175

Ala Met Leu Phe Ala Ser Gln Asn Gln Ile Thr Ser Asp Met Leu Leu
            180                 185                 190

Gln Leu Asp Ala Asp Met Glu Asp Lys Leu Ile His Gly Ile Ala Gln
        195                 200                 205

Glu Tyr Leu Ile His Ala Arg Arg Gln Glu Gln Lys Phe Pro Arg Val
    210                 215                 220

Asn Ala Ala Ala Tyr Asp Gly Phe Glu Gly His Pro Phe Gly Met Tyr
225                 230                 235                 240
```

<210> SEQ ID NO 51
<211> LENGTH: 318
<212> TYPE: PRT
<213> ORGANISM: Arabidopsis thaliana

<400> SEQUENCE: 51

```
Met Lys Cys Asn Asp Lys Met Val Val Ile Met Gly Ala Thr Gly Ser
1               5                   10                  15

Gly Lys Ser Ser Leu Ser Val Asp Leu Ala Leu His Phe Lys Ala Glu
```

```
            20                  25                  30
Ile Ile Asn Ser Asp Lys Met Gln Phe Tyr Asp Gly Leu Lys Ile Thr
            35                  40                  45

Thr Asn Gln Ser Thr Ile Glu Asp Arg Arg Gly Val Pro His His Leu
 50                  55                  60

Leu Gly Glu Leu Asn Pro Glu Ala Gly Glu Val Thr Ala Ala Glu Phe
 65                  70                  75                  80

Arg Val Met Ala Ala Glu Ala Ile Ser Glu Ile Thr Gln Arg Lys Lys
                 85                  90                  95

Leu Pro Ile Leu Ala Gly Gly Ser Asn Ser Tyr Ile His Ala Leu Leu
            100                 105                 110

Ala Lys Ser Tyr Asp Pro Glu Asn Tyr Pro Phe Ser Asp His Lys Gly
            115                 120                 125

Ser Ile Cys Ser Glu Leu Lys Tyr Asp Cys Cys Phe Ile Trp Ile Asp
            130                 135                 140

Val Asp Gln Ser Val Leu Phe Glu Tyr Leu Ser Leu Arg Leu Asp Leu
145                 150                 155                 160

Met Met Lys Ser Gly Met Phe Glu Glu Ile Ala Glu Phe His Arg Ser
                165                 170                 175

Lys Lys Ala Pro Lys Glu Pro Leu Gly Ile Trp Lys Ala Ile Gly Val
            180                 185                 190

Gln Glu Phe Asp Asp Tyr Leu Lys Met Tyr Lys Trp Asp Asn Asp Met
            195                 200                 205

Asp Lys Trp Asp Pro Met Arg Lys Glu Ala Tyr Glu Lys Ala Val Arg
210                 215                 220

Ala Ile Lys Glu Asn Thr Phe Gln Leu Thr Lys Asp Gln Ile Thr Lys
225                 230                 235                 240

Ile Asn Lys Leu Arg Asn Ala Gly Trp Asp Ile Lys Lys Val Asp Ala
                245                 250                 255

Thr Ala Ser Phe Arg Glu Ala Ile Arg Ala Ala Lys Glu Gly Glu Gly
            260                 265                 270

Val Ala Glu Met Gln Arg Lys Ile Trp Asn Lys Glu Val Leu Glu Pro
            275                 280                 285

Cys Val Lys Ile Val Arg Ser His Leu Asp Gln Pro Ile Asn Tyr Tyr
            290                 295                 300

Tyr Tyr Tyr Phe Tyr Leu Leu Lys Arg Phe Leu Ser Leu Asn
305                 310                 315

<210> SEQ ID NO 52
<211> LENGTH: 359
<212> TYPE: PRT
<213> ORGANISM: Zea mays

<400> SEQUENCE: 52

Met Glu Glu Ile Thr Gln His Phe Gly Val Gly Ala Ser Ser His Gly
 1               5                  10                  15

His Gly His Gly Gln His His His His His His His His Pro Trp
                 20                  25                  30

Ala Ser Ser Leu Ser Ala Val Val Ala Pro Leu Pro Pro Gln Pro Pro
            35                  40                  45

Ser Ala Gly Leu Pro Leu Thr Leu Asn Thr Val Ala Ala Thr Gly Asn
 50                  55                  60

Ser Gly Gly Ser Gly Asn Pro Val Leu Gln Leu Ala Asn Gly Gly Gly
 65                  70                  75                  80
```

Leu Leu Asp Ala Cys Val Lys Ala Lys Glu Pro Ser Ser Ser Pro
            85                  90                  95

Tyr Ala Gly Asp Val Glu Ala Ile Lys Ala Lys Ile Ile Ser His Pro
        100                 105                 110

His Tyr Tyr Ser Leu Leu Thr Ala Tyr Leu Glu Cys Asn Lys Val Gly
            115                 120                 125

Ala Pro Pro Glu Val Ser Ala Arg Leu Thr Glu Ile Ala Gln Glu Val
130                 135                 140

Glu Ala Arg Gln Arg Thr Ala Leu Gly Gly Leu Ala Ala Ala Thr Glu
145                 150                 155                 160

Pro Glu Leu Asp Gln Phe Met Glu Ala Tyr His Glu Met Leu Val Lys
                165                 170                 175

Phe Arg Glu Glu Leu Thr Arg Pro Leu Gln Glu Ala Met Glu Phe Met
            180                 185                 190

Arg Arg Val Glu Ser Gln Leu Asn Ser Leu Ser Ile Ser Gly Arg Ser
        195                 200                 205

Leu Arg Asn Ile Leu Ser Ser Gly Ser Ser Glu Asp Gln Glu Gly
    210                 215                 220

Ser Gly Gly Glu Thr Glu Leu Pro Glu Val Asp Ala His Gly Val Asp
225                 230                 235                 240

Gln Glu Leu Lys His His Leu Leu Lys Lys Tyr Ser Gly Tyr Leu Ser
                245                 250                 255

Ser Leu Lys Gln Glu Leu Ser Lys Lys Lys Lys Gly Lys Leu Pro
            260                 265                 270

Lys Glu Ala Arg Gln Gln Leu Leu Ser Trp Trp Asp Gln His Tyr Lys
        275                 280                 285

Trp Pro Tyr Pro Ser Glu Thr Gln Lys Val Ala Leu Ala Glu Ser Thr
290                 295                 300

Gly Leu Asp Leu Lys Gln Ile Asn Asn Trp Phe Ile Asn Gln Arg Lys
305                 310                 315                 320

Arg His Trp Lys Pro Ser Glu Glu Met His His Leu Met Met Asp Gly
                325                 330                 335

Tyr His Thr Thr Asn Ala Phe Tyr Met Asp Gly His Phe Ile Asn Asp
            340                 345                 350

Gly Gly Leu Tyr Arg Leu Gly
        355

<210> SEQ ID NO 53
<211> LENGTH: 584
<212> TYPE: PRT
<213> ORGANISM: Arabidopsis thaliana

<400> SEQUENCE: 53

Met Asn Ser Met Asn Asn Trp Leu Gly Phe Ser Leu Ser Pro His Asp
1               5                   10                  15

Gln Asn His His Arg Thr Asp Val Asp Ser Ser Thr Thr Arg Thr Ala
            20                  25                  30

Val Asp Val Ala Gly Gly Tyr Cys Phe Asp Leu Ala Ala Pro Ser Asp
        35                  40                  45

Glu Ser Ser Ala Val Gln Thr Ser Phe Leu Ser Pro Phe Gly Val Thr
    50                  55                  60

Leu Glu Ala Phe Thr Arg Asp Asn Asn Ser His Ser Arg Asp Trp Asp
65                  70                  75                  80

Ile Asn Gly Gly Ala Cys Asn Asn Ile Asn Asn Glu Gln Asn Gly
            85                  90                  95

```
Pro Lys Leu Glu Asn Phe Leu Gly Arg Thr Thr Thr Ile Tyr Asn Thr
                100                 105                 110

Asn Glu Thr Val Val Asp Gly Asn Gly Asp Cys Gly Gly Gly Asp Gly
            115                 120                 125

Gly Gly Gly Gly Ser Leu Gly Leu Ser Met Ile Lys Thr Trp Leu Ser
        130                 135                 140

Asn His Ser Val Ala Asn Ala Asn His Gln Asp Asn Gly Asn Gly Ala
145                 150                 155                 160

Arg Gly Leu Ser Leu Ser Met Asn Ser Ser Thr Ser Asp Ser Asn Asn
                165                 170                 175

Tyr Asn Asn Asp Asp Val Val Gln Glu Lys Thr Ile Val Asp Val
                180                 185                 190

Val Glu Thr Thr Pro Lys Lys Thr Ile Glu Ser Phe Gly Gln Arg Thr
            195                 200                 205

Ser Ile Tyr Arg Gly Val Thr Arg His Arg Trp Thr Gly Arg Tyr Glu
        210                 215                 220

Ala His Leu Trp Asp Asn Ser Cys Lys Arg Glu Gly Gln Thr Arg Lys
225                 230                 235                 240

Gly Arg Gln Val Tyr Leu Gly Gly Tyr Asp Lys Glu Glu Lys Ala Ala
                245                 250                 255

Arg Ala Tyr Asp Leu Ala Ala Leu Lys Tyr Trp Gly Thr Thr Thr Thr
            260                 265                 270

Thr Asn Phe Pro Leu Ser Glu Tyr Glu Lys Glu Val Glu Glu Met Lys
        275                 280                 285

His Met Thr Arg Gln Glu Tyr Val Ala Ser Leu Arg Arg Lys Ser Ser
        290                 295                 300

Gly Phe Ser Arg Gly Ala Ser Ile Tyr Arg Gly Val Thr Arg His His
305                 310                 315                 320

Gln His Gly Arg Trp Gln Ala Arg Ile Gly Arg Val Ala Gly Asn Lys
                325                 330                 335

Asp Leu Tyr Leu Gly Thr Phe Gly Thr Gln Glu Glu Ala Ala Glu Ala
            340                 345                 350

Tyr Asp Ile Ala Ala Ile Lys Phe Arg Gly Leu Ser Ala Val Thr Asn
        355                 360                 365

Phe Asp Met Asn Arg Tyr Asn Val Lys Ala Ile Leu Glu Ser Pro Ser
        370                 375                 380

Leu Pro Ile Gly Ser Ser Ala Lys Arg Leu Lys Asp Val Asn Asn Pro
385                 390                 395                 400

Val Pro Ala Met Met Ile Ser Asn Asn Val Ser Glu Ser Ala Asn Asn
                405                 410                 415

Val Ser Gly Trp Gln Asn Thr Ala Phe Gln His His Gln Gly Met Asp
            420                 425                 430

Leu Ser Leu Leu Gln Gln Gln Glu Arg Tyr Val Gly Tyr Tyr Asn
        435                 440                 445

Gly Gly Asn Leu Ser Thr Glu Ser Thr Arg Val Cys Phe Lys Gln Glu
        450                 455                 460

Glu Glu Gln Gln His Phe Leu Arg Asn Ser Pro Ser His Met Thr Asn
465                 470                 475                 480

Val Asp His His Ser Ser Thr Ser Asp Asp Ser Val Thr Val Cys Gly
                485                 490                 495

Asn Val Val Ser Tyr Gly Gly Tyr Gln Gly Phe Ala Ile Pro Val Gly
            500                 505                 510
```

```
Thr Ser Val Asn Tyr Asp Pro Phe Thr Ala Ala Glu Ile Ala Tyr Asn
            515                 520                 525

Ala Arg Asn His Tyr Tyr Tyr Ala Gln His Gln Gln Gln Gln Gln Ile
        530                 535                 540

Gln Gln Ser Pro Gly Gly Asp Phe Pro Val Ala Ile Ser Asn His
545                 550                 555                 560

Ser Ser Asn Met Tyr Phe His Gly Glu Gly Gly Glu Gly Ala Pro
                565                 570                 575

Thr Phe Ser Val Trp Asn Asp Thr
            580

<210> SEQ ID NO 54
<211> LENGTH: 661
<212> TYPE: PRT
<213> ORGANISM: Triticum aestivum

<400> SEQUENCE: 54

Met Ala Ser Gly Asn Asp Trp Leu Gly Phe Ser Leu Ser Gly Gln Glu
1               5                   10                  15

Asn Pro Gln Pro His Gln Asp Ser Pro Pro Ala Gly Ile Asp Ile
            20                  25                  30

Ser Gly Ala Ser Asp Phe Tyr Gly Val Pro Thr Gln Pro Ala Pro Asp
        35                  40                  45

Ala Gln Leu Gly Val Pro Gly His Gln Pro Ser Tyr Gly Ile Thr Glu
    50                  55                  60

Asp Phe Asn Arg Gly Ala His Glu Thr His Asp Trp Asn Met Arg Gly
65              70                  75                  80

Asp Leu Asp Tyr Asn Gly Gly Ala Ser Glu Leu Ser Met Leu Val Gly
                85                  90                  95

Ser Ser Ala Val Gly Gly Lys Arg Ala Ala Met Glu Ala Glu Thr Glu
            100                 105                 110

Pro Lys Leu Glu Asp Phe Leu Gly Cys Asn Ser Phe Val Ser Glu Gln
        115                 120                 125

Asp Gln Ala Gly Gly Phe Leu Phe Ser Gly Val Pro Met Thr Thr Ser
    130                 135                 140

Ser Asn Ser Asn Thr Gly Ser Asn Thr Met Glu Leu Ser Met Ile Lys
145                 150                 155                 160

Ser Trp Leu Arg Asp Asn Gln Leu Pro Gln Ala Pro His Pro Gln Ser
                165                 170                 175

Gln Thr Gly Ala Pro Ala Gln Gln Pro Gln Pro His Glu Glu Met Gly
            180                 185                 190

Thr Asp Ala Ser Ser Phe Asp Pro Arg Gly Arg Asn Gly Ala Leu Val
        195                 200                 205

Val Ala Gly Ser Ser Gln Ser Leu Ala Leu Ser Met Ser Thr Gly Ser
    210                 215                 220

Gly Ser His Leu Pro Met Ala Val Val Ser Gly Ser Ala Ser Gly Gly
225                 230                 235                 240

Val Ser Glu Ser Thr Ser Ser Glu Asn Lys Arg Ala Ser Gly Ala Met
                245                 250                 255

Asp Ser Pro Gly Gly Ala Val Glu Ala Val Ala Arg Lys Ser Ile Asp
            260                 265                 270

Thr Phe Gly Gln Arg Thr Ser Ile Tyr Arg Gly Val Thr Arg His Arg
        275                 280                 285

Trp Thr Gly Arg Tyr Glu Ala His Leu Trp Asp Asn Ser Cys Arg Arg
    290                 295                 300
```

Glu Gly Gln Ser Arg Lys Gly Arg Gln Val Tyr Leu Gly Gly Tyr Asp
305                 310                 315                 320

Lys Glu Asp Lys Ala Arg Ala Tyr Asp Leu Ala Ala Leu Lys Tyr
            325                 330                 335

Trp Gly Thr Thr Thr Thr Asn Phe Pro Ile Asn Thr Tyr Glu Lys
            340                 345                 350

Glu Val Asp Glu Met Lys His Met Thr Arg Gln Glu Tyr Ile Ala Tyr
            355                 360                 365

Leu Arg Arg Asn Ser Ser Gly Phe Ser Arg Gly Ala Ser Lys Tyr Arg
    370                 375                 380

Gly Val Thr Arg His His Gln His Gly Arg Trp Gln Ala Arg Ile Gly
385                 390                 395                 400

Arg Val Ala Gly Asn Lys Asp Leu Tyr Leu Gly Thr Phe Ser Thr Glu
                405                 410                 415

Glu Glu Ala Ala Glu Ala Tyr Asp Ile Ala Ala Ile Lys Phe Arg Gly
            420                 425                 430

Leu Asn Ala Val Thr Asn Phe Asp Met Ser Arg Tyr Asp Val Lys Thr
    435                 440                 445

Ile Leu Glu Ser Ser Thr Leu Pro Val Gly Gly Ala Ala Arg Arg Leu
450                 455                 460

Lys Glu Ala Ala Asp His Pro Glu Ala Gly Ala Thr Ile Trp Arg Ala
465                 470                 475                 480

Gly Met Asp Gly Ala Ile Ile Ser Gln Leu Thr Asp Val Gly Met Gly
                485                 490                 495

Ala Tyr Ala Ser Tyr His His Gly Trp Pro Thr Ile Ala Phe Gln Gln
            500                 505                 510

Pro Ser Pro Leu Ser Val His Tyr Pro Tyr Val Ala Gln Pro Pro Arg
            515                 520                 525

Gly Trp Cys Lys Pro Glu Gln Asp Ala Thr Val Ala Thr Gln Ser Leu
    530                 535                 540

Gln Asp Leu Gln Gln Leu His Leu Gly Thr Ala Ala His Asn Tyr Phe
545                 550                 555                 560

Gln Ala Ser Ser Ser Thr Val Tyr Asn Gly Gly Gly Val Gly Gly
                565                 570                 575

Tyr Gln Gln Gly Thr Gly Gly Asn Ala Phe Leu Met Pro Ala Ser Thr
            580                 585                 590

Val Val Asp Glu Gln Gly His Ser Ser Thr Ala Ala Asn Gln Gly Ser
            595                 600                 605

Thr Cys Ser Tyr Gly Asp Glu Gly Lys Leu Asn Leu Gly Tyr Asp
    610                 615                 620

Ala Met Ala Met Ala Ser Thr Gly Ala Asp Pro Tyr Ala Ala Ala Ser
625                 630                 635                 640

Thr Val Ser Ile Ala Arg Ala Asn Gly Tyr Ser Asn Asn Trp Ser Ser
                645                 650                 655

Pro Phe Ser Gly Met
            660

<210> SEQ ID NO 55
<211> LENGTH: 659
<212> TYPE: PRT
<213> ORGANISM: Triticum aestivum

<400> SEQUENCE: 55

Met Ala Ser Gly Asn Asp Trp Leu Gly Phe Ser Leu Ser Gly Gln Glu

-continued

```
1               5                   10                  15
Asn Pro Gln Pro His Gln Asp Ser Ser Pro Ala Asp Ile Asp Ile
                20                  25                  30
Ala Gly Ala Ser Gly Phe Tyr Gly Leu Pro Thr Gln Pro Ala Pro Asp
                35                  40                  45
Ala Gln Leu Gly Val Pro Gly His His Gln Pro Ser Tyr Gly Ile Thr
            50                  55                  60
Glu Ala Phe Asn Arg Gly Ala His Glu Ile His Asp Trp Asn Met Arg
65                  70                  75                  80
Gly Asp Leu Asp Tyr Asn Gly Gly Ala Ser Glu Leu Ser Met Leu Val
                    85                  90                  95
Gly Ser Ser Ala Val Gly Gly Lys Arg Ala Ala Met Glu Ala Glu Thr
                100                 105                 110
Glu Pro Lys Leu Glu Asp Phe Leu Val Gly Asn Ser Phe Val Ser Glu
                115                 120                 125
Gln Asp Gln Ala Gly Gly Phe Leu Phe Ser Gly Val Pro Met Ala Thr
            130                 135                 140
Ser Thr Asn Ser Asn Ser Arg Ser Asn Thr Met Glu Leu Ser Met Ile
145                 150                 155                 160
Lys Ser Trp Leu Arg Asp Asn Gln Val Pro Gln Ala Pro His Pro Gln
                165                 170                 175
Ser Gln Thr Gly Ala Pro Ala Gln Gln Pro Gln Pro His Glu Glu Met
                180                 185                 190
Gly Thr Asp Ala Ser Ser Phe Asp Pro Leu Gly Arg Asn Gly Ala Leu
            195                 200                 205
Val Val Ala Gly Ser Ser Gln Ser Leu Ala Leu Ser Met Ser Thr Gly
    210                 215                 220
Ser Gly Ser His Leu Pro Met Ala Val Leu Gly Gly Ser Pro Ser Gly
225                 230                 235                 240
Gly Val Ser Glu Ser Thr Ser Ser Glu Asn Lys Arg Ala Ser Gly Ala
                245                 250                 255
Met Asp Ser Pro Gly Gly Ala Val Glu Ala Val Ala Arg Lys Ser Ile
                260                 265                 270
Asp Thr Phe Gly Gln Arg Thr Ser Ile Tyr Arg Gly Val Thr Arg His
            275                 280                 285
Arg Trp Thr Gly Arg Tyr Glu Ala His Leu Trp Asp Asn Ser Cys Arg
    290                 295                 300
Arg Glu Gly Gln Ser Arg Lys Gly Arg Gln Val Tyr Leu Gly Gly Tyr
305                 310                 315                 320
Asp Lys Glu Asp Lys Ala Ala Arg Ala Tyr Asp Leu Ala Ala Leu Lys
                325                 330                 335
Tyr Trp Gly Thr Thr Thr Thr Thr Asn Phe Pro Ile Asn Thr Tyr Glu
                340                 345                 350
Lys Glu Val Asp Glu Met Lys His Met Thr Arg Gln Glu Tyr Ile Ala
            355                 360                 365
Tyr Leu Arg Arg Asn Ser Ser Gly Phe Ser Arg Gly Ala Ser Lys Tyr
    370                 375                 380
Arg Gly Val Thr Arg His His Gln His Gly Arg Trp Gln Ala Arg Ile
385                 390                 395                 400
Gly Arg Val Ala Gly Asn Lys Asp Leu Tyr Leu Gly Thr Phe Ser Thr
                405                 410                 415
Glu Glu Glu Ala Ala Glu Ala Tyr Asp Ile Ala Ala Ile Lys Phe Arg
                420                 425                 430
```

```
Gly Leu Asn Ala Val Thr Asn Phe Asp Met Ser Arg Tyr Asp Val Lys
            435                 440                 445

Thr Ile Leu Glu Ser Ser Thr Leu Pro Val Gly Gly Ala Ala Arg Arg
450                 455                 460

Pro Lys Glu Val Ala Asp His Pro Glu Ala Gly Ala Thr Ile Trp Arg
465                 470                 475                 480

Ala Gly Met Asp Gly Val Ile Ser Gln Leu Thr Asp Val Gly Met
            485                 490                 495

Gly Thr Tyr Ala Ser Tyr His His Gly Trp Pro Thr Ile Ala Phe Gln
            500                 505                 510

Gln Pro Ser Pro Leu Ser Val His Tyr Pro Tyr Val Ala Gln Pro Ser
            515                 520                 525

Arg Gly Trp Cys Lys Pro Glu Gln Asp Ala Ser Val Ala Thr Gln Ser
            530                 535                 540

Leu Gln Asp Leu Gln Gln Leu His Leu Gly Thr Ala Ala His Asn Tyr
545                 550                 555                 560

Phe Gln Ala Ser Ser Ser Ser Thr Val Tyr Asn Gly Gly Gly Tyr Gln
            565                 570                 575

Gln Gly Thr Ser Gly Asn Ala Phe Leu Met Pro Ala Ser Thr Val Val
            580                 585                 590

Asp Glu Gln Gly His Ser Ser Thr Ala Thr Asn Gln Gly Ser Thr Cys
            595                 600                 605

Ser Tyr Gly Asp Glu Glu Gly Lys Leu Asn Leu Gly Tyr Asp Ala Met
            610                 615                 620

Ala Met Ala Ser Thr Gly Ala Asp Pro Tyr Ala Ala Pro Thr Val
625                 630                 635                 640

Ser Ile Ala Arg Ala Asn Gly Tyr Ser Asn Asn Trp Ser Ser Pro Phe
            645                 650                 655

Asn Gly Met

<210> SEQ ID NO 56
<211> LENGTH: 703
<212> TYPE: PRT
<213> ORGANISM: Sorghum bicolor

<400> SEQUENCE: 56

Met Ala Thr Val Asn Asn Trp Leu Ala Phe Ser Leu Ser Pro Gln Glu
1               5                   10                  15

Leu Pro Pro Thr Gln Thr Asp Ser Thr Leu Ile Ser Ala Ala Thr Thr
            20                  25                  30

Asp Asp Val Ser Gly Asp Val Cys Phe Asn Ile Pro Gln Asp Trp Ser
            35                  40                  45

Met Arg Gly Ser Glu Leu Ser Ala Leu Val Ala Glu Pro Lys Leu Glu
    50                  55                  60

Asp Phe Leu Gly Gly Ile Ser Phe Ser Glu Gln His His Lys Ala Asn
65                  70                  75                  80

Cys Asn Met Ile Pro Ser Thr Ser Ser Thr Ala Cys Tyr Ala Ser Ser
                85                  90                  95

Gly Ala Thr Ala Gly Tyr His His Gln Leu Tyr His Gln Pro Thr Ser
            100                 105                 110

Ser Ala Leu His Phe Ala Asp Ser Val Met Val Ala Ser Ser Ala Gly
        115                 120                 125

Gly Val His Asp Gly Gly Ala Met Leu Ser Ala Ala Ser Ala Asn Gly
    130                 135                 140
```

```
Ser Ala Gly Ala Gly Ala Ala Ser Ala Asn Gly Ser Gly Ser Ile Gly
145                 150                 155                 160

Leu Ser Met Ile Lys Asn Trp Leu Arg Ser Gln Pro Ala Pro Met Gln
            165                 170                 175

Pro Arg Val Ala Ala Glu Ser Val Gln Gly Leu Ser Leu Ser Met
        180                 185                 190

Asn Met Ala Gly Ala Thr Gln Gly Ala Gly Met Pro Leu Leu Ala
            195                 200                 205

Gly Glu Arg Gly Arg Ala Pro Glu Ser Val Ser Thr Ser Ala Gln Gly
        210                 215                 220

Gly Ala Val Val Thr Ala Pro Lys Glu Asp Ser Gly Ser Gly Val
225                 230                 235                 240

Ala Ala Thr Gly Ala Leu Val Ala Val Ser Thr Asp Thr Gly Gly Ser
            245                 250                 255

Gly Ala Ser Ala Asp Asn Thr Ala Arg Lys Thr Val Asp Thr Phe Gly
            260                 265                 270

Gln Arg Thr Ser Ile Tyr Arg Gly Val Thr Arg His Arg Trp Thr Gly
        275                 280                 285

Arg Tyr Glu Ala His Leu Trp Asp Asn Ser Cys Arg Arg Glu Gly Gln
290                 295                 300

Thr Arg Lys Gly Arg Gln Val Tyr Leu Gly Gly Tyr Asp Lys Glu Glu
305                 310                 315                 320

Lys Ala Ala Arg Ala Tyr Asp Leu Ala Ala Leu Lys Tyr Trp Gly Pro
                325                 330                 335

Thr Thr Thr Thr Asn Phe Pro Val Asn Asn Tyr Glu Lys Glu Leu Glu
            340                 345                 350

Asp Met Lys His Met Thr Arg Gln Glu Phe Val Ala Ser Leu Arg Arg
            355                 360                 365

Lys Ser Ser Gly Phe Ser Arg Gly Ala Ser Ile Tyr Arg Gly Val Thr
        370                 375                 380

Arg His His Gln His Gly Arg Trp Gln Ala Arg Ile Gly Arg Val Ala
385                 390                 395                 400

Gly Asn Lys Asp Leu Tyr Leu Gly Thr Phe Ser Thr Gln Glu Glu Ala
                405                 410                 415

Ala Glu Ala Tyr Asp Ile Ala Ala Ile Lys Phe Arg Gly Leu Asn Ala
                420                 425                 430

Val Thr Asn Phe Asp Met Ser Arg Tyr Asp Val Lys Ser Ile Leu Asp
            435                 440                 445

Ser Ser Ala Leu Pro Ile Gly Ser Ala Ala Lys Arg Leu Lys Glu Ala
        450                 455                 460

Glu Ala Ala Ala Ser Ala Gln His His Ala Gly Val Val Ser Tyr Asp
465                 470                 475                 480

Val Gly Arg Ile Ala Ser Gln Leu Gly Asp Gly Gly Ala Leu Ala Ala
                485                 490                 495

Ala Tyr Gly Ala His Tyr His Gly Ala Trp Pro Thr Ile Ala Phe Gln
            500                 505                 510

Pro Ser Ala Ala Thr Gly Leu Tyr His Pro Tyr Ala Gln Pro Met Arg
            515                 520                 525

Gly Trp Cys Lys Gln Glu Gln Asp His Ala Val Ile Ala Ala Ala His
        530                 535                 540

Ser Leu Gln Glu Leu His His Leu Asn Leu Gly Ala Ala Ala Gly Ala
545                 550                 555                 560
```

```
His Asp Phe Phe Ser Ala Gly Gln Gln Ala Met His Gly Leu Gly
                565                 570                 575

Ser Met Asp Asn Ala Ser Leu Glu His Ser Thr Gly Asn Ser Val
            580                 585                 590

Val Tyr Asn Gly Val Gly Asp Ser Asn Gly Ser Thr Val Val Gly Ser
            595                 600                 605

Gly Gly Tyr Met Met Pro Met Ser Ala Ala Thr Ala Thr Ala Thr Thr
        610                 615                 620

Ala Met Val Ser His Glu Gln Val His Ala Arg Ala Gln Gly Asp His
625                 630                 635                 640

His Asp Glu Ala Lys Gln Ala Ala Gln Met Gly Tyr Glu Ser Tyr Leu
                645                 650                 655

Val Asn Ala Glu Asn Tyr Gly Gly Gly Arg Met Ser Ala Ala Trp Ala
            660                 665                 670

Thr Val Ser Ala Pro Pro Ala Ala Ser Ser Asn Asp Asn Met Ala Asp
        675                 680                 685

Val Gly His Gly Gly Ala Gln Leu Phe Ser Val Trp Asn Asp Thr
        690                 695                 700

<210> SEQ ID NO 57
<211> LENGTH: 308
<212> TYPE: PRT
<213> ORGANISM: Triticum aestivum

<400> SEQUENCE: 57

Met Asp Lys Gln Ser Val Met Trp Arg Gln Leu Gln His Gln His His
1               5                   10                  15

Gln Ala Ser Gly Ala Ala Gly Gly Asn Ala Val Ala Ala Gly Ala
                20                  25                  30

Gly Ala Thr Thr Thr Thr Ala Pro Val Arg Pro Ser Gly Ala Arg Trp
        35                  40                  45

Thr Pro Thr Pro Glu Gln Val Lys Ile Leu Lys Asp Leu Tyr Tyr Asp
    50                  55                  60

Cys Gly Ile Arg Ser Pro Thr Ala Glu Gln Ile Gln Arg Ile Ala Ala
65                  70                  75                  80

Arg Leu Arg Gln Tyr Gly Arg Ile Glu Gly Lys Asn Val Phe Tyr Trp
                85                  90                  95

Phe Gln Asn His Lys Ala Arg Glu Arg Gln Lys Lys Arg Leu Gly Val
                100                 105                 110

Asp Val Asn Gly Ser Pro Leu Ala Thr Ala Thr Ala Ala Asp Val Leu
            115                 120                 125

Ala Leu Ser Pro Ser Gly Ala Ala Ala Gly Leu Tyr Gly Ala Gly Ser
        130                 135                 140

Cys Ala Gly Arg Gly Ala Ala Val His Pro Asp Ala Ser Ala Thr Thr
145                 150                 155                 160

Thr Thr Cys Trp Gly Asp Ser Thr Leu Gln Asp Tyr Met Gly Ala Arg
                165                 170                 175

Ser Thr Ala Gly Ala Gly Asn His Gly Gly Ala Ala Ala Ala Ala Pro
            180                 185                 190

Thr Pro Trp Pro Ala Ala Ser Phe Pro Phe Ser Thr Asn Gln Thr Pro
        195                 200                 205

Pro Met Pro Pro Pro Arg Glu Leu Pro Leu Phe Pro Thr Gly Gly Gly
    210                 215                 220

Arg Gln Glu Ser Ala Asp Asp Phe Asn Gly Ser Ser Tyr His Leu Gln
225                 230                 235                 240
```

```
Pro Asn Ser Ser Gln Trp Trp Glu Ala Ala Ala Ser Asn Ala Asn
                245                 250                 255

Ala Met Ala Val Val His His Gln Leu Leu Gln Glu Gln His Glu Gln
            260                 265                 270

Gln His Ser Phe Tyr Asn Ser Ser Gly Asn Gln Gln Met Met Met
        275                 280                 285

Met Met Pro Ile Gln Asp Ala Gly Thr Ser Pro Glu Leu Thr Leu Arg
290                 295                 300

Ala Pro Tyr Met
305

<210> SEQ ID NO 58
<211> LENGTH: 327
<212> TYPE: PRT
<213> ORGANISM: Sorghum bicolor

<400> SEQUENCE: 58

Met Ala Ala Asn Val Gly Ala Gly Arg Ser Ala Val Gly Gly Gly Gly
1               5                   10                  15

Gly Gly Gly Ala Gly Gly Thr Gly Thr Ala Ala Ser Gly Ser Val
            20                  25                  30

Ala Thr Thr Ala Val Cys Arg Pro Ile Gly Ser Arg Trp Thr Pro Thr
        35                  40                  45

Pro Glu Gln Ile Arg Ile Leu Lys Glu Phe Tyr Tyr Gly Cys Gly Ile
    50                  55                  60

Arg Ser Pro Asn Ser Glu Gln Ile Gln Arg Ile Thr Ala Met Leu Arg
65                  70                  75                  80

Gln His Gly Lys Ile Glu Gly Lys Asn Val Phe Tyr Trp Phe Gln Asn
                85                  90                  95

His Lys Ala Arg Glu Arg Gln Lys Arg Arg Leu Thr Asn Leu Asp Val
            100                 105                 110

Asn Val Pro Thr Ala Ala Ala Ala Gly Ala Ala Asp Ala Ser Thr His
        115                 120                 125

Leu Gly Val Leu Ser Leu Ser Ser Pro Ser Gly Ala Ala Pro Pro Ser
130                 135                 140

Pro Thr Leu Gly Phe Tyr Ala Gly Asn Gly Gly Ala Gly Ser Thr Val
145                 150                 155                 160

Leu Leu Asp Thr Ser Ser Asp Cys Ala Ala Met Ala Thr Glu Thr Cys
                165                 170                 175

Phe Leu Gln Asp Tyr Met Gly Val Met Gly Thr Gly Ser Ala Ala Ala
            180                 185                 190

Ala Ser Pro Trp Ala Cys Phe Ser Ser Asn Thr Met Ala Ala Ala
        195                 200                 205

Ala Ala Arg Ala Pro Thr Val Thr Arg Ala Pro Glu Thr Leu Pro Leu
    210                 215                 220

Phe Pro Thr Gly Gly Asp Asp Ser Gln Pro Arg Arg Pro Arg His Gly
225                 230                 235                 240

Val Pro Val Pro Val Ala Ala Gly Glu Ala Ile Arg Gly Gly Ser Ser
                245                 250                 255

Ser Ser Arg Tyr Leu Pro Phe Trp Gly Ala Ala Pro Thr Thr Ala Ser
            260                 265                 270

Ala Thr Ser Ile Gly Ile Gln Gln Gln His Gln Leu Leu Gln Leu Gln
        275                 280                 285

Glu Gln Tyr Ser Phe Tyr Ser Asn Ala Met Pro Gly Thr Gly Ser Gln
```

```
                290                 295                 300
Asp Ala Ser Ala Ala Ser Leu Glu Leu Ser Leu Ser Ser Trp Cys Ser
305                 310                 315                 320

Pro Tyr Pro Ala Gly Thr Met
                325

<210> SEQ ID NO 59
<211> LENGTH: 260
<212> TYPE: PRT
<213> ORGANISM: Arabidopsis thaliana

<400> SEQUENCE: 59

Met Glu Asn Glu Val Asn Ala Gly Thr Ala Ser Ser Arg Trp Asn
1               5                   10                  15

Pro Thr Lys Asp Gln Ile Thr Leu Leu Glu Asn Leu Tyr Lys Glu Gly
                20                  25                  30

Ile Arg Thr Pro Ser Ala Asp Gln Ile Gln Gln Ile Thr Gly Arg Leu
            35                  40                  45

Arg Ala Tyr Gly His Ile Glu Gly Lys Asn Val Phe Tyr Trp Phe Gln
        50                  55                  60

Asn His Lys Ala Arg Gln Arg Gln Lys Gln Lys Gln Glu Arg Met Ala
65                  70                  75                  80

Tyr Phe Asn Arg Leu Leu His Lys Thr Ser Arg Phe Phe Tyr Pro Pro
                85                  90                  95

Pro Cys Ser Asn Val Gly Cys Val Ser Pro Tyr Tyr Leu Gln Gln Ala
            100                 105                 110

Ser Asp His His Met Asn Gln His Gly Ser Val Tyr Thr Asn Asp Leu
        115                 120                 125

Leu His Arg Asn Val Met Ile Pro Ser Gly Gly Tyr Glu Lys Arg
        130                 135                 140

Thr Val Thr Gln His Gln Lys Gln Leu Ser Asp Ile Arg Thr Thr Ala
145                 150                 155                 160

Ala Thr Arg Met Pro Ile Ser Pro Ser Ser Leu Arg Phe Asp Arg Phe
                165                 170                 175

Ala Leu Arg Asp Asn Cys Tyr Ala Gly Glu Asp Ile Asn Val Asn Ser
            180                 185                 190

Ser Gly Arg Lys Thr Leu Pro Leu Phe Pro Leu Gln Pro Leu Asn Ala
        195                 200                 205

Ser Asn Ala Asp Gly Met Gly Ser Ser Ser Phe Ala Leu Gly Ser Asp
    210                 215                 220

Ser Pro Val Asp Cys Ser Ser Asp Gly Ala Gly Arg Glu Gln Pro Phe
225                 230                 235                 240

Ile Asp Phe Phe Ser Gly Gly Ser Thr Ser Thr Arg Phe Asp Ser Asn
                245                 250                 255

Gly Asn Gly Leu
            260

<210> SEQ ID NO 60
<211> LENGTH: 325
<212> TYPE: PRT
<213> ORGANISM: Arabidopsis thaliana

<400> SEQUENCE: 60

Met Ser Ser Ser Asn Lys Asn Trp Pro Ser Met Phe Lys Ser Lys Pro
1               5                   10                  15

Cys Asn Asn Asn His His His Gln His Glu Ile Asp Thr Pro Ser Tyr
```

```
            20                  25                  30
Met His Tyr Ser Asn Cys Asn Leu Ser Ser Phe Ser Ser Asp Arg
                35                  40                  45
Ile Pro Asp Pro Lys Pro Arg Trp Asn Pro Lys Pro Glu Gln Ile Arg
 50                  55                  60
Ile Leu Glu Ser Ile Phe Asn Ser Gly Thr Ile Asn Pro Pro Arg Glu
 65                  70                  75                  80
Glu Ile Gln Arg Ile Arg Ile Arg Leu Gln Glu Tyr Gly Gln Ile Gly
                 85                  90                  95
Asp Ala Asn Val Phe Tyr Trp Phe Gln Asn Arg Lys Ser Arg Ala Lys
                100                 105                 110
His Lys Leu Arg Val His His Lys Ser Pro Lys Met Ser Lys Lys Asp
                115                 120                 125
Lys Thr Val Ile Pro Ser Thr Asp Ala Asp His Cys Phe Gly Phe Val
                130                 135                 140
Asn Gln Glu Thr Gly Leu Tyr Pro Val Gln Asn Asn Glu Leu Val Val
145                 150                 155                 160
Thr Glu Pro Ala Gly Phe Leu Phe Pro Val His Asn Asp Pro Ser Ala
                165                 170                 175
Ala Gln Ser Ala Phe Gly Phe Gly Asp Phe Val Pro Val Val Thr
                180                 185                 190
Glu Glu Gly Met Ala Phe Ser Thr Val Asn Asn Gly Val Asn Leu Glu
                195                 200                 205
Thr Asn Glu Asn Phe Asp Lys Ile Pro Ala Ile Asn Leu Tyr Gly Gly
                210                 215                 220
Asp Gly Asn Gly Gly Asn Cys Phe Pro Pro Leu Thr Val Pro Leu
225                 230                 235                 240
Thr Ile Asn Gln Ser Gln Glu Lys Arg Asp Val Gly Leu Ser Gly Gly
                245                 250                 255
Glu Asp Val Gly Asp Asn Val Tyr Pro Val Arg Met Thr Val Phe Ile
                260                 265                 270
Asn Glu Met Pro Ile Glu Val Val Ser Gly Leu Phe Asn Val Lys Ala
                275                 280                 285
Ala Phe Gly Asn Asp Ala Val Leu Ile Asn Ser Phe Gly Gln Pro Ile
                290                 295                 300
Leu Thr Asp Glu Phe Gly Val Thr Tyr Gln Pro Leu Gln Asn Gly Ala
305                 310                 315                 320
Ile Tyr Tyr Leu Ile
                325

<210> SEQ ID NO 61
<211> LENGTH: 1592
<212> TYPE: DNA
<213> ORGANISM: Medicago truncatula

<400> SEQUENCE: 61
actgttaata attttttaaac gtcagcgcac taaaaaaacg aaaagacgga cacgtgaaaa      60
taaaaaacac acactagttt atgacgcaat actattttac ttatgatttg ggtacattag     120
acaaaaccgt gaaagagatg tatcagctat gaaacctgta tacttcaata cagagactta     180
ctcatatcgg atacgtacgc acgaagtatc atattaatta ttttaatttt taataaatat     240
tttatcggat acttatgtga tactctacat atacacaagg atatttctaa gatactttat     300
agatacgtat cctagaaaaa catgaagagt aaaaaagtga gacaatgttg taaaaattca     360
```

```
ttataaatgt atatgattca attttagata tgcatcagta taattgattc tcgatgaaac    420
acttaaaatt atatttcttg tggaagaacg tagcgagaga ggtgattcag ttagacaaca    480
ttaaataaaa ttaatgttaa gttcttttaa tgatgtttct ctcaatatca catcatatga    540
aaatgtaata tgattataa gaaaatttt aaaaaattta ttttaataat cacatgtact     600
attttttaaa aattgtatct tttataataa tacaataata aagagtaatc agtgttaatt    660
tttcttcaaa tataagtttt attataaatc attgttaacg tatcataagt cattaccgta    720
tcgtatctta atttttttt aaaaaccgct aattcacgta cccgtattgt attgtacccg     780
cacctgtatc acaatcgatc ttagttagaa gaattgtctc gaggcggtgc aagacagcat    840
ataatagacg tggactctct tataccaaac gttgtcgtat cacaaagggt taggtaacaa    900
gtcacagttt gtccacgtgt cacgttttaa ttggaagagg tgccgttggc gtaatataac    960
agccaatcga tttttgctat aaaagcaaat caggtaaact aaacttcttc attcttttct   1020
tccccatcgc tacaaaaccg gttcctttgg aaaagagatt cattcaaacc tagcacccaa   1080
ttccgtttca aggtataatc tactttctat tcttcgatta ttttattatt attagctact   1140
atcgtttaat cgatcttttc ttttgatccg tcaaatttaa attcaattag ggttttgttc   1200
ttttctttca tctgattgaa atccttctga attgaaccgt ttacttgatt ttactgttta   1260
ttgtatgatt taatcctttg tttttcaaag acagtcttta gattgtgatt aggggttcat   1320
ataaattttt agatttggat ttttgtattg tatgattcaa aaaatacgtc ctttaattag   1380
attagtacat ggatattttt tacccgattt attgattgtc agggagaatt tgatgagcaa   1440 gttttttga tgtctgttgt aaattgaatt gattataatt gctgatctgc tgcttccagt    1500
tttcataacc catattcttt taaccttgtt gtacacacaa tgaaaattg gtgattgatt    1560 catttgtttt tctttgtttt ggattataca gg                                  1592
```

<210> SEQ ID NO 62
<211> LENGTH: 2000
<212> TYPE: DNA
<213> ORGANISM: Zea mays

<400> SEQUENCE: 62

```
gtcgtgcccc tctctagaga taaagagcat tgcatgtcta aagtataaaa aattaccaca     60 tattttttg tcacacttat ttgaagtgta gtttatctat ctctatacat atatttaaac    120
ttcactctac aaataatata gtctataata ctaaataat attagtgttt tagaggatca    180
tataaataaa ctgctagaca tggtctaaag gataattgaa tattttgaca atctacagtt   240 ttatctttt agtgtgcatg tgatctctct gtttttttg caaatagctt gacctatata    300
atacttcatc catttattta gtacatccat ttaggattta gggttgatgg tttctataga   360
ctaattttta gtacatccat tttattcttt ttagtctcta aatttttaa aactaaaact    420 ctattttagt tttttatta ataatttaga tataaaatga aataaaataa attgactaca   480
aataaaacaa atacccttta agaaataaaa aaactaagca acattttc ttgtttcgag    540 tagataatga caggctgttc aacgccgtcg acgagtctaa cggacaccaa ccagcgaacc   600
agcagcgtcg cgtcgggcca agcgaagcag acggcacggc atctctgtag ctgcctctgg   660 accctctcg agagttccgc tccaccgttg gacttgctcc gctgtcggca tccagaaatt    720
gcgtggcgga gcggcagacg tgaggcggca cggcaggcgg cctcttcctc ctctcacggc    780
accggcagct acggggatt cctttcccac cgctccttcg ctttcccttc ctcgcccgcc    840
gtaataaata gacacccct ccacaccctc ttcccaac ctcgtgttcg ttcggagcgc      900
```

```
acacacacgc aaccagatct cccccaaatc cagccgtcgg cacctccgct tcaaggtacg    960
ccgctcatcc tcccccccc cctctctcta ccttctctag atcggcgatc cggtccatgg   1020
ttagggcccg gtagttctac ttctgttcat gtttgtgtta gagcaaacat gttcatgttc   1080
atgtttgtga tgatgtggtc tggttgggcg gtcgttctag atcggagtag gatactgttt   1140
caagctacct ggtggattta ttaattttgt atctgtatgt gtgtgccata catcttcata   1200
gttacgagtt taagatgatg gatggaaata tcgatctagg ataggtatac atgttgatgc   1260
gggttttact gatgcatata cagagatgct ttttttctcg cttggttgtg atgatatggt   1320
ctggttgggc ggtcgttcta gatcggagta gaatactgtt tcaaactacc tggtggattt   1380
attaaaggat aaagggtcgt tctagatcgg agtagaatac tgtttcaaac tacctggtgg   1440
atttattaaa ggatctgtat gtatgtgcct acatcttcat agttacgagt ttaagatgat   1500
ggatggaaat atcgatctag gataggtata catgttgatg cgggttttac tgatgcatat   1560
acagagatgc tttttttcgc ttggttgtga tgatgtggtc tggttgggcg gtcgttctag   1620
atcggagtag aatactgttt caaactacct ggtggattta ttaattttgt atctttatgt   1680
gtgtgccata catcttcata gttacgagtt taagatgatg gatggaaata ttgatctagg   1740
ataggtatac atgttgatgt gggttttact gatgcatata catgatggca tatgcggcat   1800
ctattcatat gctctaacct tgagtaccta tctattataa taaacaagta tgttttataa   1860
ttattttgat cttgatatac ttggatgatg gcatatgcag cagctatatg tggattttt   1920 agccctgcct tcatacgcta tttatttgct tggtactgtt tcttttgtcc gatgctcacc   1980
ctgttgtttg gtgatacttc                                              2000

<210> SEQ ID NO 63
<211> LENGTH: 4101
<212> TYPE: DNA
<213> ORGANISM: Artificial
<220> FEATURE:
<223> OTHER INFORMATION: Cas9

<400> SEQUENCE: 63
gacaagaagt acagcatcgg gctggcgatc gggaccaact ccgtcggctg ggctgtgatt     60
accgacgagt acaaggtgcc atccaagaag ttcaaggtcc tcggcaacac tgaccggcac    120
agcattaaga gaacctgat ggggcgctg ctgttcgatt cggggagac tgcggaggcg    180 accaggctga agcggactgc gcgccggagg tacaccagga ggaagaatcg gatctgctac    240
ctccaggaga ttttctcgaa tgagatggcc aaggtggacg attccttctt ccatcgcctg    300
gaggagtcgt tcctcgttga ggaggacaag aagcatgaga ggcatcccat tttcgggaat    360
atcgttgacg aggtggctta ccatgagaag tacccgacca tctaccatct gcggaagaag    420
ctcgtcgatt cgaccgataa ggccgacctg cggctgatct acctggccct cgcgcacatg    480
attaagttcc ggggccattt cctcatcgag gcgacctca acccgacaa tcggacgtg    540 gataagctct tcattcagct cgtgcagaca tacaaccagc tcttcgagga gaatcccatt    600
aacgcctcgg gggtcgacgc taaggctatt ctctcggctc ggctgtcgaa gtcgcgccgg    660
ctggagaatc tcattgccca gctcccaggc gagaagaaga acggcctctt cggcaacctg    720
attgccctgt cgctggggct cacaccgaat ttcaagtcga acttcgacct cgccgaggac    780
gctaagctcc agctcagcaa ggatacttac gatgatgacc tcgataacct gctcgcccag    840
attggggatc agtacgcgga tctgttcctc gcggccaaga tctcagcga tgctattctc    900
```

```
ctgtcggaca ttctccgcgt caacacagag attactaagg ccccactgtc ggcgagcatg    960
attaagaggt acgatgagca tcatcaggac ctgacactgc tcaaggcgct ggtccggcag   1020
cagctccccg agaagtacaa ggagatttc ttcgatcagt caaagaatgg gtacgcgggc   1080
tacattgatg cggcgcgtc ccaggaggag ttctacaagt tcattaagcc catcctggag   1140
aagatggacg ggaccgagga gctgctggtg aagctcaatc gggaggacct gctccggaag   1200
cagcgcacat tcgacaatgg ctcgattcct caccagattc acctgggcga gctgcacgcc   1260
attctccgca ggcaggagga cttctacccg ttcctcaagg acaaccgcga agatcgag    1320
aagatcctga ccttccggat tccatactac gtggggccgc tcgcgcgggg gaactcccgg   1380
ttcgcgtgga tgactcgcaa gtccgaagaa acgattacac cgtggaattt cgaggaggtc   1440
gtcgacaagg gcgctagtgc gcagtcattc attgagagga tgaccaattt cgataagaac   1500
ctgcctaacg agaaggtgct gccgaagcat tcgctgctct acgagtactt caccgtttac   1560
aatgagctga ccaaggtgaa gtatgtgact gagggcatga ggaagccagc gttcctgagc   1620
ggcgagcaga agaaggctat cgtggacctg ctcttcaaga ctaaccggaa ggtgactgtg   1680
aagcagctca aggaggacta cttcaagaag attgagtgct tcgattccgt tgagattagc   1740
ggggtggagg atcggttcaa tgcttcgctc gggacatacc acgatctcct gaagatcatt   1800
aaggataagg acttcctcga caacgaggag aacgaggaca ttctcgaaga tattgtcctg   1860
accctcaccc tcttcgagga tcgggagatg atcgaggaga ggctcaagac atacgctcat   1920
ctgttcgatg ataaggtcat gaagcagctg aagcgcaggc ggtacacagg gtggggcgg   1980
ctgagccgga agctgatcaa cgggattcgg gataagcagt ccgggaagac aattctcgac   2040
ttcctcaagt ccgacgggtt cgctaaccgg aacttcatgc agctcattca tgatgactcg   2100
ctgacattca aggaggatat tcagaaggcg caggtttcgg ggcagggcga ctcgctccac   2160
gagcatattg cgaatctggc gggctccccc gcgattaaga agggcattct gcaaaccgtc   2220
aaggtggttg atgagctggt caaggtcatg gggcggcata agccagagaa tattgtcatc   2280
gagatggcgc gggagaatca gaccacacag aagggcaga agaactcacg ggagcggatg   2340
aagcgcatcg aggagggcat caaggagctg ggtcgcaga tcctgaagga gcatcccgtg   2400
gagaacactc agctgcaaaa tgagaagctg tacctctact acctccagaa cgggagggac   2460
atgtatgtgg atcaggagct ggatattaat aggctgagcg attacgatgt cgaccacatt   2520
gtcccacagt cgttcctgaa ggacgacagc attgacaaca aggtgctgac ccgctcggat   2580
aagaacaggg gcaagagcga taatgttcca agcgaggag ttgtgaagaa gatgaagaac   2640
tactggcggc agctcctgaa cgcgaagctc atcacacagc ggaagttcga caacctcacc   2700
aaggctgagc gcggggggct gagcgagctg gacaaggcgg ggttcattaa gaggcagctg   2760
gtcgagacac ggcagattac aaagcatgtt gcgcagattc tcgattcccg gatgaacacc   2820
aagtacgatg agaacgataa gctgattcgg gaggtcaagg taattaccct gaagtccaag   2880
ctggtgtccg acttcaggaa ggacttccag ttctacaagg ttcgggagat caacaactac   2940
caccacgcgc atgatgccta cctcaacgcg tcgtgggga ccgctctcat caagaagtac   3000
ccaaagctgg agtcagagtt cgtctacggg gattacaagg tttacgacgt gcggaagatg   3060
atcgctaaga gcgagcagga gattggcaag gctaccgcta agtacttctt ctactccaac   3120
atcatgaact tcttcaagac agagattacc ctcgcgaatg gcgagatccg gaagaggccc   3180
ctcatcgaga caaatgggga gacaggggag attgtctggg ataaggggcg ggatttcgcg   3240
accgtccgga aggtcctgtc gatgccccag gttaatattg tcaagaagac tgaggtccag   3300
```

```
actggcggct tctcaaagga gtcgattctc ccaaagagga actccgataa gctcattgct   3360
cggaagaagg attgggaccc caagaagtac gggggattcg actcccccac tgttgcttac   3420
tctgttctgg ttgttgctaa ggtggagaag gggaagtcga agaagctgaa gagcgtgaag   3480
gagctgctcg ggattacaat tatggagagg tcatccttcg agaagaatcc catcgacttc   3540
ctggaggcca agggctacaa ggaggtgaag aaggacctga ttattaagct gcccaagtac   3600
tcgctcttcg agctggagaa tgggcggaag cggatgctgg cgtccgcggg ggagctgcaa   3660
aaggggaacg agctggcgct cccctccaag tatgtgaact tcctctacct ggcgtcgcac   3720
tacgagaagc tgaaggggtc cccagaggat aatgagcaga agcagctctt cgtcgagcag   3780
cataagcact acctggacga gattatcgag cagattagcg agttctcgaa gcgggtcatc   3840
ctcgcggatg cgaacctgga taaggtgctc agcgcctaca ataagcaccg ggacaagccg   3900
attcgggagc aggcggagaa tattattcac ctcttcacac tcaccaacct cggggcacca   3960
gctgcgttca gtacttcga cactactatc gaccggaagc ggtacacctc gacgaaggag   4020
gtgctcgacg ccacccctcat tcaccagtcg atcacaggcc tgtacgagac acggattgac   4080
ctgtcccagc tcggggcgga c                                              4101

<210> SEQ ID NO 64
<211> LENGTH: 4101
<212> TYPE: DNA
<213> ORGANISM: Artificial
<220> FEATURE:
<223> OTHER INFORMATION: Cas9

<400> SEQUENCE: 64
gacaagaagt actccattgg cctggcgatt gggacaaact cggtgggtg ggccgtgatt      60
acggatgagt acaaggttcc aagcaagaag ttcaaggtcc tcgggaacac agatcggcat    120
tcgattaaga agaatctcat tggggcgctc ctcttcgact cggggagac agcggaggct    180
accaggctca agcggacagc caggcggcgg tacacaaggc ggaagaatcg catctgctac    240
ctccaggaga ttttctcgaa tgagatggcg aaggtggacg acagcttctt ccatcggctg    300
gaggagtcct tcctggtgga ggaggataag aagcacgaga ggcatccaat tttcgggaac    360
atcgtggacg aggttgcgta ccatgagaag taccctacaa tctaccatct gcggaagaag    420
ctggttgact ccacagacaa ggcggacctg aggctgatct acctgctct ggcccacatg    480
attaagttcc gcgggcattt cctgatcgag ggggacctga tcccgacaa ttcggatgtg    540
gacaagctct tcatccagct ggtgcagacc tacaaccagc tgttcgagga gaatcccatc    600
aatgcgtcgg gcgttgacgc taaggccatt ctgtccgcta ggctgtcgaa gagcaggagg    660
ctggagaacc tgatcgccca gctgccaggc gagaagaaga tgggctctt cgggaatctg    720
attgcgctct ccctggggct gacaccgaac ttcaagagca tttcgatct ggctgaggac    780
gcgaagctcc agctctcgaa ggacacttac gacgatgacc tcgataacct cctcgcgcag    840
atcgggaccc agtacgctga tctcttcctc gccgctaaga acctctcgga tgctatcctg    900
ctctccgaca ttctccgggt taataccgag attacaaagg ccccactgtc ggcgtccatg    960
atcaagcggt acgatgagca tcatcaggat ctcaccctgc tcaaggccct cgtgcggcag   1020
cagctgcccg agaagtacaa ggagatttc ttcgaccaga gcaagaatgg gtacgctggc   1080
tacattgacg gcggggcctc acaggaggag ttctacaagt tcatcaagcc aatcctggag   1140
aagatggatg gacagagga gctgctggtg aagctcaacc gggaggatct gctcaggaag   1200
```

```
cagcggacgt tcgacaacgg gtcgattccc catcagatcc acctggggga gctgcacgcg    1260
atcctgcgcc ggcaggagga tttctaccct ttcctgaagg ataatcggga gaagatcgag    1320
aagattctca ccttccggat tccctactac gtcgggccac tcgcgcgggg caatagcagg    1380
ttcgcctgga tgacacggaa gagcgaggag acaatcaccc cctggaactt cgaggaggtt    1440
gtcgacaagg gggcgtccgc ccagtcattc attgagcgga tgaccaattt cgacaagaat    1500
ctgccaaatg agaaggttct cccaaagcat agcctcctct acgagtactt cactgtttac    1560
aacgagctga ccaaggtgaa gtatgtgacc gagggcatgc ggaagcccgc gttcctgtcc    1620
ggcgagcaga agaaggccat tgtggacctc ctgttcaaga ccaatcgcaa ggtcacagtc    1680
aagcagctca aggaggatta cttcaagaag atcgagtgct cgactcggt tgagattagc     1740
ggggtggagg atcggttcaa cgcgagcctc ggcacttacc acgacctcct gaagatcatc    1800
aaggataagg acttcctcga caacgaggag aacgaggata ttctggagga catcgtgctc    1860
accctgacgc tgttcgagga tcgggagatg atcgaggagc gcctgaagac ctacgctcat    1920
ctcttcgatg ataaggtcat gaagcagctg aagaggaggc ggtacaccgg gtggggccgc    1980
ctgagcagga agctcattaa cgggatcagg acaagcaga gcggcaagac catcctggac      2040
ttcctcaaga gcgatggctt cgccaaccgg aatttcatgc agctcatcca cgacgactcc    2100
ctcaccttca aggaggacat tcagaaggct caggtcagcg ccagggcga ctcgctgcat      2160
gagcacatcg ctaacctggc gggcagccca gccatcaaga agggcatcct ccagacagtg    2220
aaggtcgtgg atgagctggt gaaggtcatg ggccggcata agcccgagaa tattgtgatt    2280
gagatggcgc gggagaatca gaccactcag aagggccaga agaactcgcg ggagcgcatg    2340
aagaggatcg aggaggggat taaggagctg ggcagccaga ttctcaagga gcaccccgtg    2400
gagaataccc agctccagaa cgagaagctg tacctctact acctcagaa tgggcgggac     2460
atgtatgttg atcaggagct ggacatcaat cgcctctcgg attacgacgt ggaccacatc    2520
gtgccccaga gcttcctgaa ggatgatagc atcgacaata aggtcctgac ccgctccgac    2580
aagaatcgcg gcaagagcga caacgtgccg agcgaggagg tcgtgaagaa gatgaagaac    2640
tactggcggc agctgctgaa cgcgaagctc attacacagc ggaagttcga taacctgacg    2700
aaggcggaga ggggcggcct ctccgagctg gacaaggcgg gcttcattaa gaggcagctc    2760
gtggagactc gccagatcac caagcacgtg gctcagatcc tcgatagccg gatgaatacg    2820
aagtacgatg agaatgacaa gctcatccgg gaggtgaagg taatcaccct gaagtcaaag    2880
ctcgttagcg atttccggaa ggacttccag ttctacaagg tgcgggagat taacaactac    2940
catcatgcgc acgatgcgta cctcaatgcg gtggtgggca cagccctgat taagaagtac    3000
cccaagctgg agagcgagtt cgtctacggg gactacaagg tgtacgatgt tcggaagatg    3060
atcgccaaga gcgagcagga gattgggaag gccaccgcta agtacttctt ctactcgaat    3120
attatgaatt tcttcaagac cgagatcaca ctcgctaatg gggagattcg gaagcggccc    3180
ctcatcgaga ctaacgggga gactggcgag attgtgtggg acaaggggcg cgacttcgct    3240
accgtgcgca aggtcctctc gatgcccag gttaatattg ttaagaagac agaggtgcag     3300
acgggcgggt tctccaagga gtctatcctg ccgaagcgga actcggacaa gctgatcgcc    3360
cgcaagaagg attgggaccc caagaagtac ggggattcg atagcccaac cgtggcttac      3420
agcgtcctgg tggtcgccaa ggttgagaag ggaagtcga agaagctcaa gagcgttaag      3480
gagctgctgg gcatcaccat catggagcgg tccagcttcg agaagaatcc tatcgacttc    3540
ctggaggcta aggggtacaa ggaggtcaag aaggacctga tcattaagct gcccaagtac    3600
```

```
tctctgttcg agctggagaa cgggaggaag cggatgctgg cgtctgctgg cgagctacag    3660
aagggcaatg agctggcgct ccccctcgaag tatgtcaact tcctctacct ggcttcccat   3720
tacgagaagc tgaagggctc gcccgaggat aatgagcaga agcagctctt cgtggagcag   3780
cacaagcact acctcgacga gatcattgag cagatttcgg agttctcgaa gcgggtcatt   3840
ctcgcggacg cgaacctcga caaggtcctc tcggcgtaca acaagcaccg ggacaagccc   3900
atccgggagc aggccgagaa cattatccac ctcttcacac tgaccaacct cggcgctccc   3960
gccgcgttca gtacttcga caccaccatt gaccgcaaga gatacacatc caccaaggag    4020
gtgctggacg cgaccctcat ccaccagagc atcacaggcc tctacgagac acggatcgac   4080
ctctcgcagc tcggggggcga t                                            4101

<210> SEQ ID NO 65
<211> LENGTH: 4092
<212> TYPE: DNA
<213> ORGANISM: Artificial
<220> FEATURE:
<223> OTHER INFORMATION: Cas9

<400> SEQUENCE: 65
gacaagaagt actcgatcgg cctggcgatt ggcacaaaca gcgtgggtg ggctgtgatc      60 actgatgagt acaaggtgcc atcgaagaag ttcaaggtgc tggggaatac agaccggcat    120
tcgatcaaga agaatctcat cggcgctctc ctcttcgatt ccggcgagac tgctgaggcg   180
acccgcctga gcgcaccgc ccggcggcgc tacactcggc ggaagaatag gatttgctac    240
ctccaggaga ttttctcgaa tgagatggcc aaggtggatg acagcttctt ccaccgcctg   300
gaggagtcgt tcctggtcga ggaggacaag aagcatgagc ggcaccctat cttcgggaat   360
atcgttgatg aggtcgccta ccacgagaag tacccccacta tctaccatct ccgcaagaag 420
ctcgtggaca gcacagataa ggccgacctc cgcctgatct acctcgccct cgcgcacatg   480
attaagttcc ggggggcactt cctcattgag ggggatctga atcccgataa ctccgacgtg  540
gacaagctgt tcatccagct ggtgcagaca taacaaccagc tgttcgagga gaatcccatc   600
aacgcgagcg gcgtggacgc taaggccatt ctgtcggcta ggctctcgaa gtcgaggcgg   660
ctggagaacc tgattgcgca gctccccggc gagaagaaga cgggctgtt cgggaatctc   720 atcgccctct ccctcggcct cacaccaaac ttcaagagca atttcgacct ggctgaggac   780
gctaagctgc aactctcaaa ggatacatac gatgacgacc tggacaatct cctggctcag   840
atcggcgacc agtacgctga cctgttcctc gcggccaaga tctgtcgga cgcgattctc   900 ctcagcgaca tcctgcgcgt caataccgag attacgaagg ctccactgtc tgcgtcaatg   960
attaagcggt acgatgagca tcaccaggat ctgaccctcc tgaaggcgct cgtgcggcag  1020
cagctgcccg agaagtacaa ggagattttc ttcgatcaga gcaagaatgg ctacgccggc  1080
tacatcgacg gggcgcgag ccaggaggag ttctacaagt tcatcaagcc catcctggag    1140
aagatggacg gcaccgagga gctactcgtg aagctcaatc gggaggatct cctccggaag  1200
cagcggacat cgataacgg gtctatccca caccagatcc acctcggcga gctgcatgcg   1260
attctgcggc ggcaggagga tttctaccct tcctgaagg acaaccggga gaagatcgag    1320
aagatcctca cattccggat tccatactac gtcggccccc tggcgagggg caatagccgg  1380
ttcgcgtgga tgacaaggaa gtccgaggag actattaccc cgtggaattt cgaggaggtg   1440
gttgacaagg gcgcttccgc gcagagcttc attgagcgga tgacaaactt cgacaagaat   1500
```

-continued

```
ctccccaacg agaaggtcct gccgaagcat agcctcctgt acgagtactt caccgtctac    1560
aatgagctaa ctaaggtcaa gtatgtgaca gagggcatga ggaagccagc cttcctctca    1620
ggcgagcaga agaaggccat tgtggacctc ctgttcaaga caaaccgcaa ggtgacagtg    1680
aagcagctga aggaggatta cttcaagaag attgagtgct tcgactcagt ggagatttca    1740
ggcgtggagg atcggttcaa cgcgagcctg gggacttacc acgacctgct gaagattatt    1800
aaggacaagg acttcctgga taacgaggag aatgaggaca tcctggagga tattgtgctc    1860
accctcaccc tgttcgagga cagggagatg attgaggaga ggctcaagac ctacgcgcac    1920
ctgttcgatg acaaggtcat gaagcagctg aagaggcggc gctacactgg gtggggccgc    1980
ctgtcgcgga agctgatcaa cggcattcgg gataagcagt ccgggaagac cattctggat    2040
ttcctgaagt cggacggctt cgccaacagg aatttcatgc agctgatcca cgacgactcc    2100
ctcaccttca aggaggacat tcagaaggcc caggttagcg gccaggggga ctcactccac    2160
gagcatattg ccaatctggc cggctctcca gctatcaaga agggcatcct gcaaacagtt    2220
aaggttgttg acgagctggt taaggtcatg ggcggcata agcccgagaa cattgtcatc    2280
gagatggctc gggagaacca gacaactcag aagggccaga agaactccag ggagcgcatg    2340
aagcggattg aggagggcat taaggagctg ggtcccaga tcctcaagga gcaccctgtc    2400
gagaacactc agctgcaaaa cgagaagctc tacctgtact acctccagaa cgggcgggat    2460
atgtatgtgg atcaggagct ggacatcaac aggctctccg actacgacgt ggatcacatt    2520
gtcccacagt ctttcctcaa ggatgattcc atcgacaaca aggtgctgac gcgcagcgac    2580
aagaataggg ggaagtcgga caacgttccg agcgaggagg tcgtgaagaa gatgaagaat    2640
tactggaggc agctcctgaa tgcgaagctg atcactcaga ggaagttcga caatctgaca    2700
aaggcggaga ggggcgggct ctcggagctg gataaggcgg gcttcatcaa gcggcagctc    2760
gttgaaaccc ggcagatcac caagcatgtc gcccagatcc tcgatagccg catgaacacc    2820
aagtacgatg agaacgacaa gctcattcgg gaggttaagg tcattacgct gaagtccaag    2880
ctcgtcagcg acttcaggaa ggatttccag ttctacaagg ttcgggagat taacaactac    2940
caccacgcgc atgatgcgta cctgaacgct gttgtcggca ctgctctcat caagaagtac    3000
ccaaagctgg agtccgagtt cgtctacggg gactacaagg tctacgatgt ccggaagatg    3060
atcgccaagt cggagcagga gatcgggaag gctactgcga agtacttctt ctacagcaac    3120
attatgaatt tcttcaagac ggagattacg ctggcgaacg gggagattag gaagaggccc    3180
ctcattgaga ctaatgggga gacaggcgag attgtttggg acaagggccg cgacttcgcg    3240
actgtgcgga aggtcctgtc catgccacag gtgaatattg ttaagaagac agaggtgcag    3300
actgggggct tctcgaagga gagcattctc ccaaagcgga acagcgataa gctcatcgcg    3360
cgcaagaagg attgggaccc taagaagtac ggcggcttcg attctcccac tgtggcctac    3420
tccgttctcg tggttgccaa ggttgagaag gggaagtcga agaagctgaa gtcggtcaag    3480
gagctgctcg ggattacaat catggagcgg agcagcttcg agaagaaccc tattgatttc    3540
ctggaggcca agggctacaa ggaggttaag aaggatctca ttatcaagct ccctaagtac    3600
tctctgttcg agctggagaa tggccggaag aggatgctgg cctcggctgg cgagctacag    3660
aaggggaatg agctggccct cccgtcgaag tatgtgaatt tcctgtacct cgcgtcgcac    3720
tacgagaagc tcaagggcag cccggaggat aatgagcaga agcagctctt cgtggagcag    3780
cataagcact acctggacga gatcattgag cagatcagcg agttctcgaa gcgggttatt    3840
ctggctgatg ctaacctgga caaggttctg agcgcctaca ataagcatcg cgacaagccg    3900
```

```
attcgcgagc aggcggagaa tattatccac ctgttcaccc tcactaacct cggggctccc    3960
gcggccttca agtacttcga taccacaata gataggaagc ggtacacctc gacgaaggag    4020
gtcctcgacg ccacactcat ccatcagtcg attacaggcc tgtacgagac acggattgac    4080
ctctcgcagc tg                                                        4092

<210> SEQ ID NO 66
<211> LENGTH: 4101
<212> TYPE: DNA
<213> ORGANISM: Artificial
<220> FEATURE:
<223> OTHER INFORMATION: Cas9

<400> SEQUENCE: 66
gacaagaagt attccatagg cctggctatc ggcaccaaca gcgtgggctg ggccgtcatc      60
accgacgagt acaaagtgcc gagtaaaaag ttcaaagtgc tcggcaacac cgaccgccac     120
tccataaaga aaaacctgat cggggcgctc ctgttcgaca cggcgagac ggcggaggcc      180 acccgcttga aacgcacggc ccgacggcgc tacacgcggc gcaagaaccg gatctgttac     240
ctacaggaga ttttctctaa cgagatggcg aaggtggacg actcgttctt tcaccgcctc     300
gaagagtcct cctcgtgga ggaggacaag aaacacgagc gccacccgat cttcggcaac      360
atcgtggacg aggtggccta ccacgagaag taccccgacca tctaccacct ccggaagaaa     420
ctcgtggaca gcacggacaa ggccgacctg aggctcatct acctcgccct ggcgcacatg     480
attaagttcc ggggccactt cctgatcgag ggcgacctga cccgacaa cagcgacgtg       540 gacaagctgt tcatccagct agtccagacc tacaaccagc ttttcgagga aaaccccatc     600
aacgccagcg gggtggacgc gaaggcgatc ctgtccgccc ggctgagcaa gtcccggcgg     660
ctggagaacc tcatcgcgca gttgcccggc gagaagaaga cgggctgtt cgggaacctg     720 atcgccctct ccctggggct caccccgaac ttcaagtcca acttcgacct cgccgaggac     780
gccaaactac agctgagcaa ggacacctac gacgacgacc tcgacaacct gctggcccag     840
atcggggacc agtacgcaga cctgttcctc gccgccaaga acctctccga cgccatcctg     900
ctgtcggaca tcctgcgggt gaacacgaag atcacgaagg ccccgctctc ggcctcgatg     960
attaaacgct acgacgagca ccaccaggac ttgaccctcc tcaaggcgct ggtccgccag    1020
cagcttcccg agaagtacaa ggaaatcttt ttcgatcaga gcaagaacgg gtacgccggg    1080
tacatcgacg gcggggcgtc ccaggaggag ttctacaagt tcatcaagcc catcctggag    1140
aaaatggacg gaccgagga gctgctcgtg aagctcaacc gcgaagattt gctccgcaag    1200
cagcgcacgt tcgacaacgg gtcgatcccg caccagatcc acctgggcga gctgcacgcg    1260
atcctcaggc gtcaggaaga cttctacccc ttcctcaagg acaaccgcga gaagatagag    1320
aagattctga ccttcagaat tccttattac gtgggcccgc tggctcgggg caactcgcgc    1380
ttcgcctgga tgacgcgcaa gtccgaggag accatcaccc cgtggaactt cgaggaggtg    1440
gtggataagg gtgcctcggc ccagtccttc atcgagcgga tgaccaactt cgacaagaac    1500
ctgccgaacg agaaggtgct cccccaagcac agcctgctct acgaatattt cacggtgtac    1560
aacgagctga cgaaggtcaa gtacgtgacc gaggaatga ggaaacctgc attcctctcc    1620
ggggagcaga gaaaagccat agtcgacctc ctgttcaaga ccaaccggaa ggtcaccgtc    1680
aagcagctca aggaggacta cttcaagaag atcgagtgct cgattcagt ggagatcagc    1740 ggcgtcgagg accggttcaa cgccagcctg ggcacctacc acgacctgct caagatcatc    1800
```

```
aaggacaagg acttcctcga caacgaggag aacgaggaca tcctggagga catcgtgctg    1860
accctgacgc tcttcgagga ccgcgagatg atcgaggagc gcctcaagac ctacgcccac    1920
ctgttcgacg acaaggtgat gaagcagctc aagcggcgga gatatactgg gtggggccgc    1980
ctctcccgga agctcattaa cggtatcagg gataagcagt ccgggaagac gatcctcgac    2040
ttcctcaagt cggacgggtt cgccaaccgc aacttcatgc agctcatcca cgacgactcc    2100
ctgacgttca aggaggacat ccagaaggcc aagtgtctg gtcaaggtga ctcgctccac      2160
gagcacatcg ccaacctcgc gggcagcccg gccatcaaga agggaatact ccagaccgtc    2220
aaggtggtgg acgagctggt gaaggtcatg ggccgccaca agccggagaa catcgtcatc    2280
gagatggcgc gggagaacca gaccacgcag aaggggcaga aaaatagccg tgagcgcatg    2340
aagcgcatcg aggagggat taaggagttg gcagccaga tcctcaagga gcaccctgtg       2400
gagaacacgc agttgcaaaa cgagaagctc tacctgtact acctccagaa cgggagggat    2460
atgtacgtgg accaagaact ggacatcaac cgcctgtccg actacgacgt ggaccacatc    2520
gtgccgcaga gcttcctcaa ggacgacagc atcgacaaca aggtgctcac ccggtccgac    2580
aagaatcggg gcaagtccga caacgtgccc agcgaggagg tcgtcaaaaa gatgaaaaac    2640
tactggcgac aactactgaa cgccaagctc atcacccagc gcaagttcga caacctcaca    2700
aaagccgagc gcggcgggtt gagcgagctg acaaggccg ggttcatcaa gcgccagctc     2760
gtcgagacgc gccagatcac gaagcacgtc gcgcagatac tcgacagccg gatgaacacc    2820
aagtacgacg agaacgacaa gctcatccgg gaggtgaagg tcatcaccct caagtcgaag    2880
ctcgtgagcg acttccgcaa ggacttccag ttctacaagg tccgggagat caacaactac    2940
caccacgccc acgatgctta tcttaacgcc gtggtgggga cggccctcat taagaaatac    3000
ccgaagctgg agtcggagtt cgtgtacggc gactacaagg tgtacgacgt caggaagatg    3060
atcgccaagt ccgaacagga gatcgggaag gccacggcga atacttcttc ctacagcaac    3120
atcatgaact tcttcaagac cgagatcacc ctcgccaacg gcgagatccg caagcgcccg    3180
ctcatcgaga cgaacgggga gaccggcgag atcgtctggg acaaggggcg cgacttcgcc    3240
actgtgcgga aggtgctgtc gatgccccag gtcaacatcg tcaagaagac ggaggtccag    3300
acgggcgggt tcagcaagga gagcatcctg ccgaagcgca acagcgacaa gctgatcgcc    3360
cgcaaaaagg actgggatcc aaaaaagtac ggcggcttcg acagcccac cgtcgcctac     3420
agcgtcctcg tcgtcgctaa agtcgagaag ggcaagtcca aaaagctcaa gagcgtcaag    3480
gagctgctcg ggatcaccat catggagcgg tccagcttcg agaagaaccc aattgatttc    3540
ctggaggcga agggctacaa ggaggtcaag aaagacctca tcataaagct gccgaagtac    3600
tcactcttcg agctggagaa cgggcgcaag cggatgctgg cgtcggccgg agagctccaa    3660
aagggcaacg agctggcgct gccgagcaag tacgtgaact tcctctacct ggcgtccac      3720
tacgagaagc tcaagggcag tccagaggat aacgagcaga agcagctatt cgtggagcag    3780
cacaagcact acctggacga gatcatcgag cagatcagcg agttctccaa gcgcgtcatc    3840
ctggcggacg ccaacctgga caaggtgctg tccgcgtaca acaagcaccg cgacaagccg    3900
atccgcgagc aagccgagaa catcatccac ctgttcaccc tcacgaacct cggggcaccc    3960
gccgccttca atatttcga cacgaccatc gaccgcaagc gctacaccag cacgaaggag    4020
gtgctcgacg ccaccctgat ccaccagagc atcaccgggc tgtacgagac ccgcatcgac    4080
ctctcgcagc tcggcgggga c                                              4101
```

<210> SEQ ID NO 67
<211> LENGTH: 4101
<212> TYPE: DNA
<213> ORGANISM: Artificial
<220> FEATURE:
<223> OTHER INFORMATION: Cas9

<400> SEQUENCE: 67

```
gacaagaagt acagtattgg attggccatc gggacgaaca gcgtgggctg ggccgtcatc    60
accgacgagt acaaggtgcc atccaagaag tttaaggttc tggggaatac cgaccgccac   120
tcgatcaaga aaatctcat cggggcgctg cttttcgaca gcggcgagac ggcggaagcg   180
acgcggctca gcggacggc tcgtcgccgt acacccggc gtaagaaccg catctgttac   240
ctccaggaga tattcagcaa cgagatggcg aaggtggacg actcctttt ccaccgtctt   300
gaggagtcct tcctggtcga ggaggacaag aagcacgagc gccacccgat cttcgggaac   360
atcgtggacg aggtggccta ccacgagaag taccccacga tctaccacct ccgcaaaaaa   420
ctcgtggact caactgacaa ggccgatttg aggcttatct acctcgccct cgcccacatg   480
attaagttcc gtgggcactt cctaatcgag ggtgacctca ccccgacaa ctctgacgtg   540
gacaagctgt tcatccagct tgtgcagacc tacaatcagc tctttgagga gaatccgatc   600
aacgcatctg tgtggacgc aaaggccatc ctcagcgcgc ggctgagcaa gtctaggcgg   660
ttggagaacc tgatcgccca actgcccggc gagaagaaaa atggcctctt cggcaacctg   720
atcgccctgt cgctggggct cacgccgaac ttcaagagta actttgacct ggcggaggac   780
gctaagctcc agctatctaa ggacacatac gacgacgacc tggacaacct gctggcccag   840
atcggcgacc agtacgccga cctcttccta gccgccaaga acctgtccga cgccatcctc   900
ctcagcgaca tcctgcgcgt gaacacggag atcacgaagg ctccgctcag cgcctccatg   960
attaagcggt acgacgagca ccaccaagac ctaactttac tcaaagccct cgtgcggcag  1020
cagcttcccg agaagtacaa agagatattt tttgatcagt ccaagaacgg ttatgcgggc  1080
tacatcgacg gcggcgcgag ccaggaggag ttctacaagt tcatcaagcc catcctggag  1140
aagatggacg gcacggagga gctgctcgtg aagctcaacc gtgaagacct cctgcgaaag  1200
cagcgaacct tcgacaacgg ttcgatcccg caccagatcc acctcgggga gctgcacgcc  1260
atcctgaggc gacaggagga cttctaccct ttcctaaagg acaaccgcga gaagattgaa  1320
aaaatcctga cgtttcgcat accctactac gtcggcccgc tggcgcgcgg caactcccgg  1380
ttcgcctgga tgacccgtaa gagcgaggag acgatcaccc cgtggaactt cgaggaggtc  1440
gtggacaagg cgcgagcgc gcagagcttc atcgagcgca tgaccaactt cgacaagaac  1500
ctcccgaacg agaaggtgct cccaaagcac tccctcctgt acgagtattt caccgtgtac  1560
aacgagttga caaggtgaa gtacgtgacg gagggaatgc ggaagcctgc gttcctctcg  1620
ggcgagcaga agaaggcaat cgtggacctg ctcttcaaga ccaaccggaa ggtgacggtg  1680
aagcagctca ggaggacta cttcaaaaaa atcgagtgct tcgactccgt ggagataagc  1740
ggcgtggagg accgattcaa cgcctccctc ggcacctacc acgacctcct taagatcatc  1800
aaggacaagg acttcctgga caacgaggag aacgaggaca tcctggagga catcgtgctc  1860
accctgaccc tcttcgagga ccgggagatg atcgaggagc gcctcaagac gtacgcccac  1920
ttgttcgacg acaaggtgat gaagcagctc aagcggcggc gatacaccgg tggggccgc  1980
ctatcccgca aacttatcaa cggcatccgc gacaagcagt ccggcaagac gatcctggat  2040
ttcctcaagt cggacgggtt cgccaaccgg aacttcatgc agctcatcca cgacgacagc  2100
```

-continued

```
ctcacgttca aggaggacat ccagaaggcc caagtgagcg gtcaaggggga cagcctccac    2160 gagcacattg cgaaccttgc tgggagccct gcgatcaaga aggggatatt gcaaaccgtg    2220
aaggtcgtgg acgagttggt gaaggtcatg gggcgacaca agcccgagaa catcgtgatc    2280
gagatggcca gggaaaatca gaccacgcag aagggccaaa aaaacagccg cgagcggatg    2340
aagcggatcg aggagggcat caaggagctg gggtcgcaga tcctcaagga gcacccggtg    2400
gagaacacgc agctccagaa cgagaagctg tacctctatt acctacagaa cgggcgggat    2460
atgtacgtgg accaggagct agacatcaac cgcctgtccg actacgacgt ggaccatatc    2520
gtcccgcagt cgttcttgaa ggacgacagc atcgacaaca aggtgctcac aagatcggat    2580
aagaatcgag gcaagtccga caacgtgccc tcggaggagg tggtcaagaa atgaaaaac    2640 tactggcggc agttgctgaa cgccaagctc attacgcagc ggaagttcga caacctgacg    2700
aaggctgaac gtggtgggct cagcgagcta gacaaggcgg ggttcatcaa gcggcagctc    2760
gtcgagaccc ggcagatcac caagcacgtg gcgcagatcc tggactcgcg catgaacacc    2820
aagtacgacg agaacgacaa gctcatccgt gaggtgaagg tcatcaccct taagtctaag    2880
ctggtcagtg acttccgcaa ggacttccag ttctacaagg tccgggagat caacaactac    2940
caccacgcgc acgacgccta cctcaacgcg gtggtgggga cggcgcttat taagaaatat    3000
cccaagctgg aaagcgagtt cgtttacggc gactacaagg tgtacgacgt ccgcaagatg    3060
atcgcaaagt cggaacagga aatcggaaag gcgacgcca aatatttctt ttactccaac    3120
atcatgaatt tttttaagac ggagatcacc ctggcgaacg gggagatccg caagcggccc    3180
ctcatcgaga ccaacgggga gacgggcgag atcgtctggg acaagggccg ggacttcgcc    3240
accgtgcgga aggtgctttc tatgcctcaa gtcaatatcg tcaaaaagac agaggtgcag    3300
accggcgggt tcagcaagga gtctatcctg ccgaagcgca actcggacaa gctcatcgcg    3360
cgcaagaaag actgggaccc caaaaaatat ggcgggttcg actcgccgac cgtcgcctac    3420
agcgtcctcg tggtggctaa ggtcgagaag ggcaagagca aaaagctaaa gtcggtgaag    3480
gagctgctgg gcatcaccat catggagcgc tcgtctttcg agaagaatcc aatcgacttc    3540
ctagaggcga aggggtacaa ggaggtcaaa aaggatctta tcatcaaact gccgaagtac    3600
agtctgttcg agctggagaa cgggcggaag cggatgctgg ctagtgcggg cgagttgcag    3660
aagggcaacg agttggcact gccctccaag tacgtgaact tcctgtacct ggcctcccac    3720
tacgagaagc tcaaggggag ccccgaggac aacgagcaga agcagctatt cgtcgagcag    3780
cacaagcact acctggacga gatcatcgag cagatcagtg agttctccaa gcgggtcatc    3840
ctcgcggacg ccaacctgga caaggtgctg agcgcgtaca acaagcacag ggacaagcca    3900
atcagggaac aggccgagaa catcatccac ctgttcaccc tgaccaacct gggtgcaccg    3960
gctgccttca agtactttga cacgaccatc gaccggaagc gctacacctc cacgaaggag    4020
gtgctggacg ccacgctgat ccaccagagc atcaccgggc tctacgagac acggatcgac    4080
ctgagccagc ttggcgggga c                                              4101
```

<210> SEQ ID NO 68
<211> LENGTH: 4092
<212> TYPE: DNA
<213> ORGANISM: Artificial
<220> FEATURE:
<223> OTHER INFORMATION: Cas9

<400> SEQUENCE: 68

```
gacaaaaagt attccattgg actcgctatc ggcacgaaca gcgtcgggtg gcggtcatc       60
```

```
actgacgagt acaaggtgcc gagcaagaag tttaaggtgc tgggaaacac cgacaggcac     120
tcgatcaaga aaatcttat cggggccta ctcttcgact ccggagaaac cgccgaggcc      180
acccggttga agcgcacggc ccgccgtcgc tacaccaggc gcaagaaccg gatctgctac    240
ctccaggaga tattcagcaa tgagatggcg aaggtggacg actcgttttt tcacaggcta    300
gaggagtctt cctcgtgga ggaggacaag aaacacgagc gccacccat cttcggcaac     360 atcgtggatg aggtggcata tcacgagaag tacccaacca tctaccacct ccgcaaaaag    420
ctcgtggact ctaccgacaa ggccgacctc cgtctgatct acctcgcgct ggcccacatg    480
attaagttcc gaggacactt tctgatcgag ggcgacctga acccagacaa cagcgacgtg    540
gacaagctgt tcatccaact tgtccagacc tacaatcagc tcttcgagga aaccctatc     600 aacgcctcgg gcgtggacgc gaaggccatc ctgtccgccc gcctgagcaa gtcgcggcgg    660
ctggagaacc tgatcgccca gctccccggc gaaaaaaaga acggcctctt cggcaacctc    720
atcgcgttgt cgctgggct caccccgaac ttcaagtcca acttcgacct ggccgaggac    780
gctaaactcc agctctcgaa ggatacctac gacgacgacc tcgacaacct gctggcccag    840
atcggcgacc agtacgcgga ccttttcctg gcggccaaga acctgagcga cgcgatcctc    900
cttagcgaca tactccgtgt gaacaccgag atcacgaagg ccccgctctc cgcgtccatg    960
attaagcgct acgacgagca ccaccaagac cttaccctgc ttaaggcgct ggtcaggcag    1020
cagttaccgg agaagtacaa ggagatcttt tttgatcaat ctaagaacgg ttacgccggg    1080
tacatcgacg gcggcgcgtc ccaggaggag ttctacaagt tcatcaagcc gatcttggag    1140
aaaatggacg ggaccgagga gctgctcgtg aagctcaacc gcgaagacct cctccgcaag    1200
cagcgcacct tcgacaacgg gagcatcccg caccagatcc acctgggaga gctgcacgcg    1260
atcctgcgga gacaagagga cttctacccc ttcctcaagg acaaccggga gaagattgaa    1320
aaaatactta cttttcgtat cccgtactac gtcgggcccc ttgcgagggg caactccaga    1380
ttcgcgtgga tgacccgcaa gtccgaggag accatcaccc cgtggaactt cgaggaggtg    1440
gtggacaagg gcgcgtcggc ccagtcgttc atcgagcgca tgaccaactt cgacaagaac    1500
cttccgaacg agaaggtgct cccgaagcac agcctgctct acgaatattt tactgtgtac    1560
aacgagctga cgaaggtcaa gtacgttacg gaggggatga ggaagcccgc cttcctctcc    1620
ggcgagcaga agaaagccat tgtggatctc ctgttcaaga ccaaccgcaa ggtgacggtg    1680
aaacagctca agaggacta cttcaagaag atcgagtgct cgactccgt agagatcagc    1740 ggggtcgagg accgcttcaa cgcctcgctg ggcacgtacc acgacctgct aaagattatc    1800
aaggacaaag acttcctaga caatgaggag aacgaggaca ttctggagga catcgtgctg    1860
actctgacgc tgttcgaaga ccgcgagatg atcgaggagc ggcttaagac gtacgcccac    1920
ctgttcgacg acaaggtgat gaagcagttg aaacggcggc gctacaccgg gtggggccgc    1980
ctctcccgca agctcatcaa cggcatccgc gacaagcagt cggggaagac gatcctggac    2040
ttcctcaaga gcgacggctt cgccaaccga aacttcatgc agctaatcca cgacgacagc    2100
ctgacgttca aggaggacat ccagaaggcc caagtgagcg gccagggaga ctcgctacac    2160
gagcatatcg ccaacctggc tggcagcccg gcgattaaga aggaatcct ccaaaccgtc    2220 aaagtggtgg acgagctggt gaaggtgatg ggccgccaca gcccgagaa cattgtgatc    2280 gagatggcgc gggagaacca gacgacgcag aagggccaaa aaaatagcag ggaaaggatg    2340
aagcgaatag aggaggggat caaggagctg ggagccaga ttctcaaaga gcacccggtc    2400
```

```
gagaacacac agctccagaa cgagaagctg tacctctact acctccaaaa cggccgcgat    2460
atgtacgtgg accaggaact agacatcaac cggctgagcg actatgacgt ggaccacatc    2520
gtgccgcagt ccttcctcaa ggacgactcg attgacaaca aagtgctcac tagatccgac    2580
aagaacagag gcaagagcga taacgtcccg tcggaggagg tcgtcaagaa aatgaaaaac    2640
tactggcggc agctcctaaa cgccaagctc atcacgcagc gtaagttcga caacctgacg    2700
aaggcggagc ggggcgggct gagcgagctg gacaaagcgg ggttcatcaa gcggcagctc    2760
gttgagacgc ggcagatcac aaagcacgtc gcgcaaatcc tcgactcccg catgaacacc    2820
aagtacgacg agaacgacaa gctcatccgg gaggtgaagg tcattaccct taaatcgaag    2880
ctcgtcagcg actttcgtaa ggacttccag ttctacaagg tcagagagat caacaactac    2940
caccacgccc acgacgccta tctgaacgcc gtggtgggca ccgcgcttat taagaagtac    3000
cccaagctgg agtccgagtt cgtgtacggc gactacaagg tttatgacgt caggaagatg    3060
atcgccaagt cggaacagga gatcggaaaa gctaccgcca aatatttctt ctatagcaac    3120
atcatgaact tcttcaaaac cgagatcacc ctcgccaacg gcgagatccg gaagcgcccg    3180
ctcatcgaga ccaacgggga gaccggggag atcgtctggg acaaggggcg ggacttcgct    3240
actgtccgaa aggtgctctc catgccacaa gtgaatatcg tcaagaaaac agaggtgcag    3300
accggagggt tcagtaagga gtccatcctg cccaagcgga actccgacaa gctaattgct    3360
cgcaaaaagg attgggatcc taaaaaatat ggcggcttcg actcgcccac ggtcgcctac    3420
tctgtgctgg tcgtggcgaa ggtggagaag ggcaagtcca agaagctcaa gagcgtcaag    3480
gagctgctgg ggatcacgat catggagcgt agttcgtttg agaagaatcc catcgacttc    3540
ctggaggcta agggctacaa ggaggtcaaa aaggacctca tcattaagct gccgaagtac    3600
agcctcttcg agctggagaa cgggcggaag cgtatgctcg cctccgctgg ggagttacaa    3660
aaggggaacg agctggcgct gccgtctaag tacgtcaact tcctgtacct ggcctcccac    3720
tacgagaagc tcaaggggtc gccggaggac aacgagcaga agcagctctt cgtagagcag    3780
cacaagcact acctggacga gatcatcgag cagatttcag agttctcaaa gcgggtcatc    3840
ctcgccgacg ccaacctgga caaggtgctc tcggcctaca caagcaccg ggacaagccg    3900 atccgcgaac aggccgaaaa catcatccac ctgttcacgc tcaccaacct cggtgccccg    3960
gcggccttca gtactttgac acgaccatc gaccggaagc gctatacctc gacgaaggag    4020
gtgctggacg ccaccctgat ccaccagtcc atcaccgggc tttacgagac ccggatcgac    4080
ctctcgcagc ta                                                         4092
```

<210> SEQ ID NO 69
<211> LENGTH: 4101
<212> TYPE: DNA
<213> ORGANISM: Artificial
<220> FEATURE:
<223> OTHER INFORMATION: Cas9

<400> SEQUENCE: 69

```
gacaagaagt atagtattgg actcgccatc ggaaccaact ctgtggggtg gctgttatt      60 acagatgaat ataaggtgcc atccaaaaag tttaaagttc tgggcaatac tgatagacac    120
tcaatcaaga gaatctgat aggtgcactt ctgtttgata gtggagagac tgccgaggca    180
accagactta aaaggactgc aagaagaaga tataccagaa gaagaatag gatttgctat    240 ttgcaggaaa tcttcagcaa cgaaatggcc aaggttgatg actcattttt ccataggttg    300
gaggagagtt tcttgtgga ggaagataag aagcacgaaa gacacccaat tttcgggaat    360
```

-continued

```
atagtggacg aggtggctta tcatgagaag tatcccacta tctaccacct gagaaagaaa      420
cttgtggact caaccgataa ggctgatctt aggcttatat acttggccct tgcacatatg      480
atcaaattca ggggccattt tcttatcgaa ggcgatctta atcccgataa ctcagatgtg      540
gacaagctgt ttatacaact tgtgcaaacc tacaatcaac tcttcgagga gaatcccatt      600
aacgcctccg gcgtggatgc aaaagccata ctgtcagcca gactgagcaa agtaggaga       660
ctggagaatc ttatagccca actgcccggt gaaaagaaga atgggctctt cggaaatctg      720
atcgctcttt cattggggtt gacacccaac tttaagagta actttgactt ggcagaagat      780
gcaaagttgc agctcagtaa agacacatat gacgatgacc ttgacaatct cttggcacaa      840
ataggggatc aatacgctga ccttttcctc gctgccaaga acctcagcga cgctatactg      900
ttgtccgaca ttcttagggt taataccgaa attacaaagg cccctcttag tgcaagtatg      960
atcaaaaggt atgatgagca tcaccaagac cttacactgc tgaaggctct ggttagacag     1020
caactccctg aaaagtataa ggaaatattc ttcgaccaaa gtaagaacgg gtacgccggt     1080
tatattgatg ggggcgcaag tcaagaagaa ttttacaaat tcatcaagcc aattcttgaa     1140
aagatggacg ggactgagga attgctggtg aaactgaata gagaggacct tcttagaaaa     1200
cagaggacat ttgacaatgg gtccatccca caccagattc atctggggga actccacgca     1260
atattgagga gacaagaaga cttttaccca ttccttaagg ataatagaga gaaaatcgaa     1320
aaaatcctga ctttcaggat tccttactat gttgggccac tggccagggg gaactcaaga     1380
ttcgcttgga tgacaaggaa gtcagaagaa accataaccc cttggaattt tgaagaggtg     1440
gttgataagg gggcatcagc ccagtctttc atagagagga tgaccaactt tgataaaaat     1500
cttccaaatg agaaggtttt gccaaaacat agtcttttgt acgagtactt tactgtttat     1560
aacgaattga ccaaggtgaa gtatgtgacc gagggaatga ggaagccagc atttttgtcc     1620
ggggagcaaa agaaagcaat cgttgatctt ctcttcaaga ccaacagaaa agtgaccgtg     1680
aaacaactga aggaagacta cttcaaaaag atagaatgtt tcgattcagt ggaaattagc     1740
ggtgttgaag acaggttcaa tgcttcattg ggtacttacc acgacctgtt gaagataatc     1800
aaagacaagg actttctcga taatgaggag aacgaagaca tcttggaaga cattgtgctt     1860
acactcactt tgtttgagga cagggaaatg attgaggaaa gactcaaaac ttacgctcat     1920
ttgtttgatg ataaggttat gaaacaacta aaaagaagaa ggtacaccgg ctggggaaga     1980
ttgagtagga aactgatcaa cggtattaga gataaacaat ccggaaagac tatcctcgat     2040
ttccttaaga gtgatggctt tgcaaatagg aattttatgc agctgattca tgacgactca     2100
cttaccttca aagaagacat ccaaaaagct caggtgtctg ggcaaggcga cagtctgcat     2160
gaacatatag ctaacttggc tgggagtccc gccatcaaga aggggatact tcaaacagtt     2220
aaagttgtgg acgaattggt gaaggtaatg ggaaggcaca agcctgaaaa tatagtgata     2280
gaaatggcaa gggaaaatca aacaacccag aaggacagaa gaacagtag ggaaaggatg     2340
aaaaggatag aagagggat caaagagctt ggtagccaga tcctcaagga acatccagtg     2400
gagaataccc aacttcaaaa cgagaaactc tatttgtact acttgcagaa cggaagagat     2460
atgtatgtgg accaagagct tgatattaac aggctgagcg attatgacgt tgaccacata     2520
gtgcccccaat cattcctcaa ggatgactct attgataata aggtgctgac aaggagtgac     2580
aagaatagag ggaaatccga caacgttcca tccgaggaag ttgtgaagaa gatgaagaac     2640
tactggaggc agttgctgaa cgctaagctc attacccaga ggaaattcga taacctgacc     2700
```

| | |
|---|---:|
| aaagcagaga gaggcgggct gagcgaactc gataaagcag gtttcatcaa gagacaactc | 2760 |
| gtggagacta ggcaaattac taagcacgtg gctcaaatac tcgacagcag gatgaacaca | 2820 |
| aagtacgacg agaacgacaa gctcattaga gaggttaagg ttattactct gaaaagtaaa | 2880 |
| ttggttagcg atttcagaaa ggatttccaa ttctataagg ttagagagat caacaattat | 2940 |
| catcatgcac atgatgccta tctgaatgct gtggttggta cagcccttat caagaagtac | 3000 |
| cctaagctag agagcgagtt tgtgtacgga gattataagg tgtatgatgt gaggaaaatg | 3060 |
| atcgctaaaa gtgagcaaga gattggaaag gctaccgcca atacttcttt ttattccaat | 3120 |
| attatgaatt tcttcaagac agaaatcacc ctggctaacg gcgagataag gaagaggccg | 3180 |
| cttatcgaaa ctaatgggga gacaggcgaa atagtgtggg acaaagggag ggatttcgca | 3240 |
| actgtgagga aggttttgag catgcctcag gtgaatatcg ttaagaaaac cgaagttcaa | 3300 |
| actggagggt tctctaagga aagcattctc cccaagagga actccgacaa gctgattgct | 3360 |
| agaaagaaag actgggaccc caagaagtat ggcggattcg actcacccac tgtggcatat | 3420 |
| agcgttctcg tggtggcaaa ggttgaaaag gtaaatcca aaaaactcaa atccgtgaag | 3480 |
| gaactccttg gcataactat tatggaaagg agtagctttg aaaagaatcc catcgacttt | 3540 |
| ctcgaagcta agggctataa ggaagttaag aaggacctta taatcaaact tccaaaatac | 3600 |
| tccctttttg agttggaaaa cggcagaaaa agaatgttgg ccagtgccgg ggagcttcaa | 3660 |
| aagggcaacg aactggctct gcctagcaaa tatgtgaact ttttgtatct ggcatcacac | 3720 |
| tacgagaaac ttaaaggctc tcctgaggac aacgagcaaa aacagctctt tgttgaacag | 3780 |
| cataagcact acctcgacga gattattgag cagatcagcg agttctcaaa gagagttatt | 3840 |
| ctggctgacg ctaatcttga caaggttttg tccgcttaca acaaacacag ggataagcca | 3900 |
| atcagggagc aggcagaaaa cataatccat ctctttaccc tgacaaacct cggtgccccc | 3960 |
| gctgctttca gtattttga tactaccatt gacaggaaga gatatacttc cactaaggaa | 4020 |
| gtgctcgacg caaccctcat acaccaaagt atcacaggcc tctatgaaac taggatagat | 4080 |
| ttgtctcaac ttgggggcga t | 4101 |

<210> SEQ ID NO 70
<211> LENGTH: 4101
<212> TYPE: DNA
<213> ORGANISM: Artificial
<220> FEATURE:
<223> OTHER INFORMATION: Cas9

<400> SEQUENCE: 70

| | |
|---|---:|
| gacaaaaagt attccatcgg gcttgctatc ggaaccaact ctgtggggtg ggcagttatt | 60 |
| accgacgaat acaaggtgcc cagcaagaag tttaaggttc tggggaacac agatagacat | 120 |
| agcataaaga aaaacctgat aggcgcactg ttgttcgact ccggggaaac agccgaagct | 180 |
| accaggctga agagaactgc aagaagaagg tacaccagaa gaaaaacag atatgttat | 240 |
| ctccaagaga ttttctctaa cgagatggcc aaggtggacg actcattctt tcacagactg | 300 |
| gaagaatctt tccttgtgga agaagataag aaacacgaga ggcaccctat ttttggcaat | 360 |
| atcgtggatg aggtggctta ccacgaaaaa tacccctacaa tataccacct caggaaaaaa | 420 |
| ttggttgata gtacagacaa ggccgacctc aggctcatct atttggccct ggcccatatg | 480 |
| attaaattca gggggcactt tctcatcgag ggagatttga ccccgacaa cagtgatgtt | 540 |
| gataagctct ttattcagct cgtgcagact acaatcagt tgtttgagga aaaccccatt | 600 |
| aatgcttccg gggtggacgc caaggcaatc cttctgcaa gactctcaaa gtcaaggaga | 660 |

| | |
|---|---|
| ctcgaaaatc tgatagcaca gcttccagga gagaagaaga acgggctctt tggaaacctg | 720 |
| atcgctctgt cactcggact cacacccaat ttcaaaagca attttgattt ggcagaggac | 780 |
| gctaagctgc aactcagtaa ggatacctac gacgatgact tggataatct gctcgcacaa | 840 |
| attggggacc agtatgcaga cctgtttctc gcagctaaga acttgagtga cgccatattg | 900 |
| ctcagtgaca tcctcagggt taataccgag attacaaaag ctccactctc tgcaagcatg | 960 |
| atcaagaggt atgacgagca ccatcaagac ctgacactcc ttaaggcgtt ggttaggcag | 1020 |
| caacttcctg aaaagtataa ggaaatcttc ttcgatcaaa gcaaaaacgg ctacgccggc | 1080 |
| tatatagacg ggggagcatc ccaagaagaa ttttataagt tcataaaacc tatattggag | 1140 |
| aagatggacg ggacagagga attgctcgtg aaactgaaca gggaggatct cctcaggaag | 1200 |
| caaaggacct tcgacaatgg ctccatccca catcagattc acctcggcga actgcacgca | 1260 |
| atactgagaa gacaagagga cttttatcct ttcctgaagg acaacaggga gaaaatcgag | 1320 |
| aaaatcttga cattcagaat cccatactac gttgggcctc tggccagagg taacagtagg | 1380 |
| ttcgcctgga tgactaggaa atcagaggag actattacac cctggaactt gaagaagtt | 1440 |
| gttgataagg gagcttcagc acaatcattc atcgaaagaa tgacaaactt gacaaaaat | 1500 |
| ctgcctaatg agaaagtgct cccaaaacat tccctgctgt atgagtattt taccgtttat | 1560 |
| aacgagctta ccaaggtgaa atacgttact gaaggtatga gaaagccagc ttttctttca | 1620 |
| ggggagcaaa agaaggctat cgtggatctt ctctttaaga ccaacagaaa ggttaccgtg | 1680 |
| aagcagctta aggaagacta ctttaaaaag atcgagtgtt ttgactcagt ggaaataagc | 1740 |
| ggtgttgaag atagattcaa cgcatccttg ggaacttatc atgatcttct taagataatc | 1800 |
| aaggataaag actttctcga caacgaggaa aacgaagata tactggagga catagttctg | 1860 |
| acacttactt tgttcgagga tagggagatg atcgaggaaa gactgaaaac atatgctcac | 1920 |
| cttttcgacg acaaagttat gaaacaactc aagagaagga gatatacagg gtgggggaga | 1980 |
| ttgagcagga aactgattaa tggtatcaga gacaaacagt caggaaaaac aatactcgac | 2040 |
| tttttgaaat cagacggggtt cgcaaatagg aatttcatgc agcttataca cgacgattca | 2100 |
| cttactttta aagaggacat tcaaaaggct caagttagtg acaaggtgaa ctccctccac | 2160 |
| gaacacatcg caaatctcgc tggcagcccct gcaattaaga agggtatact ccagacagtt | 2220 |
| aaggttgttg acgagctggt taaagtgatg ggaagacaca aacccgagaa catagtgata | 2280 |
| gagatggcca gggaaaacca aaccactcaa aagggcaga aaaattccag agagaggatg | 2340 |
| aaaaggattg aagaaggtat caaggagctg ggtagccaaa ttctgaaaga acatcctgtg | 2400 |
| gaaaacactc aactccagaa tgagaaactc tatctgtact atctgcaaaa tgggagagat | 2460 |
| atgtatgtgg accaggaact ggacataaac aggctctcag attacgatgt ggatcatatc | 2520 |
| gtgccacagt cctttcttaa ggatgatagc atcgacaata aggtgcttac caggtccgac | 2580 |
| aagaacaggg gaaagtcaga taacgtgcct tctgaagaag ttgttaaaaa gatgaagaac | 2640 |
| tactggagac agctgcttaa cgctaagctc ataacacaga ggaagtttga acttgacc | 2700 |
| aaggccgaga gaggcggact ctcagaattg gataaggcag ggttcataaa aaggcagctg | 2760 |
| gtggaaacaa ggcagataac taaacatgtg gctcagatcc tcgatagtag gatgaataca | 2820 |
| aaatacgatg agaacgacaa gctcataagg gaggttaaag tgataactct gaaatccaaa | 2880 |
| ctggttagcg atttttaggaa ggatttccag ttttacaaag ttagggagat caacaattat | 2940 |
| catcacgccc acgatgccta cttgaacgca gttgtgggta ctgcacttat caaaaagtac | 3000 |

```
cctaagctgg aatccgagtt tgtttatgga gactataagg tgtacgacgt tagaaaaatg      3060
attgcaaagt cagagcagga gatagggaaa gccactgcaa atatttctt ttatagcaat       3120 atcatgaatt tctttaagac agaaatcaca ctggccaatg gggaaataag gaagaggccc      3180
ctgatcgaaa ctaatggcga gacagggag attgtgtggg ataaaggtag ggactttgca       3240
acagtgagga aagtgctgag catgccccaa gttaatatcg ttaaaaagac cgaggttcaa      3300
acagggggct ttagtaagga aagcattttg cccaagagga atagtgacaa attgattgct      3360
aggaaaaaag attgggaccc caaaaagtat ggcggatttg atagccccac tgttgcttac      3420
tccgtgctcg tggttgcaaa ggtggagaag ggaaagagca agaaactgaa gtcagttaag      3480
gaactccttg gtatcactat catggaaaga agctcctttg agaagaaccc tattgacttc      3540
ctggaggcta aagggtacaa agaggttaag aaagacctta tcattaaatt gcccaaatat      3600
agtcttttcg agcttgaaaa cggaagaaag aggatgcttg catccgctgg cgaattgcaa      3660
aagggcaatg agcttgctct cccttccaag tatgtgaact tcctttatct tgcctcacac      3720
tatgaaaaac tcaaaggttc acccgaagac aacgaacaaa gcaactatt tgtggaacaa       3780 cacaagcact acctggacga aatcattgag caaatttctg agttttcaaa aagggtaatc      3840
ttggctgacg caaatctcga caaagttttg tcagcttaca caaacatag agataagcca       3900 attagagagc aagctgagaa tatcatccat ctgtttaccc tgactaacct tggagcgcct      3960 gctgcttta aatatttcga caccacaatc gacaggaaga ggtacactag cactaaggaa       4020
gttctcgacg ccaccctcat ccaccagagt attacaggcc tgtacgagac aagaattgat      4080
ctttctcaac ttggtggtga c                                                4101
```

<210> SEQ ID NO 71  
<211> LENGTH: 4101  
<212> TYPE: DNA  
<213> ORGANISM: Artificial  
<220> FEATURE:  
<223> OTHER INFORMATION: Cas9

<400> SEQUENCE: 71

```
gataagaagt actcaatcgg tctggcaatc ggaaccaact ctgtggggttg ggcagtgatt        60 acagatgagt ataaggtgcc aagcaaaaaa ttcaaggtgc tgggtaatac cgacagacac       120
agcattaaga gaatttgat tggagcactc ctctttgact caggggaaac agcagaggca        180
acaaggctga gaggacagc aaggcggagg tacacaaggc ggaaaaacag gatatgctac        240
ctccaggaaa tctttagcaa cgagatggct aaagtggatg atagcttttt ccatagactc       300
gaagaatcct ttcttgttga gaggacaaa aagcatgaaa ggcatcccat cttcggcaat       360
atagttgatg aggttgcata ccatgagaag tacccccacaa tctaccaccct cagaaagaaa    420 cttgtggact ccacagataa agcagacctg aggctcatat acctcgcact cgcacacatg       480
atcaagttca gagggcactt tctcatcgaa ggtgacctga atccagataa ttcagatgtg      540
gataaactgt ttatacagct ggtgcaaaca tacaaccaac ttttcgagga aaacccaatc      600
aatgcctccg gtgttgatgc aaaggccatc ctgtcagcaa gactcagcaa agcaggcggg      660
ctcgaaaacc tcatcgccca gcttcccggt gaaaagaaga cgggctcttt ggtaatctc       720 atcgcattga gccttggtct tactccaaac ttcaagagca attttgatct ggcagaggat      780
gctaaactgc aactctcaaa ggacacatat gacgatgacc ttgacaatct gttggcccag      840 atcgggggacc aatatgcaga cctcttcctg gccgcaaaga tctgtcaga tgcaatcctc      900 ttgtccgaca tactgagagt taacactgag atcacaaagg cacctctgtc cgcctccatg      960
```

```
attaagagat acgatgagca tcaccaggat ctgactttgc tcaaagccct cgttagacag   1020
cagttgccag aaaagtacaa agaaatattc tttgatcaat caaaaaacgg atatgcaggg   1080
tacatcgacg gtggggcaag ccaggaagag ttctacaaat tcatcaaacc tatcctggaa   1140
aagatggatg ggacagaaga gctgctggtt aagctgaata ggaagaccct cctcagaaag   1200
cagaggacat ttgataacgg gagcatccct catcaaatcc acctcggtga actccatgct   1260
atcctgagaa ggcaggaaga cttttatcca tttttgaagg acaatagggga gaaaatcgaa   1320 aaaatcctga cattcagaat cccatactac gttggtcctc tggcaagagg taacagtagg   1380
ttcgcatgga tgacaaggaa aagcgaggag acaatcacac cctggaattt tgaggaagtt   1440
gttgacaagg gtgccagcgc acaatccttt atcgaaagaa tgacaaattt cgacaagaat   1500
ctgcctaacg aaaaggttct cccaaagcat tcactcctgt acgaatattt tacagtttat   1560
aacgaactga ctaaagttaa atacgttacc gagggtatga ggaagccagc attcctttcc   1620
ggggaacaga agaaagctat tgtggacctc ctgttcaaga caaatagaaa agtgacagtt   1680
aagcaactca agaggattac cttcaaaaag atcgaatgtt ttgactctgt ggagatcagc   1740
ggggtggagg atagattcaa cgccagcctg ggtacatatc atgatctcct gaaaatcatt   1800
aaagacaagg acttccttga caacgaggag aacgaggaca ttctggaaga cattgttctg   1860
accctcacac tctttgagga tagggagatg attgaggaaa gactgaagac ctacgcccac   1920
ctctttgacg ataaagtgat gaaacagctc aagagaagaa ggtatacagg ttgggggaga   1980
ctgagcagga agttgatcaa tgggattagg gacaaacagt ccgggaaaac aatcctcgat   2040
tttctgaagt cagacggttt cgcaaacaga aattttatgc agctcattca cgatgacagc   2100
ttgacattca aggaagacat ccaaaaggct caagtgagcg ccaaggggga tagcctccac   2160
gagcatattg caaatctggc aggttcacca gccatcaaaa agggcatact tcagacagtt   2220
aaggttgtgg acgaattggt taaagttatg ggcaggcata agccagagaa tatcgttatc   2280
gaaatggcaa gggagaacca aacaactcaa aaagggcaga aaaatagcag agagaggatg   2340
aaaagaatcg aggaagggat caaggaactt gggtcccaaa tcctcaagga gcacccagtt   2400
gaaaatactc aactgcaaaa cgagaagctc tatctctact atctccaaaa cgggagggat   2460
atgtatgttg accaggagct ggatattaac agactgtcag attatgatgt tgatcatatc   2520
gtgccccagt cattcctgaa ggacgattcc atcgacaaca aagttctcac aaggtccgat   2580
aaaaacaggg gcaagtccga taacgttcca agcgaagaag tggtgaaaaa gatgaaaaac   2640
tattggagac aacttctgaa tgcaaagttg attactcaga gaaagtttga caacctcaca   2700
aaagcagaaa gaggcgggct tagcgaactc gataaggcag ggtttatcaa agacagctg   2760 gttgagacaa ggcagatcac aaaacatgtg gcacagatcc ttgactcaag gatgaatacc   2820
aagtatgatg agaatgataa gttgatcagg gaggttaaag ttatcacact caaatccaaa   2880
ctggtgtcag acttcaggaa agactttcaa ttttataagg tgagggagat caataactac   2940
caccatgcac atgacgccta cctgaacgca gtggtgggta cagcattgat taaaaaatac   3000
cctaagctgg agtctgagtt tgtgtacggg gactacaagg tgtacgacgt gaggaaaatg   3060
atagccaagt ccgagcagga gatcgggaaa gcaacagcta gtatttctt ttacagtaat   3120 atcatgaatt tctttaaaac tgagattact ctggcaaacg gggagatcag gaaaagaccc   3180
ctcatcgaga ctaatggtga aacaggtgag atcgtttggg acaaggggag ggattttgct   3240
actgttagaa aagttctgag tatgccacaa gtgaatattg tgaaaaagac agaagttcag   3300
```

| | |
|---|---|
| acaggtgggt tctccaaaga atccatcctg cccaagagaa attcagacaa gctcatcgca | 3360 |
| agaaagaagg actgggaccc taagaagtac ggaggatttg acagccccac cgtggcctat | 3420 |
| tccgtgcttg ttgtggcaaa ggtggagaaa gggaagagca aaaaactgaa atccgtgaaa | 3480 |
| gaactgctgg gaattaccat catggaaaga agctcctttg agaagaaccc aatcgacttc | 3540 |
| ctggaagcaa aaggatataa ggaagtgaaa aaggacctca ttatcaagct cccaaaatac | 3600 |
| tcactttcg agttggagaa cggtagaaag aggatgctgg caagcgcagg gaacttcag | 3660 |
| aaaggcaatg agctggcatt gccatcaaag tatgtgaact tcctctactt ggccagccat | 3720 |
| tacgagaaac ttaaaggtag cccagaagat aacgagcaaa aacagctctt tgtggaacag | 3780 |
| cataagcatt atctggatga gatcatagaa caaatctcag agttttccaa gagagttatc | 3840 |
| ctcgcagatg caaacctgga taaggttctc tcagcctata taagcatag agacaagcca | 3900 |
| attagagagc aagcagagaa cattatccac ttgttcactc ttacaaaccct gggggcacca | 3960 |
| gccgccttca atatttcga tacaacaata gacagaaaga ggtataccag caccaaagaa | 4020 |
| gttctcgacg ccacactgat ccatcaatca atcacaggcc tttacgaaac taggatcgac | 4080 |
| ttgtcacaac tgggtgggga t | 4101 |

<210> SEQ ID NO 72
<211> LENGTH: 3307
<212> TYPE: DNA
<213> ORGANISM: Artificial
<220> FEATURE:
<223> OTHER INFORMATION: Cas9

<400> SEQUENCE: 72

| | |
|---|---|
| gagcaaggac acctacgacg acgacttgga caacctattg gcccagatag gtgaccagta | 60 |
| tgcagacctc ttccttgcgg ccaagaactt gagtgacgct atactgctca gtgacatcct | 120 |
| gagggtgaac actgagatca ctaaggcccc tctctctgcc tcaatgatta gcgttacga | 180 |
| cgagcatcac caggatctca ccctgcttaa ggcccttgtt cggcagcagc tccctgagaa | 240 |
| gtacaaggag atattttttg accagtctaa gaacggctac gccggttaca ttgacggtgg | 300 |
| ggcaagccag gaggagttct acaagttcat caagccgatc cttgagaaga tggacggcac | 360 |
| cgaggagcta cttgtcaagt tgaaccggga agacctgctc cggaaacagc gtacattcga | 420 |
| caacggcagc atccctcacc agatccacct gggcgaacta cacgccatcc tccgacgtca | 480 |
| ggaggacttc tatccattct tgaaagataa cagggaaaaa atcgaaaaaa tacttacgtt | 540 |
| tcgaatacct tactacgtgg ggccccttgc tcggggaaac tccagattcg catggatgac | 600 |
| caggaagtca gaggagacca tcacaccctg gaactttgag gaggtggttg acaaaggtgc | 660 |
| ttctgcccag tccttcattg agcggatgac taacttcgac aagaacctgc caacgagaa | 720 |
| ggtgctgcca agcacagcc tgctctacga atactttact gtgtacaatg agctgacgaa | 780 |
| ggtgaagtac gtgacagagg ggatgcggaa gcccgctttc ctgagcggcg agcaaaaaaa | 840 |
| agcaatcgtg gacctactgt tcaagaccaa ccgaaaggtg acagtgaagc agctcaagga | 900 |
| ggactacttc aaaaaaatcg agtgcttcga ctctgttgag ataagcggcg tggaggaccg | 960 |
| attcaacgcc tcattgggaa cctatcacga cctgctcaag atcattaagg acaaggactt | 1020 |
| cctggataat gaggagaatg aggacatcct ggaggatatt gtgctgaccc ttactctatt | 1080 |
| cgaggacagg gagatgatcg aggagcgact caagacctac gctcacctgt tcgacgacaa | 1140 |
| ggttatgaag caattgaagc gtaggcgata cacggggtgg ggaagactct cccgaaaact | 1200 |
| gataaacggc atcagggaca agcagtcagg gaagacgatc ttggacttcc tgaaatccga | 1260 |

```
cgggttcgcc aaccgcaact tcatgcagct cattcacgac gactcactaa cgttcaaaga   1320
ggacattcag aaggctcaag tcagtggaca aggcgactcc ctgcacgagc acattgcaaa   1380
ccttgcgggc tccccggcga ttaaaaaggg cattctccaa acggttaagg tggtggacga   1440
gctggtgaag gtgatgggcc gacacaagcc tgagaacatc gtgatcgaga tggccaggga   1500
gaaccagact acccagaagg gtcagaagaa ctctcgggaa cgtatgaagc gtattgagga   1560
ggggattaag gagttgggct ctcaaatcct caaggagcac cctgtggaga acactcagct   1620
ccaaaacgag aagctgtacc tgtactacct gcaaaacggg cgcgatatgt acgtggatca   1680
ggagttggac atcaacaggc ttagcgatta cgacgtggac cacatcgtgc cacagtcatt   1740
cttaaaggac gacagcatcg acaacaaggt tctgacgagg agcgacaaga atcgagggaa   1800
aagtgacaat gttccatccg aggaggtggt caagaaaatg aagaactatt ggcgtcagct   1860
tctgaacgcc aagctcatca cccagcggaa attcgacaac ctgactaagg ctgagcgagg   1920
cggactctcc gagcttgaca aggctggctt catcaagcgg cagttggtcg aaacccgaca   1980
gataacgaag cacgttgccc agatacttga ctcccgtatg aacaccaagt acgacgagaa   2040
cgacaagctc atcagggagg tgaaggtcat tacccttaag tccaaactcg tcagcgactt   2100
tcgtaaggac ttccagttct acaaggtgcg cgagatcaat aactaccacc acgcacacga   2160
cgcctacctg aacgcagtgg ttggaaccgc gttgattaaa aagtacccca agttggagtc   2220
ggagttcgtt tacggggact acaaggtgta cgacgttcgg aagatgatcg ccaagtctga   2280
acaggagatc gggaaagcaa ccgccaagta tttcttctat agcaacatca tgaacttctt   2340
taaaaccgag atcacacttg ccaatggcga gatccgtaag aggccgctga tcgagacaaa   2400
tggggagact ggcgagatcg tgtgggacaa gggccgcgac ttcgcaaccg ttcggaaagt   2460
cttgtccatg cctcaagtca acatcgtcaa gaagactgag gtgcaaacag gcgggttctc   2520
gaaggagtcc atactgccca agaggaactc agacaagctc atagcacgca aaaagactg   2580 ggatccaaag aaatacggcg ggttcgactc gccgacagtc gcatactccg tgttagtggt   2640
ggctaaagtg gaaaagggga gtccaagaa gctcaagtcc gtcaaggagt tgctcgggat   2700
caccattatg gaacggtcct cattcgagaa gaatcccatt gacttcctag aggcgaaggg   2760
ctacaaagag gtcaaaaagg acctaattat taagctcccc aagtattcac tcttcgaact   2820
tgaaaatggt cgtaagcgga tgttggcaag cgctggagag cttcagaagg ggaacgagct   2880
tgcactgcct tccaagtacg tgaacttcct gtacctcgcc tctcattacg agaagttgaa   2940
gggctcaccg gaggacaacg agcagaagca gttgttcgtg gagcagcaca gcactacct   3000 cgacgagatc attgagcaga taagtgagtt cagcaaacgg gtgatccttg ccgacgctaa   3060
cctggacaag gtgctgagcg cctacaacaa gcacagagac aagccgatcc gagagcaagc   3120
ggagaacatc atacacctgt tcaccctcac gaacctcggg gctcccgcag ccttcaaata   3180 tttttgacacg accatcgacc gtaaacgcta cactagcacg aaggaggtgc tggacgctac   3240
ccttatccac cagtccatca ccggcctgta cgagacgaga atcgacttgt cgcagctcgg   3300
tggtgac                                                            3307
```

<210> SEQ ID NO 73
<211> LENGTH: 4101
<212> TYPE: DNA
<213> ORGANISM: Artificial
<220> FEATURE:
<223> OTHER INFORMATION: Cas9

<400> SEQUENCE: 73

```
gacaaaaaat actcaattgg tctggcaatt gggaccaaca gtgtcggatg ggccgtgatt      60
accgacgagt acaaggtgcc gtccaaaaaa ttcaaggtgc ttgggaacac cgaccgccac     120
tcgatcaaga aaaacctaat cggtgcgttg cttttcgaca gtggggagac cgccgaggca     180
acacgcttaa aacgcacagc taggaggaga tatacacggc gcaagaaccg aatatgctac     240
ttacaggaga tattctccaa tgagatggcg aaggtggacg actctttctt ccatcggctt     300
gaggaatcct tcctggtcga ggaggacaag aagcacgagc gacacccgat attcgggaac     360
atcgttgatg aggtggcgta ccacgagaag tacccaacga tataccactt acgcaagaag     420
ctcgtggact ctacggacaa ggccgacttg cgccttatct acttggcact ggcccacatg     480
attaagttcc gaggccactt ccttatcgag ggtgacctga ccccgataa ctccgacgtg      540
gacaagctct tcatccaact cgtccagaca tacaaccagc tattcgagga aatcctatc     600
aacgcctctg gggtggacgc taaagctatc ctctcagccc gcctgtcaaa gtcgaggagg     660
ttggagaacc taatcgccca gcttccaggc gagaagaaaa atgggctgtt cggaaaccttt    720
atcgcactct cactgggcct aaccccgaac ttcaagtcca acttcgacct ggcagaggac     780
gcgaaattgc agttgtcgaa agacacctat gacgatgacc tggacaacct gttggcccag     840
ataggggacc agtacgccga cctgttccta gcggccaaga acctgtccga cgccatcttg     900
ctgtcggata tactgcgggt gaacaccgag atcactaaag cacctctctc cgccagcatg     960
attaagcgtt acgacgagca ccaccaagat ttgaccctgc taaaggcact tgtacggcag    1020
cagcttcccg agaagtacaa ggagatcttt ttcgaccaaa gcaagaacgg ctacgccggg    1080
tacatcgacg gaggtgccag ccaggaggag ttctacaagt tcattaagcc catcctggag    1140
aagatggacg ggactgagga actacttgtg aagctgaacc gggaagactt actacggaag    1200
cagcgtacct tcgacaacgg ttctatccca catcagatcc atcttgggga gttgcacgcg    1260
atcctgcgac gccaggagga cttttacccc ttcctgaaag acaaccgcga gaaaatcgag    1320
aagatactga ccttcagaat accttactac gtcggacccc ttgcgcgagg caactcaaga    1380
ttcgcgtgga tgaccaggaa atcagaggag accatcacac cctggaattt cgaggaggtg    1440
gttgacaagg gtgcctccgc ccagtccttt atcgaacgaa tgaccaactt cgacaagaac    1500
ttgcccaacg agaaggtgct cccccaaacac agcctcctct acgaatattt cacagtgtac    1560
aacgagctta ctaaagttaa gtatgttact gagggcatga ggaaacccgc cttcctgtca    1620
ggcgagcaga agaaagctat tgtggacctc cttttcaaga ccaaccggaa ggtgacagtg    1680
aagcagctca aggaggacta cttcaagaag atagagtgct tcgacagcgt ggagatcagc    1740
ggggtggagg acagattcaa tgcctctctc ggaacatacc acgacttgct taagatcatc    1800
aaggacaagg acttcctcga caacgaggaa aacgaggata ttctggagga tattgttctg    1860
actcttaccc tgttcgagga ccgggagatg atcgaggagc gtctcaagac ctacgcccac    1920
ctgttcgacg acaaagttat gaagcagctc aagcgtcgga gatataccgg atggggccgt    1980
ctgtctcgga agctcatcaa cgggatcagg gacaagcagt cagggaagac gatcttagac    2040
ttccttaagt ctgacggctt cgccaacagg aacttcatgc agttgatcca cgacgacagc    2100
cttaccttca aggaggacat ccagaaggcc caagtgagtg gccagggtga cagcctccac    2160
gagcatattg ctaatcttgc gggttcccca gcgattaaaa aggcatact tcaaaccgtt     2220
aaggtggtgg acgagcttgt caaggtgatg ggcgacaca agcccgagaa catcgtgatc     2280
gagatggcca gggagaacca gaccacccag aaggggcaga agaatagccg agaacgcatg    2340
```

```
aagcgcatcg aggagggat taaggagcta gggagccaga tcctcaagga acatcccgtc    2400
gagaacaccc agctccagaa cgagaagcta tacctctact acttgcaaaa cgggagggat    2460
atgtacgtgg atcaggagtt ggacattaac cgcctaagcg actacgacgt agatcacatc    2520
gtgcctcagt cattcctcaa agacgacagc attgacaaca aagtcttgac ccgatccgac    2580
aagaaccgag gaaaatccga caatgtgccc tcagaggagg tcgtcaagaa aatgaagaac    2640
tattggaggc agctacttaa cgccaaactc ataacccagc ggaagttcga caacctgaca    2700
aaggctgagc ggggtgggct cagcgagctt gacaaggctg gcttcatcaa gcggcagttg    2760
gtggagacaa gacagataac gaagcacgtg gctcagatcc tggactctcg catgaacacg    2820
aagtacgacg agaacgacaa attgatccgc gaggtcaagg ttattacgct caagagcaaa    2880
cttgtcagcg atttccgcaa ggacttccag ttctacaagg tgagggagat taacaactac    2940
caccatgcac atgatgccta cttgaacgca gtggtgggga ccgcgcttat taaaaagtac    3000
cctaagttgg agtcagagtt cgtttatggg gactacaagg tgtacgacgt ccggaagatg    3060
attgcaaagt ctgaacagga aatcgggaag gccaccgcca atatttctt ctacagtaac    3120
attatgaatt tttttaagac tgaaattact ctcgcaaacg gcgagatcag gaagcgtccc    3180
ctcatcgaga caaacgggga gaccggggag atagtctggg acaaggggcg ggacttcgct    3240
acggtgagga aggtgctctc gatgccacaa gtgaacatcg tcaaaaagac agaggtgcag    3300
accggtggct tctcaaagga gtcaatcctg ccaaaacgta acagcgacaa gctcatcgcc    3360
cgcaagaaag actgggaccc taagaagtat ggtgggttcg actcaccgac ggtcgcatac    3420
tccgttctgg tcgtggcaaa ggtggaaaag ggcaagtcca aaaaactgaa atccgtgaag    3480
gagttgcttg gcattaccat catggaacgc agcagcttcg agaagaaccc cattgacttc    3540
ctggaggcta aagggtacaa ggaggtcaag aaagatttaa ttattaagct acctaagtac    3600
agcttgttcg agctggagaa cggccgaaaa cgaatgctcg catccgccgg ggaacttcaa    3660
aagggcaacg agcttgcgct gccctccaag tacgtgaact tcctgtactt ggcatcccac    3720
tacgagaaac tcaagggtag cccagaggac aacgagcaga agcagctatt cgtggagcag    3780
cacaagcact acctcgacga gataatcgag cagatcagtg agttcagtaa gcgggtgata    3840
ctcgcggacg ccaacttgga caaggtgctt agtgcctaca acaagcaccg tgacaagccc    3900
atccgagaac aggctgagaa catcatccac ctttcactc tgacaaacct cggtgctccc    3960
gccgccttca aatacttcga cactaccatc gacaggaagc gctacacatc tacgaaggaa    4020
gttcttgacg ctacgcttat tcatcagtct atcacagggc tgtacgagac aaggatcgac    4080
cttagccaac tcggcgggga t                                             4101
```

<210> SEQ ID NO 74
<211> LENGTH: 1367
<212> TYPE: PRT
<213> ORGANISM: Artificial
<220> FEATURE:
<223> OTHER INFORMATION: nCas9

<400> SEQUENCE: 74

Asp Lys Lys Tyr Ser Ile Gly Leu Ala Ile Gly Thr Asn Ser Val Gly
1               5                   10                  15

Trp Ala Val Ile Thr Asp Glu Tyr Lys Val Pro Ser Lys Lys Phe Lys
            20                  25                  30

Val Leu Gly Asn Thr Asp Arg His Ser Ile Lys Lys Asn Leu Ile Gly
        35                  40                  45

```
Ala Leu Leu Phe Asp Ser Gly Glu Thr Ala Glu Ala Thr Arg Leu Lys
 50                  55                  60

Arg Thr Ala Arg Arg Tyr Thr Arg Arg Lys Asn Arg Ile Cys Tyr
 65                  70                  75                  80

Leu Gln Glu Ile Phe Ser Asn Glu Met Ala Lys Val Asp Asp Ser Phe
                     85                  90                  95

Phe His Arg Leu Glu Glu Ser Phe Leu Val Glu Glu Asp Lys Lys His
                100                 105                 110

Glu Arg His Pro Ile Phe Gly Asn Ile Val Asp Glu Val Ala Tyr His
                115                 120                 125

Glu Lys Tyr Pro Thr Ile Tyr His Leu Arg Lys Lys Leu Val Asp Ser
            130                 135                 140

Thr Asp Lys Ala Asp Leu Arg Leu Ile Tyr Leu Ala Leu Ala His Met
145                 150                 155                 160

Ile Lys Phe Arg Gly His Phe Leu Ile Glu Gly Asp Leu Asn Pro Asp
                165                 170                 175

Asn Ser Asp Val Asp Lys Leu Phe Ile Gln Leu Val Gln Thr Tyr Asn
                180                 185                 190

Gln Leu Phe Glu Glu Asn Pro Ile Asn Ala Ser Gly Val Asp Ala Lys
            195                 200                 205

Ala Ile Leu Ser Ala Arg Leu Ser Lys Ser Arg Arg Leu Glu Asn Leu
            210                 215                 220

Ile Ala Gln Leu Pro Gly Glu Lys Lys Asn Gly Leu Phe Gly Asn Leu
225                 230                 235                 240

Ile Ala Leu Ser Leu Gly Leu Thr Pro Asn Phe Lys Ser Asn Phe Asp
                245                 250                 255

Leu Ala Glu Asp Ala Lys Leu Gln Leu Ser Lys Asp Thr Tyr Asp Asp
                260                 265                 270

Asp Leu Asp Asn Leu Leu Ala Gln Ile Gly Asp Gln Tyr Ala Asp Leu
            275                 280                 285

Phe Leu Ala Ala Lys Asn Leu Ser Asp Ala Ile Leu Leu Ser Asp Ile
            290                 295                 300

Leu Arg Val Asn Thr Glu Ile Thr Lys Ala Pro Leu Ser Ala Ser Met
305                 310                 315                 320

Ile Lys Arg Tyr Asp Glu His His Gln Asp Leu Thr Leu Leu Lys Ala
                325                 330                 335

Leu Val Arg Gln Gln Leu Pro Glu Lys Tyr Lys Glu Ile Phe Phe Asp
                340                 345                 350

Gln Ser Lys Asn Gly Tyr Ala Gly Tyr Ile Asp Gly Gly Ala Ser Gln
            355                 360                 365

Glu Glu Phe Tyr Lys Phe Ile Lys Pro Ile Leu Glu Lys Met Asp Gly
            370                 375                 380

Thr Glu Glu Leu Leu Val Lys Leu Asn Arg Glu Asp Leu Leu Arg Lys
385                 390                 395                 400

Gln Arg Thr Phe Asp Asn Gly Ser Ile Pro His Gln Ile His Leu Gly
                405                 410                 415

Glu Leu His Ala Ile Leu Arg Arg Gln Glu Asp Phe Tyr Pro Phe Leu
                420                 425                 430

Lys Asp Asn Arg Glu Lys Ile Glu Lys Ile Leu Thr Phe Arg Ile Pro
                435                 440                 445

Tyr Tyr Val Gly Pro Leu Ala Arg Gly Asn Ser Arg Phe Ala Trp Met
        450                 455                 460
```

```
Thr Arg Lys Ser Glu Glu Thr Ile Thr Pro Trp Asn Phe Glu Glu Val
465                 470                 475                 480

Val Asp Lys Gly Ala Ser Ala Gln Ser Phe Ile Glu Arg Met Thr Asn
                485                 490                 495

Phe Asp Lys Asn Leu Pro Asn Glu Lys Val Leu Pro Lys His Ser Leu
            500                 505                 510

Leu Tyr Glu Tyr Phe Thr Val Tyr Asn Glu Leu Thr Lys Val Lys Tyr
        515                 520                 525

Val Thr Glu Gly Met Arg Lys Pro Ala Phe Leu Ser Gly Glu Gln Lys
    530                 535                 540

Lys Ala Ile Val Asp Leu Leu Phe Lys Thr Asn Arg Lys Val Thr Val
545                 550                 555                 560

Lys Gln Leu Lys Glu Asp Tyr Phe Lys Lys Ile Glu Cys Phe Asp Ser
                565                 570                 575

Val Glu Ile Ser Gly Val Glu Asp Arg Phe Asn Ala Ser Leu Gly Thr
            580                 585                 590

Tyr His Asp Leu Leu Lys Ile Ile Lys Asp Lys Asp Phe Leu Asp Asn
        595                 600                 605

Glu Glu Asn Glu Asp Ile Leu Glu Asp Ile Val Leu Thr Leu Thr Leu
    610                 615                 620

Phe Glu Asp Arg Glu Met Ile Glu Glu Arg Leu Lys Thr Tyr Ala His
625                 630                 635                 640

Leu Phe Asp Asp Lys Val Met Lys Gln Leu Lys Arg Arg Arg Tyr Thr
                645                 650                 655

Gly Trp Gly Arg Leu Ser Arg Lys Leu Ile Asn Gly Ile Arg Asp Lys
            660                 665                 670

Gln Ser Gly Lys Thr Ile Leu Asp Phe Leu Lys Ser Asp Gly Phe Ala
        675                 680                 685

Asn Arg Asn Phe Met Gln Leu Ile His Asp Asp Ser Leu Thr Phe Lys
    690                 695                 700

Glu Asp Ile Gln Lys Ala Gln Val Ser Gly Gln Gly Asp Ser Leu His
705                 710                 715                 720

Glu His Ile Ala Asn Leu Ala Gly Ser Pro Ala Ile Lys Lys Gly Ile
                725                 730                 735

Leu Gln Thr Val Lys Val Val Asp Glu Leu Val Lys Val Met Gly Arg
            740                 745                 750

His Lys Pro Glu Asn Ile Val Ile Glu Met Ala Arg Glu Asn Gln Thr
        755                 760                 765

Thr Gln Lys Gly Gln Lys Asn Ser Arg Glu Arg Met Lys Arg Ile Glu
    770                 775                 780

Glu Gly Ile Lys Glu Leu Gly Ser Gln Ile Leu Lys Glu His Pro Val
785                 790                 795                 800

Glu Asn Thr Gln Leu Gln Asn Glu Lys Leu Tyr Leu Tyr Tyr Leu Gln
                805                 810                 815

Asn Gly Arg Asp Met Tyr Val Asp Gln Glu Leu Asp Ile Asn Arg Leu
            820                 825                 830

Ser Asp Tyr Asp Val Asp His Ile Val Pro Gln Ser Phe Leu Lys Asp
        835                 840                 845

Asp Ser Ile Asp Asn Lys Val Leu Thr Arg Ser Asp Lys Asn Arg Gly
    850                 855                 860

Lys Ser Asp Asn Val Pro Ser Glu Glu Val Val Lys Lys Met Lys Asn
865                 870                 875                 880

Tyr Trp Arg Gln Leu Leu Asn Ala Lys Leu Ile Thr Gln Arg Lys Phe
```

-continued

```
                885                 890                 895
Asp Asn Leu Thr Lys Ala Glu Arg Gly Gly Leu Ser Glu Leu Asp Lys
                    900                 905                 910
Ala Gly Phe Ile Lys Arg Gln Leu Val Glu Thr Arg Gln Ile Thr Lys
                    915                 920                 925
His Val Ala Gln Ile Leu Asp Ser Arg Met Asn Thr Lys Tyr Asp Glu
                    930                 935                 940
Asn Asp Lys Leu Ile Arg Glu Val Lys Val Ile Thr Leu Lys Ser Lys
945                 950                 955                 960
Leu Val Ser Asp Phe Arg Lys Asp Phe Gln Phe Tyr Lys Val Arg Glu
                    965                 970                 975
Ile Asn Asn Tyr His His Ala His Asp Ala Tyr Leu Asn Ala Val Val
                    980                 985                 990
Gly Thr Ala Leu Ile Lys Lys Tyr Pro Lys Leu Glu Ser Glu Phe Val
                    995                 1000                1005
Tyr Gly Asp Tyr Lys Val Tyr Asp Val Arg Lys Met Ile Ala Lys
                    1010                1015                1020
Ser Glu Gln Glu Ile Gly Lys Ala Thr Ala Lys Tyr Phe Phe Tyr
                    1025                1030                1035
Ser Asn Ile Met Asn Phe Phe Lys Thr Glu Ile Thr Leu Ala Asn
                    1040                1045                1050
Gly Glu Ile Arg Lys Arg Pro Leu Ile Glu Thr Asn Gly Glu Thr
                    1055                1060                1065
Gly Glu Ile Val Trp Asp Lys Gly Arg Asp Phe Ala Thr Val Arg
                    1070                1075                1080
Lys Val Leu Ser Met Pro Gln Val Asn Ile Val Lys Lys Thr Glu
                    1085                1090                1095
Val Gln Thr Gly Gly Phe Ser Lys Glu Ser Ile Leu Pro Lys Arg
                    1100                1105                1110
Asn Ser Asp Lys Leu Ile Ala Arg Lys Lys Asp Trp Asp Pro Lys
                    1115                1120                1125
Lys Tyr Gly Gly Phe Asp Ser Pro Thr Val Ala Tyr Ser Val Leu
                    1130                1135                1140
Val Val Ala Lys Val Glu Lys Gly Lys Ser Lys Lys Leu Lys Ser
                    1145                1150                1155
Val Lys Glu Leu Leu Gly Ile Thr Ile Met Glu Arg Ser Ser Phe
                    1160                1165                1170
Glu Lys Asn Pro Ile Asp Phe Leu Glu Ala Lys Gly Tyr Lys Glu
                    1175                1180                1185
Val Lys Lys Asp Leu Ile Ile Lys Leu Pro Lys Tyr Ser Leu Phe
                    1190                1195                1200
Glu Leu Glu Asn Gly Arg Lys Arg Met Leu Ala Ser Ala Gly Glu
                    1205                1210                1215
Leu Gln Lys Gly Asn Glu Leu Ala Leu Pro Ser Lys Tyr Val Asn
                    1220                1225                1230
Phe Leu Tyr Leu Ala Ser His Tyr Glu Lys Leu Lys Gly Ser Pro
                    1235                1240                1245
Glu Asp Asn Glu Gln Lys Gln Leu Phe Val Glu Gln His Lys His
                    1250                1255                1260
Tyr Leu Asp Glu Ile Ile Glu Gln Ile Ser Glu Phe Ser Lys Arg
                    1265                1270                1275
Val Ile Leu Ala Asp Ala Asn Leu Asp Lys Val Leu Ser Ala Tyr
                    1280                1285                1290
```

Asn Lys His Arg Asp Lys Pro Ile Arg Glu Gln Ala Glu Asn Ile
            1295                1300                1305

Ile His Leu Phe Thr Leu Thr Asn Leu Gly Ala Pro Ala Ala Phe
            1310                1315                1320

Lys Tyr Phe Asp Thr Thr Ile Asp Arg Lys Arg Tyr Thr Ser Thr
            1325                1330                1335

Lys Glu Val Leu Asp Ala Thr Leu Ile His Gln Ser Ile Thr Gly
            1340                1345                1350

Leu Tyr Glu Thr Arg Ile Asp Leu Ser Gln Leu Gly Gly Asp
            1355                1360                1365

<210> SEQ ID NO 75
<211> LENGTH: 1367
<212> TYPE: PRT
<213> ORGANISM: Artificial
<220> FEATURE:
<223> OTHER INFORMATION: enCas9

<400> SEQUENCE: 75

Asp Lys Lys Tyr Ser Ile Gly Leu Ala Ile Gly Thr Asn Ser Val Gly
1               5                   10                  15

Trp Ala Val Ile Thr Asp Glu Tyr Lys Val Pro Ser Lys Lys Phe Lys
            20                  25                  30

Val Leu Gly Asn Thr Asp Arg His Ser Ile Lys Lys Asn Leu Ile Gly
            35                  40                  45

Ala Leu Leu Phe Asp Ser Gly Glu Thr Ala Glu Ala Thr Arg Leu Lys
        50                  55                  60

Arg Thr Ala Arg Arg Arg Tyr Thr Arg Arg Lys Asn Arg Ile Cys Tyr
65                  70                  75                  80

Leu Gln Glu Ile Phe Ser Asn Glu Met Ala Lys Val Asp Asp Ser Phe
                85                  90                  95

Phe His Arg Leu Glu Glu Ser Phe Leu Val Glu Glu Asp Lys Lys His
            100                 105                 110

Glu Arg His Pro Ile Phe Gly Asn Ile Val Asp Glu Val Ala Tyr His
        115                 120                 125

Glu Lys Tyr Pro Thr Ile Tyr His Leu Arg Lys Lys Leu Val Asp Ser
    130                 135                 140

Thr Asp Lys Ala Asp Leu Arg Leu Ile Tyr Leu Ala Leu Ala His Met
145                 150                 155                 160

Ile Lys Phe Arg Gly His Phe Leu Ile Glu Gly Asp Leu Asn Pro Asp
                165                 170                 175

Asn Ser Asp Val Asp Lys Leu Phe Ile Gln Leu Val Gln Thr Tyr Asn
            180                 185                 190

Gln Leu Phe Glu Glu Asn Pro Ile Asn Ala Ser Gly Val Asp Ala Lys
        195                 200                 205

Ala Ile Leu Ser Ala Arg Leu Ser Lys Ser Arg Arg Leu Glu Asn Leu
    210                 215                 220

Ile Ala Gln Leu Pro Gly Glu Lys Lys Asn Gly Leu Phe Gly Asn Leu
225                 230                 235                 240

Ile Ala Leu Ser Leu Gly Leu Thr Pro Asn Phe Lys Ser Asn Phe Asp
                245                 250                 255

Leu Ala Glu Asp Ala Lys Leu Gln Leu Ser Lys Asp Thr Tyr Asp Asp
            260                 265                 270

Asp Leu Asp Asn Leu Leu Ala Gln Ile Gly Asp Gln Tyr Ala Asp Leu
        275                 280                 285

```
Phe Leu Ala Ala Lys Asn Leu Ser Asp Ala Ile Leu Leu Ser Asp Ile
    290                 295                 300
Leu Arg Val Asn Thr Glu Ile Thr Lys Ala Pro Leu Ser Ala Ser Met
305                 310                 315                 320
Ile Lys Arg Tyr Asp Glu His His Gln Asp Leu Thr Leu Leu Lys Ala
                325                 330                 335
Leu Val Arg Gln Gln Leu Pro Glu Lys Tyr Lys Glu Ile Phe Phe Asp
                340                 345                 350
Gln Ser Lys Asn Gly Tyr Ala Gly Tyr Ile Asp Gly Gly Ala Ser Gln
            355                 360                 365
Glu Glu Phe Tyr Lys Phe Ile Lys Pro Ile Leu Glu Lys Met Asp Gly
        370                 375                 380
Thr Glu Leu Leu Val Lys Leu Asn Arg Glu Asp Leu Leu Arg Lys
385                 390                 395                 400
Gln Arg Thr Phe Asp Asn Gly Ser Ile Pro His Gln Ile His Leu Gly
                405                 410                 415
Glu Leu His Ala Ile Leu Arg Arg Gln Glu Asp Phe Tyr Pro Phe Leu
            420                 425                 430
Lys Asp Asn Arg Glu Lys Ile Glu Lys Ile Leu Thr Phe Arg Ile Pro
        435                 440                 445
Tyr Tyr Val Gly Pro Leu Ala Arg Gly Asn Ser Arg Phe Ala Trp Met
    450                 455                 460
Thr Arg Lys Ser Glu Glu Thr Ile Thr Pro Trp Asn Phe Glu Glu Val
465                 470                 475                 480
Val Asp Lys Gly Ala Ser Ala Gln Ser Phe Ile Glu Arg Met Thr Asn
                485                 490                 495
Phe Asp Lys Asn Leu Pro Asn Glu Lys Val Leu Pro Lys His Ser Leu
            500                 505                 510
Leu Tyr Glu Tyr Phe Thr Val Tyr Asn Glu Leu Thr Lys Val Lys Tyr
        515                 520                 525
Val Thr Glu Gly Met Arg Lys Pro Ala Phe Leu Ser Gly Glu Gln Lys
    530                 535                 540
Lys Ala Ile Val Asp Leu Leu Phe Lys Thr Asn Arg Lys Val Thr Val
545                 550                 555                 560
Lys Gln Leu Lys Glu Asp Tyr Phe Lys Lys Ile Glu Cys Phe Asp Ser
                565                 570                 575
Val Glu Ile Ser Gly Val Glu Asp Arg Phe Asn Ala Ser Leu Gly Thr
            580                 585                 590
Tyr His Asp Leu Leu Lys Ile Ile Lys Asp Lys Asp Phe Leu Asp Asn
        595                 600                 605
Glu Glu Asn Glu Asp Ile Leu Glu Asp Ile Val Leu Thr Leu Thr Leu
    610                 615                 620
Phe Glu Asp Arg Glu Met Ile Glu Glu Arg Leu Lys Thr Tyr Ala His
625                 630                 635                 640
Leu Phe Asp Asp Lys Val Met Lys Gln Leu Lys Arg Arg Arg Tyr Thr
                645                 650                 655
Gly Trp Gly Arg Leu Ser Arg Lys Leu Ile Asn Gly Ile Arg Asp Lys
            660                 665                 670
Gln Ser Gly Lys Thr Ile Leu Asp Phe Leu Lys Ser Asp Gly Phe Ala
        675                 680                 685
Asn Arg Asn Phe Met Gln Leu Ile His Asp Asp Ser Leu Thr Phe Lys
    690                 695                 700
```

```
Glu Asp Ile Gln Lys Ala Gln Val Ser Gly Gln Gly Asp Ser Leu His
705                 710                 715                 720
Glu His Ile Ala Asn Leu Ala Gly Ser Pro Ala Ile Lys Lys Gly Ile
                725                 730                 735
Leu Gln Thr Val Lys Val Val Asp Glu Leu Val Lys Val Met Gly Arg
            740                 745                 750
His Lys Pro Glu Asn Ile Val Ile Glu Met Ala Arg Glu Asn Gln Thr
        755                 760                 765
Thr Gln Lys Gly Gln Lys Asn Ser Arg Glu Arg Met Lys Arg Ile Glu
    770                 775                 780
Glu Gly Ile Lys Glu Leu Gly Ser Gln Ile Leu Lys Glu His Pro Val
785                 790                 795                 800
Glu Asn Thr Gln Leu Gln Asn Glu Lys Leu Tyr Leu Tyr Tyr Leu Gln
                805                 810                 815
Asn Gly Arg Asp Met Tyr Val Asp Gln Glu Leu Asp Ile Asn Arg Leu
            820                 825                 830
Ser Asp Tyr Asp Val Asp His Ile Val Pro Gln Ser Phe Leu Ala Asp
        835                 840                 845
Asp Ser Ile Asp Asn Lys Val Leu Thr Arg Ser Asp Lys Asn Arg Gly
    850                 855                 860
Lys Ser Asp Asn Val Pro Ser Glu Glu Val Val Lys Lys Met Lys Asn
865                 870                 875                 880
Tyr Trp Arg Gln Leu Leu Asn Ala Lys Leu Ile Thr Gln Arg Lys Phe
                885                 890                 895
Asp Asn Leu Thr Lys Ala Glu Arg Gly Gly Leu Ser Glu Leu Asp Lys
            900                 905                 910
Ala Gly Phe Ile Lys Arg Gln Leu Val Glu Thr Arg Gln Ile Thr Lys
        915                 920                 925
His Val Ala Gln Ile Leu Asp Ser Arg Met Asn Thr Lys Tyr Asp Glu
    930                 935                 940
Asn Asp Lys Leu Ile Arg Glu Val Lys Val Ile Thr Leu Lys Ser Lys
945                 950                 955                 960
Leu Val Ser Asp Phe Arg Lys Asp Phe Gln Phe Tyr Lys Val Arg Glu
                965                 970                 975
Ile Asn Asn Tyr His His Ala His Asp Ala Tyr Leu Asn Ala Val Val
            980                 985                 990
Gly Thr Ala Leu Ile Lys Lys Tyr Pro Ala Leu Glu Ser Glu Phe Val
        995                 1000                1005
Tyr Gly Asp Tyr Lys Val Tyr Asp Val Arg Lys Met Ile Ala Lys
    1010                1015                1020
Ser Glu Gln Glu Ile Gly Lys Ala Thr Ala Lys Tyr Phe Phe Tyr
    1025                1030                1035
Ser Asn Ile Met Asn Phe Phe Lys Thr Glu Ile Thr Leu Ala Asn
    1040                1045                1050
Gly Glu Ile Arg Lys Ala Pro Leu Ile Glu Thr Asn Gly Glu Thr
    1055                1060                1065
Gly Glu Ile Val Trp Asp Lys Gly Arg Asp Phe Ala Thr Val Arg
    1070                1075                1080
Lys Val Leu Ser Met Pro Gln Val Asn Ile Val Lys Lys Thr Glu
    1085                1090                1095
Val Gln Thr Gly Gly Phe Ser Lys Glu Ser Ile Leu Pro Lys Arg
    1100                1105                1110
Asn Ser Asp Lys Leu Ile Ala Arg Lys Lys Asp Trp Asp Pro Lys
```

```
                1115                1120                1125

Lys Tyr Gly Gly Phe Asp Ser Pro Thr Val Ala Tyr Ser Val Leu
            1130                1135                1140

Val Val Ala Lys Val Glu Lys Gly Lys Ser Lys Lys Leu Lys Ser
        1145                1150                1155

Val Lys Glu Leu Leu Gly Ile Thr Ile Met Glu Arg Ser Ser Phe
    1160                1165                1170

Glu Lys Asn Pro Ile Asp Phe Leu Glu Ala Lys Gly Tyr Lys Glu
1175                1180                1185

Val Lys Lys Asp Leu Ile Ile Lys Leu Pro Lys Tyr Ser Leu Phe
    1190                1195                1200

Glu Leu Glu Asn Gly Arg Lys Arg Met Leu Ala Ser Ala Gly Glu
    1205                1210                1215

Leu Gln Lys Gly Asn Glu Leu Ala Leu Pro Ser Lys Tyr Val Asn
    1220                1225                1230

Phe Leu Tyr Leu Ala Ser His Tyr Glu Lys Leu Lys Gly Ser Pro
    1235                1240                1245

Glu Asp Asn Glu Gln Lys Gln Leu Phe Val Glu Gln His Lys His
    1250                1255                1260

Tyr Leu Asp Glu Ile Ile Glu Gln Ile Ser Glu Phe Ser Lys Arg
    1265                1270                1275

Val Ile Leu Ala Asp Ala Asn Leu Asp Lys Val Leu Ser Ala Tyr
    1280                1285                1290

Asn Lys His Arg Asp Lys Pro Ile Arg Glu Gln Ala Glu Asn Ile
    1295                1300                1305

Ile His Leu Phe Thr Leu Thr Asn Leu Gly Ala Pro Ala Ala Phe
    1310                1315                1320

Lys Tyr Phe Asp Thr Thr Ile Asp Arg Lys Arg Tyr Thr Ser Thr
    1325                1330                1335

Lys Glu Val Leu Asp Ala Thr Leu Ile His Gln Ser Ile Thr Gly
    1340                1345                1350

Leu Tyr Glu Thr Arg Ile Asp Leu Ser Gln Leu Gly Gly Asp
    1355                1360                1365

<210> SEQ ID NO 76
<211> LENGTH: 228
<212> TYPE: PRT
<213> ORGANISM: Rattus norvegicus

<400> SEQUENCE: 76

Ser Ser Glu Thr Gly Pro Val Ala Val Asp Pro Thr Leu Arg Arg Arg
1               5                   10                  15

Ile Glu Pro His Glu Phe Glu Val Phe Phe Asp Pro Arg Glu Leu Arg
            20                  25                  30

Lys Glu Thr Cys Leu Leu Tyr Glu Ile Asn Trp Gly Gly Arg His Ser
        35                  40                  45

Ile Trp Arg His Thr Ser Gln Asn Thr Asn Lys His Val Glu Val Asn
    50                  55                  60

Phe Ile Glu Lys Phe Thr Thr Glu Arg Tyr Phe Cys Pro Asn Thr Arg
65                  70                  75                  80

Cys Ser Ile Thr Trp Phe Leu Ser Trp Ser Pro Cys Gly Glu Cys Ser
                85                  90                  95

Arg Ala Ile Thr Glu Phe Leu Ser Arg Tyr Pro His Val Thr Leu Phe
                100                 105                 110
```

```
Ile Tyr Ile Ala Arg Leu Tyr His Ala Asp Pro Arg Asn Arg Gln
        115                 120                 125

Gly Leu Arg Asp Leu Ile Ser Ser Gly Val Thr Ile Gln Ile Met Thr
    130                 135                 140

Glu Gln Glu Ser Gly Tyr Cys Trp Arg Asn Phe Val Asn Tyr Ser Pro
145                 150                 155                 160

Ser Asn Glu Ala His Trp Pro Arg Tyr Pro His Leu Trp Val Arg Leu
                165                 170                 175

Tyr Val Leu Glu Leu Tyr Cys Ile Ile Leu Gly Leu Pro Pro Cys Leu
            180                 185                 190

Asn Ile Leu Arg Arg Lys Gln Pro Gln Leu Thr Phe Phe Thr Ile Ala
        195                 200                 205

Leu Gln Ser Cys His Tyr Gln Arg Leu Pro Pro His Ile Leu Trp Ala
    210                 215                 220

Thr Gly Leu Lys
225

<210> SEQ ID NO 77
<211> LENGTH: 199
<212> TYPE: PRT
<213> ORGANISM: Homo sapiens

<400> SEQUENCE: 77

Met Glu Ala Ser Pro Ala Ser Gly Pro Arg His Leu Met Asp Pro His
1               5                   10                  15

Ile Phe Thr Ser Asn Phe Asn Asn Gly Ile Gly Arg His Lys Thr Tyr
            20                  25                  30

Leu Cys Tyr Glu Val Glu Arg Leu Asp Asn Gly Thr Ser Val Lys Met
        35                  40                  45

Asp Gln His Arg Gly Phe Leu His Asn Gln Ala Lys Asn Leu Leu Cys
    50                  55                  60

Gly Phe Tyr Gly Arg His Ala Glu Leu Arg Phe Leu Asp Leu Val Pro
65                  70                  75                  80

Ser Leu Gln Leu Asp Pro Ala Gln Ile Tyr Arg Val Thr Trp Phe Ile
                85                  90                  95

Ser Trp Ser Pro Cys Phe Ser Trp Gly Cys Ala Gly Glu Val Arg Ala
            100                 105                 110

Phe Leu Gln Glu Asn Thr His Val Arg Leu Arg Ile Phe Ala Ala Arg
        115                 120                 125

Ile Tyr Asp Tyr Asp Pro Leu Tyr Lys Glu Ala Leu Gln Met Leu Arg
    130                 135                 140

Asp Ala Gly Ala Gln Val Ser Ile Met Thr Tyr Asp Glu Phe Lys His
145                 150                 155                 160

Cys Trp Asp Thr Phe Val Asp His Gln Gly Cys Pro Phe Gln Pro Trp
                165                 170                 175

Asp Gly Leu Asp Glu His Ser Gln Ala Leu Ser Gly Arg Leu Arg Ala
            180                 185                 190

Ile Leu Gln Asn Gln Gly Asn
        195

<210> SEQ ID NO 78
<211> LENGTH: 621
<212> TYPE: DNA
<213> ORGANISM: Petromyzon marinus

<400> SEQUENCE: 78
```

```
acagatgcag agtatgtgag aattcacgaa aagctggaca tctataccct caagaagcag    60
ttctttaaca ataagaagtc tgtgagccat aggtgctacg tgctgttcga gctgaagaga   120
aggggtgaaa gaagggcatg tttttggggg tatgctgtga acaagcccca gtctggaact   180
gagagaggca ttcacgccga aattttcagc atcagaaagg tggaggaata cctgagggat   240
aaccctggac agtttacaat taattggtat tctagctggt ctccatgcgc tgactgtgcc   300
gagaagatcc tggaatggta caaccaggag ctgagaggaa atggccatac cctgaagatt   360
tgggcctgca agctgtacta tgaaaagaac gcaagaaatc agatcggact gtggaacctg   420
agggataatg gtgtggggct gaacgtgatg gtgtccgagc actatcagtg ctgtagaaag   480
attttcattc agtcctcaca taatcagctg aacgagaata gatggctgga aaagactctg   540
aagagggctg agaagagaag gtccgaactg tcaattatga tccaggtgaa gatcctgcac   600
accactaagt cacctgccgt g                                             621
```

<210> SEQ ID NO 79
<211> LENGTH: 160
<212> TYPE: PRT
<213> ORGANISM: Artificial
<220> FEATURE:
<223> OTHER INFORMATION: synthetic polypeptide

<400> SEQUENCE: 79

Phe Glu Arg Asn Tyr Asp Pro Arg Glu Leu Arg Lys Glu Thr Tyr Leu
1               5                   10                  15

Leu Tyr Glu Ile Lys Trp Gly Lys Ser Gly Lys Leu Trp Arg His Trp
            20                  25                  30

Cys Gln Asn Asn Arg Thr Gln His Ala Glu Val Tyr Phe Leu Glu Asn
        35                  40                  45

Ile Phe Asn Ala Arg Arg Phe Asn Pro Ser Thr His Cys Ser Ile Thr
    50                  55                  60

Trp Tyr Leu Ser Trp Ser Pro Cys Ala Glu Cys Ser Gln Lys Ile Val
65                  70                  75                  80

Asp Phe Leu Lys Glu His Pro Asn Val Leu Glu Ile Tyr Val Ala Arg
                85                  90                  95

Leu Tyr Tyr His Glu Asp Glu Arg Asn Arg Gln Gly Leu Arg Asp Leu
            100                 105                 110

Val Asn Ser Gly Val Thr Ile Arg Ile Met Asp Leu Pro Asp Tyr Asn
        115                 120                 125

Tyr Cys Trp Lys Thr Phe Val Ser Asp Gln Gly Gly Asp Glu Asp Tyr
    130                 135                 140

Trp Pro Gly His Phe Ala Pro Trp Ile Lys Gln Tyr Ser Leu Lys Leu
145                 150                 155                 160

<210> SEQ ID NO 80
<211> LENGTH: 229
<212> TYPE: PRT
<213> ORGANISM: Rattus norvegicus

<400> SEQUENCE: 80

Met Ser Ser Glu Thr Gly Pro Val Ala Val Asp Pro Thr Leu Arg Arg
1               5                   10                  15

Arg Ile Glu Pro His Glu Phe Glu Val Phe Phe Asp Pro Arg Glu Leu
            20                  25                  30

Arg Lys Glu Thr Cys Leu Leu Tyr Glu Ile Asn Trp Gly Gly Arg His
        35                  40                  45

```
Ser Ile Trp Arg His Thr Ser Gln Asn Thr Asn Lys His Val Glu Val
 50                  55                  60

Asn Phe Ile Glu Lys Phe Thr Thr Glu Arg Tyr Phe Cys Pro Asn Thr
 65                  70                  75                  80

Arg Cys Ser Ile Thr Trp Phe Leu Ser Trp Ser Pro Cys Gly Glu Cys
                 85                  90                  95

Ser Arg Ala Ile Thr Glu Phe Leu Ser Arg Tyr Pro His Val Thr Leu
                100                 105                 110

Phe Ile Tyr Ile Ala Arg Leu Tyr His His Ala Asp Pro Arg Asn Arg
            115                 120                 125

Gln Gly Leu Arg Asp Leu Ile Ser Ser Gly Val Thr Ile Gln Ile Met
130                 135                 140

Thr Glu Gln Glu Ser Gly Tyr Cys Trp Arg Asn Phe Val Asn Tyr Ser
145                 150                 155                 160

Pro Ser Asn Glu Ala His Trp Pro Arg Tyr Pro His Leu Trp Val Arg
                165                 170                 175

Leu Tyr Val Leu Glu Leu Tyr Cys Ile Ile Leu Gly Leu Pro Pro Cys
            180                 185                 190

Leu Asn Ile Leu Arg Arg Lys Gln Pro Gln Leu Thr Phe Phe Thr Ile
            195                 200                 205

Ala Leu Gln Ser Cys His Tyr Gln Arg Leu Pro Pro His Ile Leu Trp
210                 215                 220

Ala Thr Gly Leu Lys
225

<210> SEQ ID NO 81
<211> LENGTH: 198
<212> TYPE: PRT
<213> ORGANISM: Homo sapiens

<400> SEQUENCE: 81

Met Asp Ser Leu Leu Met Asn Arg Arg Lys Phe Leu Tyr Gln Phe Lys
1               5                  10                  15

Asn Val Arg Trp Ala Lys Gly Arg Arg Glu Thr Tyr Leu Cys Tyr Val
            20                  25                  30

Val Lys Arg Arg Asp Ser Ala Thr Ser Phe Ser Leu Asp Phe Gly Tyr
        35                  40                  45

Leu Arg Asn Lys Asn Gly Cys His Val Glu Leu Leu Phe Leu Arg Tyr
 50                 55                  60

Ile Ser Asp Trp Asp Leu Asp Pro Gly Arg Cys Tyr Arg Val Thr Trp
 65                 70                  75                  80

Phe Thr Ser Trp Ser Pro Cys Tyr Asp Cys Ala Arg His Val Ala Asp
                85                  90                  95

Phe Leu Arg Gly Asn Pro Asn Leu Ser Leu Arg Ile Phe Thr Ala Arg
                100                 105                 110

Leu Tyr Phe Cys Glu Asp Arg Lys Ala Glu Pro Glu Gly Leu Arg Arg
            115                 120                 125

Leu His Arg Ala Gly Val Gln Ile Ala Ile Met Thr Phe Lys Asp Tyr
130                 135                 140

Phe Tyr Cys Trp Asn Thr Phe Val Glu Asn His Glu Arg Thr Phe Lys
145                 150                 155                 160

Ala Trp Glu Gly Leu His Glu Asn Ser Val Arg Leu Ser Arg Gln Leu
                165                 170                 175

Arg Arg Ile Leu Leu Pro Leu Tyr Glu Val Asp Asp Leu Arg Asp Ala
            180                 185                 190
```

```
Phe Arg Thr Leu Gly Leu
        195

<210> SEQ ID NO 82
<211> LENGTH: 197
<212> TYPE: PRT
<213> ORGANISM: Artificial
<220> FEATURE:
<223> OTHER INFORMATION: hAID

<400> SEQUENCE: 82

Met Asp Ser Leu Leu Met Asn Arg Arg Glu Phe Leu Tyr Gln Phe Lys
1               5                   10                  15

Asn Val Arg Trp Ala Lys Gly Arg Arg Glu Thr Tyr Leu Cys Tyr Val
            20                  25                  30

Val Lys Arg Arg Asp Ser Ala Thr Ser Phe Ser Leu Asp Phe Gly Tyr
        35                  40                  45

Leu Arg Asn Lys Asn Gly Cys His Val Glu Leu Leu Phe Leu Arg Tyr
    50                  55                  60

Ile Ser Asp Trp Asp Leu Asp Pro Gly Arg Cys Tyr Arg Val Thr Trp
65                  70                  75                  80

Phe Ile Ser Trp Ser Pro Cys Tyr Asp Cys Ala Arg His Val Ala Asp
                85                  90                  95

Phe Leu Arg Gly Asn Pro Asn Leu Ser Leu Arg Ile Phe Thr Ala Arg
            100                 105                 110

Leu Tyr Phe Cys Glu Asp Arg Lys Ala Glu Pro Glu Gly Leu Arg Arg
        115                 120                 125

Leu His Arg Ala Gly Val Gln Ile Ala Ile Met Thr Phe Lys Asp Tyr
    130                 135                 140

Phe Tyr Cys Trp Asn Thr Phe Val Glu Asn His Gly Arg Thr Phe Lys
145                 150                 155                 160

Ala Trp Glu Gly Leu His Glu Asn Ser Val Arg Leu Ser Arg Gln Leu
                165                 170                 175

Arg Arg Ile Leu Leu Pro Leu Tyr Glu Val Asp Asp Leu Arg Asp Ala
            180                 185                 190

Phe Arg Thr Cys Thr
        195

<210> SEQ ID NO 83
<211> LENGTH: 207
<212> TYPE: PRT
<213> ORGANISM: Artificial
<220> FEATURE:
<223> OTHER INFORMATION: evoCDA1

<400> SEQUENCE: 83

Thr Asp Ala Glu Tyr Val Arg Ile His Glu Lys Leu Asp Ile Tyr Thr
1               5                   10                  15

Phe Lys Lys Gln Phe Ser Asn Asn Lys Lys Ser Val Ser His Arg Cys
            20                  25                  30

Tyr Val Leu Phe Glu Leu Lys Arg Arg Gly Glu Arg Arg Ala Cys Phe
        35                  40                  45

Trp Gly Tyr Ala Val Asn Lys Pro Gln Ser Gly Thr Glu Arg Gly Ile
    50                  55                  60

His Ala Glu Ile Phe Ser Ile Arg Lys Val Glu Glu Tyr Leu Arg Asp
65                  70                  75                  80

Asn Pro Gly Gln Phe Thr Ile Asn Trp Tyr Ser Ser Trp Ser Pro Cys
```

```
                        85                  90                  95
Ala Asp Cys Ala Glu Lys Ile Leu Glu Trp Tyr Asn Gln Glu Leu Arg
                    100                 105                 110

Gly Asn Gly His Thr Leu Lys Ile Trp Val Cys Lys Leu Tyr Tyr Glu
                115                 120                 125

Lys Asn Ala Arg Asn Gln Ile Gly Leu Trp Asn Leu Arg Asp Asn Gly
            130                 135                 140

Val Gly Leu Asn Val Met Val Ser Glu His Tyr Gln Cys Cys Arg Lys
145                 150                 155                 160

Ile Phe Ile Gln Ser Ser His Asn Gln Leu Asn Glu Asn Arg Trp Leu
                165                 170                 175

Glu Lys Thr Leu Lys Arg Ala Glu Lys Arg Arg Ser Glu Leu Ser Ile
                180                 185                 190

Met Phe Gln Val Lys Ile Leu His Thr Thr Lys Ser Pro Ala Val
                195                 200                 205

<210> SEQ ID NO 84
<211> LENGTH: 228
<212> TYPE: PRT
<213> ORGANISM: Artificial
<220> FEATURE:
<223> OTHER INFORMATION: EvoAPOBEC1

<400> SEQUENCE: 84

Ser Ser Lys Thr Gly Pro Val Ala Val Asp Pro Thr Leu Arg Arg Arg
1               5                   10                  15

Ile Glu Pro His Glu Phe Glu Val Phe Phe Asp Pro Arg Glu Leu Arg
                20                  25                  30

Lys Glu Thr Cys Leu Leu Tyr Glu Ile Asn Trp Gly Gly Arg His Ser
            35                  40                  45

Ile Trp Arg His Thr Ser Gln Asn Thr Asn Lys His Val Glu Val Asn
50                  55                  60

Phe Ile Glu Lys Phe Thr Thr Glu Arg Tyr Phe Cys Pro Asn Thr Arg
65                  70                  75                  80

Cys Ser Ile Thr Trp Phe Leu Ser Trp Ser Pro Cys Gly Glu Cys Ser
                85                  90                  95

Arg Ala Ile Thr Glu Phe Leu Ser Arg Tyr Pro Asn Val Thr Leu Phe
                100                 105                 110

Ile Tyr Ile Ala Arg Leu Tyr His Leu Ala Asn Pro Arg Asn Arg Gln
                115                 120                 125

Gly Leu Arg Asp Leu Ile Ser Ser Gly Val Thr Ile Gln Ile Met Thr
            130                 135                 140

Glu Gln Glu Ser Gly Tyr Cys Trp His Asn Phe Val Asn Tyr Ser Pro
145                 150                 155                 160

Ser Asn Glu Ser His Trp Pro Arg Tyr Pro His Leu Trp Val Arg Leu
                165                 170                 175

Tyr Val Leu Glu Leu Tyr Cys Ile Ile Leu Gly Leu Pro Pro Cys Leu
                180                 185                 190

Asn Ile Leu Arg Arg Lys Gln Ser Gln Leu Thr Ser Phe Thr Ile Ala
                195                 200                 205

Leu Gln Ser Cys His Tyr Gln Arg Leu Pro Pro His Ile Leu Trp Ala
            210                 215                 220

Thr Gly Leu Lys
225
```

-continued

```
<210> SEQ ID NO 85
<211> LENGTH: 162
<212> TYPE: PRT
<213> ORGANISM: Artificial
<220> FEATURE:
<223> OTHER INFORMATION: EvoFERNY

<400> SEQUENCE: 85

Ser Phe Glu Arg Asn Tyr Asp Pro Arg Glu Leu Arg Lys Glu Thr Tyr
1               5                   10                  15

Leu Leu Tyr Glu Ile Lys Trp Gly Lys Ser Gly Lys Leu Trp Arg His
                20                  25                  30

Trp Cys Gln Asn Asn Arg Thr Gln His Ala Glu Val Tyr Phe Leu Glu
            35                  40                  45

Asn Ile Phe Asn Ala Arg Arg Phe Asn Pro Ser Thr His Cys Ser Ile
        50                  55                  60

Thr Trp Tyr Leu Ser Trp Ser Pro Cys Ala Glu Cys Ser Gln Lys Ile
65                  70                  75                  80

Val Asp Phe Leu Lys Glu His Pro Asn Val Asn Leu Glu Ile Tyr Val
                85                  90                  95

Ala Arg Leu Tyr Tyr Pro Glu Asn Glu Arg Asn Arg Gln Gly Leu Arg
                100                 105                 110

Asp Leu Val Asn Ser Gly Val Thr Ile Arg Ile Met Asp Leu Pro Asp
            115                 120                 125

Tyr Asn Tyr Cys Trp Lys Thr Phe Val Ser Asp Gln Gly Gly Asp Glu
        130                 135                 140

Asp Tyr Trp Pro Gly His Phe Ala Pro Trp Ile Lys Gln Tyr Ser Leu
145                 150                 155                 160

Lys Leu

<210> SEQ ID NO 86
<211> LENGTH: 166
<212> TYPE: PRT
<213> ORGANISM: Escherichia coli

<400> SEQUENCE: 86

Ser Glu Val Glu Phe Ser His Glu Tyr Trp Met Arg His Ala Leu Thr
1               5                   10                  15

Leu Ala Lys Arg Ala Trp Asp Glu Arg Glu Val Pro Val Gly Ala Val
                20                  25                  30

Leu Val His Asn Asn Arg Val Ile Gly Glu Gly Trp Asn Arg Pro Ile
            35                  40                  45

Gly Arg His Asp Pro Thr Ala His Ala Glu Ile Met Ala Leu Arg Gln
        50                  55                  60

Gly Gly Leu Val Met Gln Asn Tyr Arg Leu Ile Asp Ala Thr Leu Tyr
65                  70                  75                  80

Val Thr Leu Glu Pro Cys Val Met Cys Ala Gly Ala Met Ile His Ser
                85                  90                  95

Arg Ile Gly Arg Val Val Phe Gly Ala Arg Asp Ala Lys Thr Gly Ala
                100                 105                 110

Ala Gly Ser Leu Met Asp Val Leu His His Pro Gly Met Asn His Arg
            115                 120                 125

Val Glu Ile Thr Glu Gly Ile Leu Ala Asp Glu Cys Ala Ala Leu Leu
        130                 135                 140

Ser Asp Phe Phe Arg Met Arg Arg Gln Glu Ile Lys Ala Gln Lys Lys
145                 150                 155                 160
```

Ala Gln Ser Ser Thr Asp
            165

<210> SEQ ID NO 87
<211> LENGTH: 166
<212> TYPE: PRT
<213> ORGANISM: Artificial
<220> FEATURE:
<223> OTHER INFORMATION: tRNA-specific adenosine deaminase

<400> SEQUENCE: 87

Ser Glu Val Glu Phe Ser His Glu Tyr Trp Met Arg His Ala Leu Thr
1               5                   10                  15

Leu Ala Lys Arg Ala Arg Asp Glu Arg Glu Val Pro Val Gly Ala Val
            20                  25                  30

Leu Val Leu Asn Asn Arg Val Ile Gly Glu Gly Trp Asn Arg Ala Ile
        35                  40                  45

Gly Leu His Asp Pro Thr Ala His Ala Glu Ile Met Ala Leu Arg Gln
    50                  55                  60

Gly Gly Leu Val Met Gln Asn Tyr Arg Leu Ile Asp Ala Thr Leu Tyr
65                  70                  75                  80

Val Thr Phe Glu Pro Cys Val Met Cys Ala Gly Ala Met Ile His Ser
                85                  90                  95

Arg Ile Gly Arg Val Val Phe Gly Val Arg Asn Ala Lys Thr Gly Ala
            100                 105                 110

Ala Gly Ser Leu Met Asp Val Leu His Tyr Pro Gly Met Asn His Arg
        115                 120                 125

Val Glu Ile Thr Glu Gly Ile Leu Ala Asp Glu Cys Ala Ala Leu Leu
    130                 135                 140

Cys Tyr Phe Phe Arg Met Pro Arg Gln Val Phe Asn Ala Gln Lys Lys
145                 150                 155                 160

Ala Gln Ser Ser Thr Asp
            165

<210> SEQ ID NO 88
<211> LENGTH: 166
<212> TYPE: PRT
<213> ORGANISM: Artificial
<220> FEATURE:
<223> OTHER INFORMATION: tRNA-specific adenosine deaminase

<400> SEQUENCE: 88

Ser Glu Val Glu Phe Ser His Glu Tyr Trp Met Arg His Ala Leu Thr
1               5                   10                  15

Leu Ala Lys Arg Ala Trp Asp Glu Arg Glu Val Pro Val Gly Ala Val
            20                  25                  30

Leu Val Leu Asn Asn Arg Val Ile Gly Glu Gly Trp Asn Arg Ser Ile
        35                  40                  45

Gly Leu His Asp Pro Thr Ala His Ala Glu Ile Met Ala Leu Arg Gln
    50                  55                  60

Gly Gly Leu Val Met Gln Asn Tyr Arg Leu Ile Asp Ala Thr Leu Tyr
65                  70                  75                  80

Val Thr Phe Glu Pro Cys Val Met Cys Ala Gly Ala Met Ile His Ser
                85                  90                  95

Arg Ile Gly Arg Val Val Phe Gly Val Arg Asn Ala Lys Thr Gly Ala
            100                 105                 110

Ala Gly Ser Leu Met Asp Val Leu His Tyr Pro Gly Met Asn His Arg
        115                 120                 125

```
Val Glu Ile Thr Glu Gly Ile Leu Ala Asp Glu Cys Ala Ala Leu Leu
    130                 135                 140

Cys Tyr Phe Phe Arg Met Arg Arg Gln Val Phe Asn Ala Gln Lys Lys
145                 150                 155                 160

Ala Gln Ser Ser Thr Asp
                165

<210> SEQ ID NO 89
<211> LENGTH: 166
<212> TYPE: PRT
<213> ORGANISM: Artificial
<220> FEATURE:
<223> OTHER INFORMATION: tRNA-specific adenosine deaminase

<400> SEQUENCE: 89

Ser Glu Val Glu Phe Ser His Glu Tyr Trp Met Arg His Ala Leu Thr
1               5                   10                  15

Leu Ala Lys Arg Ala Leu Asp Glu Arg Glu Val Pro Val Gly Ala Val
            20                  25                  30

Leu Val Leu Asn Asn Arg Val Ile Gly Glu Gly Trp Asn Arg Ala Ile
        35                  40                  45

Gly Leu His Asp Pro Thr Ala His Ala Glu Ile Met Ala Leu Arg Gln
    50                  55                  60

Gly Gly Leu Val Met Gln Asn Tyr Arg Leu Ile Asp Ala Thr Leu Tyr
65                  70                  75                  80

Val Thr Phe Glu Pro Cys Val Met Cys Ala Gly Ala Met Ile His Ser
                85                  90                  95

Arg Ile Gly Arg Val Val Phe Gly Val Arg Asn Ala Lys Thr Gly Ala
            100                 105                 110

Ala Gly Ser Leu Met Asp Val Leu His Tyr Pro Gly Met Asn His Arg
        115                 120                 125

Val Glu Ile Thr Glu Gly Ile Leu Ala Asp Glu Cys Asn Ala Leu Leu
    130                 135                 140

Cys Tyr Phe Phe Arg Met Arg Arg Gln Val Phe Asn Ala Gln Lys Lys
145                 150                 155                 160

Ala Gln Ser Ser Thr Asp
                165

<210> SEQ ID NO 90
<211> LENGTH: 166
<212> TYPE: PRT
<213> ORGANISM: Artificial
<220> FEATURE:
<223> OTHER INFORMATION: tRNA-specific adenosine deaminase

<400> SEQUENCE: 90

Ser Glu Val Glu Phe Ser His Glu Tyr Trp Met Arg His Ala Leu Thr
1               5                   10                  15

Leu Ala Lys Arg Ala Leu Asp Glu Arg Glu Val Pro Val Gly Ala Val
            20                  25                  30

Leu Val Leu Asn Asn Arg Val Ile Gly Glu Gly Trp Asn Arg Ala Ile
        35                  40                  45

Gly Leu His Asp Pro Thr Ala His Ala Glu Ile Met Ala Leu Arg Gln
    50                  55                  60

Gly Gly Leu Val Met Gln Asn Tyr Arg Leu Ile Asp Ala Thr Leu Tyr
65                  70                  75                  80

Val Thr Phe Glu Pro Cys Val Met Cys Ala Gly Ala Met Ile His Ser
```

-continued

```
                85                   90                   95
Arg Ile Gly Arg Val Val Phe Gly Val Arg Asn Ala Lys Thr Gly Ala
                100                 105                 110

Ala Gly Ser Leu Met Asp Val Leu His Tyr Pro Gly Met Asn His Arg
                115                 120                 125

Val Glu Ile Thr Glu Gly Ile Leu Ala Asp Glu Cys Asn Ala Leu Leu
                130                 135                 140

Cys Tyr Phe Phe Arg Met Pro Arg Gln Val Phe Asn Ala Gln Lys Lys
145                 150                 155                 160

Ala Gln Ser Ser Thr Asp
                165

<210> SEQ ID NO 91
<211> LENGTH: 1763
<212> TYPE: PRT
<213> ORGANISM: Unknown
<220> FEATURE:
<223> OTHER INFORMATION: ABE7.10

<400> SEQUENCE: 91

Ser Glu Val Glu Phe Ser His Glu Tyr Trp Met Arg His Ala Leu Thr
1               5                   10                  15

Leu Ala Lys Arg Ala Trp Asp Glu Arg Glu Val Pro Val Gly Ala Val
                20                  25                  30

Leu Val His Asn Asn Arg Val Ile Gly Glu Gly Trp Asn Arg Pro Ile
                35                  40                  45

Gly Arg His Asp Pro Thr Ala His Ala Glu Ile Met Ala Leu Arg Gln
                50                  55                  60

Gly Gly Leu Val Met Gln Asn Tyr Arg Leu Ile Asp Ala Thr Leu Tyr
65              70                  75                  80

Val Thr Leu Glu Pro Cys Val Met Cys Ala Gly Ala Met Ile His Ser
                85                  90                  95

Arg Ile Gly Arg Val Val Phe Gly Ala Arg Asp Ala Lys Thr Gly Ala
                100                 105                 110

Ala Gly Ser Leu Met Asp Val Leu His His Pro Gly Met Asn His Arg
                115                 120                 125

Val Glu Ile Thr Glu Gly Ile Leu Ala Asp Glu Cys Ala Ala Leu Leu
                130                 135                 140

Ser Asp Phe Phe Arg Met Arg Arg Gln Glu Ile Lys Ala Gln Lys Lys
145                 150                 155                 160

Ala Gln Ser Ser Thr Asp Ser Gly Gly Ser Ser Gly Gly Ser Ser Gly
                165                 170                 175

Ser Glu Thr Pro Gly Thr Ser Glu Ser Ala Thr Pro Glu Ser Ser Gly
                180                 185                 190

Gly Ser Ser Gly Gly Ser Ser Glu Val Glu Phe Ser His Glu Tyr Trp
                195                 200                 205

Met Arg His Ala Leu Thr Leu Ala Lys Arg Ala Arg Asp Glu Arg Glu
                210                 215                 220

Val Pro Val Gly Ala Val Leu Val Leu Asn Asn Arg Val Ile Gly Glu
225                 230                 235                 240

Gly Trp Asn Arg Ala Ile Gly Leu His Asp Pro Thr Ala His Ala Glu
                245                 250                 255

Ile Met Ala Leu Arg Gln Gly Gly Leu Val Met Gln Asn Tyr Arg Leu
                260                 265                 270

Ile Asp Ala Thr Leu Tyr Val Thr Phe Glu Pro Cys Val Met Cys Ala
```

```
            275                 280                 285
    Gly Ala Met Ile His Ser Arg Ile Gly Arg Val Val Phe Gly Val Arg
        290                 295                 300
    Asn Ala Lys Thr Gly Ala Ala Gly Ser Leu Met Asp Val Leu His Tyr
    305                 310                 315                 320
    Pro Gly Met Asn His Arg Val Glu Ile Thr Glu Gly Ile Leu Ala Asp
                    325                 330                 335
    Glu Cys Ala Ala Leu Leu Cys Tyr Phe Phe Arg Met Pro Arg Gln Val
                340                 345                 350
    Phe Asn Ala Gln Lys Lys Ala Gln Ser Ser Thr Asp Ser Gly Gly Ser
            355                 360                 365
    Ser Gly Gly Ser Ser Gly Ser Glu Thr Pro Gly Thr Ser Glu Ser Ala
        370                 375                 380
    Thr Pro Glu Ser Ser Gly Gly Ser Ser Gly Ser Asp Lys Lys Tyr
    385                 390                 395                 400
    Ser Ile Gly Leu Ala Ile Gly Thr Asn Ser Val Gly Trp Ala Val Ile
                    405                 410                 415
    Thr Asp Glu Tyr Lys Val Pro Ser Lys Lys Phe Lys Val Leu Gly Asn
                420                 425                 430
    Thr Asp Arg His Ser Ile Lys Lys Asn Leu Ile Gly Ala Leu Leu Phe
            435                 440                 445
    Asp Ser Gly Glu Thr Ala Glu Ala Thr Arg Leu Lys Arg Thr Ala Arg
        450                 455                 460
    Arg Arg Tyr Thr Arg Arg Lys Asn Arg Ile Cys Tyr Leu Gln Glu Ile
    465                 470                 475                 480
    Phe Ser Asn Glu Met Ala Lys Val Asp Asp Ser Phe Phe His Arg Leu
                    485                 490                 495
    Glu Glu Ser Phe Leu Val Glu Glu Asp Lys Lys His Glu Arg His Pro
                500                 505                 510
    Ile Phe Gly Asn Ile Val Asp Glu Val Ala Tyr His Glu Lys Tyr Pro
            515                 520                 525
    Thr Ile Tyr His Leu Arg Lys Lys Leu Val Asp Ser Thr Asp Lys Ala
        530                 535                 540
    Asp Leu Arg Leu Ile Tyr Leu Ala Leu Ala His Met Ile Lys Phe Arg
    545                 550                 555                 560
    Gly His Phe Leu Ile Glu Gly Asp Leu Asn Pro Asp Asn Ser Asp Val
                    565                 570                 575
    Asp Lys Leu Phe Ile Gln Leu Val Gln Thr Tyr Asn Gln Leu Phe Glu
                580                 585                 590
    Glu Asn Pro Ile Asn Ala Ser Gly Val Asp Ala Lys Ala Ile Leu Ser
            595                 600                 605
    Ala Arg Leu Ser Lys Ser Arg Arg Leu Glu Asn Leu Ile Ala Gln Leu
        610                 615                 620
    Pro Gly Glu Lys Lys Asn Gly Leu Phe Gly Asn Leu Ile Ala Leu Ser
    625                 630                 635                 640
    Leu Gly Leu Thr Pro Asn Phe Lys Ser Asn Phe Asp Leu Ala Glu Asp
                    645                 650                 655
    Ala Lys Leu Gln Leu Ser Lys Asp Thr Tyr Asp Asp Asp Leu Asp Asn
                660                 665                 670
    Leu Leu Ala Gln Ile Gly Asp Gln Tyr Ala Asp Leu Phe Leu Ala Ala
            675                 680                 685
    Lys Asn Leu Ser Asp Ala Ile Leu Leu Ser Asp Ile Leu Arg Val Asn
        690                 695                 700
```

-continued

```
Thr Glu Ile Thr Lys Ala Pro Leu Ser Ala Ser Met Ile Lys Arg Tyr
705                 710                 715                 720

Asp Glu His His Gln Asp Leu Thr Leu Leu Lys Ala Leu Val Arg Gln
                725                 730                 735

Gln Leu Pro Glu Lys Tyr Lys Glu Ile Phe Phe Asp Gln Ser Lys Asn
            740                 745                 750

Gly Tyr Ala Gly Tyr Ile Asp Gly Gly Ala Ser Gln Glu Glu Phe Tyr
        755                 760                 765

Lys Phe Ile Lys Pro Ile Leu Glu Lys Met Asp Gly Thr Glu Glu Leu
    770                 775                 780

Leu Val Lys Leu Asn Arg Glu Asp Leu Leu Arg Lys Gln Arg Thr Phe
785                 790                 795                 800

Asp Asn Gly Ser Ile Pro His Gln Ile His Leu Gly Glu Leu His Ala
                805                 810                 815

Ile Leu Arg Arg Gln Glu Asp Phe Tyr Pro Phe Leu Lys Asp Asn Arg
            820                 825                 830

Glu Lys Ile Glu Lys Ile Leu Thr Phe Arg Ile Pro Tyr Tyr Val Gly
        835                 840                 845

Pro Leu Ala Arg Gly Asn Ser Arg Phe Ala Trp Met Thr Arg Lys Ser
    850                 855                 860

Glu Glu Thr Ile Thr Pro Trp Asn Phe Glu Glu Val Val Asp Lys Gly
865                 870                 875                 880

Ala Ser Ala Gln Ser Phe Ile Glu Arg Met Thr Asn Phe Asp Lys Asn
                885                 890                 895

Leu Pro Asn Glu Lys Val Leu Pro Lys His Ser Leu Leu Tyr Glu Tyr
            900                 905                 910

Phe Thr Val Tyr Asn Glu Leu Thr Lys Val Lys Tyr Val Thr Glu Gly
        915                 920                 925

Met Arg Lys Pro Ala Phe Leu Ser Gly Glu Gln Lys Lys Ala Ile Val
    930                 935                 940

Asp Leu Leu Phe Lys Thr Asn Arg Lys Val Thr Val Lys Gln Leu Lys
945                 950                 955                 960

Glu Asp Tyr Phe Lys Lys Ile Glu Cys Phe Asp Ser Val Glu Ile Ser
                965                 970                 975

Gly Val Glu Asp Arg Phe Asn Ala Ser Leu Gly Thr Tyr His Asp Leu
            980                 985                 990

Leu Lys Ile Ile Lys Asp Lys Asp  Phe Leu Asp Asn Glu  Glu Asn Glu
        995                 1000                1005

Asp Ile  Leu Glu Asp Ile Val  Leu Thr Leu Thr Leu  Phe Glu Asp
    1010                1015                1020

Arg Glu  Met Ile Glu Glu Arg  Leu Lys Thr Tyr Ala  His Leu Phe
    1025                1030                1035

Asp Asp  Lys Val Met Lys Gln  Leu Lys Arg Arg Arg  Tyr Thr Gly
    1040                1045                1050

Trp Gly  Arg Leu Ser Arg Lys  Leu Ile Asn Gly Ile  Arg Asp Lys
    1055                1060                1065

Gln Ser  Gly Lys Thr Ile Leu  Asp Phe Leu Lys Ser  Asp Gly Phe
    1070                1075                1080

Ala Asn  Arg Asn Phe Met Gln  Leu Ile His Asp Asp  Ser Leu Thr
    1085                1090                1095

Phe Lys  Glu Asp Ile Gln Lys  Ala Gln Val Ser Gly  Gln Gly Asp
    1100                1105                1110
```

```
Ser Leu His Glu His Ile Ala Asn Leu Ala Gly Ser Pro Ala Ile
1115                1120                1125

Lys Lys Gly Ile Leu Gln Thr Val Lys Val Val Asp Glu Leu Val
1130                1135                1140

Lys Val Met Gly Arg His Lys Pro Glu Asn Ile Val Ile Glu Met
1145                1150                1155

Ala Arg Glu Asn Gln Thr Thr Gln Lys Gly Gln Lys Asn Ser Arg
1160                1165                1170

Glu Arg Met Lys Arg Ile Glu Glu Gly Ile Lys Glu Leu Gly Ser
1175                1180                1185

Gln Ile Leu Lys Glu His Pro Val Glu Asn Thr Gln Leu Gln Asn
1190                1195                1200

Glu Lys Leu Tyr Leu Tyr Tyr Leu Gln Asn Gly Arg Asp Met Tyr
1205                1210                1215

Val Asp Gln Glu Leu Asp Ile Asn Arg Leu Ser Asp Tyr Asp Val
1220                1225                1230

Asp His Ile Val Pro Gln Ser Phe Leu Lys Asp Asp Ser Ile Asp
1235                1240                1245

Asn Lys Val Leu Thr Arg Ser Asp Lys Asn Arg Gly Lys Ser Asp
1250                1255                1260

Asn Val Pro Ser Glu Glu Val Val Lys Lys Met Lys Asn Tyr Trp
1265                1270                1275

Arg Gln Leu Leu Asn Ala Lys Leu Ile Thr Gln Arg Lys Phe Asp
1280                1285                1290

Asn Leu Thr Lys Ala Glu Arg Gly Gly Leu Ser Glu Leu Asp Lys
1295                1300                1305

Ala Gly Phe Ile Lys Arg Gln Leu Val Glu Thr Arg Gln Ile Thr
1310                1315                1320

Lys His Val Ala Gln Ile Leu Asp Ser Arg Met Asn Thr Lys Tyr
1325                1330                1335

Asp Glu Asn Asp Lys Leu Ile Arg Glu Val Lys Val Ile Thr Leu
1340                1345                1350

Lys Ser Lys Leu Val Ser Asp Phe Arg Lys Asp Phe Gln Phe Tyr
1355                1360                1365

Lys Val Arg Glu Ile Asn Asn Tyr His His Ala His Asp Ala Tyr
1370                1375                1380

Leu Asn Ala Val Val Gly Thr Ala Leu Ile Lys Lys Tyr Pro Lys
1385                1390                1395

Leu Glu Ser Glu Phe Val Tyr Gly Asp Tyr Lys Val Tyr Asp Val
1400                1405                1410

Arg Lys Met Ile Ala Lys Ser Glu Gln Glu Ile Gly Lys Ala Thr
1415                1420                1425

Ala Lys Tyr Phe Phe Tyr Ser Asn Ile Met Asn Phe Phe Lys Thr
1430                1435                1440

Glu Ile Thr Leu Ala Asn Gly Glu Ile Arg Lys Arg Pro Leu Ile
1445                1450                1455

Glu Thr Asn Gly Glu Thr Gly Glu Ile Val Trp Asp Lys Gly Arg
1460                1465                1470

Asp Phe Ala Thr Val Arg Lys Val Leu Ser Met Pro Gln Val Asn
1475                1480                1485

Ile Val Lys Lys Thr Glu Val Gln Thr Gly Gly Phe Ser Lys Glu
1490                1495                1500

Ser Ile Leu Pro Lys Arg Asn Ser Asp Lys Leu Ile Ala Arg Lys
```

```
                    1505                1510                1515

Lys Asp Trp Asp Pro Lys Lys Tyr Gly Gly Phe Asp Ser Pro Thr
    1520                1525                1530

Val Ala Tyr Ser Val Leu Val Ala Lys Val Glu Lys Gly Lys
    1535                1540                1545

Ser Lys Lys Leu Lys Ser Val Lys Glu Leu Leu Gly Ile Thr Ile
    1550                1555                1560

Met Glu Arg Ser Ser Phe Glu Lys Asn Pro Ile Asp Phe Leu Glu
    1565                1570                1575

Ala Lys Gly Tyr Lys Glu Val Lys Lys Asp Leu Ile Ile Lys Leu
    1580                1585                1590

Pro Lys Tyr Ser Leu Phe Glu Leu Glu Asn Gly Arg Lys Arg Met
    1595                1600                1605

Leu Ala Ser Ala Gly Glu Leu Gln Lys Gly Asn Glu Leu Ala Leu
    1610                1615                1620

Pro Ser Lys Tyr Val Asn Phe Leu Tyr Leu Ala Ser His Tyr Glu
    1625                1630                1635

Lys Leu Lys Gly Ser Pro Glu Asp Asn Glu Gln Lys Gln Leu Phe
    1640                1645                1650

Val Glu Gln His Lys His Tyr Leu Asp Glu Ile Ile Glu Gln Ile
    1655                1660                1665

Ser Glu Phe Ser Lys Arg Val Ile Leu Ala Asp Ala Asn Leu Asp
    1670                1675                1680

Lys Val Leu Ser Ala Tyr Asn Lys His Arg Asp Lys Pro Ile Arg
    1685                1690                1695

Glu Gln Ala Glu Asn Ile Ile His Leu Phe Thr Leu Thr Asn Leu
    1700                1705                1710

Gly Ala Pro Ala Ala Phe Lys Tyr Phe Asp Thr Thr Ile Asp Arg
    1715                1720                1725

Lys Arg Tyr Thr Ser Thr Lys Glu Val Leu Asp Ala Thr Leu Ile
    1730                1735                1740

His Gln Ser Ile Thr Gly Leu Tyr Glu Thr Arg Ile Asp Leu Ser
    1745                1750                1755

Gln Leu Gly Gly Asp
    1760

<210> SEQ ID NO 92
<211> LENGTH: 1565
<212> TYPE: PRT
<213> ORGANISM: Unknown
<220> FEATURE:
<223> OTHER INFORMATION: ABE8e

<400> SEQUENCE: 92

Ser Glu Val Glu Phe Ser His Glu Tyr Trp Met Arg His Ala Leu Thr
1               5                   10                  15

Leu Ala Lys Arg Ala Arg Asp Glu Arg Glu Val Pro Val Gly Ala Val
            20                  25                  30

Leu Val Leu Asn Asn Arg Val Ile Gly Glu Gly Trp Asn Arg Ala Ile
        35                  40                  45

Gly Leu His Asp Pro Thr Ala His Ala Glu Ile Met Ala Leu Arg Gln
    50                  55                  60

Gly Gly Leu Val Met Gln Asn Tyr Arg Leu Ile Asp Ala Thr Leu Tyr
65                  70                  75                  80

Val Thr Phe Glu Pro Cys Val Met Cys Ala Gly Ala Met Ile His Ser
```

-continued

```
                85                  90                  95
Arg Ile Gly Arg Val Phe Gly Val Arg Asn Ser Lys Arg Gly Ala
            100                 105                 110
Ala Gly Ser Leu Met Asn Val Leu Asn Tyr Pro Gly Met Asn His Arg
            115                 120                 125
Val Glu Ile Thr Glu Gly Ile Leu Ala Asp Glu Cys Ala Ala Leu Leu
130                 135                 140
Cys Asp Phe Tyr Arg Met Pro Arg Gln Val Phe Asn Ala Gln Lys Lys
145                 150                 155                 160
Ala Gln Ser Ser Ile Asn Ser Gly Ser Gly Gly Ser Ser Gly
            165                 170                 175
Ser Glu Thr Pro Gly Thr Ser Glu Ser Ala Thr Pro Glu Ser Ser Gly
            180                 185                 190
Gly Ser Ser Gly Gly Ser Asp Lys Lys Tyr Ser Ile Gly Leu Ala Ile
            195                 200                 205
Gly Thr Asn Ser Val Gly Trp Ala Val Ile Thr Asp Glu Tyr Lys Val
            210                 215                 220
Pro Ser Lys Lys Phe Lys Val Leu Gly Asn Thr Asp Arg His Ser Ile
225                 230                 235                 240
Lys Lys Asn Leu Ile Gly Ala Leu Leu Phe Asp Ser Gly Glu Thr Ala
                245                 250                 255
Glu Ala Thr Arg Leu Lys Arg Thr Ala Arg Arg Arg Tyr Thr Arg Arg
            260                 265                 270
Lys Asn Arg Ile Cys Tyr Leu Gln Glu Ile Phe Ser Asn Glu Met Ala
            275                 280                 285
Lys Val Asp Asp Ser Phe Phe His Arg Leu Glu Glu Ser Phe Leu Val
290                 295                 300
Glu Glu Asp Lys Lys His Glu Arg His Pro Ile Phe Gly Asn Ile Val
305                 310                 315                 320
Asp Glu Val Ala Tyr His Glu Lys Tyr Pro Thr Ile Tyr His Leu Arg
                325                 330                 335
Lys Lys Leu Val Asp Ser Thr Asp Lys Ala Asp Leu Arg Leu Ile Tyr
            340                 345                 350
Leu Ala Leu Ala His Met Ile Lys Phe Arg Gly His Phe Leu Ile Glu
            355                 360                 365
Gly Asp Leu Asn Pro Asp Asn Ser Asp Val Asp Lys Leu Phe Ile Gln
            370                 375                 380
Leu Val Gln Thr Tyr Asn Gln Leu Phe Glu Glu Asn Pro Ile Asn Ala
385                 390                 395                 400
Ser Gly Val Asp Ala Lys Ala Ile Leu Ser Ala Arg Leu Ser Lys Ser
                405                 410                 415
Arg Arg Leu Glu Asn Leu Ile Ala Gln Leu Pro Gly Glu Lys Lys Asn
            420                 425                 430
Gly Leu Phe Gly Asn Leu Ile Ala Leu Ser Leu Gly Leu Thr Pro Asn
            435                 440                 445
Phe Lys Ser Asn Phe Asp Leu Ala Glu Asp Ala Lys Leu Gln Leu Ser
450                 455                 460
Lys Asp Thr Tyr Asp Asp Asp Leu Asp Asn Leu Leu Ala Gln Ile Gly
465                 470                 475                 480
Asp Gln Tyr Ala Asp Leu Phe Leu Ala Ala Lys Asn Leu Ser Asp Ala
                485                 490                 495
Ile Leu Leu Ser Asp Ile Leu Arg Val Asn Thr Glu Ile Thr Lys Ala
            500                 505                 510
```

```
Pro Leu Ser Ala Ser Met Ile Lys Arg Tyr Asp Glu His His Gln Asp
            515                 520                 525

Leu Thr Leu Leu Lys Ala Leu Val Arg Gln Gln Leu Pro Glu Lys Tyr
        530                 535                 540

Lys Glu Ile Phe Phe Asp Gln Ser Lys Asn Gly Tyr Ala Gly Tyr Ile
545                 550                 555                 560

Asp Gly Gly Ala Ser Gln Glu Glu Phe Tyr Lys Phe Ile Lys Pro Ile
                565                 570                 575

Leu Glu Lys Met Asp Gly Thr Glu Glu Leu Leu Val Lys Leu Asn Arg
            580                 585                 590

Glu Asp Leu Leu Arg Lys Gln Arg Thr Phe Asp Asn Gly Ser Ile Pro
        595                 600                 605

His Gln Ile His Leu Gly Glu Leu His Ala Ile Leu Arg Arg Gln Glu
    610                 615                 620

Asp Phe Tyr Pro Phe Leu Lys Asp Asn Arg Glu Lys Ile Glu Lys Ile
625                 630                 635                 640

Leu Thr Phe Arg Ile Pro Tyr Tyr Val Gly Pro Leu Ala Arg Gly Asn
                645                 650                 655

Ser Arg Phe Ala Trp Met Thr Arg Lys Ser Glu Glu Thr Ile Thr Pro
            660                 665                 670

Trp Asn Phe Glu Glu Val Val Asp Lys Gly Ala Ser Ala Gln Ser Phe
        675                 680                 685

Ile Glu Arg Met Thr Asn Phe Asp Lys Asn Leu Pro Asn Glu Lys Val
    690                 695                 700

Leu Pro Lys His Ser Leu Leu Tyr Glu Tyr Phe Thr Val Tyr Asn Glu
705                 710                 715                 720

Leu Thr Lys Val Lys Tyr Val Thr Glu Gly Met Arg Lys Pro Ala Phe
                725                 730                 735

Leu Ser Gly Glu Gln Lys Lys Ala Ile Val Asp Leu Leu Phe Lys Thr
            740                 745                 750

Asn Arg Lys Val Thr Val Lys Gln Leu Lys Glu Asp Tyr Phe Lys Lys
        755                 760                 765

Ile Glu Cys Phe Asp Ser Val Glu Ile Ser Gly Val Glu Asp Arg Phe
    770                 775                 780

Asn Ala Ser Leu Gly Thr Tyr His Asp Leu Leu Lys Ile Ile Lys Asp
785                 790                 795                 800

Lys Asp Phe Leu Asp Asn Glu Glu Asn Glu Asp Ile Leu Glu Asp Ile
                805                 810                 815

Val Leu Thr Leu Thr Leu Phe Glu Asp Arg Glu Met Ile Glu Glu Arg
            820                 825                 830

Leu Lys Thr Tyr Ala His Leu Phe Asp Asp Lys Val Met Lys Gln Leu
        835                 840                 845

Lys Arg Arg Arg Tyr Thr Gly Trp Gly Arg Leu Ser Arg Lys Leu Ile
    850                 855                 860

Asn Gly Ile Arg Asp Lys Gln Ser Gly Lys Thr Ile Leu Asp Phe Leu
865                 870                 875                 880

Lys Ser Asp Gly Phe Ala Asn Arg Asn Phe Met Gln Leu Ile His Asp
                885                 890                 895

Asp Ser Leu Thr Phe Lys Glu Asp Ile Gln Lys Ala Gln Val Ser Gly
            900                 905                 910

Gln Gly Asp Ser Leu His Glu His Ile Ala Asn Leu Ala Gly Ser Pro
        915                 920                 925
```

```
Ala Ile Lys Lys Gly Ile Leu Gln Thr Val Lys Val Val Asp Glu Leu
    930             935             940

Val Lys Val Met Gly Arg His Lys Pro Glu Asn Ile Val Ile Glu Met
945             950             955             960

Ala Arg Glu Asn Gln Thr Thr Gln Lys Gly Gln Lys Asn Ser Arg Glu
                965             970             975

Arg Met Lys Arg Ile Glu Glu Gly Ile Lys Glu Leu Gly Ser Gln Ile
            980             985             990

Leu Lys Glu His Pro Val Glu Asn  Thr Gln Leu Gln Asn  Glu Lys Leu
        995             1000                1005

Tyr Leu  Tyr Tyr Leu Gln Asn  Gly Arg Asp Met Tyr  Val Asp Gln
    1010             1015            1020

Glu Leu  Asp Ile Asn Arg Leu  Ser Asp Tyr Asp Val  Asp His Ile
    1025             1030            1035

Val Pro  Gln Ser Phe Leu Lys  Asp Asp Ser Ile Asp  Asn Lys Val
    1040             1045            1050

Leu Thr  Arg Ser Asp Lys Asn  Arg Gly Lys Ser Asp  Asn Val Pro
    1055             1060            1065

Ser Glu  Glu Val Val Lys Lys  Met Lys Asn Tyr Trp  Arg Gln Leu
    1070             1075            1080

Leu Asn  Ala Lys Leu Ile Thr  Gln Arg Lys Phe Asp  Asn Leu Thr
    1085             1090            1095

Lys Ala  Glu Arg Gly Gly Leu  Ser Glu Leu Asp Lys  Ala Gly Phe
    1100             1105            1110

Ile Lys  Arg Gln Leu Val Glu  Thr Arg Gln Ile Thr  Lys His Val
    1115             1120            1125

Ala Gln  Ile Leu Asp Ser Arg  Met Asn Thr Lys Tyr  Asp Glu Asn
    1130             1135            1140

Asp Lys  Leu Ile Arg Glu Val  Lys Val Ile Thr Leu  Lys Ser Lys
    1145             1150            1155

Leu Val  Ser Asp Phe Arg Lys  Asp Phe Gln Phe Tyr  Lys Val Arg
    1160             1165            1170

Glu Ile  Asn Asn Tyr His His  Ala His Asp Ala Tyr  Leu Asn Ala
    1175             1180            1185

Val Val  Gly Thr Ala Leu Ile  Lys Lys Tyr Pro Lys  Leu Glu Ser
    1190             1195            1200

Glu Phe  Val Tyr Gly Asp Tyr  Lys Val Tyr Asp Val  Arg Lys Met
    1205             1210            1215

Ile Ala  Lys Ser Glu Gln Glu  Ile Gly Lys Ala Thr  Ala Lys Tyr
    1220             1225            1230

Phe Phe  Tyr Ser Asn Ile Met  Asn Phe Phe Lys Thr  Glu Ile Thr
    1235             1240            1245

Leu Ala  Asn Gly Glu Ile Arg  Lys Arg Pro Leu Ile  Glu Thr Asn
    1250             1255            1260

Gly Glu  Thr Gly Glu Ile Val  Trp Asp Lys Gly Arg  Asp Phe Ala
    1265             1270            1275

Thr Val  Arg Lys Val Leu Ser  Met Pro Gln Val Asn  Ile Val Lys
    1280             1285            1290

Lys Thr  Glu Val Gln Thr Gly  Gly Phe Ser Lys Glu  Ser Ile Leu
    1295             1300            1305

Pro Lys  Arg Asn Ser Asp Lys  Leu Ile Ala Arg Lys  Lys Asp Trp
    1310             1315            1320

Asp Pro  Lys Lys Tyr Gly Gly  Phe Asp Ser Pro Thr  Val Ala Tyr
```

```
                    1325               1330               1335

Ser Val Leu Val Val Ala Lys Val Glu Lys Gly Lys Ser Lys Lys
            1340               1345               1350

Leu Lys Ser Val Lys Glu Leu Leu Gly Ile Thr Ile Met Glu Arg
            1355               1360               1365

Ser Ser Phe Glu Lys Asn Pro Ile Asp Phe Leu Glu Ala Lys Gly
            1370               1375               1380

Tyr Lys Glu Val Lys Lys Asp Leu Ile Ile Lys Leu Pro Lys Tyr
            1385               1390               1395

Ser Leu Phe Glu Leu Glu Asn Gly Arg Lys Arg Met Leu Ala Ser
            1400               1405               1410

Ala Gly Glu Leu Gln Lys Gly Asn Glu Leu Ala Leu Pro Ser Lys
            1415               1420               1425

Tyr Val Asn Phe Leu Tyr Leu Ala Ser His Tyr Glu Lys Leu Lys
            1430               1435               1440

Gly Ser Pro Glu Asp Asn Glu Gln Lys Gln Leu Phe Val Glu Gln
            1445               1450               1455

His Lys His Tyr Leu Asp Glu Ile Ile Glu Gln Ile Ser Glu Phe
            1460               1465               1470

Ser Lys Arg Val Ile Leu Ala Asp Ala Asn Leu Asp Lys Val Leu
            1475               1480               1485

Ser Ala Tyr Asn Lys His Arg Asp Lys Pro Ile Arg Glu Gln Ala
            1490               1495               1500

Glu Asn Ile Ile His Leu Phe Thr Leu Thr Asn Leu Gly Ala Pro
            1505               1510               1515

Ala Ala Phe Lys Tyr Phe Asp Thr Thr Ile Asp Arg Lys Arg Tyr
            1520               1525               1530

Thr Ser Thr Lys Glu Val Leu Asp Ala Thr Leu Ile His Gln Ser
            1535               1540               1545

Ile Thr Gly Leu Tyr Glu Thr Arg Ile Asp Leu Ser Gln Leu Gly
            1550               1555               1560

Gly Asp
    1565

<210> SEQ ID NO 93
<211> LENGTH: 1565
<212> TYPE: PRT
<213> ORGANISM: Unknown
<220> FEATURE:
<223> OTHER INFORMATION: ABE8.20m

<400> SEQUENCE: 93

Ser Glu Val Glu Phe Ser His Glu Tyr Trp Met Arg His Ala Leu Thr
1               5                   10                  15

Leu Ala Lys Arg Ala Arg Asp Glu Arg Glu Val Pro Val Gly Ala Val
                20                  25                  30

Leu Val Leu Asn Asn Arg Val Ile Gly Glu Gly Trp Asn Arg Ala Ile
            35                  40                  45

Gly Leu His Asp Pro Thr Ala His Ala Glu Ile Met Ala Leu Arg Gln
        50                  55                  60

Gly Gly Leu Val Met Gln Asn Tyr Arg Leu Tyr Asp Ala Thr Leu Tyr
65                  70                  75                  80

Ser Thr Phe Glu Pro Cys Val Met Cys Ala Gly Ala Met Ile His Ser
                85                  90                  95

Arg Ile Gly Arg Val Val Phe Gly Val Arg Asn Ala Lys Thr Gly Ala
```

```
                100             105               110
Ala Gly Ser Leu Met Asp Val Leu His His Pro Gly Met Asn His Arg
            115                 120             125
Val Glu Ile Thr Glu Gly Ile Leu Ala Asp Glu Cys Ala Ala Leu Leu
        130                 135             140
Cys Arg Phe Phe Arg Met Pro Arg Arg Val Phe Asn Ala Gln Lys Lys
145                 150                 155                 160
Ala Gln Ser Ser Thr Asp Ser Gly Gly Ser Gly Gly Ser Ser Gly
                165                 170                 175
Ser Glu Thr Pro Gly Thr Ser Glu Ser Ala Thr Pro Glu Ser Ser Gly
                180                 185                 190
Gly Ser Ser Gly Gly Ser Asp Lys Lys Tyr Ser Ile Gly Leu Ala Ile
            195                 200                 205
Gly Thr Asn Ser Val Gly Trp Ala Val Ile Thr Asp Glu Tyr Lys Val
        210                 215                 220
Pro Ser Lys Lys Phe Lys Val Leu Gly Asn Thr Asp Arg His Ser Ile
225                 230                 235                 240
Lys Lys Asn Leu Ile Gly Ala Leu Leu Phe Asp Ser Gly Glu Thr Ala
                245                 250                 255
Glu Ala Thr Arg Leu Lys Arg Thr Ala Arg Arg Arg Tyr Thr Arg Arg
                260                 265                 270
Lys Asn Arg Ile Cys Tyr Leu Gln Glu Ile Phe Ser Asn Glu Met Ala
                275                 280                 285
Lys Val Asp Asp Ser Phe Phe His Arg Leu Glu Glu Ser Phe Leu Val
        290                 295                 300
Glu Glu Asp Lys Lys His Glu Arg His Pro Ile Phe Gly Asn Ile Val
305                 310                 315                 320
Asp Glu Val Ala Tyr His Glu Lys Tyr Pro Thr Ile Tyr His Leu Arg
                325                 330                 335
Lys Lys Leu Val Asp Ser Thr Asp Lys Ala Asp Leu Arg Leu Ile Tyr
                340                 345                 350
Leu Ala Leu Ala His Met Ile Lys Phe Arg Gly His Phe Leu Ile Glu
            355                 360                 365
Gly Asp Leu Asn Pro Asp Asn Ser Asp Val Asp Lys Leu Phe Ile Gln
            370                 375                 380
Leu Val Gln Thr Tyr Asn Gln Leu Phe Glu Glu Asn Pro Ile Asn Ala
385                 390                 395                 400
Ser Gly Val Asp Ala Lys Ala Ile Leu Ser Ala Arg Leu Ser Lys Ser
                405                 410                 415
Arg Arg Leu Glu Asn Leu Ile Ala Gln Leu Pro Gly Glu Lys Lys Asn
                420                 425                 430
Gly Leu Phe Gly Asn Leu Ile Ala Leu Ser Leu Gly Leu Thr Pro Asn
            435                 440                 445
Phe Lys Ser Asn Phe Asp Leu Ala Glu Asp Ala Lys Leu Gln Leu Ser
            450                 455                 460
Lys Asp Thr Tyr Asp Asp Asp Leu Asp Asn Leu Leu Ala Gln Ile Gly
465                 470                 475                 480
Asp Gln Tyr Ala Asp Leu Phe Leu Ala Ala Lys Asn Leu Ser Asp Ala
                485                 490                 495
Ile Leu Leu Ser Asp Ile Leu Arg Val Asn Thr Glu Ile Thr Lys Ala
            500                 505                 510
Pro Leu Ser Ala Ser Met Ile Lys Arg Tyr Asp Glu His His Gln Asp
            515                 520                 525
```

```
Leu Thr Leu Leu Lys Ala Leu Val Arg Gln Gln Leu Pro Glu Lys Tyr
    530                 535                 540
Lys Glu Ile Phe Phe Asp Gln Ser Lys Asn Gly Tyr Ala Gly Tyr Ile
545                 550                 555                 560
Asp Gly Gly Ala Ser Gln Glu Glu Phe Tyr Lys Phe Ile Lys Pro Ile
                565                 570                 575
Leu Glu Lys Met Asp Gly Thr Glu Glu Leu Leu Val Lys Leu Asn Arg
            580                 585                 590
Glu Asp Leu Leu Arg Lys Gln Arg Thr Phe Asp Asn Gly Ser Ile Pro
        595                 600                 605
His Gln Ile His Leu Gly Glu Leu His Ala Ile Leu Arg Arg Gln Glu
    610                 615                 620
Asp Phe Tyr Pro Phe Leu Lys Asp Asn Arg Glu Lys Ile Glu Lys Ile
625                 630                 635                 640
Leu Thr Phe Arg Ile Pro Tyr Tyr Val Gly Pro Leu Ala Arg Gly Asn
                645                 650                 655
Ser Arg Phe Ala Trp Met Thr Arg Lys Ser Glu Glu Thr Ile Thr Pro
            660                 665                 670
Trp Asn Phe Glu Glu Val Val Asp Lys Gly Ala Ser Ala Gln Ser Phe
        675                 680                 685
Ile Glu Arg Met Thr Asn Phe Asp Lys Asn Leu Pro Asn Glu Lys Val
    690                 695                 700
Leu Pro Lys His Ser Leu Leu Tyr Glu Tyr Phe Thr Val Tyr Asn Glu
705                 710                 715                 720
Leu Thr Lys Val Lys Tyr Val Thr Glu Gly Met Arg Lys Pro Ala Phe
                725                 730                 735
Leu Ser Gly Glu Gln Lys Lys Ala Ile Val Asp Leu Leu Phe Lys Thr
            740                 745                 750
Asn Arg Lys Val Thr Val Lys Gln Leu Lys Glu Asp Tyr Phe Lys Lys
        755                 760                 765
Ile Glu Cys Phe Asp Ser Val Glu Ile Ser Gly Val Glu Asp Arg Phe
    770                 775                 780
Asn Ala Ser Leu Gly Thr Tyr His Asp Leu Leu Lys Ile Ile Lys Asp
785                 790                 795                 800
Lys Asp Phe Leu Asp Asn Glu Glu Asn Glu Asp Ile Leu Glu Asp Ile
                805                 810                 815
Val Leu Thr Leu Thr Leu Phe Glu Asp Arg Glu Met Ile Glu Glu Arg
            820                 825                 830
Leu Lys Thr Tyr Ala His Leu Phe Asp Asp Lys Val Met Lys Gln Leu
        835                 840                 845
Lys Arg Arg Arg Tyr Thr Gly Trp Gly Arg Leu Ser Arg Lys Leu Ile
    850                 855                 860
Asn Gly Ile Arg Asp Lys Gln Ser Gly Lys Thr Ile Leu Asp Phe Leu
865                 870                 875                 880
Lys Ser Asp Gly Phe Ala Asn Arg Asn Phe Met Gln Leu Ile His Asp
                885                 890                 895
Asp Ser Leu Thr Phe Lys Glu Asp Ile Gln Lys Ala Gln Val Ser Gly
            900                 905                 910
Gln Gly Asp Ser Leu His Glu His Ile Ala Asn Leu Ala Gly Ser Pro
        915                 920                 925
Ala Ile Lys Lys Gly Ile Leu Gln Thr Val Lys Val Val Asp Glu Leu
    930                 935                 940
```

-continued

```
Val Lys Val Met Gly Arg His Lys Pro Glu Asn Ile Val Ile Glu Met
945                 950                 955                 960

Ala Arg Glu Asn Gln Thr Thr Gln Lys Gly Gln Lys Asn Ser Arg Glu
                965                 970                 975

Arg Met Lys Arg Ile Glu Glu Gly Ile Lys Glu Leu Gly Ser Gln Ile
            980                 985                 990

Leu Lys Glu His Pro Val Glu Asn Thr Gln Leu Gln Asn Glu Lys Leu
        995                 1000                1005

Tyr Leu Tyr Tyr Leu Gln Asn Gly Arg Asp Met Tyr Val Asp Gln
    1010                1015                1020

Glu Leu Asp Ile Asn Arg Leu Ser Asp Tyr Asp Val Asp His Ile
    1025                1030                1035

Val Pro Gln Ser Phe Leu Lys Asp Asp Ser Ile Asp Asn Lys Val
    1040                1045                1050

Leu Thr Arg Ser Asp Lys Asn Arg Gly Lys Ser Asp Asn Val Pro
    1055                1060                1065

Ser Glu Glu Val Val Lys Lys Met Lys Asn Tyr Trp Arg Gln Leu
    1070                1075                1080

Leu Asn Ala Lys Leu Ile Thr Gln Arg Lys Phe Asp Asn Leu Thr
    1085                1090                1095

Lys Ala Glu Arg Gly Gly Leu Ser Glu Leu Asp Lys Ala Gly Phe
    1100                1105                1110

Ile Lys Arg Gln Leu Val Glu Thr Arg Gln Ile Thr Lys His Val
    1115                1120                1125

Ala Gln Ile Leu Asp Ser Arg Met Asn Thr Lys Tyr Asp Glu Asn
    1130                1135                1140

Asp Lys Leu Ile Arg Glu Val Lys Val Ile Thr Leu Lys Ser Lys
    1145                1150                1155

Leu Val Ser Asp Phe Arg Lys Asp Phe Gln Phe Tyr Lys Val Arg
    1160                1165                1170

Glu Ile Asn Asn Tyr His His Ala His Asp Ala Tyr Leu Asn Ala
    1175                1180                1185

Val Val Gly Thr Ala Leu Ile Lys Lys Tyr Pro Lys Leu Glu Ser
    1190                1195                1200

Glu Phe Val Tyr Gly Asp Tyr Lys Val Tyr Asp Val Arg Lys Met
    1205                1210                1215

Ile Ala Lys Ser Glu Gln Glu Ile Gly Lys Ala Thr Ala Lys Tyr
    1220                1225                1230

Phe Phe Tyr Ser Asn Ile Met Asn Phe Phe Lys Thr Glu Ile Thr
    1235                1240                1245

Leu Ala Asn Gly Glu Ile Arg Lys Arg Pro Leu Ile Glu Thr Asn
    1250                1255                1260

Gly Glu Thr Gly Glu Ile Val Trp Asp Lys Gly Arg Asp Phe Ala
    1265                1270                1275

Thr Val Arg Lys Val Leu Ser Met Pro Gln Val Asn Ile Val Lys
    1280                1285                1290

Lys Thr Glu Val Gln Thr Gly Gly Phe Ser Lys Glu Ser Ile Leu
    1295                1300                1305

Pro Lys Arg Asn Ser Asp Lys Leu Ile Ala Arg Lys Lys Asp Trp
    1310                1315                1320

Asp Pro Lys Lys Tyr Gly Gly Phe Asp Ser Pro Thr Val Ala Tyr
    1325                1330                1335

Ser Val Leu Val Val Ala Lys Val Glu Lys Gly Lys Ser Lys Lys
```

```
               1340                1345                1350

Leu Lys Ser Val Lys Glu Leu Leu Gly Ile Thr Ile Met Glu Arg
    1355                1360                1365

Ser Ser Phe Glu Lys Asn Pro Ile Asp Phe Leu Glu Ala Lys Gly
    1370                1375                1380

Tyr Lys Glu Val Lys Lys Asp Leu Ile Ile Lys Leu Pro Lys Tyr
    1385                1390                1395

Ser Leu Phe Glu Leu Glu Asn Gly Arg Lys Arg Met Leu Ala Ser
    1400                1405                1410

Ala Gly Glu Leu Gln Lys Gly Asn Glu Leu Ala Leu Pro Ser Lys
    1415                1420                1425

Tyr Val Asn Phe Leu Tyr Leu Ala Ser His Tyr Glu Lys Leu Lys
    1430                1435                1440

Gly Ser Pro Glu Asp Asn Glu Gln Lys Gln Leu Phe Val Glu Gln
    1445                1450                1455

His Lys His Tyr Leu Asp Glu Ile Ile Glu Gln Ile Ser Glu Phe
    1460                1465                1470

Ser Lys Arg Val Ile Leu Ala Asp Ala Asn Leu Asp Lys Val Leu
    1475                1480                1485

Ser Ala Tyr Asn Lys His Arg Asp Lys Pro Ile Arg Glu Gln Ala
    1490                1495                1500

Glu Asn Ile Ile His Leu Phe Thr Leu Thr Asn Leu Gly Ala Pro
    1505                1510                1515

Ala Ala Phe Lys Tyr Phe Asp Thr Thr Ile Asp Arg Lys Arg Tyr
    1520                1525                1530

Thr Ser Thr Lys Glu Val Leu Asp Ala Thr Leu Ile His Gln Ser
    1535                1540                1545

Ile Thr Gly Leu Tyr Glu Thr Arg Ile Asp Leu Ser Gln Leu Gly
    1550                1555                1560

Gly Asp
    1565

<210> SEQ ID NO 94
<211> LENGTH: 364
<212> TYPE: PRT
<213> ORGANISM: Unknown
<220> FEATURE:
<223> OTHER INFORMATION: ABE7.10

<400> SEQUENCE: 94

Ser Glu Val Glu Phe Ser His Glu Tyr Trp Met Arg His Ala Leu Thr
1               5                   10                  15

Leu Ala Lys Arg Ala Trp Asp Glu Arg Glu Val Pro Val Gly Ala Val
            20                  25                  30

Leu Val His Asn Asn Arg Val Ile Gly Glu Gly Trp Asn Arg Pro Ile
        35                  40                  45

Gly Arg His Asp Pro Thr Ala His Ala Glu Ile Met Ala Leu Arg Gln
    50                  55                  60

Gly Gly Leu Val Met Gln Asn Tyr Arg Leu Ile Asp Ala Thr Leu Tyr
65                  70                  75                  80

Val Thr Leu Glu Pro Cys Val Met Cys Ala Gly Ala Met Ile His Ser
                85                  90                  95

Arg Ile Gly Arg Val Val Phe Gly Ala Arg Asp Ala Lys Thr Gly Ala
            100                 105                 110

Ala Gly Ser Leu Met Asp Val Leu His His Pro Gly Met Asn His Arg
```

```
               115                 120                 125
Val Glu Ile Thr Glu Gly Ile Leu Ala Asp Glu Cys Ala Ala Leu Leu
130                 135                 140

Ser Asp Phe Phe Arg Met Arg Arg Gln Glu Ile Lys Ala Gln Lys Lys
145                 150                 155                 160

Ala Gln Ser Ser Thr Asp Ser Gly Gly Ser Gly Gly Ser Ser Gly
                165                 170                 175

Ser Glu Thr Pro Gly Thr Ser Glu Ser Ala Thr Pro Glu Ser Ser Gly
                180                 185                 190

Gly Ser Ser Gly Gly Ser Ser Glu Val Glu Phe Ser His Glu Tyr Trp
                195                 200                 205

Met Arg His Ala Leu Thr Leu Ala Lys Arg Ala Arg Asp Glu Arg Glu
210                 215                 220

Val Pro Val Gly Ala Val Leu Val Leu Asn Asn Arg Val Ile Gly Glu
225                 230                 235                 240

Gly Trp Asn Arg Ala Ile Gly Leu His Asp Pro Thr Ala His Ala Glu
                245                 250                 255

Ile Met Ala Leu Arg Gln Gly Gly Leu Val Met Gln Asn Tyr Arg Leu
                260                 265                 270

Ile Asp Ala Thr Leu Tyr Val Thr Phe Glu Pro Cys Val Met Cys Ala
                275                 280                 285

Gly Ala Met Ile His Ser Arg Ile Gly Arg Val Val Phe Gly Val Arg
                290                 295                 300

Asn Ala Lys Thr Gly Ala Ala Gly Ser Leu Met Asp Val Leu His Tyr
305                 310                 315                 320

Pro Gly Met Asn His Arg Val Glu Ile Thr Glu Gly Ile Leu Ala Asp
                325                 330                 335

Glu Cys Ala Ala Leu Leu Cys Tyr Phe Phe Arg Met Pro Arg Gln Val
                340                 345                 350

Phe Asn Ala Gln Lys Lys Ala Gln Ser Ser Thr Asp
                355                 360

<210> SEQ ID NO 95
<211> LENGTH: 167
<212> TYPE: PRT
<213> ORGANISM: Unknown
<220> FEATURE:
<223> OTHER INFORMATION: TadA8.20m

<400> SEQUENCE: 95

Met Ser Glu Val Glu Phe Ser His Glu Tyr Trp Met Arg His Ala Leu
1               5                   10                  15

Thr Leu Ala Lys Arg Ala Arg Asp Glu Arg Glu Val Pro Val Gly Ala
                20                  25                  30

Val Leu Val Leu Asn Asn Arg Val Ile Gly Glu Gly Trp Asn Arg Ala
                35                  40                  45

Ile Gly Leu His Asp Pro Thr Ala His Ala Glu Ile Met Ala Leu Arg
        50                  55                  60

Gln Gly Gly Leu Val Met Gln Asn Tyr Arg Leu Tyr Asp Ala Thr Leu
65                  70                  75                  80

Tyr Ser Thr Phe Glu Pro Cys Val Met Cys Ala Gly Ala Met Ile His
                85                  90                  95

Ser Arg Ile Gly Arg Val Val Phe Gly Val Arg Asn Ala Lys Thr Gly
                100                 105                 110

Ala Ala Gly Ser Leu Met Asp Val Leu His His Pro Gly Met Asn His
```

```
                115                 120                 125
Arg Val Glu Ile Thr Glu Gly Ile Leu Ala Asp Glu Cys Ala Ala Leu
            130                 135                 140

Leu Cys Arg Phe Phe Arg Met Pro Arg Val Phe Asn Ala Gln Lys
145                 150                 155                 160

Lys Ala Gln Ser Ser Thr Asp
                165

<210> SEQ ID NO 96
<211> LENGTH: 167
<212> TYPE: PRT
<213> ORGANISM: Unknown
<220> FEATURE:
<223> OTHER INFORMATION: TadA8e

<400> SEQUENCE: 96

Met Ser Glu Val Glu Phe Ser His Glu Tyr Trp Met Arg His Ala Leu
1               5                   10                  15

Thr Leu Ala Lys Arg Ala Arg Asp Glu Arg Glu Val Pro Val Gly Ala
            20                  25                  30

Val Leu Val Leu Asn Asn Arg Val Ile Gly Glu Gly Trp Asn Arg Ala
        35                  40                  45

Ile Gly Leu His Asp Pro Thr Ala His Ala Glu Ile Met Ala Leu Arg
    50                  55                  60

Gln Gly Gly Leu Val Met Gln Asn Tyr Arg Leu Ile Asp Ala Thr Leu
65                  70                  75                  80

Tyr Val Thr Phe Glu Pro Cys Val Met Cys Ala Gly Ala Met Ile His
                85                  90                  95

Ser Arg Ile Gly Arg Val Val Phe Gly Val Arg Asn Ser Lys Arg Gly
            100                 105                 110

Ala Ala Gly Ser Leu Met Asn Val Leu Asn Tyr Pro Gly Met Asn His
        115                 120                 125

Arg Val Glu Ile Thr Glu Gly Ile Leu Ala Asp Glu Cys Ala Ala Leu
    130                 135                 140

Leu Cys Asp Phe Tyr Arg Met Pro Arg Gln Val Phe Asn Ala Gln Lys
145                 150                 155                 160

Lys Ala Gln Ser Ser Ile Asn
                165

<210> SEQ ID NO 97
<211> LENGTH: 83
<212> TYPE: PRT
<213> ORGANISM: Unknown
<220> FEATURE:
<223> OTHER INFORMATION: Bacillus phage AR9

<400> SEQUENCE: 97

Thr Asn Leu Ser Asp Ile Ile Glu Lys Glu Thr Gly Lys Gln Leu Val
1               5                   10                  15

Ile Gln Glu Ser Ile Leu Met Leu Pro Glu Glu Val Glu Glu Val Ile
            20                  25                  30

Gly Asn Lys Pro Glu Ser Asp Ile Leu Val His Thr Ala Tyr Asp Glu
        35                  40                  45

Ser Thr Asp Glu Asn Val Met Leu Leu Thr Ser Asp Ala Pro Glu Tyr
    50                  55                  60

Lys Pro Trp Ala Leu Val Ile Gln Asp Ser Asn Gly Glu Asn Lys Ile
65                  70                  75                  80
```

Lys Met Leu

<210> SEQ ID NO 98
<211> LENGTH: 19
<212> TYPE: PRT
<213> ORGANISM: Artificial
<220> FEATURE:
<223> OTHER INFORMATION: RNA Spacer

<400> SEQUENCE: 98

Asn Asn Asn Asn Asn Asn Asn Asn Asn Asn Asn Asn Asn Asn Asn Asn
1               5                   10                  15

Asn Asn Asn

<210> SEQ ID NO 99
<211> LENGTH: 21
<212> TYPE: PRT
<213> ORGANISM: Artificial
<220> FEATURE:
<223> OTHER INFORMATION: Target strand

<400> SEQUENCE: 99

Ala Ala Ala Asn Asn Asn Asn Asn Asn Asn Asn Asn Asn Asn Asn Asn
1               5                   10                  15

Asn Asn Asn Asn Asn
            20

<210> SEQ ID NO 100
<211> LENGTH: 22
<212> TYPE: PRT
<213> ORGANISM: Artificial
<220> FEATURE:
<223> OTHER INFORMATION: Non-target strand

<400> SEQUENCE: 100

Thr Thr Thr Asn Asn Asn Asn Asn Asn Asn Asn Asn Asn Asn Asn Asn
1               5                   10                  15

Asn Asn Asn Asn Asn Asn
            20

<210> SEQ ID NO 101
<211> LENGTH: 66
<212> TYPE: DNA
<213> ORGANISM: Unknown
<220> FEATURE:
<223> OTHER INFORMATION: Telomerase Ku binding motif

<400> SEQUENCE: 101
ttcttgtcgt acttatagat cgctacgtta tttcaattttt gaaaatctga gtcctgggag    60
tgcgga                                                                66

<210> SEQ ID NO 102
<211> LENGTH: 605
<212> TYPE: PRT
<213> ORGANISM: Unknown
<220> FEATURE:
<223> OTHER INFORMATION: Ku heterodimer

<400> SEQUENCE: 102

Met Ser Gly Trp Glu Ser Tyr Tyr Lys Thr Glu Gly Asp Glu Glu Ala
1               5                   10                  15

Glu Glu Glu Gln Glu Glu Asn Leu Glu Ala Ser Gly Asp Tyr Lys Tyr
            20                  25                  30

```
Ser Gly Arg Asp Ser Leu Ile Phe Leu Val Asp Ala Ser Lys Ala Met
         35                  40                  45
Phe Glu Ser Gln Ser Glu Asp Glu Leu Thr Pro Phe Asp Met Ser Ile
 50                  55                  60
Gln Cys Ile Gln Ser Val Tyr Ile Ser Lys Ile Ile Ser Ser Asp Arg
 65                  70                  75                  80
Asp Leu Leu Ala Trp Phe Tyr Gly Thr Glu Lys Asp Lys Asn Ser Val
                 85                  90                  95
Asn Phe Lys Ile Tyr Val Leu Gln Glu Leu Asp Asn Pro Gly Ala Lys
             100                 105                 110
Arg Ile Leu Glu Leu Asp Gln Phe Lys Gly Gln Gln Gly Gln Lys Arg
             115                 120                 125
Phe Gln Asp Met Met Gly His Gly Ser Asp Tyr Ser Leu Ser Glu Val
130                 135                 140
Leu Trp Val Cys Ala Asn Leu Phe Ser Asp Val Gln Phe Lys Met Ser
145                 150                 155                 160
His Lys Arg Ile Met Leu Phe Thr Asn Glu Asp Asn Pro His Gly Asn
                165                 170                 175
Asp Ser Ala Lys Ala Ser Arg Ala Arg Thr Lys Ala Gly Asp Leu Arg
            180                 185                 190
Asp Thr Gly Ile Phe Leu Asp Leu His Leu Lys Lys Pro Gly Gly Phe
            195                 200                 205
Asp Ile Ser Leu Phe Tyr Arg Asp Ile Ile Ser Ile Ala Glu Asp Glu
            210                 215                 220
Asp Leu Arg Val His Phe Glu Glu Ser Ser Lys Leu Glu Asp Leu Leu
225                 230                 235                 240
Arg Lys Val Arg Ala Lys Glu Thr Arg Lys Arg Ala Leu Ser Arg Leu
                245                 250                 255
Lys Leu Lys Leu Asn Lys Asp Ile Val Ile Ser Val Gly Ile Tyr Asn
                260                 265                 270
Leu Val Gln Lys Ala Leu Lys Pro Pro Ile Lys Leu Tyr Arg Glu
            275                 280                 285
Thr Asn Glu Pro Val Lys Thr Lys Thr Arg Thr Phe Asn Thr Ser Thr
290                 295                 300
Gly Gly Leu Leu Leu Pro Ser Asp Thr Lys Arg Ser Gln Ile Tyr Gly
305                 310                 315                 320
Ser Arg Gln Ile Ile Leu Glu Lys Glu Glu Thr Glu Glu Leu Lys Arg
                325                 330                 335
Phe Asp Asp Pro Gly Leu Met Leu Met Gly Phe Lys Pro Leu Val Leu
                340                 345                 350
Leu Lys Lys His His Tyr Leu Arg Pro Ser Leu Phe Val Tyr Pro Glu
            355                 360                 365
Glu Ser Leu Val Ile Gly Ser Ser Thr Leu Phe Ser Ala Leu Leu Ile
370                 375                 380
Lys Cys Leu Glu Lys Glu Val Ala Ala Leu Cys Arg Tyr Thr Pro Arg
385                 390                 395                 400
Arg Asn Ile Pro Pro Tyr Phe Val Ala Leu Val Pro Gln Glu Glu Glu
                405                 410                 415
Leu Asp Asp Gln Lys Ile Gln Val Thr Pro Pro Gly Phe Gln Leu Val
            420                 425                 430
Phe Leu Pro Phe Ala Asp Asp Lys Arg Lys Met Pro Phe Thr Glu Lys
            435                 440                 445
Ile Met Ala Thr Pro Glu Gln Val Gly Lys Met Lys Ala Ile Val Glu
```

```
                    450                 455                 460
Lys Leu Arg Phe Thr Tyr Arg Ser Asp Ser Phe Glu Asn Pro Val Leu
465                 470                 475                 480

Gln Gln His Phe Arg Asn Leu Glu Ala Leu Ala Leu Asp Leu Met Glu
                    485                 490                 495

Pro Glu Gln Ala Val Asp Leu Thr Leu Pro Lys Val Glu Ala Met Asn
                500                 505                 510

Lys Arg Leu Gly Ser Leu Val Asp Glu Phe Lys Glu Leu Val Tyr Pro
                515                 520                 525

Pro Asp Tyr Asn Pro Glu Gly Lys Val Thr Lys Arg Lys His Asp Asn
                530                 535                 540

Glu Gly Ser Gly Ser Lys Arg Pro Lys Val Glu Tyr Ser Glu Glu Glu
545                 550                 555                 560

Leu Lys Thr His Ile Ser Lys Gly Thr Leu Gly Lys Phe Thr Val Pro
                565                 570                 575

Leu Lys Glu Ala Cys Arg Ala Tyr Gly Leu Lys Ser Gly Leu Lys Lys
                580                 585                 590

Gln Glu Leu Leu Glu Ala Leu Thr Lys His Phe Gln Asp
                595                 600                 605

<210> SEQ ID NO 103
<211> LENGTH: 482
<212> TYPE: PRT
<213> ORGANISM: Artificial
<220> FEATURE:
<223> OTHER INFORMATION: polypeptide

<400> SEQUENCE: 103

Met Val Arg Ser Gly Asn Lys Ala Ala Trp Leu Cys Met Asp Val Gly
1               5                   10                  15

Phe Thr Met Ser Asn Ser Ile Pro Gly Ile Glu Ser Pro Phe Glu Gln
                20                  25                  30

Ala Lys Lys Val Ile Thr Met Phe Val Gln Arg Gln Val Phe Ala Glu
            35                  40                  45

Asn Lys Asp Glu Ile Ala Leu Val Leu Phe Gly Thr Asp Gly Thr Asp
50                  55                  60

Asn Pro Leu Ser Gly Gly Asp Gln Tyr Gln Asn Ile Thr Val His Arg
65                  70                  75                  80

His Leu Met Leu Pro Asp Phe Asp Leu Leu Glu Asp Ile Glu Ser Lys
                85                  90                  95

Ile Gln Pro Gly Ser Gln Gln Ala Asp Phe Leu Asp Ala Leu Ile Val
            100                 105                 110

Ser Met Asp Val Ile Gln His Glu Thr Ile Gly Lys Lys Phe Glu Lys
                115                 120                 125

Arg His Ile Glu Ile Phe Thr Asp Leu Ser Ser Arg Phe Ser Lys Ser
            130                 135                 140

Gln Leu Asp Ile Ile His Ser Leu Lys Lys Cys Asp Ile Ser Glu
145                 150                 155                 160

Arg His Ser Ile His Trp Pro Cys Arg Leu Thr Ile Gly Ser Asn Leu
                165                 170                 175

Ser Ile Arg Ile Ala Ala Tyr Lys Ser Ile Leu Gln Glu Arg Val Lys
            180                 185                 190

Lys Thr Thr Trp Asp Ala Lys Thr Leu Lys Lys Glu Asp Ile Gln Lys
        195                 200                 205

Glu Thr Val Tyr Cys Leu Asn Asp Asp Asp Glu Thr Glu Val Leu Lys
```

```
            210                 215                 220

Glu Asp Ile Ile Gln Gly Phe Arg Tyr Gly Ser Asp Ile Val Pro Phe
225                 230                 235                 240

Ser Lys Val Asp Glu Glu Gln Met Lys Tyr Lys Ser Glu Gly Lys Cys
                245                 250                 255

Phe Ser Val Leu Gly Phe Cys Lys Ser Ser Gln Val Gln Arg Arg Phe
            260                 265                 270

Phe Met Gly Asn Gln Val Leu Lys Val Phe Ala Ala Arg Asp Asp Glu
        275                 280                 285

Ala Ala Ala Val Ala Leu Ser Ser Leu Ile His Ala Leu Asp Asp Leu
    290                 295                 300

Asp Ile Trp Ala Ile Val Arg Tyr Ala Tyr Asp Lys Arg Ala Asn Pro
305                 310                 315                 320

Gln Val Gly Val Ala Phe Pro His Ile Lys His Asn Tyr Glu Cys Leu
                325                 330                 335

Val Tyr Val Gln Leu Pro Phe Met Glu Asp Leu Arg Gln Tyr Met Phe
            340                 345                 350

Ser Ser Leu Lys Asn Ser Lys Lys Tyr Ala Pro Thr Glu Ala Gln Leu
        355                 360                 365

Asn Ala Val Asp Ala Leu Ile Asp Ser Met Ser Leu Ala Lys Lys Asp
    370                 375                 380

Glu Lys Thr Asp Thr Leu Glu Asp Leu Phe Pro Thr Thr Lys Ile Pro
385                 390                 395                 400

Asn Pro Arg Phe Gln Arg Leu Phe Gln Cys Leu Leu His Arg Ala Leu
                405                 410                 415

His Pro Arg Glu Pro Leu Pro Pro Ile Gln Gln His Ile Trp Asn Met
            420                 425                 430

Leu Asn Pro Pro Ala Glu Val Thr Thr Lys Ser Gln Ile Pro Leu Ser
        435                 440                 445

Lys Ile Lys Thr Leu Phe Pro Leu Ile Glu Ala Lys Lys Lys Asp Gln
    450                 455                 460

Val Thr Ala Gln Glu Ile Phe Gln Asp Asn His Glu Asp Gly Pro Thr
465                 470                 475                 480

Ala Lys

<210> SEQ ID NO 104
<211> LENGTH: 10
<212> TYPE: DNA
<213> ORGANISM: Unknown
<220> FEATURE:
<223> OTHER INFORMATION: Sm consensus site

<400> SEQUENCE: 104
aatttttgga                                                          10

<210> SEQ ID NO 105
<211> LENGTH: 83
<212> TYPE: PRT
<213> ORGANISM: Unknown
<220> FEATURE:
<223> OTHER INFORMATION: Monomeric Sm

<400> SEQUENCE: 105

Gly Ser Val Ile Asp Val Ser Ser Gln Arg Val Asn Val Gln Arg Pro
1               5                   10                  15

Leu Asp Ala Leu Gly Asn Ser Leu Asn Ser Pro Val Ile Ile Lys Leu
            20                  25                  30
```

```
Lys Gly Asp Arg Glu Phe Arg Gly Val Leu Lys Ser Phe Asp Leu His
         35                  40                  45

Met Asn Leu Val Leu Asn Asp Ala Glu Glu Leu Glu Asp Gly Glu Val
     50                  55                  60

Thr Arg Arg Leu Gly Thr Val Leu Ile Arg Gly Asp Asn Ile Val Tyr
 65                  70                  75                  80

Ile Ser Pro

<210> SEQ ID NO 106
<211> LENGTH: 25
<212> TYPE: DNA
<213> ORGANISM: Unknown
<220> FEATURE:
<223> OTHER INFORMATION: bacteriophage MS2

<400> SEQUENCE: 106
gcgcacatga ggatcaccca tgtgc                                           25

<210> SEQ ID NO 107
<211> LENGTH: 116
<212> TYPE: PRT
<213> ORGANISM: Unknown
<220> FEATURE:
<223> OTHER INFORMATION: bacteriophage MS2

<400> SEQUENCE: 107

Met Ala Ser Asn Phe Thr Gln Phe Val Leu Val Asp Asn Gly Gly Thr
 1               5                  10                  15

Gly Asp Val Thr Val Ala Pro Ser Asn Phe Ala Asn Gly Ile Ala Glu
             20                  25                  30

Ile Ser Ser Asn Ser Arg Ser Gln Ala Tyr Lys Val Thr Cys Ser Val
         35                  40                  45

Arg Gln Ser Ser Ala Gln Asn Arg Lys Tyr Thr Ile Lys Val Glu Val
 50                  55                  60

Pro Lys Gly Ala Trp Arg Ser Tyr Leu Asn Met Glu Leu Thr Ile Pro
 65                  70                  75                  80

Ile Phe Ala Thr Asn Ser Asp Cys Glu Leu Ile Val Lys Ala Met Gln
             85                  90                  95

Gly Leu Leu Lys Asp Gly Asn Pro Ile Pro Ser Ala Ile Ala Ala Asn
            100                 105                 110

Ser Gly Ile Tyr
        115

<210> SEQ ID NO 108
<211> LENGTH: 26
<212> TYPE: DNA
<213> ORGANISM: Unknown
<220> FEATURE:
<223> OTHER INFORMATION: bacteriophage PP7

<400> SEQUENCE: 108
ataaggagtt tatatggaaa ccctta                                          26

<210> SEQ ID NO 109
<211> LENGTH: 127
<212> TYPE: PRT
<213> ORGANISM: Unknown
<220> FEATURE:
<223> OTHER INFORMATION: bacteriophage PP7

<400> SEQUENCE: 109
```

```
Met Ser Lys Thr Ile Val Leu Ser Val Gly Glu Ala Thr Arg Thr Leu
1               5                   10                  15

Thr Glu Ile Gln Ser Thr Ala Asp Arg Gln Ile Phe Glu Glu Lys Val
            20                  25                  30

Gly Pro Leu Val Gly Arg Leu Arg Leu Thr Ala Ser Leu Arg Gln Asn
            35                  40                  45

Gly Ala Lys Thr Ala Tyr Arg Val Asn Leu Lys Leu Asp Gln Ala Asp
        50                  55                  60

Trp Asp Cys Ser Thr Ser Val Cys Gly Glu Leu Pro Lys Val Arg Tyr
65                  70                  75                  80

Thr Gln Val Trp Ser His Asp Val Thr Ile Val Ala Asn Ser Thr Glu
                85                  90                  95

Ala Ser Arg Lys Ser Leu Tyr Asp Leu Thr Lys Ser Leu Val Ala Thr
            100                 105                 110

Ser Gln Val Glu Asp Leu Val Val Asn Leu Val Pro Leu Gly Arg
        115                 120                 125
```

<210> SEQ ID NO 110
<211> LENGTH: 19
<212> TYPE: DNA
<213> ORGANISM: Zea mays

<400> SEQUENCE: 110
ctgaatgcct gcgagcatc                                              19

<210> SEQ ID NO 111
<211> LENGTH: 62
<212> TYPE: PRT
<213> ORGANISM: Zea mays

<400> SEQUENCE: 111

```
Met Lys Ser Ile Arg Cys Lys Asn Cys Asn Lys Leu Leu Phe Lys Ala
1               5                   10                  15

Asp Ser Phe Asp His Ile Glu Ile Arg Cys Pro Arg Cys Lys Arg His
            20                  25                  30

Ile Ile Met Leu Asn Ala Cys Glu His Pro Thr Glu Lys His Cys Gly
        35                  40                  45

Lys Arg Glu Lys Ile Thr His Ser Asp Glu Thr Val Arg Tyr
    50                  55                  60
```

<210> SEQ ID NO 112
<211> LENGTH: 24
<212> TYPE: PRT
<213> ORGANISM: Artificial
<220> FEATURE:
<223> OTHER INFORMATION: GCN4 sequence

<400> SEQUENCE: 112

```
Glu Glu Leu Leu Ser Lys Asn Tyr His Leu Glu Asn Glu Val Ala Arg
1               5                   10                  15

Leu Lys Lys Gly Ser Gly Ser Gly
            20
```

<210> SEQ ID NO 113
<211> LENGTH: 241
<212> TYPE: PRT
<213> ORGANISM: Artificial
<220> FEATURE:
<223> OTHER INFORMATION: 10-mer GCN4 sequence

<400> SEQUENCE: 113

Glu Glu Glu Leu Leu Ser Lys Asn Tyr His Leu Glu Asn Glu Val Ala
1               5                   10                  15

Arg Leu Lys Lys Gly Ser Gly Ser Gly Glu Glu Leu Leu Ser Lys Asn
            20                  25                  30

Tyr His Leu Glu Asn Glu Val Ala Arg Leu Lys Lys Gly Ser Gly Ser
                35                  40                  45

Gly Glu Glu Leu Leu Ser Lys Asn Tyr His Leu Glu Asn Glu Val Ala
    50                  55                  60

Arg Leu Lys Lys Gly Ser Gly Ser Gly Glu Glu Leu Leu Ser Lys Asn
65                  70                  75                  80

Tyr His Leu Glu Asn Glu Val Ala Arg Leu Lys Lys Gly Ser Gly Ser
                85                  90                  95

Gly Glu Glu Leu Leu Ser Lys Asn Tyr His Leu Glu Asn Glu Val Ala
                100                 105                 110

Arg Leu Lys Lys Gly Ser Gly Ser Gly Glu Glu Leu Leu Ser Lys Asn
            115                 120                 125

Tyr His Leu Glu Asn Glu Val Ala Arg Leu Lys Lys Gly Ser Gly Ser
            130                 135                 140

Gly Glu Glu Leu Leu Ser Lys Asn Tyr His Leu Glu Asn Glu Val Ala
145                 150                 155                 160

Arg Leu Lys Lys Gly Ser Gly Ser Gly Glu Glu Leu Leu Ser Lys Asn
                165                 170                 175

Tyr His Leu Glu Asn Glu Val Ala Arg Leu Lys Lys Gly Ser Gly Ser
                180                 185                 190

Gly Glu Glu Leu Leu Ser Lys Asn Tyr His Leu Glu Asn Glu Val Ala
            195                 200                 205

Arg Leu Lys Lys Gly Ser Gly Ser Gly Glu Glu Leu Leu Ser Lys Asn
        210                 215                 220

Tyr His Leu Glu Asn Glu Val Ala Arg Leu Lys Lys Gly Ser Gly Ser
225                 230                 235                 240

Gly

<210> SEQ ID NO 114
<211> LENGTH: 277
<212> TYPE: PRT
<213> ORGANISM: Artificial
<220> FEATURE:
<223> OTHER INFORMATION: ScFv antibody

<400> SEQUENCE: 114

Met Gly Pro Asp Ile Val Met Thr Gln Ser Pro Ser Ser Leu Ser Ala
1               5                   10                  15

Ser Val Gly Asp Arg Val Thr Ile Thr Cys Arg Ser Ser Thr Gly Ala
            20                  25                  30

Val Thr Thr Ser Asn Tyr Ala Ser Trp Val Gln Glu Lys Pro Gly Lys
                35                  40                  45

Leu Phe Lys Gly Leu Ile Gly Gly Thr Asn Asn Arg Ala Pro Gly Val
    50                  55                  60

Pro Ser Arg Phe Ser Gly Ser Leu Ile Gly Asp Lys Ala Thr Leu Thr
65                  70                  75                  80

Ile Ser Ser Leu Gln Pro Glu Asp Phe Ala Thr Tyr Phe Cys Ala Leu
                85                  90                  95

Trp Tyr Ser Asn His Trp Val Phe Gly Gln Gly Thr Lys Val Glu Leu
                100                 105                 110

```
Lys Arg Gly Gly Gly Ser Gly Gly Gly Ser Gly Gly Gly
        115                 120                 125

Ser Ser Gly Gly Ser Glu Val Lys Leu Leu Glu Ser Gly Gly Gly
        130                 135                 140

Leu Val Gln Pro Gly Gly Ser Leu Lys Leu Ser Cys Ala Val Ser Gly
145                 150                 155                 160

Phe Ser Leu Thr Asp Tyr Gly Val Asn Trp Val Arg Gln Ala Pro Gly
                165                 170                 175

Arg Gly Leu Glu Trp Ile Gly Val Ile Trp Gly Asp Gly Ile Thr Asp
                180                 185                 190

Tyr Asn Ser Ala Leu Lys Asp Arg Phe Ile Ile Ser Lys Asp Asn Gly
            195                 200                 205

Lys Asn Thr Val Tyr Leu Gln Met Ser Lys Val Arg Ser Asp Asp Thr
    210                 215                 220

Ala Leu Tyr Tyr Cys Val Thr Gly Leu Phe Asp Tyr Trp Gly Gln Gly
225                 230                 235                 240

Thr Leu Val Thr Val Ser Ser Tyr Pro Tyr Asp Val Pro Asp Tyr Ala
                245                 250                 255

Gly Gly Gly Gly Ser Gly Gly Gly Ser Gly Gly Gly Ser
                260                 265                 270

Gly Gly Gly Gly Ser
        275

<210> SEQ ID NO 115
<211> LENGTH: 1227
<212> TYPE: PRT
<213> ORGANISM: Artificial
<220> FEATURE:
<223> OTHER INFORMATION: LbCpf1

<400> SEQUENCE: 115

Ser Lys Leu Glu Lys Phe Thr Asn Cys Tyr Ser Leu Ser Lys Thr Leu
1               5                   10                  15

Arg Phe Lys Ala Ile Pro Val Gly Lys Thr Gln Glu Asn Ile Asp Asn
                20                  25                  30

Lys Arg Leu Leu Val Glu Asp Glu Lys Arg Ala Glu Asp Tyr Lys Gly
            35                  40                  45

Val Lys Lys Leu Leu Asp Arg Tyr Tyr Leu Ser Phe Ile Asn Asp Val
        50                  55                  60

Leu His Ser Ile Lys Leu Lys Asn Leu Asn Asn Tyr Ile Ser Leu Phe
65              70                  75                  80

Arg Lys Lys Thr Arg Thr Glu Lys Glu Asn Lys Glu Leu Glu Asn Leu
                85                  90                  95

Glu Ile Asn Leu Arg Lys Glu Ile Ala Lys Ala Phe Lys Gly Asn Glu
                100                 105                 110

Gly Tyr Lys Ser Leu Phe Lys Lys Asp Ile Ile Glu Thr Ile Leu Pro
            115                 120                 125

Glu Phe Leu Asp Asp Lys Asp Glu Ile Ala Leu Val Asn Ser Phe Asn
        130                 135                 140

Gly Phe Thr Thr Ala Phe Thr Gly Phe Phe Asp Asn Arg Glu Asn Met
145                 150                 155                 160

Phe Ser Glu Glu Ala Lys Ser Thr Ser Ile Ala Phe Arg Cys Ile Asn
                165                 170                 175

Glu Asn Leu Thr Arg Tyr Ile Ser Asn Met Asp Ile Phe Glu Lys Val
                180                 185                 190
```

-continued

Asp Ala Ile Phe Asp Lys His Glu Val Gln Glu Ile Lys Glu Lys Ile
            195                 200                 205

Leu Asn Ser Asp Tyr Asp Val Glu Asp Phe Phe Gly Glu Phe Phe
        210                 215                 220

Asn Phe Val Leu Thr Gln Glu Gly Ile Asp Val Tyr Asn Ala Ile Ile
225                 230                 235                 240

Gly Gly Phe Val Thr Glu Ser Gly Glu Lys Ile Lys Gly Leu Asn Glu
                245                 250                 255

Tyr Ile Asn Leu Tyr Asn Gln Lys Thr Lys Gln Lys Leu Pro Lys Phe
                260                 265                 270

Lys Pro Leu Tyr Lys Gln Val Leu Ser Asp Arg Glu Ser Leu Ser Phe
            275                 280                 285

Tyr Gly Glu Gly Tyr Thr Ser Asp Glu Glu Val Leu Glu Val Phe Arg
            290                 295                 300

Asn Thr Leu Asn Lys Asn Ser Glu Ile Phe Ser Ser Ile Lys Lys Leu
305                 310                 315                 320

Glu Lys Leu Phe Lys Asn Phe Asp Glu Tyr Ser Ser Ala Gly Ile Phe
                325                 330                 335

Val Lys Asn Gly Pro Ala Ile Ser Thr Ile Ser Lys Asp Ile Phe Gly
            340                 345                 350

Glu Trp Asn Val Ile Arg Asp Lys Trp Asn Ala Glu Tyr Asp Asp Ile
            355                 360                 365

His Leu Lys Lys Lys Ala Val Val Thr Glu Lys Tyr Glu Asp Asp Arg
            370                 375                 380

Arg Lys Ser Phe Lys Lys Ile Gly Ser Phe Ser Leu Glu Gln Leu Gln
385                 390                 395                 400

Glu Tyr Ala Asp Ala Asp Leu Ser Val Val Glu Lys Leu Lys Glu Ile
                405                 410                 415

Ile Ile Gln Lys Val Asp Glu Ile Tyr Lys Val Tyr Gly Ser Ser Glu
            420                 425                 430

Lys Leu Phe Asp Ala Asp Phe Val Leu Glu Lys Ser Leu Lys Lys Asn
            435                 440                 445

Asp Ala Val Val Ala Ile Met Lys Asp Leu Leu Asp Ser Val Lys Ser
            450                 455                 460

Phe Glu Asn Tyr Ile Lys Ala Phe Phe Gly Glu Gly Lys Glu Thr Asn
465                 470                 475                 480

Arg Asp Glu Ser Phe Tyr Gly Asp Phe Val Leu Ala Tyr Asp Ile Leu
                485                 490                 495

Leu Lys Val Asp His Ile Tyr Asp Ala Ile Arg Asn Tyr Val Thr Gln
            500                 505                 510

Lys Pro Tyr Ser Lys Asp Lys Phe Lys Leu Tyr Phe Gln Asn Pro Gln
            515                 520                 525

Phe Met Gly Gly Trp Asp Lys Asp Lys Glu Thr Asp Tyr Arg Ala Thr
530                 535                 540

Ile Leu Arg Tyr Gly Ser Lys Tyr Tyr Leu Ala Ile Met Asp Lys Lys
545                 550                 555                 560

Tyr Ala Lys Cys Leu Gln Lys Ile Asp Lys Asp Asp Val Asn Gly Asn
                565                 570                 575

Tyr Glu Lys Ile Asn Tyr Lys Leu Leu Pro Gly Pro Asn Lys Met Leu
            580                 585                 590

Pro Lys Val Phe Phe Ser Lys Lys Trp Met Ala Tyr Tyr Asn Pro Ser
            595                 600                 605

-continued

Glu Asp Ile Gln Lys Ile Tyr Lys Asn Gly Thr Phe Lys Lys Gly Asp
610                615                620

Met Phe Asn Leu Asn Asp Cys His Lys Leu Ile Asp Phe Phe Lys Asp
625                630                635                640

Ser Ile Ser Arg Tyr Pro Lys Trp Ser Asn Ala Tyr Asp Phe Asn Phe
                645                650                655

Ser Glu Thr Glu Lys Tyr Lys Asp Ile Ala Gly Phe Tyr Arg Glu Val
                660                665                670

Glu Glu Gln Gly Tyr Lys Val Ser Phe Glu Ser Ala Ser Lys Lys Glu
                675                680                685

Val Asp Lys Leu Val Glu Glu Gly Lys Leu Tyr Met Phe Gln Ile Tyr
690                695                700

Asn Lys Asp Phe Ser Asp Lys Ser His Gly Thr Pro Asn Leu His Thr
705                710                715                720

Met Tyr Phe Lys Leu Leu Phe Asp Glu Asn Asn His Gly Gln Ile Arg
                725                730                735

Leu Ser Gly Gly Ala Glu Leu Phe Met Arg Arg Ala Ser Leu Lys Lys
                740                745                750

Glu Glu Leu Val Val His Pro Ala Asn Ser Pro Ile Ala Asn Lys Asn
                755                760                765

Pro Asp Asn Pro Lys Lys Thr Thr Leu Ser Tyr Asp Val Tyr Lys
770                775                780

Asp Lys Arg Phe Ser Glu Asp Gln Tyr Glu Leu His Ile Pro Ile Ala
785                790                795                800

Ile Asn Lys Cys Pro Lys Asn Ile Phe Lys Ile Asn Thr Glu Val Arg
                805                810                815

Val Leu Leu Lys His Asp Asp Asn Pro Tyr Val Ile Gly Ile Ala Arg
                820                825                830

Gly Glu Arg Asn Leu Leu Tyr Ile Val Val Asp Gly Lys Gly Asn
                835                840                845

Ile Val Glu Gln Tyr Ser Leu Asn Glu Ile Ile Asn Asn Phe Asn Gly
                850                855                860

Ile Arg Ile Lys Thr Asp Tyr His Ser Leu Leu Asp Lys Lys Glu Lys
865                870                875                880

Glu Arg Phe Glu Ala Arg Gln Asn Trp Thr Ser Ile Glu Asn Ile Lys
                885                890                895

Glu Leu Lys Ala Gly Tyr Ile Ser Gln Val Val His Lys Ile Cys Glu
                900                905                910

Leu Val Glu Lys Tyr Asp Ala Val Ile Ala Leu Glu Asp Leu Asn Ser
                915                920                925

Gly Phe Lys Asn Ser Arg Val Lys Val Glu Lys Gln Val Tyr Gln Lys
930                935                940

Phe Glu Lys Met Leu Ile Asp Lys Leu Asn Tyr Met Val Asp Lys Lys
945                950                955                960

Ser Asn Pro Cys Ala Thr Gly Gly Ala Leu Lys Gly Tyr Gln Ile Thr
                965                970                975

Asn Lys Phe Glu Ser Phe Lys Ser Met Ser Thr Gln Asn Gly Phe Ile
                980                985                990

Phe Tyr Ile Pro Ala Trp Leu Thr Ser Lys Ile Asp Pro Ser Thr Gly
                995                1000                1005

Phe Val Asn Leu Leu Lys Thr Lys Tyr Thr Ser Ile Ala Asp Ser
                1010                1015                1020

Lys Lys Phe Ile Ser Ser Phe Asp Arg Ile Met Tyr Val Pro Glu

```
                1025                1030                1035

Glu  Asp  Leu  Phe  Glu  Phe  Ala  Leu  Asp  Tyr  Lys  Asn  Phe  Ser  Arg
               1040                1045                1050

Thr  Asp  Ala  Asp  Tyr  Ile  Lys  Lys  Trp  Lys  Leu  Tyr  Ser  Tyr  Gly
               1055                1060                1065

Asn  Arg  Ile  Arg  Ile  Phe  Arg  Asn  Pro  Lys  Lys  Asn  Asn  Val  Phe
               1070                1075                1080

Asp  Trp  Glu  Glu  Val  Cys  Leu  Thr  Ser  Ala  Tyr  Lys  Glu  Leu  Phe
               1085                1090                1095

Asn  Lys  Tyr  Gly  Ile  Asn  Tyr  Gln  Gln  Gly  Asp  Ile  Arg  Ala  Leu
               1100                1105                1110

Leu  Cys  Glu  Gln  Ser  Asp  Lys  Ala  Phe  Tyr  Ser  Ser  Phe  Met  Ala
               1115                1120                1125

Leu  Met  Ser  Leu  Met  Leu  Gln  Met  Arg  Asn  Ser  Ile  Thr  Gly  Arg
               1130                1135                1140

Thr  Asp  Val  Asp  Phe  Leu  Ile  Ser  Pro  Val  Lys  Asn  Ser  Asp  Gly
               1145                1150                1155

Ile  Phe  Tyr  Asp  Ser  Arg  Asn  Tyr  Glu  Ala  Gln  Glu  Asn  Ala  Ile
               1160                1165                1170

Leu  Pro  Lys  Asn  Ala  Asp  Ala  Asn  Gly  Ala  Tyr  Asn  Ile  Ala  Arg
               1175                1180                1185

Lys  Val  Leu  Trp  Ala  Ile  Gly  Gln  Phe  Lys  Lys  Ala  Glu  Asp  Glu
               1190                1195                1200

Lys  Leu  Asp  Lys  Val  Lys  Ile  Ala  Ile  Ser  Asn  Lys  Glu  Trp  Leu
               1205                1210                1215

Glu  Tyr  Ala  Gln  Thr  Ser  Val  Lys  His
               1220                1225

<210> SEQ ID NO 116
<211> LENGTH: 1307
<212> TYPE: PRT
<213> ORGANISM: Unknown
<220> FEATURE:
<223> OTHER INFORMATION: Acidaminococcus sp.

<400> SEQUENCE: 116

Met  Thr  Gln  Phe  Glu  Gly  Phe  Thr  Asn  Leu  Tyr  Gln  Val  Ser  Lys  Thr
1                   5                   10                  15

Leu  Arg  Phe  Glu  Leu  Ile  Pro  Gln  Gly  Lys  Thr  Leu  Lys  His  Ile  Gln
                    20                  25                  30

Glu  Gln  Gly  Phe  Ile  Glu  Glu  Asp  Lys  Ala  Arg  Asn  Asp  His  Tyr  Lys
            35                  40                  45

Glu  Leu  Lys  Pro  Ile  Ile  Asp  Arg  Ile  Tyr  Lys  Thr  Tyr  Ala  Asp  Gln
        50                  55                  60

Cys  Leu  Gln  Leu  Val  Gln  Leu  Asp  Trp  Glu  Asn  Leu  Ser  Ala  Ala  Ile
65                  70                  75                  80

Asp  Ser  Tyr  Arg  Lys  Glu  Lys  Thr  Glu  Glu  Thr  Arg  Asn  Ala  Leu  Ile
                85                  90                  95

Glu  Glu  Gln  Ala  Thr  Tyr  Arg  Asn  Ala  Ile  His  Asp  Tyr  Phe  Ile  Gly
            100                 105                 110

Arg  Thr  Asp  Asn  Leu  Thr  Asp  Ala  Ile  Asn  Lys  Arg  His  Ala  Glu  Ile
        115                 120                 125

Tyr  Lys  Gly  Leu  Phe  Lys  Ala  Glu  Leu  Phe  Asn  Gly  Lys  Val  Leu  Lys
    130                 135                 140

Gln  Leu  Gly  Thr  Val  Thr  Thr  Thr  Glu  His  Glu  Asn  Ala  Leu  Leu  Arg
```

```
145                 150                 155                 160
Ser Phe Asp Lys Phe Thr Thr Tyr Phe Ser Gly Phe Tyr Glu Asn Arg
                165                 170                 175

Lys Asn Val Phe Ser Ala Glu Asp Ile Ser Thr Ala Ile Pro His Arg
                180                 185                 190

Ile Val Gln Asp Asn Phe Pro Lys Phe Lys Glu Asn Cys His Ile Phe
                195                 200                 205

Thr Arg Leu Ile Thr Ala Val Pro Ser Leu Arg Glu His Phe Glu Asn
            210                 215                 220

Val Lys Lys Ala Ile Gly Ile Phe Val Ser Thr Ser Ile Glu Glu Val
225                 230                 235                 240

Phe Ser Phe Pro Phe Tyr Asn Gln Leu Leu Thr Gln Thr Gln Ile Asp
                245                 250                 255

Leu Tyr Asn Gln Leu Leu Gly Gly Ile Ser Arg Glu Ala Gly Thr Glu
                260                 265                 270

Lys Ile Lys Gly Leu Asn Glu Val Leu Asn Leu Ala Ile Gln Lys Asn
                275                 280                 285

Asp Glu Thr Ala His Ile Ile Ala Ser Leu Pro His Arg Phe Ile Pro
            290                 295                 300

Leu Phe Lys Gln Ile Leu Ser Asp Arg Asn Thr Leu Ser Phe Ile Leu
305                 310                 315                 320

Glu Glu Phe Lys Ser Asp Glu Glu Val Ile Gln Ser Phe Cys Lys Tyr
                325                 330                 335

Lys Thr Leu Leu Arg Asn Glu Asn Val Leu Glu Thr Ala Glu Ala Leu
                340                 345                 350

Phe Asn Glu Leu Asn Ser Ile Asp Leu Thr His Ile Phe Ile Ser His
                355                 360                 365

Lys Lys Leu Glu Thr Ile Ser Ser Ala Leu Cys Asp His Trp Asp Thr
            370                 375                 380

Leu Arg Asn Ala Leu Tyr Glu Arg Arg Ile Ser Glu Leu Thr Gly Lys
385                 390                 395                 400

Ile Thr Lys Ser Ala Lys Glu Lys Val Gln Arg Ser Leu Lys His Glu
                405                 410                 415

Asp Ile Asn Leu Gln Glu Ile Ile Ser Ala Ala Gly Lys Glu Leu Ser
                420                 425                 430

Glu Ala Phe Lys Gln Lys Thr Ser Glu Ile Leu Ser His Ala His Ala
                435                 440                 445

Ala Leu Asp Gln Pro Leu Pro Thr Thr Leu Lys Lys Gln Glu Glu Lys
            450                 455                 460

Glu Ile Leu Lys Ser Gln Leu Asp Ser Leu Leu Gly Leu Tyr His Leu
465                 470                 475                 480

Leu Asp Trp Phe Ala Val Asp Glu Ser Asn Glu Val Asp Pro Glu Phe
                485                 490                 495

Ser Ala Arg Leu Thr Gly Ile Lys Leu Glu Met Glu Pro Ser Leu Ser
                500                 505                 510

Phe Tyr Asn Lys Ala Arg Asn Tyr Ala Thr Lys Lys Pro Tyr Ser Val
                515                 520                 525

Glu Lys Phe Lys Leu Asn Phe Gln Met Pro Thr Leu Ala Ser Gly Trp
                530                 535                 540

Asp Val Asn Lys Glu Lys Asn Asn Gly Ala Ile Leu Phe Val Lys Asn
545                 550                 555                 560

Gly Leu Tyr Tyr Leu Gly Ile Met Pro Lys Gln Lys Gly Arg Tyr Lys
                565                 570                 575
```

```
Ala Leu Ser Phe Glu Pro Thr Glu Lys Thr Ser Glu Gly Phe Asp Lys
            580                 585                 590

Met Tyr Tyr Asp Tyr Phe Pro Asp Ala Ala Lys Met Ile Pro Lys Cys
        595                 600                 605

Ser Thr Gln Leu Lys Ala Val Thr Ala His Phe Gln Thr His Thr Thr
    610                 615                 620

Pro Ile Leu Leu Ser Asn Asn Phe Ile Glu Pro Leu Glu Ile Thr Lys
625                 630                 635                 640

Glu Ile Tyr Asp Leu Asn Asn Pro Glu Lys Glu Pro Lys Lys Phe Gln
                645                 650                 655

Thr Ala Tyr Ala Lys Lys Thr Gly Asp Gln Lys Gly Tyr Arg Glu Ala
            660                 665                 670

Leu Cys Lys Trp Ile Asp Phe Thr Arg Asp Phe Leu Ser Lys Tyr Thr
        675                 680                 685

Lys Thr Thr Ser Ile Asp Leu Ser Ser Leu Arg Pro Ser Ser Gln Tyr
    690                 695                 700

Lys Asp Leu Gly Glu Tyr Tyr Ala Glu Leu Asn Pro Leu Leu Tyr His
705                 710                 715                 720

Ile Ser Phe Gln Arg Ile Ala Glu Lys Glu Ile Met Asp Ala Val Glu
                725                 730                 735

Thr Gly Lys Leu Tyr Leu Phe Gln Ile Tyr Asn Lys Asp Phe Ala Lys
            740                 745                 750

Gly His His Gly Lys Pro Asn Leu His Thr Leu Tyr Trp Thr Gly Leu
        755                 760                 765

Phe Ser Pro Glu Asn Leu Ala Lys Thr Ser Ile Lys Leu Asn Gly Gln
    770                 775                 780

Ala Glu Leu Phe Tyr Arg Pro Lys Ser Arg Met Lys Arg Met Ala His
785                 790                 795                 800

Arg Leu Gly Glu Lys Met Leu Asn Lys Lys Leu Lys Asp Gln Lys Thr
                805                 810                 815

Pro Ile Pro Asp Thr Leu Tyr Gln Glu Leu Tyr Asp Tyr Val Asn His
            820                 825                 830

Arg Leu Ser His Asp Leu Ser Asp Glu Ala Arg Ala Leu Leu Pro Asn
        835                 840                 845

Val Ile Thr Lys Glu Val Ser His Glu Ile Ile Lys Asp Arg Arg Phe
850                 855                 860

Thr Ser Asp Lys Phe Phe Phe His Val Pro Ile Thr Leu Asn Tyr Gln
865                 870                 875                 880

Ala Ala Asn Ser Pro Ser Lys Phe Asn Gln Arg Val Asn Ala Tyr Leu
                885                 890                 895

Lys Glu His Pro Glu Thr Pro Ile Ile Gly Ile Asp Arg Gly Glu Arg
            900                 905                 910

Asn Leu Ile Tyr Ile Thr Val Ile Asp Ser Thr Gly Lys Ile Leu Glu
        915                 920                 925

Gln Arg Ser Leu Asn Thr Ile Gln Gln Phe Asp Tyr Gln Lys Lys Leu
    930                 935                 940

Asp Asn Arg Glu Lys Glu Arg Val Ala Ala Arg Gln Ala Trp Ser Val
945                 950                 955                 960

Val Gly Thr Ile Lys Asp Leu Lys Gln Gly Tyr Leu Ser Gln Val Ile
                965                 970                 975

His Glu Ile Val Asp Leu Met Ile His Tyr Gln Ala Val Val Val Leu
            980                 985                 990
```

```
Glu Asn Leu Asn Phe Gly Phe Lys Ser Lys Arg Thr Gly Ile Ala Glu
            995                 1000                1005

Lys Ala Val Tyr Gln Gln Phe Glu Lys Met Leu Ile Asp Lys Leu
        1010                1015                1020

Asn Cys Leu Val Leu Lys Asp Tyr Pro Ala Glu Lys Val Gly Gly
        1025                1030                1035

Val Leu Asn Pro Tyr Gln Leu Thr Asp Gln Phe Thr Ser Phe Ala
        1040                1045                1050

Lys Met Gly Thr Gln Ser Gly Phe Leu Phe Tyr Val Pro Ala Pro
        1055                1060                1065

Tyr Thr Ser Lys Ile Asp Pro Leu Thr Gly Phe Val Asp Pro Phe
        1070                1075                1080

Val Trp Lys Thr Ile Lys Asn His Glu Ser Arg Lys His Phe Leu
        1085                1090                1095

Glu Gly Phe Asp Phe Leu His Tyr Asp Val Lys Thr Gly Asp Phe
        1100                1105                1110

Ile Leu His Phe Lys Met Asn Arg Asn Leu Ser Phe Gln Arg Gly
        1115                1120                1125

Leu Pro Gly Phe Met Pro Ala Trp Asp Ile Val Phe Glu Lys Asn
        1130                1135                1140

Glu Thr Gln Phe Asp Ala Lys Gly Thr Pro Phe Ile Ala Gly Lys
        1145                1150                1155

Arg Ile Val Pro Val Ile Glu Asn His Arg Phe Thr Gly Arg Tyr
        1160                1165                1170

Arg Asp Leu Tyr Pro Ala Asn Glu Leu Ile Ala Leu Leu Glu Glu
        1175                1180                1185

Lys Gly Ile Val Phe Arg Asp Gly Ser Asn Ile Leu Pro Lys Leu
        1190                1195                1200

Leu Glu Asn Asp Asp Ser His Ala Ile Asp Thr Met Val Ala Leu
        1205                1210                1215

Ile Arg Ser Val Leu Gln Met Arg Asn Ser Asn Ala Ala Thr Gly
        1220                1225                1230

Glu Asp Tyr Ile Asn Ser Pro Val Arg Asp Leu Asn Gly Val Cys
        1235                1240                1245

Phe Asp Ser Arg Phe Gln Asn Pro Glu Trp Pro Met Asp Ala Asp
        1250                1255                1260

Ala Asn Gly Ala Tyr His Ile Ala Leu Lys Gly Gln Leu Leu Leu
        1265                1270                1275

Asn His Leu Lys Glu Ser Lys Asp Leu Lys Leu Gln Asn Gly Ile
        1280                1285                1290

Ser Asn Gln Asp Trp Leu Ala Tyr Ile Gln Glu Leu Arg Asn
        1295                1300                1305

<210> SEQ ID NO 117
<211> LENGTH: 1241
<212> TYPE: PRT
<213> ORGANISM: Unknown
<220> FEATURE:
<223> OTHER INFORMATION: Butyrivibrio proteoclasticus

<400> SEQUENCE: 117

Met Leu Leu Tyr Glu Asn Tyr Thr Lys Arg Asn Gln Ile Thr Lys Ser
1               5                   10                  15

Leu Arg Leu Glu Leu Arg Pro Gln Gly Lys Thr Leu Arg Asn Ile Lys
            20                  25                  30
```

-continued

Glu Leu Asn Leu Leu Glu Gln Asp Lys Ala Ile Tyr Ala Leu Leu Glu
            35                  40                  45

Arg Leu Lys Pro Val Ile Asp Glu Gly Ile Lys Asp Ile Ala Arg Asp
 50                  55                  60

Thr Leu Lys Asn Cys Glu Leu Ser Phe Glu Lys Leu Tyr Glu His Phe
65                  70                  75                  80

Leu Ser Gly Asp Lys Lys Ala Tyr Ala Lys Glu Ser Glu Arg Leu Lys
                85                  90                  95

Lys Glu Ile Val Lys Thr Leu Ile Lys Asn Leu Pro Glu Gly Ile Gly
            100                 105                 110

Lys Ile Ser Glu Ile Asn Ser Ala Lys Tyr Leu Asn Gly Val Leu Tyr
            115                 120                 125

Asp Phe Ile Asp Lys Thr His Lys Asp Ser Glu Glu Lys Gln Asn Ile
            130                 135                 140

Leu Ser Asp Ile Leu Glu Thr Lys Gly Tyr Leu Ala Leu Phe Ser Lys
145                 150                 155                 160

Phe Leu Thr Ser Arg Ile Thr Thr Leu Glu Gln Ser Met Pro Lys Arg
                165                 170                 175

Val Ile Glu Asn Phe Glu Ile Tyr Ala Ala Asn Ile Pro Lys Met Gln
            180                 185                 190

Asp Ala Leu Glu Arg Gly Ala Val Ser Phe Ala Ile Glu Tyr Glu Ser
            195                 200                 205

Ile Cys Ser Val Asp Tyr Tyr Asn Gln Ile Leu Ser Gln Glu Asp Ile
            210                 215                 220

Asp Ser Tyr Asn Arg Leu Ile Ser Gly Ile Met Asp Glu Asp Gly Ala
225                 230                 235                 240

Lys Glu Lys Gly Ile Asn Gln Thr Ile Ser Glu Lys Asn Ile Lys Ile
                245                 250                 255

Lys Ser Glu His Leu Glu Glu Lys Pro Phe Arg Ile Leu Lys Gln Leu
            260                 265                 270

His Lys Gln Ile Leu Glu Glu Arg Glu Lys Ala Phe Thr Ile Asp His
            275                 280                 285

Ile Asp Ser Asp Glu Glu Val Val Gln Val Thr Lys Glu Ala Phe Glu
            290                 295                 300

Gln Thr Lys Glu Gln Trp Glu Asn Ile Lys Lys Ile Asn Gly Phe Tyr
305                 310                 315                 320

Ala Lys Asp Pro Gly Asp Ile Thr Leu Phe Ile Val Val Gly Pro Asn
                325                 330                 335

Gln Thr His Val Leu Ser Gln Leu Ile Tyr Gly Glu His Asp Arg Ile
            340                 345                 350

Arg Leu Leu Leu Glu Glu Tyr Glu Lys Asn Thr Leu Glu Val Leu Pro
            355                 360                 365

Arg Arg Thr Lys Ser Glu Asp Ala Arg Tyr Asp Lys Phe Val Asn Ala
            370                 375                 380

Val Pro Lys Lys Val Ala Lys Glu Ser His Thr Phe Asp Gly Leu Gln
385                 390                 395                 400

Lys Met Thr Gly Asp Asp Arg Leu Phe Ile Leu Tyr Arg Asp Glu Leu
                405                 410                 415

Ala Arg Asn Tyr Met Arg Ile Lys Glu Ala Tyr Gly Thr Phe Glu Arg
            420                 425                 430

Asp Ile Leu Lys Ser Arg Arg Gly Ile Lys Gly Asn Arg Asp Val Gln
            435                 440                 445

Glu Ser Leu Val Ser Phe Tyr Asp Glu Leu Thr Lys Phe Arg Ser Ala

```
            450                 455                 460
Leu Arg Ile Ile Asn Ser Gly Asn Asp Glu Lys Ala Asp Pro Ile Phe
465                 470                 475                 480

Tyr Asn Thr Phe Asp Gly Ile Phe Glu Lys Ala Asn Arg Thr Tyr Lys
                    485                 490                 495

Ala Glu Asn Leu Cys Arg Asn Tyr Val Thr Lys Ser Pro Ala Asp Asp
                500                 505                 510

Ala Arg Ile Met Ala Ser Cys Leu Gly Thr Pro Ala Arg Leu Arg Thr
                515                 520                 525

His Trp Trp Asn Gly Glu Asn Phe Ala Ile Asn Asp Val Ala Met
                530                 535                 540

Ile Arg Arg Gly Asp Glu Tyr Tyr Phe Val Leu Thr Pro Asp Val
545                 550                 555                 560

Lys Pro Val Asp Leu Lys Thr Lys Asp Glu Thr Asp Ala Gln Ile Phe
                565                 570                 575

Val Gln Arg Lys Gly Ala Lys Ser Phe Leu Gly Leu Pro Lys Ala Leu
                580                 585                 590

Phe Lys Cys Ile Leu Glu Pro Tyr Phe Glu Ser Pro Glu His Lys Asn
                595                 600                 605

Asp Lys Asn Cys Val Ile Glu Glu Tyr Val Ser Lys Pro Leu Thr Ile
                610                 615                 620

Asp Arg Arg Ala Tyr Asp Ile Phe Lys Asn Gly Thr Phe Lys Lys Thr
625                 630                 635                 640

Asn Ile Gly Ile Asp Gly Leu Thr Glu Glu Lys Phe Lys Asp Asp Cys
                645                 650                 655

Arg Tyr Leu Ile Asp Val Tyr Lys Glu Phe Ile Ala Val Tyr Thr Arg
                660                 665                 670

Tyr Ser Cys Phe Asn Met Ser Gly Leu Lys Arg Ala Asp Glu Tyr Asn
                675                 680                 685

Asp Ile Gly Glu Phe Phe Ser Asp Val Asp Thr Arg Leu Cys Thr Met
                690                 695                 700

Glu Trp Ile Pro Val Ser Phe Glu Arg Ile Asn Asp Met Val Asp Lys
705                 710                 715                 720

Lys Glu Gly Leu Leu Phe Leu Val Arg Ser Met Phe Leu Tyr Asn Arg
                725                 730                 735

Pro Arg Lys Pro Tyr Glu Arg Thr Phe Ile Gln Leu Phe Ser Asp Ser
                740                 745                 750

Asn Met Glu His Thr Ser Met Leu Leu Asn Ser Arg Ala Met Ile Gln
                755                 760                 765

Tyr Arg Ala Ala Ser Leu Pro Arg Arg Val Thr His Lys Lys Gly Ser
                770                 775                 780

Ile Leu Val Ala Leu Arg Asp Ser Asn Gly His Ile Pro Met His
785                 790                 795                 800

Ile Arg Glu Ala Ile Tyr Lys Met Lys Asn Asn Phe Asp Ile Ser Ser
                805                 810                 815

Glu Asp Phe Ile Met Ala Lys Ala Tyr Leu Ala Glu His Asp Val Ala
                820                 825                 830

Ile Lys Lys Ala Asn Glu Asp Ile Ile Arg Asn Arg Tyr Thr Glu
                835                 840                 845

Asp Lys Phe Phe Leu Ser Leu Ser Tyr Thr Lys Asn Ala Asp Ile Ser
                850                 855                 860

Ala Arg Thr Leu Asp Tyr Ile Asn Asp Lys Val Glu Glu Asp Thr Gln
865                 870                 875                 880
```

-continued

```
Asp Ser Arg Met Ala Val Ile Val Thr Arg Asn Leu Lys Asp Leu Thr
                885                 890                 895

Tyr Val Ala Val Val Asp Glu Lys Asn Asn Val Leu Glu Glu Lys Ser
            900                 905                 910

Leu Asn Glu Ile Asp Gly Val Asn Tyr Arg Glu Leu Leu Lys Glu Arg
        915                 920                 925

Thr Lys Ile Lys Tyr His Asp Lys Thr Arg Leu Trp Gln Tyr Asp Val
    930                 935                 940

Ser Ser Lys Gly Leu Lys Glu Ala Tyr Val Glu Leu Ala Val Thr Gln
945                 950                 955                 960

Ile Ser Lys Leu Ala Thr Lys Tyr Asn Ala Val Val Val Glu Ser
                965                 970                 975

Met Ser Ser Thr Phe Lys Asp Lys Phe Ser Phe Leu Asp Glu Gln Ile
            980                 985                 990

Phe Lys Ala Phe Glu Ala Arg Leu Cys Ala Arg Met Ser Asp Leu Ser
        995                 1000                1005

Phe Asn Thr Ile Lys Glu Gly Glu Ala Gly Ser Ile Ser Asn Pro
    1010                1015                1020

Ile Gln Val Ser Asn Asn Gly Asn Ser Tyr Gln Asp Gly Val
    1025                1030                1035

Ile Tyr Phe Leu Asn Asn Ala Tyr Thr Arg Thr Leu Cys Pro Asp
    1040                1045                1050

Thr Gly Phe Val Asp Val Phe Asp Lys Thr Arg Leu Ile Thr Met
    1055                1060                1065

Gln Ser Lys Arg Gln Phe Phe Ala Lys Met Lys Asp Ile Arg Ile
    1070                1075                1080

Asp Asp Gly Glu Met Leu Phe Thr Phe Asn Leu Glu Glu Tyr Pro
    1085                1090                1095

Thr Lys Arg Leu Leu Asp Arg Lys Glu Trp Thr Val Lys Ile Ala
    1100                1105                1110

Gly Asp Gly Ser Tyr Phe Asp Lys Asp Lys Gly Glu Tyr Val Tyr
    1115                1120                1125

Val Asn Asp Ile Val Arg Glu Gln Ile Ile Pro Ala Leu Leu Glu
    1130                1135                1140

Asp Lys Ala Val Phe Asp Gly Asn Met Ala Glu Lys Phe Leu Asp
    1145                1150                1155

Lys Thr Ala Ile Ser Gly Lys Ser Val Glu Leu Ile Tyr Lys Trp
    1160                1165                1170

Phe Ala Asn Ala Leu Tyr Gly Ile Ile Thr Lys Lys Asp Gly Glu
    1175                1180                1185

Lys Ile Tyr Arg Ser Pro Ile Thr Gly Thr Glu Ile Asp Val Ser
    1190                1195                1200

Lys Asn Thr Thr Tyr Asn Phe Gly Lys Lys Phe Met Phe Lys Gln
    1205                1210                1215

Glu Tyr Arg Gly Asp Gly Asp Phe Leu Asp Ala Phe Leu Asn Tyr
    1220                1225                1230

Met Gln Ala Gln Asp Ile Ala Val
    1235                1240

<210> SEQ ID NO 118
<211> LENGTH: 1238
<212> TYPE: PRT
<213> ORGANISM: Unknown
<220> FEATURE:
```

<223> OTHER INFORMATION: Candidatus Methanoplasma termitum

<400> SEQUENCE: 118

```
Met Asn Asn Tyr Asp Glu Phe Thr Lys Leu Tyr Pro Ile Gln Lys Thr
  1               5                  10                  15

Ile Arg Phe Glu Leu Lys Pro Gln Gly Arg Thr Met Glu His Leu Glu
             20                  25                  30

Thr Phe Asn Phe Phe Glu Glu Asp Arg Asp Arg Ala Glu Lys Tyr Lys
         35                  40                  45

Ile Leu Lys Glu Ala Ile Asp Glu Tyr His Lys Lys Phe Ile Asp Glu
     50                  55                  60

His Leu Thr Asn Met Ser Leu Asp Trp Asn Ser Leu Lys Gln Ile Ser
 65                  70                  75                  80

Glu Lys Tyr Tyr Lys Ser Arg Glu Glu Lys Asp Lys Val Phe Leu
                 85                  90                  95

Ser Glu Gln Lys Arg Met Arg Gln Glu Ile Val Ser Glu Phe Lys Lys
                100                 105                 110

Asp Asp Arg Phe Lys Asp Leu Phe Ser Lys Lys Leu Phe Ser Glu Leu
            115                 120                 125

Leu Lys Glu Glu Ile Tyr Lys Lys Gly Asn His Gln Glu Ile Asp Ala
130                 135                 140

Leu Lys Ser Phe Asp Lys Phe Ser Gly Tyr Phe Ile Gly Leu His Glu
145                 150                 155                 160

Asn Arg Lys Asn Met Tyr Ser Asp Gly Asp Glu Ile Thr Ala Ile Ser
                165                 170                 175

Asn Arg Ile Val Asn Glu Asn Phe Pro Lys Phe Leu Asp Asn Leu Gln
            180                 185                 190

Lys Tyr Gln Glu Ala Arg Lys Lys Tyr Pro Glu Trp Ile Ile Lys Ala
        195                 200                 205

Glu Ser Ala Leu Val Ala His Asn Ile Lys Met Asp Ile Val Phe Ser
210                 215                 220

Leu Glu Tyr Phe Asn Lys Val Leu Asn Gln Glu Gly Ile Gln Arg Tyr
225                 230                 235                 240

Asn Leu Ala Leu Gly Gly Tyr Val Thr Lys Ser Gly Glu Lys Met Met
                245                 250                 255

Gly Leu Asn Asp Ala Leu Asn Leu Ala His Gln Ser Gly Lys Ser Ser
            260                 265                 270

Lys Gly Arg Ile His Met Thr Pro Leu Phe Lys Gln Ile Leu Ser Glu
        275                 280                 285

Lys Glu Ser Phe Ser Tyr Ile Pro Asp Val Phe Thr Glu Asp Ser Gln
290                 295                 300

Leu Leu Pro Ser Ile Gly Gly Phe Phe Ala Gln Ile Glu Asn Asp Lys
305                 310                 315                 320

Asp Gly Asn Ile Phe Asp Arg Ala Leu Glu Leu Ile Ser Ser Tyr Ala
                325                 330                 335

Glu Tyr Asp Thr Glu Arg Ile Tyr Ile Arg Gln Ala Asp Ile Asn Arg
            340                 345                 350

Val Ser Asn Val Ile Phe Gly Glu Trp Gly Thr Leu Gly Gly Leu Met
        355                 360                 365

Arg Glu Tyr Lys Ala Asp Ser Ile Asn Asp Ile Asn Leu Glu Arg Thr
370                 375                 380

Cys Lys Lys Val Asp Lys Trp Leu Asp Ser Lys Glu Phe Ala Leu Ser
385                 390                 395                 400
```

-continued

Asp Val Leu Glu Ala Ile Asp Arg Thr Gly Asn Asn Asp Ala Phe Asn
             405                 410                 415

Glu Tyr Ile Ser Lys Met Arg Thr Ala Arg Glu Lys Ile Asp Ala Ala
         420                 425                 430

Arg Lys Glu Met Lys Phe Ile Ser Glu Lys Ile Ser Gly Asp Glu Glu
     435                 440                 445

Ser Ile His Ile Ile Lys Thr Leu Leu Asp Ser Val Gln Gln Phe Leu
 450                 455                 460

His Phe Phe Asn Leu Phe Lys Ala Arg Gln Asp Ile Pro Leu Asp Gly
465                 470                 475                 480

Ala Phe Tyr Ala Glu Phe Asp Glu Val His Ser Lys Leu Phe Ala Ile
             485                 490                 495

Val Pro Leu Tyr Asn Lys Val Arg Asn Tyr Leu Thr Lys Asn Asn Leu
         500                 505                 510

Asn Thr Lys Lys Ile Lys Leu Asn Phe Lys Asn Pro Thr Leu Ala Asn
     515                 520                 525

Gly Trp Asp Gln Asn Lys Val Tyr Asp Tyr Ala Ser Leu Ile Phe Leu
 530                 535                 540

Arg Asp Gly Asn Tyr Tyr Leu Gly Ile Ile Asn Pro Lys Arg Lys Lys
545                 550                 555                 560

Asn Ile Lys Phe Glu Gln Gly Ser Gly Asn Gly Pro Phe Tyr Arg Lys
             565                 570                 575

Met Val Tyr Lys Gln Ile Pro Gly Pro Asn Lys Asn Leu Arg Pro Val
         580                 585                 590

Phe Leu Thr Ser Thr Lys Gly Lys Lys Glu Tyr Lys Pro Ser Lys Glu
     595                 600                 605

Ile Ile Glu Gly Tyr Glu Ala Asp Lys His Ile Arg Gly Asp Lys Phe
 610                 615                 620

Asp Leu Asp Phe Cys His Lys Leu Ile Asp Phe Phe Lys Glu Ser Ile
625                 630                 635                 640

Glu Lys His Lys Asp Trp Ser Lys Phe Asn Phe Tyr Phe Ser Pro Thr
             645                 650                 655

Glu Ser Tyr Gly Asp Ile Ser Glu Phe Tyr Leu Asp Val Glu Lys Gln
         660                 665                 670

Gly Tyr Arg Met His Phe Glu Asn Ile Ser Ala Glu Thr Ile Asp Glu
     675                 680                 685

Tyr Val Glu Lys Gly Asp Leu Phe Leu Phe Gln Ile Tyr Asn Lys Asp
 690                 695                 700

Phe Val Lys Ala Ala Thr Gly Lys Lys Asp Met His Thr Ile Tyr Trp
705                 710                 715                 720

Asn Ala Ala Phe Ser Pro Glu Asn Leu Gln Asp Val Val Lys Leu
             725                 730                 735

Asn Gly Glu Ala Glu Leu Phe Tyr Arg Asp Lys Ser Asp Ile Lys Glu
         740                 745                 750

Ile Val His Arg Glu Gly Glu Ile Leu Val Asn Arg Thr Tyr Asn Gly
     755                 760                 765

Arg Thr Pro Val Pro Asp Lys Ile His Lys Lys Leu Thr Asp Tyr His
 770                 775                 780

Asn Gly Arg Thr Lys Asp Leu Gly Glu Ala Lys Glu Tyr Leu Asp Lys
785                 790                 795                 800

Val Arg Tyr Phe Lys Ala His Tyr Asp Ile Thr Lys Asp Arg Arg Tyr
             805                 810                 815

Leu Asn Asp Lys Ile Tyr Phe His Val Pro Leu Thr Leu Asn Phe Lys

-continued

```
                820             825             830
Ala Asn Gly Lys Lys Asn Leu Asn Lys Met Val Ile Glu Lys Phe Leu
                835             840             845
Ser Asp Glu Lys Ala His Ile Ile Gly Ile Asp Arg Gly Glu Arg Asn
    850             855             860
Leu Leu Tyr Tyr Ser Ile Ile Asp Arg Ser Gly Lys Ile Ile Asp Gln
865             870             875             880
Gln Ser Leu Asn Val Ile Asp Gly Phe Asp Tyr Arg Glu Lys Leu Asn
                885             890             895
Gln Arg Glu Ile Glu Met Lys Asp Ala Arg Gln Ser Trp Asn Ala Ile
        900             905             910
Gly Lys Ile Lys Asp Leu Lys Glu Gly Tyr Leu Ser Lys Ala Val His
        915             920             925
Glu Ile Thr Lys Met Ala Ile Gln Tyr Asn Ala Ile Val Val Met Glu
        930             935             940
Glu Leu Asn Tyr Gly Phe Lys Arg Gly Arg Phe Lys Val Glu Lys Gln
945             950             955             960
Ile Tyr Gln Lys Phe Glu Asn Met Leu Ile Asp Lys Met Asn Tyr Leu
            965             970             975
Val Phe Lys Asp Ala Pro Asp Glu Ser Pro Gly Gly Val Leu Asn Ala
            980             985             990
Tyr Gln Leu Thr Asn Pro Leu Glu Ser Phe Ala Lys Leu Gly Lys Gln
            995             1000            1005
Thr Gly Ile Leu Phe Tyr Val Pro Ala Ala Tyr Thr Ser Lys Ile
    1010            1015            1020
Asp Pro Thr Thr Gly Phe Val Asn Leu Phe Asn Thr Ser Ser Lys
    1025            1030            1035
Thr Asn Ala Gln Glu Arg Lys Glu Phe Leu Gln Lys Phe Glu Ser
    1040            1045            1050
Ile Ser Tyr Ser Ala Lys Asp Gly Gly Ile Phe Ala Phe Ala Phe
    1055            1060            1065
Asp Tyr Arg Lys Phe Gly Thr Ser Lys Thr Asp His Lys Asn Val
    1070            1075            1080
Trp Thr Ala Tyr Thr Asn Gly Glu Arg Met Arg Tyr Ile Lys Glu
    1085            1090            1095
Lys Lys Arg Asn Glu Leu Phe Asp Pro Ser Lys Glu Ile Lys Glu
    1100            1105            1110
Ala Leu Thr Ser Ser Gly Ile Lys Tyr Asp Gly Gly Gln Asn Ile
    1115            1120            1125
Leu Pro Asp Ile Leu Arg Ser Asn Asn Asn Gly Leu Ile Tyr Thr
    1130            1135            1140
Met Tyr Ser Ser Phe Ile Ala Ala Ile Gln Met Arg Val Tyr Asp
    1145            1150            1155
Gly Lys Glu Asp Tyr Ile Ile Ser Pro Ile Lys Asn Ser Lys Gly
    1160            1165            1170
Glu Phe Phe Arg Thr Asp Pro Lys Arg Arg Glu Leu Pro Ile Asp
    1175            1180            1185
Ala Asp Ala Asn Gly Ala Tyr Asn Ile Ala Leu Arg Gly Glu Leu
    1190            1195            1200
Thr Met Arg Ala Ile Ala Glu Lys Phe Asp Pro Asp Ser Glu Lys
    1205            1210            1215
Met Ala Lys Leu Glu Leu Lys His Lys Asp Trp Phe Glu Phe Met
    1220            1225            1230
```

```
Gln Thr Arg Gly Asp
    1235

<210> SEQ ID NO 119
<211> LENGTH: 1281
<212> TYPE: PRT
<213> ORGANISM: Eubacterium eligens

<400> SEQUENCE: 119

Met Asn Gly Asn Arg Ser Ile Val Tyr Arg Glu Phe Val Gly Val Ile
1               5                   10                  15

Pro Val Ala Lys Thr Leu Arg Asn Glu Leu Arg Pro Val Gly His Thr
            20                  25                  30

Gln Glu His Ile Ile Gln Asn Gly Leu Ile Gln Glu Asp Glu Leu Arg
        35                  40                  45

Gln Glu Lys Ser Thr Glu Leu Lys Asn Ile Met Asp Asp Tyr Tyr Arg
    50                  55                  60

Glu Tyr Ile Asp Lys Ser Leu Ser Gly Val Thr Asp Leu Asp Phe Thr
65                  70                  75                  80

Leu Leu Phe Glu Leu Met Asn Leu Val Gln Ser Ser Pro Ser Lys Asp
                85                  90                  95

Asn Lys Lys Ala Leu Glu Lys Glu Gln Ser Lys Met Arg Glu Gln Ile
            100                 105                 110

Cys Thr His Leu Gln Ser Asp Ser Asn Tyr Lys Asn Ile Phe Asn Ala
        115                 120                 125

Lys Leu Leu Lys Glu Ile Leu Pro Asp Phe Ile Lys Asn Tyr Asn Gln
    130                 135                 140

Tyr Asp Val Lys Asp Lys Ala Gly Lys Leu Glu Thr Leu Ala Leu Phe
145                 150                 155                 160

Asn Gly Phe Ser Thr Tyr Phe Thr Asp Phe Phe Glu Lys Arg Lys Asn
                165                 170                 175

Val Phe Thr Lys Glu Ala Val Ser Thr Ser Ile Ala Tyr Arg Ile Val
            180                 185                 190

His Glu Asn Ser Leu Ile Phe Leu Ala Asn Met Thr Ser Tyr Lys Lys
        195                 200                 205

Ile Ser Glu Lys Ala Leu Asp Glu Ile Glu Val Ile Glu Lys Asn Asn
    210                 215                 220

Gln Asp Lys Met Gly Asp Trp Glu Leu Asn Gln Ile Phe Asn Pro Asp
225                 230                 235                 240

Phe Tyr Asn Met Val Leu Ile Gln Ser Gly Ile Asp Phe Tyr Asn Glu
                245                 250                 255

Ile Cys Gly Val Val Asn Ala His Met Asn Leu Tyr Cys Gln Gln Thr
            260                 265                 270

Lys Asn Asn Tyr Asn Leu Phe Lys Met Arg Lys Leu His Lys Gln Ile
        275                 280                 285

Leu Ala Tyr Thr Ser Thr Ser Phe Glu Val Pro Lys Met Phe Glu Asp
    290                 295                 300

Asp Met Ser Val Tyr Asn Ala Val Asn Ala Phe Ile Asp Glu Thr Glu
305                 310                 315                 320

Lys Gly Asn Ile Ile Gly Lys Leu Lys Asp Ile Val Asn Lys Tyr Asp
                325                 330                 335

Glu Leu Asp Glu Lys Arg Ile Tyr Ile Ser Lys Asp Phe Tyr Glu Thr
            340                 345                 350

Leu Ser Cys Phe Met Ser Gly Asn Trp Asn Leu Ile Thr Gly Cys Val
```

-continued

```
            355                 360                 365
Glu Asn Phe Tyr Asp Glu Asn Ile His Ala Lys Gly Lys Ser Lys Glu
            370                 375                 380
Glu Lys Val Lys Lys Ala Val Lys Glu Asp Lys Tyr Lys Ser Ile Asn
385                 390                 395                 400
Asp Val Asn Asp Leu Val Glu Lys Tyr Ile Asp Glu Lys Glu Arg Asn
                    405                 410                 415
Glu Phe Lys Asn Ser Asn Ala Lys Gln Tyr Ile Arg Glu Ile Ser Asn
                    420                 425                 430
Ile Ile Thr Asp Thr Glu Thr Ala His Leu Glu Tyr Asp Asp His Ile
                435                 440                 445
Ser Leu Ile Glu Ser Glu Lys Ala Asp Glu Met Lys Lys Arg Leu
            450                 455                 460
Asp Met Tyr Met Asn Met Tyr His Trp Ala Lys Ala Phe Ile Val Asp
465                 470                 475                 480
Glu Val Leu Asp Arg Asp Glu Met Phe Tyr Ser Asp Ile Asp Asp Ile
                    485                 490                 495
Tyr Asn Ile Leu Glu Asn Ile Val Pro Leu Tyr Asn Arg Val Arg Asn
                    500                 505                 510
Tyr Val Thr Gln Lys Pro Tyr Asn Ser Lys Lys Ile Lys Leu Asn Phe
                515                 520                 525
Gln Ser Pro Thr Leu Ala Asn Gly Trp Ser Gln Ser Lys Glu Phe Asp
            530                 535                 540
Asn Asn Ala Ile Ile Leu Ile Arg Asp Asn Lys Tyr Tyr Leu Ala Ile
545                 550                 555                 560
Phe Asn Ala Lys Asn Lys Pro Asp Lys Lys Ile Ile Gln Gly Asn Ser
                    565                 570                 575
Asp Lys Lys Asn Asp Asn Asp Tyr Lys Lys Met Val Tyr Asn Leu Leu
                    580                 585                 590
Pro Gly Ala Asn Lys Met Leu Pro Lys Val Phe Leu Ser Lys Lys Gly
                595                 600                 605
Ile Glu Thr Phe Lys Pro Ser Asp Tyr Ile Ile Ser Gly Tyr Asn Ala
            610                 615                 620
His Lys His Ile Lys Thr Ser Glu Asn Phe Asp Ile Ser Phe Cys Arg
625                 630                 635                 640
Asp Leu Ile Asp Tyr Phe Lys Asn Ser Ile Glu Lys His Ala Glu Trp
                    645                 650                 655
Arg Lys Tyr Glu Phe Lys Phe Ser Ala Thr Asp Ser Tyr Ser Asp Ile
                    660                 665                 670
Ser Glu Phe Tyr Arg Glu Val Glu Met Gln Gly Tyr Arg Ile Asp Trp
                675                 680                 685
Thr Tyr Ile Ser Glu Ala Asp Ile Asn Lys Leu Asp Glu Glu Gly Lys
            690                 695                 700
Ile Tyr Leu Phe Gln Ile Tyr Asn Lys Asp Phe Ala Glu Asn Ser Thr
705                 710                 715                 720
Gly Lys Glu Asn Leu His Thr Met Tyr Phe Lys Asn Ile Phe Ser Glu
                    725                 730                 735
Glu Asn Leu Asp Lys Ile Ile Lys Leu Asn Gly Gln Ala Glu Leu Phe
                    740                 745                 750
Tyr Arg Arg Ala Ser Val Lys Asn Pro Val Lys His Lys Lys Asp Ser
                755                 760                 765
Val Leu Val Asn Lys Thr Tyr Lys Asn Gln Leu Asp Asn Gly Asp Val
            770                 775                 780
```

```
Val Arg Ile Pro Ile Pro Asp Asp Ile Tyr Asn Glu Ile Tyr Lys Met
785                 790                 795                 800

Tyr Asn Gly Tyr Ile Lys Glu Ser Asp Leu Ser Glu Ala Ala Lys Glu
                805                 810                 815

Tyr Leu Asp Lys Val Glu Val Arg Thr Ala Gln Lys Asp Ile Val Lys
            820                 825                 830

Asp Tyr Arg Tyr Thr Val Asp Lys Tyr Phe Ile His Thr Pro Ile Thr
        835                 840                 845

Ile Asn Tyr Lys Val Thr Ala Arg Asn Asn Val Asn Asp Met Val Val
850                 855                 860

Lys Tyr Ile Ala Gln Asn Asp Asp Ile His Val Ile Gly Ile Asp Arg
865                 870                 875                 880

Gly Glu Arg Asn Leu Ile Tyr Ile Ser Val Ile Asp Ser His Gly Asn
                885                 890                 895

Ile Val Lys Gln Lys Ser Tyr Asn Ile Leu Asn Asn Tyr Asp Tyr Lys
                900                 905                 910

Lys Lys Leu Val Glu Lys Glu Lys Thr Arg Glu Tyr Ala Arg Lys Asn
            915                 920                 925

Trp Lys Ser Ile Gly Asn Ile Lys Glu Leu Lys Glu Gly Tyr Ile Ser
    930                 935                 940

Gly Val Val His Glu Ile Ala Met Leu Ile Val Glu Tyr Asn Ala Ile
945                 950                 955                 960

Ile Ala Met Glu Asp Leu Asn Tyr Gly Phe Lys Arg Gly Arg Phe Lys
                965                 970                 975

Val Glu Arg Gln Val Tyr Gln Lys Phe Glu Ser Met Leu Ile Asn Lys
            980                 985                 990

Leu Asn Tyr Phe Ala Ser Lys Glu Lys Ser Val Asp Glu Pro Gly Gly
        995                 1000                1005

Leu Leu Lys Gly Tyr Gln Leu Thr Tyr Val Pro Asp Asn Ile Lys
    1010                1015                1020

Asn Leu Gly Lys Gln Cys Gly Val Ile Phe Tyr Val Pro Ala Ala
    1025                1030                1035

Phe Thr Ser Lys Ile Asp Pro Ser Thr Gly Phe Ile Ser Ala Phe
    1040                1045                1050

Asn Phe Lys Ser Ile Ser Thr Asn Ala Ser Arg Lys Gln Phe Phe
    1055                1060                1065

Met Gln Phe Asp Glu Ile Arg Tyr Cys Ala Glu Lys Asp Met Phe
    1070                1075                1080

Ser Phe Gly Phe Asp Tyr Asn Asn Phe Asp Thr Tyr Asn Ile Thr
    1085                1090                1095

Met Gly Lys Thr Gln Trp Thr Val Tyr Thr Asn Gly Glu Arg Leu
    1100                1105                1110

Gln Ser Glu Phe Asn Asn Ala Arg Arg Thr Gly Lys Thr Lys Ser
    1115                1120                1125

Ile Asn Leu Thr Glu Thr Ile Lys Leu Leu Leu Glu Asp Asn Glu
    1130                1135                1140

Ile Asn Tyr Ala Asp Gly His Asp Ile Arg Ile Asp Met Glu Lys
    1145                1150                1155

Met Asp Glu Asp Lys Lys Ser Glu Phe Phe Ala Gln Leu Leu Ser
    1160                1165                1170

Leu Tyr Lys Leu Thr Val Gln Met Arg Asn Ser Tyr Thr Glu Ala
    1175                1180                1185
```

```
Glu Glu Gln Glu Asn Gly Ile Ser Tyr Asp Lys Ile Ile Ser Pro
    1190            1195            1200

Val Ile Asn Asp Glu Gly Phe Phe Asp Ser Asp Asn Tyr Lys
    1205            1210            1215

Glu Ser Asp Asp Lys Glu Cys Lys Met Pro Lys Asp Ala Asp Ala
    1220            1225            1230

Asn Gly Ala Tyr Cys Ile Ala Leu Lys Gly Leu Tyr Glu Val Leu
    1235            1240            1245

Lys Ile Lys Ser Glu Trp Thr Glu Asp Gly Phe Asp Arg Asn Cys
    1250            1255            1260

Leu Lys Leu Pro His Ala Glu Trp Leu Asp Phe Ile Gln Asn Lys
    1265            1270            1275

Arg Tyr Glu
    1280

<210> SEQ ID NO 120
<211> LENGTH: 1300
<212> TYPE: PRT
<213> ORGANISM: Unknown
<220> FEATURE:
<223> OTHER INFORMATION: Francisella novicida

<400> SEQUENCE: 120

Met Ser Ile Tyr Gln Glu Phe Val Asn Lys Tyr Ser Leu Ser Lys Thr
1               5                   10                  15

Leu Arg Phe Glu Leu Ile Pro Gln Gly Lys Thr Leu Glu Asn Ile Lys
                20                  25                  30

Ala Arg Gly Leu Ile Leu Asp Asp Glu Lys Arg Ala Lys Asp Tyr Lys
            35                  40                  45

Lys Ala Lys Gln Ile Ile Asp Lys Tyr His Gln Phe Phe Ile Glu Glu
        50                  55                  60

Ile Leu Ser Ser Val Cys Ile Ser Glu Asp Leu Leu Gln Asn Tyr Ser
65                  70                  75                  80

Asp Val Tyr Phe Lys Leu Lys Lys Ser Asp Asp Asn Leu Gln Lys
                85                  90                  95

Asp Phe Lys Ser Ala Lys Asp Thr Ile Lys Lys Gln Ile Ser Glu Tyr
            100                 105                 110

Ile Lys Asp Ser Glu Lys Phe Lys Asn Leu Phe Asn Gln Asn Leu Ile
        115                 120                 125

Asp Ala Lys Lys Gly Gln Glu Ser Asp Leu Ile Leu Trp Leu Lys Gln
    130                 135                 140

Ser Lys Asp Asn Gly Ile Glu Leu Phe Lys Ala Asn Ser Asp Ile Thr
145                 150                 155                 160

Asp Ile Asp Glu Ala Leu Glu Ile Ile Lys Ser Phe Lys Gly Trp Thr
                165                 170                 175

Thr Tyr Phe Lys Gly Phe His Glu Asn Arg Lys Val Asn Tyr Ser Ser
            180                 185                 190

Asn Asp Ile Pro Thr Ser Ile Ile Tyr Arg Ile Val Asp Asn Leu
        195                 200                 205

Pro Lys Phe Leu Glu Asn Lys Ala Lys Tyr Glu Ser Leu Lys Asp Lys
    210                 215                 220

Ala Pro Glu Ala Ile Asn Tyr Glu Gln Ile Lys Lys Asp Leu Ala Glu
225                 230                 235                 240

Glu Leu Thr Phe Asp Ile Asp Tyr Lys Thr Ser Glu Val Asn Gln Arg
                245                 250                 255
```

```
Val Phe Ser Leu Asp Glu Val Phe Glu Ile Ala Asn Phe Asn Asn Tyr
            260                 265                 270

Leu Asn Gln Ser Gly Ile Thr Lys Phe Asn Thr Ile Ile Gly Gly Lys
        275                 280                 285

Phe Val Asn Gly Glu Asn Thr Lys Arg Lys Gly Ile Asn Glu Tyr Ile
    290                 295                 300

Asn Leu Tyr Ser Gln Gln Ile Asn Asp Lys Thr Leu Lys Lys Tyr Lys
305                 310                 315                 320

Met Ser Val Leu Phe Lys Gln Ile Leu Ser Asp Thr Glu Ser Lys Ser
                325                 330                 335

Phe Val Ile Asp Lys Leu Glu Asp Asp Ser Asp Val Val Thr Thr Met
            340                 345                 350

Gln Ser Phe Tyr Glu Gln Ile Ala Ala Phe Lys Thr Val Glu Glu Lys
        355                 360                 365

Ser Ile Lys Glu Thr Leu Ser Leu Leu Phe Asp Asp Leu Lys Ala Gln
    370                 375                 380

Lys Leu Asp Leu Ser Lys Ile Tyr Phe Lys Asn Asp Lys Ser Leu Thr
385                 390                 395                 400

Asp Leu Ser Gln Gln Val Phe Asp Asp Tyr Ser Val Ile Gly Thr Ala
                405                 410                 415

Val Leu Glu Tyr Ile Thr Gln Gln Ile Ala Pro Lys Asn Leu Asp Asn
            420                 425                 430

Pro Ser Lys Lys Glu Gln Glu Leu Ile Ala Lys Lys Thr Glu Lys Ala
        435                 440                 445

Lys Tyr Leu Ser Leu Glu Thr Ile Lys Leu Ala Leu Glu Glu Phe Asn
    450                 455                 460

Lys His Arg Asp Ile Asp Lys Gln Cys Arg Phe Glu Glu Ile Leu Ala
465                 470                 475                 480

Asn Phe Ala Ala Ile Pro Met Ile Phe Asp Glu Ile Ala Gln Asn Lys
                485                 490                 495

Asp Asn Leu Ala Gln Ile Ser Ile Lys Tyr Gln Asn Gln Gly Lys Lys
            500                 505                 510

Asp Leu Leu Gln Ala Ser Ala Glu Asp Asp Val Lys Ala Ile Lys Asp
        515                 520                 525

Leu Leu Asp Gln Thr Asn Asn Leu Leu His Lys Leu Lys Ile Phe His
    530                 535                 540

Ile Ser Gln Ser Glu Asp Lys Ala Asn Ile Leu Asp Lys Asp Glu His
545                 550                 555                 560

Phe Tyr Leu Val Phe Glu Glu Cys Tyr Phe Glu Leu Ala Asn Ile Val
                565                 570                 575

Pro Leu Tyr Asn Lys Ile Arg Asn Tyr Ile Thr Gln Lys Pro Tyr Ser
            580                 585                 590

Asp Glu Lys Phe Lys Leu Asn Phe Glu Asn Ser Thr Leu Ala Asn Gly
        595                 600                 605

Trp Asp Lys Asn Lys Glu Pro Asp Asn Thr Ala Ile Leu Phe Ile Lys
    610                 615                 620

Asp Asp Lys Tyr Tyr Leu Gly Val Met Asn Lys Lys Asn Asn Lys Ile
625                 630                 635                 640

Phe Asp Asp Lys Ala Ile Lys Glu Asn Lys Gly Glu Gly Tyr Lys Lys
                645                 650                 655

Ile Val Tyr Lys Leu Leu Pro Gly Ala Asn Lys Met Leu Pro Lys Val
            660                 665                 670

Phe Phe Ser Ala Lys Ser Ile Lys Phe Tyr Asn Pro Ser Glu Asp Ile
```

-continued

```
                675                 680                 685
Leu Arg Ile Arg Asn His Ser Thr His Thr Lys Asn Gly Ser Pro Gln
        690                 695                 700
Lys Gly Tyr Glu Lys Phe Glu Phe Asn Ile Glu Asp Cys Arg Lys Phe
705                 710                 715                 720
Ile Asp Phe Tyr Lys Gln Ser Ile Ser Lys His Pro Glu Trp Lys Asp
                725                 730                 735
Phe Gly Phe Arg Phe Ser Asp Thr Gln Arg Tyr Asn Ser Ile Asp Glu
                740                 745                 750
Phe Tyr Arg Glu Val Glu Asn Gln Gly Tyr Lys Leu Thr Phe Glu Asn
                755                 760                 765
Ile Ser Glu Ser Tyr Ile Asp Ser Val Val Asn Gln Gly Lys Leu Tyr
770                 775                 780
Leu Phe Gln Ile Tyr Asn Lys Asp Phe Ser Ala Tyr Ser Lys Gly Arg
785                 790                 795                 800
Pro Asn Leu His Thr Leu Tyr Trp Lys Ala Leu Phe Asp Glu Arg Asn
                805                 810                 815
Leu Gln Asp Val Val Tyr Lys Leu Asn Gly Glu Ala Glu Leu Phe Tyr
                820                 825                 830
Arg Lys Gln Ser Ile Pro Lys Lys Ile Thr His Pro Ala Lys Glu Ala
                835                 840                 845
Ile Ala Asn Lys Asn Lys Asp Asn Pro Lys Lys Glu Ser Val Phe Glu
850                 855                 860
Tyr Asp Leu Ile Lys Asp Lys Arg Phe Thr Glu Asp Lys Phe Phe Phe
865                 870                 875                 880
His Cys Pro Ile Thr Ile Asn Phe Lys Ser Ser Gly Ala Asn Lys Phe
                885                 890                 895
Asn Asp Glu Ile Asn Leu Leu Leu Lys Glu Lys Ala Asn Asp Val His
                900                 905                 910
Ile Leu Ser Ile Asp Arg Gly Glu Arg His Leu Ala Tyr Tyr Thr Leu
                915                 920                 925
Val Asp Gly Lys Gly Asn Ile Ile Lys Gln Asp Thr Phe Asn Ile Ile
        930                 935                 940
Gly Asn Asp Arg Met Lys Thr Asn Tyr His Asp Lys Leu Ala Ala Ile
945                 950                 955                 960
Glu Lys Asp Arg Asp Ser Ala Arg Lys Asp Trp Lys Lys Ile Asn Asn
                965                 970                 975
Ile Lys Glu Met Lys Glu Gly Tyr Leu Ser Gln Val Val His Glu Ile
                980                 985                 990
Ala Lys Leu Val Ile Glu Tyr Asn Ala Ile Val Val Phe Glu Asp Leu
        995                 1000                1005
Asn Phe Gly Phe Lys Arg Gly Arg Phe Lys Val Glu Lys Gln Val
        1010                1015                1020
Tyr Gln Lys Leu Glu Lys Met Leu Ile Glu Lys Leu Asn Tyr Leu
        1025                1030                1035
Val Phe Lys Asp Asn Glu Phe Asp Lys Thr Gly Gly Val Leu Arg
        1040                1045                1050
Ala Tyr Gln Leu Thr Ala Pro Phe Glu Thr Phe Lys Lys Met Gly
        1055                1060                1065
Lys Gln Thr Gly Ile Ile Tyr Tyr Val Pro Ala Gly Phe Thr Ser
        1070                1075                1080
Lys Ile Cys Pro Val Thr Gly Phe Val Asn Gln Leu Tyr Pro Lys
        1085                1090                1095
```

```
Tyr Glu  Ser Val Ser Lys Ser  Gln Glu Phe Phe Ser  Lys Phe Asp
    1100         1105              1110

Lys Ile Cys Tyr Asn Leu Asp  Lys Gly Tyr Phe Glu  Phe Ser Phe
    1115         1120              1125

Asp Tyr  Lys Asn Phe Gly Asp  Lys Ala Ala Lys Gly  Lys Trp Thr
    1130         1135              1140

Ile Ala  Ser Phe Gly Ser Arg  Leu Ile Asn Phe Arg  Asn Ser Asp
    1145         1150              1155

Lys Asn  His Asn Trp Asp Thr  Arg Glu Val Tyr Pro  Thr Lys Glu
    1160         1165              1170

Leu Glu  Lys Leu Leu Lys Asp  Tyr Ser Ile Glu Tyr  Gly His Gly
    1175         1180              1185

Glu Cys  Ile Lys Ala Ala Ile  Cys Gly Glu Ser Asp  Lys Lys Phe
    1190         1195              1200

Phe Ala  Lys Leu Thr Ser Val  Leu Asn Thr Ile Leu  Gln Met Arg
    1205         1210              1215

Asn Ser  Lys Thr Gly Thr Glu  Leu Asp Tyr Leu Ile  Ser Pro Val
    1220         1225              1230

Ala Asp  Val Asn Gly Asn Phe  Phe Asp Ser Arg Gln  Ala Pro Lys
    1235         1240              1245

Asn Met  Pro Gln Asp Ala Asp  Ala Asn Gly Ala Tyr  His Ile Gly
    1250         1255              1260

Leu Lys  Gly Leu Met Leu Leu  Gly Arg Ile Lys Asn  Asn Gln Glu
    1265         1270              1275

Gly Lys  Lys Leu Asn Leu Val  Ile Lys Asn Glu Glu  Tyr Phe Glu
    1280         1285              1290

Phe Val  Gln Asn Arg Asn Asn
    1295         1300

<210> SEQ ID NO 121
<211> LENGTH: 1206
<212> TYPE: PRT
<213> ORGANISM: Unknown
<220> FEATURE:
<223> OTHER INFORMATION: Lachnospiraceae bacterium

<400> SEQUENCE: 121

Met Tyr Tyr Glu Ser Leu Thr Lys Gln Tyr Pro Val Ser Lys Thr Ile
1               5                   10                  15

Arg Asn Glu Leu Ile Pro Ile Gly Lys Thr Leu Asp Asn Ile Arg Gln
            20                  25                  30

Asn Asn Ile Leu Glu Ser Asp Val Lys Arg Lys Gln Asn Tyr Glu His
        35                  40                  45

Val Lys Gly Ile Leu Asp Glu Tyr His Lys Gln Leu Ile Asn Glu Ala
    50                  55                  60

Leu Asp Asn Cys Thr Leu Pro Ser Leu Lys Ile Ala Ala Glu Ile Tyr
65                  70                  75                  80

Leu Lys Asn Gln Lys Glu Val Ser Asp Arg Glu Asp Phe Asn Lys Thr
                85                  90                  95

Gln Asp Leu Leu Arg Lys Glu Val Val Glu Lys Leu Lys Ala His Glu
            100                 105                 110

Asn Phe Thr Lys Ile Gly Lys Lys Asp Ile Leu Asp Leu Leu Glu Lys
        115                 120                 125

Leu Pro Ser Ile Ser Glu Asp Asp Tyr Asn Ala Leu Glu Ser Phe Arg
    130                 135                 140
```

```
Asn Phe Tyr Thr Tyr Phe Thr Ser Tyr Asn Lys Val Arg Glu Asn Leu
145                 150                 155                 160

Tyr Ser Asp Lys Glu Lys Ser Ser Thr Val Ala Tyr Arg Leu Ile Asn
                165                 170                 175

Glu Asn Phe Pro Lys Phe Leu Asp Asn Val Lys Ser Tyr Arg Phe Val
            180                 185                 190

Lys Thr Ala Gly Ile Leu Ala Asp Gly Leu Gly Glu Glu Gln Asp
        195                 200                 205

Ser Leu Phe Ile Val Glu Thr Phe Asn Lys Thr Leu Thr Gln Asp Gly
210                 215                 220

Ile Asp Thr Tyr Asn Ser Gln Val Gly Lys Ile Asn Ser Ser Ile Asn
225                 230                 235                 240

Leu Tyr Asn Gln Lys Asn Gln Lys Ala Asn Gly Phe Arg Lys Ile Pro
                245                 250                 255

Lys Met Lys Met Leu Tyr Lys Gln Ile Leu Ser Asp Arg Glu Glu Ser
            260                 265                 270

Phe Ile Asp Glu Phe Gln Ser Asp Glu Val Leu Ile Asp Asn Val Glu
        275                 280                 285

Ser Tyr Gly Ser Val Leu Ile Glu Ser Leu Lys Ser Ser Lys Val Ser
290                 295                 300

Ala Phe Phe Asp Ala Leu Arg Glu Ser Lys Gly Lys Asn Val Tyr Val
305                 310                 315                 320

Lys Asn Asp Leu Ala Lys Thr Ala Met Ser Val Ile Val Phe Glu Asn
                325                 330                 335

Trp Arg Thr Phe Asp Asp Leu Leu Asn Gln Gly Tyr Asp Leu Ala Asn
            340                 345                 350

Glu Asn Lys Lys Lys Asp Asp Lys Tyr Phe Glu Lys Arg Gln Lys Glu
        355                 360                 365

Leu Lys Lys Asn Lys Ser Tyr Ser Leu Glu His Leu Cys Asn Leu Ser
370                 375                 380

Glu Asp Ser Cys Asn Leu Ile Glu Asn Tyr Ile His Gln Ile Ser Asp
385                 390                 395                 400

Asp Ile Glu Asn Ile Ile Asn Asn Glu Thr Phe Leu Arg Ile Val
                405                 410                 415

Ile Asn Glu His Asp Arg Ser Arg Lys Leu Ala Lys Asn Arg Lys Ala
            420                 425                 430

Val Lys Ala Ile Lys Asp Phe Leu Asp Ser Ile Lys Val Leu Glu Arg
        435                 440                 445

Glu Leu Lys Leu Ile Asn Ser Ser Gly Gln Glu Leu Glu Lys Asp Leu
        450                 455                 460

Ile Val Tyr Ser Ala His Glu Glu Leu Leu Val Glu Leu Lys Gln Val
465                 470                 475                 480

Asp Ser Leu Tyr Asn Met Thr Arg Asn Tyr Leu Thr Lys Lys Pro Phe
                485                 490                 495

Ser Thr Glu Lys Val Lys Leu Asn Phe Asn Arg Ser Thr Leu Leu Asn
            500                 505                 510

Gly Trp Asp Arg Asn Lys Glu Thr Asp Asn Leu Gly Val Leu Leu Leu
        515                 520                 525

Lys Asp Gly Lys Tyr Tyr Leu Gly Ile Met Asn Thr Ser Ala Asn Lys
        530                 535                 540

Ala Phe Val Asn Pro Pro Val Ala Lys Thr Glu Lys Val Phe Lys Lys
545                 550                 555                 560
```

-continued

Val Asp Tyr Lys Leu Leu Pro Val Pro Asn Gln Met Leu Pro Lys Val
            565                 570                 575

Phe Phe Ala Lys Ser Asn Ile Asp Phe Tyr Asn Pro Ser Ser Glu Ile
            580                 585                 590

Tyr Ser Asn Tyr Lys Lys Gly Thr His Lys Lys Gly Asn Met Phe Ser
            595                 600                 605

Leu Glu Asp Cys His Asn Leu Ile Asp Phe Phe Lys Glu Ser Ile Ser
            610                 615                 620

Lys His Glu Asp Trp Ser Lys Phe Gly Phe Lys Phe Asp Thr Gln Ala
625                 630                 635                 640

Ser Tyr Asn Asp Ile Ser Glu Phe Tyr Arg Glu Val Glu Lys Gln Gly
            645                 650                 655

Tyr Lys Leu Thr Tyr Thr Asp Ile Asp Glu Thr Tyr Ile Asn Asp Leu
            660                 665                 670

Ile Glu Arg Asn Glu Leu Tyr Leu Phe Gln Ile Tyr Asn Lys Asp Phe
            675                 680                 685

Ser Met Tyr Ser Lys Gly Lys Leu Asn Leu His Thr Leu Tyr Phe Met
            690                 695                 700

Met Leu Phe Asp Gln Arg Asn Ile Asp Asp Val Val Tyr Lys Leu Asn
705                 710                 715                 720

Gly Glu Ala Glu Val Phe Tyr Arg Pro Ala Ser Ile Ser Glu Asp Glu
            725                 730                 735

Leu Ile Ile His Lys Ala Gly Glu Glu Ile Lys Asn Lys Asn Pro Asn
            740                 745                 750

Arg Ala Arg Thr Lys Glu Thr Ser Thr Phe Ser Tyr Asp Ile Val Lys
            755                 760                 765

Asp Lys Arg Tyr Ser Lys Asp Lys Phe Thr Leu His Ile Pro Ile Thr
            770                 775                 780

Met Asn Phe Gly Val Asp Glu Val Lys Arg Phe Asn Asp Ala Val Asn
785                 790                 795                 800

Ser Ala Ile Arg Ile Asp Glu Asn Val Asn Val Ile Gly Ile Asp Arg
            805                 810                 815

Gly Glu Arg Asn Leu Leu Tyr Val Val Val Ile Asp Ser Lys Gly Asn
            820                 825                 830

Ile Leu Glu Gln Ile Ser Leu Asn Ser Ile Ile Asn Lys Glu Tyr Asp
            835                 840                 845

Ile Glu Thr Asp Tyr His Ala Leu Leu Asp Glu Arg Glu Gly Gly Arg
            850                 855                 860

Asp Lys Ala Arg Lys Asp Trp Asn Thr Val Glu Asn Ile Arg Asp Leu
865                 870                 875                 880

Lys Ala Gly Leu Tyr Leu Gln Val Val Asn Val Val Ala Lys Leu Val
            885                 890                 895

Leu Lys Tyr Asn Ala Ile Ile Cys Leu Glu Asp Leu Asn Phe Gly Phe
            900                 905                 910

Lys Arg Gly Arg Gln Lys Val Glu Lys Gln Val Tyr Gln Lys Phe Glu
            915                 920                 925

Lys Met Leu Ile Asp Lys Leu Asn Tyr Leu Val Ile Asp Lys Ser Arg
930                 935                 940

Glu Gln Thr Ser Pro Lys Glu Leu Gly Gly Ala Leu Asn Ala Leu Gln
945                 950                 955                 960

Leu Thr Ser Lys Phe Lys Ser Phe Lys Glu Leu Gly Lys Gln Ser Gly
            965                 970                 975

Val Ile Tyr Tyr Val Pro Ala Tyr Leu Thr Ser Lys Ile Asp Pro Thr

```
                980             985             990
Thr Gly Phe Ala Asn Leu Phe Tyr Met Lys Cys Glu Asn Val Glu Lys
            995                 1000                1005

Ser Lys Arg Phe Phe Asp Gly Phe Asp Phe Ile Arg Phe Asn Ala
    1010            1015                1020

Leu Glu Asn Val Phe Glu Phe Gly Phe Asp Tyr Arg Ser Phe Thr
    1025            1030                1035

Gln Arg Ala Cys Gly Ile Asn Ser Lys Trp Thr Val Cys Thr Asn
    1040            1045                1050

Gly Glu Arg Ile Ile Lys Tyr Arg Asn Pro Asp Lys Asn Asn Met
    1055            1060                1065

Phe Asp Glu Lys Val Val Val Thr Asp Glu Met Lys Asn Leu
    1070            1075                1080

Phe Glu Gln Tyr Lys Ile Pro Tyr Glu Asp Gly Arg Asn Val Lys
    1085            1090                1095

Asp Met Ile Ile Ser Asn Glu Glu Ala Glu Phe Tyr Arg Arg Leu
    1100            1105                1110

Tyr Arg Leu Leu Gln Gln Thr Leu Gln Met Arg Asn Ser Thr Ser
    1115            1120                1125

Asp Gly Thr Arg Asp Tyr Ile Ile Ser Pro Val Lys Asn Lys Arg
    1130            1135                1140

Glu Ala Tyr Phe Asn Ser Glu Leu Ser Asp Gly Ser Val Pro Lys
    1145            1150                1155

Asp Ala Asp Ala Asn Gly Ala Tyr Asn Ile Ala Arg Lys Gly Leu
    1160            1165                1170

Trp Val Leu Glu Gln Ile Arg Gln Lys Ser Glu Gly Glu Lys Ile
    1175            1180                1185

Asn Leu Ala Met Thr Asn Ala Glu Trp Leu Glu Tyr Ala Gln Thr
    1190            1195                1200

His Leu Leu
    1205

<210> SEQ ID NO 122
<211> LENGTH: 1233
<212> TYPE: PRT
<213> ORGANISM: Unknown
<220> FEATURE:
<223> OTHER INFORMATION: Lachnospiraceae bacterium

<400> SEQUENCE: 122

Met Asp Tyr Gly Asn Gly Gln Phe Glu Arg Arg Ala Pro Leu Thr Lys
1               5                   10                  15

Thr Ile Thr Leu Arg Leu Lys Pro Ile Gly Glu Thr Arg Glu Thr Ile
            20                  25                  30

Arg Glu Gln Lys Leu Leu Glu Gln Asp Ala Ala Phe Arg Lys Leu Val
        35                  40                  45

Glu Thr Val Thr Pro Ile Val Asp Asp Cys Ile Arg Lys Ile Ala Asp
    50                  55                  60

Asn Ala Leu Cys His Phe Gly Thr Glu Tyr Asp Phe Ser Cys Leu Gly
65                  70                  75                  80

Asn Ala Ile Ser Lys Asn Asp Ser Lys Ala Ile Lys Lys Glu Thr Glu
                85                  90                  95

Lys Val Glu Lys Leu Leu Ala Lys Val Leu Thr Glu Asn Leu Pro Asp
            100                 105                 110

Gly Leu Arg Lys Val Asn Asp Ile Asn Ser Ala Ala Phe Ile Gln Asp
```

```
              115                 120                 125
Thr Leu Thr Ser Phe Val Gln Asp Asp Ala Asp Lys Arg Val Leu Ile
    130                 135                 140
Gln Glu Leu Lys Gly Lys Thr Val Leu Met Gln Arg Phe Leu Thr Thr
145                 150                 155                 160
Arg Ile Thr Ala Leu Thr Val Trp Leu Pro Asp Arg Val Phe Glu Asn
                165                 170                 175
Phe Asn Ile Phe Ile Glu Asn Ala Glu Lys Met Arg Ile Leu Leu Asp
            180                 185                 190
Ser Pro Leu Asn Glu Lys Ile Met Lys Phe Asp Pro Asp Ala Glu Gln
        195                 200                 205
Tyr Ala Ser Leu Glu Phe Tyr Gly Gln Cys Leu Ser Gln Lys Asp Ile
    210                 215                 220
Asp Ser Tyr Asn Leu Ile Ile Ser Gly Ile Tyr Ala Asp Asp Glu Val
225                 230                 235                 240
Lys Asn Pro Gly Ile Asn Glu Ile Val Lys Glu Tyr Asn Gln Gln Ile
                245                 250                 255
Arg Gly Asp Lys Asp Glu Ser Pro Leu Pro Lys Leu Lys Lys Leu His
            260                 265                 270
Lys Gln Ile Leu Met Pro Val Glu Lys Ala Phe Phe Val Arg Val Leu
        275                 280                 285
Ser Asn Asp Ser Asp Ala Arg Ser Ile Leu Glu Lys Ile Leu Lys Asp
    290                 295                 300
Thr Glu Met Leu Pro Ser Lys Ile Ile Glu Ala Met Lys Glu Ala Asp
305                 310                 315                 320
Ala Gly Asp Ile Ala Val Tyr Gly Ser Arg Leu His Glu Leu Ser His
                325                 330                 335
Val Ile Tyr Gly Asp His Gly Lys Leu Ser Gln Ile Ile Tyr Asp Lys
            340                 345                 350
Glu Ser Lys Arg Ile Ser Glu Leu Met Glu Thr Leu Ser Pro Lys Glu
        355                 360                 365
Arg Lys Glu Ser Lys Lys Arg Leu Glu Gly Leu Glu Glu His Ile Arg
    370                 375                 380
Lys Ser Thr Tyr Thr Phe Asp Glu Leu Asn Arg Tyr Ala Glu Lys Asn
385                 390                 395                 400
Val Met Ala Ala Tyr Ile Ala Val Glu Glu Ser Cys Ala Glu Ile
                405                 410                 415
Met Arg Lys Glu Lys Asp Leu Arg Thr Leu Leu Ser Lys Glu Asp Val
            420                 425                 430
Lys Ile Arg Gly Asn Arg His Asn Thr Leu Ile Val Lys Asn Tyr Phe
        435                 440                 445
Asn Ala Trp Thr Val Phe Arg Asn Leu Ile Arg Ile Leu Arg Arg Lys
    450                 455                 460
Ser Glu Ala Glu Ile Asp Ser Asp Phe Tyr Asp Val Leu Asp Asp Ser
465                 470                 475                 480
Val Glu Val Leu Ser Leu Thr Tyr Lys Gly Glu Asn Leu Cys Arg Ser
                485                 490                 495
Tyr Ile Thr Lys Lys Ile Gly Ser Asp Leu Lys Pro Glu Ile Ala Thr
            500                 505                 510
Tyr Gly Ser Ala Leu Arg Pro Asn Ser Arg Trp Trp Ser Pro Gly Glu
        515                 520                 525
Lys Phe Asn Val Lys Phe His Thr Ile Val Arg Arg Asp Gly Arg Leu
    530                 535                 540
```

```
Tyr Tyr Phe Ile Leu Pro Lys Gly Ala Lys Pro Val Glu Leu Glu Asp
545                 550                 555                 560

Met Asp Gly Asp Ile Glu Cys Leu Gln Met Arg Lys Ile Pro Asn Pro
            565                 570                 575

Thr Ile Phe Leu Pro Lys Leu Val Phe Lys Asp Pro Glu Ala Phe Phe
            580                 585                 590

Arg Asp Asn Pro Glu Ala Asp Glu Phe Val Phe Leu Ser Gly Met Lys
            595                 600                 605

Ala Pro Val Thr Ile Thr Arg Glu Thr Tyr Glu Ala Tyr Arg Tyr Lys
610                 615                 620

Leu Tyr Thr Val Gly Lys Leu Arg Asp Gly Val Ser Glu Glu Glu
625                 630                 635                 640

Tyr Lys Arg Ala Leu Leu Gln Val Leu Thr Ala Tyr Lys Glu Phe Leu
            645                 650                 655

Glu Asn Arg Met Ile Tyr Ala Asp Leu Asn Phe Gly Phe Lys Asp Leu
            660                 665                 670

Glu Glu Tyr Lys Asp Ser Ser Glu Phe Ile Lys Gln Val Glu Thr His
            675                 680                 685

Asn Thr Phe Met Cys Trp Ala Lys Val Ser Ser Gln Leu Asp Asp
690                 695                 700

Leu Val Lys Ser Gly Asn Gly Leu Leu Phe Glu Ile Trp Ser Glu Arg
705                 710                 715                 720

Leu Glu Ser Tyr Tyr Lys Tyr Gly Asn Glu Lys Val Leu Arg Gly Tyr
            725                 730                 735

Glu Gly Val Leu Leu Ser Ile Leu Lys Asp Glu Asn Leu Val Ser Met
            740                 745                 750

Arg Thr Leu Leu Asn Ser Arg Pro Met Leu Val Tyr Arg Pro Lys Glu
            755                 760                 765

Ser Ser Lys Pro Met Val Val His Arg Asp Gly Ser Arg Val Val Asp
770                 775                 780

Arg Phe Asp Lys Asp Gly Lys Tyr Ile Pro Pro Glu Val His Asp Glu
785                 790                 795                 800

Leu Tyr Arg Phe Phe Asn Asn Leu Leu Ile Lys Glu Lys Leu Gly Glu
            805                 810                 815

Lys Ala Arg Lys Ile Leu Asp Asn Lys Lys Val Lys Val Lys Val Leu
            820                 825                 830

Glu Ser Glu Arg Val Lys Trp Ser Lys Phe Tyr Asp Glu Gln Phe Ala
            835                 840                 845

Val Thr Phe Ser Val Lys Lys Asn Ala Asp Cys Leu Asp Thr Thr Lys
            850                 855                 860

Asp Leu Asn Ala Glu Val Met Glu Gln Tyr Ser Glu Ser Asn Arg Leu
865                 870                 875                 880

Ile Leu Ile Arg Asn Thr Thr Asp Ile Leu Tyr Tyr Leu Val Leu Asp
            885                 890                 895

Lys Asn Gly Lys Val Leu Lys Gln Arg Ser Leu Asn Ile Ile Asn Asp
            900                 905                 910

Gly Ala Arg Asp Val Asp Trp Lys Glu Arg Phe Arg Gln Val Thr Lys
            915                 920                 925

Asp Arg Asn Glu Gly Tyr Asn Glu Trp Asp Tyr Ser Arg Thr Ser Asn
            930                 935                 940

Asp Leu Lys Glu Val Tyr Leu Asn Tyr Ala Leu Lys Glu Ile Ala Glu
945                 950                 955                 960
```

```
Ala Val Ile Glu Tyr Asn Ala Ile Leu Ile Glu Lys Met Ser Asn
                965                 970                 975

Ala Phe Lys Asp Lys Tyr Ser Phe Leu Asp Asp Val Thr Phe Lys Gly
            980                 985                 990

Phe Glu Thr Lys Lys Leu Ala Lys Leu Ser Asp Leu His Phe Arg Gly
        995                1000                1005

Ile Lys Asp Gly Glu Pro Cys Ser Phe Thr Asn Pro Leu Gln Leu
    1010                1015                1020

Cys Gln Asn Asp Ser Asn Lys Ile Leu Gln Asp Gly Val Ile Phe
    1025                1030                1035

Met Val Pro Asn Ser Met Thr Arg Ser Leu Asp Pro Asp Thr Gly
    1040                1045                1050

Phe Ile Phe Ala Ile Asn Asp His Asn Ile Arg Thr Lys Lys Ala
    1055                1060                1065

Lys Leu Asn Phe Leu Ser Lys Phe Asp Gln Leu Lys Val Ser Ser
    1070                1075                1080

Glu Gly Cys Leu Ile Met Lys Tyr Ser Gly Asp Ser Leu Pro Thr
    1085                1090                1095

His Asn Thr Asp Asn Arg Val Trp Asn Cys Cys Asn His Pro
    1100                1105                1110

Ile Thr Asn Tyr Asp Arg Glu Thr Lys Lys Val Glu Phe Ile Glu
    1115                1120                1125

Glu Pro Val Glu Glu Leu Ser Arg Val Leu Glu Glu Asn Gly Ile
    1130                1135                1140

Glu Thr Asp Thr Glu Leu Asn Lys Leu Asn Glu Arg Glu Asn Val
    1145                1150                1155

Pro Gly Lys Val Val Asp Ala Ile Tyr Ser Leu Val Leu Asn Tyr
    1160                1165                1170

Leu Arg Gly Thr Val Ser Gly Val Ala Gly Gln Arg Ala Val Tyr
    1175                1180                1185

Tyr Ser Pro Val Thr Gly Lys Lys Tyr Asp Ile Ser Phe Ile Gln
    1190                1195                1200

Ala Met Asn Leu Asn Arg Lys Cys Asp Tyr Tyr Arg Ile Gly Ser
    1205                1210                1215

Lys Glu Arg Gly Glu Trp Thr Asp Phe Val Ala Gln Leu Ile Asn
    1220                1225                1230

<210> SEQ ID NO 123
<211> LENGTH: 1227
<212> TYPE: PRT
<213> ORGANISM: Unknown
<220> FEATURE:
<223> OTHER INFORMATION: Lachnospiraceae bacterium

<400> SEQUENCE: 123

Met Ser Lys Leu Glu Lys Phe Thr Asn Cys Tyr Ser Leu Ser Lys Thr
1               5                   10                  15

Leu Arg Phe Lys Ala Ile Pro Val Gly Lys Thr Gln Glu Asn Ile Asp
            20                  25                  30

Asn Lys Arg Leu Leu Val Glu Asp Glu Lys Arg Ala Glu Asp Tyr Lys
        35                  40                  45

Gly Val Lys Lys Leu Leu Asp Arg Tyr Tyr Leu Ser Phe Ile Asn Asp
    50                  55                  60

Val Leu His Ser Ile Lys Leu Lys Asn Leu Asn Asn Tyr Ile Ser Leu
65                  70                  75                  80
```

```
Phe Arg Lys Lys Thr Arg Thr Glu Lys Glu Asn Lys Glu Leu Glu Asn
                 85                  90                  95

Leu Glu Ile Asn Leu Arg Lys Glu Ile Ala Lys Ala Phe Lys Gly Asn
            100                 105                 110

Glu Gly Tyr Lys Ser Leu Phe Lys Lys Asp Ile Ile Glu Thr Ile Leu
            115                 120                 125

Pro Glu Phe Leu Asp Asp Lys Asp Glu Ile Ala Leu Val Asn Ser Phe
130                 135                 140

Asn Gly Phe Thr Thr Ala Phe Thr Gly Phe Phe Asp Asn Arg Glu Asn
145                 150                 155                 160

Met Phe Ser Glu Glu Ala Lys Ser Thr Ser Ile Ala Phe Arg Cys Ile
                165                 170                 175

Asn Glu Asn Leu Thr Arg Tyr Ile Ser Asn Met Asp Ile Phe Glu Lys
            180                 185                 190

Val Asp Ala Ile Phe Asp Lys His Glu Val Gln Glu Ile Lys Glu Lys
            195                 200                 205

Ile Leu Asn Ser Asp Tyr Asp Val Glu Asp Phe Phe Glu Gly Glu Phe
    210                 215                 220

Phe Asn Phe Val Leu Thr Gln Glu Gly Ile Asp Val Tyr Asn Ala Ile
225                 230                 235                 240

Ile Gly Gly Phe Val Thr Glu Ser Gly Glu Lys Ile Lys Gly Leu Asn
                245                 250                 255

Glu Tyr Ile Asn Leu Tyr Asn Gln Lys Thr Lys Gln Lys Leu Pro Lys
            260                 265                 270

Phe Lys Pro Leu Tyr Lys Gln Val Leu Ser Asp Arg Glu Ser Leu Ser
            275                 280                 285

Phe Tyr Gly Glu Gly Tyr Thr Ser Asp Glu Glu Val Leu Glu Val Phe
    290                 295                 300

Arg Asn Thr Leu Asn Lys Asn Ser Glu Ile Phe Ser Ser Ile Lys Lys
305                 310                 315                 320

Leu Glu Lys Leu Phe Lys Asn Phe Asp Glu Tyr Ser Ser Ala Gly Ile
                325                 330                 335

Phe Val Lys Asn Gly Pro Ala Ile Ser Thr Ile Ser Lys Asp Ile Phe
            340                 345                 350

Gly Glu Trp Asn Val Ile Arg Asp Lys Trp Asn Ala Glu Tyr Asp Asp
            355                 360                 365

Ile His Leu Lys Lys Lys Ala Val Thr Glu Lys Tyr Glu Asp Asp
    370                 375                 380

Arg Arg Lys Ser Phe Lys Lys Ile Gly Ser Phe Ser Leu Glu Gln Leu
385                 390                 395                 400

Gln Glu Tyr Ala Asp Ala Asp Leu Ser Val Val Glu Lys Leu Lys Glu
                405                 410                 415

Ile Ile Ile Gln Lys Val Asp Glu Ile Tyr Lys Val Tyr Gly Ser Ser
            420                 425                 430

Glu Lys Leu Phe Asp Ala Asp Phe Val Leu Glu Lys Ser Leu Lys Lys
            435                 440                 445

Asn Asp Ala Val Val Ala Ile Met Lys Asp Leu Leu Asp Ser Val Lys
450                 455                 460

Ser Phe Glu Asn Tyr Ile Lys Ala Phe Phe Gly Glu Gly Lys Glu Thr
465                 470                 475                 480

Asn Arg Asp Glu Ser Phe Tyr Gly Asp Phe Val Leu Ala Tyr Asp Ile
                485                 490                 495

Leu Leu Lys Val Asp His Ile Tyr Asp Ala Ile Arg Asn Tyr Val Thr
```

```
                500             505             510
Gln Lys Pro Tyr Ser Lys Asp Lys Phe Lys Leu Tyr Phe Gln Asn Pro
            515                 520                 525

Gln Phe Met Gly Gly Trp Asp Lys Asp Lys Glu Thr Asp Tyr Arg Ala
        530                 535                 540

Thr Ile Leu Arg Tyr Gly Ser Lys Tyr Tyr Leu Ala Ile Met Asp Lys
545                 550                 555                 560

Lys Tyr Ala Lys Cys Leu Gln Lys Ile Asp Lys Asp Val Asn Gly
                565                 570                 575

Asn Tyr Glu Lys Ile Asn Tyr Lys Leu Leu Pro Gly Pro Asn Lys Met
            580                 585                 590

Leu Pro Lys Val Phe Phe Ser Lys Lys Trp Met Ala Tyr Tyr Asn Pro
        595                 600                 605

Ser Glu Asp Ile Gln Lys Ile Tyr Lys Asn Gly Thr Phe Lys Lys Gly
    610                 615                 620

Asp Met Phe Asn Leu Asn Asp Cys His Lys Leu Ile Asp Phe Phe Lys
625                 630                 635                 640

Asp Ser Ile Ser Arg Tyr Pro Lys Trp Ser Asn Ala Tyr Asp Phe Asn
                645                 650                 655

Phe Ser Glu Thr Glu Lys Tyr Lys Asp Ile Ala Gly Phe Tyr Arg Glu
            660                 665                 670

Val Glu Glu Gln Gly Tyr Lys Val Ser Phe Glu Ser Ala Ser Lys Lys
        675                 680                 685

Glu Val Asp Lys Leu Val Glu Glu Gly Lys Leu Tyr Met Phe Gln Ile
    690                 695                 700

Tyr Asn Lys Asp Phe Ser Asp Lys Ser His Gly Thr Pro Asn Leu His
705                 710                 715                 720

Thr Met Tyr Phe Lys Leu Leu Phe Asp Glu Asn Asn His Gly Gln Ile
                725                 730                 735

Arg Leu Ser Gly Gly Ala Glu Leu Phe Met Arg Arg Ala Ser Leu Lys
            740                 745                 750

Lys Glu Glu Leu Val Val His Pro Ala Asn Ser Pro Ile Ala Asn Lys
        755                 760                 765

Asn Pro Asp Asn Pro Lys Lys Thr Thr Thr Leu Ser Tyr Asp Val Tyr
    770                 775                 780

Lys Asp Lys Arg Phe Ser Glu Asp Gln Tyr Glu Leu His Ile Pro Ile
785                 790                 795                 800

Ala Asn Ile Asn Lys Cys Pro Lys Asn Ile Phe Lys Ile Asn Thr Glu
                805                 810                 815

Val Arg Val Leu Leu Lys His Asp Asp Asn Pro Tyr Val Ile Gly Ile
            820                 825                 830

Asp Arg Gly Glu Arg Asn Leu Leu Tyr Ile Val Val Asp Gly Lys
        835                 840                 845

Gly Asn Ile Val Glu Gln Tyr Ser Leu Asn Glu Ile Ile Asn Asn Phe
    850                 855                 860

Asn Gly Ile Arg Ile Lys Thr Asp Tyr His Ser Leu Leu Asp Lys Lys
865                 870                 875                 880

Glu Lys Glu Arg Phe Glu Ala Arg Gln Asn Trp Thr Ser Ile Glu Asn
                885                 890                 895

Ile Lys Glu Leu Lys Ala Gly Tyr Ile Ser Gln Val Val His Lys Ile
            900                 905                 910

Cys Glu Leu Val Glu Lys Tyr Asp Ala Val Ile Ala Leu Glu Asp Leu
        915                 920                 925
```

Asn Ser Gly Phe Lys Asn Ser Arg Val Lys Val Glu Lys Gln Val Tyr
            930                 935                 940

Gln Lys Phe Glu Lys Met Leu Ile Asp Lys Leu Asn Tyr Met Val Asp
945                 950                 955                 960

Lys Lys Ser Asn Pro Cys Ala Thr Gly Gly Ala Leu Lys Gly Tyr Gln
                965                 970                 975

Ile Thr Asn Lys Phe Glu Ser Phe Lys Ser Met Ser Thr Gln Asn Gly
            980                 985                 990

Phe Ile Phe Tyr Ile Pro Ala Trp Leu Thr Ser Lys Ile Asp Pro Ser
        995                 1000                1005

Thr Gly Phe Val Asn Leu Leu Lys Thr Lys Tyr Thr Ser Ile Ala
    1010                1015                1020

Asp Lys Lys Phe Ile Ser Ser Phe Asp Arg Ile Met Tyr Val Pro
    1025                1030                1035

Glu Glu Asp Leu Phe Glu Phe Ala Leu Asp Tyr Lys Asn Phe Ser
    1040                1045                1050

Arg Thr Asp Ala Asp Tyr Ile Lys Lys Trp Lys Leu Tyr Ser Tyr
    1055                1060                1065

Gly Asn Arg Ile Arg Ile Phe Arg Asn Pro Lys Lys Asn Asn Val
    1070                1075                1080

Phe Asp Trp Glu Glu Val Cys Leu Thr Ser Ala Tyr Lys Glu Leu
    1085                1090                1095

Phe Asn Lys Tyr Gly Ile Asn Tyr Gln Gln Gly Asp Ile Arg Ala
    1100                1105                1110

Leu Leu Cys Glu Gln Ser Asp Lys Ala Phe Tyr Ser Ser Phe Met
    1115                1120                1125

Ala Leu Met Ser Leu Met Leu Gln Met Arg Asn Ser Ile Thr Gly
    1130                1135                1140

Arg Thr Asp Val Asp Phe Leu Ile Ser Pro Val Lys Asn Ser Asp
    1145                1150                1155

Gly Ile Phe Tyr Asp Ser Arg Asn Tyr Glu Ala Gln Glu Asn Ala
    1160                1165                1170

Ile Leu Pro Lys Asn Ala Asp Ala Asn Gly Ala Tyr Asn Ile Ala
    1175                1180                1185

Arg Lys Val Leu Trp Ala Ile Gly Gln Phe Lys Lys Ala Glu Asp
    1190                1195                1200

Glu Lys Leu Asp Lys Val Lys Ile Ala Ser Asn Lys Glu Trp Leu
    1205                1210                1215

Glu Tyr Ala Gln Thr Ser Val Lys His
    1220                1225

<210> SEQ ID NO 124
<211> LENGTH: 1264
<212> TYPE: PRT
<213> ORGANISM: Unknown
<220> FEATURE:
<223> OTHER INFORMATION: Lachnospiraceae bacterium

<400> SEQUENCE: 124

Met Glu Asp Tyr Ser Gly Phe Val Asn Ile Tyr Ser Ile Gln Lys Thr
1               5                   10                  15

Leu Arg Phe Glu Leu Lys Pro Val Gly Lys Thr Leu Glu His Ile Glu
            20                  25                  30

Lys Lys Gly Phe Leu Lys Lys Asp Lys Ile Arg Ala Glu Asp Tyr Lys
        35                  40                  45

```
Ala Val Lys Lys Ile Ile Asp Lys Tyr His Arg Ala Tyr Ile Glu Glu
         50                  55                  60

Val Phe Asp Ser Val Leu His Gln Lys Lys Lys Asp Lys Thr Arg
 65                  70                  75                  80

Phe Ser Thr Gln Phe Ile Lys Glu Ile Lys Glu Phe Ser Glu Leu Tyr
                     85                  90                  95

Tyr Lys Thr Glu Lys Asn Ile Pro Asp Lys Glu Arg Leu Glu Ala Leu
                100                 105                 110

Ser Glu Lys Leu Arg Lys Met Leu Val Gly Ala Phe Lys Gly Glu Phe
            115                 120                 125

Ser Glu Glu Val Ala Glu Lys Tyr Asn Lys Asn Leu Phe Ser Lys Glu
            130                 135                 140

Leu Ile Arg Asn Glu Ile Glu Lys Phe Cys Glu Thr Asp Glu Glu Arg
145                 150                 155                 160

Lys Gln Val Ser Asn Phe Lys Ser Phe Thr Thr Tyr Phe Thr Gly Phe
                165                 170                 175

His Ser Asn Arg Gln Asn Ile Tyr Ser Asp Glu Lys Lys Ser Thr Ala
                180                 185                 190

Ile Gly Tyr Arg Ile Ile His Gln Asn Leu Pro Lys Phe Leu Asp Asn
            195                 200                 205

Leu Lys Ile Ile Glu Ser Ile Gln Arg Arg Phe Lys Asp Phe Pro Trp
210                 215                 220

Ser Asp Leu Lys Lys Asn Leu Lys Lys Ile Asp Lys Asn Ile Lys Leu
225                 230                 235                 240

Thr Glu Tyr Phe Ser Ile Asp Gly Phe Val Asn Val Leu Asn Gln Lys
                245                 250                 255

Gly Ile Asp Ala Tyr Asn Thr Ile Leu Gly Gly Lys Ser Glu Glu Ser
            260                 265                 270

Gly Glu Lys Ile Gln Gly Leu Asn Glu Tyr Ile Asn Leu Tyr Arg Gln
            275                 280                 285

Lys Asn Asn Ile Asp Arg Lys Asn Pro Leu Asn Val Lys Ile Leu Phe
            290                 295                 300

Lys Gln Ile Leu Gly Asp Arg Glu Thr Lys Ser Phe Ile Pro Glu Ala
305                 310                 315                 320

Phe Pro Asp Asp Gln Ser Val Leu Asn Ser Ile Thr Glu Phe Ala Lys
                325                 330                 335

Tyr Leu Lys Leu Asp Lys Lys Lys Ser Ile Ile Ala Glu Leu Lys
                340                 345                 350

Lys Phe Leu Ser Ser Phe Asn Arg Tyr Glu Leu Asp Gly Ile Tyr Leu
            355                 360                 365

Ala Asn Asp Asn Ser Leu Ala Ser Ile Ser Thr Phe Leu Phe Asp Asp
            370                 375                 380

Trp Ser Phe Ile Lys Lys Ser Val Ser Phe Lys Tyr Asp Glu Ser Val
385                 390                 395                 400

Gly Asp Pro Lys Lys Ile Lys Ser Pro Leu Lys Tyr Glu Lys Glu
                405                 410                 415

Lys Glu Lys Trp Leu Lys Gln Leu Tyr Tyr Thr Ile Ser Phe Leu Asn
            420                 425                 430

Asp Ala Ile Glu Ser Tyr Ser Lys Ser Gln Asp Glu Lys Arg Val Lys
            435                 440                 445

Ile Arg Leu Glu Ala Tyr Phe Ala Glu Phe Lys Ser Lys Asp Asp Ala
    450                 455                 460
```

```
Lys Lys Gln Phe Asp Leu Leu Glu Arg Ile Glu Ala Tyr Ala Ile
465                 470                 475                 480

Val Glu Pro Leu Leu Gly Ala Glu Tyr Pro Arg Asp Arg Asn Leu Lys
            485                 490                 495

Ala Asp Lys Lys Glu Val Gly Lys Ile Lys Asp Phe Leu Asp Ser Ile
            500                 505                 510

Lys Ser Leu Gln Phe Phe Leu Lys Pro Leu Leu Ser Ala Glu Ile Phe
            515                 520                 525

Asp Glu Lys Asp Leu Gly Phe Tyr Asn Gln Leu Gly Tyr Tyr Glu
530                 535                 540

Glu Ile Asp Ile Ser Gly His Leu Tyr Asn Lys Val Arg Asn Tyr Leu
545                 550                 555                 560

Thr Gly Lys Ile Tyr Ser Lys Glu Lys Phe Lys Leu Asn Phe Glu Asn
            565                 570                 575

Ser Thr Leu Leu Lys Gly Trp Asp Glu Asn Arg Glu Val Ala Asn Leu
            580                 585                 590

Cys Val Ile Phe Arg Glu Asp Gln Lys Tyr Tyr Leu Gly Val Met Asp
    595                 600                 605

Lys Glu Asn Asn Thr Ile Leu Ser Asp Ile Pro Lys Val Lys Pro Asn
610                 615                 620

Glu Leu Phe Tyr Glu Lys Met Val Tyr Lys Leu Ile Pro Thr Pro His
625                 630                 635                 640

Met Gln Leu Pro Arg Ile Ile Phe Ser Ser Asp Asn Leu Ser Ile Tyr
                645                 650                 655

Asn Pro Ser Lys Ser Ile Leu Lys Ile Arg Glu Ala Lys Ser Phe Lys
            660                 665                 670

Glu Gly Lys Asn Phe Lys Leu Lys Asp Cys His Lys Phe Ile Asp Phe
            675                 680                 685

Tyr Lys Glu Ser Ile Ser Lys Asn Glu Asp Trp Ser Arg Phe Asp Phe
690                 695                 700

Lys Phe Ser Lys Thr Ser Ser Tyr Glu Asn Ile Ser Glu Phe Tyr Arg
705                 710                 715                 720

Glu Val Glu Arg Gln Gly Tyr Asn Leu Asp Phe Lys Lys Val Ser Lys
                725                 730                 735

Phe Tyr Ile Asp Ser Leu Val Glu Asp Gly Lys Leu Tyr Leu Phe Gln
                740                 745                 750

Ile Tyr Asn Lys Asp Phe Ser Ile Phe Ser Lys Gly Lys Pro Asn Leu
            755                 760                 765

His Thr Ile Tyr Phe Arg Ser Leu Phe Ser Lys Glu Asn Leu Lys Asp
770                 775                 780

Val Cys Leu Lys Leu Asn Gly Glu Ala Glu Met Phe Phe Arg Lys Lys
785                 790                 795                 800

Ser Ile Asn Tyr Asp Glu Lys Lys Arg Glu Gly His His Pro Glu
            805                 810                 815

Leu Phe Glu Lys Leu Lys Tyr Pro Ile Leu Lys Asp Lys Arg Tyr Ser
            820                 825                 830

Glu Asp Lys Phe Gln Phe His Leu Pro Ile Ser Leu Asn Phe Lys Ser
            835                 840                 845

Lys Glu Arg Leu Asn Phe Asn Leu Lys Val Asn Glu Phe Leu Lys Arg
            850                 855                 860

Asn Lys Asp Ile Asn Ile Ile Gly Ile Asp Arg Gly Glu Arg Asn Leu
865                 870                 875                 880

Leu Tyr Leu Val Met Ile Asn Gln Lys Gly Glu Ile Leu Lys Gln Thr
```

-continued

```
                    885                 890                 895
Leu Leu Asp Ser Met Gln Ser Gly Lys Gly Arg Pro Glu Ile Asn Tyr
                900                 905                 910
Lys Glu Lys Leu Gln Glu Lys Glu Ile Glu Arg Asp Lys Ala Arg Lys
            915                 920                 925
Ser Trp Gly Thr Val Glu Asn Ile Lys Glu Leu Lys Glu Gly Tyr Leu
        930                 935                 940
Ser Ile Val Ile His Gln Ile Ser Lys Leu Met Val Glu Asn Asn Ala
945                 950                 955                 960
Ile Val Val Leu Glu Asp Leu Asn Ile Gly Phe Lys Arg Gly Arg Gln
                965                 970                 975
Lys Val Glu Arg Gln Val Tyr Gln Lys Phe Glu Lys Met Leu Ile Asp
                980                 985                 990
Lys Leu Asn Phe Leu Val Phe Lys  Glu Asn Lys Pro Thr  Glu Pro Gly
                995                 1000                1005
Gly Val  Leu Lys Ala Tyr Gln  Leu Thr Asp Glu Phe  Gln Ser Phe
    1010                1015                1020
Glu Lys  Leu Ser Lys Gln Thr  Gly Phe Leu Phe Tyr  Val Pro Ser
    1025                1030                1035
Trp Asn  Thr Ser Lys Ile Asp  Pro Arg Thr Gly Phe  Ile Asp Phe
    1040                1045                1050
Leu His  Pro Ala Tyr Glu Asn  Ile Glu Lys Ala Lys  Gln Trp Ile
    1055                1060                1065
Asn Lys  Phe Asp Ser Ile Arg  Phe Asn Ser Lys Met  Asp Trp Phe
    1070                1075                1080
Glu Phe  Thr Ala Asp Thr Arg  Lys Phe Ser Glu Asn  Leu Met Leu
    1085                1090                1095
Gly Lys  Asn Arg Val Trp Val  Ile Cys Thr Thr Asn  Val Glu Arg
    1100                1105                1110
Tyr Phe  Thr Ser Lys Thr Ala  Asn Ser Ser Ile Gln  Tyr Asn Ser
    1115                1120                1125
Ile Gln  Ile Thr Glu Lys Leu  Lys Glu Leu Phe Val  Asp Ile Pro
    1130                1135                1140
Phe Ser  Asn Gly Gln Asp Leu  Lys Pro Glu Ile Leu  Arg Lys Asn
    1145                1150                1155
Asp Ala  Val Phe Phe Lys Ser  Leu Leu Phe Tyr Ile  Lys Thr Thr
    1160                1165                1170
Leu Ser  Leu Arg Gln Asn Asn  Gly Lys Lys Gly Glu  Glu Glu Lys
    1175                1180                1185
Asp Phe  Ile Leu Ser Pro Val  Val Asp Ser Lys Gly  Arg Phe Phe
    1190                1195                1200
Asn Ser  Leu Glu Ala Ser Asp  Asp Glu Pro Lys Asp  Ala Asp Ala
    1205                1210                1215
Asn Gly  Ala Tyr His Ile Ala  Leu Lys Gly Leu Met  Asn Leu Leu
    1220                1225                1230
Val Leu  Asn Glu Thr Lys Glu  Glu Asn Leu Ser Arg  Pro Lys Trp
    1235                1240                1245
Lys Ile  Lys Asn Lys Asp Trp  Leu Glu Phe Val Trp  Glu Arg Asn
    1250                1255                1260
Arg
```

<210> SEQ ID NO 125
<211> LENGTH: 1373

```
<212> TYPE: PRT
<213> ORGANISM: Unknown
<220> FEATURE:
<223> OTHER INFORMATION: Moraxella bovoculi

<400> SEQUENCE: 125
```

| | | | | | | | | | | | | | | |
|---|---|---|---|---|---|---|---|---|---|---|---|---|---|---|
| Met | Leu | Phe | Gln | Asp | Phe | Thr | His | Leu | Tyr | Pro | Leu | Ser | Lys | Thr | Val |
| 1 | | | | 5 | | | | | 10 | | | | | 15 | |
| Arg | Phe | Glu | Leu | Phe | Ile | Asp | Arg | Thr | Leu | Glu | His | Ile | His | Ala | Lys |
| | | | 20 | | | | | 25 | | | | | 30 | | |
| Asn | Phe | Leu | Ser | Gln | Asp | Glu | Thr | Met | Ala | Asp | Met | His | Gln | Lys | Val |
| | | | | 35 | | | | | 40 | | | | | 45 | |
| Lys | Val | Ile | Leu | Asp | Asp | Tyr | His | Arg | Asp | Phe | Ile | Ala | Asp | Met | Met |
| 50 | | | | | 55 | | | | | 60 | | | | | |
| Gly | Glu | Val | Lys | Leu | Thr | Lys | Leu | Ala | Glu | Phe | Tyr | Asp | Val | Tyr | Leu |
| 65 | | | | | 70 | | | | | 75 | | | | | 80 |
| Lys | Phe | Arg | Lys | Asn | Pro | Lys | Asp | Asp | Glu | Leu | Gln | Lys | Ala | Gln | Leu |
| | | | | 85 | | | | | 90 | | | | | 95 | |
| Lys | Asp | Leu | Gln | Ala | Val | Leu | Arg | Lys | Glu | Ile | Val | Lys | Pro | Ile | Gly |
| | | | 100 | | | | | 105 | | | | | 110 | | |
| Asn | Gly | Gly | Lys | Tyr | Lys | Ala | Gly | Tyr | Asp | Arg | Leu | Phe | Gly | Ala | Lys |
| | | | | 115 | | | | | 120 | | | | | 125 | |
| Leu | Phe | Lys | Asp | Gly | Lys | Glu | Leu | Gly | Asp | Leu | Ala | Lys | Phe | Val | Ile |
| | | | 130 | | | | | 135 | | | | | 140 | | |
| Ala | Gln | Glu | Gly | Glu | Ser | Ser | Pro | Lys | Leu | Ala | His | Leu | Ala | His | Phe |
| 145 | | | | | 150 | | | | | 155 | | | | | 160 |
| Glu | Lys | Phe | Ser | Thr | Tyr | Phe | Thr | Gly | Phe | His | Asp | Asn | Arg | Lys | Asn |
| | | | | 165 | | | | | 170 | | | | | 175 | |
| Met | Tyr | Ser | Asp | Glu | Asp | Lys | His | Thr | Ala | Ile | Ala | Tyr | Arg | Leu | Ile |
| | | | 180 | | | | | 185 | | | | | 190 | | |
| His | Glu | Asn | Leu | Pro | Arg | Phe | Ile | Asp | Asn | Leu | Gln | Ile | Leu | Thr | Thr |
| | | | | 195 | | | | | 200 | | | | | 205 | |
| Ile | Lys | Gln | Lys | His | Ser | Ala | Leu | Tyr | Asp | Gln | Ile | Ile | Asn | Glu | Leu |
| | 210 | | | | | 215 | | | | | 220 | | | | |
| Thr | Ala | Ser | Gly | Leu | Asp | Val | Ser | Leu | Ala | Ser | His | Leu | Asp | Gly | Tyr |
| 225 | | | | | 230 | | | | | 235 | | | | | 240 |
| His | Lys | Leu | Leu | Thr | Gln | Glu | Gly | Ile | Thr | Ala | Tyr | Asn | Thr | Leu | Leu |
| | | | | 245 | | | | | 250 | | | | | 255 | |
| Gly | Gly | Ile | Ser | Gly | Glu | Ala | Gly | Ser | Pro | Lys | Ile | Gln | Gly | Ile | Asn |
| | | | 260 | | | | | 265 | | | | | 270 | | |
| Glu | Leu | Ile | Asn | Ser | His | His | Asn | Gln | His | Cys | His | Lys | Ser | Glu | Arg |
| | | | | 275 | | | | | 280 | | | | | 285 | |
| Ile | Ala | Lys | Leu | Arg | Pro | Leu | His | Lys | Gln | Ile | Leu | Ser | Asp | Gly | Met |
| | 290 | | | | | 295 | | | | | 300 | | | | |
| Ser | Val | Ser | Phe | Leu | Pro | Ser | Lys | Phe | Ala | Asp | Asp | Ser | Glu | Met | Cys |
| 305 | | | | | 310 | | | | | 315 | | | | | 320 |
| Gln | Ala | Val | Asn | Glu | Phe | Tyr | Arg | His | Tyr | Ala | Asp | Val | Phe | Ala | Lys |
| | | | | 325 | | | | | 330 | | | | | 335 | |
| Val | Gln | Ser | Leu | Phe | Asp | Gly | Phe | Asp | Asp | His | Gln | Lys | Asp | Gly | Ile |
| | | | 340 | | | | | 345 | | | | | 350 | | |
| Tyr | Val | Glu | His | Lys | Asn | Leu | Asn | Glu | Leu | Ser | Lys | Gln | Ala | Phe | Gly |
| | | | | 355 | | | | | 360 | | | | | 365 | |
| Asp | Phe | Ala | Leu | Leu | Gly | Arg | Val | Leu | Asp | Gly | Tyr | Tyr | Val | Asp | Val |
| | 370 | | | | | 375 | | | | | 380 | | | | |

-continued

Val Asn Pro Glu Phe Asn Glu Arg Phe Ala Lys Ala Lys Thr Asp Asn
385                 390                 395                 400

Ala Lys Ala Lys Leu Thr Lys Glu Lys Asp Lys Phe Ile Lys Gly Val
            405                 410                 415

His Ser Leu Ala Ser Leu Glu Gln Ala Ile Glu His Tyr Thr Ala Arg
            420                 425                 430

His Asp Glu Ser Val Gln Ala Gly Lys Leu Gly Gln Tyr Phe Lys
            435                 440                 445

His Gly Leu Ala Gly Val Asp Asn Pro Ile Gln Lys Ile His Asn Asn
450                 455                 460

His Ser Thr Ile Lys Gly Phe Leu Glu Arg Glu Arg Pro Ala Gly Glu
465                 470                 475                 480

Arg Ala Leu Pro Lys Ile Lys Ser Gly Lys Asn Pro Glu Met Thr Gln
            485                 490                 495

Leu Arg Gln Leu Lys Glu Leu Leu Asp Asn Ala Leu Asn Val Ala His
            500                 505                 510

Phe Ala Lys Leu Leu Thr Thr Lys Thr Thr Leu Asp Asn Gln Asp Gly
            515                 520                 525

Asn Phe Tyr Gly Glu Phe Gly Val Leu Tyr Asp Glu Leu Ala Lys Ile
530                 535                 540

Pro Thr Leu Tyr Asn Lys Val Arg Asp Tyr Leu Ser Gln Lys Pro Phe
545                 550                 555                 560

Ser Thr Glu Lys Tyr Lys Leu Asn Phe Gly Asn Pro Thr Leu Leu Asn
            565                 570                 575

Gly Trp Asp Leu Asn Lys Glu Lys Asp Asn Phe Gly Val Ile Leu Gln
            580                 585                 590

Lys Asp Gly Cys Tyr Tyr Leu Ala Leu Leu Asp Lys Ala His Lys Lys
            595                 600                 605

Val Phe Asp Asn Ala Pro Asn Thr Gly Lys Ser Ile Tyr Gln Lys Met
610                 615                 620

Ile Tyr Lys Tyr Leu Glu Val Arg Lys Gln Phe Pro Lys Val Phe Phe
625                 630                 635                 640

Ser Lys Glu Ala Ile Ala Ile Asn Tyr His Pro Ser Lys Glu Leu Val
            645                 650                 655

Glu Ile Lys Asp Lys Gly Arg Gln Arg Ser Asp Asp Glu Arg Leu Lys
            660                 665                 670

Leu Tyr Arg Phe Ile Leu Glu Cys Leu Lys Ile His Pro Lys Tyr Asp
            675                 680                 685

Lys Lys Phe Glu Gly Ala Ile Gly Asp Ile Gln Leu Phe Lys Lys Asp
            690                 695                 700

Lys Lys Gly Arg Glu Val Pro Ile Ser Glu Lys Asp Leu Phe Lys Asp
705                 710                 715                 720

Ile Asn Gly Ile Phe Ser Ser Lys Pro Lys Leu Glu Met Glu Asp Phe
            725                 730                 735

Phe Ile Gly Glu Phe Lys Arg Tyr Asn Pro Ser Gln Asp Leu Val Asp
            740                 745                 750

Gln Tyr Asn Ile Tyr Lys Lys Ile Asp Ser Asn Asp Asn Arg Lys Lys
            755                 760                 765

Glu Asn Phe Tyr Asn Asn His Pro Lys Phe Lys Lys Asp Leu Val Arg
            770                 775                 780

Tyr Tyr Tyr Glu Ser Met Cys Lys His Glu Glu Trp Glu Glu Ser Phe
785                 790                 795                 800

Glu Phe Ser Lys Lys Leu Gln Asp Ile Gly Cys Tyr Val Asp Val Asn

```
                805                 810                 815
Glu Leu Phe Thr Glu Ile Glu Thr Arg Arg Leu Asn Tyr Lys Ile Ser
                820                 825                 830
Phe Cys Asn Ile Asn Ala Asp Tyr Ile Asp Glu Leu Val Glu Gln Gly
                835                 840                 845
Gln Leu Tyr Leu Phe Gln Ile Tyr Asn Lys Asp Phe Ser Pro Lys Ala
                850                 855                 860
His Gly Lys Pro Asn Leu His Thr Leu Tyr Phe Lys Ala Leu Phe Ser
865                 870                 875                 880
Glu Asp Asn Leu Ala Asp Pro Ile Tyr Lys Leu Asn Gly Glu Ala Gln
                885                 890                 895
Ile Phe Tyr Arg Lys Ala Ser Leu Asp Met Asn Glu Thr Thr Ile His
                900                 905                 910
Arg Ala Gly Glu Val Leu Glu Asn Lys Asn Pro Asp Asn Pro Lys Lys
                915                 920                 925
Arg Gln Phe Val Tyr Asp Ile Ile Lys Asp Lys Arg Tyr Thr Gln Lys
                930                 935                 940
Asp Phe Met Leu His Val Pro Ile Thr Met Asn Phe Gly Val Gln Gly
945                 950                 955                 960
Met Thr Ile Lys Glu Phe Asn Lys Lys Val Asn Gln Ser Ile Gln Gln
                965                 970                 975
Tyr Asp Glu Val Asn Val Ile Gly Ile Asp Arg Gly Glu Arg His Leu
                980                 985                 990
Leu Tyr Leu Thr Val Ile Asn Ser   Lys Gly Glu Ile Leu  Glu Gln Cys
                995                1000                1005
Ser Leu  Asn Asp Ile Thr Thr  Ala Ser Ala Asn Gly  Thr Gln Met
    1010                1015                1020
Thr Thr  Pro Tyr His Lys Ile  Leu Asp Lys Arg Glu   Ile Glu Arg
    1025                1030                1035
Leu Asn  Ala Arg Val Gly Trp  Gly Glu Ile Glu Thr   Ile Lys Glu
    1040                1045                1050
Leu Lys  Ser Gly Tyr Leu Ser  His Val Val His Gln   Ile Ser Gln
    1055                1060                1065
Leu Met  Leu Lys Tyr Asn Ala  Ile Val Val Leu Glu   Asp Leu Asn
    1070                1075                1080
Phe Gly  Phe Lys Arg Gly Arg  Phe Lys Val Glu Lys   Gln Ile Tyr
    1085                1090                1095
Gln Asn  Phe Glu Asn Ala Leu  Ile Lys Lys Leu Asn   His Leu Val
    1100                1105                1110
Leu Lys  Asp Lys Ala Asp Asp  Glu Ile Gly Ser Tyr   Lys Asn Ala
    1115                1120                1125
Leu Gln  Leu Thr Asn Asn Phe  Thr Asp Leu Lys Ser   Ile Gly Lys
    1130                1135                1140
Gln Thr  Gly Phe Leu Phe Tyr  Val Pro Ala Trp Asn   Thr Ser Lys
    1145                1150                1155
Ile Asp  Pro Glu Thr Gly Phe  Val Asp Leu Leu Lys   Pro Arg Tyr
    1160                1165                1170
Glu Asn  Ile Gln Ala Ser Gln  Ala Phe Phe Gly Lys   Phe Asp Lys
    1175                1180                1185
Ile Cys  Tyr Asn Ala Asp Lys  Asp Tyr Phe Glu Phe   His Ile Asp
    1190                1195                1200
Tyr Ala  Lys Phe Thr Asp Lys  Ala Lys Asn Ser Arg   Gln Ile Trp
    1205                1210                1215
```

```
Thr Ile Cys Ser His Gly Asp Lys Arg Tyr Val Tyr Asp Lys Thr
1220                1225                1230

Ala Asn Gln Asn Lys Gly Ala Ala Lys Gly Ile Asn Val Asn Asp
1235                1240                1245

Ile Leu Lys Ser Leu Phe Ala Arg His His Ile Asn Glu Lys Gln
1250                1255                1260

Pro Asn Leu Val Met Asp Ile Cys Gln Asn Asn Asp Lys Glu Phe
1265                1270                1275

His Lys Ser Leu Met Tyr Leu Leu Lys Thr Leu Leu Ala Leu Arg
1280                1285                1290

Tyr Ser Asn Ala Ser Ser Asp Glu Asp Phe Ile Leu Ser Pro Val
1295                1300                1305

Ala Asn Asp Glu Gly Val Phe Phe Asn Ser Ala Leu Ala Asp Asp
1310                1315                1320

Thr Gln Pro Gln Asn Ala Asp Ala Asn Gly Ala Tyr His Ile Ala
1325                1330                1335

Leu Lys Gly Leu Trp Leu Leu Asn Glu Leu Lys Asn Ser Asp Asp
1340                1345                1350

Leu Asn Lys Val Lys Leu Ala Ile Asp Asn Gln Thr Trp Leu Asn
1355                1360                1365

Phe Ala Gln Asn Arg
1370

<210> SEQ ID NO 126
<211> LENGTH: 1352
<212> TYPE: PRT
<213> ORGANISM: Unknown
<220> FEATURE:
<223> OTHER INFORMATION: Parcubacteria bacterium

<400> SEQUENCE: 126

Met Glu Asn Ile Phe Asp Gln Phe Ile Gly Lys Tyr Ser Leu Ser Lys
1               5                   10                  15

Thr Leu Arg Phe Glu Leu Lys Pro Val Gly Lys Thr Glu Asp Phe Leu
                20                  25                  30

Lys Ile Asn Lys Val Phe Glu Lys Asp Gln Thr Ile Asp Asp Ser Tyr
            35                  40                  45

Asn Gln Ala Lys Phe Tyr Phe Asp Ser Leu His Gln Lys Phe Ile Asp
        50                  55                  60

Ala Ala Leu Ala Ser Asp Lys Thr Ser Glu Leu Ser Phe Gln Asn Phe
65                  70                  75                  80

Ala Asp Val Leu Glu Lys Gln Asn Lys Ile Ile Leu Asp Lys Lys Arg
                85                  90                  95

Glu Met Gly Ala Leu Arg Lys Arg Asp Lys Asn Ala Val Gly Ile Asp
                100                 105                 110

Arg Leu Gln Lys Glu Ile Asn Asp Ala Glu Asp Ile Ile Gln Lys Glu
            115                 120                 125

Lys Glu Lys Ile Tyr Lys Asp Val Arg Thr Leu Phe Asp Asn Glu Ala
        130                 135                 140

Glu Ser Trp Lys Thr Tyr Tyr Gln Glu Arg Glu Val Asp Gly Lys Lys
145                 150                 155                 160

Ile Thr Glu Ser Lys Ala Asp Leu Lys Gln Lys Gly Ala Asp Phe Leu
                165                 170                 175

Thr Ala Ala Gly Ile Leu Lys Val Leu Lys Tyr Glu Phe Pro Glu Glu
                180                 185                 190
```

```
Lys Glu Lys Glu Phe Gln Ala Lys Asn Gln Pro Ser Leu Phe Val Glu
        195                 200                 205

Glu Lys Glu Asn Pro Gly Gln Lys Arg Tyr Ile Phe Asp Ser Phe Asp
    210                 215                 220

Lys Phe Ala Gly Tyr Leu Thr Lys Phe Gln Gln Thr Lys Lys Asn Leu
225                 230                 235                 240

Tyr Ala Ala Asp Gly Thr Ser Thr Ala Val Ala Thr Arg Ile Ala Asp
                245                 250                 255

Asn Phe Ile Ile Phe His Gln Asn Thr Lys Val Phe Arg Asp Lys Tyr
                260                 265                 270

Lys Asn Asn His Thr Asp Leu Gly Phe Asp Glu Glu Asn Ile Phe Glu
            275                 280                 285

Ile Glu Arg Tyr Lys Asn Cys Leu Leu Gln Arg Glu Ile Glu His Ile
        290                 295                 300

Lys Asn Glu Asn Ser Tyr Asn Lys Ile Ile Gly Arg Ile Asn Lys Lys
305                 310                 315                 320

Ile Lys Glu Tyr Arg Asp Gln Lys Ala Lys Asp Thr Lys Leu Thr Lys
                325                 330                 335

Ser Asp Phe Pro Phe Lys Asn Leu Asp Lys Gln Ile Leu Gly Glu
            340                 345                 350

Val Glu Lys Glu Lys Gln Leu Ile Glu Lys Thr Arg Glu Lys Thr Glu
        355                 360                 365

Glu Asp Val Leu Ile Glu Arg Phe Lys Glu Phe Ile Glu Asn Asn Glu
    370                 375                 380

Glu Arg Phe Thr Ala Ala Lys Lys Leu Met Asn Ala Phe Cys Asn Gly
385                 390                 395                 400

Glu Phe Glu Ser Glu Tyr Glu Gly Ile Tyr Leu Lys Asn Lys Ala Ile
                405                 410                 415

Asn Thr Ile Ser Arg Arg Trp Phe Val Ser Asp Arg Asp Phe Glu Leu
                420                 425                 430

Lys Leu Pro Gln Gln Lys Ser Lys Asn Lys Ser Glu Lys Asn Glu Pro
        435                 440                 445

Lys Val Lys Lys Phe Ile Ser Ile Ala Glu Ile Lys Asn Ala Val Glu
        450                 455                 460

Glu Leu Asp Gly Asp Ile Phe Lys Ala Val Phe Tyr Asp Lys Lys Ile
465                 470                 475                 480

Ile Ala Gln Gly Gly Ser Lys Leu Glu Gln Phe Leu Val Ile Trp Lys
                485                 490                 495

Tyr Glu Phe Glu Tyr Leu Phe Arg Asp Ile Glu Arg Glu Asn Gly Glu
                500                 505                 510

Lys Leu Leu Gly Tyr Asp Ser Cys Leu Lys Ile Ala Lys Gln Leu Gly
            515                 520                 525

Ile Phe Pro Gln Glu Lys Glu Ala Arg Glu Lys Ala Thr Ala Val Ile
        530                 535                 540

Lys Asn Tyr Ala Asp Ala Gly Leu Gly Ile Phe Gln Met Met Lys Tyr
545                 550                 555                 560

Phe Ser Leu Asp Asp Lys Asp Arg Lys Asn Thr Pro Gly Gln Leu Ser
                565                 570                 575

Thr Asn Phe Tyr Ala Glu Tyr Asp Gly Tyr Tyr Lys Asp Phe Glu Phe
            580                 585                 590

Ile Lys Tyr Tyr Asn Glu Phe Arg Asn Phe Ile Thr Lys Lys Pro Phe
        595                 600                 605
```

-continued

```
Asp Glu Asp Lys Ile Lys Leu Asn Phe Glu Asn Gly Ala Leu Leu Lys
610                 615                 620

Gly Trp Asp Glu Asn Lys Glu Tyr Asp Phe Met Gly Val Ile Leu Lys
625                 630                 635                 640

Lys Glu Gly Arg Leu Tyr Leu Gly Ile Met His Lys Asn His Arg Lys
                645                 650                 655

Leu Phe Gln Ser Met Gly Asn Ala Lys Gly Asp Asn Ala Asn Arg Tyr
                660                 665                 670

Gln Lys Met Ile Tyr Lys Gln Ile Ala Asp Ala Ser Lys Asp Val Pro
            675                 680                 685

Arg Leu Leu Leu Thr Ser Lys Lys Ala Met Glu Lys Phe Lys Pro Ser
        690                 695                 700

Gln Glu Ile Leu Arg Ile Lys Lys Glu Lys Thr Phe Lys Arg Glu Ser
705                 710                 715                 720

Lys Asn Phe Ser Leu Arg Asp Leu His Ala Leu Ile Glu Tyr Tyr Arg
                725                 730                 735

Asn Cys Ile Pro Gln Tyr Ser Asn Trp Ser Phe Tyr Asp Phe Gln Phe
                740                 745                 750

Gln Asp Thr Gly Lys Tyr Gln Asn Ile Lys Glu Phe Thr Asp Asp Val
            755                 760                 765

Gln Lys Tyr Gly Tyr Lys Ile Ser Phe Arg Asp Ile Asp Asp Glu Tyr
        770                 775                 780

Ile Asn Gln Ala Leu Asn Glu Gly Lys Met Tyr Leu Phe Glu Val Val
785                 790                 795                 800

Asn Lys Asp Ile Tyr Asn Thr Lys Asn Gly Ser Lys Asn Leu His Thr
                805                 810                 815

Leu Tyr Phe Glu His Ile Leu Ser Ala Glu Asn Leu Asn Asp Pro Val
                820                 825                 830

Phe Lys Leu Ser Gly Met Ala Glu Ile Phe Gln Arg Gln Pro Ser Val
            835                 840                 845

Asn Glu Arg Glu Lys Ile Thr Thr Gln Lys Asn Gln Cys Ile Leu Asp
        850                 855                 860

Lys Gly Asp Arg Ala Tyr Lys Tyr Arg Arg Tyr Thr Glu Lys Lys Ile
865                 870                 875                 880

Met Phe His Met Ser Leu Val Leu Asn Thr Gly Lys Gly Glu Ile Lys
                885                 890                 895

Gln Val Gln Phe Asn Lys Ile Ile Asn Gln Arg Ile Ser Ser Ser Asp
            900                 905                 910

Asn Glu Met Arg Val Asn Val Ile Gly Ile Asp Arg Gly Glu Lys Asn
        915                 920                 925

Leu Leu Tyr Tyr Ser Val Val Lys Gln Asn Gly Glu Ile Ile Glu Gln
930                 935                 940

Ala Ser Leu Asn Glu Ile Asn Gly Val Asn Tyr Arg Asp Lys Leu Ile
945                 950                 955                 960

Glu Arg Glu Lys Glu Arg Leu Lys Asn Arg Gln Ser Trp Lys Pro Val
                965                 970                 975

Val Lys Ile Lys Asp Leu Lys Lys Gly Tyr Ile Ser His Val Ile His
                980                 985                 990

Lys Ile Cys Gln Leu Ile Glu Lys  Tyr Ser Ala Ile Val  Val Leu Glu
            995                 1000                 1005

Asp Leu  Asn Met Arg Phe Lys  Gln Ile Arg Gly Gly  Ile Glu Arg
    1010                 1015                 1020

Ser Val  Tyr Gln Gln Phe Glu  Lys Ala Leu Ile Asp  Lys Leu Gly
```

```
                    1025                1030                1035

Tyr Leu Val Phe Lys Asp Asn Arg Asp Leu Arg Ala Pro Gly Gly
        1040                1045                1050

Val Leu Asn Gly Tyr Gln Leu Ser Ala Pro Phe Val Ser Phe Glu
        1055                1060                1065

Lys Met Arg Lys Gln Thr Gly Ile Leu Phe Tyr Thr Gln Ala Glu
        1070                1075                1080

Tyr Thr Ser Lys Thr Asp Pro Ile Thr Gly Phe Arg Lys Asn Val
        1085                1090                1095

Tyr Ile Ser Asn Ser Ala Ser Leu Asp Lys Ile Lys Glu Ala Val
        1100                1105                1110

Lys Lys Phe Asp Ala Ile Gly Trp Asp Gly Lys Glu Gln Ser Tyr
        1115                1120                1125

Phe Phe Lys Tyr Asn Pro Tyr Asn Leu Ala Asp Glu Lys Tyr Lys
        1130                1135                1140

Asn Ser Thr Val Ser Lys Glu Trp Ala Ile Phe Ala Ser Ala Pro
        1145                1150                1155

Arg Ile Arg Arg Gln Lys Gly Glu Asp Gly Tyr Trp Lys Tyr Asp
        1160                1165                1170

Arg Val Lys Val Asn Glu Glu Phe Glu Lys Leu Leu Lys Val Trp
        1175                1180                1185

Asn Phe Val Asn Pro Lys Ala Thr Asp Ile Lys Gln Glu Ile Ile
        1190                1195                1200

Lys Lys Ile Lys Ala Gly Asp Leu Gln Gly Glu Lys Glu Leu Asp
        1205                1210                1215

Gly Arg Leu Arg Asn Phe Trp His Ser Phe Ile Tyr Leu Phe Asn
        1220                1225                1230

Leu Val Leu Glu Leu Arg Asn Ser Phe Ser Leu Gln Ile Lys Ile
        1235                1240                1245

Lys Ala Gly Glu Val Ile Ala Val Asp Glu Gly Val Asp Phe Ile
        1250                1255                1260

Ala Ser Pro Val Lys Pro Phe Phe Thr Thr Pro Asn Pro Tyr Ile
        1265                1270                1275

Pro Ser Asn Leu Cys Trp Leu Ala Val Glu Asn Ala Asp Ala Asn
        1280                1285                1290

Gly Ala Tyr Asn Ile Ala Arg Lys Gly Val Met Ile Leu Lys Lys
        1295                1300                1305

Ile Arg Glu His Ala Lys Lys Asp Pro Glu Phe Lys Lys Leu Pro
        1310                1315                1320

Asn Leu Phe Ile Ser Asn Ala Glu Trp Asp Glu Ala Ala Arg Asp
        1325                1330                1335

Trp Gly Lys Tyr Ala Gly Thr Thr Ala Leu Asn Leu Asp His
        1340                1345                1350

<210> SEQ ID NO 127
<211> LENGTH: 1260
<212> TYPE: PRT
<213> ORGANISM: Unknown
<220> FEATURE:
<223> OTHER INFORMATION: Porphyromonas crevioricanis

<400> SEQUENCE: 127

Met Asp Ser Leu Lys Asp Phe Thr Asn Leu Tyr Pro Val Ser Lys Thr
1               5                   10                  15

Leu Arg Phe Glu Leu Lys Pro Val Gly Lys Thr Leu Glu Asn Ile Glu
```

```
            20                  25                  30
Lys Ala Gly Ile Leu Lys Glu Asp Glu His Arg Ala Glu Ser Tyr Arg
             35                  40                  45
Arg Val Lys Lys Ile Ile Asp Thr Tyr His Lys Val Phe Ile Asp Ser
 50                  55                  60
Ser Leu Glu Asn Met Ala Lys Met Gly Ile Glu Asn Glu Ile Lys Ala
 65                  70                  75                  80
Met Leu Gln Ser Phe Cys Glu Leu Tyr Lys Lys Asp His Arg Thr Glu
                 85                  90                  95
Gly Glu Asp Lys Ala Leu Asp Lys Ile Arg Ala Val Leu Arg Gly Leu
            100                 105                 110
Ile Val Gly Ala Phe Thr Gly Val Cys Gly Arg Arg Glu Asn Thr Val
            115                 120                 125
Gln Asn Glu Lys Tyr Glu Ser Leu Phe Lys Glu Lys Leu Ile Lys Glu
            130                 135                 140
Ile Leu Pro Asp Phe Val Leu Ser Thr Glu Ala Glu Ser Leu Pro Phe
145                 150                 155                 160
Ser Val Glu Glu Ala Thr Arg Ser Leu Lys Glu Phe Asp Ser Phe Thr
                165                 170                 175
Ser Tyr Phe Ala Gly Phe Tyr Glu Asn Arg Lys Asn Ile Tyr Ser Thr
                180                 185                 190
Lys Pro Gln Ser Thr Ala Ile Ala Tyr Arg Leu Ile His Glu Asn Leu
            195                 200                 205
Pro Lys Phe Ile Asp Asn Ile Leu Val Phe Gln Lys Ile Lys Glu Pro
            210                 215                 220
Ile Ala Lys Glu Leu Glu His Ile Arg Ala Asp Phe Ser Ala Gly Gly
225                 230                 235                 240
Tyr Ile Lys Lys Asp Glu Arg Leu Glu Asp Ile Phe Ser Leu Asn Tyr
                245                 250                 255
Tyr Ile His Val Leu Ser Gln Ala Gly Ile Glu Lys Tyr Asn Ala Leu
                260                 265                 270
Ile Gly Lys Ile Val Thr Glu Gly Asp Gly Glu Met Lys Gly Leu Asn
            275                 280                 285
Glu His Ile Asn Leu Tyr Asn Gln Gln Arg Gly Arg Glu Asp Arg Leu
            290                 295                 300
Pro Leu Phe Arg Pro Leu Tyr Lys Gln Ile Leu Ser Asp Arg Glu Gln
305                 310                 315                 320
Leu Ser Tyr Leu Pro Glu Ser Phe Glu Lys Asp Glu Glu Leu Leu Arg
                325                 330                 335
Ala Leu Lys Glu Phe Tyr Asp His Ile Ala Glu Asp Ile Leu Gly Arg
                340                 345                 350
Thr Gln Gln Leu Met Thr Ser Ile Ser Glu Tyr Asp Leu Ser Arg Ile
            355                 360                 365
Tyr Val Arg Asn Asp Ser Gln Leu Thr Asp Ile Ser Lys Lys Met Leu
            370                 375                 380
Gly Asp Trp Asn Ala Ile Tyr Met Ala Arg Glu Arg Ala Tyr Asp His
385                 390                 395                 400
Glu Gln Ala Pro Lys Arg Ile Thr Ala Lys Tyr Glu Arg Asp Arg Ile
                405                 410                 415
Lys Ala Leu Lys Gly Glu Glu Ser Ile Ser Leu Ala Asn Leu Asn Ser
            420                 425                 430
Cys Ile Ala Phe Leu Asp Asn Val Arg Asp Cys Arg Val Asp Thr Tyr
            435                 440                 445
```

```
Leu Ser Thr Leu Gly Gln Lys Glu Gly Pro His Gly Leu Ser Asn Leu
    450                 455                 460
Val Glu Asn Val Phe Ala Ser Tyr His Glu Ala Glu Gln Leu Leu Ser
465                 470                 475                 480
Phe Pro Tyr Pro Glu Glu Asn Asn Leu Ile Gln Asp Lys Asp Asn Val
                485                 490                 495
Val Leu Ile Lys Asn Leu Leu Asp Asn Ile Ser Asp Leu Gln Arg Phe
                500                 505                 510
Leu Lys Pro Leu Trp Gly Met Gly Asp Glu Pro Asp Lys Asp Glu Arg
            515                 520                 525
Phe Tyr Gly Glu Tyr Asn Tyr Ile Arg Gly Ala Leu Asp Gln Val Ile
    530                 535                 540
Pro Leu Tyr Asn Lys Val Arg Asn Tyr Leu Thr Arg Lys Pro Tyr Ser
545                 550                 555                 560
Thr Arg Lys Val Lys Leu Asn Phe Gly Asn Ser Gln Leu Leu Ser Gly
                565                 570                 575
Trp Asp Arg Asn Lys Glu Lys Asp Asn Ser Cys Val Ile Leu Arg Lys
            580                 585                 590
Gly Gln Asn Phe Tyr Leu Ala Ile Met Asn Asn Arg His Lys Arg Ser
    595                 600                 605
Phe Glu Asn Lys Met Leu Pro Glu Tyr Lys Glu Gly Glu Pro Tyr Phe
610                 615                 620
Glu Lys Met Asp Tyr Lys Phe Leu Pro Asp Pro Asn Lys Met Leu Pro
625                 630                 635                 640
Lys Val Phe Leu Ser Lys Lys Gly Ile Glu Ile Tyr Lys Pro Ser Pro
                645                 650                 655
Lys Leu Leu Glu Gln Tyr Gly His Gly Thr His Lys Lys Gly Asp Thr
            660                 665                 670
Phe Ser Met Asp Asp Leu His Glu Leu Ile Asp Phe Phe Lys His Ser
    675                 680                 685
Ile Glu Ala His Glu Asp Trp Lys Gln Phe Gly Phe Lys Phe Ser Asp
    690                 695                 700
Thr Ala Thr Tyr Glu Asn Val Ser Ser Phe Tyr Arg Glu Val Glu Asp
705                 710                 715                 720
Gln Gly Tyr Lys Leu Ser Phe Arg Lys Val Ser Glu Ser Tyr Val Tyr
                725                 730                 735
Ser Leu Ile Asp Gln Gly Lys Leu Tyr Leu Phe Gln Ile Tyr Asn Lys
            740                 745                 750
Asp Phe Ser Pro Cys Ser Lys Gly Thr Pro Asn Leu His Thr Leu Tyr
    755                 760                 765
Trp Arg Met Leu Phe Asp Glu Arg Asn Leu Ala Asp Val Ile Tyr Lys
    770                 775                 780
Leu Asp Gly Lys Ala Glu Ile Phe Phe Arg Glu Lys Ser Leu Lys Asn
785                 790                 795                 800
Asp His Pro Thr His Pro Ala Gly Lys Pro Ile Lys Lys Ser Arg
                805                 810                 815
Gln Lys Lys Gly Glu Glu Ser Leu Phe Glu Tyr Asp Leu Val Lys Asp
            820                 825                 830
Arg Arg Tyr Thr Met Asp Lys Phe Gln Phe His Val Pro Ile Thr Met
    835                 840                 845
Asn Phe Lys Cys Ser Ala Gly Ser Lys Val Asn Asp Met Val Asn Ala
850                 855                 860
```

```
His Ile Arg Glu Ala Lys Asp Met His Val Ile Gly Ile Asp Arg Gly
865                 870                 875                 880

Glu Arg Asn Leu Leu Tyr Ile Cys Val Ile Asp Ser Arg Gly Thr Ile
                885                 890                 895

Leu Asp Gln Ile Ser Leu Asn Thr Ile Asn Asp Ile Asp Tyr His Asp
            900                 905                 910

Leu Leu Glu Ser Arg Asp Lys Asp Arg Gln Gln Glu His Arg Asn Trp
        915                 920                 925

Gln Thr Ile Glu Gly Ile Lys Glu Leu Lys Gln Gly Tyr Leu Ser Gln
    930                 935                 940

Ala Val His Arg Ile Ala Glu Leu Met Val Ala Tyr Lys Ala Val Val
945                 950                 955                 960

Ala Leu Glu Asp Leu Asn Met Gly Phe Lys Arg Gly Arg Gln Lys Val
                965                 970                 975

Glu Ser Ser Val Tyr Gln Gln Phe Glu Lys Gln Leu Ile Asp Lys Leu
            980                 985                 990

Asn Tyr Leu Val Asp Lys Lys Lys Arg Pro Glu Asp Ile Gly Gly Leu
        995                 1000                1005

Leu Arg Ala Tyr Gln Phe Thr Ala Pro Phe Lys Ser Phe Lys Glu
    1010                1015                1020

Met Gly Lys Gln Asn Gly Phe Leu Phe Tyr Ile Pro Ala Trp Asn
    1025                1030                1035

Thr Ser Asn Ile Asp Pro Thr Thr Gly Phe Val Asn Leu Phe His
    1040                1045                1050

Val Gln Tyr Glu Asn Val Asp Lys Ala Lys Ser Phe Phe Gln Lys
    1055                1060                1065

Phe Asp Ser Ile Ser Tyr Asn Pro Lys Lys Asp Trp Phe Glu Phe
    1070                1075                1080

Ala Phe Asp Tyr Lys Asn Phe Thr Lys Lys Ala Glu Gly Ser Arg
    1085                1090                1095

Ser Met Trp Ile Leu Cys Thr His Gly Ser Arg Ile Lys Asn Phe
    1100                1105                1110

Arg Asn Ser Gln Lys Asn Gly Gln Trp Asp Ser Glu Glu Phe Ala
    1115                1120                1125

Leu Thr Glu Ala Phe Lys Ser Leu Phe Val Arg Tyr Glu Ile Asp
    1130                1135                1140

Tyr Thr Ala Asp Leu Lys Thr Ala Ile Val Asp Glu Lys Gln Lys
    1145                1150                1155

Asp Phe Phe Val Asp Leu Leu Lys Leu Phe Lys Leu Thr Val Gln
    1160                1165                1170

Met Arg Asn Ser Trp Lys Glu Lys Asp Leu Asp Tyr Leu Ile Ser
    1175                1180                1185

Pro Val Ala Gly Ala Asp Gly Arg Phe Phe Asp Thr Arg Glu Gly
    1190                1195                1200

Asn Lys Ser Leu Pro Lys Asp Ala Asp Ala Asn Gly Ala Tyr Asn
    1205                1210                1215

Ile Ala Leu Lys Gly Leu Trp Ala Leu Arg Gln Ile Arg Gln Thr
    1220                1225                1230

Ser Glu Gly Gly Lys Leu Lys Leu Ala Ile Ser Asn Lys Glu Trp
    1235                1240                1245

Leu Gln Phe Val Gln Glu Arg Ser Tyr Glu Lys Asp
    1250                1255                1260
```

<210> SEQ ID NO 128
<211> LENGTH: 1324
<212> TYPE: PRT
<213> ORGANISM: Prevotella disiens

<400> SEQUENCE: 128

```
Met Glu Asn Tyr Gln Glu Phe Thr Asn Leu Phe Gln Leu Asn Lys Thr
1               5                   10                  15

Leu Arg Phe Glu Leu Lys Pro Ile Gly Lys Thr Cys Glu Leu Leu Glu
            20                  25                  30

Glu Gly Lys Ile Phe Ala Ser Gly Ser Phe Leu Glu Lys Asp Lys Val
        35                  40                  45

Arg Ala Asp Asn Val Ser Tyr Val Lys Lys Glu Ile Asp Lys Lys His
    50                  55                  60

Lys Ile Phe Ile Glu Glu Thr Leu Ser Ser Phe Ser Ile Ser Asn Asp
65                  70                  75                  80

Leu Leu Lys Gln Tyr Phe Asp Cys Tyr Asn Glu Leu Lys Ala Phe Lys
                85                  90                  95

Lys Asp Cys Lys Ser Asp Glu Glu Val Lys Lys Thr Ala Leu Arg
            100                 105                 110

Asn Lys Cys Thr Ser Ile Gln Arg Ala Met Arg Glu Ala Ile Ser Gln
            115                 120                 125

Ala Phe Leu Lys Ser Pro Gln Lys Lys Leu Leu Ala Ile Lys Asn Leu
        130                 135                 140

Ile Glu Asn Val Phe Lys Ala Asp Glu Asn Val Gln His Phe Ser Glu
145                 150                 155                 160

Phe Thr Ser Tyr Phe Ser Gly Phe Glu Thr Asn Arg Glu Asn Phe Tyr
                165                 170                 175

Ser Asp Glu Glu Lys Ser Thr Ser Ile Ala Tyr Arg Leu Val His Asp
            180                 185                 190

Asn Leu Pro Ile Phe Ile Lys Asn Ile Tyr Ile Phe Glu Lys Leu Lys
        195                 200                 205

Glu Gln Phe Asp Ala Lys Thr Leu Ser Glu Ile Phe Glu Asn Tyr Lys
    210                 215                 220

Leu Tyr Val Ala Gly Ser Ser Leu Asp Glu Val Phe Ser Leu Glu Tyr
225                 230                 235                 240

Phe Asn Asn Thr Leu Thr Gln Lys Gly Ile Asp Asn Tyr Asn Ala Val
                245                 250                 255

Ile Gly Lys Ile Val Lys Glu Asp Lys Gln Glu Ile Gln Gly Leu Asn
            260                 265                 270

Glu His Ile Asn Leu Tyr Asn Gln Lys His Lys Asp Arg Arg Leu Pro
        275                 280                 285

Phe Phe Ile Ser Leu Lys Lys Gln Ile Leu Ser Asp Arg Glu Ala Leu
    290                 295                 300

Ser Trp Leu Pro Asp Met Phe Lys Asn Asp Ser Glu Val Ile Asp Ala
305                 310                 315                 320

Leu Lys Gly Phe Tyr Ile Glu Asp Gly Phe Glu Asn Asn Val Leu Thr
                325                 330                 335

Pro Leu Ala Thr Leu Leu Ser Ser Leu Asp Lys Tyr Asn Leu Asn Gly
            340                 345                 350

Ile Phe Ile Arg Asn Asn Glu Ala Leu Ser Ser Leu Ser Gln Asn Val
        355                 360                 365

Tyr Arg Asn Phe Ser Ile Asp Glu Ala Ile Asp Ala Gln Asn Ala Glu
    370                 375                 380
```

```
Leu Gln Thr Phe Asn Asn Tyr Glu Leu Ile Ala Asn Ala Leu Arg Ala
385                 390                 395                 400

Lys Ile Lys Lys Glu Thr Lys Gln Gly Arg Lys Ser Phe Glu Lys Tyr
            405                 410                 415

Glu Glu Tyr Ile Asp Lys Lys Val Lys Ala Ile Asp Ser Leu Ser Ile
            420                 425                 430

Gln Glu Ile Asn Glu Leu Val Glu Asn Tyr Val Ser Glu Phe Asn Ser
            435                 440                 445

Asn Ser Gly Asn Met Pro Arg Lys Val Glu Asp Tyr Phe Ser Leu Met
        450                 455                 460

Arg Lys Gly Asp Phe Gly Ser Asn Asp Leu Ile Glu Asn Ile Lys Thr
465                 470                 475                 480

Lys Leu Ser Ala Ala Glu Lys Leu Leu Gly Thr Lys Tyr Gln Glu Thr
                485                 490                 495

Ala Lys Asp Ile Phe Lys Lys Asp Glu Asn Ser Lys Leu Ile Lys Glu
                500                 505                 510

Leu Leu Asp Ala Thr Lys Gln Phe Gln His Phe Ile Lys Pro Leu Leu
            515                 520                 525

Gly Thr Gly Glu Glu Ala Asp Arg Asp Leu Val Phe Tyr Gly Asp Phe
530                 535                 540

Leu Pro Leu Tyr Glu Lys Phe Glu Glu Leu Thr Leu Leu Tyr Asn Lys
545                 550                 555                 560

Val Arg Asn Arg Leu Thr Gln Lys Pro Tyr Ser Lys Asp Lys Ile Arg
                565                 570                 575

Leu Cys Phe Asn Lys Pro Lys Leu Met Thr Gly Trp Val Asp Ser Lys
                580                 585                 590

Thr Glu Lys Ser Asp Asn Gly Thr Gln Tyr Gly Gly Tyr Leu Phe Arg
            595                 600                 605

Lys Lys Asn Glu Ile Gly Glu Tyr Asp Tyr Phe Leu Gly Ile Ser Ser
        610                 615                 620

Lys Ala Gln Leu Phe Arg Lys Asn Glu Ala Val Ile Gly Asp Tyr Glu
625                 630                 635                 640

Arg Leu Asp Tyr Tyr Gln Pro Lys Ala Asn Thr Ile Tyr Gly Ser Ala
                645                 650                 655

Tyr Glu Gly Glu Asn Ser Tyr Lys Glu Asp Lys Lys Arg Leu Asn Lys
                660                 665                 670

Val Ile Ile Ala Tyr Ile Glu Gln Ile Lys Gln Thr Asn Ile Lys Lys
            675                 680                 685

Ser Ile Ile Glu Ser Ile Ser Lys Tyr Pro Asn Ile Ser Asp Asp Asp
        690                 695                 700

Lys Val Thr Pro Ser Ser Leu Leu Glu Lys Ile Lys Lys Val Ser Ile
705                 710                 715                 720

Asp Ser Tyr Asn Gly Ile Leu Ser Phe Lys Ser Phe Gln Ser Val Asn
                725                 730                 735

Lys Glu Val Ile Asp Asn Leu Leu Lys Thr Ile Ser Pro Leu Lys Asn
            740                 745                 750

Lys Ala Glu Phe Leu Asp Leu Ile Asn Lys Asp Tyr Gln Ile Phe Thr
            755                 760                 765

Glu Val Gln Ala Val Ile Asp Glu Ile Cys Lys Gln Lys Thr Phe Ile
            770                 775                 780

Tyr Phe Pro Ile Ser Asn Val Glu Leu Glu Lys Glu Met Gly Asp Lys
785                 790                 795                 800

Asp Lys Pro Leu Cys Leu Phe Gln Ile Ser Asn Lys Asp Leu Ser Phe
```

```
                805                 810                 815
Ala Lys Thr Phe Ser Ala Asn Leu Arg Lys Lys Arg Gly Ala Glu Asn
                820                 825                 830
Leu His Thr Met Leu Phe Lys Ala Leu Met Glu Gly Asn Gln Asp Asn
                835                 840                 845
Leu Asp Leu Gly Ser Gly Ala Ile Phe Tyr Arg Ala Lys Ser Leu Asp
                850                 855                 860
Gly Asn Lys Pro Thr His Pro Ala Asn Glu Ala Ile Lys Cys Arg Asn
865                 870                 875                 880
Val Ala Asn Lys Asp Lys Val Ser Leu Phe Thr Tyr Asp Ile Tyr Lys
                885                 890                 895
Asn Arg Arg Tyr Met Glu Asn Lys Phe Leu Phe His Leu Ser Ile Val
                900                 905                 910
Gln Asn Tyr Lys Ala Ala Asn Asp Ser Ala Gln Leu Asn Ser Ser Ala
                915                 920                 925
Thr Glu Tyr Ile Arg Lys Ala Asp Asp Leu His Ile Ile Gly Ile Asp
                930                 935                 940
Arg Gly Glu Arg Asn Leu Leu Tyr Tyr Ser Val Ile Asp Met Lys Gly
945                 950                 955                 960
Asn Ile Val Glu Gln Asp Ser Leu Asn Ile Ile Arg Asn Asn Asp Leu
                965                 970                 975
Glu Thr Asp Tyr His Asp Leu Leu Asp Lys Arg Glu Lys Glu Arg Lys
                980                 985                 990
Ala Asn Arg Gln Asn Trp Glu Ala Val Glu Gly Ile Lys Asp Leu Lys
                995                 1000                1005
Lys Gly Tyr Leu Ser Gln Ala Val His Gln Ile Ala Gln Leu Met
                1010                1015                1020
Leu Lys Tyr Asn Ala Ile Ile Ala Leu Glu Asp Leu Gly Gln Met
                1025                1030                1035
Phe Val Thr Arg Gly Gln Lys Ile Glu Lys Ala Val Tyr Gln Gln
                1040                1045                1050
Phe Glu Lys Ser Leu Val Asp Lys Leu Ser Tyr Leu Val Asp Lys
                1055                1060                1065
Lys Arg Pro Tyr Asn Glu Leu Gly Gly Ile Leu Lys Ala Tyr Gln
                1070                1075                1080
Leu Ala Ser Ser Ile Thr Lys Asn Asn Ser Asp Lys Gln Asn Gly
                1085                1090                1095
Phe Leu Phe Tyr Val Pro Ala Trp Asn Thr Ser Lys Ile Asp Pro
                1100                1105                1110
Val Thr Gly Phe Thr Asp Leu Leu Arg Pro Lys Ala Met Thr Ile
                1115                1120                1125
Lys Glu Ala Gln Asp Phe Phe Gly Ala Phe Asp Asn Ile Ser Tyr
                1130                1135                1140
Asn Asp Lys Gly Tyr Phe Glu Phe Glu Thr Asn Tyr Asp Lys Phe
                1145                1150                1155
Lys Ile Arg Met Lys Ser Ala Gln Thr Arg Trp Thr Ile Cys Thr
                1160                1165                1170
Phe Gly Asn Arg Ile Lys Arg Lys Lys Asp Lys Asn Tyr Trp Asn
                1175                1180                1185
Tyr Glu Glu Val Glu Leu Thr Glu Glu Phe Lys Lys Leu Phe Lys
                1190                1195                1200
Asp Ser Asn Ile Asp Tyr Glu Asn Cys Asn Leu Lys Glu Glu Ile
                1205                1210                1215
```

-continued

```
Gln Asn Lys Asp Asn Arg Lys Phe Phe Asp Asp Leu Ile Lys Leu
    1220                1225                1230

Leu Gln Leu Thr Leu Gln Met Arg Asn Ser Asp Lys Gly Asn
    1235                1240                1245

Asp Tyr Ile Ile Ser Pro Val Ala Asn Ala Glu Gly Gln Phe Phe
    1250                1255                1260

Asp Ser Arg Asn Gly Asp Lys Lys Leu Pro Leu Asp Ala Asp Ala
    1265                1270                1275

Asn Gly Ala Tyr Asn Ile Ala Arg Lys Gly Leu Trp Asn Ile Arg
    1280                1285                1290

Gln Ile Lys Gln Thr Lys Asn Lys Asp Asp Leu Asn Leu Ser Ile
    1295                1300                1305

Ser Ser Thr Glu Trp Leu Asp Phe Val Arg Glu Lys Pro Tyr Leu
    1310                1315                1320

Lys

<210> SEQ ID NO 129
<211> LENGTH: 1484
<212> TYPE: PRT
<213> ORGANISM: Unknown
<220> FEATURE:
<223> OTHER INFORMATION: Peregrinibacteria bacterium
<220> FEATURE:
<221> NAME/KEY: misc_feature
<222> LOCATION: (1073)..(1073)
<223> OTHER INFORMATION: Xaa can be any naturally occurring amino acid

<400> SEQUENCE: 129

Met Ser Asn Phe Phe Lys Asn Phe Thr Asn Leu Tyr Glu Leu Ser Lys
1               5                   10                  15

Thr Leu Arg Phe Glu Leu Lys Pro Val Gly Asp Thr Leu Thr Asn Met
            20                  25                  30

Lys Asp His Leu Glu Tyr Asp Glu Lys Leu Gln Thr Phe Leu Lys Asp
        35                  40                  45

Gln Asn Ile Asp Asp Ala Tyr Gln Ala Leu Lys Pro Gln Phe Asp Glu
    50                  55                  60

Ile His Glu Glu Phe Ile Thr Asp Ser Leu Glu Ser Lys Lys Ala Lys
65                  70                  75                  80

Glu Ile Asp Phe Ser Glu Tyr Leu Asp Leu Phe Gln Glu Lys Lys Glu
            85                  90                  95

Leu Asn Asp Ser Glu Lys Lys Leu Arg Asn Lys Ile Gly Glu Thr Phe
        100                 105                 110

Asn Lys Ala Gly Glu Lys Trp Lys Lys Glu Lys Tyr Pro Gln Tyr Glu
    115                 120                 125

Trp Lys Lys Gly Ser Lys Ile Ala Asn Gly Ala Asp Ile Leu Ser Cys
130                 135                 140

Gln Asp Met Leu Gln Phe Ile Lys Tyr Lys Asn Pro Glu Asp Glu Lys
145                 150                 155                 160

Ile Lys Asn Tyr Ile Asp Asp Thr Leu Lys Gly Phe Phe Thr Tyr Phe
            165                 170                 175

Gly Gly Phe Asn Gln Asn Arg Ala Asn Tyr Tyr Glu Thr Lys Lys Glu
        180                 185                 190

Ala Ser Thr Ala Val Ala Thr Arg Ile Val His Glu Asn Leu Pro Lys
    195                 200                 205

Phe Cys Asp Asn Val Ile Gln Phe Lys His Ile Ile Lys Arg Lys Lys
210                 215                 220
```

Asp Gly Thr Val Glu Lys Thr Glu Arg Lys Thr Glu Tyr Leu Asn Ala
225                 230                 235                 240

Tyr Gln Tyr Leu Lys Asn Asn Lys Ile Thr Gln Ile Lys Asp Ala
        245                 250                 255

Glu Thr Glu Lys Met Ile Glu Ser Thr Pro Ile Ala Lys Ile Phe
            260                 265                 270

Asp Val Tyr Tyr Phe Ser Ser Cys Leu Ser Gln Lys Gln Ile Glu Glu
        275                 280                 285

Tyr Asn Arg Ile Ile Gly His Tyr Asn Leu Leu Ile Asn Leu Tyr Asn
290                 295                 300

Gln Ala Lys Arg Ser Glu Gly Lys His Leu Ser Ala Asn Glu Lys Lys
305                 310                 315                 320

Tyr Lys Asp Leu Pro Lys Phe Lys Thr Leu Tyr Lys Gln Ile Gly Cys
                325                 330                 335

Gly Lys Lys Lys Asp Leu Phe Tyr Thr Ile Lys Cys Asp Thr Glu Glu
            340                 345                 350

Glu Ala Asn Lys Ser Arg Asn Glu Gly Lys Glu Ser His Ser Val Glu
                355                 360                 365

Glu Ile Ile Asn Lys Ala Gln Glu Ala Ile Asn Lys Tyr Phe Lys Ser
370                 375                 380

Asn Asn Asp Cys Glu Asn Ile Asn Thr Val Pro Asp Phe Ile Asn Tyr
385                 390                 395                 400

Ile Leu Thr Lys Glu Asn Tyr Glu Gly Val Tyr Trp Ser Lys Ala Ala
                405                 410                 415

Met Asn Thr Ile Ser Asp Lys Tyr Phe Ala Asn Tyr His Asp Leu Gln
                420                 425                 430

Asp Arg Leu Lys Glu Ala Lys Val Phe Gln Lys Ala Asp Lys Lys Ser
                435                 440                 445

Glu Asp Asp Ile Lys Ile Pro Glu Ala Ile Glu Leu Ser Gly Leu Phe
450                 455                 460

Gly Val Leu Asp Ser Leu Ala Asp Trp Gln Thr Thr Leu Phe Lys Ser
465                 470                 475                 480

Ser Ile Leu Ser Asn Glu Lys Leu Lys Ile Ile Thr Asp Ser Gln Thr
                485                 490                 495

Pro Ser Glu Ala Leu Leu Lys Met Ile Phe Asn Asp Ile Glu Lys Asn
                500                 505                 510

Met Glu Ser Phe Leu Lys Glu Thr Asn Asp Ile Ile Thr Leu Lys Lys
                515                 520                 525

Tyr Lys Gly Asn Lys Glu Gly Thr Glu Lys Ile Lys Gln Trp Phe Asp
                530                 535                 540

Tyr Thr Leu Ala Ile Asn Arg Met Leu Lys Tyr Phe Leu Val Lys Glu
545                 550                 555                 560

Asn Lys Ile Lys Gly Asn Ser Leu Asp Thr Asn Ile Ser Glu Ala Leu
                565                 570                 575

Lys Thr Leu Ile Tyr Ser Asp Asp Ala Glu Trp Phe Lys Trp Tyr Asp
                580                 585                 590

Ala Leu Arg Asn Tyr Leu Thr Gln Lys Pro Gln Asp Glu Ala Lys Glu
                595                 600                 605

Asn Lys Leu Lys Leu Asn Phe Asp Asn Pro Ser Leu Ala Gly Gly Trp
                610                 615                 620

Asp Val Asn Lys Glu Cys Ser Asn Phe Cys Val Ile Leu Lys Asp Lys
625                 630                 635                 640

```
Asn Glu Lys Lys Tyr Leu Ala Met Ile Lys Lys Gly Glu Asn Thr Leu
                645                 650                 655

Phe Gln Lys Glu Trp Thr Glu Gly Arg Gly Lys Asn Leu Thr Lys Lys
            660                 665                 670

Ser Asn Pro Leu Phe Glu Ile Asn Asn Cys Glu Ile Leu Ser Lys Met
        675                 680                 685

Glu Tyr Asp Phe Trp Ala Asp Val Ser Lys Met Ile Pro Lys Cys Ser
    690                 695                 700

Thr Gln Leu Lys Ala Val Val Asn His Phe Lys Gln Ser Asp Asn Glu
705                 710                 715                 720

Phe Ile Phe Pro Ile Gly Tyr Lys Val Thr Ser Gly Glu Lys Phe Arg
                725                 730                 735

Glu Glu Cys Lys Ile Ser Lys Gln Asp Phe Glu Leu Asn Asn Lys Val
            740                 745                 750

Phe Asn Lys Asn Glu Leu Ser Val Thr Ala Met Arg Tyr Asp Leu Ser
        755                 760                 765

Ser Thr Gln Glu Lys Gln Tyr Ile Lys Ala Phe Gln Lys Glu Tyr Trp
    770                 775                 780

Glu Leu Leu Phe Lys Gln Glu Lys Arg Asp Thr Lys Leu Thr Asn Asn
785                 790                 795                 800

Glu Ile Phe Asn Glu Trp Ile Asn Phe Cys Asn Lys Lys Tyr Ser Glu
                805                 810                 815

Leu Leu Ser Trp Glu Arg Lys Tyr Lys Asp Ala Leu Thr Asn Trp Ile
            820                 825                 830

Asn Phe Cys Lys Tyr Phe Leu Ser Lys Tyr Pro Lys Thr Thr Leu Phe
        835                 840                 845

Asn Tyr Ser Phe Lys Glu Ser Glu Asn Tyr Asn Ser Leu Asp Glu Phe
    850                 855                 860

Tyr Arg Asp Val Asp Ile Cys Ser Tyr Lys Leu Asn Ile Asn Thr Thr
865                 870                 875                 880

Ile Asn Lys Ser Ile Leu Asp Arg Leu Val Glu Glu Gly Lys Leu Tyr
                885                 890                 895

Leu Phe Glu Ile Lys Asn Gln Asp Ser Asn Asp Gly Lys Ser Ile Gly
            900                 905                 910

His Lys Asn Asn Leu His Thr Ile Tyr Trp Asn Ala Ile Phe Glu Asn
        915                 920                 925

Phe Asp Asn Arg Pro Lys Leu Asn Gly Glu Ala Glu Ile Phe Tyr Arg
    930                 935                 940

Lys Ala Ile Ser Lys Asp Lys Leu Gly Ile Val Lys Gly Lys Lys Thr
945                 950                 955                 960

Lys Asn Gly Thr Trp Ile Ile Lys Asn Tyr Arg Phe Ser Lys Glu Lys
                965                 970                 975

Phe Ile Leu His Val Pro Ile Thr Leu Asn Phe Cys Ser Asn Asn Glu
            980                 985                 990

Tyr Val Asn Asp Ile Val Asn Thr  Lys Phe Tyr Asn Phe  Ser Asn Leu
        995                 1000                1005

His Phe Leu Gly Ile Asp Arg  Gly Glu Lys His  Leu Ala Tyr Tyr
    1010                1015                1020

Ser Leu Val Asn Lys Asn Gly  Glu Ile Val Asp Gln  Gly Thr Leu
    1025                1030                1035

Asn Leu Pro Phe Thr Asp Lys  Asp Gly Asn Gln Arg  Ser Ile Lys
    1040                1045                1050

Lys Glu Lys Tyr Phe Tyr Asn  Lys Gln Glu Asp Lys  Trp Glu Ala
```

```
                1055                1060                1065
Lys Glu Val Asp Xaa Trp Asn Tyr Asn Asp Leu Leu Asp Ala Met
    1070                1075                1080
Ala Ser Asn Arg Asp Met Ala Arg Lys Asn Trp Gln Arg Ile Gly
    1085                1090                1095
Thr Ile Lys Glu Ala Lys Asn Gly Tyr Val Ser Leu Val Ile Arg
    1100                1105                1110
Lys Ile Ala Asp Leu Ala Val Asn Asn Glu Arg Pro Ala Phe Ile
    1115                1120                1125
Val Leu Glu Asp Leu Asn Thr Gly Phe Lys Arg Ser Arg Gln Lys
    1130                1135                1140
Ile Asp Lys Ser Val Tyr Gln Lys Phe Glu Leu Ala Leu Ala Lys
    1145                1150                1155
Lys Leu Asn Phe Leu Val Asp Lys Asn Ala Lys Arg Asp Glu Ile
    1160                1165                1170
Gly Ser Pro Thr Lys Ala Leu Gln Leu Thr Pro Pro Val Asn Asn
    1175                1180                1185
Tyr Gly Asp Ile Glu Asn Lys Lys Gln Ala Gly Ile Met Leu Tyr
    1190                1195                1200
Thr Arg Ala Asn Tyr Thr Ser Gln Thr Asp Pro Ala Thr Gly Trp
    1205                1210                1215
Arg Lys Thr Ile Tyr Leu Lys Ala Gly Pro Glu Glu Thr Thr Tyr
    1220                1225                1230
Lys Lys Asp Gly Lys Ile Lys Asn Lys Ser Val Lys Asp Gln Ile
    1235                1240                1245
Ile Glu Thr Phe Thr Asp Ile Gly Phe Asp Gly Lys Asp Tyr Tyr
    1250                1255                1260
Phe Glu Tyr Asp Lys Gly Phe Val Asp Glu Lys Thr Gly Glu
    1265                1270                1275
Ile Lys Pro Lys Lys Trp Arg Leu Tyr Ser Gly Glu Asn Gly Lys
    1280                1285                1290
Ser Leu Asp Arg Phe Arg Gly Glu Arg Glu Lys Asp Lys Tyr Glu
    1295                1300                1305
Trp Lys Ile Asp Lys Ile Asp Ile Val Lys Ile Leu Asp Asp Leu
    1310                1315                1320
Phe Val Asn Phe Asp Lys Asn Ile Ser Leu Leu Lys Gln Leu Lys
    1325                1330                1335
Glu Gly Val Glu Leu Thr Arg Asn Asn Glu His Gly Thr Gly Glu
    1340                1345                1350
Ser Leu Arg Phe Ala Ile Asn Leu Ile Gln Gln Ile Arg Asn Thr
    1355                1360                1365
Gly Asn Asn Glu Arg Asp Asn Asp Phe Ile Leu Ser Pro Val Arg
    1370                1375                1380
Asp Glu Asn Gly Lys His Phe Asp Ser Arg Glu Tyr Trp Asp Lys
    1385                1390                1395
Glu Thr Lys Gly Glu Lys Ile Ser Met Pro Ser Ser Gly Asp Ala
    1400                1405                1410
Asn Gly Ala Phe Asn Ile Ala Arg Lys Gly Ile Ile Met Asn Ala
    1415                1420                1425
His Ile Leu Ala Asn Ser Asp Ser Lys Asp Leu Ser Leu Phe Val
    1430                1435                1440
Ser Asp Glu Glu Trp Asp Leu His Leu Asn Asn Lys Thr Glu Trp
    1445                1450                1455
```

-continued

```
Lys Lys Gln Leu Asn Ile Phe Ser Ser Arg Lys Ala Met Ala Lys
    1460                1465                1470

Arg Lys Lys Lys Arg Pro Ala Ala Thr Lys Lys
    1475                1480

<210> SEQ ID NO 130
<211> LENGTH: 1245
<212> TYPE: PRT
<213> ORGANISM: Porphyromonas macacae

<400> SEQUENCE: 130

Met Lys Thr Gln His Phe Phe Glu Asp Phe Thr Ser Leu Tyr Ser Leu
1               5                   10                  15

Ser Lys Thr Ile Arg Phe Glu Leu Lys Pro Ile Gly Lys Thr Leu Glu
                20                  25                  30

Asn Ile Lys Lys Asn Gly Leu Ile Arg Arg Asp Glu Gln Arg Leu Asp
            35                  40                  45

Asp Tyr Glu Lys Leu Lys Lys Val Ile Asp Glu Tyr His Glu Asp Phe
        50                  55                  60

Ile Ala Asn Ile Leu Ser Ser Phe Ser Phe Ser Glu Glu Ile Leu Gln
65                  70                  75                  80

Ser Tyr Ile Gln Asn Leu Ser Ile Ser Glu Ala Arg Ala Lys Ile Glu
                85                  90                  95

Lys Thr Met Arg Asp Thr Leu Ala Lys Ala Phe Ser Glu Asp Glu Arg
            100                 105                 110

Tyr Lys Ser Ile Phe Lys Lys Glu Leu Val Lys Lys Asp Ile Pro Val
        115                 120                 125

Trp Cys Pro Ala Tyr Lys Ser Leu Cys Lys Lys Phe Asp Asn Phe Thr
    130                 135                 140

Thr Ser Leu Val Pro Phe His Glu Asn Arg Lys Asn Leu Tyr Thr Ser
145                 150                 155                 160

Asn Glu Ile Thr Ala Ser Ile Pro Tyr Arg Ile Val His Val Asn Leu
                165                 170                 175

Pro Lys Phe Ile Gln Asn Ile Glu Ala Leu Cys Glu Leu Gln Lys Lys
            180                 185                 190

Met Gly Ala Asp Leu Tyr Leu Glu Met Met Glu Asn Leu Arg Asn Val
        195                 200                 205

Trp Pro Ser Phe Val Lys Thr Pro Asp Asp Leu Cys Asn Leu Lys Thr
    210                 215                 220

Tyr Asn His Leu Met Val Gln Ser Ser Ile Ser Glu Tyr Asn Arg Phe
225                 230                 235                 240

Val Gly Gly Tyr Ser Thr Glu Asp Gly Thr Lys His Gln Gly Ile Asn
                245                 250                 255

Glu Trp Ile Asn Ile Tyr Arg Gln Arg Asn Lys Glu Met Arg Leu Pro
            260                 265                 270

Gly Leu Val Phe Leu His Lys Gln Ile Leu Ala Lys Val Asp Ser Ser
        275                 280                 285

Ser Phe Ile Ser Asp Thr Leu Glu Asn Asp Asp Gln Val Phe Cys Val
    290                 295                 300

Leu Arg Gln Phe Arg Lys Leu Phe Trp Asn Thr Val Ser Ser Lys Glu
305                 310                 315                 320

Asp Asp Ala Ala Ser Leu Lys Asp Leu Phe Cys Gly Leu Ser Gly Tyr
                325                 330                 335

Asp Pro Glu Ala Ile Tyr Val Ser Asp Ala His Leu Ala Thr Ile Ser
```

```
                340                 345                 350
Lys Asn Ile Phe Asp Arg Trp Asn Tyr Ile Ser Asp Ala Ile Arg Arg
            355                 360                 365
Lys Thr Glu Val Leu Met Pro Arg Lys Lys Glu Ser Val Glu Arg Tyr
        370                 375                 380
Ala Glu Lys Ile Ser Lys Gln Ile Lys Lys Arg Gln Ser Tyr Ser Leu
385                 390                 395                 400
Ala Glu Leu Asp Asp Leu Leu Ala His Tyr Ser Glu Glu Ser Leu Pro
                405                 410                 415
Ala Gly Phe Ser Leu Leu Ser Tyr Phe Thr Ser Leu Gly Gly Gln Lys
            420                 425                 430
Tyr Leu Val Ser Asp Gly Glu Val Ile Leu Tyr Glu Glu Gly Ser Asn
        435                 440                 445
Ile Trp Asp Glu Val Leu Ile Ala Phe Arg Asp Leu Gln Val Ile Leu
    450                 455                 460
Asp Lys Asp Phe Thr Glu Lys Lys Leu Gly Lys Asp Glu Glu Ala Val
465                 470                 475                 480
Ser Val Ile Lys Lys Ala Leu Asp Ser Ala Leu Arg Leu Arg Lys Phe
                485                 490                 495
Phe Asp Leu Leu Ser Gly Thr Gly Ala Glu Ile Arg Arg Asp Ser Ser
            500                 505                 510
Phe Tyr Ala Leu Tyr Thr Asp Arg Met Asp Lys Leu Lys Gly Leu Leu
        515                 520                 525
Lys Met Tyr Asp Lys Val Arg Asn Tyr Leu Thr Lys Lys Pro Tyr Ser
    530                 535                 540
Ile Glu Lys Phe Lys Leu His Phe Asp Asn Pro Ser Leu Leu Ser Gly
545                 550                 555                 560
Trp Asp Lys Asn Lys Glu Leu Asn Asn Leu Ser Val Ile Phe Arg Gln
                565                 570                 575
Asn Gly Tyr Tyr Tyr Leu Gly Ile Met Thr Pro Lys Gly Lys Asn Leu
            580                 585                 590
Phe Lys Thr Leu Pro Lys Leu Gly Ala Glu Glu Met Phe Tyr Glu Lys
        595                 600                 605
Met Glu Tyr Lys Gln Ile Ala Glu Pro Met Leu Met Leu Pro Lys Val
    610                 615                 620
Phe Phe Pro Lys Lys Thr Lys Pro Ala Phe Ala Pro Asp Gln Ser Val
625                 630                 635                 640
Val Asp Ile Tyr Asn Lys Lys Thr Phe Lys Thr Gly Gln Lys Gly Phe
                645                 650                 655
Asn Lys Lys Asp Leu Tyr Arg Leu Ile Asp Phe Tyr Lys Glu Ala Leu
            660                 665                 670
Thr Val His Glu Trp Lys Leu Phe Asn Phe Ser Phe Ser Pro Thr Glu
        675                 680                 685
Gln Tyr Arg Asn Ile Gly Glu Phe Phe Asp Glu Val Arg Glu Gln Ala
    690                 695                 700
Tyr Lys Val Ser Met Val Asn Val Pro Ala Ser Tyr Ile Asp Glu Ala
705                 710                 715                 720
Val Glu Asn Gly Lys Leu Tyr Leu Phe Gln Ile Tyr Asn Lys Asp Phe
                725                 730                 735
Ser Pro Tyr Ser Lys Gly Ile Pro Asn Leu His Thr Leu Tyr Trp Lys
            740                 745                 750
Ala Leu Phe Ser Glu Gln Asn Gln Ser Arg Val Tyr Lys Leu Cys Gly
        755                 760                 765
```

-continued

Gly Gly Glu Leu Phe Tyr Arg Lys Ala Ser Leu His Met Gln Asp Thr
770                 775                 780

Thr Val His Pro Lys Gly Ile Ser Ile His Lys Lys Asn Leu Asn Lys
785                 790                 795                 800

Lys Gly Glu Thr Ser Leu Phe Asn Tyr Asp Leu Val Lys Asp Lys Arg
            805                 810                 815

Phe Thr Glu Asp Lys Phe Phe Phe His Val Pro Ile Ser Ile Asn Tyr
            820                 825                 830

Lys Asn Lys Lys Ile Thr Asn Val Asn Gln Met Val Arg Asp Tyr Ile
            835                 840                 845

Ala Gln Asn Asp Asp Leu Gln His Gly Ile Asp Arg Gly Glu Arg Asn
850                 855                 860

Leu Leu Tyr Ile Ser Arg Ile Asp Thr Arg Gly Asn Leu Leu Glu Gln
865                 870                 875                 880

Phe Ser Leu Asn Val Ile Glu Ser Asp Lys Gly Asp Leu Arg Thr Asp
                885                 890                 895

Tyr Gln Lys Ile Leu Gly Asp Arg Glu Gln Glu Arg Leu Arg Arg Arg
            900                 905                 910

Gln Glu Trp Lys Ser Ile Glu Ser Ile Lys Asp Leu Lys Asp Gly Tyr
            915                 920                 925

Met Ser Gln Val Val His Lys Ile Cys Asn Met Val Val Glu His Lys
930                 935                 940

Ala Ile Val Val Leu Glu Asn Leu Asn Leu Ser Phe Met Lys Gly Arg
945                 950                 955                 960

Lys Lys Val Glu Lys Ser Val Tyr Glu Lys Phe Glu Arg Met Leu Val
                965                 970                 975

Asp Lys Leu Asn Tyr Leu Val Val Asp Lys Lys Asn Leu Ser Asn Glu
            980                 985                 990

Pro Gly Gly Leu Tyr Ala Ala Tyr Gln Leu Thr Asn Pro Leu Phe Ser
            995                 1000                1005

Phe Glu Glu Leu His Arg Tyr Pro Gln Ser Gly Ile Leu Phe Phe
    1010                1015                1020

Val Asp Pro Trp Asn Thr Ser Leu Thr Asp Pro Ser Thr Gly Phe
    1025                1030                1035

Val Asn Leu Leu Gly Arg Ile Asn Tyr Thr Asn Val Gly Asp Ala
    1040                1045                1050

Arg Lys Phe Phe Asp Arg Phe Asn Ala Ile Arg Tyr Asp Gly Lys
    1055                1060                1065

Gly Asn Ile Leu Phe Asp Leu Asp Leu Ser Arg Phe Asp Val Arg
    1070                1075                1080

Val Glu Thr Gln Arg Lys Leu Trp Thr Leu Thr Thr Phe Gly Ser
    1085                1090                1095

Arg Ile Ala Lys Ser Lys Lys Ser Gly Lys Trp Met Val Glu Arg
    1100                1105                1110

Ile Glu Asn Leu Ser Leu Cys Phe Leu Glu Leu Phe Glu Gln Phe
    1115                1120                1125

Asn Ile Gly Tyr Arg Val Glu Lys Asp Leu Lys Lys Ala Ile Leu
    1130                1135                1140

Ser Gln Asp Arg Lys Glu Phe Tyr Val Arg Leu Ile Tyr Leu Phe
    1145                1150                1155

Asn Leu Met Met Gln Ile Arg Asn Ser Asp Gly Glu Glu Asp Tyr
    1160                1165                1170

-continued

```
Ile Leu Ser Pro Ala Leu Asn Glu Lys Asn Leu Gln Phe Asp Ser
1175                1180                1185

Arg Leu Ile Glu Ala Lys Asp Leu Pro Val Asp Ala Asp Ala Asn
1190                1195                1200

Gly Ala Tyr Asn Val Ala Arg Lys Gly Leu Met Val Val Gln Arg
1205                1210                1215

Ile Lys Arg Gly Asp His Glu Ser Ile His Arg Ile Gly Arg Ala
1220                1225                1230

Gln Trp Leu Arg Tyr Val Gln Glu Gly Ile Val Glu
1235                1240                1245

<210> SEQ ID NO 131
<211> LENGTH: 1250
<212> TYPE: PRT
<213> ORGANISM: Unknown
<220> FEATURE:
<223> OTHER INFORMATION: Smithella sp.

<400> SEQUENCE: 131

Met Gln Thr Leu Phe Glu Asn Phe Thr Asn Gln Tyr Pro Val Ser Lys
1               5                   10                  15

Thr Leu Arg Phe Glu Leu Ile Pro Gln Gly Lys Thr Lys Asp Phe Ile
            20                  25                  30

Glu Gln Lys Gly Leu Leu Lys Lys Asp Glu Asp Arg Ala Glu Lys Tyr
        35                  40                  45

Lys Lys Val Lys Asn Ile Ile Asp Glu Tyr His Lys Asp Phe Ile Glu
    50                  55                  60

Lys Ser Leu Asn Gly Leu Lys Leu Asp Gly Leu Glu Lys Tyr Lys Thr
65                  70                  75                  80

Leu Tyr Leu Lys Gln Glu Lys Asp Asp Lys Asp Lys Lys Ala Phe Asp
                85                  90                  95

Lys Glu Lys Glu Asn Leu Arg Lys Gln Ile Ala Asn Ala Phe Arg Asn
            100                 105                 110

Asn Glu Lys Phe Lys Thr Leu Phe Ala Lys Glu Leu Ile Lys Asn Asp
        115                 120                 125

Leu Met Ser Phe Ala Cys Glu Glu Asp Lys Lys Asn Val Lys Glu Phe
130                 135                 140

Glu Ala Phe Thr Thr Tyr Phe Thr Gly Phe His Gln Asn Arg Ala Asn
145                 150                 155                 160

Met Tyr Val Ala Asp Glu Lys Arg Thr Ala Ile Ala Ser Arg Leu Ile
                165                 170                 175

His Glu Asn Leu Pro Lys Phe Ile Asp Asn Ile Lys Ile Phe Glu Lys
            180                 185                 190

Met Lys Lys Glu Ala Pro Glu Leu Leu Ser Pro Phe Asn Gln Thr Leu
        195                 200                 205

Lys Asp Met Lys Asp Val Ile Lys Gly Thr Thr Leu Glu Glu Ile Phe
    210                 215                 220

Ser Leu Asp Tyr Phe Asn Lys Thr Leu Thr Gln Ser Gly Ile Asp Ile
225                 230                 235                 240

Tyr Asn Ser Val Ile Gly Gly Arg Thr Pro Glu Glu Gly Lys Thr Lys
                245                 250                 255

Ile Lys Gly Leu Asn Glu Tyr Ile Asn Thr Asp Phe Asn Gln Lys Gln
            260                 265                 270

Thr Asp Lys Lys Lys Arg Gln Pro Lys Phe Lys Gln Leu Tyr Lys Gln
        275                 280                 285
```

-continued

```
Ile Leu Ser Asp Arg Gln Ser Leu Ser Phe Ile Ala Glu Ala Phe Lys
290                 295                 300

Asn Asp Thr Glu Ile Leu Glu Ala Ile Glu Lys Phe Tyr Val Asn Glu
305                 310                 315                 320

Leu Leu His Phe Ser Asn Glu Gly Lys Ser Thr Asn Val Leu Asp Ala
            325                 330                 335

Ile Lys Asn Ala Val Ser Asn Leu Glu Ser Phe Asn Leu Thr Lys Met
        340                 345                 350

Tyr Phe Arg Ser Gly Ala Ser Leu Thr Asp Val Ser Arg Lys Val Phe
    355                 360                 365

Gly Glu Trp Ser Ile Ile Asn Arg Ala Leu Asp Asn Tyr Tyr Ala Thr
370                 375                 380

Thr Tyr Pro Ile Lys Pro Arg Glu Lys Ser Glu Lys Tyr Glu Glu Arg
385                 390                 395                 400

Lys Glu Lys Trp Leu Lys Gln Asp Phe Asn Val Ser Leu Ile Gln Thr
            405                 410                 415

Ala Ile Asp Glu Tyr Asp Asn Glu Thr Val Lys Gly Lys Asn Ser Gly
        420                 425                 430

Lys Val Ile Ala Asp Tyr Phe Ala Lys Phe Cys Asp Asp Lys Glu Thr
    435                 440                 445

Asp Leu Ile Gln Lys Val Asn Glu Gly Tyr Ile Ala Val Lys Asp Leu
450                 455                 460

Leu Asn Thr Pro Cys Pro Glu Asn Glu Lys Leu Gly Ser Asn Lys Asp
465                 470                 475                 480

Gln Val Lys Gln Ile Lys Ala Phe Met Asp Ser Ile Met Asp Ile Met
            485                 490                 495

His Phe Val Arg Pro Leu Ser Leu Lys Asp Thr Asp Lys Glu Lys Asp
        500                 505                 510

Glu Thr Phe Tyr Ser Leu Phe Thr Pro Leu Tyr Asp His Leu Thr Gln
    515                 520                 525

Thr Ile Ala Leu Tyr Asn Lys Val Arg Asn Tyr Leu Thr Gln Lys Pro
530                 535                 540

Tyr Ser Thr Glu Lys Ile Lys Leu Asn Phe Glu Asn Ser Thr Leu Leu
545                 550                 555                 560

Gly Gly Trp Asp Leu Asn Lys Glu Thr Asp Asn Thr Ala Ile Ile Leu
            565                 570                 575

Arg Lys Asp Asn Leu Tyr Tyr Leu Gly Ile Met Asp Lys Arg His Asn
        580                 585                 590

Arg Ile Phe Arg Asn Val Pro Lys Ala Asp Lys Asp Phe Cys Tyr
    595                 600                 605

Glu Lys Met Val Tyr Lys Leu Leu Pro Gly Ala Asn Lys Met Leu Pro
610                 615                 620

Lys Val Phe Phe Ser Gln Ser Arg Ile Gln Glu Phe Thr Pro Ser Ala
625                 630                 635                 640

Lys Leu Leu Glu Asn Tyr Ala Asn Glu Thr His Lys Lys Gly Asp Asn
            645                 650                 655

Phe Asn Leu Asn His Cys His Lys Leu Ile Asp Phe Phe Lys Asp Ser
        660                 665                 670

Ile Asn Lys His Glu Asp Trp Lys Asn Phe Asp Phe Arg Phe Ser Ala
    675                 680                 685

Thr Ser Thr Tyr Ala Asp Leu Ser Gly Phe Tyr His Glu Val Glu His
690                 695                 700

Gln Gly Tyr Lys Ile Ser Phe Gln Ser Val Ala Asp Ser Phe Ile Asp
```

```
             705                 710                 715                 720
Asp Leu Val Asn Glu Gly Lys Leu Tyr Leu Phe Gln Ile Tyr Asn Lys
                    725                 730                 735
Asp Phe Ser Pro Phe Ser Lys Gly Lys Pro Asn Leu His Thr Leu Tyr
                    740                 745                 750
Trp Lys Met Leu Phe Asp Glu Asn Asn Leu Lys Asp Val Val Tyr Lys
                    755                 760                 765
Leu Asn Gly Glu Ala Glu Val Phe Tyr Arg Lys Ser Ile Ala Glu
                    770                 775                 780
Lys Asn Thr Thr Ile His Lys Ala Asn Glu Ser Ile Ile Asn Lys Asn
785                 790                 795                 800
Pro Asp Asn Pro Lys Ala Thr Ser Thr Phe Asn Tyr Asp Ile Val Lys
                    805                 810                 815
Asp Lys Arg Tyr Thr Ile Asp Lys Phe Gln Phe His Ile Pro Ile Thr
                    820                 825                 830
Met Asn Phe Lys Ala Glu Gly Ile Phe Asn Met Asn Gln Arg Val Asn
                    835                 840                 845
Gln Phe Leu Lys Ala Asn Pro Asp Ile Asn Ile Ile Gly Ile Asp Arg
    850                 855                 860
Gly Glu Arg His Leu Leu Tyr Tyr Ala Leu Ile Asn Gln Lys Gly Lys
865                 870                 875                 880
Ile Leu Lys Gln Asp Thr Leu Asn Val Ile Ala Asn Glu Lys Gln Lys
                    885                 890                 895
Val Asp Tyr His Asn Leu Leu Asp Lys Lys Glu Gly Asp Arg Ala Thr
                    900                 905                 910
Ala Arg Gln Glu Trp Gly Val Ile Glu Thr Ile Lys Glu Leu Lys Glu
                    915                 920                 925
Gly Tyr Leu Ser Gln Val Ile His Lys Leu Thr Asp Leu Met Ile Glu
                    930                 935                 940
Asn Asn Ala Ile Ile Val Met Glu Asp Leu Asn Phe Gly Phe Lys Arg
945                 950                 955                 960
Gly Arg Gln Lys Val Glu Lys Gln Val Tyr Gln Lys Phe Glu Lys Met
                    965                 970                 975
Leu Ile Asp Lys Leu Asn Tyr Leu Val Asp Lys Asn Lys Lys Ala Asn
                    980                 985                 990
Glu Leu Gly Gly Leu Leu Asn Ala Phe Gln Leu Ala Asn Lys Phe Glu
                    995                 1000                1005
Ser Phe Gln Lys Met Gly Lys Gln Asn Gly Phe Ile Phe Tyr Val
    1010                1015                1020
Pro Ala Trp Asn Thr Ser Lys Thr Asp Pro Ala Thr Gly Phe Ile
    1025                1030                1035
Asp Phe Leu Lys Pro Arg Tyr Glu Asn Leu Asn Gln Ala Lys Asp
    1040                1045                1050
Phe Phe Glu Lys Phe Asp Ser Ile Arg Leu Asn Ser Lys Ala Asp
    1055                1060                1065
Tyr Phe Glu Phe Ala Phe Asp Phe Lys Asn Phe Thr Glu Lys Ala
    1070                1075                1080
Asp Gly Gly Arg Thr Lys Trp Thr Val Cys Thr Thr Asn Glu Asp
    1085                1090                1095
Arg Tyr Gln Trp Asn Arg Ala Leu Asn Asn Asn Arg Gly Ser Gln
    1100                1105                1110
Glu Lys Tyr Asp Ile Thr Ala Glu Leu Lys Ser Leu Phe Asp Gly
    1115                1120                1125
```

```
Lys Val Asp Tyr Lys Ser Gly Lys Asp Leu Lys Gln Gln Ile Ala
        1130                1135                1140

Ser Gln Glu Ser Ala Asp Phe Phe Lys Ala Leu Met Lys Asn Leu
    1145                1150                1155

Ser Ile Thr Leu Ser Leu Arg His Asn Asn Gly Glu Lys Gly Asp
    1160                1165                1170

Asn Glu Gln Asp Tyr Ile Leu Ser Pro Val Ala Asp Ser Lys Gly
    1175                1180                1185

Arg Phe Phe Asp Ser Arg Lys Ala Asp Asp Met Pro Lys Asn
    1190                1195                1200

Ala Asp Ala Asn Gly Ala Tyr His Ile Ala Leu Lys Gly Leu Trp
    1205                1210                1215

Cys Leu Glu Gln Ile Ser Lys Thr Asp Asp Leu Lys Lys Val Lys
    1220                1225                1230

Leu Ala Ile Ser Asn Lys Glu Trp Leu Glu Phe Val Gln Thr Leu
    1235                1240                1245

Lys Gly
    1250

<210> SEQ ID NO 132
<211> LENGTH: 3987
<212> TYPE: DNA
<213> ORGANISM: Artificial
<220> FEATURE:
<223> OTHER INFORMATION: enAsCpf1-ver1

<400> SEQUENCE: 132
atggccggga gcaagaagcg ccggataaag caggacacgc agttcgaggg cttcaccaac      60
ctgtaccaag tctccaagac gctccggttc gagcttatcc cgcaagggaa gaccctgaaa     120
cacatccagg aacaaggttt catcgaggag acaaggccc gcaacgacca ctacaaggag      180
ctcaagccca taatcgatcg gatctacaag acgtacgccg accagtgcct ccaactggtg     240
cagctcgact gggagaacct gagcgccgcc attgacagct accgcaagga aaagacggag     300
gagacgcgca cgcccttat tgaggagcaa gccacctacc gcaacgccat ccacgactac      360
ttcatcgggc gcaccgacaa cctgacggac gcgatcaaca gcgccacgc ggaaatctac       420
aagggccttt tcaaggccga gctcttcaac gggaaggtcc taaaacagct cgggactgtc     480
acgacaaccg agcatgagaa cgccctcctt cgcagcttcg acaagttcac cacatacttc     540
tcgggcttct accggaaccg caagaacgtt ttcagcgccg aggacatctc caccgccatc     600
ccgcacagga tcgtccagga caacttcccc aagttcaagg agaactgcca catcttcacg     660
cgcctgatta cagccgtacc ttcacttcgt gagcacttcg agaacgtcaa aaaggccatc     720
gggatcttcg tctccacgtc catcgaggag gtattctctt tcccgttcta taaccagctc     780
ctgacccaga cgcagatcga cctctacaac cagctactgg gcggcatcag ccggaggcc      840
gggaccgaga aaataaaggg cctcaacgaa gttctcaacc tggccatcca agaaacgac      900
gagaccgcgc atatcatcgc atccctgccg catcgcttca ttccttttgtt caagcagata     960
ttgagcgacc ggaacaccct ctcgttcatc ctcgaagaat tcaagagcga cgaggaggtc    1020
attcagtctt tctgcaagta caagacgctc ctacggaatg agaatgtgct ggagaccgcg    1080
gaggcactct tcaatgagct gaactccatt gacctgaccc acatcttcat tagccacaag    1140
aaactggaga cgatctccag cgccctgtgc gaccactggg acactctccg caacgccctc    1200
tacgaacgcc ggatctccga acttaccggc aagataacta gtcggctaa ggagaaggtg    1260
```

-continued

```
caacggagcc tcaagcacga ggacatcaac cttcaggaaa tcatctcagc cgcgggcaag    1320
gagctgagcg aggcgtttaa gcagaaaaca tcggagatac tgagccacgc gcacgcggcc    1380
ctggatcaac cgctgccgac gactctcaag aagcaagagg agaaggaaat ccttaagtcc    1440
cagctcgact cgctgctcgg cctctatcac ttgctcgact ggttcgcggt tgatgagtcc    1500
aacgaggtgg acccggagtt ctccgcgcgc ctcacgggta ttaagctgga gatggagcca    1560
agcttaagct tctacaacaa ggcccgcaac tacgcgacca aaaaaccgta ctcagtcgag    1620
aaattcaagc tgaatttcca gatgcctaca ttggcgaggg ggtgggacgt gaaccgcgag    1680
aagaacaatg gagccatcct gttcgtcaaa aatgggttgt actacctggg catcatgccc    1740
aagcagaagg gccgttacaa ggccctgtca ttcgagccta ccgagaagac ctcggagggc    1800
ttcgacaaga tgtactacga ctatttcccg gacgccgcca agatgatccc gaagtgctcc    1860
acgcagctca agccgtcac ggcccacttc agacgcata ccacgccgat acttctgagc    1920
aacaacttca ttgagccgct agagatcacg aaggagatat acgacctaaa caaccccgaa    1980
aaggagccca agaagttcca gacagcctac gctaagaaga caggtgatca aagggatat    2040 agggaggcac tctgcaagtg gatcgacttc acgcgcgact tcctgtcgaa atatacaaag    2100
acgaccagca ttgacctaag ttctctccgc ccatcctccc agtacaagga tctgggcgag    2160
tattatgcgg agctgaaccc attgctgtac cacatcagct tccagaggat cgccgagaag    2220
gagattatgg acgcggtgga gacggggaaa ctatacctgt tccaaatata taacaaggac    2280
ttcgctaaag ggaccacgg gaagcccaac ctgcacacac tctactggac gggcttgttt    2340
tcgccagaaa atttggccaa gacttcgatc aagctcaacg gccaggcgga gttgttttac    2400
cgtcccaagt ctcgcatgaa gcgcatggcg catcgcctcg agagaaaat gcttaacaag    2460 aagctcaagg atcagaagac gcccatacct gatacgttgt accaggaatt gtacgactac    2520
gtgaaccacc gcctatcgca cgacctctca gacgaggccc gcgccctcct cccaaacgtg    2580
attactaagg aggtttccca tgaaataatc aaggaccgac ggttcaccag cgacaaattt    2640
tttttccacg tgcctatcac gctcaattac caggcggcca actccccatc gaagttcaac    2700
cagcgcgtga acgcctacct taaggagcac ccggagaccc caatcatcgg gatcgaccgt    2760
ggcgagcgga acctgatcta tattacggtg atcgatagca ccggaagat cctggagcag    2820 cgctccctga cacaatcca gcagtttgac taccagaaga aactcgacaa ccgggagaag    2880
gagcgcgtcg cagcccggca agcatggagt gtggtcggca ccataaagga cctgaaacag    2940
ggttacctaa gtcaagttat ccacgagatc gttgacctga tgatacacta tcaagccgta    3000
gtcgtgctgg agaacctcaa cttcgggttt aagtccaagc gcaccggcat cgcggagaag    3060
gcggtgtacc agcagttcga gaagatgctg atcgacaagc tgaactgcct ggtgctcaag    3120
gactaccctg cggagaaggt cggcgggtc ttgaacccgt accagctaac cgaccagttc    3180
acgagcttcg ccaaaatggg cacgcagtcc ggattcttgt tttatgtccc ggctccatat    3240
acaagtaaga tcgacccgct gacagggttt gttgacccat tcgtgtggaa gaccatcaag    3300
aaccacgaga gcaggaaaca cttcttagag ggcttcgact tcctgcatta cgacgttaag    3360
acaggcgact tcatcctgca cttcaagatg aaccgcaacc tgtcgttcca gaggggcctg    3420
cccggcttca tgcccgcctg ggatatcgtc tttgagaaga tgagacgca gttcgacgcg    3480 aaggggacgc cgttcatcgc tggaaagcgg atcgtgccgg tcatcgagaa ccaccgcttc    3540
acgggtcgct accgagattt ataccccgcc aacgaactaa ttgcgctgct ggaggagaag    3600
```

```
gggatcgtgt tccgagatgg cagcaacatt ctcccgaagc tgctggagaa cgacgactcg    3660
cacgctattg acacgatggt cgccctcata cggagcgtgc ttcagatgcg gaacagtaac    3720
gctgccacgg gcgaggacta cattaactcc cccgtccgcg acctcaacgg ggtctgcttc    3780
gatagccgct tccagaaccc ggagtggcct atggatgcgg acgcgaacgg ggcctaccac    3840
atcgccctca agggccaact cctgctcaac cacttgaagg aaagcaaaga cctcaaattg    3900
cagaatggca tcagtaacca ggactggctc gcgtacatcc aggaactgag aaacgggtcc    3960
aagaagcggc gtatcaagca agattga                                        3987
```

<210> SEQ ID NO 133
<211> LENGTH: 3987
<212> TYPE: DNA
<213> ORGANISM: Artificial
<220> FEATURE:
<223> OTHER INFORMATION: enAsCpf1-ver2

<400> SEQUENCE: 133

```
atggcgggaa gcaaaaagcg ccggattaag caagacacgc agttcgaggg cttcacgaac      60
ctctaccaag tcagcaagac cctccggttc gagctgatac acagggaaa gacgctcaag      120 cacatccagg aacagggctt catcgaggag gacaaggcgc gcaacgacca ctacaaggag     180
ttgaaaccga tcatcgaccg catctacaag acgtacgccg accagtgcct ccagctcgtg     240
cagctcgact gggagaacct tccgccgcc attgactcgt accggaagga gaagactgag     300
gagacccgca acgccctgat cgaggagcaa gcaacctacc ggaacgccat ccacgactac    360
ttcatcggcc gcaccgacaa cctcaccgac gcgatcaaca gcggcacgc ggagatatac     420 aaagggctgt tcaaggcgga gctgttcaac ggcaaggtgc tcaagcagct agggacggtg    480
accacgaccg agcacgagaa cgcgctcctc cgcagcttcg acaagttcac cacctacttc    540
agcggcttct accggaaccg caagaatgtg ttcagcgcgg aggacatcag cacggccatc    600
ccgcaccgca tcgtccagga caacttcccg aagttcaagg agaactgcca catcttcacc    660
cgcctgataa ccgccgtccc ctccctgcgg gagcacttcg agaacgtcaa aaaggcaatt    720
gggatcttcg tctcgaccag cattgaggag tgttcagct tcccttcta caaccagctc    780 ctcacccaga cgcagatcga cctgtacaat cagttgctcg gcgggataag ccgcgaggcg    840
ggaaccgaaa aaatcaaggg gctgaacgaa gtgttgaacc tcgccatcca agaagaacgac    900 gagaccgcgc acatcatcgc ctccctgccc caccggttca tcccgctgtt caagcagatc    960
ctctctgacc ggaacaccct gtccttcatt cttgaggagt tcaagtcgga cgaggaggtc    1020
atccagagct tctgcaagta caagacgctg ctacggaacg agaacgtgct ggagacggcg    1080
gaggcactgt tcaacgagct aaacagcatc gacctcacgc acatcttcat cagtcacaag    1140
aaactggaga ccatctcctc cgcgctgtgc gaccactggg acacgctcag gaacgcgctc    1200
tacgagcgcc gaatcagtga gctgacgggc aagatcacga gtccgcgaa ggagaaggtg    1260 cagcggtccc tcaagcacga ggacatcaac tccaggaga tcatctcagc ggctgggaaa    1320
gagctgtccg aggcgttcaa gcagaaaacg agcgaaatcc tgtcccacgc gcacgcggcc    1380
ctggatcagc tctgccgac gaccctcaag aaacaagaag aaaggaaat cctcaagtcg    1440 cagctcgact cgctgctggg cctgtaccat ctcctcgact ggttcgccgt ggacgagagc    1500
aacgaggtgg accccgagtt ctccgcgcgg cttacgggga tcaagctgga gatggagccc    1560
agcctgtcct tctacaacaa ggcgcgcaac tacgccacca gaagccctta cagcgtggag    1620
aagttcaagc tcaacttcca gatgcccact ctcgcacgtg ggtgggacgt caaccgcgaa    1680
```

```
aaaaataatg gggcgatcct gttcgtcaag aacggcctgt actacttggg catcatgccg   1740
aaacagaagg gccgctacaa ggccctgagc ttcgaaccga ccgagaaaac gagcgagggg   1800
ttcgacaaga tgtactacga ctacttcccc gacgccgcga agatgattcc aaagtgctcc   1860
acgcagctta aggccgtgac ggcccacttc cagacgcaca cgaccccgat cctcctcagc   1920
aacaacttca tcgagcccct ggagatcacg aaggagatat acgacctgaa caacccggag   1980
aaggagccca agaaattcca gaccgcctac gccaagaaga caggcgacca aaagggttac   2040
agggaggccc tctgcaagtg gatcgacttc actagggact tcctgtccaa gtacaccaag   2100
actacctcta tcgacctgtc cagcctccgc ccgtcgtccc agtacaaaga tttgggcgag   2160
tattacgcgg agctgaaccc actgctctac cacatcagct tccagcgcat cgcggagaag   2220
gagatcatgg acgcagtgga gacgggcaag ctatacctat ttcagatata caacaaagac   2280
ttcgctaagg gacaccacgg caagcctaac ctgcacaccc tctactggac ggggctcttc   2340
agcccggaga acctcgccaa gacctcgatc aagctcaacg gccaggccga gctgttctac   2400
cggcccaagt cccgcatgaa gcggatggcc caccggctcg gggagaaaat gctcaacaag   2460
aaattgaagg accaaaaaac gccgataccc gacaccctat accaggagct gtacgactat   2520
gtgaaccacc gcctgagcca cgacctcagc gacgaggcgc gggccctcct gccgaacgtc   2580
atcacaaagg aggtcagcca cgagatcatc aaggaccggc gcttcacctc cgacaagttt   2640
ttctttcacg tgcccatcac gctcaactac caggccgcca actcgccgtc caagttcaac   2700
cagcgcgtga cgcctacct caaggagcac cccgagaccc cgatcatcgg gattgaccga   2760
ggggagcgga acctcatcta catcaccgtc atcgacagca ccgggaagat ccttgaacag   2820
cggtcgctca acaccatcca gcagttcgac taccagaaga aactcgacaa ccgggagaag   2880
gagagagtgg cggcccgcca ggcttggtcc gtcgtcggga cgattaagga cttgaaacaa   2940
ggttacctgt cgcaagtgat ccacgagatc gttgacctga tgatccacta ccaagccgtc   3000
gtggtcctgg agaacctcaa cttcggcttc aagagcaaac gaaccggcat cgcggagaag   3060
gccgtgtacc agcagttcga aaaaatgctg atcgacaagc tgaactgcct cgtgctcaag   3120
gactaccccg ctgagaaggt cggcggggtg ctgaacccgt accagctcac tgaccagttc   3180
accagcttcg caaagatggg cacccagtcc ggcttcctgt tctacgtgcc tgcgccatac   3240
acctcgaaga tcgacccgct caccgggttc gtggaccccct tcgtctggaa gaccatcaag   3300
aaccacgaga gccgcaagca cttcctggag ggcttcgact tcctccacta cgacgtcaag   3360
accgggagct tcatcctgca cttcaagatg aaccgcaacc tcagtttcca gcgcggcctg   3420
ccggggttca tgcccgcttg ggatatagtc ttcgagaaga atgagacgca gttcgacgcg   3480
aagggcaccc cgttcatcgc cgggaagcgc atcgtgccgg tcatcgagaa ccaccggttc   3540
accgggcgct accgcgacct ataccccggcg aacgagttga tcgccctcct ggaggagaag   3600
ggcatcgtgt tccgcgacgg ctccaacatc ctcccgaagc tgctcgaaaa cgacgactcc   3660
cacgccatcg acacgatggt cgcgctgatc cggtcggtgc tccagatgcg gaactccaac   3720
gccgcgacgg gcgaggacta catcaacagt ccggtccgcg atctgaacgg cgtctgcttc   3780
gactcccggt tccagaaccc cgagtggccg atggacgcgc acgcgaacgg cgcataccac   3840
atcgccctaa aagggcaatt gctgctcaac cacctcaagg aatccaaaga cctaaagctc   3900
cagaacggca tctccaacca ggactggctg gcgtacatcc aggaactgcg gaacgggagc   3960
aaaaaacgtc ggatcaagca agattga                                      3987
```

<210> SEQ ID NO 134
<211> LENGTH: 3987
<212> TYPE: DNA
<213> ORGANISM: Artificial
<220> FEATURE:
<223> OTHER INFORMATION: enAsCpf1-ver3

<400> SEQUENCE: 134

```
atggcgggct ccaagaaacg ccggattaag caagataccc agttcgaggg gttcacgaac     60
ctctaccaag tgagcaagac cctccgattc gaactgattc ctcagggaa gaccctcaag    120
cacatccagg agcaagggtt catcgaggag acaaggcgc ggaacgacca ctacaaggaa    180
ctcaaaccca tcatcgaccg catctacaag acctacgccg atcagtgcct ccagctcgtg    240
cagttggact gggagaacct cagcgcggcc attgactcct accggaagga gaaaacggag    300
gagacgcgca acgcgctcat cgaggaacag gcaacctatc gcaacgccat ccacgactac    360
ttcatcggga ggactgacaa cctcactgac gcgattaaca gcgccacgc ggagatatac    420
aagggactct tcaaagcgga gctgtttaac ggcaaggttc tcaagcaact cggcactgtg    480
accacgaccg agcatgagaa cgccctgctc cgctccttcg acaagttcac cacctacttc    540
tccggttct accgcaaccg caagaatgtc ttcagcgcgg aggacatcag cacggccatt    600
ccacatcgaa tcgtccaaga taacttcccg aagttcaagg agaactgcca catcttcacc    660
cgactcatta ctgctgtacc gtcgttacgc gaacacttcg agaacgtcaa gaaggcaatt    720
ggaatcttcg tctctacgtc aatagaggag gtgttcagct ccctttcta caaccagctc    780
cttacgcaga cccagataga cctgtacaat cagctcctcg gtgggatcag ccggaggcg    840
gggactgaga agattaaagg gctcaacgag gtcttgaacc tggccatcca aaaaaacgat    900
gagacggcgc acatcatcgc ctcgctgccc caccggttca tcccgctgtt caagcagatc    960
ctcagtgaca ggaacaccct tgagctttat ctagaggagt tcaagagcga cgaggaggtg   1020
atccagagct ctgcaagta caaaaccctg ctgaggaacg agaacgtcct ggagacggcg   1080
gaggcgctgt tcaacgagct gaactctatc gacttaactc acatattcat ctcgcacaag   1140
aagctggaga ctattagctc tgcactctgc gaccactggg acacccctcg caacgcgctc   1200
tacgagcgcc gcatctcgga gctgaccggg aagatcacca atccgcgaa ggaaaaggtc   1260
cagcgttccc tcaaacacga ggatattaac ttacaggaga ttatctcagc ggctgggaag   1320
gagttgtcag aggcgttcaa gcagaaaact tccgagatcc tgagccacgc gcacgcagcg   1380
ctcgaccagc ctctgcccac caccctcaaa aagcaggaag aaaagagat cctcaagagc   1440
cagttggact ccctgctggg gctctatcac cttctcgact ggttcgccgt cgatgagtcg   1500
aacgaggtgg acccgagtt ctccgcccgg ctgaccggca tcaagctaga gatggagccg   1560
tccctcagct tctacaataa ggcccgcaac tacgcgacca aaaaaccta cagcgtggag   1620
aagttcaagc tgaacttcca gatgccgacc ttagcacgcg gtgggacgt aaacaggag   1680
agaacaatg agccatcct gttcgtcaag aacgggcttt actacctcgg ataatgccc   1740
aagcagaagg gccgctacaa ggcccttttcc ttcgagccga cggagaaaac ctccgagggg   1800
ttcgacaaga gtgtactacga ctacttcccc gacgccgcca gatgatccc gaagtgctca   1860
acgcagctaa agccgtgac cgcccacttc cagacccaca cgacgccgat cctgctgagc   1920
aacaacttca tcgagcccct tgagatcact aaggagatat acgacctgaa caaccccgag   1980
aaggagccca gaagtttca aaccgcctac gccaaaaaaa ctggcgacca aaagggctac   2040
agggaggcgc tgtgtaagtg gatcgacttc acacgcgact tcctttcgaa gtatacgaag   2100
```

```
acaacctcta ttgacctgag cagcctgcgt cctagctccc agtacaaaga tttgggcgag    2160
tactacgcgg agcttaatcc actactctac cacatctcat tccagcgcat cgctgagaag    2220
gaaatcatgg acgcggtgga gacaggcaaa ctgtacctct tccagatata caacaaagac    2280
ttcgctaagg ggcaccacgg gaagcccaac cttcatacgc tctactggac gggcctattc    2340
agccccgaaa atctggccaa gacctccatc aagctgaacg ccaagcgga gctgttctac     2400 agacccaaga gccggatgaa gcggatggcc cacaggctcg gcgagaaaat gcttaacaaa    2460
aagttgaagg accagaaaac ccctatcccc gacaccctct accaggaact gtacgactac    2520
gtgaaccaca ggctctcgca cgacctttcc gacgaggccc gtgccctact cccgaacgtc    2580
attaccaaag aggtttcgca cgagatcatc aaggaccggc ggttcacgag cgacaagttt    2640
ttctttcacg tccccatcac ccttaactac caggcggcca actccccatc aagttcaac     2700 cagcgtgtga atgcctacct caaggagcac ccagagaccc cgatcattgg gatcgaccgg    2760
ggcgagcgga acctgatcta catcaccgtc atcgactcga cgggcaagat tcttgagcag    2820
agatcgttga ataccataca gcagttcgac taccagaaga aactcgacaa ccgcgagaag    2880
gagcgcgtgg cggcccgcca ggcgtggtcc gtcgttggga cgattaagga cttgaaacaa    2940
ggttatctgt cccaagtcat ccacgagatc gttgatctga tgatccacta tcaggcagtg    3000
gtggtgctgg agaatctcaa cttcggcttc aagagtaagc ggacgggaat cgccgagaag    3060
gccgtgtacc agcagttcga gaagatgctg atcgacaagc tcaactgcct tgtgctgaaa    3120
gactacccgg ccgagaaggt cggcggcgtc ctcaacccgt accaacttac cgaccagttc    3180
acctccttcg ccaagatggg cactcagtcc gggttcttgt tctacgtccc cgcaccttac    3240
acctctaaga tcgaccctct gactggcttc gtagatccat tcgtgtggaa gaccattaag    3300
aaccacgaga gccgcaagca cttcctggag ggcttcgact tcctgcacta cgacgtgaag    3360 accgggact tcatccttca cttcaagatg aaccggaacc tcagcttcca gcggggcctg     3420
ccggggttca tgcccgcctg ggacatcgtg ttcgagaaga acgagaccca gttcgacgcg    3480
aagggcacgc ccttcatcgc cgggaagcgt atcgtgccgg tgatcgagaa ccatcgtttc    3540
acgggtcgct accgtgacct ctacccggcg aacgagctta tcgcactcct ggaggagaag    3600
ggcatcgtct tccgggacgg ctccaacatc ctcccgaaac tgctggaaaa cgacgactct    3660
cacgccatcg acacgatggt ggccctcatc cggtccgtgc tccaaatgcg gaacagcaac    3720
gccgccaccg tgaggacta catcaacagc ccggtccggg atctgaacgg ggtgtgcttc     3780
gattcgcggt tccagaatcc tgagtggccg atggacgcgg atgcaaacgg ggcgtaccac    3840
atcgcgctca agggccagtt acttctgaac caccttaagg agtctaaaga tttgaaactc    3900
cagaacggga tctcgaacca ggactggctg gcctacatcc aagagttgcg gaacggcagc    3960
aagaagcggc ggattaagca agattag                                        3987
```

<210> SEQ ID NO 135
<211> LENGTH: 9
<212> TYPE: PRT
<213> ORGANISM: Artificial Sequence
<220> FEATURE:
<223> OTHER INFORMATION: Synthetic: Homing endonuclease conserved
      sequence motif

<400> SEQUENCE: 135

Leu Ala Gly Leu Ile Asp Ala Asp Gly
1               5